(12) United States Patent
Jackson et al.

(10) Patent No.: US 11,466,032 B2
(45) Date of Patent: Oct. 11, 2022

(54) CYTOTOXIC AGENTS

(71) Applicant: FEMTOGENIX LIMITED, Hertfordshire (GB)

(72) Inventors: Paul Joseph Mark Jackson, Hertfordshire (GB); David Edwin Thurston, Hertfordshire (GB); Khondaker Mirazur Rahman, Hertfordshire (GB)

(73) Assignee: Femtogenix Limited

( * ) Notice: Subject to any disclaimer, the term of this patent is extended or adjusted under 35 U.S.C. 154(b) by 115 days.

(21) Appl. No.: 16/644,269

(22) PCT Filed: Sep. 4, 2018

(86) PCT No.: PCT/GB2018/052501
§ 371 (c)(1),
(2) Date: Mar. 4, 2020

(87) PCT Pub. No.: WO2019/043417
PCT Pub. Date: Mar. 7, 2019

(65) Prior Publication Data
US 2021/0107923 A1 Apr. 15, 2021

(30) Foreign Application Priority Data
Sep. 4, 2017 (GB) ..................................... 1714115

(51) Int. Cl.
*C07D 519/00* (2006.01)
*A61K 47/68* (2017.01)
*A61P 35/00* (2006.01)

(52) U.S. Cl.
CPC ........ *C07D 519/00* (2013.01); *A61K 47/6803* (2017.08)

(58) Field of Classification Search
CPC .... C07D 519/00; A61K 47/6803; A61P 35/00
See application file for complete search history.

(56) References Cited

U.S. PATENT DOCUMENTS

2015/0315196 A1* 11/2015 Howard .................. A61P 35/02
540/496

FOREIGN PATENT DOCUMENTS

| WO | 2013055990 | 4/2013 |
|---|---|---|
| WO | 2014140862 | 9/2014 |
| WO | 2015028850 | 3/2015 |
| WO | 2016115191 | 7/2016 |
| WO | 2016115201 | 7/2016 |
| WO | 2016198869 | 12/2016 |

OTHER PUBLICATIONS

Donnez, J., "Uterine fibroid management: from the present to the future." Human reproduction update 22.6 (2016): 665-686.*
WebMD, Psoriasis, Jan. 9, 2012; http://www.webmd.com/skin-problems-and-treatments/psoriasis/psoriasis-prevention;accessed online May 4, 2014.*
Verweij, M., 2000 Preventive Medicine Between Obligation and Aspiration 2000, Springer Science and Business Media p. 1-190; Ch. 3; 31 p.*
Skin Cancer Prevention—The Skin Cancer Foundation, 2015 p. 1-3; https://www.skincancer.org/skin-cancer-prevention.*
Belge, K., "Advances in treating psoriasis." F1000prime reports 6 (2014): 1-8.*
Ghoreschi, K., "Selectivity and therapeutic inhibition of kinases: to be or not to be?." Nature immunology 10.4 (2009): 356-360.*
Guspanova, Jana, Written Opinion and Search Report of Int'l Search Authority (PCT/GB2018/052501), dated Nov. 28, 2018.

\* cited by examiner

*Primary Examiner* — John M Mauro
(74) *Attorney, Agent, or Firm* — Maynard Cooper & Gale, P. C.; Matthew J. Parker

(57) ABSTRACT

The invention relates to a compound of formula (I) or formula (II) or pharmaceutically acceptable salts, solvates, tautomers, stereoisomers or mixtures thereof; which are useful as medicaments, in particular as anti-proliferative agents and for use as a drug in an antibody-drug conjugate and in the treatment of proliferative diseases.

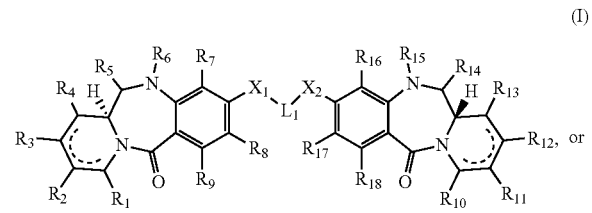

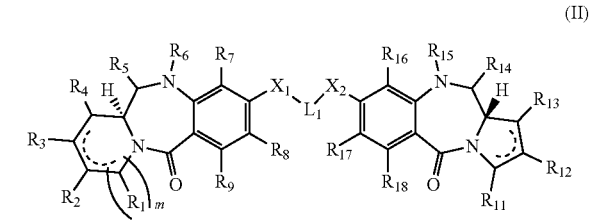

18 Claims, 10 Drawing Sheets
Specification includes a Sequence Listing.

HexA

5'GGATCCCGGGATATCGATATATGGCGCCAAATTTAGCTATAGATCTAGAATTCCGG
ACCGCGGTTTAAACGTTAACCGGTACCTAGGCCTGCAGCTGCGCATGCTAGCGCTTAA
GTACTAGTGCACGTGGCCATGGATCC-3'

TyrT

3'-AAGGCCAATGGAAATTAGGCAATGCCTACTTTTAATGCGTTGGTCAAGAAAAAA
GAGAAGGATTGTGAAATGTCGCCGCGCAGTAAACTATACTACGCGGGGCGAAGGG
CTATTCCCTCGTCCGGTCATTTTTCGTAATGGGGCACCACCCCAAGGGCT-5'

MS1

5'-GGATCCATATGCGGCAATACACATGGCCGATTTCCAACTGCACTAGTCGTAGCGC
GATCAAGGTTAAGCTCCCGTTCTATCCTGGTATAGCAATTAGGGCGTGAAGAGTTAT
GTAAAGTACGTCCGGTGGGGTCTGTTTTGTCATCTCAGCCTCGAATGCGGATCC-3'

FIG. 5

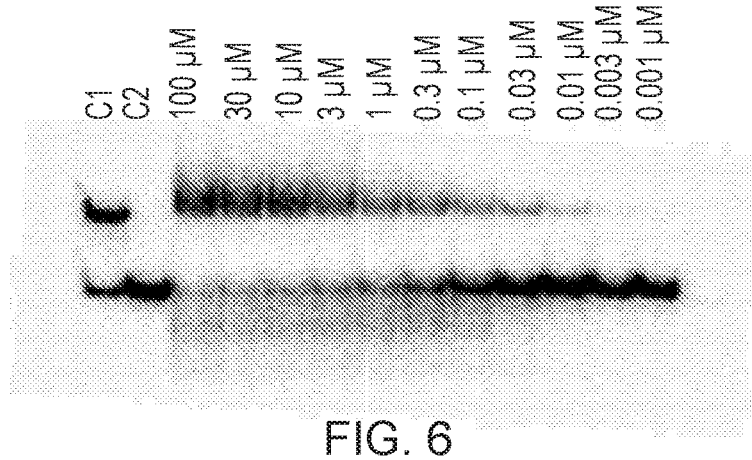

FIG. 6

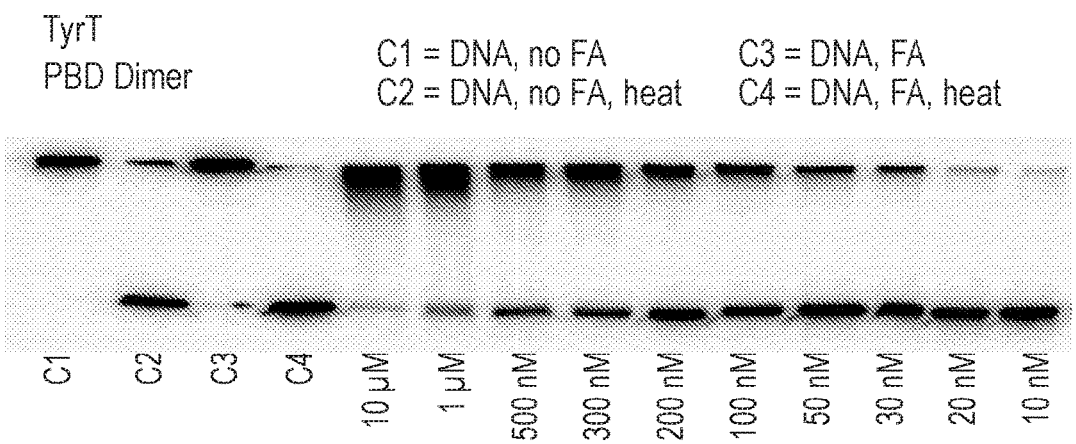

SEQUENCE LISTING

```
<160> NUMBER OF SEQ ID NOS: 64

<210> SEQ ID NO 1
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Arg Ser Ser Gln Ser Ile Val His Ser Val Gly Asn Thr Phe Leu Glu
1               5                   10                  15

<210> SEQ ID NO 2
<211> LENGTH: 7
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 2

Lys Val Ser Asn Arg Phe Ser
1               5

<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Phe Gln Gly Ser Gln Phe Pro Tyr Thr
1               5

<210> SEQ ID NO 4
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Tyr Glu Phe Ser Arg Ser Trp Met Asn
1               5                   10

<210> SEQ ID NO 5
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Arg Ile Tyr Pro Gly Asp Gly Asp Thr Asn Tyr Ser Gly Lys Phe
1               5                   10                  15

Lys Gly

<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Asp Gly Ser Ser Trp Asp Trp Tyr Phe Asp Val
1               5                   10

<210> SEQ ID NO 7
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Asn Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Glu Leu Pro Trp
                85                  90                  95

Thr Phe Gly Gln Gly Thr Lys Val Glu Ile Lys
            100                 105

<210> SEQ ID NO 8
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Glu Val Gln Leu Val Glu Ser Gly Pro Ala Leu Val Lys Pro Thr Gln
1               5                   10                  15

Thr Leu Thr Leu Thr Cys Thr Val Ser Gly Phe Ser Leu Thr Gly Tyr
            20                  25                  30

Ser Val Asn Trp Ile Arg Gln Pro Pro Gly Lys Ala Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Arg Asp Tyr Tyr Phe Asn Tyr Ala Ser Trp Phe Ala Tyr Trp Gly Gln
            100                 105                 110

Gly Thr Leu Val Thr Val Ser Ser
        115                 120

<210> SEQ ID NO 9
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ser Ala Ser Gln Gly Ile Ser Asn Tyr Leu Asn
1               5                   10

<210> SEQ ID NO 10
<211> LENGTH: 7

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Tyr Thr Ser Asn Leu His Ser
1               5

<210> SEQ ID NO 11
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gln Gln Tyr Ser Glu Leu Pro Trp Thr
1               5

<210> SEQ ID NO 12
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Phe Ser Leu Thr Gly Tyr Ser Val Asn
1               5                   10

<210> SEQ ID NO 13
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Met Ile Trp Gly Asp Gly Ser Thr Asp Tyr Asn Ser Ala Leu Lys Ser
1               5                   10                  15

<210> SEQ ID NO 14
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Asp Tyr Tyr Val Asn Tyr Ala Ser Trp Phe Ala Tyr
1               5                   10

<210> SEQ ID NO 15
<211> LENGTH: 214
<212> TYPE: PRT
<213> ORGANISM: Artificial Sequence
<220> FEATURE:
<221> NAME/KEY: source
```

<223> OTHER INFORMATION: /note="Description of Artificial Sequence:
Synthetic polypeptide"

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Glu Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Cys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 16

Glu Val Gln Leu Val Glu Ser Gly Pro Ala Leu Val Lys Pro Thr Gln
1               5                   10                  15

Thr Leu Thr Leu Thr Cys Thr Val Ser Gly Phe Ser Leu Thr Gly Tyr
            20                  25                  30

Ser Val Asn Trp Ile Arg Gln Pro Pro Gly Lys Ala Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Arg Asp Tyr Tyr Phe Asn Tyr Ala Ser Trp Phe Ala Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 17
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

-continued

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Gly Ser
            20                  25                  30

Arg Phe Thr Tyr Met His Trp Tyr Gln Gln Lys Pro Gly Gln Pro Pro
        35                  40                  45

Lys Leu Leu Ile Lys Tyr Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Pro Trp Thr Phe Gly Gln Gly Thr Lys Val Glu Ile Lys
            100                 105                 110

<210> SEQ ID NO 18
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 18

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Trp Met Asn Trp Val Arg Gln Ala Pro Gly Gln Gly Leu Glu Trp Ile
        35                  40                  45

Gly Met Ile His Pro Leu Asp Ala Glu Ile Arg Ala Asn Gln Lys Phe
    50                  55                  60

Arg Asp Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Thr Tyr Asp Gly Gly Phe Glu Tyr Trp Gly Gln Gly Thr
            100                 105                 110

Leu Val Thr Val Ser Ser
        115

<210> SEQ ID NO 19
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 19

Arg Ala Ser Gln Ser Val Ser Gly Ser Arg Phe Thr Tyr Met His
1               5                   10                  15

<210> SEQ ID NO 20
<211> LENGTH: 7
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"

<400> SEQUENCE: 20

Tyr Ala Ser Ile Leu Glu Ser
1               5

<210> SEQ ID NO 21
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gln His Ser Trp Glu Ile Pro Pro Trp Thr
1               5                   10

<210> SEQ ID NO 22
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gly Tyr Trp Met Asn
1               5

<210> SEQ ID NO 23
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Met Ile His Pro Leu Asp Ala Glu Ile Arg Ala Asn Gln Lys Phe Arg
1               5                   10                  15

Asp

<210> SEQ ID NO 24
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gly Thr Tyr Asp Gly Gly Phe Glu Tyr
1               5

<210> SEQ ID NO 25
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Gly Ser
            20                  25                  30

Arg Phe Thr Tyr Met His Trp Tyr Gln Gln Lys Pro Gly Gln Pro Pro
        35                  40                  45

Lys Leu Leu Ile Lys Tyr Ala Ser Ile Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 26
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Trp Met Asn Trp Val Arg Gln Ala Pro Gly Gln Gly Leu Glu Trp Ile
        35                  40                  45

Gly Met Ile His Pro Leu Asp Ala Glu Ile Arg Ala Asn Gln Lys Phe
    50                  55                  60

Arg Asp Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Thr Tyr Asp Gly Gly Phe Glu Tyr Trp Gly Gln Gly Thr
            100                 105                 110

Leu Val Thr Val Ser Ser Ala Ser Thr Lys Gly Pro Ser Val Phe Pro

```
                  115                 120                 125
Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 27
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Met Ile His Pro Met Asp Ser Glu Ile Arg Ala Asn Gln Lys Phe Arg
1               5                   10                  15

Asp
```

<210> SEQ ID NO 28
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 28

Met Ile His Pro Leu Asp Ser Glu Ile Arg Ala Asn Gln Lys Phe Arg
1               5                   10                  15

Asp

<210> SEQ ID NO 29
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 29

Gly Thr Tyr Asp Gly Gly Phe Lys Tyr
1               5

<210> SEQ ID NO 30
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 30

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Ser Gly Ser
                20                  25                  30

Arg Phe Thr Tyr Met His Trp Tyr Gln Gln Lys Pro Gly Gln Pro Pro
            35                  40                  45

Lys Leu Leu Ile Lys Tyr Ala Ser Ile Leu Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Cys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

```
Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 31
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Trp Met Asn Trp Val Arg Gln Ala Pro Gly Gln Gly Leu Glu Trp Ile
        35                  40                  45

Gly Met Ile His Pro Leu Asp Ala Glu Ile Arg Ala Asn Gln Lys Phe
    50                  55                  60

Arg Asp Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Thr Tyr Asp Gly Gly Phe Glu Tyr Trp Gly Gln Gly Thr
            100                 105                 110

Leu Val Thr Val Ser Ser Cys Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320
```

-continued

```
Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 32
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 32

```
Lys Ala Ser Asp Leu Ile His Asn Trp Leu Ala
1               5                   10
```

<210> SEQ ID NO 33
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 33

```
Tyr Gly Ala Thr Ser Leu Glu Thr
1               5
```

<210> SEQ ID NO 34
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 34

```
Gln Gln Tyr Trp Thr Thr Pro Phe Thr
1               5
```

<210> SEQ ID NO 35
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<400> SEQUENCE: 35

Gly Tyr Ser Ile Thr Asn Asp Tyr Ala Trp Asn
1               5                   10

<210> SEQ ID NO 36
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Gly Tyr Ile Ser Tyr Ser Gly Tyr Thr Thr Tyr Asn Pro Ser Leu Lys
1               5                   10                  15

Ser

<210> SEQ ID NO 37
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Ala Arg Trp Ala Ser Gly Leu Asp Tyr
1               5

<210> SEQ ID NO 38
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Leu Ile His Asn Trp
            20                  25                  30

Leu Ala Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Trp Thr Thr Pro Phe
                85                  90                  95

Thr Phe Gly Gln Gly Thr Lys Val Glu Ile Lys Arg
            100                 105

<210> SEQ ID NO 39
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 39

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr Asn Asp
            20                  25                  30

Tyr Ala Trp Asn Trp Val Arg Gln Ala Pro Gly Lys Gly Leu Glu Trp
        35                  40                  45

Val Gly Tyr Ile Ser Tyr Ser Gly Tyr Thr Thr Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Ala Ser Gly Leu Asp Tyr Trp Gly Gln Gly Thr Leu Val
            100                 105                 110

Thr Val Ser Ser
        115
```

<210> SEQ ID NO 40
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 40

```
Gly Tyr Ser Ile Thr Ser Asp Tyr Ala Trp Asn
1               5                   10
```

<210> SEQ ID NO 41
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 41

```
Gly Tyr Ile Ser Asn Ser Gly Ser Thr Ser Tyr Asn Pro Ser Leu Lys
1               5                   10                  15

Ser
```

<210> SEQ ID NO 42
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 42

```
Glu Arg Asn Tyr Asp Tyr Asp Asp Tyr Tyr Ala Met Asp Tyr
1               5                   10              15
```

<210> SEQ ID NO 43
<211> LENGTH: 17
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic peptide"

<400> SEQUENCE: 43

Lys Ser Ser Gln Ser Leu Leu Tyr Arg Ser Asn Gln Lys Asn Tyr Leu
1               5                   10                  15

Ala

<210> SEQ ID NO 44
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Trp Ala Ser Thr Arg Glu Ser
1               5

<210> SEQ ID NO 45
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Gln Gln Tyr Tyr Asn Tyr Pro Arg Thr
1               5

<210> SEQ ID NO 46
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Asp
            20                  25                  30

Tyr Ala Trp Asn Trp Val Arg Gln Ala Pro Gly Lys Gly Leu Glu Trp
        35                  40                  45

Val Gly Tyr Ile Ser Asn Ser Gly Ser Thr Tyr Asn Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Asn Tyr Asp Tyr Asp Tyr Tyr Ala Met Asp
            100                 105                 110

Tyr Trp Gly Gln Gly Thr Leu Val Thr Val Ser Ser
        115                 120
```

```
<210> SEQ ID NO 47
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Tyr Arg
            20                  25                  30

Ser Asn Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Asn Tyr Pro Arg Thr Phe Gly Gln Gly Thr Lys Val Glu Ile
            100                 105                 110

Lys

<210> SEQ ID NO 48
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Gly Phe Ser Phe Ser Asp Phe Ala Met Ser
1               5                   10

<210> SEQ ID NO 49
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Ala Thr Ile Gly Arg Val Ala Phe His Thr Tyr Tyr Pro Asp Ser Met
1               5                   10                  15

Lys Gly

<210> SEQ ID NO 50
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Ala Arg His Arg Gly Phe Asp Val Gly His Phe Asp Phe
```

```
<210> SEQ ID NO 51
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Arg Ser Ser Glu Thr Leu Val His Ser Ser Gly Asn Thr Tyr Leu Glu
1               5                   10                  15

<210> SEQ ID NO 52
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Arg Val Ser Asn Arg Phe Ser
1               5

<210> SEQ ID NO 53
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Phe Gln Gly Ser Phe Asn Pro Leu Thr
1               5

<210> SEQ ID NO 54
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp Phe
            20                  25                  30

Ala Met Ser Trp Val Arg Gln Ala Pro Gly Lys Gly Leu Glu Trp Val
        35                  40                  45

Ala Thr Ile Gly Arg Val Ala Phe His Thr Tyr Tyr Pro Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Arg Gly Phe Asp Val Gly His Phe Asp Phe Trp Gly Gln
            100                 105                 110
```

```
Gly Thr Leu Val Thr Val Ser Ser
        115                 120

<210> SEQ ID NO 55
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Thr Leu Val His Ser
            20                  25                  30

Ser Gly Asn Thr Tyr Leu Glu Trp Tyr Gln Gln Lys Pro Gly Lys Ala
        35                  40                  45

Pro Lys Leu Leu Ile Tyr Arg Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Phe Asn Pro Leu Thr Phe Gly Gln Gly Thr Lys Val Glu Ile Lys
            100                 105                 110

Arg

<210> SEQ ID NO 56
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Gly Asp Thr Asn Tyr Asn Glu Ile Phe
    50                  55                  60

Lys Gly Arg Ala Thr Phe Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110

Val Thr Val Ser Ser
        115

<210> SEQ ID NO 57
<211> LENGTH: 112
<212> TYPE: PRT
```

<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Asp Ile Gln Leu Thr Gln Ser Pro Ser Ser Leu Ser Ala Ser Val Gly
1               5                   10                  15
Asp Arg Val Thr Ile Thr Cys Lys Ala Ser Gln Ser Val Asp Tyr Glu
            20                  25                  30
Gly Asp Ser Phe Leu Asn Trp Tyr Gln Gln Lys Pro Gly Lys Ala Pro
        35                  40                  45
Lys Leu Leu Ile Tyr Ala Ala Ser Asn Leu Glu Ser Gly Val Pro Ser
    50                  55                  60
Arg Phe Ser Gly Ser Gly Ser Gly Thr Asp Phe Thr Leu Thr Ile Ser
65                  70                  75                  80
Ser Leu Gln Pro Glu Asp Phe Ala Thr Tyr Tyr Cys Gln Gln Ser Asn
                85                  90                  95
Glu Asp Pro Leu Thr Phe Gly Gln Gly Thr Lys Val Glu Ile Lys Arg
            100                 105                 110

<210> SEQ ID NO 58
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Gly Tyr Thr Phe Ser Ser Tyr Trp Ile Glu
1               5                   10

<210> SEQ ID NO 59
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Gly Glu Ile Leu Pro Gly Gly Gly Asp Thr Asn Tyr Asn Glu Ile Phe
1               5                   10                  15
Lys Gly

<210> SEQ ID NO 60
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Thr Arg Arg Val Pro Ile Arg Leu Asp Tyr
1               5                   10

<210> SEQ ID NO 61
<211> LENGTH: 15

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Lys Ala Ser Gln Ser Val Asp Tyr Glu Gly Asp Ser Phe Leu Asn
1               5                   10                  15

<210> SEQ ID NO 62
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Ala Ala Ser Asn Leu Glu Ser
1               5

<210> SEQ ID NO 63
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gln Gln Ser Asn Glu Asp Pro Leu Thr
1               5

<210> SEQ ID NO 64
<211> LENGTH: 1255
<212> TYPE: PRT
<213> ORGANISM: Homo sapiens

<400> SEQUENCE: 64

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160
```

```
Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
    530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575
```

-continued

```
Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
                660                 665                 670

Ile Leu Ile Lys Arg Arg Gln Gln Lys Ile Arg Lys Tyr Thr Met Arg
                675                 680                 685

Arg Leu Leu Gln Glu Thr Glu Leu Val Glu Pro Leu Thr Pro Ser Gly
            690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
                740                 745                 750

Lys Val Leu Arg Glu Asn Thr Ser Pro Lys Ala Asn Lys Glu Ile Leu
                755                 760                 765

Asp Glu Ala Tyr Val Met Ala Gly Val Gly Ser Pro Tyr Val Ser Arg
            770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
                820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
                900                 905                 910

Trp Glu Leu Met Thr Phe Gly Ala Lys Pro Tyr Asp Gly Ile Pro Ala
                915                 920                 925
```

-continued

```
Arg Glu Ile Pro Asp Leu Leu Glu Lys Gly Glu Arg Leu Pro Gln Pro
    930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
                980                 985                 990

Asp Leu Gly Pro Ala Ser Pro Leu Asp Ser Thr Phe Tyr Arg Ser Leu
                995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255
```

CYTOTOXIC AGENTS

CROSS-REFERENCE TO RELATED APPLICATIONS

This application is a national stage under 35 U.S.C. 371 of International Application No. PCT/GB2018/052501 having an international filing date of Sep. 4, 2018 (currently published). International Application No. PCT/GB2018/052501 cites the priority of GB Patent Application No. 1714115.1, filed Sep. 4, 2017 (abandoned).

FIELD OF THE INVENTION

The invention relates to DNA-alkylating units comprising fused rings. In particular it relates to compounds comprising a naked C-ring and C-ring substituted (e.g., aryl) pyrridino-benzodiazepine group linked via the A-ring to other aromatic alkylating units (e.g., PBD), and to pharmaceutically acceptable salts thereof, which are useful as medicaments, in particular as anti-proliferative agents.

BACKGROUND

The pyrrolobenzodiazepines (PBDs) are a group of compounds some of which have been shown to be sequence-selective DNA minor-groove binding agents. The PBDs were originally discovered in *Streptomyces* species[2-6] They are tricyclic in nature, and are comprised of fused 6-7-5-membered rings and can be identified as an anthranilate (A ring), a diazepine (B ring) and a pyrrolidine (C ring) 4 They are characterized by an electrophilic N10=C11 imine group (as shown below) or the hydrated equivalent, a carbinolamine [NH—CH(OH)], or a carbinolamine alkyl ether ([NH—CH(OR), where R=alkyl)] which can form a covalent bond to a C2-amino group of guanine in DNA to form a DNA adduct[7]. The natural products interact in the minor groove of the DNA helix with excellent fit (i.e., good "isohelicity") due to a right-handed longitudinal twist induced by a chiral C11a-position which has the (S)-configuration[8].

The DNA adduct has been reported to inhibit a number of biological processes including the binding of transcription factors[9, 10, 11] and the function of enzymes such as endonucleases[12, 13] and RNA polymerase[14]. PBD monomers (e.g., anthramycin) have been shown by footprinting[8], NMR[15, 16], molecular modeling[17] and X-ray crystallography[18] to span three base pairs and to have a thermodynamic preference for the sequence 5'-Pu-G-Pu-3' (where Pu=purine, and G is the reacting guanine)[19] and a kinetic preference for the sequence 5'-Py-G-Py-3'. PBDs are thought to interact with DNA by first locating at a low-energy binding sequence (i.e., a 5'-Pu-G-Pu-3' triplet) through Van der Waals, hydrogen bonding and electrostatic interactions 9. Then, once in place, a nucleophilic attack by the exocyclic C2-amino group of the central guanine occurs to form the covalent adduct[9] (FIG. 2). Once bound, the PBD remains anchored in the DNA minor groove, avoiding DNA repair by causing negligible distortion of the DNA helix[18]. The ability of PBDs to form an adduct in the minor groove and crosslink DNA enables them to interfere with DNA processing and, hence, their potential for use as antiproliferative agents.

WO 2004/087711, WO 2011/117882 and WO 2013/164593 disclose PBD (6-7-5) dimers linked via their A-rings, and more recently WO2012128868 and WO2016115191 disclose G-alkylating agents containing a D-ring (i.e., 6-7-5-6 and 6-7-6-6 respectively), all of which have been shown to act as cytotoxic agents in vitro and as anti-tumour agents in vivo in animal tumour models. Furthermore, the C8/C8'-linked PBD dimer SJG-136[20] has completed Phase I clinical trials for leukaemia and ovarian cancer[21] and has shown sufficient therapeutic benefit to progress to Phase II studies, and two antibody-drug conjugates (ADCs) containing PBD dimers have now entered Phase III clinical trials.

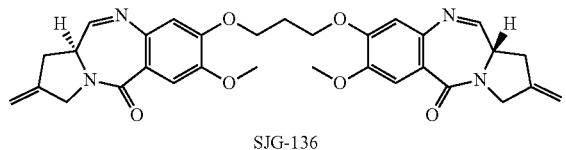

SJG-136

The present application reports pyrridinobenzodiazepines (PDDs) and aryl-PDDs, which are related to PBDs but contain an expanded 6-membered C-ring as compared to the 5-membered C-ring of PBDs, and/or contain an extra bulky group on the C-ring. The PDD is coupled to various G-alkylating moieties through its A-ring. The inventors have discovered that symmetrical and unsymmetrical dimers based on the PDD or C-ring substituted PDD provide properties, such as cytoxicity and DNA binding, that results in effective compounds. In addition, compounds according

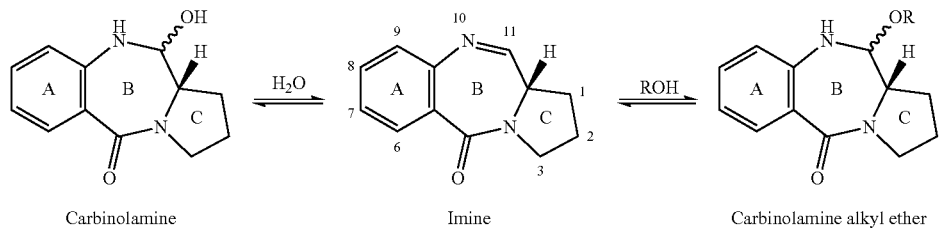

Carbinolamine      Imine      Carbinolamine alkyl ether to the present invention are less hydrophobic than currently available dimer compounds. Hydrophobicity is a key problem associated with the conjugation of PBD dimers to antibodies and other scaffolds and it can have a considerable impact on the successful use of such compounds as therapeutics. The disclosed PBD dimers also show sequence selectivity.

The present invention seeks to overcome problem(s) associated with the prior art.

SUMMARY

In a first aspect, the present invention provides a compound of formula (I) or formula (II):

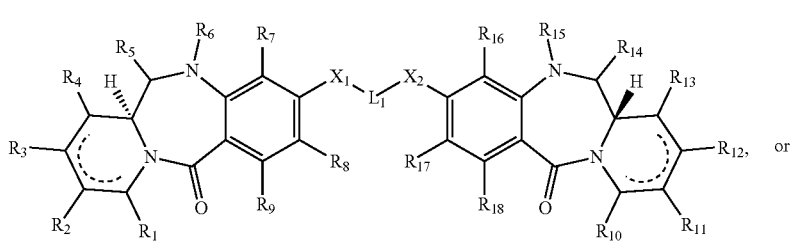

(I)

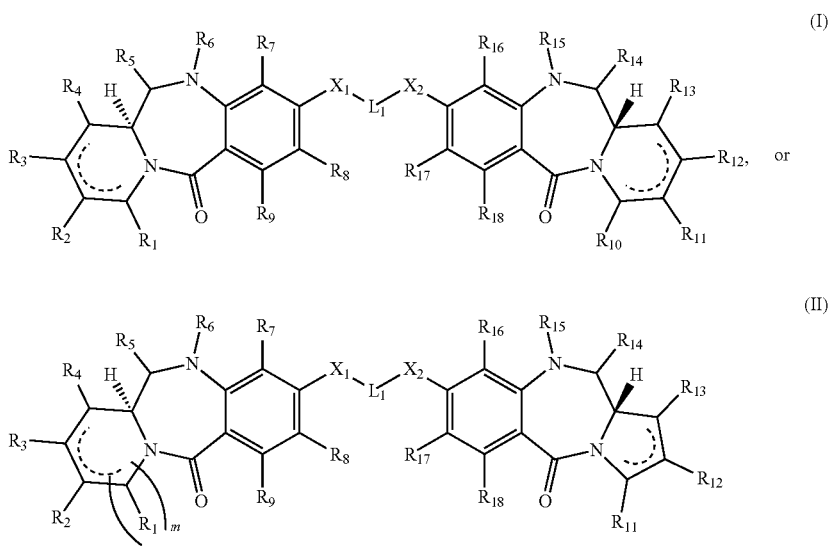

(II)

wherein;

each double line independently represents a single bond or a double bond;

m is 0 or 1;

$R_1$, $R_2$, $R_3$ and $R_4$ are independently selected from H and $R_{19}$; or one of $R_1$ and $R_2$, $R_2$ and $R_3$, or $R_3$ and $R_4$, together with the carbon atoms to which they are attached form a 6-membered aryl, or a 5- or 6-membered cyclic, heterocyclic, or heteroaryl ring optionally substituted with 1, 2 or 3 independently selected optional $R_{20}$ groups;

$R_5$ and $R_6$ are selected such that either (i) $R_5$ is selected from H, OH and $OC_{1-6}$ alkyl; and $R_6$ is selected from H, $SO_3H$, nitrogen protecting groups, -$L_2$-$R_{28}$ and $R_A$; (ii) $R_5$ is oxo or H, and $R_6$ is H or $C_{1-6}$ alkyl; or (iii) $R_5$ and $R_6$ together form a double bond;

$R_7$, $R_9$, $R_{16}$ and $R_{18}$ are independently selected from H and $R_{20}$;

$R_8$ and $R_{17}$ are independently selected from H, $SR_{22}$, $SCH_2Ph$ and $R_{20}$;

$R_{10}$, $R_{11}$, $R_{12}$ and $R_{13}$, are independently selected from H and $R_{19}$; or one of $R_{10}$ and $R_{11}$, $R_{11}$ and $R_{12}$, $R_{12}$ and $R_{13}$, or $R_{13}$ and $R_{14}$ together with the carbon atoms to which they are attached form a 6-membered aryl, or a 5- or 6-membered cyclic, heterocyclic, or heteroaryl ring optionally substituted with 1, 2 or 3 independently selected optional $R_{20}$ groups;

$R_{14}$ and $R_{15}$ are selected such that either (iv) $R_{14}$ is selected from H, OH and $OC_{1-6}$ alkyl; and $R_{15}$ is selected from H, $SO_3H$, nitrogen protecting groups, -$L_2$-$R_2$ and $R_B$; (v) $R_{14}$ is oxo or H, and $R_{15}$ is H or $C_{1-6}$ alkyl; or (vi) $R_{14}$ and $R_{15}$ together form a double bond; with the proviso that if $R_5$ and $R_6$ are selected from (ii) then $R_{14}$ and $R_{15}$ are selected from (iv) and (vi); and if $R_{14}$ and $R_{15}$ are selected from (v) then $R_5$ and $R_6$ are selected from (i) and (iii);

each $R_A$ and $R_B$ is independently selected from $(CH_2)_j$—OH, $(CH_2)_j$—$CO_2R_{26}$, $C(=O)$—O—$(CH_2)_k$—$NR_{26}R_{27}$, $(CH_2)_j$—$NR_{26}R_{27}$, $C(=O)$—NH—$(CH_2)_j$—$NR_{26}R_{27}$ and $C(=O)$—NH—$(CH_2)_k$—$C(=NH)NR_{26}R_{27}$;

$X_1$ is O, S, $NR_{24}$, $CR_{24}R_{25}$, $CR_{24}R_{25}O$, $C(=O)$, $C(=O)NR_{24}$, $NR_{24}C(=O)$, O—$C(O)$, $C(O)$—O or is absent;

$L_1$ is selected from an amino acid, a peptide chain having from 2 to 12 amino acids, a paraformaldehyde chain —$(OCH_2)_{1-24}$—, a polyethylene glycol chain —$(OCH_2CH_2)_{1-12}$— and —$(CH_2)_n$—$Y_1$—$(CH_2)_p$— wherein n is selected from 0, 1, 2, 3, 4, 5, 6, 7, 8, 9, 10, 11 or 12;

p is selected from 0, 1, 2, 3, 4, 5, 6, 7, 8, 9, 10, 11 or 12; and $Y_1$ is selected from —$(CH_2)_{1-5}$—, —$C(O)$—NH—, —NH—, —$S(O)_{0-2}$—, —$C[(CH_2)_{0-5}Y_2]$—, —$Ar_1$—$C(O)$—NH—$(Ar_2)_{0-1}$—$Ar_3$—, —$Ar_3$—$(Ar_2)_{0-1}$—NH—$C(O)$—$Ar_1$—, optionally substituted 3- to 7-membered cycloalkylene or heterocycloalkene, optionally substituted 6-membered arylene, and optionally substituted 5- to 9-membered heteroarylene;

$Y_2$ is H or $R_{20}$;

$Ar_1$ is an optionally substituted 5-membered heteroarylene;

$Ar_2$ is an optionally substituted 6-membered arylene or heteroarylene;

$Ar_3$ is an optionally substituted 5- to 9-membered heteroaryl ring;

wherein the optionally substituted groups of $Y_1$, $Ar_1$, $Ar_2$ and $Ar_3$ are optionally substituted with 1, 2 or 3 independently selected optional $R_{20}$ groups;

$X_2$ is O, S, $NR_{24}$, $CR_{24}R_{25}$, $CR_{24}R_{25}O$, $C(=O)$, $C(=O)NR_{24}$, $NR_{24}C(=O)$, O—$C(O)$, $C(O)$—O or is absent;

each $R_{19}$ is independently selected from $R_{20}$, $R_{21}$, $=CH_2$, $=CH$—$(CH_2)_s$—$CH_3$, $=CH$—$(CH_2)_s$—$R_{21}$, $=O$, $(CH_2)_s$—$OR_{21}$, $(CH_2)_s$—$CO_2R_{21}$, $(CH_2)_s$—$NR_{21}R_{23}$, O—$(CH_2)_t$—$NR_{21}R_{23}$, NH—$C(O)$—$R_{21}$, O—$(CH_2)_t$—NH—$C(O)$—$R_{21}$, O—$(CH_2)_t$—$C(O)$—NH—$R_{21}$, $(CH_2)_s$—$SO_2R_{21}$, O—$SO_2R_{21}$, $(CH_2)_s$—$C(O)R_{21}$ and $(CH_2)_s$—$C(O)NR_{21}R_{23}$;

each $R_{20}$ is independently selected from F, Cl, Br, $(CH_2)_j$—OH, $C_{1-6}$ alkyl, $OC_{1-6}$ alkyl, $OCH_2Ph$, $(CH_2)_j$—$CO_2R_{26}$, O—$(CH_2)_k$—$NR_{26}R_{26}$, $C(=O)$—O—$(CH_2)_k$—$NR_{26}R_{27}$, $C(=O)$—$NR_{26}R_{27}$, $(CH_2)_j$—$NR_{26}R_{27}$, $NR_{26}NH_2$, $C(=O)$—NH—$(CH_2)_j$—$NR_{26}R_{27}$, $C(=O)$—NH—$C_6H_4$—$(CH_2)_j$—$R_{26}$, $C(=O)$—NH—$(CH_2)_k$—$C(=NH)NR_{26}R_{27}$, -$L_2$-$R_{28}$, $S(O)_2$—$(C_{1-6}$ alkyl), O—$(CH_2)_k$—O—$(C_{1-6}$ alkyl), $(CH_2)_j$—$S(O)_2$—$NR_{26}R_{27}$, $C(=NH)$—O—$(C_{1-6}$ alkyl), $(CH_2)_k$—O—$(C_{1-6}$ alkyl), CN, NCO, Cy, $C(O)$—NH—$(CH_2)_j$-Cy, $C(O)$-Cy, NH—$C(O)$—$NR_{26}R_{27}$ and

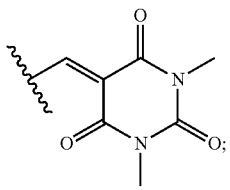 [SMILES: *C=C1C(=O)N(C)C(=O)N(C)C1=O]

each j and s is independently selected from 0, 1, 2, 3, 4, 5 or 6;

each k and t is independently selected from 1, 2, 3, 4, 5 or 6;

each $R_{21}$ is independently selected from H, $C_{1-12}$ alkyl, $C_{5-6}$ heterocyclyl, $C_{5-9}$ heteroaryl, $C_{6-15}$ heteroarylalkyl, phenyl and $C_{7-12}$ aralkyl groups; wherein the heterocyclyl, heteroaryl, heteroarylalkyl, phenyl and aralkyl groups are optionally substituted with 1, 2 or 3 independently selected optional $R_{20}$ groups;

each $R_{22}$, $R_{23}$, $R_{24}$, $R_{25}$, $R_{26}$ and $R_{27}$ is independently selected from H and $C_{1-12}$alkyl;

each Cy is independently selected from a $C_{5-6}$ heterocyclyl or $C_{5-6}$ heteroaryl group, wherein the heterocyclyl or heteroaryl groups are optionally substituted with 1 or 2 $R_{20}$ groups;

$L_2$ is a bond or a linker moiety having 1-200 non-hydrogen atoms selected from C, N, O, S or halogen, and optionally incorporates ether, oxo, carboxamidyl, urethanyl, branched, cyclic, unsaturated, heterocyclyl, aryl or heteroaryl moieties; and $R_{28}$ is an azide, alkyne, bisulfone, carbohydrazide, hydrazine, hydroxylamine, iodoacetamide, isothiocyanate, maleimide, phosphine, pyrridopyridazine, semihydrazide, succinimidyl ester, sulfodichlorophenol ester, sulfonyl halide, sulfosuccinimidyl ester, 4-sulfotetrafluorophenyl ester, tetrafluorophenyl ester, thiazole, $R_4$, O—$(CH_2)_k$—$NR_{26}R_{26}$, $NHNH_2$, or is a targeting agent wherein the targeting agent is selected from a protein, a portion of a protein, a peptide, a nucleic acid, or an antibody;

or pharmaceutically acceptable salts, solvates, tautomers, stereoisomers or mixtures thereof;

with the proviso that either the compound is:
(a) a compound of formula (I), wherein at least one of $R_3$ or $R_{12}$ is an optionally substituted $C_{5-6}$ heterocyclyl, an optionally substituted $C_{5-9}$ heteroaryl or an optionally substituted phenyl;
(b) a compound of formula (I), wherein both $R_2$ and $R_3$, and R and $R_{12}$, together with the carbon atoms to which they are attached form an optionally substituted 5-membered cyclic, heterocyclic, or heteroaryl ring;
(c) a compound of formula (II), wherein m is 1; $R_{12}$ is an optionally substituted $C_{5-6}$ heterocyclyl, an optionally substituted $C_{5-9}$ heteroaryl or an optionally substituted phenyl; and $R_1$, $R_2$, $R_3$, $R_4$, $R_{10}$, $R_{11}$ and $R_{13}$ are independently selected from H and $R_{19}$;
(d) a compound of formula (II), wherein m is 1; $R_{11}$ and $R_{12}$, or $R_{12}$ and $R_{13}$, together with the carbon atoms to which they are attached form an optionally substituted 6-membered aryl, or a 5- or 6-membered cyclic, heterocyclic, or heteroaryl ring; and $R_1$, $R_2$, $R_3$, $R_4$, are independently selected from H and $R_{19}$;
(e) a compound of formula (II), wherein m is 0; $R_{12}$ is an optionally substituted $C_{5-6}$ heterocyclyl, an optionally substituted $C_{5-9}$ heteroaryl or an optionally substituted phenyl; and $R_2$ and $R_3$, or $R_3$ and $R_4$, together with the carbon atoms to which they are attached form an optionally substituted 6-membered aryl, or a 5- or 6-membered cyclic, heterocyclic, or heteroaryl ring; or
(f) a compound of formula (II), wherein m is 1; $R_{12}$ is =$CH_2$, =CH—$(CH_2)_s$—$CH_3$ or =CH—$(CH_2)_s$—$R_{21}$; and $R_1$, $R_2$, $R_3$, $R_4$, $R_{10}$, $R_{11}$, $R_{12}$ and $R_{13}$ are independently selected from H and $R_{19}$.

In another aspect, the present invention provides a compound of formula (I) or formula (II), or pharmaceutically acceptable salts, solvates, tautomers, stereoisomers or mixtures thereof, for use as a medicament.

In a further aspect, there is provided a compound of formula (I) or formula (II), or pharmaceutically acceptable salts, solvates, tautomers, stereoisomers or mixtures thereof, for use in a method of therapy.

In another aspect, the present invention provides a pharmaceutical composition comprising a compound of formula (I) or formula (II), or pharmaceutically acceptable salts, solvates, tautomers, stereoisomers or mixtures thereof, and a pharmaceutically acceptable carrier or diluent. The pharmaceutical composition of the present invention may further comprise one or more (e.g. two, three or four) further active agents.

In another aspect, the present invention provides a compound of formula (I) or formula (II) or pharmaceutically acceptable salts, solvates, tautomers, stereoisomers or mixtures thereof, or a pharmaceutical composition comprising a compound of formula (I) or formula (II), for use in the treatment of a proliferative disease.

In a further aspect, the present invention provides a method of treatment of a patient suffering from a proliferative disease, comprising administering to said patient a therapeutically effective amount of a compound of formula (I) or formula (II) or pharmaceutically acceptable salts, solvates, tautomers, stereoisomers or mixtures thereof, or a pharmaceutical composition comprising a compound of formula (I) or formula (II).

In a further aspect, the compound of formula (I) or formula (II) or pharmaceutically acceptable salts, solvates, tautomers, stereoisomers or mixtures thereof, may be administered alone or in combination with other treatments, either simultaneously or sequentially depending upon the condition to be treated.

In a further aspect, the present invention provides a compound of formula (I) or formula (II) or pharmaceutically acceptable salts, solvates, tautomers, stereoisomers or mixtures thereof, for use as a drug in an antibody-drug conjugate.

In certain aspects, the compound of formula (I) or formula (II) or pharmaceutically acceptable salts, solvates, tautomers, stereoisomers or mixtures thereof, may be used as a payload on a tumour-targeting agent (e.g., antibody, antibody fragment, hormone, etc.).

In a further aspect, the compound of formula (I) or formula (II) or pharmaceutically acceptable salts, solvates, tautomers, stereoisomers or mixtures thereof, may be linked, either directly or indirectly, to a targeting agent (e.g., antibody, antibody fragment, hormone, etc.) to provide a targeted conjugate. The target conjugates of the present disclosure may contain one or multiple compounds of formula (I) or pharmaceutically acceptable salts, solvates, tautomers, stereoisomers or mixtures thereof. A variety of target conjugates are known in the art and may be used with a compound of formula (I) and salts or solvates thereof. For example, in a particular aspect the target conjugate is an antibody-drug conjugate, wherein one or more compounds of formula (I) are linked, directly or indirectly, to the antibody. Therefore, the compound of formula (I) and salts or solvates thereof, may be used as a payload on a targeted conjugate.

Further particular and preferred aspects are set out in the accompanying independent and dependent claims. Features of the dependent claims may be combined with features of the independent claims as appropriate, and in combinations other than those explicitly set out in the claims.

Definitions

The following abbreviations are used throughout the specification: Ac acetyl; Alloc allyloxycarbonyl; BAIB bis(acetoxy)iodobenzene/(diacetoxyiodo)benzene; Boc tert-butoxycarbonyl; DCM dichloromethane; DMAP 4-dimethylaminopyridine; DMF dimethylformamide; DMSO dimethylsulfoxide; Et ethyl; Et$_2$O diethyl ether; EtOAc ethyl acetate; EtOH ethanol; HATU (1-[Bis(dimethylamino)methylene]-1H-1,2,3-triazolo[4,5-b]-pyridinium 3-oxid hexafluorophosphate); Me methyl; MeOH methanol; PBDs pyrrolo[2,1-c][1,4]benzo-diazepines; PDDs pyrridinobenzodiazepines; Ph phenyl; Pyr pyridine; TBAF tetrabutylammonium fluoride; TEMPO (2,2,6,6-tetramethyl-piperidin-1-yl)oxyl; and TBS-Cl/TBDMSCl tert-butyldimethylsilyl chloride.

"Substituted", when used in connection with a chemical substituent or moiety (e.g., an alkyl group), means that one or more hydrogen atoms of the substituent or moiety have been replaced with one or more non-hydrogen atoms or groups, provided that valence requirements are met and that a chemically stable compound results from the substitution.

"Optionally substituted" refers to a parent group which may be unsubstituted or which may be substituted with one or more substituents. Suitably, unless otherwise specified, when optional substituents are present the optional substituted parent group comprises from one to three optional substituents. Where a group may be "optionally substituted with 1, 2 or 3 optional groups", this means that the group may be substituted with 0, 1, 2 or 3 of the optional substituents. Suitably, the group is substituted with 1, 2 or 3 of the optional substituents. Where a group may be "optionally substituted with one or two optional substituents", this means that the group may be substituted with 0, 1 or 2 of the optional substituents. Suitably groups may be optionally substituted with 0 or 1 optional substituents. In some aspects, suitably the group is not optionally substituted. In other aspects, suitably the group is substituted with 1 of the optional substituents.

Optional substituents may be selected from $C_{1-7}$ alkyl, $C_{2-7}$ alkenyl, $C_{2-7}$ alkynyl, $C_{5-20}$ aryl, $C_{3-10}$ cycloalkyl, $C_{3-10}$ cycloalkenyl, $C_{3-10}$ cycloalkynyl, $C_{3-20}$ heterocyclyl, $C_{3-10}$ heteroaryl, acetal, acyl, acylamido, acyloxy, amidino, amido, amino, aminocarbonyloxy, azido, carboxy, cyano, ether, formyl, guanidino, halo, hemiacetal, hemiketal, hydroxamic acid, hydroxyl, imidic acid, imino, ketal, nitro, nitroso, oxo, oxycarbonyl, oxycarboyloxy, sulfamino, sulfamyl, sulfate, sulfhydryl, sulfinamino, sulfinate, sulfino, sulfinyl, sulfinyloxy, sulfo, sulfonamido, sulfonamino, sulfonate, sulfonyl, sulfonyloxy, uredio groups.

"Independently selected" is used in the context of statement that, for example, "each $R_{21}$ and $R_{22}$ are independently selected from H and $C_{1-6}$ alkyl, . . . " and means that each instance of the functional group, e.g. $R_{21}$, is selected from the listed options independently of any other instance of $R_{21}$ or $R_{22}$ in the compound. Hence, for example, H may be selected for the first instance of $R_{21}$ in the compound; methyl may be selected for the next instance of $R_{21}$ in the compound; and ethyl may be selected for the first instance of $R_{22}$ in the compound.

$C_{1-12}$ alkyl: refers to straight chain and branched saturated hydrocarbon groups, generally having from 1 to 12 carbon atoms; more suitably $C_{1-7}$ alkyl; more suitably $C_{1-6}$ alkyl; more suitably $C_{1-3}$ alkyl. Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, n-heptyl, and the like.

"Alkylene" refers to a divalent radical derived from an alkane which may be a straight chain or branched, as exemplified by —CH$_2$CH$_2$CH$_2$CH$_2$—.

"Monocyclic cycloalkylene" refers to a divalent radical derived from a saturated monocyclic hydrocarbon group (or cycloalkane). The cycloalkylene group may be attached to the rest of the compound at any ring atom unless such attachment would violate valence requirements. Suitably, the monocylic cycloalkylene group is a $C_{3-10}$ cycloalkylene group that is a cycloalkyl group having from 3 to 10 carbon atoms that comprise the ring. Suitably the monocylic cycloalkylene group is a $C_{3-7}$ cycloalkylene group, more suitably a $C_6$ cycloalkylene group (i.e. a cyclohexylene group).

The term "amino acid" refers to both the twenty "canonical" or "natural" amino acids, as well "non-canonical" amino acids, also referred to as "unnatural" amino acids, such as modified or synthetic amino acids, as well as amino acid analogs and amino acid mimetics that function similarly to naturally occurring amino acids. Naturally occurring amino acids are those encoded by the genetic code, i.e. they are amino acids selected from alanine, argenine, asparagine, aspartic acid, cysteine, glutamine, glutamic acid, glycine, histidine, isoleucine, leucine, lysine, methionine, phenylalanine, proline, serine, threonine, tryptophan, tyrosine and valine. Modified amino acids include, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

"Aryl": refers to fully unsaturated monocyclic, bicyclic and polycyclic aromatic hydrocarbons having at least one aromatic ring and having a specified number of carbon atoms that comprise their ring members (e.g., 6-membered aryl refers to an aryl group having 6 carbon atoms as ring members and $C_{6-14}$ aryl refers to an aryl group having 6 to 14 carbon atoms as ring members). The aryl group may be attached to a parent group or to a substrate at any ring atom and may include one or more non-hydrogen substituents unless such attachment or substitution would violate valence requirements. Suitably, a $C_{6-14}$ aryl is selected from a $C_{6-12}$ aryl, more suitably, a $C_{6-10}$ aryl. Examples of aryl groups include phenyl.

"Arylene" refers to a divalent radical derived from an aryl group, e.g. —C$_6$H$_4$— which is the arylene derived from phenyl.

"$C_{7-12}$ aralkyl" refers to an arylalkyl group having 7 to 12 carbon atoms and comprising an alkyl group substituted with an aryl group. Suitably the alkyl group is a $C_{1-6}$ alkyl group and the aryl group is phenyl. Examples of $C_{7-12}$ aralkyl include benzyl and phenethyl. In some cases the $C_{7-12}$ aralkyl group may be optionally substituted and an example of an optionally substituted $C_{7-12}$ aralkyl group is 4-methoxybenzyl.

"$C_3$-$C_8$ carbocyclyl" by itself or as part of another term, is a 3-, 4-, 5-, 6-, 7- or 8-membered monovalent, substituted or unsubstituted, saturated or unsaturated non-aromatic monocyclic or bicyclic carbocyclic ring derived by the removal of one hydrogen atom from a ring atom of a parent ring system. Representative $C_3$-$C_8$ carbocyclyl include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, cyclooctadienyl, bicyclo(1.1.1.)pentane, and bicyclo(2.2.2.)octane. A $C_3$-$C_8$ carbocyclyl group can be optionally substituted.

Halogen: refers to a group selected from F, Cl, Br, and I. Suitably, the halogen is Cl.

"heteroalkyl," refers to a stable straight or branched chain hydrocarbon, or combinations thereof, fully saturated or containing from 1 to 3 degrees of unsaturation, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Up to two heteroatoms may be consecutive. Heteroalkyl groups typically comprise from 1 to 15 carbon atoms, preferably from 1 to 12 carbon atoms, more preferably from 1 to 8 carbon atoms, and most preferably from 1 to 4 carbon atoms. Heteroalkyl groups may be optionally substituted.

"heteroalkylene" refers to a divalent group derived from heteroalkyl (as discussed above). For heteroalkylene groups, heteroatoms can also occupy either or both of the chain termini. Heteroalkylene groups may be optionally substituted.

"$C_{5-9}$ heteroaryl": refers to unsaturated monocyclic or bicyclic aromatic groups comprising from 5 to 9 ring atoms, whether carbon or heteroatoms, of which from 1 to 5 are ring heteroatoms. Suitably, any monocyclic heteroaryl ring has from 5 to 6 ring atoms and from 1 to 3 ring heteroatoms. Suitably each ring heteroatom is independently selected from nitrogen, oxygen, and sulfur. The bicyclic rings include fused ring systems and, in particular, include bicyclic groups in which a monocyclic heterocycle comprising 5 ring atoms is fused to a benzene ring. The heteroaryl group may be attached to a parent group or to a substrate at any ring atom and may include one or more non-hydrogen substituents unless such attachment or substitution would violate valence requirements or result in a chemically unstable compound.

Examples of monocyclic heteroaryl groups include, but are not limited to, those derived from:
$N_1$: pyrrole, pyridine;
$O_1$: furan;
$S_1$: thiophene;
$N_1O_1$: oxazole, isoxazole, isoxazine;
$N_2O_1$: oxadiazole (e.g. 1-oxa-2,3-diazolyl, 1-oxa-2,4-diazolyl, 1-oxa-2,5-diazolyl, 1-oxa-3,4-diazolyl);
$N_3O_1$: oxatriazole;
$N_1S_1$: thiazole, isothiazole;
$N_2$: imidazole, pyrazole, pyridazine, pyrimidine, pyrazine;
$N_3$: triazole, triazine; and,
$N_4$: tetrazole.

Examples of heteroaryl which comprise fused rings, include, but are not limited to, those derived from:
$O_1$: benzofuran, isobenzofuran;
$N_1$: indole, isoindole, indolizine, isoindoline;
$S_1$: benzothiofuran;
$N_1O_1$: benzoxazole, benzisoxazole;
$N_1S_1$: benzothiazole;
$N_2$: benzimidazole, indazole;
$O_2$: benzodioxole;
$N_2O_1$: benzofurazan;
$N_2S_1$: benzothiadiazole;
$N_3$: benzotriazole; and
$N_4$: purine (e.g., adenine, guanine), pteridine;

"5- or 6-membered heteroaryl": refers to unsaturated monocyclic aromatic groups comprising from 5 or 6 ring atoms, whether carbon or heteroatoms, of which from 1 to 5 are ring heteroatoms. Suitably, any monocyclic heteroaryl ring has from 5 to 6 ring atoms and from 1 to 3 ring heteroatoms. Suitably each ring heteroatom is independently selected from nitrogen, oxygen, and sulfur. The heteroaryl group may be attached to a parent group or to a substrate at any ring atom and may include one or more non-hydrogen substituents unless such attachment or substitution would violate valence requirements or result in a chemically unstable compound. Examples of monocyclic heteroaryl groups include, but are not limited to, those derived from the list given above in relation to the definition for $C_{5-9}$ heteroaryl.

"heteroarylene" refers to a divalent radical derived from a heteroaryl group (such as those described above) and preferably contain 5-14, 6-14, or 6-20 carbon atoms in addition to one, two or three heteroatoms. Heteroarylenes may be monocyclic, bicyclic, or tricyclic ring systems. Representative heteroarylenes, are not limited to, but may be selected from triazolylene, tetrazolylene, oxadiazolylene, pyridylene, furylene, benzofuranylene, thiophenylene, benzothiophenylene, quinolinylene, pyrrolylene, indolylene, oxazolylene, benzoxazolylene, imidazolylene, benzimidazolylene, thiazolylene, benzothiazolylene, isoxazolylene, pyrazolylene, isothiazolylene, pyridazinylene, pyrimidinylene, pyrazinylene, triazinylene, cinnolinylene, phthalazinylene, quinazolinylene, pyrimidylene, azepinylene, oxepinylene, and quinoxalinylene. Heteroarylenes are optionally substituted.

"Monocyclic heteroarylene" refers to a divalent radical derived from a monocyclic heteroaryl group (in particular those derived from this list of monocyclic heteroaryl groups provided above).

"$C_{6-15}$ heteroarylalkyl" refers to an alkyl group substituted with a heteroaryl group. Suitably the alkyl is a $C_{1-6}$ alkyl group and the heteroaryl group is $C_{5-9}$ heteroaryl as defined above. Examples of $C_{6-15}$ heteroarylalkyl groups include pyrrol-2-ylmethyl, pyrrol-3-ylmethyl, pyrrol-4-ylmethyl, pyrrol-3-ylethyl, pyrrol-4-ylethyl, imidazol-2-ylmethyl, imidazol-4-ylmethyl, imidazol-4-ylethyl, thiophen-3-ylmethyl, furan-3-ylmethyl, pyridin-2-ylmethyl, pyridin-2-ylethyl, thiazol-2-ylmethyl, thiazol-4-ylmethyl, thiazol-2-ylethyl, pyrimidin-2-ylpropyl, and the like.

"$C_{3-20}$ heterocyclyl", "heterocyclic" or "heterocyclo": refers to saturated or partially unsaturated monocyclic, bicyclic or polycyclic groups having ring atoms composed of 3 to 20 ring atoms, whether carbon atoms or heteroatoms, of which from 1 to 10 are ring heteroatoms. Suitably, each ring has from 3 to 7 ring atoms and from 1 to 4 ring heteroatoms (e.g., suitably $C_{3-5}$ heterocyclyl refers to a heterocyclyl group having 3 to 5 ring atoms and 1 to 4 heteroatoms as ring members). The ring heteroatoms are independently selected from nitrogen, oxygen, and sulphur.

As with bicyclic cycloalkyl groups, bicyclic heterocyclyl groups may include isolated rings, spiro rings, fused rings, and bridged rings. The heterocyclyl group may be attached to a parent group or to a substrate at any ring atom and may include one or more non-hydrogen substituents unless such attachment or substitution would violate valence requirements or result in a chemically unstable compound.

Examples of monocyclic heterocyclyl groups include, but are not limited to, those derived from:

$N_1$: aziridine, azetidine, pyrrolidine, pyrroline, 2H-pyrrole or 3H-pyrrole, piperidine, dihydropyridine, tetrahydropyridine, azepine;

$O_1$: oxirane, oxetane, tetrahydrofuran, dihydrofuran, tetrahydropyran, dihydropyran, pyran, oxepin;

$S_1$: thiirane, thietane, tetrahydrothiophene, tetrahydrothiopyran, thiepane;

$O_2$: dioxolane, dioxane, and dioxepane;

$O_3$: trioxane;

$N_2$: imidazolidine, pyrazolidine, imidazoline, pyrazoline, piperazine, uracil;

$N_1O_1$: tetrahydrooxazole, dihydrooxazole, tetrahydroisoxazole, dihydroisoxazole, morpholine, tetrahydrooxazine, dihydrooxazine, oxazine;

$N_1S_1$: thiazoline, thiazolidine, thiomorpholine;

$N_2O_1$: oxadiazine;

$O_1S_1$: oxathiole and oxathiane (thioxane); and $N_1O_1S_1$: oxathiazine.

Examples of substituted monocyclic heterocyclyl groups include those derived from saccharides, in cyclic form, for example, furanoses, such as arabinofuranose, lyxofuranose, ribofuranose, and xylofuranse, and pyranoses, such as aliopyranose, altropyranose, glucopyranose, mannopyranose, gulopyranose, idopyranose, galactopyranose, and talopyranose.

"5- or 6-membered heterocyclic" refers to saturated or partially unsaturated monocyclic examples of "$C_{3-20}$ heterocyclyl" groups. 5- or 6-membered heterocyclic having ring atoms composed of 5 to 6 ring atoms, whether carbon atoms or heteroatoms, of which from 1 to 4 are ring heteroatoms. More suitably, each ring has from 5 to 6 ring atoms and from 1 to 2 ring heteroatoms. The ring heteroatoms are independently selected from nitrogen, oxygen, and sulphur.

"Monocyclic heterocyclylene" refers to a divalent radical derived from a monocyclic heterocyclyl group (in particular those derived from this list of monocyclic heterocyclyl groups provided above).

"Monocyclic cycloalkenylene" refers to a divalent radical derived from a cycloalkyl that contains at least one double bond. Suitably, the cycloalkenylene group comprises one or two double bonds. The cycloalkenylene group may be attached to the rest of the compound at any ring atom unless such attachment would violate valence requirements. Suitably the monocylic cycloalkenylene group is a $C_{3-7}$ cycloalkenylene group, more suitably a $C_6$ cycloalkenylene group (i.e. a cyclohexenylene group).

"Nucleic acid", refers to a linear polymer of nucleosides (including deoxyribo-nucleosides, ribonucleosides, or analogs thereof) joined by inter-nucleosidic linkages. Nucleic acid may encompass the term "polynucleotide" as well as "oligonucleotide". The linear polymer may be represented by a sequence of letters, such as "ATGCCTG," where it will be understood that the nucleotides are in 5' to 3' order from left to right and that "A" denotes deoxyadenosine, "C" denotes deoxycytidine, "G" denotes deoxyguanosine, and "T" denotes deoxythymidine, unless otherwise noted. Another natural nucleotide is "U", denoting uridine. The letters A, C, G, T and U can be used to refer to the bases themselves, to nucleosides, or to nucleotides comprising the bases, as is standard in the art. In naturally occurring nucleic acids, the inter-nucleoside linkage is typically a phosphodiester bond, and the subunits are referred to as "nucleotides." Nucleic acids may also include other inter-nucleoside linkages, such as phosphoro-thioate linkages, and the like. Such analogs of nucleotides that do not include a phosphate group are considered to fall within the scope of the term "nucleotid"" as used herein, and nucleic acids comprising one or more inter-nucleoside linkages that are not phosphodiester linkages are still referred to as "polynucleotides", "oligonucleotides", etc.

Nitrogen Protecting Groups

Nitrogen protecting groups are well known in the art and are groups that block or protect the nitrogen groups from further reaction. Nitrogen protecting groups are exemplified by carbamates, such as methyl or ethyl carbamate, 9-fluorenylmethyloxy-carbonyl (Fmoc), substituted ethyl carbamates, carbamates cleaved by 1,6-beta-elimination, ureas, amides, peptides, alkyl and aryl derivatives. Carbamate protecting groups have the general formula:

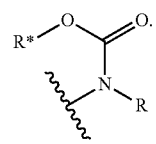

In this specification a zig-zag line indicates the point of attachment of the shown group (e.g. the protecting group above) to the rest of the compound of formula (I) or formula (II). Suitable nitrogen protecting groups may be selected from acetyl, trifluoroacetyl, t-butyloxycarbonyl (BOC), benzyloxycarbonyl (Cbz) and 9-fluorenylmethyloxy-carbonyl (Fmoc).

A large number of possible carbamate nitrogen protecting groups are listed on pages 706 to 771 of Wuts, P. G. M. and Greene, T. W., Protective Groups in Organic Synthesis, 4$^{th}$ Edition, Wiley-Interscience, 2007, and in P. Kocienski, *Protective Groups,* 3rd Edition (2005) which are incorporated herein by reference.

Particularly preferred protecting groups include Alloc (allyloxycarbonyl), Troc (2,2,2-Trichloroethyl carbonate), Teoc [2-(Trimethylsilyl)ethoxycarbony], BOC (tert-butyloxycarbonyl), Doc (2,4-dimethylpent-3-yloxycarbonyl), Hoc (cyclohexyloxy-carbonyl), TcBOC (2,2,2-trichloro-tert-butyloxycarbonyl), Fmoc (9-fluorenylmethyloxycarbonyl), 1-Adoc (1-Adamantyloxycarbonyl) and 2-Adoc (2-adamantyloxycarbonyl).

Hydroxyl Protecting Groups

Hydroxyl protecting groups are well known in the art, a large number of suitable groups are described on pages 16 to 366 of Wuts, P. G. M. and Greene, T. W., Protective Groups in Organic Synthesis, 4$^{th}$ Edition, Wiley-Interscience, 2007, and in P. Kocienski, *Protective Groups,* 3rd Edition (2005) which are incorporated herein by reference.

Classes of particular interest include silyl ethers, methyl ethers, alkyl ethers, benzyl ethers, esters, benzoates, carbonates, and sulfonates. Particularly preferred protecting groups include THP (tetrahydropyranyl ether).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgGi, IgG2, IgG3, IgG4, IgAi, and IgA2. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

By "co-administering" is meant intravenously administering two (or more) drugs during the same administration, rather than sequential infusions of the two or more drugs. Generally, this will involve combining the two (or more) drugs into the same IV bag prior to co-administration thereof.

A drug that is administered "concurrently" with one or more other drugs is administered during the same treatment cycle, on the same day of treatment as the one or more other drugs, and, optionally, at the same time as the one or more other drugs. For instance, for cancer therapies given every 3 weeks, the concurrently administered drugs are each administered on day-1 of a 3-week cycle.

A "chemotherapeutic agent" refers to a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gammail and calicheamicin omegali (see, e.g., Nicolaou et al., *Angew. Chem Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including ADRIAMYCIN, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethyl ornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g., celecoxib or etoricoxib), proteosome inhibitor (e.g., PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors; serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and non-steroidal aromatase inhibitors such as anastrazole (ARFMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

"Effector functions" refer to those biological activities attributable to the Fc region of an antibody, which vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "epitope" refers to the particular site on an antigen molecule to which an antibody binds.

The "epitope 4D5" or "4D5 epitope" or "4D5" is the region in the extracellular domain of HER2 to which the antibody 4D5 (ATCC CRL 10463) and trastuzumab bind. This epitope is close to the transmembrane domain of HER2, and within domain IV of HER2. To screen for antibodies which bind to the 4D5 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 550 to about residue 610, inclusive, of HER2 (SEQ ID NO: 39).

The "epitope 2C4" or "2C4 epitope" is the region in the extracellular domain of HER2 to which the antibody 2C4 binds. In order to screen for antibodies which bind to the 2C4 epitope, a routine cross-blocking assay such as that described in Antibodies, A Laboratory Manual, Cold Spring Harbor Laboratory, Ed Harlow and David Lane (1988), can be performed. Alternatively, epitope mapping can be performed to assess whether the antibody binds to the 2C4 epitope of HER2. Epitope 2C4 comprises residues from domain II in the extracellular domain of HER2. The 2C4 antibody and pertuzumab bind to the extracellular domain of HER2 at the junction of domains I, II and III (Franklin et al. Cancer Cell 5:317-328 (2004)). Anti-HER2 murine antibody 7C2 binds to an epitope in domain I of HER2. See, e.g., PCT Publication No. WO 98/17797. This epitope is distinct from the epitope bound by trastuzumab, which binds to domain IV of HER2, and the epitope bound by pertuzumab, which binds to domain II of HER2. By binding domain IV, trastuzumab disrupts ligand-independent HER2-HER3 complexes, thereby inhibiting downstream signaling (e.g. PI3K/AKT). In contrast, pertuzumab binding to domain II prevents ligand-driven HER2 interaction with other HER family members (e.g. HER3, HER1 or HER4), thus also preventing downstream signal transduction. Binding of MAb 7C2 to domain I does not result in interference of trastuzumab or pertuzumab binding to domains IV and II, respectively, thereby offering the potential of combining a MAb 7C2 ADC with trastuzumab, trastuzumab emtansine (T-DM-1), and/or pertuzumab. Murine antibody 7C2, 7C2.B9, is described in PCT Publication No. WO 98/17797. An anti-HER2 7C2 humanized antibody is disclosed in WO2016/040723 A1.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H(L)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of LI, 50-55 of L2, 89-96 of L3, 31-35B of HI, 50-58 of H2, and 95-102 of H3. (See Almagro and Fransson, Front. Biosci. 13: 1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

The term "immunosuppressive agent" as used herein for adjunct therapy refers to substances that act to suppress or mask the immune system of the mammal being treated herein. This would include substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); non-steroidal anti-inflammatory drugs (NSAIDs); ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids or glucocorticosteroids or glucocorticoid analogs, e.g., prednisone, methylprednisolone, including SOLU-MEDROL® methylprednisolone sodium succinate, and dexamethasone; dihydrofolate reductase inhibitors such as methotrexate (oral or subcutaneous); anti-malarial agents such as chloroquine and hydroxychloroquine; sulfasalazine; leflunomide; cytokine or cytokine receptor antibodies including anti-interferon-alpha, -beta, or -gamma antibodies, antitumor necrosis factor (TNF)-alpha antibodies (infliximab (REMICADE®) or adalimumab), anti-TNF-alpha immunoadhesin (etanercept), anti-TNF-beta antibodies, anti-interleukin-2 (IL-2) antibodies and anti-IL-2 receptor antibodies, and anti-interleukin-6 (IL-6) receptor antibodies and antagonists (such as ACTEMRA™ (tocilizumab)); anti-LFA-1 antibodies, including anti-CD11a and anti-CD18 antibodies; anti-L3T4 antibodies; heterologous anti-lymphocyte globulin; pan-T antibodies, preferably anti-CD3 or anti-CD4/CD4a antibodies; soluble peptide containing a LFA-3 binding domain (WO 90/08187); streptokinase; transforming growth factor-beta (TGF-beta); streptodornase; RNA or DNA from the host; FK506; RS-61443; chlorambucil; deoxyspergualin; rapamycin; T-cell receptor (Cohen et al, U.S. Pat. No. 5,114,721); T-cell receptor fragments (Offner et al, Science, 251: 430-432 (1991); WO 90/11294; Ianeway, Nature, 341: 482 (1989); and WO 91/01133); BAFF antagonists such as BAFF antibodies and BR3 antibodies and zTNF4 antagonists (for review, see Mackay and Mackay, Trends Immunol, 23: 113-5 (2002) and see also definition below); biologic agents that interfere with T cell helper signals, such as anti-CD40 receptor or anti-CD40 ligand (CD 154), including blocking antibodies to CD40-CD40 ligand (e.g., Durie et al, Science, 261: 1328-30 (1993); Mohan et al, J. Immunol, 154: 1470-80 (1995)) and CTLA4-Ig (Finck et al, Science, 265: 1225-7 (1994)); and T-cell receptor antibodies (EP 340,109) such as T10B9. Some preferred immunosuppressive agents herein include cyclophosphamide, chlorambucil, azathioprine, leflunomide, MMF, or methotrexate.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "HER2," as used herein, refers to any native, mature HER2 which results from processing of a HER2 precursor protein in a cell. The term includes HER2 from any vertebrate source, including mammals such as primates (e.g. humans and cynomolgus monkeys) and rodents (e.g., mice and rats), unless otherwise indicated. The term also includes naturally occurring variants of HER2, e.g., splice variants or allelic variants. The amino acid sequence of an exemplary human HER2 precursor protein, with signal sequence (with signal sequence, amino acids 1-22) is shown in SEQ ID NO: 64. The amino acid sequence of an exemplary mature human HER2 is amino acids 23-1255 of SEQ ID NO: 64.

The term "HER2-positive cell" refers to a cell that expresses HER2 on its surface. The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CHI, $CH_2$, and $CH_3$). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 (nivolumab) described herein. In another specific aspect, a PD-1 binding antagonist is MK-3475 (lambrolizumab) described herein. In another specific aspect, a PD-1 binding antagonist is CT-01 1 (pidilizumab) described herein. In another specific aspect, a PD-1 binding antagonist is AMP-224 described herein.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signalling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55. S70 described herein. In another specific aspect, an anti-PD-L1 antibody is MDX-1105 described herein. In still another specific aspect, an anti-PD-L1 antibody is MPDL3280A described herein. In still another specific aspect, an anti-PD-L1 antibody is MEDI4736 described herein.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

A "fixed" or "flat" dose of a therapeutic agent herein refers to a dose that is administered to a human patient without regard for the weight (WT) or body surface area (BSA) of the patient. The fixed or flat dose is therefore not provided as a mg/kg dose or a mg/m$^2$ dose, but rather as an absolute amount of the therapeutic agent.

A "loading" dose herein generally comprises an initial dose of a therapeutic agent administered to a patient, and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dose(s) are administered more frequently than the maintenance dose(s), so as to achieve the desired steady-state concentration of the therapeutic agent earlier than can be achieved with the maintenance dose(s).

A "maintenance" dose herein refers to one or more doses of a therapeutic agent administered to the patient over a treatment period. Usually, the maintenance doses are administered at spaced treatment intervals, such as approximately every week, approximately every 2 weeks, approximately every 3 weeks, or approximately every 4 weeks, preferably every 3 weeks.

"Infusion" or "infusing" refers to the introduction of a drug-containing solution into the body through a vein for therapeutic purposes. Generally, this is achieved via an intravenous (IV) bag.

An "intravenous bag" or "IV bag" is a bag that can hold a solution which can be administered via the vein of a patient. In one embodiment, the solution is a saline solution (e.g. about 0.9% or about 0.45% NaCl). Optionally, the IV bag is formed from polyolefin or polyvinal chloride.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

A "free cysteine amino acid" refers to a cysteine amino acid residue which has been engineered into a parent antibody, has a thiol functional group (—SH), and is not paired as an intramolecular or intermolecular disulfide bridge.

"Drug", "drug substance", "active pharmaceutical ingredient", and the like, refer to a compound (e.g., compounds of Formula (I) and compounds specifically named above) that may be used for treating a subject in need of treatment.

"Excipient" refers to any substance that may influence the bioavailability of a drug, but is otherwise pharmacologically inactive.

The term "or pharmaceutically acceptable salts, solvates, tautomers, stereoisomers or mixtures thereof" means that pharmaceutically acceptable salt, solvate, tautomeric, stereoisomeric forms of the shown structure are also included. Mixtures thereof means that mixture of these forms may be present, for example, the compounds of the invention may include both a tautomeric form and a pharmaceutically acceptable salt.

"Pharmaceutically acceptable" substances refers to those substances which are within the scope of sound medical judgment suitable for use in contact with the tissues of subjects without undue toxicity, irritation, allergic response, and the like, commensurate with a reasonable benefit-to-risk ratio, and effective for their intended use.

"Pharmaceutical composition" refers to the combination of one or more drug substances and one or more excipients.

The term "subject" as used herein refers to a human or non-human mammal. Examples of non-human mammals include livestock animals such as sheep, horses, cows, pigs, goats, rabbits and deer; and companion animals such as cats, dogs, rodents, and horses.

"Therapeutically effective amount" of a drug refers to the quantity of the drug or composition that is effective in treating a subject and thus producing the desired therapeutic, ameliorative, inhibitory or preventative effect. The therapeutically effective amount may depend on the weight and age of the subject and the route of administration, among other things.

"Treating" refers to reversing, alleviating, inhibiting the progress of, or preventing a disorder, disease or condition to which such term applies, or to reversing, alleviating, inhibiting the progress of, or preventing one or more symptoms of such disorder, disease or condition.

"Treatment" refers to the act of "treating", as defined immediately above.

As used herein the term "comprising" means "including at least in part of" and is meant to be inclusive or open ended. When interpreting each statement in this specification that includes the term "comprising", features, elements and/or steps other than that or those prefaced by the term may also be present. Related terms such as "comprise" and "comprises" are to be interpreted in the same manner.

The term "consisting essentially of" limits the scope of a claim to the specified materials or steps "and those that do not materially affect the basic and novel characteristic(s)" of the claimed invention. When the phrase "consisting essentially of" appears in a clause of the body of a claim, rather than immediately following the preamble, it limits only the element set forth in that clause.

The term "consisting of" excludes any element, step, or ingredient not specified in the claim; "consisting of" defined as "closing the claim to the inclusion of materials other than those recited except for impurities ordinarily associated therewith. When the phrase "consists of" appears in a clause of the body of a claim, rather than immediately following the preamble, it limits only the element set forth in that clause; other elements are not excluded from the claim as a whole. It should be understood that while various embodiments in the specification are presented using "comprising" language, under various circumstances, a related embodiment is also described using "consisting essentially of" or "consisting of" language.

Provisos

The compound of formula (I) or formula (II) is a compound according to proviso (a); (b); (c); (d); (e) or (f). Suitably, the compound of formula (I) or formula (II) is a compound according to proviso (a); (b); (c); (d) or (e). Suitably, the compound of formula (I) or formula (II) is a compound according to proviso (a); (b); (c) or (d). Suitably, the compound of formula (I) or formula (II) is a compound according to proviso (a); (b) or (c). More suitably, the compound of formula (I) or formula (II) is a compound according to proviso (a) or (b). Most suitably, the compound of formula (I) or formula (II) is a compound according to proviso (a).

Proviso (a)

Suitably, the compound of formula (I) or formula (II) is (a) a compound of formula (I), wherein at least one of $R_3$ or $R_{12}$ is an optionally substituted $C_{5-6}$ heterocyclyl, an optionally substituted $C_{5-9}$ heteroaryl or an optionally substituted phenyl. Suitably, such a compound may be represented as a compound having the structure of formula (A1) or (A2):

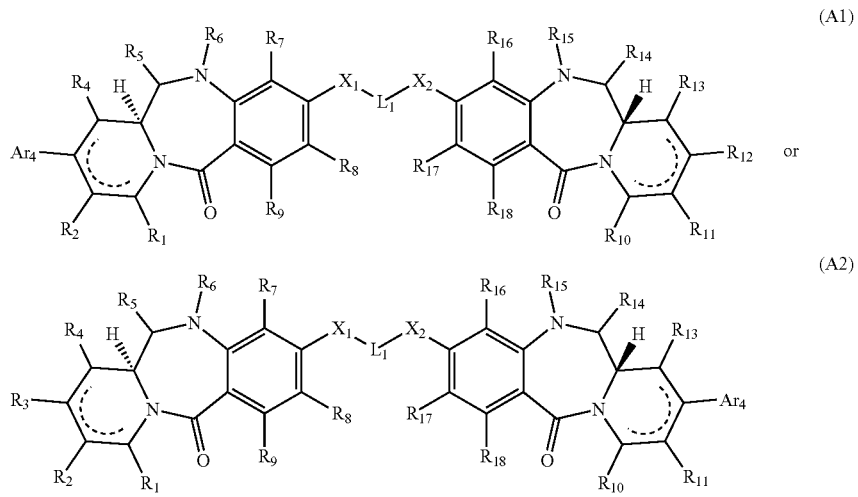

wherein $Ar_4$ is an optionally substituted an optionally substituted $C_{5-6}$ heterocyclyl, $C_{5-9}$ heteroaryl or an optionally substituted phenyl, optionally substituted with 1, 2 or 3 independently selected optional $R_{20}$ groups.

Suitably, (A1) or (A2) has a single double bond in the C-ring between $R_4$ and $Ar_4$. More suitably, (A1) or (A2) has a single double bond in the C-ring between $Ar_4$ and $R_2$.

In an aspect, suitably, both $R_3$ and $R_{12}$ are selected from an optionally substituted $C_{5-6}$ heterocyclyl, an optionally substituted $C_{5-9}$ heteroaryl or an optionally substituted phenyl. Suitably, such a compound may be represented as a compound having the structure of formula (A3):

(A3)

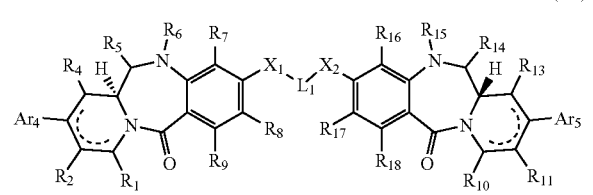

wherein $Ar_4$ and $Ar_5$ are independently selected from an optionally substituted $C_{5-6}$ heterocyclyl, optionally substituted $C_{5-9}$ heteroaryl or optionally substituted phenyl, optionally substituted with 1, 2 or 3 independently selected optional $R_{20}$ groups. Suitably, (A3) contains a single double bond in each C-ring and those double bonds are between $R_4$ and $Ar_4$; and between $R_{13}$ and $Ar_5$.

Suitably, the compound of formula (I) or formula (II) has the structure of formula (A4):

(A4)

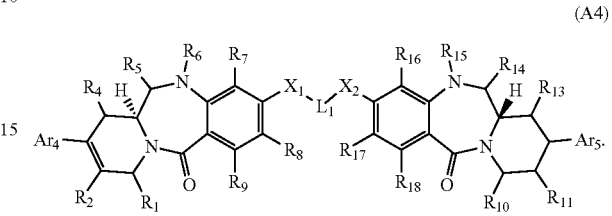

More suitably, the compound of formula (I) or formula (II), or formula (A4) has the structure of formula (A5):

(A5)

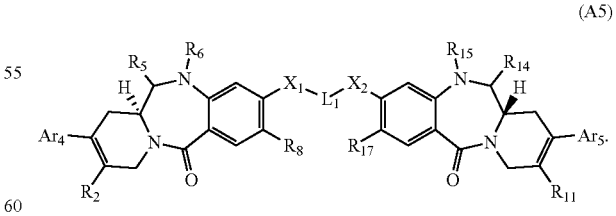

More suitably, the compound of formula (I) or formula (II) has the structure of formula (A6):

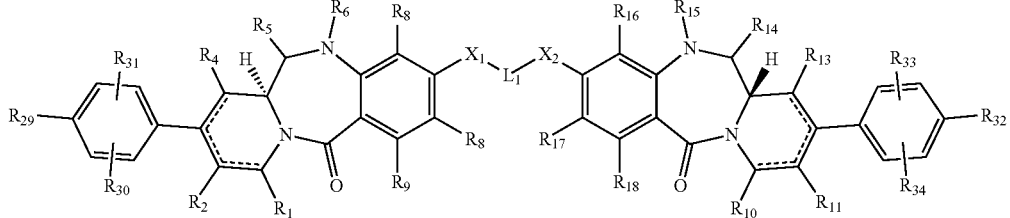
(A6)

wherein $R_{29}$, $R_{30}$, $R_{31}$, $R_{32}$, $R_{33}$ and $R_{34}$ are each independently selected from H and $R_{20}$. Hence, $R_{29}$, $R_{30}$, $R_{31}$, $R_{32}$, $R_{33}$ and $R_{34}$ represent the optional substituent groups.

The above structures are drawn showing the bonds for groups $R_{29}$ and $R_{30}$ going into the middle of the phenyl ring on the left-hand side of the molecule (A6). This indicates that these groups are attached to this phenyl ring without specifying the exact positions of the $R_{29}$ and $R_{30}$ groups. Hence, these groups may be present on any of the four available position of phenyl ring on the left-hand side that would meet the valence requirements (i.e. the four positons for which no bound is shown).

More suitably, the compound of formula (I), formula (II), or formula (A6) has the structure of formula (A7) or formula (A8):

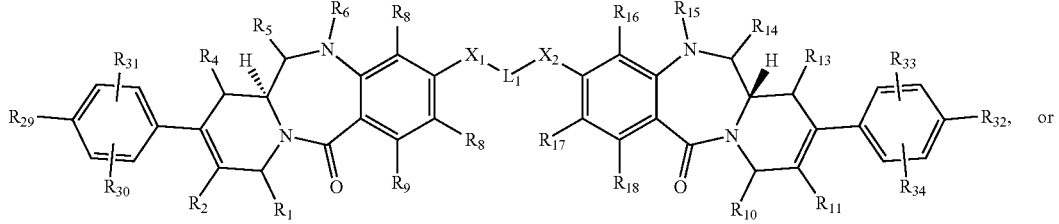
(A7) or

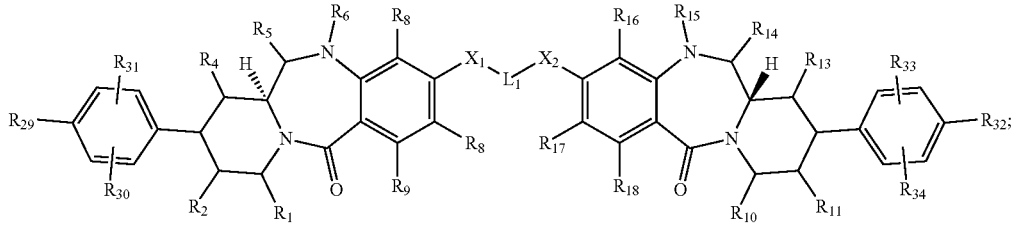
(A8)

wherein $R_{29}$, $R_{30}$ and $R_{31}$ are each independently selected from H and $R_{20}$.

More suitably, the compound of formula (I), formula (II), formula (A6) or formula (A7) has the structure of formula (A9) or formula (A10):

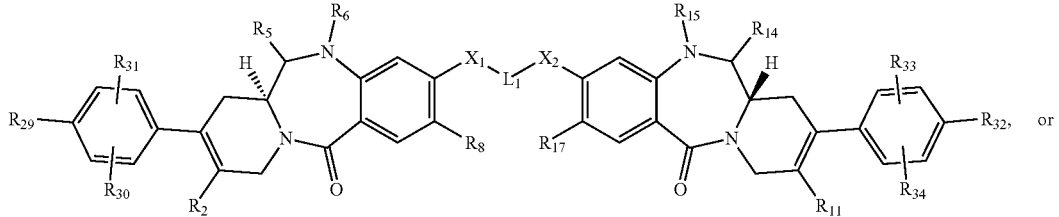
(A9) or

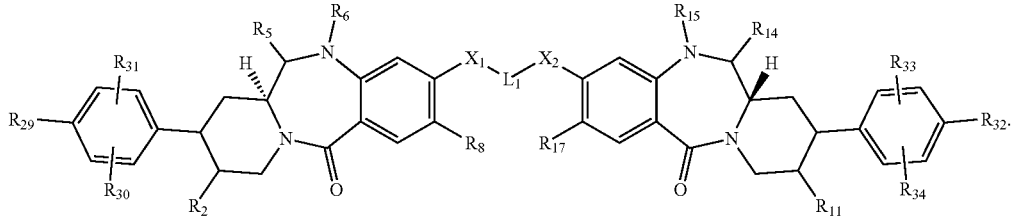

(A10)

In another aspect, suitably, either (i) R₃ is an optionally substituted an optionally substituted C₅₋₆ heterocyclyl, C₅₋₉ heteroaryl or an optionally substituted phenyl, and Ru and R₁₂, together with the carbon atoms to which they are attached form an optionally substituted 6-membered aryl, or a 5- or 6-membered heteroaryl ring; or (ii) R₁₂ is an optionally substituted C₅₋₆ heterocyclyl, an optionally substituted C₅₋₉ heteroaryl or an optionally substituted phenyl, and R₂ and R₃, together with the carbon atoms to which they are attached form an optionally substituted 6-membered aryl, or a 5- or 6-membered heteroaryl ring. The optionally substituted 6-membered aryl, or a 5- or 6-membered heteroaryl rings are optionally substituted with 1, 2 or 3 independently selected optional R₂₀ groups. Suitably, such a compound may be represented as a compound having the structure of formula (A11), (A12), (A13) or (A14):

(A11)

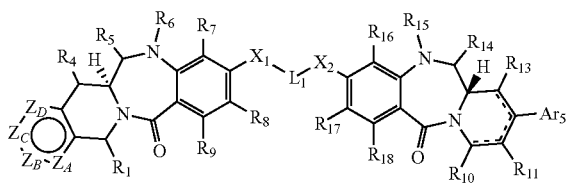

or (A12)

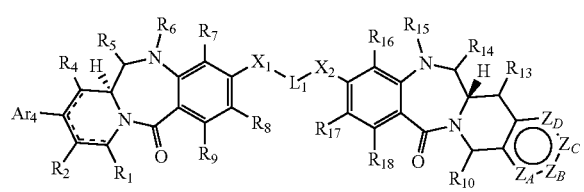

(A13)

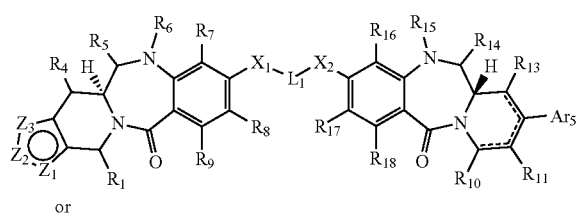

or (A14)

wherein one of $Z_A$, $Z_B$, $Z_C$ and $Z_D$ is CH, one of $Z_A$, $Z_B$, $Z_C$ and $Z_D$ is C—R₃₅, one of $Z_A$, $Z_B$,
$Z_C$ and $Z_D$ is N or C—R₃₆, and the remaining one of $Z_A$, $Z_B$, $Z_C$ and $Z_D$ is N or C—R₃₇; R₃₅, R₃₆ and R₃₇ are independently selected from H and R₂₀; and
Z₁ is selected from NH, N(C₁₋₆ alkyl), S and O; and Z₂ and Z₃ are independently selected
  from N, CH, C—R₂₀; or Z₁ and Z₂ are independently selected from N, CH, C—R₂₀;
and Z₃ is selected from NH, N(C₁₋₆ alkyl), S and O.

In this aspect, where there is more than one R₂₀ group present, each R₂₀ group is independently selected. Again, Ar₄ and Ar₅ are independently selected from an optionally substituted C₅₋₆ heterocyclyl, optionally substituted C₅₋₉ heteroaryl or optionally substituted phenyl, wherein these groups are optionally substituted with 1, 2 or 3 independently selected optional R₂₀ groups.

Thus, for (A11) and (A12), the 6-membered D-ring containing groups Z₁, Z₂ and Z₃ is either an optionally substituted heterocyclic ring (i.e. is selected from an optionally substituted pyridine, pyridazine, pyrimidine or a pyrazine ring) or is an optionally substituted phenyl ring. For (A13) and (A14), the 5-membered D-ring containing groups Z₁, Z₂ and Z₃ is a heterocyclic ring.

More suitably, the compound of formula (I), (II), (A1), (A2), (A11) or (A12) has the structure of formula (A15) or (A16):

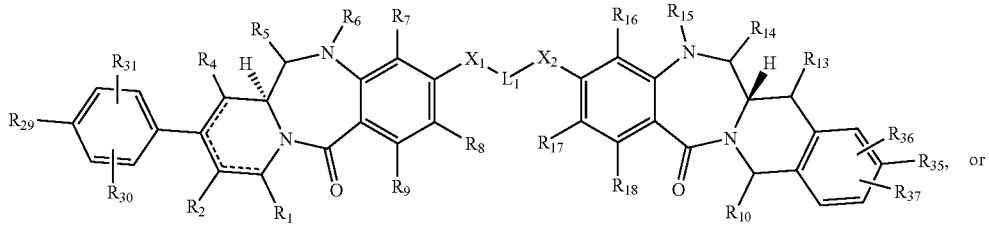

(A15)

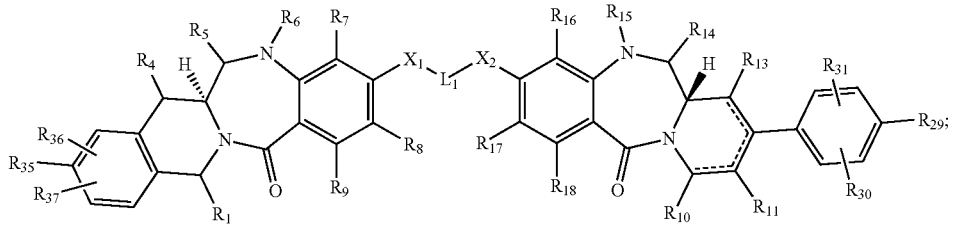

(A16)

wherein $R_{29}$, $R_{30}$, $R_{31}$, $R_{35}$, $R_{36}$ and $R_{37}$ are each independently selected from H and $R_{20}$.

More suitably, the compound of formula (I), (II), (A1), (A2), (A11), (A12) (A15) or (A16) has the structure of formula (A17) or (A18):

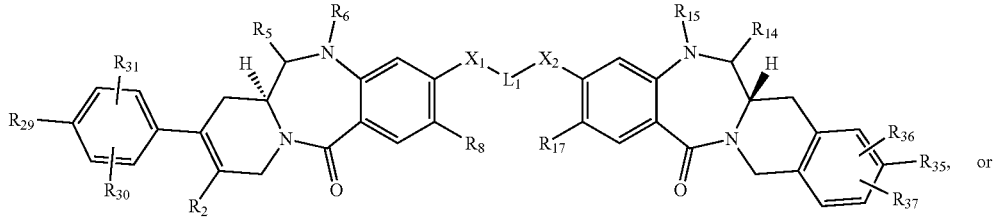

(A17)

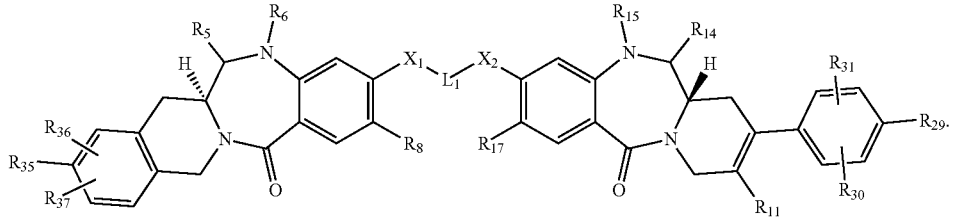

(A18)

In another aspect, suitably the compound of formula (I) or formula (II), has the structure of formula (A1), or formula (A2), wherein $R_1$, $R_2$, $R_3$, $R_4$, $R_{10}$, $R_{11}$, $R_{12}$ and $R_{19}$ are independently selected from H and $R_{20}$; wherein $Ar_4$ is an optionally substituted $C_{5-6}$ heterocyclyl, an optionally substituted $C_{5-9}$ heteroaryl or an optionally substituted phenyl, optionally substituted with 1, 2 or 3 independently selected optional $R_{20}$ groups.

Suitably, the compound of formula (I), formula (II), formula (A1) or formula (A2), has the structure of formula (A19), or formula (A20):

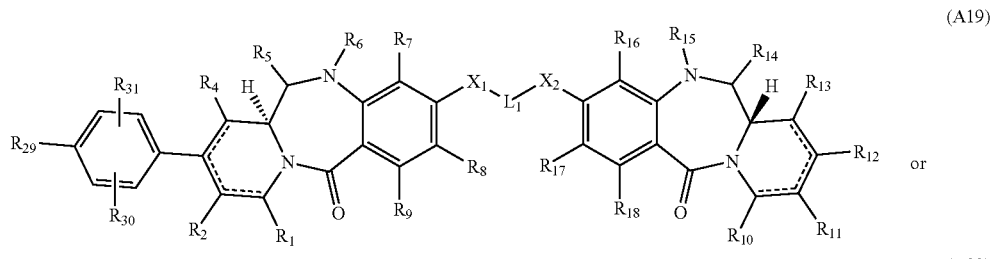

(A19)

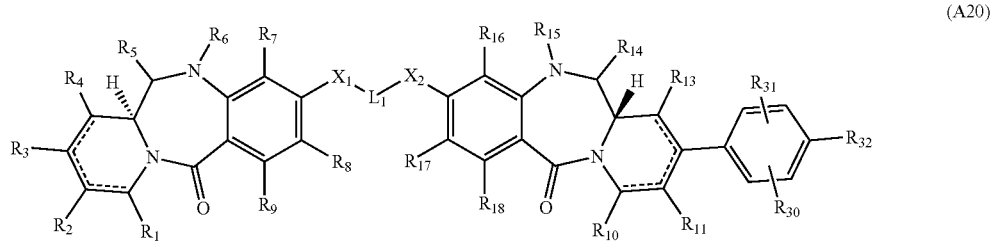

(A20)

wherein $R_1$, $R_2$, $R_3$, $R_4$, $R_{10}$, $R_{11}$, $R_{12}$ and $R_{13}$ are independently selected from H and $R_{20}$.

Suitably, the compound of formula (I), (II), (A1), (A2), (A3) or (A6) is

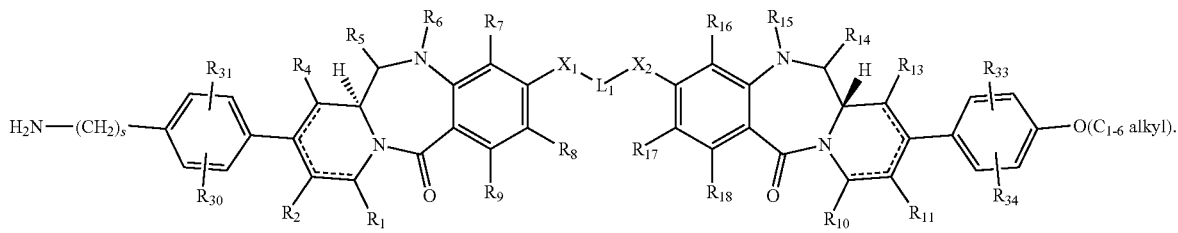

(A21)

In some aspects, suitably, the compound of formula (I) or formula (II) is a compound of formula (A1), (A2), (A3), (A11), (A12), (A13) or (A14); suitably, a compound of formula (A1), (A2), (A3), (A11) or (A12). More suitably, the compound of formula (I) or formula (II) is a compound of formula (A1), (A2) or (A3).

Proviso (b)

Suitably, the compound of formula (I) or formula (II) is (b) a compound of formula (I) wherein both $R_2$ and $R_3$, and $R_{11}$ and $R_{12}$, together with the carbon atoms to which they are attached form an optionally substituted 5-membered cyclic, heterocyclic, or heteroaryl ring. Suitably, the optionally substituted 5-membered cyclic, heterocyclic, or heteroaryl rings are optionally substituted with 1, 2 or 3 independently selected optional $R_{20}$ groups. Suitably, such a compound may be represented as a compound having the structure of formula (B1) or (B2):

(B1)

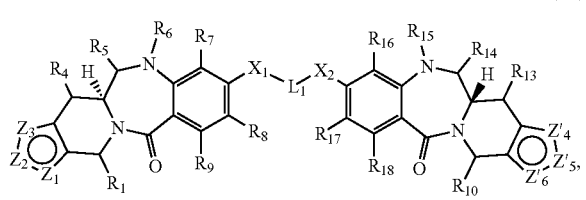

-continued or (B2)

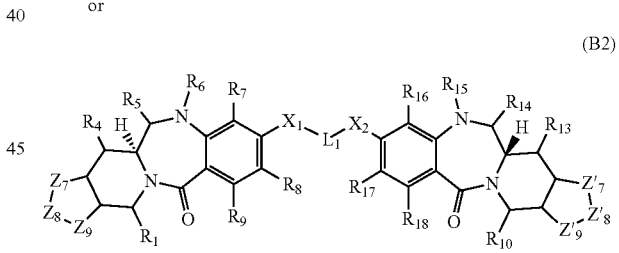

wherein $Z_4$ is selected from NH, N($C_{1-6}$ alkyl), S and O; and $Z_5$ and $Z_6$ are independently selected from N, CH, C—$R_2$; or $Z_4$ and $Z_5$ are independently selected from N, CH, C—$R_{20}$, and $Z_6$ is selected from NH, N($C_{1-6}$ alkyl), S and O; and $Z'_4$ is selected from NH, N($C_{1-6}$ alkyl), S and O; and $Z'_5$ and $Z'_6$ are independently selected from N, CH, C—$R_{20}$; or $Z'_4$ and $Z'_5$ are independently selected from N, CH, C—$R_{20}$, and $Z'_6$ is selected from NH, N($C_{1-6}$ alkyl), S and O.

$Z_7$, $Z_8$, $Z'_6$, $Z'_7$, $Z'_8$ and $Z'_9$ are each independently selected from NH, N($C_{1-6}$ alkyl), S, O and CH$R_{38}$ wherein each $R_{38}$ is independently selected from H and $R_2$.

Suitably, the compound of formula (I), formula (II) is a compound having the structure of formula (B1).

Suitably, the compound of formula (I), or formula (II) is a compound having the structure of formula (B1) or formula (B2), wherein $Z_4=Z'_4$, $Z_5=Z'_5$ and $Z_6=Z'_6$; and $Z_7=Z'_7$, $Z_8=Z'_8$ and $Z_9=Z'_9$. Hence, suitably, the D-rings are the same.

More suitably, both $R_2$ and $R_3$, and $R_{11}$ and $R_{12}$, together with the carbon atoms to which they are attached form an optionally substituted 5-membered heteroaryl ring.

More suitably, the compound of formula (I), formula (II) or formula (B1) is a compound having the structure of formula (B3) or formula (B4):

(B3)

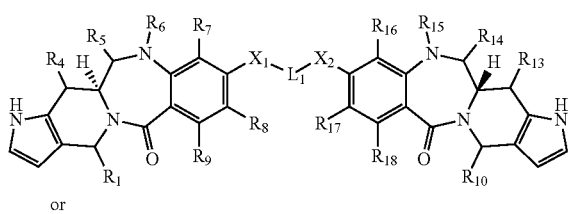

or (B4)

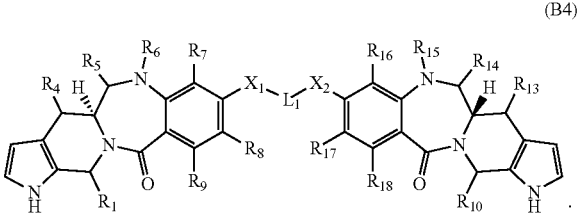

Proviso (c)

Suitably, the compound of formula (I) or formula (II) is (c) a compound of formula (II), wherein $R_{12}$ is an optionally substituted C, heterocyclyl, an optionally substituted $C_{5-9}$ heteroaryl or an optionally substituted phenyl and $R_1$, $R_2$, $R_3$, $R_4$, $R_{10}$, $R_{11}$, and $R_{13}$ are independently selected from H and $R_{19}$. Suitably, such a compound may be represented as a compound having the structure of formula (C1):

(C1)

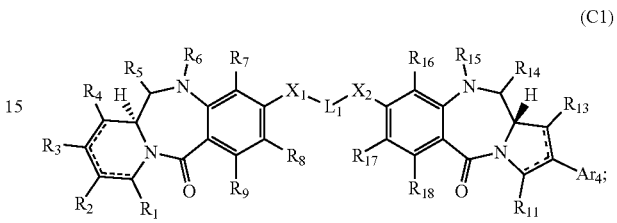

wherein $Ar_4$ is selected from optionally substituted $C_{5-6}$ heterocyclyl, optionally substituted $C_{5-9}$ heteroaryl or optionally substituted phenyl, optionally substituted with 1, 2 or 3 independently selected optional $R_{20}$ groups.

Suitably, the compound of formula (I), formula (II), or formula (C1) is a compound having the structure of formula (C2):

(C2)

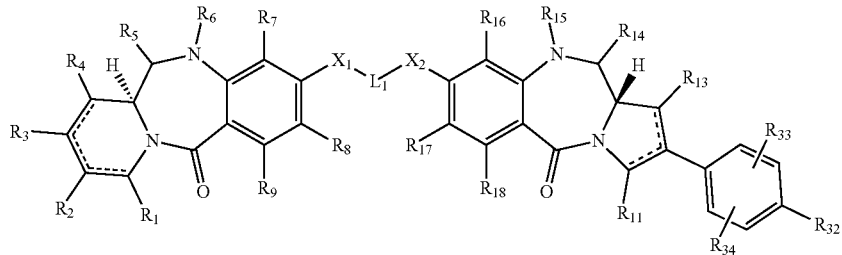

wherein $R_{22}$, $R_{33}$ and $R_{34}$ are each independently selected from H and $R_{20}$.

Suitably, the compound of formula (I), formula (II), formula (C1) or formula (C2) is a compound having the structure of formula (C3):

(C3)

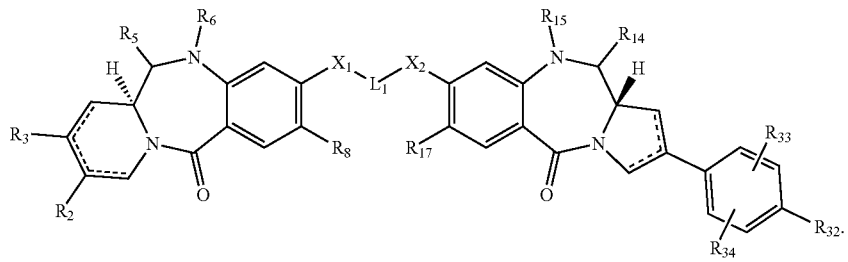

Proviso (d)

Suitably, the compound of formula (I) or formula (II) is (d) a compound of formula (II), wherein $R_{11}$ and $R_{12}$, or $R_{12}$ and $R_{13}$, together with the carbon atoms to which they are attached form an optionally substituted 6-membered aryl, or a 5- or 6-membered cyclic, heterocyclic, or heteroaryl ring, and $R_1$, $R_2$, $R_3$, $R_4$, are independently selected from H and $R_{19}$. Suitably, the 6-membered aryl, or a 5- or 6-membered cyclic, heterocyclic, or heteroaryl rings are optionally substituted with 1, 2 or 3 independently selected optional $R_{20}$ groups. Suitably, such a compound may be represented as a compound having the structure of formula (D1), (D2), (D3) or (D4):

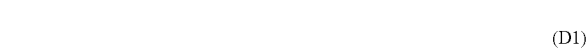

(D1)

(D2)

(D3)


or (D4)

wherein w is 0 or 1, and
- when w is 1, then $D_1$, $D_2$, $D_3$ and $D_4$ are independently selected from N and C—$R_{39}$; with the proviso that no more than two of $D_1$, $D_2$, $D_3$ and $D_4$ are N;
- when w is 0, then $D_2$ is selected from NH, N($C_{1-6}$ alkyl), S and O; and $D_3$ and $D_4$ are independently selected from N, C—$R_{39}$; or $D_2$ and $D_3$ are independently selected from N, C—$R_{39}$, and $D_4$ is selected from NH, N($C_{1-6}$ alkyl), S and O; and
- when w is 1, then $D'_1$, $D'_2$, $D'_3$ and $D'_4$ are independently selected from S, O, N—$R_{39}$ and CH—$R_{39}$; with the proviso that 1, 2, 3, or 4 of $D'_1$, $D'_2$, $D'_3$ and $D'_4$ are CH—$R_{39}$;

$D'_1$, $D'_2$, $D'_3$ and $D'_4$ are independently selected from S, O, NH, N($C_{1-6}$ alkyl) and CH—$R_{39}$; and
each $R_{39}$ is independently selected from H and $R_{20}$.

The proviso that no more than two of $D_1$, $D_2$, $D_3$ and $D_4$ are N means that 0, 1 or 2 of $D_1$, $D_2$, $D_3$ and $D_4$ are N.

Suitably, the compound of formula (I) or formula (II) is a compound of formula (D1) or (D2).

Suitably, the compound of formula (I), (II), (D1) or (D2) is a compound of formula (D5) or (D6):

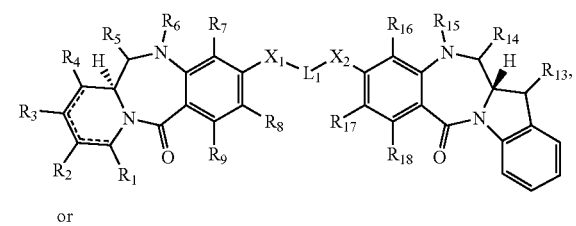

(D5)

or

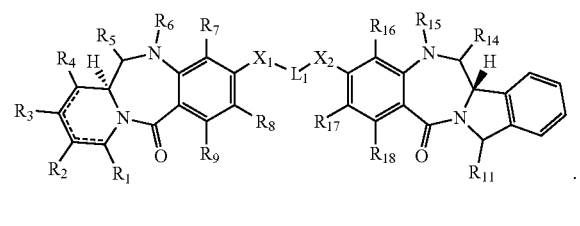

(D6)

Proviso (e)

Suitably, the compound of formula (I) or formula (II) is (e) a compound of formula (II), wherein m is 0; $R_{12}$ is an optionally substituted $C_{5-6}$ heterocyclyl, an optionally substituted $C_{5-9}$ heteroaryl or an optionally substituted phenyl; and $R_2$ and $R_3$, or $R_3$ and $R_4$, together with the carbon atoms to which they are attached form an optionally substituted 6-membered aryl, or an optionally substituted 5- or 6-membered cyclic, heterocyclic, or an optionally substituted heteroaryl ring. Suitably, each optionally substituted ring may be optionally substituted with 1, 2 or 3 independently selected optional $R_{20}$ groups. Suitably, such a compound may be represented as a compound having the structure of formula (E1), (E2), (E3) or (E4):

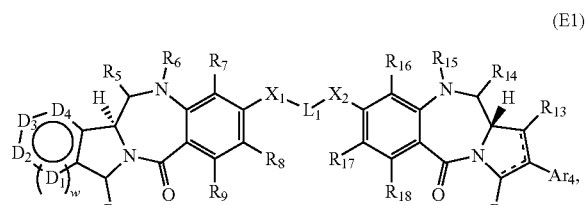

(E1)

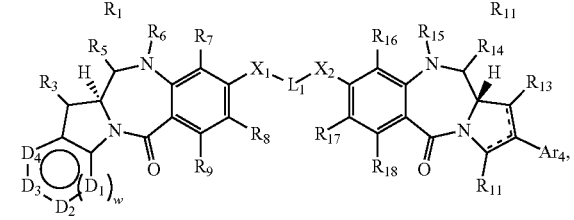

(E3)

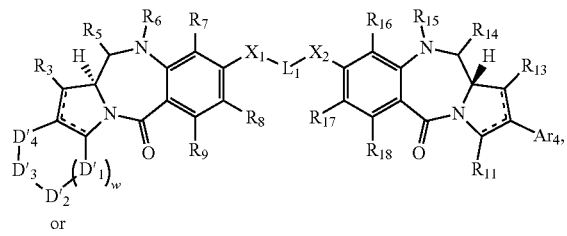

or (E4)

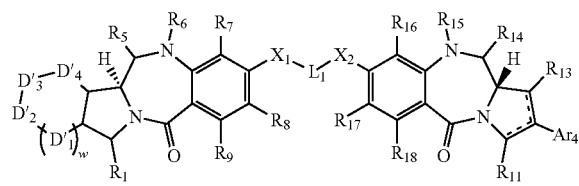

wherein w is 0 or 1, and
when w is 1, then $D_1$, $D_2$, $D_3$ and $D_4$ are independently selected from N and C—$R_{39}$; with the proviso that no more than two of $D_1$, $D_2$, $D_3$ and $D_4$ are N;
when w is 0, then $D_2$ is selected from NH, N($C_{1-6}$ alkyl), S and O; and $D_3$ and $D_4$ are independently selected from N, C—$R_{39}$; or $D_2$ and $D_3$ are independently selected from N, C—$R_{39}$, and $D_4$ is selected from NH, N($C_{1-6}$ alkyl), S and O; and
when w is 1, then $D'_1$, $D'_2$, $D'_3$ and $D'_4$ are independently selected from S, O, N—$R_{39}$ and CH—$R_{39}$; with the proviso that 1, 2, 3, or 4 of $D'_1$, $D'_2$, $D'_3$ and $D'_4$ are CH—$R_{39}$;
$D'_1$, $D'_2$, $D'_3$ and $D'_4$ are independently selected from S, O, NH, N($C_{1-6}$ alkyl) and CH—$R_{39}$;

each $R_{39}$ is independently selected from H and $R_{20}$; and
$Ar_4$ is selected from optionally substituted $C_{5-6}$ heterocyclyl, optionally substituted $C_{5-9}$ heteroaryl or optionally substituted phenyl, optionally substituted with 1, 2 or 3 independently selected optional $R_{20}$ groups.

The proviso that no more than two of $D_1$, $D_2$, $D_3$ and $D_4$ are N means that 0, 1 or 2 of $D_1$, $D_2$, $D_3$ and $D_4$ are N.

Suitably, the compound of formula (I) or formula (II) is a compound of formula (E1), (E2), (E3) or (E4), wherein $Ar_4$ is an optionally substituted phenyl.

Suitably, the compound of formula (I), (II), (E2) or (E4) is a compound having the formula (E5) or (E6):

(E5)

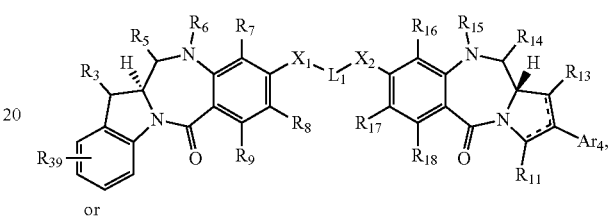

or (E6)

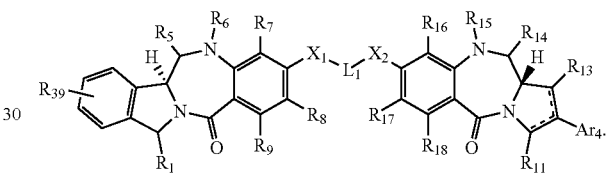

More suitably, the compound of formula (I), (II), (E2), (E4), (E5) or (E6) is a compound having the formula (E7) or (E8):

(E7)

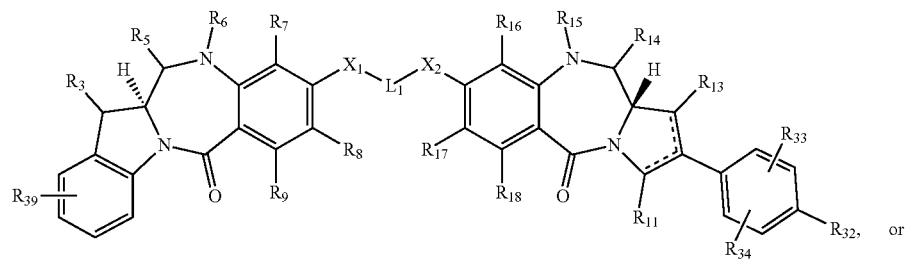

or (E8)

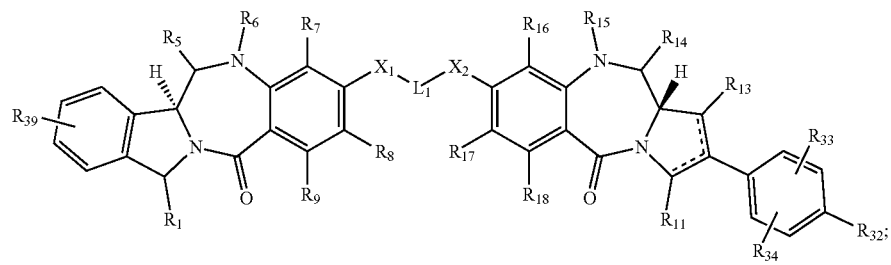

wherein $R_{32}$, $R_{33}$ and $R_{34}$ are each independently selected from H and $R_{20}$.

More suitably, the compound according to proviso (e) is a compound of formula (II), wherein m is 0; $R_{12}$ is an optionally substituted $C_{5-6}$ heterocyclyl, an optionally substituted $C_{5-9}$ heteroaryl or an optionally substituted phenyl; and $R_3$ and $R_4$, together with the carbon atoms to which they are attached form an optionally substituted 6-membered aryl, or a 5- or 6-membered cyclic, heterocyclic, or heteroaryl ring.

Alternatively, more suitably, the compound according to proviso (e) is a compound of formula (II), wherein m is 0; $R_{12}$ is an optionally substituted $C_{5-6}$ heterocyclyl, an optionally substituted $C_{5-9}$ heteroaryl or an optionally substituted phenyl; and $R_2$ and $R_3$, or $R_3$ and $R_4$, together with the carbon atoms to which they are attached form an optionally substituted 5- or 6-membered cyclic, heterocyclic, or heteroaryl ring.

Alternatively, more suitably, where the compound is a compound according to proviso (e) $Y_1$ is selected from —(CH$_2$)$_{1-5}$—, —C(O)—NH—, —NH— or —S(O)$_{0-2}$—.

Proviso (f)

Suitably, the compound of formula (I) or formula (II) is (f) a compound of formula (II), wherein m is 1; $R_{12}$ is =CH$_2$, =CH—(CH$_2$)$_s$—CH$_3$ or =CH—(CH$_2$)$_s$—R$_{21}$; and $R_1$, $R_2$, $R_3$, $R_4$, $R_{10}$, $R_{11}$, $R_{12}$ and $R_{13}$ are independently selected from H and $R_{19}$. Suitably, such a compound may be represented as a compound having the structure of formula (F1):

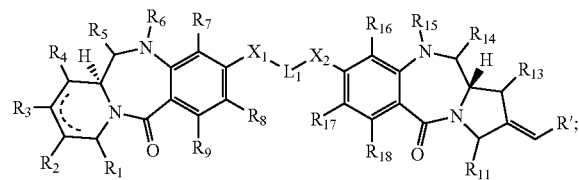

(F1)

wherein R' is H, —(CH$_2$)$_s$—CH$_3$ or (CH$_2$)$_s$—R$_{21}$.

Suitably, the compound of formula (I), (II) or (F1) is a compound having the structure of formula (F2):

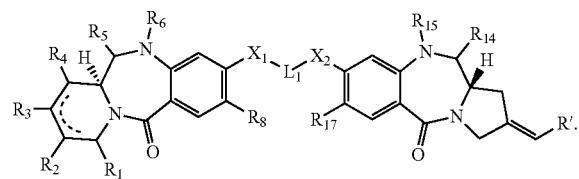

(F2)

Other Structures

In some aspects, suitably, the compound of formula (I) or formula (II) is a compound having the structure of formula (O1):

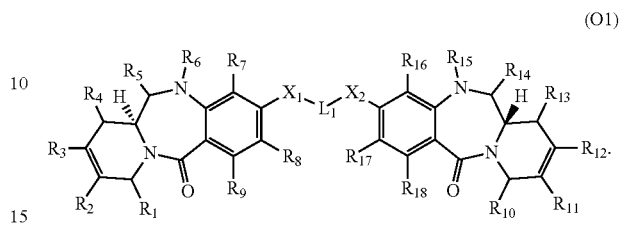

(O1)

Suitably, the compound of formula (I), (II) or (O1) is a compound having the structure of formula (O2):

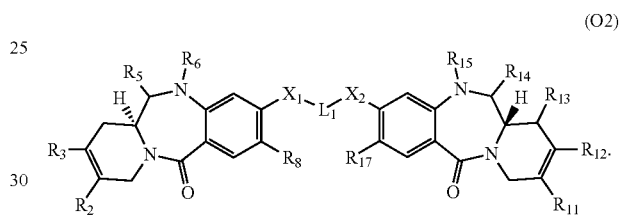

(O2)

In some aspects, suitably, the compound of formula (I) or formula (II) is a compound having the structure of formula (O3):

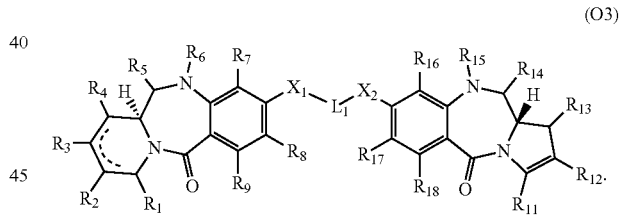

(O3)

In some aspects, the compound of formula (I) or formula (II) is a compound according to proviso (c) or (e) having the structure of formula (O4):

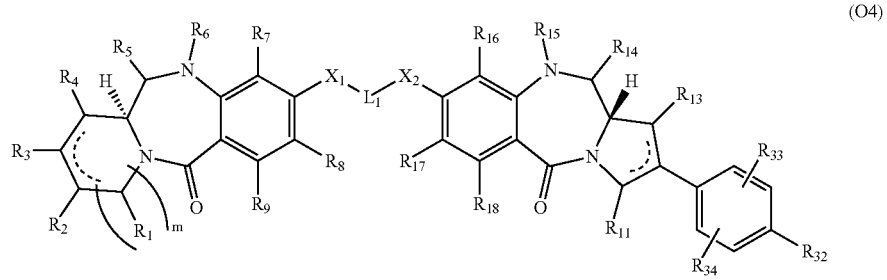

(O4)

wherein $R_{32}$, $R_{33}$ and $R_{34}$ are each independently selected from H and $R_{20}$.

Optional Double Bonds in the C-Ring of the PBD or PDD Moieties

The compounds of formula (I) or formula (II) comprise PBD or PDD moieties with C-rings containing dotted lines --- that indicate the optional presence of one or more double bonds. Thus, for example, for compounds of formula (I) or for compounds of formula (II) when m is 1, and an optional double bond is present in the C-ring, the left hand side moiety may have one or more double bonds and may be selected from:

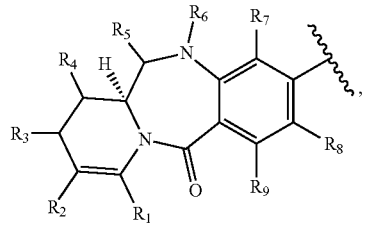
(DB1)

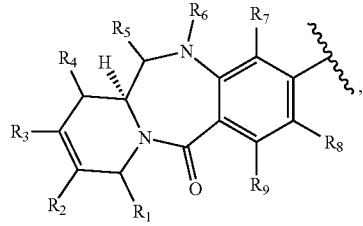
(DB2)

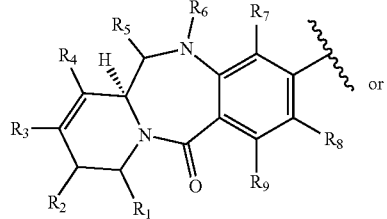
(DB3) or

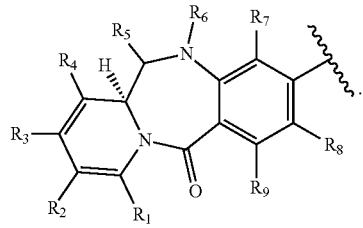
(DB4)

Suitably, the compound has a double bond and the left hand side moiety is selected from (DB2) or (DB3).

Suitably, where the compounds have an optional double bond present, the left hand side moiety is (DB3).

More suitably, where the compounds have an optional double bond present, the left hand side moiety is (DB2).

Similarly, for compounds of formula (I) when an optional double bond is present in the C-ring, the right hand side moiety may have one or more double bonds and may be selected from:

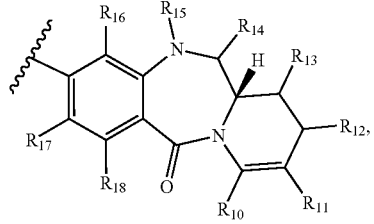
(DB5)

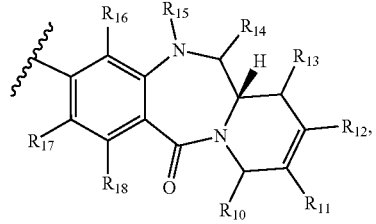
(DB6)

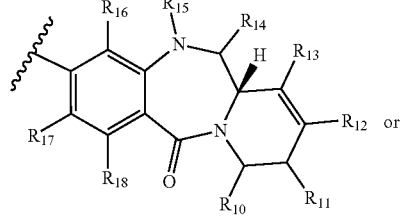
(DB7) or

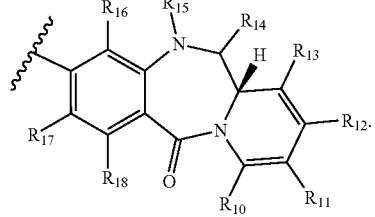
(DB8)

Suitably, the compound has a double bond and the left hand side moiety is selected from (DB6) or (DB7).

Suitably, where the compounds have an optional double bond present, the left hand side moiety is (DB7).

More suitably, where the compounds of formula (I) have an optional double bond present, the right hand side moiety is (DB6).

For compounds of formula (II) when an optional double bond is present in the C-ring, the right hand side moiety may have a double bond as shown below:

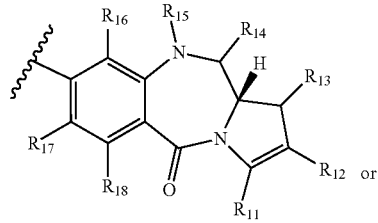
(DB9) or

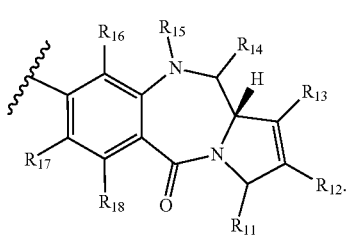

(DB10)

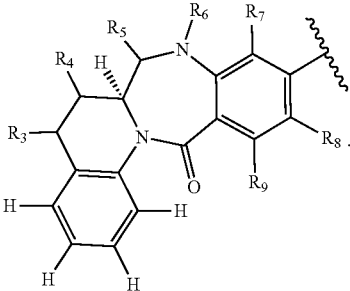

(LMH2)

Suitably, where the compounds of formula (II) have an optional double bond present, the right hand side moiety is (DB10).

More suitably, where the compounds of formula (II) have an optional double bond present, the right hand side moiety is (DB9).

In some aspects, optional double bonds are absent from the compounds of formula (I) or formula (II).

$R_1$, $R_2$, R, and $R_4$

For the options where any of $R_1$, $R_2$, $R_3$ and $R_4$ are each independently selected from =$CH_2$, =CH—$(CH_2)_s$—$CH_3$, =CH—$(CH_2)_s$—$R_{21}$ and =O, the carbon of the C-ring to which it is attached cannot have an optional double bond in order for the valence requirements of the molecule to be met. For example, if $R_4$ is =$CH_2$ then there must be a single bond between the carbons to which $R_4$ and $R_3$ are attached, this may be represented as follows (LHM1):

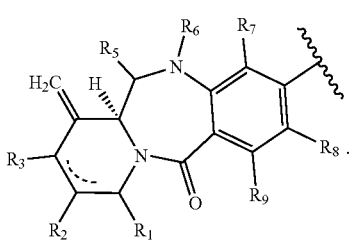

(LMH1)

In the aspects where one of $R_1$ and $R_2$, $R_2$ and $R_3$, or $R_3$ and $R_4$ together with the carbon atoms to which they are attached form a 6-membered aryl, or a 5- or 6-membered cyclic, heterocyclic, or heteroaryl ring optionally substituted with up to three optional substituent groups, groups then the left hand moiety contains a further fused ring [not drawn in formula (I) or (II)]. In these aspects, then the remaining groups (from $R_1$, $R_2$, $R_3$ and $R_4$) that do not form the further fused ring are each independently selected from the normal specified list of groups, i.e. from H and $R_{19}$. For example, where $R_1$ and $R_2$ together with the carbon atoms to which they are attached form a 6-membered aryl ring the structure of the left hand moiety can be shown as follows (LMH2):

In LMH2 groups $R_3$ and $R_4$ do not form the further fused ring and so are each independently selected from the normal specified list of groups for $R_3$ and $R_4$, i.e. from H and $R_{19}$. In addition, the H groups shown on the further fused ring of (LMH2) may be substituted with up to three independently selected optional $R_{20}$ groups.

Suitably, $R_1$, $R_2$, $R_3$ and $R_4$ are each independently selected from H, $R_{20}$, $R_{21}$, =$CH_2$, =CH—$(CH_2)_s$—$CH_3$, =CH—$(CH_2)_s$—$R_{21}$, $(CH_2)_s$—$OR_{21}$, $(CH_2)_s$—$CO_2R_{21}$, $(CH_2)_s$—$NR_{21}R_{23}$, O—$(CH_2)_t$—$NR_{21}R_{23}$, NH—C(O)—$R_{21}$, O—$(CH_2)_t$—NH—C(O)—$R_{21}$, O—$(CH_2)_t$—C(O)—NH—$R_{21}$, $(CH_2)_s$—C(O)$R_{21}$ and $(CH_2)_s$—C(O)$NR_{21}R_{23}$;

or one of $R_1$ and $R_2$, $R_2$ and $R_3$, or $R_3$ and $R_4$ together with the carbon atoms to which they are attached form a 6-membered aryl, or a 5- or 6-membered cyclic, heterocyclic, or heteroaryl ring optionally substituted with 1, 2 or 3 independently selected optional $R_{20}$ groups.

Suitably, $R_1$, $R_2$, $R_3$ and $R_4$ are each independently selected from H, $R_{20}$, $R_{21}$, $(CH_2)_s$—$OR_{21}$, $(CH_2)_s$—$CO_2R_{21}$, $(CH_2)_s$—$NR_{21}R_{23}$, NH—C(O)—$R_{21}$, $(CH_2)_s$—C(O)$R_{21}$ and $(CH_2)_s$—C(O)$NR_{21}R_{23}$;

or one of $R_1$ and $R_2$, $R_2$ and $R_3$, or $R_3$ and $R_4$ together with the carbon atoms to which they are attached form a 6-membered aryl, or a 5- or 6-membered cyclic, heterocyclic, or heteroaryl ring optionally substituted with 1, 2 or 3 independently selected optional $R_{20}$ groups.

Suitably, where one of $R_1$ and $R_2$, $R_2$ and $R_3$, or $R_3$ and $R_4$ together with the carbon atoms to which they are attached form an optionally substituted 5- or 6-membered heterocyclic or heteroaryl ring the heterocyclic or heteroaryl ring comprises one nitrogen atom. Suitably, the optionally substituted 5- or 6-membered heterocyclic or heteroaryl ring is a pyrrolyl, N-methylpyrrolyl or a pyridyl ring. An N-methylpyrrolyl is an example of where the 5- or 6-membered heterocyclic or heteroaryl ring is optionally substituted with a methyl group.

Suitably, where one of $R_1$ and $R_2$, $R_2$ and $R_3$, or $R_3$ and $R_4$ together with the carbon atoms to which they are attached form an optionally substituted 6-membered aryl, or an optionally substituted 5- or 6-membered cyclic, heterocyclic, or heteroaryl ring, the ring is selected from optionally substituted phenyl, pyrrolyl, N-methylpyrrolyl and pyridyl rings.

In some aspects, suitably $R_1$, $R_2$, $R_3$ and $R_4$ are each independently selected from H and $R_{20}$.

In another aspect, suitably $R_2$ and $R_3$ together with the carbon atoms to which they are attached form a 6-membered aryl, or a 5- or 6-membered cyclic, heterocyclic, or heteroaryl ring optionally substituted with 1, 2 or 3 independently selected optional $R_{20}$ groups. Suitably $R_2$ and $R_3$ together with the carbon atoms to which they are attached form optionally substituted phenyl, pyrrolyl, N-methylpyrrolyl and pyridyl rings.

Suitably 1, 2, 3 or 4 of $R_1$, $R_2$, $R_3$ and $R_4$ are H.
More suitably, $R_1$ is H.
More suitably, $R_2$ is H.
More suitably, $R_3$ is selected from H, optionally substituted $C_{5-9}$ heteroaryl and optionally substituted phenyl; wherein the heteroaryl and phenyl groups are optionally substituted with 1, 2 or 3 independently selected optional $R_{20}$ groups.
More suitably, $R_3$ is H or optionally substituted phenyl.
In some aspects, suitably, $R_4$ is H.

$R_5$ and $R_6$

Suitably, $R_5$ and $R_6$ are (i), wherein $R_5$ is selected from H, OH and $OCH_3$ or $OCH_2CH_3$; and $R_6$ is selected from H, $SO_3H$, nitrogen protecting groups, OH, $OCH_3$, $OCH_2CH_3$, $OCH_2Ph$, $(CH_2)_j$—$CO_2H$, $(CH_2)_j$—$CO_2CH_3$, $(CH_2)_j$—$CO_2CH_2CH_3$, O—$(CH_2)_k$—$NH_2$, O—$(CH_2)_k$—NH—$CH_3$, C(=O)—O—$(CH_2)_k$—$NH_2$, C(=O)—O—$(CH_2)_k$—NH—$CH_3$, $(CH_2)_j$—$NH_2$, $(CH_2)_j$—NH—$CH_3$, C(=O)—NH—$(CH_2)_k$—$NH_2$, C(=O)—NH—$(CH_2)_k$—NH—$CH_3$, C(=O)—NH—$C_6H_4$—$(CH_2)_j$—H, C(=O)—NH—$(CH_2)_k$—C(=NH)$NH_2$, C(=O)—NH—$(CH_2)_k$—C(=NH)NH—$CH_3$ and -$L_2$-$R_{28}$; (ii) $R_5$ is oxo or H, and $R_6$ is H or $C_{1-6}$ alkyl; or (iii) $R_5$ and $R_6$ together form a double bond.

More suitably, $R_5$ and $R_6$ are (i), wherein $R_5$ is selected from H, OH and $OCH_3$ or $OCH_2CH_3$; and $R_6$ is selected from H, $SO_3H$, OH, $OCH_3$, $OCH_2CH_3$, $CO_2H$, $CO_2CH_3$, $CO_2CH_2CH_3$, O—$(CH_2)_k$—$NH_2$, C(=O)—O—$(CH_2)_k$—$NH_2$, $(CH_2)_j$—$NH_2$ and -$L_2$-$R_{28}$; (ii) $R_5$ is oxo or H, and $R_6$ is H or $C_{1-6}$ alkyl; or (iii) $R_5$ and $R_6$ together form a double bond.

Suitably, $R_5$ and $R_6$ are (i), wherein $R_5$ is selected from H, OH and $OCH_3$ or $OCH_2CH_3$; and $R_6$ is selected from H, $SO_3H$, OH, $OCH_3$, $OCH_2CH_3$, $CO_2H$, $CO_2CH_3$, $CO_2CH_2CH_3$, O—$(CH_2)_k$—$NH_2$C(=O)—O—$(CH_2)_k$—$NH_2$ and -$L_2$-$R_{28}$; (ii) $R_5$ is oxo or H, and $R_6$ is H or $C_{1-6}$ alkyl; or (iii) $R_5$ and $R_6$ together form a double bond.

More suitably, either:
(1) $R_5$ is H or OH, and $R_6$ is $SO_3H$, OH, $OCH_3$, $OCH_2CH_3$, O—$(CH_2)_k$—$NH_2$ or -$L_2$-$R_{28}$;
(2) $R_5$ is OH, $OCH_3$ or $OCH_2CH_3$, and $R_6$ is H;
(3) $R_5$ is oxo or H, and $R_6$ is H or $C_{1-6}$ alkyl; or
(4) $R_5$ and $R_6$ together form a double bond.

In some aspects, $R_5$ and $R_6$ are (ii) wherein $R_5$ is oxo or H, and $R_6$ is H or $C_{1-6}$ alkyl in such aspects then the left hand moiety of the compound of formula (I) will not alkylate DNA. In such aspects, the options for $R_{14}$ and $R_{15}$ are limited to options (iv) and (vi) which are those that ensure that the right hand moiety of the compound of formula (I) does alkylate with DNA. Examples of compounds such of formula (I) are shown below:

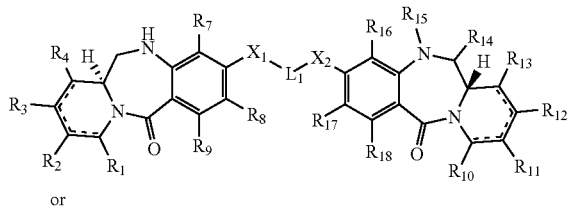

or

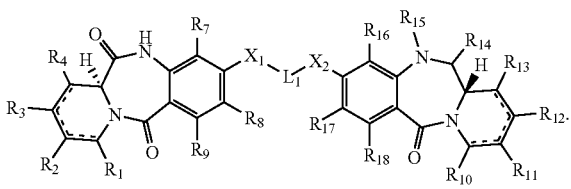

Most suitably, $R_5$ and $R_6$ are (iii), wherein $R_5$ and $R_6$ together form a double bond.

In some aspects, $R_6$ is $SO_3H$ and the compound of formula (I) is a salt thereof. Suitably, in this aspect, $R_6$ is $SO_3H$ and the compound of formula (I) is an alkali metal salt thereof $(AM)^+$; hence, in this aspect, $R_6$ may be written as $SO_3^-(AM)^+$. Suitably, $R_6$ is $SO_3H$ and the compound of formula (I) is an alkali metal salt thereof chosen from $Li^+$, $Na^+$ and $K^+$. More suitably, $R_6$ is $SO_3H$ and the compound of formula (I) is a $Na^+$ salt thereof; hence, in this aspect, $R_6$ may be written as $SO_3$—$Na^+$.

$R_7$, $R_9$, $R_{16}$ and $R_{18}$

Suitably, $R_7$, $R_9$, $R_{16}$ and $R_{18}$ are independently selected from H, $(CH_2)_j$—OH, methyl, ethyl, $OCH_3$, $OCH_2CH_3$, $OCH_2Ph$, $CO_2H$, $CO_2CH_3$, $CO_2CH_2CH_3$, O—$(CH_2)_k$—$NH_2$, O—$(CH_2)_k$—NH—$CH_3$, $(CH_2)_j$—$NH_2$, $(CH_2)_j$—NH—$CH_3$ and -$L_2$-$R_{28}$.

Suitably, $R_7$, $R_9$, $R_{16}$ and $R_{18}$ are independently selected from H, OH, methyl, ethyl, $OCH_3$, $OCH_2CH_3$, $CO_2H$, $CO_2CH_3$, $CO_2CH_2CH_3$, $(CH_2)_j$—$NH_2$ and -$L_2$-$R_{28}$.

More suitably, $R_7$, $R_9$, $R_{16}$ and $R_{18}$ are independently selected from H, OH, methyl, ethyl, $OCH_3$ and $OCH_2CH_3$.

Most suitably, $R_7$ is H.
Most suitably, $R_9$ is H.
Most suitably, $R_{16}$ is H.
Most suitably, $R_{18}$ is H.

$R_8$ and $R_{17}$

Suitably, $R_8$ and $R_{17}$ are independently selected from H, SH, $SCH_3$, $SCH_2Ph$, $(CH_2)_j$—OH, methyl, ethyl, $OCH_3$, $OCH_2CH_3$, $OCH_2Ph$, $CO_2H$, $CO_2CH_3$, $CO_2CH_2CH_3$, O—$(CH_2)_k$—$NH_2$, O—$(CH_2)_k$—NH—$CH_3$, $(CH_2)_j$—$NH_2$, $(CH_2)_j$—NH—$CH_3$ and -$L_2$-$R_{28}$.

Suitably, $R_8$ and $R_{17}$ are independently selected from H, OH, methyl, ethyl, $OCH_3$, $OCH_2CH_3$, $OCH_2Ph$, $CO_2H$, $CO_2CH_3$, $CO_2CH_2CH_3$, O—$(CH_2)_k$—$NH_2$, $(CH_2)_j$—$NH_2$ and -$L_2$-$R_{28}$.

More suitably, $R_8$ and $R_{17}$ are independently selected from $OCH_3$, $OCH_2CH_3$ and $OCH_2Ph$.

More suitably, $R_8$ and $R_{17}$ are $OCH_3$.

$R_{10}$, $R_{11}$, $R_{12}$ and $R_{13}$

Suitably, $R_{10}$, $R_{11}$, $R_{12}$ and $R_{13}$ are each independently selected from H, $R_{20}$, $R_{21}$, =$CH_2$, =CH—$(CH_2)_s$—$CH_3$, =CH—$(CH_2)_s$—$R_{21}$, $(CH_2)_s$—$OR_{21}$, $(CH_2)$—$CO_2R_{21}$, $(CH_2)_s$—$NR_{21}R_{23}$, O—$(CH_2)_t$—$NR_{21}R_{23}$, NH—C(O)—$R_{21}$, O—$(CH_2)_t$—NH—C(O)—$R_{21}$, O—$(CH_2)_t$—C(O)—NH—$R_{21}$, $(CH_2)_s$—C(O)$R_{21}$ and $(CH_2)_s$—C(O)$NR_{21}R_{23}$;
or one of $R_{10}$ and $R_{11}$, $R_{11}$ and $R_{12}$, or $R_{12}$ and $R_{13}$ together with the carbon atoms to which they are attached form a 6-membered aryl, or a 5- or 6-membered cyclic, heterocyclic, or heteroaryl ring optionally substituted with 1, 2 or 3 independently selected optional $R_{20}$ groups.

Suitably, $R_{10}$, $R_{11}$, $R_{12}$ and $R_{13}$ are each independently selected from H, $R_{20}$, $R_{21}$, =$CH_2$, =CH—$(CH_2)_s$—$CH_3$, =CH—$(CH_2)_s$—$R_{21}$, $(CH_2)_s$—$OR_{21}$, $(CH_2)_s$—$CO_2R_{21}$, $(CH_2)_s$—$NR_{21}R_{23}$, NH—C(O)—$R_{21}$, $(CH_2)_s$—C(O)$R_{21}$ and $(CH_2)_s$—C(O)$NR_{21}R_{23}$;
or one of $R_{10}$ and $R_{11}$, $R_{11}$ and $R_{12}$, or $R_{12}$ and $R_{13}$ together with the carbon atoms to which they are attached form a 6-membered aryl, or a 5- or 6-membered cyclic, heterocyclic, or heteroaryl ring optionally substituted with 1, 2 or 3 independently selected optional $R_{20}$ groups.

In some aspects, suitably $R_{10}$, $R_{11}$, $R_{12}$ and $R_{13}$ are each independently selected from H and $R_{20}$.

Suitably, where one of $R_{10}$ and $R_{11}$, $R_{11}$ and $R_{12}$, or $R_{12}$ and $R_{13}$ together with the carbon atoms to which they are attached form an optionally substituted 5- or 6-membered heterocyclic or heteroaryl ring the heterocyclic or heteroaryl ring comprises one nitrogen atom. Suitably, the optionally substituted 5- or 6-membered heterocyclic or heteroaryl ring is a pyrrolyl, N-methylpyrrolyl or a pyridyl ring. An N-methylpyrrolyl is an example of where the 5- or 6-membered heterocyclic or heteroaryl ring is optionally substituted with a methyl group.

Suitably, where one of $R_{10}$ and $R_{11}$, R and $R_{12}$, or $R_{12}$ and $R_{13}$ together with the carbon atoms to which they are attached form an optionally substituted 6-membered aryl, or an optionally substituted 5- or 6-membered cyclic, heterocyclic, or heteroaryl ring, the ring is an optionally substituted phenyl, pyrrolyl, N-methylpyrrolyl or pyridyl ring.

In another aspect, suitably $R_{11}$ and $R_{12}$ together with the carbon atoms to which they are attached form a 6-membered aryl, or a 5- or 6-membered cyclic, heterocyclic, or heteroaryl ring optionally substituted with 1, 2 or 3 independently selected optional $R_2$ groups. Suitably $R_{11}$ and $R_{12}$ together with the carbon atoms to which they are attached form an optionally substituted phenyl, pyrrolyl, N-methylpyrrolyl or pyridyl ring.

Suitably 1, 2, 3 or 4 of $R_{10}$, $R_{11}$, $R_{12}$ and $R_{13}$ are H.

More suitably, $R_{10}$ is H.

Suitably, $R_{11}$ is H.

More suitably, $R_{12}$ is selected from H, =$CH_2$, =CH—$(CH_2)_s$—$CH_3$, =CH—$(CH_2)_s$—$R_{21}$, optionally substituted $C_{5-9}$ heteroaryl and optionally substituted phenyl; wherein the heteroaryl and phenyl groups are optionally substituted with 1, 2 or 3 independently selected optional $R_{20}$ groups.

More suitably, $R_{12}$ is selected from H, =$CH_2$, =CH—$(CH_2)_s$—$CH_3$, =CH—$(CH_2)_s$—$R_{21}$ and optionally substituted phenyl.

More suitably, $R_{13}$ is H.

$R_{14}$ and $R_{15}$

Suitably, $R_{14}$ and $R_{15}$ are (iv), wherein $R_{14}$ is selected from H, OH and $OCH_3$ or $OCH_2CH_3$; and $R_{15}$ is selected from H, $SO_3H$, nitrogen protecting groups, OH, $OCH_3$, $OCH_2CH_3$, $OCH_2Ph$, $(CH_2)_j$—$CO_2H$, $(CH_2)_j$—$CO_2CH_3$, $(CH_2)_j$—$CO_2CH_2CH_3$, O—$(CH_2)_k$—$NH_2$, O—$(CH_2)_k$—NH—$CH_3$, C(=O)—O—$(CH_2)_k$—$NH_2$, C(=O)—O—$(CH_2)_k$—NH—$CH_3$, $(CH_2)_j$—$NH_2$, $(CH_2)_j$—NH—$CH_3$, C(=O)—NH—$(CH_2)_k$—$NH_2$, C(=O)—NH—$(CH_2)_k$—NH—$CH_3$, C(=O)—NH—$C_6H_4$—$(CH_2)_j$—H, C(=O)—NH—$(CH_2)_k$—C(=NH)$NH_2$, C(=O)—NH—$(CH_2)_k$—C(=NH)NH—$CH_3$ and -$L_2$—$R_{28}$; (v) $R_{14}$ is oxo or H, and $R_{15}$ is H or $C_{1-6}$ alkyl; or (vi) $R_{14}$ and $R_{15}$ together form a double bond.

More suitably, $R_{14}$ and $R_{15}$ are (iv), wherein $R_{14}$ is selected from H, OH and $OCH_3$ or $OCH_2CH_3$; and $R_{15}$ is selected from H, $SO_3H$, OH, $OCH_3$, $OCH_2CH_3$, $CO_2H$, $CO_2CH_3$, $CO_2CH_2CH_3$, O—$(CH_2)_k$—$NH_2$, C(=O)—$(CH_2)_k$—$NH_2$, $(CH_2)_j$—$NH_2$ and -$L_2$—$R_{28}$; (v) $R_{14}$ is oxo or H, and $R_{15}$ is H or $C_{1-6}$ alkyl; or (vi) $R_{14}$ and $R_{15}$ together form a double bond.

Suitably, $R_{14}$ and $R_{15}$ are (iv), wherein $R_{14}$ is selected from H, OH and $OCH_3$ or $OCH_2CH_3$; and $R_{15}$ is selected from H, $SO_3H$, OH, $OCH_3$, $OCH_2CH_3$, $CO_2H$, $CO_2CH_3$, $CO_2CH_2CH_3$, O—$(CH_2)_k$—$NH_2$C(=O)—O—$(CH_2)_k$—$NH_2$ and -$L_2$—$R_{28}$; (v) $R_{14}$ is oxo or H, and $R_{15}$ is H or $C_{1-6}$ alkyl; or (vi) $R_{14}$ and $R_6$ together form a double bond.

More suitably, either:

(1) $R_{14}$ is H or OH, and $R_{15}$ is $SO_3H$, OH, $OCH_3$, $OCH_2CH_3$, O—$(CH_2)_k$—$NH_2$ or -$L_2$-$R_{28}$;

(2) $R_{14}$ is OH, $OCH_3$ or $OCH_2CH_3$, and $R_{15}$ is H;

(3) $R_{14}$ is oxo or H, and $R_{15}$ is H or $C_{1-6}$ alkyl; or (4) $R_{14}$ and $R_{15}$ together form a double bond.

In some aspects, $R_{14}$ and $R_{15}$ are (v) wherein $R_{14}$ is oxo or H, and $R_{15}$ is H or $C_{1-6}$ alkyl; in such aspects then the right hand moiety of the compound of formula (I) will not alkylate DNA. In such aspects, the options for $R_5$ and $R_6$ are limited to options (i) and (iii) which are those that ensure that the left hand moiety of the compound of formula (I) does alkylate with DNA. Examples of compounds such of formula (I) are shown below:

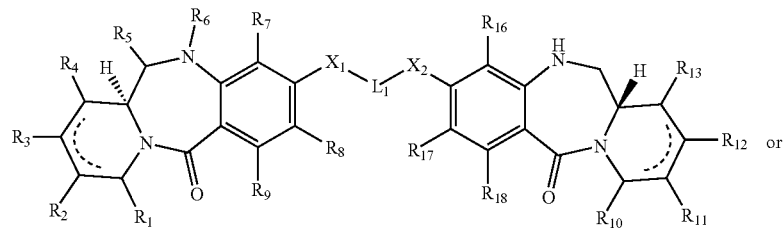

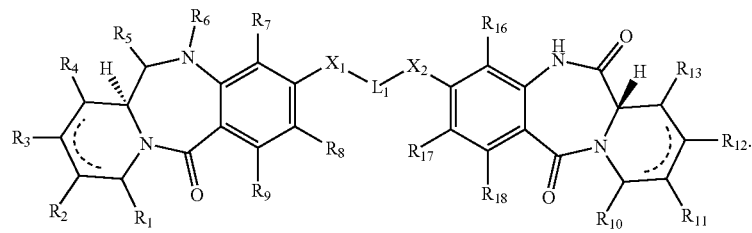

Most suitably, $R_{14}$ and $R_{15}$ are (vi), wherein $R_{14}$ and $R_{15}$ together form a double bond.

In some aspects, $R_{15}$ is $SO_3H$ and the compound of formula (I) is a salt thereof. Suitably, in this aspect, $R_{15}$ is $SO_3H$ and the compound of formula (I) is an alkali metal salt thereof $(AM)^+$; hence, in this aspect, $R_{15}$ may be written as $SO_3^-(AM)^+$. Suitably, $R_{15}$ is $SO_3H$ and the compound of formula (I) is an alkali metal salt thereof chosen from $Li^+$, $Na^+$ and $K^+$. More suitably, $R_{15}$ is $SO_3H$ and the compound of formula (I) is a $Na^+$ salt thereof; hence, in this aspect, $R_{15}$ may be written as $SO_3^-$—$Na^+$.

Suitably, the group is substituted with 1, 2 or 3 of the optional substituents. Where a group may be "optionally substituted with one or two optional substituents", this means that the group may be substituted with 0, 1 or 2 of the optional substituents.

$R_{19}$

Suitably, each $R_{19}$ is independently selected from $R_{20}$, $R_{21}$, =$CH_2$, =CH—$(CH_2)_s$—$CH_3$, =CH—$(CH_2)_s$—$R_{21}$, $(CH_2)_s$—$OR_{21}$, $(CH_2)_s$—$CO_2R_{21}$, $(CH_2)_s$—$NR_{21}R_{23}$, O—$(CH_2)_t$—$NR_{21}R_{23}$, NH—C(O)—$R_{21}$, O—$(CH_2)_t$—NH—C(O)—$R_{21}$, O—$(CH_2)_t$—C(O)—NH—$R_{21}$, $(CH_2)_s$—C(O)$R_{21}$ and $(CH_2)_s$—C(O)$NR_{21}R_{23}$.

Suitably, each $R_{19}$ is independently selected from $R_{20}$, $R_{21}$, =$CH_2$, =CH—$(CH_2)_s$—$CH_3$, =CH—$(CH_2)_s$—$R_{21}$, $(CH_2)_s$—$OR_{21}$, $(CH_2)_s$—$CO_2R_{21}$, $(CH_2)_s$—$NR_{21}R_{23}$, NH—C(O)—$R_{21}$, $(CH_2)_s$—C(O)$R_{21}$ and $(CH_2)$—C(O)$NR_{21}R_{23}$.

In one aspect, suitably, one $R_{19}$ is $R_{21}$; and each of the remaining $R_{19}$ groups are independently selected from $R_{20}$, =$CH_2$, =CH—$(CH_2)_s$—$CH_3$, =CH—$(CH_2)_s$—$R_{21}$, $(CH_2)_s$—$OR_{21}$, $(CH_2)_s$—$CO_2R_{21}$, $(CH_2)_s$—$NR_{21}R_{23}$, O—$(CH_2)_t$—$NR_{21}R_{23}$, NH—C(O)—$R_{21}$, O—$(CH_2)_t$—NH—C(O)—$R_{21}$, O—$(CH_2)_t$—C(O)—NH—$R_{21}$, $(CH_2)_s$—C(O)$R_{21}$ and $(CH_2)_s$—C(O)$NR_{21}R_{23}$.

In another aspect, suitably, two $R_{19}$ groups are independently selected $R_{21}$ groups; and each of the remaining $R_{19}$ groups are independently selected from $R_{20}$, =$CH_2$, =CH—$(CH_2)_s$—$CH_3$, =CH—$(CH_2)_s$—$R_{21}$, $(CH_2)_s$—$OR_{21}$, $(CH_2)_s$—$CO_2R_{21}$, $(CH_2)_s$—$NR_{21}R_{23}$, O—$(CH_2)_t$—$NR_{21}R_{23}$, NH—C(O)—$R_{21}$, O—$(CH_2)_t$—NH—C(O)—$R_{21}$, O—$(CH_2)_t$—C(O)—NH—$R_{21}$, $(CH_2)_s$—C(O)$R_{21}$ and $(CH_2)_s$—C(O)$NR_{21}R_{23}$.

Suitably, each $R_{19}$ is independently selected from $R_{20}$, $R_{21}$, =$CH_2$, =CH—$(CH_2)_s$—$CH_3$, =CH—$(CH_2)_s$—$R_{21}$, $(CH_2)_s$—$OR_{21}$, $(CH_2)$—$CO_2R_{21}$, $(CH_2)_s$—$NR_{21}R_{23}$, NH—C(O)—$R_{21}$, $(CH_2)_s$—C(O)$R_{21}$ and $(CH_2)_s$—C(O)$NR_{21}R_{23}$.

More suitably, each $R_{19}$ is independently selected from $R_{20}$, =$CH_2$, =CH—$(CH_2)_s$—$CH_3$, =CH—$(CH_2)_s$—$R_{21}$ and $CH_2$—$CH_2$—C(O)—$N(CH_3)_2$.

In some aspects, each $R_{19}$ is independently selected from H, $C_{1-12}$ alkyl, F, Cl, Br, $(CH_2)_j$—OH, $OC_{1-6}$ alkyl, $OCH_2Ph$, =$CH_2$, =CH—$(CH_2)_s$—$CH_3$, =CH—$(CH_2)_s$—$R_{21}$ and an optionally substituted $C_{5-6}$ heterocyclyl, optionally substituted $C_{5-9}$ heteroaryl or an optionally substituted phenyl; optionally substituted with 1, 2, 3 optional groups, independently selected from F, Cl, Br, methyl, ethyl, $OCH_3$, $OCH_2CH_3(CH_2)_j$—$NR_{26}R_{27}$, $NR_{26}NH_2$, C(=O)—NH—$(CH_2)_j$—$NR_{26}R_{27}$, C(=O)—NH—$C_6H_4$—$(CH_2)_j$—$R_{26}$, C(=O)—NH—$(CH_2)_k$—C(=NH)$NR_{26}R_{27}$, -$L_2$-$R_{28}$, $C_{5-6}$ heterocyclyl, —S(O)$_2$—($C_{1-6}$ alkyl), O—$(CH_2)_k$—O—($C_{1-6}$ alkyl), $(CH_2)_j$—S(O)$_2$—$NR_{26}R_{27}$, C(=O)—O—($C_{1-6}$ alkyl), $(CH_2)_k$—O—($C_{1-6}$ alkyl), CN, NCO, C(O)—NH—$(CH_2)_j$-Cy, C(O)-Cy, NH—C(O)—$NR_{26}R_{27}$ and

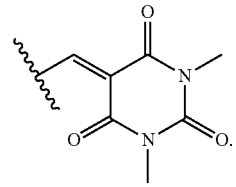 [SMILES: *C=C1C(=O)N(C)C(=O)N(C)C1=O]

In some aspects, each $R_{19}$ is independently selected from H, $C_{1-12}$ alkyl, F, Cl, Br, $(CH_2)_j$—OH, $OC_{1-6}$ alkyl, $OCH_2Ph$, =$CH_2$, =CH—$(CH_2)_s$—$CH_3$, =CH—$(CH_2)_s$—$R_{21}$ and an optionally substituted $C_{5-6}$ heterocyclyl, an optionally substituted $C_{5-9}$ heteroaryl or an optionally substituted phenyl; optionally substituted with 1, 2, 3 independently selected optional $R_{20}$ groups; wherein each $R_{20}$ group is independently selected from F, Cl, Br, methyl, ethyl, $OCH_3$ and $OCH_2CH_3$. Suitably, in this aspect $R_{19}$ is independently selected from H, $C_{1-12}$ alkyl, F, Cl, Br, $(CH_2)_j$—OH, $OC_{1-6}$ alkyl, $OCH_2Ph$, =$CH_2$, =CH—$(CH_2)_s$—$CH_3$ and =CH—$(CH_2)_s$—$R_{21}$.

In this aspect, suitably, each $R_{19}$ is independently selected from H, methyl, ethyl, F, Cl, Br, $OCH_3$, $OCH_2CH_3$ and $OCH_2Ph$.

Suitably, where an $R_{19}$ group may be optionally substituted it is substituted with 1, 2 or 3 of the optional substituents; suitably, an $R_{19}$ group is substituted with 1 or 2 of the optional substituents. More suitably, an $R_{19}$ group is substituted with 1 of the optional substituents. Alternatively, suitably an $R_{19}$ group is not substituted.

$R_{20}$

Suitably, each $R_{20}$ is independently selected from F, Cl, Br, $(CH_2)_j$—OH, methyl, ethyl, $OCH_3$, $OCH_2CH_3$, $OCH_2Ph$, $(CH_2)_j$—$CO_2R_{26}$, O—$(CH_2)_k$—$NR_{26}R_{27}$, C(=O)—O—$(CH_2)_k$—$NR_{26}R_{27}$, C(=O)—$NR_{26}R_{27}$, $(CH_2)_j$—$NR_{26}R_{27}$, $NR_{26}NH_2$, C(=O)—NH—$(CH_2)_j$—$NR_{26}R_{27}$, C(=O)—NH—$C_6H_4$—$(CH_2)_j$—$R_{26}$, C(=O)—NH—$(CH_2)_k$—C(=NH)$NR_{26}R_{27}$, -$L_2$-$R_{28}$, S(O)$_2$—($C_{1-6}$ alkyl), O—$(CH_2)_k$—O—($C_{1-6}$ alkyl), $(CH_2)_j$—S(O)$_2$—$NR_{26}R_{27}$, C(=NH)—O—($C_{1-6}$ alkyl), $(CH_2)_k$—O—($C_{1-6}$ alkyl), CN, NCO, Cy, C(O)—NH—$(CH_2)_j$-Cy, C(O)-Cy, NH—C(O)—$NR_{26}R_{27}$ and

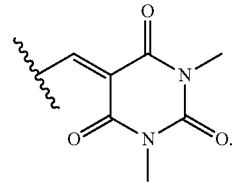 [SMILES: *C=C1C(=O)N(C)C(=O)N(C)C1=O]

Suitably, each $R_{20}$ is independently selected from $(CH_2)_j$—OH, methyl, ethyl, $OCH_3$, $OCH_2CH_3$, $OCH_2Ph$, $(CH_2)_j$—$CO_2H$, $(CH_2)_j$—$CO_2CH_3$, $(CH_2)_j$—$CO_2CH_2CH_3$, O—$(CH_2)_k$—$NH_2$, O—$(CH_2)_k$—NH—$CH_3$, C(=O)—O—$(CH_2)_k$—$NH_2$, C(=O)—O—$(CH_2)_k$—NH—$CH_3$, $(CH_2)_j$—$NH_2$, $(CH_2)_j$—NH—$CH_3$, C(=O)—$NH_2$, $N(CH_3)$—$NH_2$, $NHNH_2$, C(=O)—NH—$NH_2$, C(=O)—NH—$CH_2$—$NH_2$, C(=O)—NH—$(CH_2)_j$—$NH_2$, C(=O)—NH—$(CH_2)_k$—NH—$CH_3$, C(=O)—NH—$C_6H_4$—$(CH_2)_j$—H, C(=O)—NH—$(CH_2)_k$—C(=NH)$NH_2$, C(=O)—NH—$(CH_2)_k$—C(=NH)NH—$CH_3$, -$L_2$-$R_{28}$, S(O)$_2$—$CH_3$, S(O)$_2$—$CH_2CH_3$, S(O)$_2$—CH($CH_3$)$_2$, O—$CH_2$—O—$CH_3$, O—$CH_2$—O—$CH_2CH_3$, S(O)$_2$—$NH_2$, S(O)$_2$—$NHCH_3$, S(O)$_2$—$N(CH_3)_2$, C(=NH)—O—$CH_3$, C(=NH)—O—

$CH_2CH_3$, $CH_2$—O—$CH_3$, $CH_2$—O—$CH_2CH_3$, CN, NCO, Cy, C(O)—NH-Cy, C(O)—NH—$CH_2$-Cy, C(O)-Cy, NH—C(O)—$NH_2$, NH—C(O)—$NH_2$ and

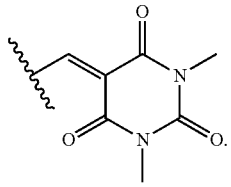 [SMILES: *C=C1C(=O)N(C)C(=O)N(C)C1=O]

More suitably, each $R_{20}$ is independently selected from $(CH_2)_j$—OH, methyl, ethyl, $OCH_3$, $OCH_2CH_3$, $CO_2H$, $CO_2CH_3$, $CO_2CH_2CH_3$, O—$(CH_2)_k$—$NH_2$, C(=O)—O—$(CH_2)_k$—$NH_2$, $(CH_2)_j$—$NH_2$, NH—$CH_3$, -$L_2$-$R_{28}$, $S(O)_2$—$CH_3$, $S(O)_2$—$CH_2CH_3$, $S(O)_2$—$CH(CH_3)_2$, O—$CH_2$—O—$CH_3$, O—$CH_2$—O—$CH_2CH_3$, $S(O)_2$—$NHCH_3$, $S(O)_2$—$N(CH_3)_2$, C(=NH)—O—$CH_3$, C(=NH)—O—$CH_2CH_3$, $CH_2$—O—$CH_3$, $CH_2$—O—$CH_2CH_3$, Cy, C(O)—NH-Cy, C(O)—NH—$CH_2$—Cy, C(O)-Cy, NH—C(O)—$NH_2$ and NH—C(O)—$NH_2$.

In some aspects, suitably, one $R_{20}$ group is selected from $(CH_2)_j$—$CO_2R_{26}$, O—$(CH_2)_k$—$NR_{26}R_{27}$, C(=O)—O—$(CH_2)_k$—$NR_{26}R_{27}$, $(CH_2)_j$—$NR_{26}R_{27}$, $NHNH_2$, C(=O)—NH—$(CH_2)_j$—$NR_{26}R_{27}$, C(=O)—NH—$C_6H_4$—$(CH_2)_j$—$R_{26}$, C(=O)—NH—$(CH_2)_k$—C(=NH)$NR_{26}R_{27}$ and -$L_2$-$R_{28}$; and the remaining $R_{20}$ groups are each independently selected from F, Cl, Br, $(CH_2)_j$—OH, $C_{1-6}$ alkyl, $OC_{1-6}$ alkyl, $OCH_2Ph$, $S(O)_2$—$CH_3$, $S(O)_2$—$CH(CH_3)_2$, $S(O)_2$—$NHCH_3$, $S(O)_2$—$N(CH_3)_2$, O—$CH_2$—O—$CH_2CH_3$, Cy, C(O)—NH—$CH_2$—Cy, NH—C(O)—$NH_2$ and NH—C(O)—$NH_2$.

In one aspect, more suitably, one $R_{20}$ group is -$L_2$-$R_{28}$; and the remaining $R_{20}$ groups are each independently selected from F, Cl, Br, $(CH_2)_j$—OH, $C_{1-6}$ alkyl, $OC_{1-6}$ alkyl, $OCH_2Ph$, $S(O)_2$—$CH_3$, $S(O)_2$—$CH(CH_3)_2$, $S(O)_2$—$NHCH_3$, $S(O)_2$—$N(CH_3)_2$, O—$CH_2$—O—$CH_2CH_3$, Cy, C(O)—NH—$CH_2$—Cy, NH—C(O)—$NH_2$ and NH—C(O)—$NH_2$.

More suitably, one $R_{20}$ group is selected from $(CH_2)_j$—$CO_2H$, $(CH_2)_j$—$CO_2CH_3$, O—$(CH_2)_k$—$NH_2$, O—$(CH_2)_k$—NH—$CH_3$, C(=O)—O—$(CH_2)_k$—$NH_2$, C(=O)—O—$(CH_2)_k$—NH—$CH_3$, $(CH_2)_j$—$NH_2$, $(CH_2)_j$—NH—$CH_3$, C(=O)—NH—$(CH_2)_k$—$NH_2$, C(=O)—NH—$(CH_2)_k$—NH—$CH_3$, C(=O)—NH—$C_6H_4$—$(CH_2)_j$—H, C(=O)—NH—$(CH_2)_k$—C(=NH)$NH_2$ and C(=O)—NH—$(CH_2)_k$—C(=NH)NH—$CH_3$; and the remaining $R_{20}$ groups are each independently selected from F, Cl, Br, $(CH_2)_j$—OH, methyl, ethyl, $OCH_3$, $OCH_2CH_3$, $OCH_2Ph$, $S(O)_2$—$NHCH_3$ and $S(O)_2$—$N(CH_3)_2$. More suitably, the remaining $R_{20}$ groups are each independently selected from F, Cl, Br, methyl, ethyl, $OCH_3$ and $OCH_2CH_3$.

More suitably, one $R_{20}$ group is selected from $(CH_2)_j$—$CO_2H$, $(CH_2)_j$—$CO_2CH_3$, O—$(CH_2)_k$—$NH_2$, O—$(CH_2)_k$—NH—$CH_3$, C(=O)—O—$(CH_2)_k$—$NH_2$, C(=O)—O—$(CH_2)_k$—NH—$CH_3$, $(CH_2)_j$—$NH_2$, $(CH_2)_j$—NH—$CH_3$, C(=O)—NH—$(CH_2)_k$—$NH_2$, C(=O)—NH—$(CH_2)_k$—NH—$CH_3$, C(=O)—NH—$C_6H_4$—$(CH_2)_j$—H, C(=O)—NH—$(CH_2)_k$—C(=NH)$NH_2$ and C(=O)—NH—$(CH_2)_k$—C(=NH)NH—$CH_3$; and the remaining $R_{20}$ groups are each independently selected from F, Cl, Br, $(CH_2)_j$—OH, methyl, ethyl, $OCH_3$, $OCH_2CH_3$ and $OCH_2Ph$.

More suitably, one $R_{20}$ group is selected from O—$(CH_2)_k$—$NH_2$ and $(CH_2)_j$—$NH_2$; and the remaining $R_{20}$ groups are each independently selected from F, Cl, Br, methyl, ethyl, $OCH_3$ and $OCH_2CH_3$.

$R_{21}$

In some aspects, suitably $R_{21}$ is selected from $C_{5-6}$ heterocyclyl, $C_{5-9}$ heteroaryl, $C_{6-15}$ heteroarylalkyl, phenyl, benzyl and phenethyl; wherein the heterocyclyl, heteroaryl, heteroarylalkyl, phenyl and aralkyl groups are optionally substituted with 1, 2 or 3 optional groups independently selected optional $R_{20}$ groups.

In another aspect, suitably $R_{21}$ is selected from H, $C_{1-12}$ alkyl, N-methylpyrrolyl, furanyl, thiophenyl, imidazolyl, N-methylimidazolyl, oxazolyl, thiazolyl, pyridyl, pyrimidinyl, uracilyl, tetrahydropyridinyl, indolyl, N-methylindolyl, benzofuranyl, benzothiophenyl, benzimidazolyl, N-methylbenzo-imidazolyl, benzooxazolyl, benzothiazolyl, pyrrol-3-ylmethyl, pyrrol-4-ylmethyl, imidazol-2-ylmethyl, imidazol-4-ylmethyl, thiophen-3-ylmethyl, furan-3-ylmethyl, phenyl, benzyl and phenethyl; wherein the heterocyclyl, heteroaryl, heteroarylalkyl, phenyl and aralkyl groups are optionally substituted with 1, 2 or 3 independently selected optional $R_{20}$ groups.

Suitably $R_{21}$ is selected from H, $C_{1-6}$ alkyl, N-methylpyrrolyl, furanyl, thiophenyl, imidazolyl, N-methylimidazolyl, oxazolyl, thiazolyl, pyridyl, pyrimidinyl, uracilyl, tetrahydropyridinyl, indolyl, N-methylindolyl, benzofuranyl, benzothiophenyl, benzimidazolyl, N-methylbenzoimidazolyl, benzooxazolyl, benzothiazolyl, pyrrol-3-ylmethyl, pyrrol-4-ylmethyl, imidazol-2-ylmethyl, imidazol-4-ylmethyl, thiophen-3-ylmethyl, furan-3-ylmethyl, phenyl, benzyl and phenethyl; wherein the heterocyclyl, heteroaryl, heteroarylalkyl, phenyl and aralkyl groups are optionally substituted with 1, 2 or 3 independently selected optional $R_{20}$ groups.

Suitably $R_{21}$ is selected from H, methyl, ethyl, n-propyl, i-propyl, n-butyl, s-butyl, i-butyl, t-butyl, N-methylpyrrolyl, furanyl, thiophenyl, imidazolyl, N-methylimidazolyl, oxazolyl, thiazolyl, pyridyl, pyrimidinyl, uracilyl, tetrahydropyridinyl, indolyl, N-methylindolyl, benzofuranyl, benzothiophenyl, benzimidazolyl, N-methylbenzoimidazolyl, benzooxazolyl, benzothiazolyl, pyrrol-3-ylmethyl, pyrrol-4-ylmethyl, imidazol-2-ylmethyl, imidazol-4-ylmethyl, thiophen-3-ylmethyl, furan-3-ylmethyl, phenyl, benzyl and phenethyl optionally substituted with 1, 2 or 3 independently selected optional $R_{20}$ groups.

Suitably $R_{21}$ is selected from H, methyl, ethyl, n-propyl, i-propyl, n-butyl, s-butyl, i-butyl, t-butyl, N-methylpyrrolyl, furanyl, thiophenyl, imidazolyl, N-methylimidazolyl, oxazolyl, thiazolyl, pyridyl, pyrimidinyl, uracilyl, tetrahydropyridinyl, indolyl, N-methylindolyl, benzofuranyl, benzothiophenyl, benzimidazolyl, N-methylbenzoimidazolyl, benzooxazolyl, benzothiazolyl, phenyl, benzyl and phenethyl optionally substituted with 1, 2 or 3 independently selected optional $R_{20}$ groups.

Suitably, the heterocyclyl, heteroaryl, heteroarylalkyl, phenyl and aralkyl groups are optionally substituted with 1, 2 or 3 optional groups independently selected from F, Cl, Br, methyl, ethyl, $OCH_3$, $OCH_2CH_3$, $(CH_2)_j$—$NR_{26}R_{27}$, $NR_{26}NH_2$, C(=O)—NH—$(CH_2)_j$—$NR_{26}R_{27}$, C(=O)—NH—$C_6H_4$—$(CH_2)_j$—$R_{26}$, C(=O)—NH—$(CH_2)_k$—C(=NH)$NR_{26}R_{27}$, -$L_2$-$R_{28}$, $C_{5-6}$ heterocyclyl, —$S(O)_2$—($C_{1-6}$ alkyl), O—$(CH_2)_k$—O—($C_{1-6}$alkyl), $(CH_2)_j$—$S(O)_2$—$NR_{26}R_{27}$, C(=NH)—O—($C_{1-6}$ alkyl), $(CH_2)_k$—O—($C_{1-6}$ alkyl), CN, NCO, C(O)—NH—$(CH_2)_j$-Cy, C(O)-Cy, NH—C(O)—$NR_{26}R_{27}$ and

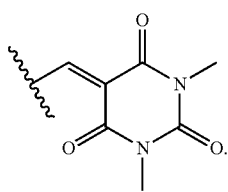 [SMILES: *C=C1C(=O)N(C)C(=O)N(C)C1=O]

In some aspects, suitably, each $R_{21}$ is independently selected from:

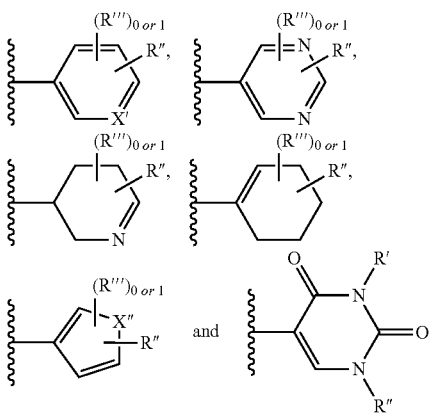

wherein X' is N, CH or CR''';

X" is O, NH, N—($C_{1-6}$ alkyl) or S; and each R" and R''' are independently selected from H, $S(O)_2$—($C_{1-6}$ alkyl), O—$(CH_2)_k$—O—($C_{1-6}$ alkyl), $(CH_2)_j$—$NR_{26}R_{27}$, $NR_{26}NH_2$, -$L_2$-$R_{28}$, $(CH_2)_j$—$S(O)_2$—$NR_{26}R_{27}$, C(=NH)—O—($C_{1-6}$ alkyl), $(CH_2)_k$—O—($C_{1-6}$ alkyl), CN, NCO, Cy, C(O)—NH—$(CH_2)_j$-Cy, C(O)-Cy, NH—C(O)—$NR_{26}R_{27}$, $R_{20}$ groups and

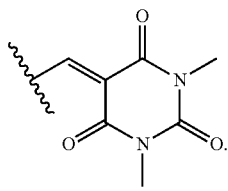 [SMILES: *C=C1C(=O)N(C)C(=O)N(C)C1=O]

More suitably, each R" and R''' are independently selected from $S(O)_2$—($C_{1-6}$ alkyl), O—$(CH_2)_k$—O—($C_{1-6}$ alkyl), $(CH_2)_j$—$NR_{26}R_{27}$, $NR_{26}NH_2$, $(CH_2)_j$—$S(O)_2$—$NR_{26}R_{27}$, C(=NH)—O—($C_{1-6}$ alkyl), $(CH_2)_k$—O—($C_{1-6}$ alkyl), CN, NCO, Cy, C(O)—NH—$(CH_2)_j$-Cy, C(O)-Cy, NH—C(O)—$NR_{26}R_{27}$, $R_{20}$ groups and

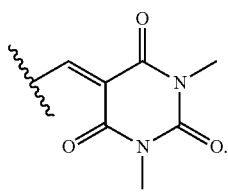 [SMILES: *C=C1C(=O)N(C)C(=O)N(C)C1=O]

In some embodiments, $R_{21}$ is selected from:

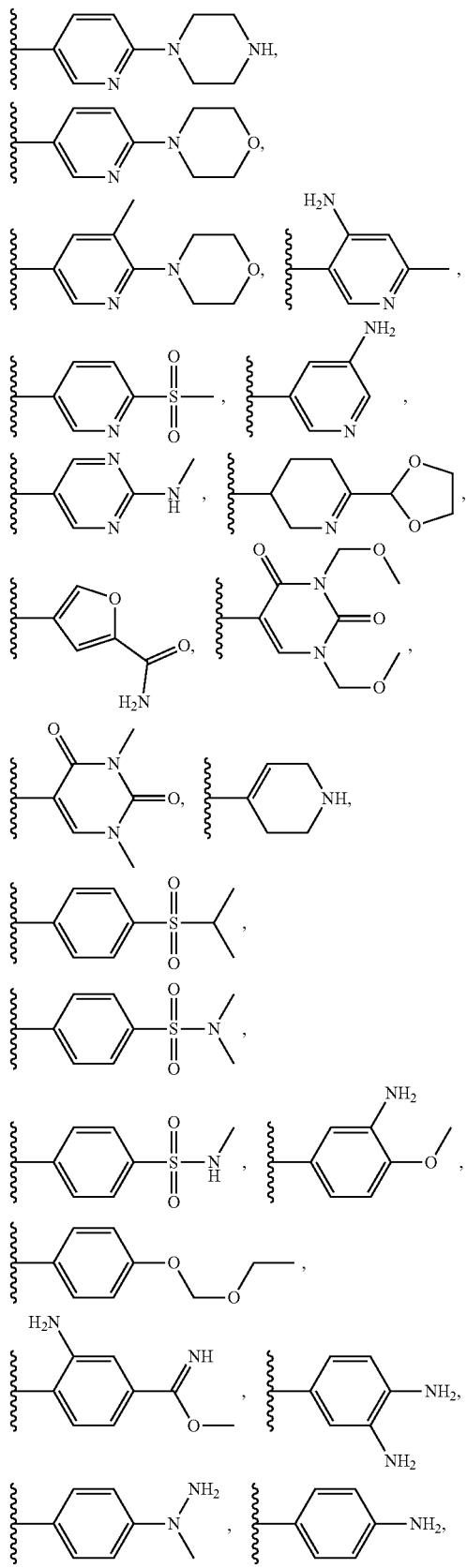

-continued

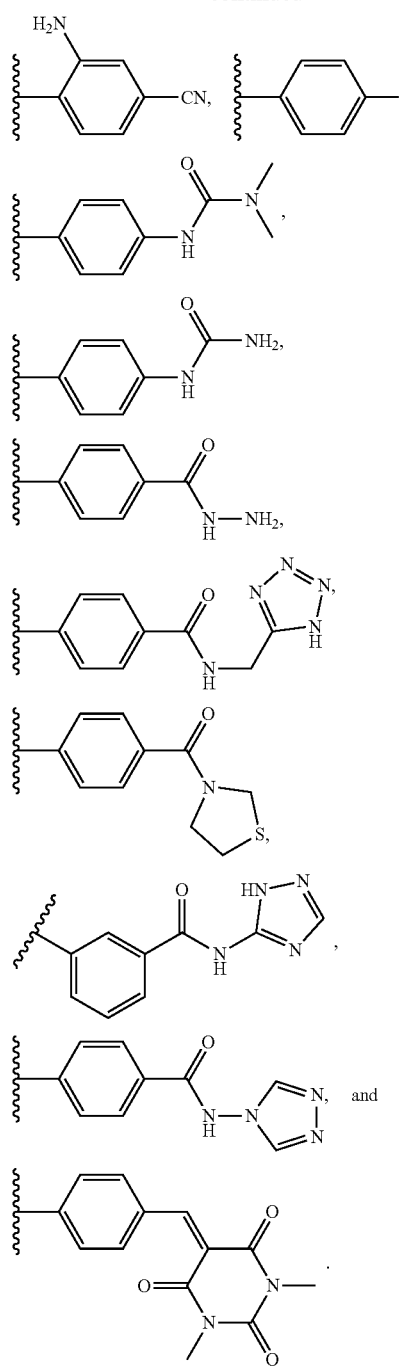

In some embodiments, more suitably $R^{21}$ is selected from:

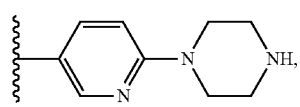

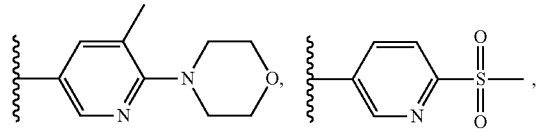

-continued

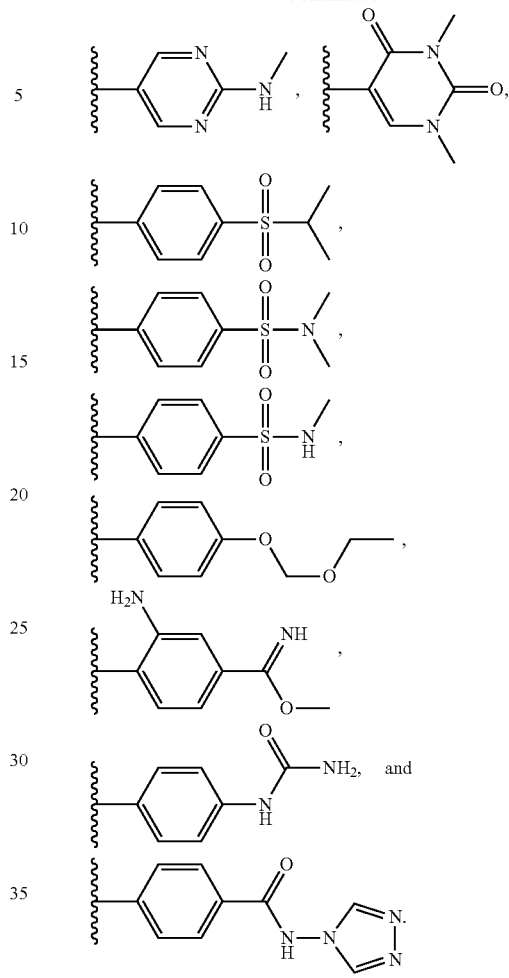

In some embodiments, $R_{21}$ is selected from H, methyl, ethyl, n-propyl, i-propyl, n-butyl, s-butyl, i-butyl, t-butyl.

Suitably, where an $R_{21}$ group may be optionally substituted it is substituted with 1, 2 or 3 of the optional substituents; suitably, an $R_{21}$ group is substituted with 1 or 2 of the optional substituents. More suitably, an $R_{21}$ group is substituted with 1 of the optional substituents. Alternatively, suitably an $R_{21}$ group is not substituted.

Cy

Suitably, each Cy is independently selected from a $C_5$ heterocyclyl or C heteroaryl group, wherein the heterocyclyl or heteroaryl groups are optionally substituted with 1 or 2 $R_{20}$ groups.

Suitably, each Cy is independently selected from pyrrolyl, tetrazolyl, triazolyl, furanyl, thiazolidinyl and pyrrolidinyl, wherein these groups are optionally substituted with 1 or 2 $R_{20}$ groups.

More suitably, each Cy is independently selected from:

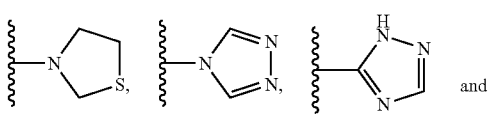

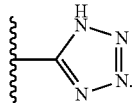

$R_{22}$, $R_{21}$, $R_{24}$, $R_{25}$, $R_{26}$ and $R_{27}$,

Suitably each $R_{22}$, $R_{23}$, $R_{24}$, $R_{25}$, $R_{26}$ and $R_{27}$ is independently H, $C_1$ alkyl, $C_2$ alkyl, $C_3$ alkyl, $C_4$ alkyl, $C_5$ alkyl, $C_6$ alkyl, $C_7$ alkyl, $C_8$ alkyl, $C_9$ alkyl, $C_{10}$ alkyl or $C_{11}$ alkyl.

Suitably, each $R_{22}$, $R_{23}$, $R_{24}$, $R_{25}$, $R_{26}$ and $R_{27}$ is independently selected from H and $C_{1-6}$ alkyl.

Suitably each $R_{22}$, $R_{23}$, $R_{24}$, $R_{25}$, $R_{26}$ and $R_{27}$ is independently selected from H, methyl, ethyl, n-propyl, i-propyl, n-butyl, s-butyl, i-butyl and t-butyl.

More suitably each $R_{22}$, $R_{23}$, $R_{24}$, $R_{25}$, $R_{26}$ and $R_{27}$ is independently selected from H, methyl, and ethyl. More suitably each $R_{22}$, $R_{23}$, $R_{24}$, $R_{25}$, $R_{26}$ and $R_{27}$ is independently selected from H and methyl.

$X_1$

Suitably, $X_1$ is O, S, $NR_{24}$, $CR_{24}R_{25}$, C(=O), C(=O)$NR_{24}$, $NR_{24}$C(=O) or is absent.

The amide is drawn in both directions, i.e. C(=O)$NR_{24}$ and $NR_{24}$C(=O). Hence, it may be attached in either direction. Thus, for example, $X_1$ may be C(=O)$NR_{28}$ that links the left hand moiety to group $L_1$ as follows: —C(=O)$NR_2$-$L_1$-$X_2$—, whereas when $X_1$ is $NR_{28}$C(=O) then the left hand moiety is linked to group $L_1$ as follows: —$NR_{28}$C(=O)-$L_1$-$X_2$—.

In some aspects, suitably, $X_1$ is O, S, NH, N—$CH_3$, $CH_2$, $CH_2$O, C(=O), C(=O)NH, C(=O)$NCH_3$, NHC(=O), $NCH_3$C(=O), O—C(O), C(O)—O or is absent.

More suitably, $X_1$ is O, NH, $CH_2$, C(=O), C(=O)NH, NHC(=O) or is absent.

In one aspect, suitably, X, is O.

$L_1$

In one aspect, suitably, $L_1$ is an amino acid or a peptide chain having 2, 3, 4, 5, 6, 7, 8, 9, 10, 11 or 12 amino acids.

In another aspect, suitably, $L_1$ is a paraformaldehyde chain —(OCH$_2$)$_{1-24}$—having 1, 2, 3, 4, 5, 6, 7, 8, 9, 10, 11, 12, 13, 14, 15, 16, 17, 18, 19, 20, 21, 22, 23 or 24 repeating units; or a polyethylene glycol chain —(OCH$_2$CH$_2$)$_{1-12}$— having 1, 2, 3, 4, 5, 6, 7, 8, 9, 10, 11 or 12 repeating units.

In another aspect, more suitably, $L_1$ is —(CH$_2$)$_n$—Y$_1$—(CH$_2$)$_p$—.

More suitably, $L_1$ is selected from —(CH$_2$)$_m$—(CH$_2$)$_q$—(CH$_2$)$_n$—, —(CH$_2$)$_m$—Ar$_1$—C(O)—NH—(Ar$_2$)$_{0-1}$—Ar$_3$—(CH$_2$)$_n$—, —(CH$_2$)$_m$—Ar$_3$—(Ar$_2$)$_{0-1}$—NH—C(O)—Ar$_1$—(CH$_2$)$_n$—,

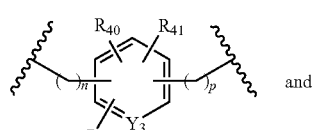

and

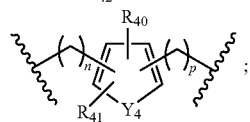

wherein q is 1, 2, 3, 4 or 5;

$Y_3$ is C—H or N;

$Y_4$ is N—$R_{43}$, O or S; and $R_{40}$, $R_{41}$ and $R_{42}$ are independently selected from H and $R_{21}$; and $R_{43}$ is H or methyl.

The above structures are drawn without specifying the positions of any of the groups, i.e. groups $R_{40}$, $R_{41}$, $R_{42}$, and the two groups (shown by bonds that end in a zig-zag line) where the ring is attached to the rest of the molecule. Hence, these groups may be present on any position of the ring except for $Y_3$ or $Y_4$ (as positioning a group, such as $R_{20}$ at $Y_3$ or $Y_4$ would not meet the valence requirements). The linker groups —(CH$_2$)$_m$—Ar$_1$—C(O)—NH—(Ar$_2$)$_{0-1}$—Ar$_3$—(CH$_2$)$_n$— and —(CH$_2$)$_m$—Ar$_3$—(Ar$_2$)$_{0-1}$—NH—C(O)—Ar$_1$—(CH$_2$)$_n$— are drawn in both directions and can be attached to $X_1$ and $X_2$ in either direction.

More suitably, L is selected from —(CH$_2$)$_m$—(CH$_2$)$_q$—(CH$_2$)$_n$—,

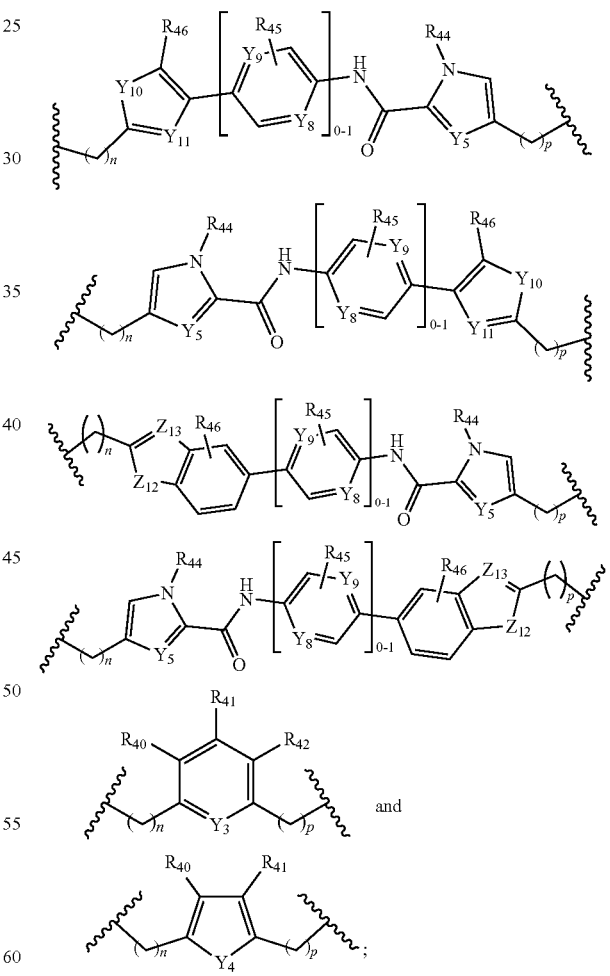

wherein $R_{44}$ is H or methyl;

$R_{45}$ and $R_{46}$ are independently selected from H or $R_{20}$.

More suitably, L is selected from —(CH$_2$)$_{0-10}$—(CH$_2$)$_{1-5}$—(CH$_2$)$_{0-10}$— and

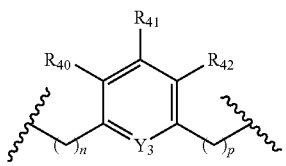

More suitably, L is selected from —CH$_2$—, —CH$_2$—CH$_2$—, —CH$_2$—CH$_2$—CH$_2$—, —CH$_2$—CH$_2$—CH$_2$—CH$_2$—, —CH$_2$—CH$_2$—CH$_2$—CH$_2$—CH$_2$—, —CH$_2$—CH$_2$—CH$_2$—CH$_2$—CH$_2$—CH$_2$—, —CH$_2$—CH$_2$—CH$_2$—CH$_2$—CH$_2$—CH$_2$—CH$_2$—, —CH$_2$—CH$_2$—CH$_2$—CH$_2$—CH$_2$—CH$_2$—CH$_2$—CH$_2$— and

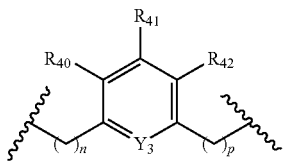

In another aspect, suitably one of $R_{40}$, $R_{41}$ and $R_{42}$ is $R_{20}$; and the remaining of $R_{40}$, $R_{41}$ and $R_{42}$ are H. More suitably, one of $R_{40}$, $R_{41}$ and $R_{42}$ is selected from $(CH_2)_j$—$CO_2R_{26}$, O—$(CH_2)_k$—$NR_{26}R_{27}$, C(=O)—O—$(CH_2)_k$—$NR_{26}R_{27}$, C(=O)—$NR_{26}R_{27}$, $(CH_2)_j$—$NR_{26}R_{27}$, $NR_{26}NH_2$, C(=O)—NH—$(CH_2)_j$—$NR_{26}R_{27}$, C(=O)—NH—$C_6H_4$—$(CH_2)_j$—$R_{26}$, C(=O)—NH—$(CH_2)_k$—C(=NH)$NR_{26}R_{27}$, -$L_2$-$R_{28}$, $(CH_2)_j$—S(O)$_2$—$NR_{26}R_{27}$ and NH—C(O)—$NR_{26}R_{27}$; and remaining of $R_{40}$, $R_{41}$ and $R_{42}$ are H. More suitably, one of $R_{40}$, $R_{41}$ and $R_{42}$ is $(CH_2)_j$—$NR_{26}R_{27}$ or -$L_2$-$R_{28}$; and remaining of $R_{40}$, $R_{41}$ and $R_{42}$ are H.

$X_2$

Suitably, $X_2$ is O, S, $NR_{24}$, $CR_{24}R_{25}$, C(=O), C(=O)$NR_{24}$, $NR_{24}$C(=O) or is absent.

In some aspects, suitably, $X_2$ is O, S, NH, N—$CH_3$, $CH_2$, $CH_2$O, C(=O), C(=O)NH, C(=O)$NCH_3$, NHC(=O), $NCH_3$C(=O), O—C(O), C(O)—O or is absent.

More suitably, $X_2$ is O, NH, $CH_2$, C(=O), C(=O)NH, NHC(=O) or is absent.

In one aspect, suitably, $X_2$ is O or is absent.

j

Suitably, each j is independently selected from 0, 1, 2 or 3.

In some aspects, j is 1.

In other aspects, j is 0.

k

Suitably, each k is independently selected from 1, 2 or 3.

More suitably, k is 1 or 2.

In some aspects, k is 1.

m

Suitably m is 0.

More suitably, m is 1.

n

Suitably, n is selected from 0, 1, 2, 3, 4, 5 or 6. Suitably, n is selected from 0, 1, 2 or 3. In one aspect, suitably n is 1, 2, 3, 4, 5 or 6; suitably, n is 1, 2 or 3; suitably, n is 1.

p

Suitably, p is selected from 0, 1, 2, 3, 4, 5 or 6. Suitably, p is selected from 0, 1, 2 or 3.

In one aspect, suitably p is 1, 2, 3, 4, 5 or 6; suitably, p is 1, 2 or 3; suitably, p is 1.

q

Suitably, q is selected from 1, 2 or 3.

More suitably, q is 1.

s

Suitably, each s is independently selected from 0, 1, 2 or 3.

In some aspects, s is 1.

In other aspects, s is 0.

t

Suitably, each t is independently selected from 1, 2 or 3.

More suitably, t is 1 or 2.

In some aspects, t is 1.

w

Suitably w is 0.

More suitably, w is 1.

Suitably, $Ar_1$ is selected from pyrrolylene, N-methylpyrrolylene, furanylene, thiophenylene, imidazolylene, N-methylimidazolylene, oxazolylene or thiazolylene, wherein these groups may be optionally substituted with 1, 2 or 3 independently selected optional $R_{20}$ groups.

Suitably, $Ar_1$ is:

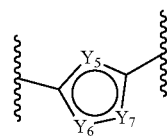

wherein one of $Y_6$ and $Y_7$ is independently selected from N—$R_{42}$, S and O; and the other of $Y_6$ and $Y_7$ is CH; and $Y_5$ is independently selected from C—$R_{42}$, N, S and COH; and $R_{42}$ is selected from H or $R_{20}$.

Suitably, $Ar_1$ is selected from pyrrolylene, N-methylpyrrolylene, imidazolylene or N-methylimidazolylene, wherein these groups may be optionally substituted with 1 or 2 independently selected optional $R_{20}$ groups.

Suitably, $Ar_1$ is:

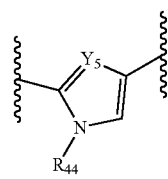

wherein $R_{44}$ is H or methyl.

$Ar_2$

Suitably, $Ar_2$ is an optionally substituted phenylene or pyridylene.

More suitably, $Ar_2$ is:

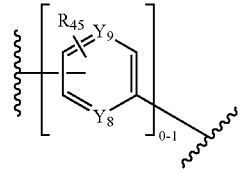

wherein $Y_8$ is N or CH; $Y_9$ is N or CH; and wherein at least one of $Y_8$ and $Y_9$ is CH; and $R_{45}$ is H or $R_{20}$.

More suitably, $Ar_2$ is an optionally substituted phenylene.

$Ar_3$

Suitably, $Ar_3$ is selected from pyrrolylene, N-methylpyrrolylene, furanylene, thiophenylene, imidazolylene, N-methylimidazolylene, oxazolylene, thiazolylene, pyridylene, indolylene, N-methylindolylene, benzofuranylene, benzothiophenylene, benzimidazolylene, N-methylbenzoimidazolylene, benzooxazolylene or benzothiazolylene wherein these groups may be optionally substituted with 1, 2 or 3 independently selected optional $R_{20}$ groups.

pyrrolylene, N-methylpyrrolylene, thiophenylene, imidazolylene, N-methylimidazolylene, oxazolylene, thiazolylene, indolylene, N-methylindolylene, benzofuranylene, benzothiophenylene, benzimidazolylene, N-methylbenzoimidazolylene, Suitably, $Ar_3$ is selected from pyrrolyl, N-methylpyrrolyl, thiophenyl, N-methylimidazolyl, oxazolyl, thiazolyl, benzothiophenyl, N-methylbenzoimidazolyl and benzothiazolyl wherein these groups may be optionally substituted with 1, 2 or 3 independently selected optional $R_{20}$ groups.

Suitably, $Ar_3$ is

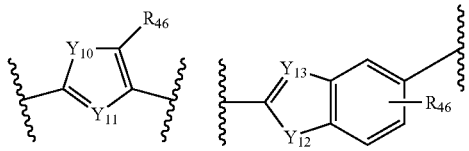

wherein $Z_{10}$ is selected from NH, N—$CH_3$, S and O;
$Z_{11}$ is selected from CH and N;
$Z_{12}$ is selected from NH, N—$CH_3$, S and O;
$Z_{13}$ is selected from CH and N; and
$R_{46}$ is selected from H and $R_{20}$.

$Ar_4$ and $Ar_4$

Suitably, $Ar_4$ and $Ar_5$ are independently selected from pyrrolyl, N-methylpyrrolyl, furanyl, thiophenyl, imidazolyl, N-methylimidazolyl, oxazolyl, thiazolyl, pyridyl, pyrimidinyl, pyridazinyl, indolyl, N-methylindolyl, benzofuranyl, benzothiophenyl, benzimidazolyl, N-methylbenzoimidazolyl, benzooxazolyl, benzothiazolyl or phenyl wherein these groups may be optionally substituted with 1, 2 or 3 independently selected optional $R_{20}$ groups.

More suitably, $Ar_4$ and $Ar_5$ are independently selected from pyrrolyl, N-methylpyrrolyl, furanyl, thiophenyl, imidazolyl, N-methylimidazolyl, oxazolyl, thiazolyl, pyridyl, pyrimidinyl or phenyl wherein these groups may be optionally substituted with 1, 2 or 3 independently selected optional $R_{20}$ groups.

Suitably, $Ar_4$ and $Ar_5$ are independently selected from pyrrolyl, N-methylpyrrolyl, furanyl, thiophenyl, imidazolyl, N-methylimidazolyl, oxazolyl, thiazolyl, pyridyl, indolyl, N-methylindolyl, benzofuranyl, benzothiophenyl, benzimidazolyl, N-methylbenzoimidazolyl, benzooxazolyl, benzothiazolyl or phenyl wherein these groups may be optionally substituted with 1, 2 or 3 independently selected optional $R_{20}$ groups.

More suitably, $Ar_4$ and $Ar_5$ are independently selected from pyrrolyl, N-methylpyrrolyl, furanyl, thiophenyl, imidazolyl, N-methylimidazolyl, oxazolyl, thiazolyl, pyridyl or phenyl wherein these groups may be optionally substituted with 1, 2 or 3 independently selected optional $R_{20}$ groups.

More suitably, $Ar_4$ and $Ar_5$ are independently selected from pyrrolyl, N-methylpyrrolyl, furanyl, thiophenyl, imidazolyl, N-methylimidazolyl, oxazolyl, thiazolyl, pyridyl or phenyl wherein these groups may be optionally substituted with 1, 2 or 3 independently selected optional $R_{20}$ groups.

More suitably, $Ar_4$ and $Ar_5$ are independently selected from pyrrolyl, N-methylpyrrolyl, pyridyl or phenyl wherein these groups may be optionally substituted with 1, 2 or 3 independently selected optional $R_{20}$ groups.

Suitably, $Ar_4$ is a group that is substituted with 1, 2 or 3 independently selected $R_{20}$ groups. More suitably, $Ar_4$ is a group that is substituted with one $R_{20}$ group.

Suitably, Ar is a group that is substituted with 1, 2 or 3 independently selected $R_{20}$ groups. More suitably, $Ar_5$ is a group that is substituted with one $R_{20}$ group.

More suitably, $Ar_4$ and $Ar_5$ are identical groups.

$R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{45}$ and $R_{46}$ Suitably, $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{45}$ and $R_{46}$ are each independently selected from H, F, Cl, Br, $(CH_2)_j$—OH, methyl, ethyl, $OCH_3$, $OCH_2CH_3$, $OCH_2Ph$, $(CH_2)_j$—$CO_2R_{26}$, O—$(CH_2)_k$—$NR_{26}R_{27}$, C(=O)—O—$(CH_2)_k$—$NR_{26}R_{27}$, $(CH_2)_j$—$NR_{26}R_{27}$, $NHNH_2$, C(=O)—NH—$(CH_2)_j$—$NR_{26}R_{27}$, C(=O)—NH—$C_6H_4$—$(CH_2)_j$—$R_{26}$, C(=O)—NH—$(CH_2)_k$—C(=NH)$NR_{26}R_{27}$ and $-L_2$-$R_{28}$.

Suitably, $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{45}$ and $R_{46}$ are each independently selected from H, $(CH_2)_j$—OH, methyl, ethyl, $OCH_3$, $OCH_2CH_3$, $OCH_2Ph$, $(CH_2)_j$—$CO_2H$, $(CH_2)_j$—$CO_2CH_3$, $(CH_2)_j$—$CO_2CH_2CH_3$, O—$(CH_2)_k$—$NH_2$, O—$(CH_2)_k$—NH—$CH_3$, C(=O)—O—$(CH_2)_k$—$NH_2$, C(=O)—O—$(CH_2)_k$—NH—$CH_3$, $(CH_2)_j$—$NH_2$, $(CH_2)_j$—NH—$CH_3$, $NHNH_2$, C(=O)—NH—$(CH_2)_k$—$NH_2$, C(=O)—NH—$(CH_2)_k$—NH—$CH_3$, C(=O)—NH—$C_6H_4$—$(CH_2)_j$—H, C(=O)—NH—$(CH_2)_k$—C(=NH)$NH_2$, C(=O)—NH—$(CH_2)_k$—C(=NH)NH—$CH_3$ and $-L_2$-$R_{28}$.

More suitably, $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{45}$ and $R_{46}$ are each independently selected from H, $(CH_2)_j$—OH, methyl, ethyl, $OCH_3$, $OCH_2CH_3$, $CO_2H$, $CO_2CH_3$, $CO_2CH_2CH_3$, O—$(CH_2)_k$—$NH_2$, C(=O)—O—$(CH_2)_k$—$NH_2$, $(CH_2)_j$—$NH_2$ and $-L_2$-$R_{28}$.

In one aspect, suitably, one of $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{45}$ and $R_{46}$ is selected from $(CH_2)_j$—$CO_2R_{27}$, O—$(CH_2)_k$—$NR_{27}R_{28}$, C(=O)—O—$(CH_2)_k$—$NR_{26}R_{27}$, $(CH_2)_j$—$NR_{27}R_{28}$, $NHNH_2$, C(=O)—NH—$(CH_2)_k$—$NR_{27}R_{28}$; C(=O)—NH—$C_6H_4$—$(CH_2)_j$—$R_{27}$, C(=O)—NH—$(CH_2)_k$—C(=NH)$NR_{27}R_{28}$ and $-L_2$-$R_{28}$; and the remaining of $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{45}$ and $R_{46}$ are each independently selected from H, F, Cl, Br, $(CH_2)_j$—OH, $C_{1-6}$ alkyl, $OC_{1-6}$ alkyl and $OCH_2Ph$.

In this aspect, suitably, one of $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{45}$ and $R_{46}$ is selected from $(CH_2)_j$—$CO_2H$, $(CH_2)_j$—$CO_2CH_3$, O—$(CH_2)_k$—$NH_2$, O—$(CH_2)_k$—NH—$CH_3$, C(=O)—O—$(CH_2)_k$—$NH_2$, C(=O)—O—$(CH_2)_k$—NH—$CH_3$, $(CH_2)_j$—$NH_2$, $(CH_2)_j$—NH—$CH_3$, C(=O)—NH—$(CH_2)_k$—$NH_2$, C(=O)—NH—$(CH_2)_k$—NH—$CH_3$, C(=O)—NH—$C_6H_4$—$(CH_2)_j$—H, C(=O)—NH—$(CH_2)_k$—C(=NH)$NH_2$ and C(=O)—NH—$(CH_2)_k$—C(=NH)NH—$CH_3$; and the remaining of $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{45}$ and $R_{46}$ are each independently selected from F, Cl, Br, $(CH_2)_j$—OH, methyl, ethyl, $OCH_3$, $OCH_2CH_3$ and $OCH_2Ph$.

In this aspect, more suitably, one of $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{45}$ and $R_{46}$ is selected from O—$(CH_2)_k$—$NH_2$ and $(CH_2)_j$—$NH_2$; and the remaining $R_{29}$, $R_{30}$, $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{45}$ and $R_{46}$ groups are each independently selected from $(CH_2)_j$—OH, methyl, ethyl, $OCH_3$ and $OCH_2CH_3$.

$R_{43}$

In one embodiment, $R_{43}$ is H.

More suitably, $R_{43}$ is methyl.

$R_{44}$

In one embodiment, $R_{44}$ is H.

More suitably, $R_{44}$ is methyl.

$R_A$ and $R_B$

Suitably, each $R_A$ and $R_B$ is independently selected from $(CH_2)_j$—OH, $(CH_2)_j$—$CO_2H$, $(CH_2)_j$—$CO_2CH_3$, $(CH_2)_j$—$CO_2CH_2CH_3$, C(=O)—O—$(CH_2)_k$—$NH_2$, C(=O)—O—$(CH_2)_k$—NH—$CH_3$, $(CH_2)_j$—$NH_2$, $(CH_2)_j$—NH—$CH_3$, C(=O)—NH—$(CH_2)_k$—$NH_2$, C(=O)—NH—$(CH_2)_k$—NH—$CH_3$, C(=O)—NH—$(CH_2)_k$—C(=NH)$NH_2$ and C(=O)—NH—$(CH_2)_k$—C(=NH)NH—$CH_3$.

More suitably, each $R_A$ and $R_B$ is independently selected from $(CH_2)_j$—OH, $CO_2H$, $CO_2CH_3$, $CO_2CH_2CH_3$, C(=O)—O—$(CH_2)_k$—$NH_2$ and $(CH_2)_j$—$NH_2$.

$L_2$

Linker $L_2$ is a bond or is a moiety having 1-200 nonhydrogen atoms selected from C, N, O, S, or halogen, and optionally incorporates alkyl, ether, oxo, carboxyl, carboxamide, carboxamidyl, urethanyl, branched, cyclic, unsaturated, amino acid, heterocyclyl, aryl or heteroaryl moieties. Linker $L_2$ may be unbranched or branched, flexible or rigid, short or long and may incorporate any combination of moieties as deemed useful. In some embodiments, at least a portion of the linker $L_2$ may have a polyalkylene oxide polymeric region, which may enhance solubility of the compound of formula (I) or (II). In some embodiments, the linker $L_2$ may have a repeating unit of ethylene glycol, and may have a number of repeating ethylene glycol units of about 1 to about 25, or any number therebetween. In some embodiments, $L_2$ may include about 3 to about 20, about 4 to about 15, about 5 to about 12 or about 6 to about 10 ethylene glycol units. In some embodiments, at least a portion of Linker $L_2$ may include one or more amino acid moieties which may provide enhanced solubility for the compound of formula (I) or (II) or may provide amino acid sequences to enhance target binding, enhance compatibility with a targeting agent, or enhance target binding recognition. In other embodiments, the linker $L_2$ may include one or more amino acid moieties that provide a suitable substrate motif for a protease. When a set of amino acid moieties are incorporated into the linker $L_2$ that provide a substrate motif specific for a selected protease, the cytotoxic drug compound of formula (I) or (II) may be released from a target bound conjugate to provide localized cytotoxic effects. In other embodiments, the linker $L_2$ may include an alkylene chain. Suitably, the alkylene chain is 1, 2, 3, 4, 5, 6, 7, 8, 9, 10, 11 or 12 carbons in length; and suitably the alkylene chain comprises —$CH_2$— groups. Such substrate motifs are known in the art and may be incorporated into the linker $L_2$ as desired to provide selective release from the target bound conjugate. This selectivity can be based on known presence of a desired protease within the localized delivery region of the conjugate drug. Other polymeric types of moieties may be incorporated in the linker $L_2$, such as polyacids, polysaccharides, or polyamines. Other moieties such as substituted aromatic or heteroaromatic moieties may be used to enhance rigidity or provide synthetically accessible sites on substituents therein for linking to reactive moieties or to the compound of formula (I) or (II).

For example, the linker $L_2$ can include ethylene glycol repeating units, and/or an amino acid sequence. In some embodiments, linker $L_2$ includes the formula:

—[$CH_2CH_2O$]$_{0-50}$—$X_{AA}$— wherein $X_{AA}$ is an amino acid sequence.

Any suitable number of ethylene glycol units can be used in the linker L of the present invention. For example, the linker $L_2$ can include 1, 2, 3, 4, 5, 6, 7, 8, 9, 10, 11, 12, 15, 16, 19, 20, 23, 24, 35, 36, 37, 48, 49, or more ethylene glycol units. In some embodiments, the linker $L_2$ can include 8 ethylene glycol units. Several commercially available ethylene glycol groups (polyethylene glycol, PEG) are suitable in the linker $L_2$, such as $H_2N$-dPEG®$_8$—C(O)OH, having a discrete ("d") polyethylene glycol having 8 ethylene glycol repeating units. Other discrete PEG units are commercially available and known to one of skill in the art, such as by Advanced ChemTech. In some embodiments, the linker $L_2$ includes the formula:

—HN-PEG-C(O)—$X_{AA}$— wherein PEG has 1-50 ethylene glycol units, and $X_{AA}$ is an amino acid sequence.

In another example, the linker $L_2$ can include an alkylene chain, and/or an amino acid sequence. In some embodiments, linker $L_2$ includes the formula:

—[$CH_2$]$_{0-12}$—$X_{AA}$— wherein $X_A$ is an amino acid sequence; and the linker $L_2$ can include 1, 2, 3, 4, 5, 6, 7, 8, 9, 10, or more —$CH_2$— moieties.

The amino acid portion of the linker $L_2$ can include any suitable number of amino acid moieties, as described above. For example, the amino acid sequence $X_{AA}$ can include from 1 to 100 amino acid moieties, or from 1 to 10 amino acid moieties, or from 1 to 5 amino acid moieties. The linker $L_2$ can include 1, 2, 3, 4, 5, 6, 7, 8, 9, 10, or more amino acid moieties. In some embodiments, the linker $L_2$ includes 2 amino acid moieties. In some embodiments, the linker $L_2$ includes the amino acid sequence Val-Ala. In some embodiments, the linker $L_2$ includes the formula:

—HN-PEG$_8$-C(O)-Val-Alawherein PEG$_8$ has 8 ethylene glycol units.

The linker $L_2$ can also include a variety of other connecting groups that connect the ethylene glycol portion to the amino acid sequence, or connect the ethylene glycol or amino acid sequence to $R_{28}$, or the compound of formula (I) or (II). For example, the amino acid sequence can be connected to the compound of formula (I) or (II) via a 4-amino benzyl carboxylate group. In some embodiments, the ethylene glycol portion ca be directly linked to $R_{28}$. In some embodiments, the linker $L_2$ has the formula:

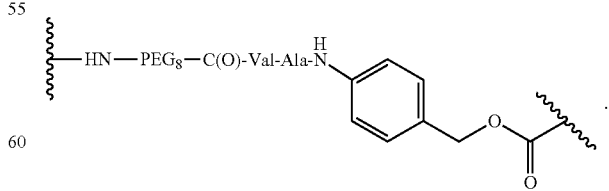

$R_{28}$ $R_{28}$ is an azide, alkyne, bisulfone, carbohydrazide, hydrazine, hydroxylamine, iodoacetamide, isothiocyanate, maleimide, phosphine, pyrridopyridazine, semihydrazide, succinimidyl ester, sulfodichlorophenol ester, sulfonyl halide, sulfosuccinimidyl ester, 4-sulfotetrafluorophenyl ester, tetrafluorophenyl ester, thiazole, $R_A$, O—$(CH_2)_k$—$NR_{26}R_{26}$, $NHNH_2$, or is a targeting agent wherein the targeting agent is selected from a protein, a portion of a protein, a peptide, a nucleic acid, or an antibody.

Hence, $R_{28}$ is a reactive moiety capable of reacting with a targeting agent, or is a targeting agent. Where $R_{28}$ is a reactive moiety it can react with functional groups such as aldehdes, amines, disulfides, ketones thiols in the targeting agent, or in Staudinger reactions, Pictet-Spengler reactions and/or Click-type chemistry with the targeting agent. For some reactive moieties suitable coupling reagents are used to react the reactive moiety with a targeting agent, e.g. where $R_{28}$ is a carboxylic acid [when $R_A$ is $(CH_2)_j$—$CO_2R_{26}$] carbodiimide coupling reagents may be used.

Suitably, $R_{28}$ is an azide, alkynes, bisulfone, carbohydrazide, hydroxylamine, iodoacetamide, isothiocyanate, maleimide, phosphine, semihydrazide, succinimidyl ester and sulfonyl halide, $R_A$ or is a targeting agent wherein the targeting agent is selected from a protein, a portion of a protein, a peptide, a nucleic acid, or an antibody.

In one aspect, suitably, $R_{28}$ is an azide, alkynes, bisulfone, carbohydrazide, hydroxylamine, iodoacetamide, isothiocyanate, maleimide, phosphine, semihydrazide, succinimidyl ester and sulfonyl halide or $R_A$.

A number of other chemistries are known for attachment of compounds to antibodies. U.S. Pat. No. 7,595,292 (Brocchini et al.) refers to linkers that form thioesters with the sulfurs in a disulfide bond of an antibody. U.S. Pat. No. 7,985,783 (Carico et al.) refers to the introduction of aldehyde residues into antibodies, which are used to couple compounds to the antibody.

In another aspect, $R_{28}$ is a targeting agent wherein the targeting agent is selected from a protein, a portion of a protein, a peptide, a nucleic acid, or an antibody. The targeting agent may bind to a tumor-associated antigen, a cancer-stem-cell associated antigen or a viral antigen.

In various embodiments, the targeting agent may bind to a target selected from an acute myeloid leukemia (AML M4) cell, an acute promyelocytic leukemia cell, an acute lymphoblastic leukemia cell, an acute lymphocytic leukemia cell, a chronic lymphocytic leukemia cell, a chronic myeloid leukemia cell, a chronic T-cell lymphocytic leukemia, a myelodysplasia syndromic cell, a multiple myeloma cell, a prostate carcinoma cell, a renal cell adenocarcinoma cell, a pancreatic adenocarcinoma cell, a lung carcinoma cell or a gastric adenocarcinoma cell, a gastric adenocarcinoma cell, a breast cancer cell, a colon cancer cell, a melanoma cell, a thyroid cancer cell, an ovarian cancer cell, a bladder cancer cell, a liver cancer cell, a head and neck cancer cell, an esophageal cancer cell, a hodgkin lymphoma cell, a non-hodgkin lymphoma cell, a mesothelioma cell, a neuroblastoma cell, a neuroendocrine tumor cell, a neurofibromatosis type 1 (NF1) cell, a neurofibromatosis type 2 (NF2) or an osteosarcoma cell.

Other Features

Suitably, the compound of formula (I) or formula (II) is selected with the proviso that when -$L_2$-$R_{28}$ is present in the compound of formula (I) or (II), there is only one -$L_2$-$R_{28}$ group present.

In some embodiments, -$L_2$-$R_{28}$ is absent from the compound of formula (I) or (II).

Suitably, the compound of formula (I) or formula (II) contains only one primary or secondary amine.

Suitably, the compound of formula (I) or formula (II) contains only one primary amine, secondary amine or -$L_2$-$R_{28}$ group.

Suitably, the compound of formula (I) or formula (II) contains only one primary amine, secondary amine, $R_A$, $R_B$ or -$L_2$-$R_{28}$ group.

In another aspect, each $R_{19}$ is independently selected from H, $C_{1-12}$ alkyl, F, Cl, Br, $OC_{1-6}$ alkyl, $OCH_2Ph$, =$CH_2$, =CH—$(CH_2)_s$—$CH_3$, =CH—$(CH_2)_s$—$R_{21}$ and an optionally substituted $C_{5-9}$ heteroaryl or an optionally substituted phenyl; optionally substituted with 1, 2, 3 independently selected optional $R_{20}$ groups; and each $R_{20}$ group is independently selected from F, Cl, Br, methyl, ethyl, $OCH_3$ and $OCH_2CH_3$; and either:

(i) $R_6$ is $R_A$ or -$L_2$-$R_{28}$; and $R_{15}$ is selected from H, $SO_3H$, and nitrogen protecting groups or together with $R_{14}$ forms a double bond; or (ii) $R_{15}$ is $R_B$ or -$L_2$-$R_{28}$; and $R_6$ is selected from H, $SO_3H$, and nitrogen protecting groups or together with $R_5$ forms a double bond.

In another aspect, one $R_{20}$ group is selected from $(CH_2)_j$—$CO_2H$, $(CH_2)_j$—$CO_2CH_3$, O—$(CH_2)_k$—$NH_2$, O—$(CH_2)_k$—NH—$CH_3$, C(=O)—O—$(CH_2)_k$—$NH_2$, C(=O)—O—$(CH_2)_k$—NH—$CH_3$, $(CH_2)_j$—$NH_2$, $(CH_2)_j$—NH—$CH_3$, C(=O)—NH—$(CH_2)_k$—$NH_2$, C(=O)—NH—$(CH_2)_k$—NH—$CH_3$, C(=O)—NH—$C_6H_4$—$(CH_2)_j$—H, C(=O)—NH—$(CH_2)_k$—C(=NH)$NH_2$ and C(=O)—NH—$(CH_2)_k$—C(=NH)NH—$CH_3$;

the remaining $R_{20}$ groups are each independently selected from F, Cl, Br, $(CH_2)_j$—OH, methyl, ethyl, $OCH_3$, $OCH_2CH_3$ and $OCH_2Ph$;

each $R_{19}$ is independently selected from H, methyl, ethyl, F, Cl, Br, $OCH_3$, $OCH_2CH_3$ and $OCH_2Ph$;

$R_5$ is selected from H, OH and $OC_{1-6}$ alkyl; and $R_6$ is selected from H, $SO_3H$ and nitrogen protecting groups; or $R_5$ and $R_6$ together form a double bond; and $R_{14}$ is selected from H, OH and $OC_{1-6}$ alkyl; and $R_{15}$ is selected from H, $SO_3H$ and nitrogen protecting groups; or $R_{14}$ and $R_{15}$ together form a double bond.

Applications

The invention finds application in the treatment of disease, more specifically of a proliferative disease.

In certain aspects a method of treating a proliferative disease is provided, the method comprising administering to a subject a therapeutically effective amount of a compound of the formula (I) or formula (II) or pharmaceutically acceptable salts, solvates, tautomers, stereoisomers or mixtures thereof, or a composition comprising a compound of formula (I) formula (I) or formula (II) or pharmaceutically acceptable salts, solvates, tautomers, stereoisomers or mixtures thereof.

In certain aspects a method of treating a proliferative disease is provided, the method comprising administering to a subject a therapeutically effective amount of a targeted conjugate comprising a compound of the formula (I) or formula (II) or pharmaceutically acceptable salts, solvates, tautomers, stereoisomers or mixtures thereof.

In certain aspects a method of treating a proliferative disease is provided, the method comprising administering to a subject a therapeutically effective amount of an antibody-drug conjugate comprising a compound of the formula (I) or formula (II) or pharmaceutically acceptable salts, solvates, tautomers, stereoisomers or mixtures thereof.

The term "proliferative disease" refers to an unwanted or uncontrolled cellular proliferation of excessive or abnormal cells which is undesired, such as, neoplastic or hyperplastic growth, whether in vitro or in vivo. Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, hepatocellular cancer, gastric or stomach cancer including gastrointestinal cancer, bowel cancer, colon cancer, hepatoma, breast cancer, glioblastoma, cervical cancer, ovarian cancer, oesophageal [or esophageal] cancer, oral cancer, prostate cancer, testicular cancer, liver cancer, rectal cancer, colorectal cancer, endometrial or uterine carcinoma, uterine cancer, salivary gland carcinoma, kidney or renal cancer, prostate cancer, vulval cancer, thyroid cancer, hepatic carcinoma, anal carcinoma, penile carcinoma, head and neck cancer, bladder cancer, pancreas cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Suitably the proliferative disease is selected from bladder cancer, bone cancer, bowel cancer, brain cancer, breast cancer, cervical cancer, colon cancer, head and neck cancer, leukemia, liver cancer, lung cancer, lymphoma, melanoma, oesophageal cancer, oral cancer, ovarian cancer, pancreatic cancer, prostate cancer, rectal cancer, renal cancer, retinoblastoma, sarcoma, skin cancer, stomach cancer, testicular cancer, thyroid cancer and uterine cancer. Suitably the proliferative disease is selected from breast cancer and cervical cancer.

Any type of cell may be treated, including but not limited to, bone, eye, head and neck, lung, gastrointestinal (including, e.g. mouth, oesophagus, bowel, colon), breast (mammary), cervix, ovarian, uterus, prostate, liver (hepatic), kidney (renal), bladder, pancreas, brain, and skin.

A skilled person is readily able to determine whether or not a candidate compound treats a proliferative condition for any particular cell type.

Suitably subjects are human, livestock animals and companion animals.

In a further aspect, the compound of formula (I) or formula (II) or pharmaceutically acceptable salts, solvates, tautomers, stereoisomers or mixtures thereof, may be linked, either directly or indirectly, to a targeting agent (e.g., antibody, antibody fragment, hormone, etc.) to provide a targeted conjugate. The target conjugates of the present disclosure may contain one or multiple compounds of formula (I) or formula (II) or pharmaceutically acceptable salts, solvates, tautomers, stereoisomers or mixtures thereof. A variety of target conjugates are known in the art and may be used with a compound of formula (I) or formula (II) or pharmaceutically acceptable salts, solvates, tautomers, stereoisomers or mixtures thereof. For example, in a particular aspect the target conjugate is an antibody-drug conjugate, wherein one or more compounds of formula (I) or formula (II) or pharmaceutically acceptable salts, solvates, tautomers, stereoisomers or mixtures thereof, are linked, directly or indirectly, to the antibody. Therefore, the compound of formula (I) or formula (II) or pharmaceutically acceptable salts, solvates, tautomers, stereoisomers or mixtures thereof, may be used as a payload on a targeted conjugate.

Suitably, a compound of formula (I) and salts and solvates thereof, for use as a drug in targeted conjugate is prepared by attaching a compound of formula (I) or formula (II) or pharmaceutically acceptable salts, solvates, tautomers, stereoisomers or mixtures thereof, to a targeting agent, either directly or via an optional linker group. Suitably, the compound of formula (I) or formula (II) or pharmaceutically acceptable salts, solvates, tautomers, stereoisomers or mixtures thereof, is attached to a targeting agent via a linker group. Suitably, the targeted conjugate is for use in the treatment of a disease, more specifically of a proliferative disease. Suitably, the drug may be attached by any suitable functional group that it contains to the targeting agent either directly or via a linker group. Typically, the drug contains, or can be modified to contain, one or more functional groups such as amine, hydroxyl or carboxylic acid groups for attaching the drug to the targeting agent either directly or via a linker group. In some aspects, one or more atoms or groups of the compound of formula (I) or (II) may be eliminated during the attachment of the drug to the antibody. In some aspects, the targeting agent binds to a cell surface receptor or a tumor-associated antigen. In some aspects, the targeting agent is an antibody. In some aspects, the targeting agent is a hormone. In some aspects, the targeting agent is a protein. In some aspects, the targeting agent is a polypeptide. In some aspects, the targeting agent is a small molecule (for example, folic acid).

In some aspects, the present invention relates to a compound of formula (I) or formula (II) or pharmaceutically acceptable salts, solvates, tautomers, stereoisomers or mixtures thereof, for use as a drug in an antibody-drug conjugate. Suitably, a compound of formula (I) or formula (II) or pharmaceutically acceptable salts, solvates, tautomers, stereoisomers or mixtures thereof, for use as a drug in an antibody-drug conjugate is prepared by attaching to an antibody or an antibody fragment either directly or via an optional linker group. Suitably, the compound of formula (I) or formula (II) or pharmaceutically acceptable salts, solvates, tautomers, stereoisomers or mixtures thereof, is attached to an antibody or an antibody fragment via a linker group. Suitably, the antibody-drug conjugate is for use in the treatment of a disease, more specifically of a proliferative disease.

In some aspects, the present invention relates to the use of a compound of formula (I) or formula (II) or pharmaceutically acceptable salts, solvates, tautomers, stereoisomers or mixtures thereof, as a drug in an antibody-drug conjugate. Suitably, the use of a compound of formula (I) or formula (II) or pharmaceutically acceptable salts, solvates, tautomers, stereoisomers or mixtures thereof, as a drug in an antibody-drug conjugate is accomplished by attaching to a compound of formula (I) and salts and solvates thereof to an antibody or an antibody fragment either directly or via an optional linker group. Suitably, the compound of formula (I) or formula (II) or pharmaceutically acceptable salts, solvates, tautomers, stereoisomers or mixtures thereof, is attached to an antibody or an antibody fragment either directly or via a linker group. Suitably, the antibody-drug conjugate is for use in the treatment of a disease, more specifically of a proliferative disease.

In such aspects, suitably, the drug may be attached by any suitable functional group that it contains to the antibody or antibody fragment either directly or via a linker group. Typically, the drug contains, or can be modified to contain, one or more functional groups such as amine, hydroxyl or carboxylic acid groups for attaching the drug to the antibody or antibody fragment either directly or via a linker group.

The compounds of formula (I) or formula (II) or pharmaceutically acceptable salts, solvates, tautomers, stereoisomers or mixtures thereof, find application as payloads for antibodies or antibody fragments or other targeting moieties (e.g. hormones, proteins and small molecule targeting agents such as folic acid). The compounds of formula (I) or formula (II) or pharmaceutically acceptable salts, solvates, tautomers, stereoisomers or mixtures thereof, readily allow conjugation to antibodies or antibody fragments or other targeting moieties.

Suitably, a compound of formula (I) or formula (II) or pharmaceutically acceptable salts, solvates, tautomers, stereoisomers or mixtures thereof, may be used in preparing a targeting conjugate by being modified to contain one or more linker groups, wherein the targeting agent (such as an antibody) is attached to the drug through one or more linker groups. Therefore, the present invention provides for a compound of formula (I) or formula (II) further comprising one or more linker groups or pharmaceutically acceptable salts, solvates, tautomers, stereoisomers or mixtures thereof. Suitably, a compound of formula (I) or formula (II) further comprises 1, 2 or 3 linker groups. Suitably, a compound of formula (I) or formula (II) further comprises 1 or 2 linker groups. Suitably, a compound of formula (I) or formula (II) further comprise 1 linker group. In some aspects, one or more atoms or groups (such as H atoms or hydroxyl groups) of the compound of formula (I) or formula (II) may be eliminated during the attachment of the drug to the targeting agent (such as an antibody) or the attachment of the linker to the drug or the modification of the drug to contain one or more functional groups (such as amine, hydroxyl or carboxylic acid groups) for attaching the drug to the antibody either directly or via a linker group. In some aspects, where the compound of formula (I) or formula (II) further comprises a linker group that is attached to the rest of the compound of formula (I) or formula (II) by eliminating one or more atoms or groups, such as H atom or atoms or hydroxyl groups.

Linkers can either be cleavable or non-cleavable, with cleavable linkers normally represented by combinations of amino acids. The list of cleavable linkers includes, but is not limited to, valine-citruline, valine-alanine and any combination of two to eight amino acids. A self-immolative unit (e.g., a PAB spacer) can be included to assist with clean cleavage, and optionally hydrophilic groups (e.g., PEG) can be added to increase hydrophilicity of the construct. In some aspects, more suitably, the linker group comprises a self-immolative unit. A range of self immolative units are known in the art, e.g. A. Blencowe, A. T. Russell, F. Greco, W. Hayes, D. W. Thornthwaite *Polymer Chemistry* (2011) 2, 773-790; and have been described in, for example, U.S. Pat. No. 7,754,681, European Patent Publication No. 0624377.

A variety of suitable linker groups are known in the art and may be used as described herein. For example, the maleimide methodology is routinely used as a method to attach antibodies to drug compounds by providing a linker attached to the drug with a terminal maleimide group. In addition, methodologies using diarylcyclooctyne moieties (such as, but not limited to, DBCO, dibenzylcyclooctyne) are known in the art. Diarylcyclooctynes react with stable azides to provide attachment via the formation of stable triazoles. Diarylcyclooctynes are thermostable with very narrow and specific reactivity toward azides, resulting in almost quantitative yields of stable triazoles. Furthermore, the reaction does not require a cytotoxic Cu(I) catalyst (that is toxic to most organisms) and thus, prevents its use in many biological systems. Still further, alkoxyamine methodologies are also alternatives in the art. For site-specific conjugation of the drug to the antibody, the antibodies may comprise a "tag" (which may be proprietary) that will react with a diarylcyclooctyne (for example DBCO), an alkoxyamine and/or maleimide group to attach the antibody to the drug. The tag in some instances may be a mutated amino acid. Suitably linker groups incorporating the various groups described above are available in the art.

The substituent groups of the compounds of formula (I) or formula (II) or pharmaceutically acceptable salts, solvates, tautomers, stereoisomers or mixtures thereof, may interact with DNA sequences and may be selected so as to target specific sequences.

Antibody and Antibody Fragments

The term "antibody" specifically covers monoclonal antibodies, polyclonal antibodies, dimers, multimers, multispecific antibodies (e.g., bispecific antibodies), intact antibodies and antibody fragments, so long as they exhibit the desired biological activity, for example, the ability to bind CD19 (Miller et al (2003) Journal, of Immunology 170:4854-4861). Antibodies may be murine, human, humanized, chimeric, or derived from other species. An antibody is a protein generated by the immune system that is capable of recognizing and binding to a specific antigen. (Janeway, C, Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. lgG1, lgG2, lgG3, lgG4, lgA1 and lgA2) or subclass, or allotype (e.g. human G1 m1, G1 m2, G1 m3, non-G1 m1[ that, is any allotype other than G1 m1], G1 m17, G2m23, G3m21, G3m28, G3m11, G3m5, G3m13, G3m14, G3m10, G3m15, G3m16, G3m6, G3m24, G3m26, G3m27, A2 m1, A2m2, Km1, Km2 and Km3) of immunoglobulin molecule. The immunoglobulins can be derived from any species, including human, murine, or rabbit origin.

As used herein, "binds an epitope" is used to mean the antibody binds an epitope with a higher affinity than a non-specific partner such as Bovine Serum Albumin (BSA, Genbank accession no. CAA76847, version no. CAA76847.1 Gl:3336842, record update date: Jan. 7, 2011 02:30 PM). In some embodiments the antibody binds an epitope with an association constant (Ka) at least 2, 3, 4, 5, 10, 20, 50, 100, 200, 500, 1000, 2000, 5000, $10^4$, $10^5$ or $10^6$-fold higher than the antibody's association constant for BSA, when measured at physiological conditions.

"Antibody fragments" comprise a portion of a full length antibody, generally the antigen binding or variable region thereof. Examples of antibody fragments include Fab, Fab', F(ab')2, and scFv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments. The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256:495, or may be made by recombinant DNA methods (see, U.S. Pat. No. 4,816,567). The monoclonal antibodies may also be isolated from phage antibody libraries using the techniques described in Clackson et al (1991) Nature, 352:624-628; Marks et al (1991) J. Mol. Biol., 222:581-597 or from transgenic mice carrying a fully human immunoglobulin system (Lonberg (2008) Curr. Opinion 20(4):450-459).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies include "primatized" antibodies comprising variable domain antigen-binding sequences derived from a non-human primate (e.g. Old World Monkey or Ape) and human constant region sequences. An "intact antibody" herein is one comprising VL and VH domains, as well as a light chain constant domain (CL) and heavy chain constant domains, CH1, CH2 and CH3. The constant domains may be native sequence constant domains (e.g. human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1 q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." vThere are five major classes of intact antibodies: IgA, IgD, IgE, IgG, and IgM, and several of these may be further divided into "subclasses" (isotypes), e.g., lgG1, lgG2, lgG3, lgG4, IgA, and lgA2. The heavy-chain constant domains that correspond to the different classes of antibodies are called α, δ, ε, γ, and μ, respectively. The subunit structures and three-dimensional configurations of different classes of immunoglobulins are well known.

The antibodies disclosed herein may be modified. For example, to make them less immunogenic to a human subject. This may be achieved using any of a number of techniques familiar to the person skilled in the art, such as humanisation.

Antibody-Drug Conjugates

Antibody therapy has been established for the targeted treatment of patients with cancer, immunological and angiogenic disorders (Carter, P. (2006) Nature Reviews Immunology 6:343-357). The use of antibody-drug conjugates (ADC), i.e. immunoconjugates, for the local delivery of cytotoxic or cytostatic agents, i.e. drugs to kill or inhibit tumor cells in the treatment of cancer, targets delivery of the drug moiety to tumors, and intracellular accumulation therein, whereas systemic administration of these unconjugated drug agents may result in unacceptable levels of toxicity to normal cells (Xie et al (2006) Expert. Opin. Biol. Ther. 6(3):281-291; Kovtun ef a/(2006) Cancer Res. 66(6): 3214-3121; Law et al (2006) CancerRes. 66(4):2328-2337; Wu et al (2005) Nature Biotech. 23(9): 1137-1145; Lambert J. (2005) Current Opin. in Pharmacol. 5:543-549; Hamann P. (2005) Expert Opin. Ther. Patents 15(9): 1087-1 103; Payne, G. (2003) Cancer Cell 3:207-212; Trail ef a/(2003) Cancer Immunol. Immunother. 52:328-337; Syrigos and Epenetos (1999) Anticancer Research 19:605-614).

Maximal efficacy with minimal toxicity is sought thereby. Efforts to design and refine ADC have focused on the selectivity of monoclonal antibodies (mAbs) as well as drug mechanism of action, drug-linking, drug/antibody ratio (loading), and drug-releasing properties (Junutula, et al., 2008b Nature Biotech., 26(8):925-932; Doman ef a/(2009) Blood 114(13):2721-2729; U.S. Pat. Nos. 7,521,541; 7,723, 485; WO2009/052249; McDonagh (2006) Protein Eng. Design & Sel. 19(7): 299-307; Doronina ef a/(2006) Bioconj. Chem. 17:114-124; Erickson ef a/(2006) CancerRes. 66(8): 1-8; Sanderson et a/(2005) Clin. CancerRes. 11:843-852; Jeffrey et al (2005) J. Med. Chem. 48:1344-1358; Hamblett et al (2004) Clin. Cancer Res. 10:7063-7070). Drug moieties may impart their cytotoxic and cytostatic effects by mechanisms including tubulin binding, DNA binding, proteasome and/or topoisomerase inhibition. Some cytotoxic drugs tend to be inactive or less active when conjugated to large antibodies or protein receptor ligands.

Tumor-Associated Antigens:

(1) BMPRIB (bone morphogenetic protein receptor-type IB, Genbank accession no. NM_001203)

ten Dijke, P., et al Science 264 (5155): 101-104 (1994), Oncogene 14 (11): 1377-1382 (1997); WO2004063362 (Claim 2); WO2003042661 (Claim 12); US203134790-A1 (Page 38-39); WO2002102235 (Claim 13; Page 296); WO2003055443 (Page 91-92); WO200299122 (Example 2; Page 528-530); WO2003029421 (Claim 6); WO2003024392 (Claim 2; FIG. 112); WO200298358 (Claim 1; Page 183); WO200254940 (Page 100-101); WO200259377 (Page 349-350); WO200230268 (Claim 27; Page 376); WO200148204 (Example; FIG. 4) NP_001194 bone morphogenetic protein receptor, type IB/pid=NP_001194.1—Cross-references: MIM:603248; NP_001194.1; AY065994

(2) E16 (LAT1, SLC7A5, Genbank accession no. NM_003486) Biochem. Biophys. Res. Commun. 255 (2), 283-288 (1999), Nature 395 (6699):288-291 (1998), Gaugitsch, H. W., et al (1992) J. Biol. Chem. 267 (16): 11267-11273); WO2004048938 (Example 2); WO2004032842 (Example TV); WO2003042661 (Claim 12); WO2003016475 (Claim 1); WO200278524 (Example 2); WO200299074 (Claim 19; Page 127-129); WO200286443 (Claim 27; Pages 222, 393); WO2003003906 (Claim 10; Page 293); WO200264798 (Claim 33; Page 93-95); WO200014228 (Claim 5; Page 133-136); US2003224454 (FIG. 3); WO2003025138 (Claim 12; Page 150); NP_003477 solute carrier family 7 (cationic amino acid transporter, y+ system), member 5/pid=NP_003477.3—

*Homo sapiens*; Cross-references: MIM:600182; NP_003477.3; NM_015923; NM0003486_1

(3) STEAP1 (six transmembrane epithelial antigen of prostate, Genbank accession no. NM_012449) *Cancer Res.* 61 (15), 5857-5860 (2001), Hubert, R. S., et al (1999) *Proc. Natl. Acad. Sci. U.S.A.* 96 (25): 14523-14528); WO2004065577 (Claim 6); WO2004027049 (FIG. 1L); EP1394274 (Example 11); WO2004016225 (Claim 2); WO2003042661 (Claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A); NP_036581 six transmembrane epithelial antigen of the prostate; Cross-references: MIM: 604415; NP_036581.1; NM_012449_1

(4) 0772P (CA125, MUC16, Genbank accession no. AF361486) *J. Biol. Chem.* 276 (29):27371-27375 (2001)); WO2004045553 (Claim 14); WO200292836 (Claim 6; FIG. 12); WO200283866 (Claim 15; Page 116-121); US2003124140 (Example 16); US 798959; Cross-references: GI:34501467; AAK74120.3; AF361486_1

(5) MPF (MPF, MSLN, SMR, megakaryocyte potentiating factor, mesothelin, Genbank accession no. NM_005823) Yamaguchi, N., et al *Biol. Chem.* 269 (2), 805-808 (1994), *Proc. Natl. Acad. Sci. U.S.A.* 96 (20): 11531-11536 (1999), *Proc. Natl. Acad. Sci. U.S.A.* 93 (1): 136-140 (1996), *J. Biol. Chem.* 270 (37):21984-21990 (1995)); WO2003101283 (Claim 14); (WO2002102235 (Claim 13; Page 287-288); WO2002101075 (Claim 4; Page 308-309); WO200271928 (Page 320-321); WO9410312 (Page 52-57); Cross-references: MIM:601051; NP_005814.2; NM_005823_1

(6) Napi2b (Napi3b, NAPI-3B, NPTIIb, SLC34A2, solute carrier family 34 (sodium phosphate), member 2, type II sodium-dependent phosphate transporter 3b, Genbank accession no. NM_006424) *J. Biol. Chem.* 277 (22): 19665-19672 (2002), *Genomics* 62 (2):281-284 (1999), Feild, J. A., et al (1999) *Biochem. Biophys. Res. Commun.* 258 (3):578-582); WO2004022778 (Claim 2); EP1394274 (Example 11); WO2002102235 (Claim 13; Page 326); EP875569 (Claim 1; Page 17-19); WO200157188 (Claim 20; Page 329); WO2004032842 (Example IV); WO200175177 (Claim 24; Page 139-140); Cross-references: MIM:604217; NP_006415.1; NM_06424_1

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878) Nagase T., et al (2000) *DNA Res.* 7 (2): 143-150); WO2004000997 (Claim 1); WO2003003984 (Claim 1); WO200206339 (Claim 1; Page 50); WO200188133 (Claim 1; Page 41-43, 48-58); WO2003054152 (Claim 20); WO2003101400 (Claim 11); Accession: Q9P283; EMBL; AB040878; BAA95969.1. Genew; HGNC: 10737;

(8) PSCA hlg (2700050C12Rik, C530008O16Rik, RIKEN cDNA 2700050C12, RIKEN cDNA 2700050C12 gene, Genbank accession no. AY358628); Ross et al (2002) *Cancer Res.* 62:2546-2553; US2003129192 (Claim 2); US2004044180 (Claim 12); US2004044179 (Claim 11); US2003096961 (Claim 11); US2003232056 (Example 5); WO2003105758 (Claim 12); US2003025148 (Example 5); EP1347046 (Claim 1); WO2003025148 (Claim 20); Cross-references: GI:37182378; AAQ88991.1; AY358628_1

(9) ETBR (Endothelin type B receptor, Genbank accession no. AY275463); Nakamuta M., et al *Biochem. Biophys. Res. Commun.* 177, 34-39, 1991; Ogawa Y., et al *Biochem. Biophys. Res. Commun.* 178, 248-255, 1991; Arai H., et al *Jpn. Circ. J.* 56, 1303-1307, 1992; Arai H., et al *J. Biol. Chem.* 268, 3463-3470, 1993; Sakamoto A., Yanagisawa M., et al *Biochem. Biophys. Res. Commun.* 178, 656-663, 1991; Elshourbagy N. A., et al *J. Biol. Chem.* 268, 3873-3879, 1993; Haendler B., et al *J. Cardiovasc. Pharmacol.* 20, S1-S4, 1992; Tsutsumi M., et al *Gene* 228, 43-49, 1999; Strausberg R. L., et al *Proc. Natl. Acad. Sci. U.S.A.* 99, 16899-16903, 2002; Bourgeois C, et al *J. Clin. Endocrinol. Metab.* 82, 3116-3123, 1997; Okamoto Y., et al *Biol. Chem.* 272, 21589-21596, 1997; Verheij J. B., et al *Am. J. Med. Genet.* 108, 223-225, 2002; Hofstra R. M. W., et al *Eur. J. Hum. Genet.* 5, 180-185, 1997; Puffenberger E. G., et al *Cell* 79, 1257-1266, 1994; Attie T., et al, *Hum. Mol. Genet.* 4, 2407-2409, 1995; Auricchio A., et al *Hum. Mol. Genet.* 5:351-354, 1996; Amiel J., et al *Hum. Mol. Genet.* 5, 355-357, 1996; Hofstra R. M. W., et al *Nat. Genet.* 12, 445-447, 1996; Svensson P J., et al *Hum. Genet.* 103, 145-148, 1998; Fuchs S., et al *Mol. Med.* 7, 115-124, 2001; Pingault V., et al (2002) *Hum. Genet.* 111, 198-206; WO2004045516 (Claim 1); WO2004048938 (Example 2); WO2004040000 (Claim 151); WO2003087768 (Claim 1); WO2003016475 (Claim 1); WO2003016475 (Claim 1); WO200261087 (FIG. 1); WO2003016494 (FIG. 6); WO2003025138 (Claim 12; Page 144); WO200198351 (Claim 1; Page 124-125); EP522868 (Claim 8; FIG. 2); WO200177172 (Claim 1; Page 297-299); US2003109676; U.S. Pat. No. 6,518,404 (FIG. 3); U.S. Pat. No. 5,773,223 (Claim 1a; Col 31-34); WO2004001004;

(10) MSG783 (RNF124, hypothetical protein FLJ20315, Genbank accession no. NM_017763);

WO2003104275 (Claim 1); WO2004046342 (Example 2); WO2003042661 (Claim 12); WO2003083074 (Claim 14; Page 61); WO2003018621 (Claim 1); WO2003024392 (Claim 2; FIG. 93); WO200166689 (Example 6); Cross-references: LocusID: 54894; NP_060233.2; NM0017763_1

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138)

*Lab. Invest.* 82 (11): 1573-1582 (2002); WO2003087306; US2003064397 (Claim 1; FIG. 1); WO200272596 (Claim 13; Page 54-55); WO200172962 (Claim 1; FIG. 4B); WO2003104270 (Claim 11); WO2003104270 (Claim 16); US2004005598 (Claim 22); WO2003042661 (Claim 12); US2003060612 (Claim 12; FIG. 10); WO200226822 (Claim 23; FIG. 2); WO200216429 (Claim 12; FIG. 10); Cross-references: GI:22655488; AAN0408.1; AF455138_1

(12) TrpM4 (BR22450, FLJ20041, TRPM4, TRPM4B, transient receptor potential cation channel, subfamily M, member 4, Genbank accession no. NM_017636) Xu, X. Z., et al *Proc. Natl. Acad. Sci. U.S.A.* 98 (19): 10692-10697 (2001), *Cell* 109 (3):397-407 (2002), *J. Biol. Chem.* 278 (33):30813-30820 (2003); US2003143557 (Claim 4); WO200040614 (Claim 14; Page 100-103); WO200210382 (Claim 1; FIG. 9A); WO2003042661 (Claim 12); WO200230268 (Claim 27; Page 391); US2003219806 (Claim 4); WO200162794 (Claim 14; FIG. 1A-D); Cross-references: MIM:606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212) Ciccodicola, A., et al *EMBO J.* 8 (7): 1987-1991 (1989), *Am. J. Hum. Genet.* 49 (3):555-565 (1991); US2003224411 (Claim 1); WO2003083041 (Example 1); WO2003034984 (Claim 12); WO200288170 (Claim 2; Page 52-53); WO2003024392 (Claim 2; FIG. 58);

WO200216413 (Claim 1; Page 94-95, 105); WO200222808 (Claim 2; FIG. 1); U.S. Pat. No. 5,854,399 (Example 2; Col 17-18); U.S. Pat. No. 5,792,616 (FIG. 2); Cross-references: MIM: 187395; NP_003203.1; NM_003212_1

(14) CD21 (CR2 (Complement receptor 2) or C3DR (C3d/Epstein Barr virus receptor) or Hs.73792 Genbank accession no. M26004) Fujisaku et al (1989) *J. Biol. Chem.* 264 (4):2118-2125); Weis J. J., et al *J. Exp. Med.* 167, 1047-1066, 1988; Moore M., et al *Proc. Natl. Acad. Sci. U.S.A.* 84, 9194-9198, 1987; Barel M., et al *Mol. Immunol.* 35, 1025-1031, 1998; Weis J. J., et al *Proc. Natl. Acad. Sci. U.S.A.* 83, 5639-5643, 1986; Sinha S. K., et al (1993) *J. Immunol.* 150, 5311-5320; WO2004045520 (Example 4); US2004005538 (Example 1); WO2003062401 (Claim 9); WO2004045520 (Example 4); WO9102536 (FIGS. 9.1-9.9); WO2004020595 (Claim 1); Accession: P20023; Q13866; Q14212; EMBL; M26004; AAA35786.1.

(15) CD79b (CD79B, CD79β, IGb (immunoglobulin-associated beta), B29, Genbank accession no. NM_000626 or 11038674) *Proc. Natl. Acad. Sci. U.S.A.* (2003) 100 (7):4126-4131, *Blood* (2002) 100 (9):3068-3076, Muller et al (1992) *Eur. J. Immunol.* 22 (6): 1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146); Cross-references: MIM: 147245; NP_000617.1; NM_000626_1

(16) FcRH2 (IFGP4, IRTA4, SPAP1A (SH2 domain containing phosphatase anchor protein 1a), SPAP1B, SPAP1C, Genbank accession no. NM_30764, AY358130) *Genome Res.* 13 (10):2265-2270 (2003), *Immunogenetics* 54 (2):87-95 (2002), *Blood* 99 (8):2662-2669 (2002), *Proc. Natl. Acad. Sci. U.S.A.* 98 (17):9772-9777 (2001), Xu, M. J., et al (2001) *Biochem. Biophys. Res. Commun.* 280 (3):768-775; WO2004016225 (Claim 2); WO2003077836; WO200138490 (Claim 5; FIG. 18D-1-18D-2); WO2003097803 (Claim 12); WO2003089624 (Claim 25); Cross-references: MIM:606509; NP_110391.2; NM_030764_1

(17) HER2 (ErbB2, Genbank accession no. M11730) Coussens L., et al *Science* (1985) 230(4730): 1132-1139); Yamamoto T., et al *Nature* 319, 230-234, 1986; Semba K., et al *Proc. Natl. Acad. Sci. U.S.A.* 82, 6497-6501, 1985; Swiercz J. M., et al *J. Cell Biol.* 165, 869-880, 2004; Kuhns J. J., et al *J. Biol. Chem.* 274, 36422-36427, 1999; Cho H.-S., et al *Nature* 421, 756-760, 2003; Ehsani A, et al (1993) *Genomics* 15, 426-429; WO2004048938 (Example 2); WO2004027049 (FIG. 1I); WO2004009622; WO2003081210; WO2003089904 (Claim 9); WO2003016475 (Claim 1); US2003118592; WO2003008537 (Claim 1); WO2003055439 (Claim 29; FIG. 1 A-B); WO2003025228 (Claim 37; FIG. 5C); WO200222636 (Example 13; Page 95-107); WO200212341 (Claim 68; FIG. 7); WO200213847 (Page 71-74); WO200214503 (Page 114-117); WO200153463 (Claim 2; Page 41-46); WO200141787 (Page 15); WO200044899 (Claim 52; FIG. 7); WO200020579 (Claim 3; FIG. 2); U.S. Pat. No. 5,869,445 (Claim 3; Col 31-38); WO9630514 (Claim 2; Page 56-61); EP1439393 (Claim 7); WO2004043361 (Claim 7); WO2004022709; WO200100244 (Example 3; FIG. 4); Accession: P04626; EMBL; M11767; AAA35808.1. EMBL; M11761; AAA35808.1.

(18) NCA (CEACAM6, Genbank accession no. M18728); Barnett T., et al *Genomics* 3, 59-66, 1988; Tawaragi Y., et al *Biochem. Biophys. Res. Commun.* 150, 89-96, 1988; Strausberg R. L., et al *Proc. Natl. Acad. Sci. U.S.A.* 99: 16899-16903, 2002; WO2004063709; EP 1439393 (Claim 7); WO2004044178 (Example 4); WO2004031238; WO2003042661 (Claim 12); WO200278524 (Example 2); WO200286443 (Claim 27; Page 427); WO200260317 (Claim 2); Accession: P40199; Q14920; EMBL; M29541; AAA59915.1. EMBL; M18728;

(19) MDP (DPEP1, Genbank accession no. BCo17023) *Proc. Natl. Acad. Sci. U.S.A.* 99 (26): 16899-16903 (2002); WO2003016475 (Claim 1); WO200264798 (Claim 33; Page 85-87); JP05003790 (FIG. 6-8); WO9946284 (FIG. 9); Cross-references: MIM: 179780; AAH17023.1; BC017023_1

(20) IL20Rα (IL20Ra, ZCYTOR7, Genbank accession no. AF 184971); Clark H. F., et al *Genome Res.* 13, 2265-2270, 2003; Mungall A. J., et al *Nature* 425, 805-811, 2003; Blumberg H., et al *Cell* 104, 9-19, 2001; Dumoutier L., et al *J. Immunol.* 167, 3545-3549, 2001; Parrish-Novak J., et al *J. Biol. Chem.* 277, 47517-47523, 2002; Pletnev S., et al (2003) *Biochemistry* 42: 12617-12624; Sheikh F., et al (2004) *J. Immunol.* 172, 2006-2010; EP1394274 (Example 11); US2004005320 (Example 5); WO2003029262 (Page 74-75); WO2003002717 (Claim 2; Page 63); WO200222153 (Page 45-47); US2002042366 (Page 20-21); WO200146261 (Page 57-59); WO200146232 (Page 63-65); WO9837193 (Claim 1; Page 55-59); Accession: Q9UHF4; Q6UWA9; Q96SH8; EMBL; AF 184971; AAF01320.1.

(21) Brevican (BCAN, BEHAB, Genbank accession no. AF229053) Gary S. C., et al *Gene* 256, 139-147, 2000; Clark H. F., et al *Genome Res.* 13, 2265-2270, 2003; Strausberg R. L., et al *Proc. Natl. Acad. Sci. U.S.A.* 99, 16899-16903, 2002; US2003186372 (Claim 11); US2003186373 (Claim 11); US2003119131 (Claim 1; FIG. 52); US2003119122 (Claim 1; FIG. 52); US2003119126 (Claim 1); US2003119121 (Claim 1; FIG. 52); US2003119129 (Claim 1); US2003119130 (Claim 1); US2003119128 (Claim 1; FIG. 52); US2003119125 (Claim 1); WO2003016475 (Claim 1); WO200202634 (Claim 1);

(22) EphB2R (DRT, ERK, Hek5, EPHT3, Tyro5, Genbank accession no. NM_004442) Chan, J. and Watt, V. M., *Oncogene* 6 (6), 1057-1061 (1991) *Oncogene* 10 (5):897-905 (1995), *Annu. Rev. Neurosci.* 21:309-345 (1998), *Int. Rev. Cytol.* 196: 177-244 (2000); WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42); Cross-references: MIM: 600997; NP_004433.2; NM_004442_1

(23) ASLG659 (B7h, Genbank accession no. AX092328) US20040101899 (Claim 2); WO2003104399 (Claim 11); WO2004000221 (FIG. 3); US2003165504 (Claim 1); US2003124140 (Example 2); US2003065143 (FIG. 60); WO2002102235 (Claim 13; Page 299); US2003091580 (Example 2); WO200210187 (Claim 6; FIG. 10); WO200194641 (Claim 12; FIG. 7*b*); WO200202624 (Claim 13; FIG. 1A-1B); US2002034749 (Claim 54; Page 45-46); WO200206317 (Example 2; Page 320-321, Claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (Claim 12); WO2003004989 (Claim 1); WO200271928 (Page 233-234, 452-453); WO 0116318;

(24) PSCA (Prostate stem cell antigen precursor, Genbank accession no. AJ297436) Reiter R. E., et al *Proc. Natl. Acad. Sci. U.S.A.* 95, 1735-1740, 1998; Gu Z., et al *Oncogene* 19, 1288-1296, 2000; *Biochem. Biophys. Res. Commun.* (2000) 275(3):783-788; WO2004022709; EP1394274 (Example 11); US2004018553 (Claim 17); WO2003008537 (Claim 1); WO200281646 (Claim 1; Page 164); WO2003003906 (Claim 10; Page 288); WO200140309 (Example 1; FIG. 17); US2001055751 (Example 1; FIG. 1b); WO200032752 (Claim 18; FIG. 1); WO9851805 (Claim 17; Page 97); WO9851824 (Claim 10; Page 94); WO9840403 (Claim 2; FIG. 1B); Accession: 043653; EMBL; AF043498; AAC39607.1.

(25) GEDA (Genbank accession No. AY260763); AAP14954 lipoma HMGIC fusion-partner-like protein/pid=AAP14954.1—*Homo sapiens* Species: *Homo sapiens* (human) WO2003054152 (Claim 20); WO20030000842 (Claim 1); WO2003023013 (Example 3, Claim 20); US2003194704 (Claim 45); Cross-references: GI:30102449; AAP14954.1; AY260763_1

(26) BAFF-R (B cell-activating factor receptor, BLyS receptor 3, BR3, Genbank accession No. AF116456); BAFF receptor/pid=NP_443177.1—*Homo sapiens* Thompson, J. S., et al *Science* 293 (5537), 2108-2111 (2001); WO2004058309; WO2004011611; WO2003045422 (Example; Page 32-33); WO2003014294 (Claim 35; FIG. 6B); WO2003035846 (Claim 70; Page 615-616); WO2002294852 (Col 136-137); WO200238766 (Claim 3; Page 133); WO200224909 (Example 3; FIG. 3); Cross-references: MIM:606269; NP_443177.1; NM_052945_1; AF132600

(27) CD22 (B-cell receptor CD22-B isoform, BL-CAM, Lyb-8, Lyb8, SIGLEC-2, FLJ22814, Genbank accession No. AK026467); Wilson et al (1991) J. Exp. Med. 173: 137-146; WO2003072036 (Claim 1; FIG. 1); Cross-references: MIM: 107266; NP_001762.1; NM_001771_1

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.10)
WO2003088808, US20030228319; WO2003062401 (claim 9); US2002150573 (claim 4, pages 13-14); WO9958658 (claim 13, FIG. 16); WO9207574 (FIG. 1); U.S. Pat. No. 5,644,033; Ha et al (1992) *J. Immunol.* 148(5):1526-1531; Mueller et al (1992) *Eur. J. Biochem.* 22: 1621-1625; Hashimoto et al (1994) *Immunogenetics* 40(4): 287-295; Preud'homme et al (1992) *Clin. Exp. Immunol.* 90(1): 141-146; Yu et al (1992) *J. Immunol.* 148(2) 633-637; Sakaguchi et al (1988) *EMBO J.* 7(11):3457-3464;

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] *Gene* Chromosome: 1 1q23.3, Genbank accession No. NP_001707.1)
WO2004040000; WO2004015426; US2003105292 (Example 2); U.S. Pat. No. 6,555,339 (Example 2); WO200261087 (FIG. 1); WO200157188 (Claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58); WO9217497 (claim 7, FIG. 5); Dobner et al (1992) *Eur. J. Immunol.* 22:2795-2799; Barella et al (1995) *Biochem. J.* 309:773-779;

(30) HLA-DOB (Beta subunit of MHC class II molecule (1a antigen) that binds peptides and presents them to CD4+ T lymphocytes); 273 aa, pI: 6.56 MW: 30820 TM: 1 [P] Gene Chromosome: 6p21.3, Genbank accession No. NP_002111.1)
Tonnelle et al (1985) *EMBO J.* 4(11):2839-2847; Jonsson et al (1989) *Immunogenetics* 29(6):411-413; Beck et al (1992) *J. Mol. Biol.* 228:433-441; Strausberg et al (2002) *Proc. Natl. Acad. Sci USA* 99: 16899-16903; Servenius et al (1987) *J. Biol. Chem.* 262:8759-8766; Beck et al (1996) *J. Mol. Biol.* 255: 1-13; Naruse et al (2002) Tissue Antigens 59:512-519; WO9958658 (claim 13, FIG. 15); U.S. Pat. No. 6,153,408 (Col 35-38); U.S. Pat. No. 5,976,551 (col 168-170); US6011146 (col 145-146); Kasahara et al (1989) *Immunogenetics* 30(1):66-68; Larhammar et al (1985) *J. Biol. Chem.* 260(26): 14111-14119;

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] *Gene* Chromosome: 17p13.3, Genbank accession No. NP_002552.2) Le et al (1997) *FEBS Lett.* 418(1-2): 195-199; WO2004047749; WO2003072035 (claim 10); Touchman et al (2000) *Genome Res.* 10: 165-173; WO200222660 (claim 20); WO2003093444 (claim 1); WO2003087768 (claim 1); WO2003029277 (page 82);

(32) CD72 (B-cell differentiation antigen CD72, Lyb-2) PROTEIN SEQUENCE Full maeaity . . . tafrfpd (1 . . . 359; 359 aa), pI: 8.66, MW: 40225 TM: 1 [P] Gene Chromosome: 9p13.3, Genbank accession No. NP_001773.1) WO2004042346 (claim 65); WO2003026493 (pages 51-52, 57-58); WO200075655 (pages 105-106); Von Hoegen et al (1990) *J. Immunol.* 144(12):4870-4877; Strausberg et al (2002) *Proc. Natl. Acad. Sci USA* 99: 16899-16903;

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.1)
US2002193567; WO9707198 (claim 11, pages 39-42); Miura et al (1996) *Genomics* 38(3):299-304; Miura et al (1998) *Blood* 92:2815-2822; WO2003083047; WO9744452 (claim 8, pages 57-61); WO200012130 (pages 24-26);

(34) FcRH1 (Fc receptor-like protein 1, a putative receptor for the immunoglobulin Fe domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1) WO2003077836; WO200138490 (claim 6, FIG. 18E-1-18-E-2); Davis et al (2001) *Proc. Natl. Acad. Sci USA* 98(17):9772-9777; WO2003089624 (claim 8); EP1347046 (claim 1); WO2003089624 (claim 7);

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88 MW: 106468 TM: 1 [P] *Gene* Chromosome: 1q21, Genbank accession No. Human: AF343662, AF343663, AF343664, AF343665, AF369794, AF397453, AK090423, AK090475, AL834187, AY358085; Mouse: AK089756, AY158090, AY56558; NP_112571.1 WO2003024392 (claim 2, FIG. 97); Nakayama et al (2000) *Biochem. Biophys. Res. Commun.* 277(1): 124-127; WO2003077836; WO200138490 (claim 3, FIG. 18B-1-18B-2);

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436

WO2004074320 (SEQ ID NO 810); JP2004113151 (SEQ ID NOS 2, 4, 8); WO2003042661 (SEQ ID NO 580); WO2003009814 (SEQ ID NO 411); EP1295944 (pages 69-70); WO200230268 (page 329); WO200190304 (SEQ ID NO 2706); US2004249130; US2004022727; WO2004063355; US2004197325; US2003232350; US2004005563; US2003124579; Horie et al (2000) *Genomics* 67: 146-152; Uchida et al (1999) *Biochem. Biophys. Res. Commun.* 266:593-602; Liang et al (2000) *Cancer Res.* 60:4907-12; Glynne-Jones et al (2001) *Int J Cancer*. October 15; 94(2): 178-84;

(37) PMEL17 (silver homolog; SILV; D12S53E; PMEL17; SI; SIL); ME20; gp100) BC001414; BT007202; M32295; M77348; NM_0 6928; McGlinchey, R. P. et al (2009) *Proc. Natl. Acad. Sci. U.S.A.* 106 (33), 13731-13736; Kummer, M. P. et al (2009) *J. Biol. Chem.* 284 (4), 2296-2306;

(38) TMEFF1 (transmembrane protein with EGF-like and two follistatin-like domains 1; Tomoregulin-1); H7365; C9ORF2; C9ORF2; U19878; X83961; NM_080655; NM_003692; Harms, P. W. (2003) *Genes Dev.* 17 (21), 2624-2629; Gery, S. et al (2003) *Oncogene* 22 (18):2723-2727;

(39) GDNF-Ra1 (GDNF family receptor alpha 1; GFRA1; GDNFR; GDNFRA; RETL1; TRNR1; RET1L; GDNFR-alpha1; GFR-ALPHA-1); U95847; BC014962; NM_145793 NM_005264; Kim, M. H. et al (2009) *Mol. Cell. Biol.* 29 (8), 2264-2277; Treanor, J. J. et al (1996) *Nature* 382 (6586):80-83;

(40) Ly6E (lymphocyte antigen 6 complex, locus E, Ly67, RIG-E, SCA-2, TSA-l); NP_002337.1; NM_002346.2; de Nooij-van Dalen, A G. et al (2003) *Int. J. Cancer* 103 (6), 768-774; Zammit, D. J. et al (2002) *Mol. Cell. Biol.* 22 (3):946-952; WO 2013/17705;

(41) TMEM46 (shisa homolog 2 (*Xenopus laevis*); SHISA2); NP_001007539.1; NM_001007538.1; Furushima, K. et al (2007) *Dev. Biol.* 306 (2), 480-492; Clark, H. F. et al (2003) *Genome Res.* 13 (10):2265-2270;

(42) Ly6G6D (lymphocyte antigen 6 complex, locus G6D; Ly6-D, MEGT1); NP_067079.2; NM_021246.2; Mallya, M. et al (2002) *Genomics* 80 (1): 113-123; Ribas, G. et al (1999) *J. Immunol.* 163 (1):278-287;

(43) LGR5 (leucine-rich repeat-containing G protein-coupled receptor 5; GPR49, GPR67); NP_003658.1; NM_003667.2; Salanti, G. et al (2009) *Am. J. Epidemiol.* 170 (5):537-545; Yamamoto, Y. et al (2003) *Hepatology* 37 (3):528-533;

(44) RET (ret proto-oncogene; MEN2A; HSCR1; MEN2B; MTC1; PTC; CDHF12; Hs.168114; RET51; RETELE1); NP_066124.1; NM_020975.4; Tsukamoto, H. et al (2009) *Cancer Sci.* 100 (10): 1895-1901; Narita, N. et al (2009) *Oncogene* 28 (34):3058-3068;

(45) LY6K (lymphocyte antigen 6 complex, locus K; LY6K; HSJ001348; FLJ35226); NP_059997.3; NM_017527.3; Ishikawa, N. et al (2007) *Cancer Res.* 67 (24): 11601-11611; de Nooij-van Dalen, A G. et al (2003) *Int. J. Cancer* 103 (6):768-774;

(46) GPR19 (G protein-coupled receptor 19; Mm.4787); NP_006134.1; NM_06143.2; Montpetit, A. and Sinnett, D. (1999) *Hum. Genet.* 105 (1-2): 162-164; O'Dowd, B. F. et al (1996) *FEBS Lett.* 394 (3):325-329;

(47) GPR54 (KISS1 receptor; KISS1R; GPR54; HOT7T175; AXOR12); NP_115940.2; NM 032551.4; Navenot, J. M. et al (2009) *Mol. Pharmacol.* 75 (6): 1300-1306; Hata, K. et al (2009) *Anticancer Res.* 29 (2):617-623;

(48) ASPHD1 (aspartate beta-hydroxylase domain containing 1; LOC253982); NP_859069.2; NM_181718.3; Gerhard, D. S. et al (2004) *Genome Res.* 14 (10B):2121-2127;

(49) Tyrosinase (TYR; OCA1A; OCA1A; tyrosinase; SHEP3); NP_000363.1; NM_000372.4; Bishop, D. T. et al (2009) *Nat. Genet.* 41(8):920-925; Nan, H. et al (2009) *Int. J. Cancer* 125 (4): 909-917;

(50) TMEM118 (ring finger protein, transmembrane 2; RNFT2; FLJ14627); NP_001103373.1; NM 001109903.1; Clark, H. F. et al (2003) *Genome Res.* 13 (10):2265-2270; Scherer, S. E. et al (2006) *Nature* 440 (7082):346-351

(51) GPR172A (G protein-coupled receptor 172A; GPCR41; FLJ11856; D15Ertd747e); NP_078807.1; NM_024531.3; Ericsson, T. A. et al (2003) *Proc. Natl. Acad. Sci. U.S.A.* 100 (11):6759-6764; Takeda, S. et al (2002) *FEBS Lett.* 520 (1-3):97-101.

(52) CD33, a member of the sialic acid binding, immunoglobulin-like lectin family, is a 67-kDa glycosylated transmembrane protein. CD33 is expressed on most myeloid and monocytic leukemia cells in addition to committed myelomonocytic and erythroid progenitor cells. It is not seen on the earliest pluripotent stem cells, mature granulocytes, lymphoid cells, or nonhematopoietic cells (Sabbath et al., (1985) *J. Clin. Invest.* 75:756-56; Andrews et al., (1986) *Blood* 68: 1030-5). CD33 contains two tyrosine residues on its cytoplasmic tail, each of which is followed by hydrophobic residues similar to the immunoreceptor tyrosine-based inhibitory motif (ITIM) seen in many inhibitory receptors.

(53) CLL-1 (CLEC12A, MICL, and DCAL2), encodes a member of the C-type lectin/C-type lectin-like domain (CTL/CTLD) superfamily. Members of this family share a common protein fold and have diverse functions, such as cell adhesion, cell-cell signalling, glycoprotein turnover, and roles in inflammation and immune response. The protein encoded by this gene is a negative regulator of granulocyte and monocyte function. Several alternatively spliced transcript variants of this gene have been described, but the full-length nature of some of these variants has not been determined. This gene is closely linked to other CTL/CTLD superfamily members in the natural killer gene complex region on chromosome 12p13 (Drickamer K (1999) *Curr. Opin. Struct. Biol.* 9 (5):585-90; van Rhenen A, et al., (2007) *Blood* 110 (7):2659-66; Chen C H, et al. (2006) *Blood* 107 (4): 1459-67; Marshall A S, et al. (2006) *Eur. J. Immunol.* 36 (8):2159-69; Bakker A B, et al (2005) *Cancer Res.* 64 (22):8443-50; Marshall A S, et al (2004) *J. Biol. Chem.* 279 (15): 14792-802). CLL-1 has been shown to be a type II transmembrane receptor comprising a single C-type lectin-like domain (which is not predicted to bind either calcium or sugar), a stalk region, a transmembrane domain and a short cytoplasmic tail containing an ITIM motif.

Anti-CD22 Antibodies

In certain embodiments, the anti-CD22 antibodies of an ADC comprises three light chain hypervariable regions (HVR-L1, HVR-L2 and HVR-L3) and three heavy chain hypervariable regions (HVR-H1, HVR-H2 and HVR-H3), according to U.S. Pat. No. 8,226,945:

```
HVR-L1
                         (SEQ ID NO: 1)
RSSQSIVHSVGNTFLE

HVR-L2
                         (SEQ ID NO: 2)
KVSNRFS

HVR-L3
                         (SEQ ID NO: 3)
FQGSQFPYT

HVR-H1
                         (SEQ ID NO: 4)
GYEFSRSWMN

HVR-H2
                         (SEQ ID NO: 5)
GRIYPGDGDTNYSGKFKG

HVR-H3
                         (SEQ ID NO: 6)
DGSSWDWYFDV
```

Anti-Ly6E Antibodies

In certain embodiments, an ADC comprises anti-Ly6E antibodies. Lymphocyte antigen 6 complex, locus E (Ly6E), also known as retinoic acid induced gene E (RIG-E) and stem cell antigen 2 (SCA-2). It is a GPI linked, 131 amino acid length, ~8.4 kDa protein of unknown function with no known binding partners. It was initially identified as a transcript expressed in immature thymocyte, thymic medullary epithelial cells in mice (Mao, et al. (1996) *Proc. Natl. Acad. Sci. U.S.A.* 93:5910-5914). In some embodiments, the invention provides an immunoconjugate comprising an anti-Ly6E antibody described in PCT Publication No. WO 2013/177055.

In some embodiments, the invention provides an antibody-drug conjugate comprising an anti-Ly6E antibody comprising at least one, two, three, four, five, or six HVRs selected from (a) HVR-H1 comprising the amino acid sequence of SEQ ID NO: 12; (b) HVR-H2 comprising the amino acid sequence of SEQ ID NO: 13; (c) HVR-H3 comprising the amino acid sequence of SEQ ID NO: 14; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11.

In one aspect, the invention provides an antibody-drug conjugate comprising an antibody that comprises at least one, at least two, or all three VH HVR sequences selected from (a) HVR-H1 comprising the amino acid sequence of SEQ ID NO: 12; (b) HVR-H2 comprising the amino acid sequence of SEQ ID NO: 13; and (c) HVR-H3 comprising the amino acid sequence of SEQ ID NO: 14. In a further embodiment, the antibody comprises (a) HVR-H1 comprising the amino acid sequence of SEQ ID NO: 12; (b) HVR-H2 comprising the amino acid sequence of SEQ ID NO: 13; and (c) HVR-H3 comprising the amino acid sequence of SEQ ID NO: 14.

In another aspect, the invention provides an antibody-drug conjugate comprising an antibody that comprises at least one, at least two, or all three VL HVR sequences selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11. In one embodiment, the antibody comprises (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11.

In another aspect, an antibody-drug conjugate of the invention comprises an antibody comprising (a) a VH domain comprising at least one, at least two, or all three VH HVR sequences selected from (i) HVR-H1 comprising the amino acid sequence of SEQ ID NO: 12, (ii) HVR-H2 comprising the amino acid sequence of SEQ ID NO: 13, and (iii) HVR-H3 comprising an amino acid sequence selected from SEQ ID NO: 14; and (b) a VL domain comprising at least one, at least two, or all three VL HVR sequences selected from (i) HVR-L1 comprising the amino acid sequence of SEQ ID NO: 9, (ii) HVR-L2 comprising the amino acid sequence of SEQ ID NO: 10, and (c) HVR-L3 comprising the amino acid sequence of SEQ ID NO: 11.

In another aspect, the invention provides an antibody-drug conjugate comprising an antibody that comprises (a) HVR-H1 comprising the amino acid sequence of SEQ ID NO: 12; (b) HVR-H2 comprising the amino acid sequence of SEQ ID NO: 13; (c) HVR-H3 comprising the amino acid sequence of SEQ ID NO: 14; (d) HVR-L1 comprising the amino acid sequence of SEQ ID NO: 9; (e) HVR-L2 comprising the amino acid sequence of SEQ ID NO: 10; and (f) HVR-L3 comprising the amino acid sequence of SEQ ID NO: 11.

In any of the above embodiments, an anti-Ly6E antibody of an antibody-drug conjugate is humanized. In one embodiment, an anti-Ly6E antibody comprises HVRs as in any of the above embodiments, and further comprises a human acceptor framework, e.g. a human immunoglobulin framework or a human consensus framework.

In another aspect, an anti-Ly6E antibody of an antibody-drug conjugate comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 8. In certain embodiments, a VH sequence having at least 90%, 91%, 92%, 93%, 94%, 95%, 96%, 97%, 98%, or 99% identity to the amino acid sequence of SEQ ID NO: 8 contains substitutions (e.g., conservative substitutions), insertions, or deletions relative to the reference sequence, but an anti-Ly6E antibody comprising that sequence retains the ability to bind to Ly6E. In certain embodiments, a total of 1 to 10 amino acids have been substituted, inserted and/or deleted in SEQ ID NO: 8. In certain embodiments, a total of 1 to 5 amino acids have been substituted, inserted and/or deleted in SEQ ID NO: 8. In certain embodiments, substitutions, insertions, or deletions occur in regions outside the HVRs (i.e., in the FRs). Optionally, the anti-Ly6E antibody comprises the VH sequence of SEQ ID NO: 8, including post-translational modifications of that sequence. In a particular embodiment, the VH comprises one, two or three HVRs selected from: (a) HVR-H1 comprising the amino acid sequence of SEQ ID NO: 12, (b) HVR-H2 comprising the amino acid sequence of SEQ ID NO: 13, and (c) HVR-H3 comprising the amino acid sequence of SEQ ID NO: 14.

In another aspect, an anti-Ly6E antibody of an antibody-drug conjugate is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 7. In certain embodiments, a VL sequence having at least 90%, 91%, 92%, 93%, 94%, 95%, 96%, 97%, 98%, or 99% identity to the amino acid sequence of SEQ ID NO:7 contains substitutions (e.g., conservative substitutions), insertions, or deletions relative to the reference sequence, but an anti-Ly6E antibody comprising that sequence retains the ability to bind to Ly6E. In certain embodiments, a total of 1 to 10 amino acids have been substituted, inserted and/or deleted in SEQ ID NO: 7. In certain embodiments, a total of 1 to 5 amino acids have been substituted, inserted and/or deleted in SEQ ID NO: 7. In certain embodiments, the substitutions, insertions, or deletions occur in regions outside the HVRs (i.e., in the FRs). Optionally, the anti-Ly6E antibody comprises the VL sequence of SEQ ID NO: 7, including post-translational modifications of that sequence. In a particular embodiment, the VL comprises one, two or three HVRs selected from (a) HVR-L1 comprising the amino acid sequence of SEQ ID NO: 9; (b) HVR-L2 comprising the amino acid sequence of SEQ ID NO: 10; and (c) HVR-L3 comprising the amino acid sequence of SEQ ID NO: 11.

In another aspect, an antibody-drug conjugate comprising an anti-Ly6E antibody is provided, wherein the antibody comprises a VH as in any of the embodiments provided above, and a VL as in any of the embodiments provided above.

In one embodiment, an antibody-drug conjugate is provided, wherein the antibody comprises the VH and VL sequences in SEQ ID NO: 8 and SEQ ID NO: 7, respectively, including post-translational modifications of those sequences.

In a further aspect, provided herein are antibody-drug conjugate comprising antibodies that bind to the same epitope as an anti-Ly6E antibody provided herein. For example, in certain embodiments, an immunoconjugate is provided comprising an antibody that binds to the same epitope as an anti-Ly6E antibody comprising a VH sequence of SEQ ID NO: 8 and a VL sequence of SEQ ID NO: 7, respectively.

In a further aspect of the invention, an anti-Ly6E antibody of an antibody-drug conjugate according to any of the above embodiments is a monoclonal antibody, including a human antibody. In one embodiment, an anti-Ly6E antibody of an antibody-drug conjugate is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein. In some embodiments, an immunconjugate (ADC) comprises an anti-Ly6E antibody comprising a heavy chain and a light chain comprising the amino acid sequences of SEQ ID NO: 16 and 15, respectively.

Table of Ly6E AntibodySequences

| SEQ ID NO | Description | Sequence |
|---|---|---|
| 7 | anti-Ly6E antibody hU9B12 V12 light chain variable region | DIQMTQSPSS LSASVGDRVT ITCSASQGIS NYLNWYQQKP GKTVKLLIYY TSNLHSGVPS RFSGSGSGTD YTLTISSLQP EDFATYYCQQ YSELPWTFGQ GTKVEIK |
| 8 | anti-Ly6E antibody hU9B12 V12 heavy chain variable region | EVQLVESGPA LVKPTQTLTL TCTVSGFSLT GYSVNWIRQPPGKAL EWLGMIWGDG STDYNSALKS RLTISKDTSK NQVVLTMTNM DPVDTATYYC ARDYYFNYAS WFAYWGQGTL VTVSS |
| 9 | anti-Ly6E antibody hU9B12 V12 HVR-L1 | SASQGISNYLN |
| 10 | anti-Ly6E antibody hU9B12 V12 HVR-L2 | YTSNLHS |
| 11 | anti-Ly6E antibody hU9B12 V12 HVR-L3 | QQYSELPWT |
| 12 | anti-Ly6E antibody hU9B12 V12 HVR-H1 | GFSLTGYSVN |
| 13 | anti-Ly6E antibody hU9B12 V12 HVR-H2 | MIWGDGSTDY NSALKS |
| 14 | anti-Ly6E antibody hU9B12 V12 HVR-H3 | DYYVNYASWFAY |
| 15 | anti-Ly6E antibody | DIQMTQSPSS LSASVGDRVT ITCSASQGIS NYLNWYQQKP GKTVKLLIYY TSNLHSGVPS RFSGSGSGTD YTLTISSLQP |

Table of Ly6E AntibodySequences

| SEQ ID NO | Description | Sequence |
|---|---|---|
|  | hU9B12 V12 K149C kappa light chain | EDFATYYCQQ YSELPWTFGQ GTKVEIK RTVAAPSVFIF PPSDEQLKSG TASVVCLLNN FYPREAKVQW CVDNALQSGN SQESVTEQDS KDSTYSLSST LTLSKADYEK HKVYACEVTH QGLSSPVTKS FNRGEC |
| 16 | anti-Ly6E antibody hu9B12 V12 IgG1 heavy chain | EVQL VESGPA LVKPTQTLTL TCTVSGFSLT GYSVNWIRQP PGKALEWLGM IWGDGSTDYN SALKSRLTIS KDTSKNQVVL TMTNMDPVDT ATYYCARDYY FNYASWFAYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |

Anti-HER2 Antibodies

In certain embodiments, an ADC comprises anti-HER2 antibodies. In one embodiment of the invention, an anti-HER2 antibody of an ADC of the invention comprises a humanized anti-HER2 antibody, e.g., huMAb4D5-1, huMAb4D5-2, huMAb4D5-3, huMAb4D5-4, huMAb4D5-5, huMAb4D5-6, huMAb4D5-7 and huMAb4D5-8, as described in Table 3 of U.S. Pat. No. 5,821,337, which is specifically incorporated by reference herein. Those antibodies contain human framework regions with the complementarity-determining regions of a murine antibody (4D5) that binds to HER2. The humanized antibody huMAb4D5-8 is also referred to as trastuzumab, commercially available under the tradename HERCEPTIN®. In another embodiment of the invention, an anti-HER2 antibody of an ADC of the invention comprises a humanized anti-HER2 antibody, e.g., humanized 2C4, as described in U.S. Pat. No. 7,862,817. An exemplary humanized 2C4 antibody is pertuzumab, commercially available under the tradename PERJETA®.

In another embodiment of the invention, an anti-HER2 antibody of an ADC of the invention comprises a humanized 7C2 anti-HER2 antibody. A humanized 7C2 antibody is an anti-HER2 antibody.

In some embodiments, the invention provides an antibody-drug conjugate comprising an anti-HER2 antibody comprising at least one, two, three, four, five, or six HVRs selected from (a) HVR-H1 comprising the amino acid sequence of SEQ ID NO: 22; (b) HVR-H2 comprising the amino acid sequence of SEQ ID NO: 23, 27, or 28; (c) HVR-H3 comprising the amino acid sequence of SEQ ID NO: 24 or 29; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21. In some embodiments, the invention provides an antibody-drug conjugate comprising an anti-HER2 antibody comprising at least one, two, three, four, five, or six HVRs selected from (a) HVR-H1 comprising the amino acid sequence of SEQ ID NO: 22; (b) HVR-H2 comprising the amino acid sequence of SEQ ID NO: 23; (c) HVR-H3 comprising the amino acid sequence of SEQ ID NO: 24; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21.

In one aspect, the invention provides an antibody-drug conjugate comprising an antibody that comprises at least one, at least two, or all three VH HVR sequences selected from (a) HVR-H1 comprising the amino acid sequence of SEQ ID NO: 22; (b) HVR-H2 comprising the amino acid sequence of SEQ ID NO: 23, 27, or 28; and (c) HVR-H3 comprising the amino acid sequence of SEQ ID NO: 24 or 29. In one aspect, the invention provides an immunoconjugate comprising an antibody that comprises at least one, at least two, or all three VH HVR sequences selected from (a) HVR-H1 comprising the amino acid sequence of SEQ ID NO: 22; (b) HVR-H2 comprising the amino acid sequence of SEQ ID NO: 23; and (c) HVR-H3 comprising the amino acid sequence of SEQ ID NO: 24. In a further embodiment, the antibody comprises (a) HVR-H1 comprising the amino acid sequence of SEQ ID NO: 22; (b) HVR-H2 comprising the amino acid sequence of SEQ ID NO: 23, 27, or 28; and (c) HVR-H3 comprising the amino acid sequence of SEQ ID NO: 24 or 29. In a further embodiment, the antibody comprises (a) HVR-H1 comprising the amino acid sequence of SEQ ID NO: 22; (b) HVR-H2 comprising the amino acid sequence of SEQ ID NO: 23; and (c) HVR-H3 comprising the amino acid sequence of SEQ ID NO: 24.

In another aspect, the invention provides an antibody-drug conjugate comprising an antibody that comprises at least one, at least two, or all three VL HVR sequences selected from (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21. In one embodiment, the antibody comprises (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO:21.

In another aspect, an antibody-drug conjugate of the invention comprises an antibody comprising (a) a VH domain comprising at least one, at least two, or all three VH HVR sequences selected from (i) HVR-H1 comprising the amino acid sequence of SEQ ID NO: 22, (ii) HVR-H2 comprising the amino acid sequence of SEQ ID NO: 23, 27, or 28, and (iii) HVR-H3 comprising an amino acid sequence selected from SEQ ID NO: 24 or 29; and (b) a VL domain comprising at least one, at least two, or all three VL HVR sequences selected from (i) HVR-L1 comprising the amino acid sequence of SEQ ID NO: 19, (ii) HVR-L2 comprising the amino acid sequence of SEQ ID NO: 20, and (c) HVR-L3 comprising the amino acid sequence of SEQ ID NO: 21. In another aspect, an antibody-drug conjugate of the invention comprises an antibody comprising (a) a VH domain comprising at least one, at least two, or all three VH HVR sequences selected from (i) HVR-H1 comprising the amino acid sequence of SEQ ID NO: 22, (ii) HVR-H2 comprising the amino acid sequence of SEQ ID NO: 23, and (iii) HVR-H3 comprising an amino acid sequence selected from SEQ ID NO: 24; and (b) a VL domain comprising at least one, at least two, or all three VL HVR sequences selected from (i) HVR-L1 comprising the amino acid sequence of SEQ ID NO: 19, (ii) HVR-L2 comprising the amino acid sequence of SEQ ID NO: 20, and (c) HVR-L3 comprising the amino acid sequence of SEQ ID NO: 21.

In another aspect, the invention provides an antibody-drug conjugate comprising an antibody that comprises (a) HVR-H1 comprising the amino acid sequence of SEQ ID NO: 22; (b) HVR-H2 comprising the amino acid sequence of SEQ ID NO: 23, 27, or 28; (c) HVR-H3 comprising the amino acid sequence of SEQ ID NO: 24 or 29; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21. In another aspect, the invention provides an antibody-drug conjugate comprising an antibody that comprises (a) HVR-H1 comprising the amino acid sequence of SEQ ID NO: 22; (b) HVR-H2 comprising the amino acid sequence of SEQ ID NO: 23; (c) HVR-H3 comprising the amino acid sequence of SEQ ID NO: 24; (d) HVR-L1 comprising the amino acid sequence of SEQ ID NO: 19; (e) HVR-L2 comprising the amino acid sequence of SEQ ID NO: 20; and (f) HVR-L3 comprising the amino acid sequence of SEQ ID NO: 21.

In any of the above embodiments, an anti-HER2 antibody of an antibody-drug conjugate is humanized. In one embodiment, an anti-HER2 antibody of an antibody-drug conjugate comprises HVRs as in any of the above embodiments, and further comprises a human acceptor framework, e.g. a human immunoglobulin framework or a human consensus framework.

In another aspect, an anti-HER2 antibody of an antibody-drug conjugate comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 18. In certain embodiments, a VH sequence having at least 90%, 91%, 92%, 93%, 94%, 95%, 96%, 97%, 98%, or 99% identity to the amino acid sequence of SEQ ID NO: 18 contains substitutions (e.g., conservative substitutions), insertions, or deletions relative to the reference sequence, but an anti-HER2 antibody comprising that sequence retains the ability to bind to HER2. In certain embodiments, a total of 1 to 10 amino acids have been substituted, inserted and/or deleted in SEQ ID NO: 18. In certain embodiments, a total of 1 to 5 amino acids have been substituted, inserted and/or deleted in SEQ ID NO: 18. In certain embodiments, substitutions, insertions, or deletions occur in regions outside the HVRs (i.e., in the FRs). Optionally, the anti-HER2 antibody comprises the VH sequence of SEQ ID NO: 18, including post-translational modifications of that sequence. In a particular embodiment, the VH comprises one, two or three HVRs selected from: (a) HVR-H1 comprising the amino acid sequence of SEQ ID NO: 22, (b) HVR-H2 comprising the amino acid sequence of SEQ ID NO: 23, and (c) HVR-H3 comprising the amino acid sequence of SEQ ID NO: 24.

In another aspect, an anti-HER2 antibody of an antibody-drug conjugate is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 17. In certain embodiments, a VL sequence having at least 90%, 91%, 92%, 93%, 94%, 95%, 96%, 97%, 98%, or 99% identity to the amino acid sequence of SEQ ID NO: 17 contains substitutions (e.g., conservative substitutions), insertions, or deletions relative to the reference sequence, but an anti-HER2 antibody comprising that sequence retains the ability to bind to HER2. In certain embodiments, a total of 1 to 10 amino acids have been substituted, inserted and/or deleted in SEQ ID NO: 17. In certain embodiments, a total of 1 to 5 amino acids have been substituted, inserted and/or deleted in SEQ ID NO: 17. In certain embodiments, the substitutions, insertions, or deletions occur in regions outside the HVRs (i.e., in the FRs). Optionally, the anti-HER2 antibody comprises the VL sequence of SEQ ID NO: 17, including post-translational modifications of that sequence. In a particular embodiment, the VL comprises one, two or three HVRs selected from (a) HVR-L1 comprising the amino acid sequence of SEQ ID NO: 19; (b) HVR-L2 comprising the amino acid sequence of SEQ ID NO: 20; and (c) HVR-L3 comprising the amino acid sequence of SEQ ID NO: 21.

In another aspect, an antibody-drug conjugate comprising an anti-HER2 antibody is provided, wherein the antibody comprises a VH as in any of the embodiments provided above, and a VL as in any of the embodiments provided above.

In one embodiment, an antibody-drug conjugate comprising an antibody is provided, wherein the antibody comprises the VH and VL sequences in SEQ ID NO: 18 and SEQ ID NO: 17, respectively, including post-translational modifications of those sequences.

In one embodiment, an antibody-drug conjugate comprising an antibody is provided, wherein the antibody comprises the humanized 7C2.v2.2.LA (hu7C2) K149C kappa light chain sequence of SEQ ID NO: 30

In one embodiment, an antibody-drug conjugate comprising an antibody is provided, wherein the antibody comprises the Hu7C2 A118C IgG1 heavy chain sequence of SEQ ID NO: 31

In a further aspect, provided herein are antibody-drug conjugates comprising antibodies that bind to the same epitope as an anti-HER2 antibody provided herein. For example, in certain embodiments, an immunoconjugate is provided, comprising an antibody that binds to the same epitope as an anti-HER2 antibody comprising a VH sequence of SEQ ID NO: 18 and a VL sequence of SEQ ID NO: 17, respectively.

In a further aspect of the invention, an anti-HER2 antibody of an antibody-drug conjugate according to any of the above embodiments is a monoclonal antibody, including a human antibody. In one embodiment, an anti-HER2 antibody of an immunoconjugate is an antibody fragment, e.g., a Fv, Fab, Fab', scFv, diabody, or F(ab')$_2$ fragment. In another embodiment, an immunoconjugate comprises an antibody that is a substantially full length antibody, e.g., an IgG1 antibody, IgG2a antibody or other antibody class or isotype as defined herein.

| | Table of humanized 7C2 anti-HER2 antibody sequences | |
|---|---|---|
| SEQ ID NO | Description | Sequence |
| 17 | Humanized 7C2.V2.2.LA ("hu7C2") light chain variable region | DIVMTQSPDS LAVSLGERAT INCRASQSVS GSRETYMHWY QQKPGQPPKL LIKYASILES GVPDRFSGSG SGTDFTLTIS SLQAEDVAVY YCQHSWEIPP WTFGQGTKVE IK |
| 18 | Humanized 7C2.v2.2.LA ("hu7C2") heavy chain variable region | EVQLVQSGAE VKKPGASVKV SCKASGYSFT GYWMNWVRQA PGQGLEWIGM IHPLDAEIRA NQKFRDRVTI TVDTSTSTAY LELSSLRSED TAVYYCARGT YDGGFEYWGQ GTLVTVSS |
| 19 | hu7C2 HVR-L1 | RASQSVSGSRETYMH |
| 20 | hu7C2 HVR-L2 | YASILES |
| 21 | hu7C2 HVR-L3 | QHSWEIPPWT |
| 22 | hu7C2 HVR-H1 | GYWMN |
| 23 | hu7C2 HVR-H2 | MIHPLDAEIRANQKFRD |
| 24 | hu7C2 HVR-H3 | GTYDGGFEY |
| 25 | Humanized 7C2.V2.2.LA (hu7C2) kappa light chain | DIVMTQSPDS LAVSLGERAT INCRASQSVS GSRETYMHWY QQKPGQPPKL LIKYASILES GVPDRFSGSG SGTDFTLTIS SLQAEDVAVY YCQHSWEIPP WTFGQGTKVE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 26 | Humanized 7C2.v2.2.LA (hu7C2) IgG1 heavy chain | EVQLVQSGAE VKKPGASVKV SCKASGYSFT GYWMNWVRQA PGQGLEWIGM IHPLDAEIRA NQKFRDRVTI TVDTSTSTAY LELSSLRSED TAVYYCARGT YDGGFEYWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 27 | Hu7C2.v2.1.S53M HVR-H2 | MIHPMDSEIRANQKFRD |
| 28 | Hu7C2.v2.1.S53L HVR-H2 | MIHPLDSEIRANQKFRD |
| 29 | Hu7C2.v2.1.E101K HVR-H3 | GTYDGGFKY |
| 30 | Humanized 7C2.V2.2.LA (hu7C2) K149C | DIVMTQSPDS LAVSLGERAT INCRASQSVS GSRETYMHWY QQKPGQPPKL LIKYASILES GVPDRFSGSG SGTDFTLTIS SLQAEDVAVY |

-continued

Table of humanized 7C2 anti-HER2 antibody sequences

| SEQ ID NO | Description | Sequence |
|---|---|---|
| | kappa light chain | YCQHSWEIPP WTFGQGTKVE IKRTVAAPSV<br>FIFPPSDEQL KSGTASVVCL LNNFYPREAK<br>VQWCVDNALQ SGNSQESVTE QDSKDSTYSL<br>SSTLTLSKAD YEKHKVYACE VTHQGLSSPV<br>TKSFNRGEC |
| 31 | Humanized 7C2.v2.2.LA (hu7C2) A118C IgG1 heavy chain | EVQLVQSGAE VKKPGASVKV SCKASGYSFT<br>GYWMNWVRQA PGQGLEWIGM IHPLDAEIRA<br>NQKFRDRVTI TVDTSTSTAY LELSSLRSED<br>TAVYYCARGT YDGGFEYWGQ GTLVTVSSCS<br>TKGPSVFPLA PSSKSTSGGT AALGCLVKDY<br>FPEPVTVSWN SGALTSGVHT FPAVLQSSGL<br>YSLSSVVTVP SSSLGTQTYI CNVNHKPSNT<br>KVDKKVEPKS CDKTHTCPPC PAPELLGGPS<br>VFLFPPKPKD TLMISRTPEV TCVVVDVSHE<br>DPEVKFNWYV DGVEVHNAKT KPREEQYNST<br>YRVVSVLTVL HQDWLNGKEY KCKVSNKALP<br>APIEKTISKA KGQPREPQVY TLPPSREEMT<br>KNQVSLTCLV KGFYPSDIAV EWESNGQPEN<br>NYKTTPPVLD SDGSFFLYSK LTVDKSRWQQ<br>GNVFSCSVMH EALHNHYTQK SLSLSPGK |

Anti-MUC16 Antibodies

In certain embodiments, an ADC comprises anti-MUC16 antibodies.

In some embodiments, the invention provides an antibody-drug conjugate comprising an anti-MUC16 antibody comprising at least one, two, three, four, five, or six HVRs selected from (a) HVR-H1 comprising the amino acid sequence of SEQ ID NO: 35; (b) HVR-H$_2$ comprising the amino acid sequence of SEQ ID NO: 36; (c) HVR-H3 comprising the amino acid sequence of SEQ ID NO: 37; (d) HVR-L1 comprising the amino acid sequence of SEQ ID NO: 32; (e) HVR-L2 comprising the amino acid sequence of SEQ ID NO: 33 and (f) HVR-L3 comprising the amino acid sequence of SEQ ID NO: 34.

In one aspect, the invention provides an antibody-drug conjugate comprising an antibody that comprises at least one, at least two, or all three VH HVR sequences selected from (a) HVR-H1 comprising the amino acid sequence of SEQ ID NO: 35; (b) HVR-H$_2$ comprising the amino acid sequence of SEQ ID NO: 36; (c) HVR-H3 comprising the amino acid sequence of SEQ ID NO: 37. In a further embodiment, the antibody comprises (a) HVR-H1 comprising the amino acid sequence of SEQ ID NO: 35; (b) HVR-H$_2$ comprising the amino acid sequence of SEQ ID NO: 36; (c) HVR-H3 comprising the amino acid sequence of SEQ ID NO: 37.

In another aspect, the invention provides an antibody-drug conjugate comprising an antibody that comprises at least one, at least two, or all three VL HVR sequences selected from (a) HVR-L1 comprising the amino acid sequence of SEQ ID NO: 32; (b) HVR-L2 comprising the amino acid sequence of SEQ ID NO: 33; and (c) HVR-L3 comprising the amino acid sequence of SEQ ID NO: 34. In one embodiment, the antibody comprises (a) HVR-L1 comprising the amino acid sequence of SEQ ID NO: 32; (b) HVR-L2 comprising the amino acid sequence of SEQ ID NO: 33; and (c) HVR-L3 comprising the amino acid sequence of SEQ ID NO: 34.

In another aspect, an antibody-drug conjugate of the invention comprises an antibody comprising (a) a VH domain comprising at least one, at least two, or all three VH HVR sequences selected from (i) HVR-H1 comprising the amino acid sequence of SEQ ID NO: 35, (ii) HVR-H$_2$ comprising the amino acid sequence of SEQ ID NO: 36, and (iii) HVR-H3 comprising an amino acid sequence selected from SEQ ID NO: 37; and (b) a VL domain comprising at least one, at least two, or all three VL HVR sequences selected from (i) HVR-L1 comprising the amino acid sequence of SEQ ID NO: 32, (ii) HVR-L2 comprising the amino acid sequence of SEQ ID NO: 33, and (c) HVR-L3 comprising the amino acid sequence of SEQ ID NO: 34.

In another aspect, the invention provides an antibody-drug conjugate comprising an antibody that comprises (a) HVR-H1 comprising the amino acid sequence of SEQ ID NO: 35 (b) HVR-H$_2$ comprising the amino acid sequence of SEQ ID NO: 36; (c) HVR-H3 comprising the amino acid sequence of SEQ ID NO: 37; (d) HVR-L1 comprising the amino acid sequence of SEQ ID NO: 32; (e) HVR-L2 comprising the amino acid sequence of SEQ ID NO: 33; and (f) HVR-L3 comprising the amino acid sequence of SEQ ID NO: 34.

In any of the above embodiments, an anti-MUC16 antibody of an antibody-drug conjugate is humanized. In one embodiment, an anti-MUC16 antibody comprises HVRs as in any of the above embodiments, and further comprises a human acceptor framework, e.g. a human immunoglobulin framework or a human consensus framework.

In another aspect, an anti-MUC16 antibody of an antibody-drug conjugate comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 39. In certain embodiments, a VH sequence having at least 90%, 91%, 92%, 93%, 94%, 95%, 96%, 97%, 98%, or 99% identity to the amino acid sequence of SEQ ID NO: 39 contains substitutions (e.g., conservative substitutions), insertions, or deletions relative to the reference sequence, but an anti-MUC16 antibody comprising that sequence retains the ability to bind to MUC16. In certain embodiments, a total of 1 to 10 amino acids have been substituted, inserted and/or deleted in SEQ ID NO: 39. In certain embodiments, a total of 1 to 5 amino acids have been substituted, inserted and/or deleted in SEQ ID NO: 39. In certain embodiments, substitutions, insertions, or deletions occur in regions outside the HVRs (i.e., in the FRs). Optionally, the anti-MUC16 antibody comprises the VH sequence of SEQ ID NO: 39, including post-translational modifications of that sequence. In a particular embodiment, the VH comprises one, two or three HVRs selected from: (a) HVR-H1 comprising the amino acid sequence of SEQ ID NO: 35, (b) HVR-H$_2$ comprising the amino acid sequence of SEQ ID NO: 36, and (c) HVR-H3 comprising the amino acid sequence of SEQ ID NO: 37.

In another aspect, an anti-MUC16 antibody of an antibody-drug conjugate is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 38. In certain embodiments, a VL sequence having at least 90%, 91%, 92%, 93%, 94%, 95%, 96%, 97%, 98%, or 99% identity to the amino acid sequence of SEQ ID NO:38 contains substitutions (e.g., conservative substitutions), insertions, or deletions relative to the reference sequence, but an anti-MUC16 antibody comprising that sequence retains the ability to bind to MUC16. In certain embodiments, a total of 1 to 10 amino acids have been substituted, inserted and/or deleted in SEQ ID NO: 38. In certain embodiments, a total of 1 to 5 amino acids have been substituted, inserted and/or deleted in SEQ ID NO: 38. In certain embodiments, the substitutions, insertions, or deletions occur in regions outside the HVRs (i.e., in the FRs). Optionally, the anti-MUC16 antibody comprises the VL sequence of SEQ ID NO: 38, including post-translational modifications of that sequence. In a particular embodiment, the VL comprises one, two or three HVRs selected from (a) HVR-L1 comprising the amino acid sequence of SEQ ID NO: 32; (b) HVR-L2 comprising the amino acid sequence of SEQ ID NO: 33; and (c) HVR-L3 comprising the amino acid sequence of SEQ ID NO: 34.

In another aspect, an antibody-drug conjugate comprising an anti-MUC16 antibody is provided, wherein the antibody comprises a VH as in any of the embodiments provided above, and a VL as in any of the embodiments provided above.

In one embodiment, an antibody-drug conjugate is provided, wherein the antibody comprises the VH and VL sequences in SEQ ID NO:39 and SEQ ID NO:38, respectively, including post-translational modifications of those sequences.

In a further aspect, provided herein are antibody-drug conjugate comprising antibodies that bind to the same epitope as an anti-MUC6 antibody provided herein. For example, in certain embodiments, an immunoconjugate is provided comprising an antibody that binds to the same epitope as an anti-MUC6 antibody comprising a VH sequence of SEQ ID NO: 39 and a VL sequence of SEQ ID NO: 38, respectively.

In a further aspect of the invention, an anti-MUC16 antibody of an antibody-drug conjugate according to any of the above embodiments is a monoclonal antibody, including a human antibody. In one embodiment, an anti-MUC6 antibody of an antibody-drug conjugate is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

Table of MUC16 Antibody Sequences

| SEQ ID NO | Description | Sequence |
|---|---|---|
| 32 | Anti-Muc16 antibody HVR-L1 | KASDLIHNWL A |
| 33 | Anti-Muc16 antibody HVR-L2 | YGATSLET |
| 34 | Anti-Muc16 antibody HVR-L3 | QQYWTTPFT |
| 35 | Anti-Muc16 antibody HVR-H1 | GYSITNDYAW N |
| 36 | Anti-Muc16 antibody HVR-H2 | GYISYSGYTT YNPSLKS |
| 37 | Anti-Muc16 antibody HVR-H3 | ARWASGLDY |
| 38 | Anti-Muc16 antibody light chain variable region | DIQMTQSPSS LSASVGDRVT ITCKASDLIH NWLAWYQQKP GKAPKLLIYG ATSLETGVPS RFSGSGSGTD FTLTISSLQP EDFATYYCQQ YWTTPFTFGQ GTKVEIKR |
| 39 | Anti-Muc16 antibody heavy chain variable region | EVQLVESCGC LVQPCGSLRL SCAASCYSIT NDYAWNWVRQ APGKGLEWVG YISYSGYTTY NPSLKSRFTI SRDTSKNTLY LQMNSLRAED TAVYYCARWA SGLDYWGQGT LVTVSS |

Anti-STEAP-1 Antibodies

In certain embodiments, an ADC comprises anti-STEAP-1 antibodies.

In some embodiments, the invention provides an antibody-drug conjugate comprising an anti-STEAP-1 antibody comprising at least one, two, three, four, five, or six HVRs selected from (a) HVR-H1 comprising the amino acid sequence of SEQ ID NO: 40; (b) HVR-H$_2$ comprising the amino acid sequence of SEQ ID NO: 41; (c) HVR-H3 comprising the amino acid sequence of SEQ ID NO: 42; (d) HVR-L1 comprising the amino acid sequence of SEQ ID NO: 43; (e) HVR-L2 comprising the amino acid sequence of SEQ ID NO: 44 and (f) HVR-L3 comprising the amino acid sequence of SEQ ID NO: 45.

In one aspect, the invention provides an antibody-drug conjugate comprising an antibody that comprises at least one, at least two, or all three VH HVR sequences selected from (a) HVR-H1 comprising the amino acid sequence of SEQ ID NO: 40; (b) HVR-H$_2$ comprising the amino acid sequence of SEQ ID NO: 41; (c) HVR-H3 comprising the amino acid sequence of SEQ ID NO: 42. In a further embodiment, the antibody comprises (a) HVR-H1 comprising the amino acid sequence of SEQ ID NO: 40; (b) HVR-H$_2$ comprising the amino acid sequence of SEQ ID NO: 41; (c) HVR-H3 comprising the amino acid sequence of SEQ ID NO: 42.

In another aspect, the invention provides an antibody-drug conjugate comprising an antibody that comprises at least one, at least two, or all three VL HVR sequences selected from (a) HVR-L1 comprising the amino acid sequence of SEQ ID NO: 43; (b) HVR-L2 comprising the amino acid sequence of SEQ ID NO: 44; and (c) HVR-L3 comprising the amino acid sequence of SEQ ID NO: 45. In one embodiment, the antibody comprises (a) HVR-L1 comprising the amino acid sequence of SEQ ID NO: 43; (b) HVR-L2 comprising the amino acid sequence of SEQ ID NO: 44; and (c) HVR-L3 comprising the amino acid sequence of SEQ ID NO: 45.

In another aspect, an antibody-drug conjugate of the invention comprises an antibody comprising (a) a VH domain comprising at least one, at least two, or all three VH HVR sequences selected from (i) HVR-H1 comprising the amino acid sequence of SEQ ID NO: 40, (ii) HVR-H$_2$ comprising the amino acid sequence of SEQ ID NO: 41, and (iii) HVR-H3 comprising an amino acid sequence selected from SEQ ID NO: 42; and (b) a VL domain comprising at least one, at least two, or all three VL HVR sequences selected from (i) HVR-L1 comprising the amino acid sequence of SEQ ID NO: 43, (ii) HVR-L2 comprising the amino acid sequence of SEQ ID NO: 44, and (c) HVR-L3 comprising the amino acid sequence of SEQ ID NO: 45.

In another aspect, the invention provides an antibody-drug conjugate comprising an antibody that comprises (a) HVR-H1 comprising the amino acid sequence of SEQ ID NO: 40 (b) HVR-H$_2$ comprising the amino acid sequence of SEQ ID NO: 41; (c) HVR-H3 comprising the amino acid sequence of SEQ ID NO: 42; (d) HVR-L1 comprising the amino acid sequence of SEQ ID NO: 43; (e) HVR-L2 comprising the amino acid sequence of SEQ ID NO: 44; and (f) HVR-L3 comprising the amino acid sequence of SEQ ID NO: 45.

In any of the above embodiments, an anti-STEAP-1 antibody of an antibody-drug conjugate is humanized. In one embodiment, an anti-STEAP-1 antibody comprises HVRs as in any of the above embodiments, and further comprises a human acceptor framework, e.g. a human immunoglobulin framework or a human consensus framework.

In another aspect, an anti-STEAP-1 antibody of an antibody-drug conjugate comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 46. In certain embodiments, a VH sequence having at least 90%, 91%, 92%, 93%, 94%, 95%, 96%, 97%, 98%, or 99% identity to the amino acid sequence of SEQ ID NO: 46 contains substitutions (e.g., conservative substitutions), insertions, or deletions relative to the reference sequence, but an anti-STEAP-1 antibody comprising that sequence retains the ability to bind to STEAP-1. In certain embodiments, a total of 1 to 10 amino acids have been substituted, inserted and/or deleted in SEQ ID NO: 46. In certain embodiments, a total of 1 to 5 amino acids have been substituted, inserted and/or deleted in SEQ ID NO: 46. In certain embodiments, substitutions, insertions, or deletions occur in regions outside the HVRs (i.e., in the FRs). Optionally, the anti-STEAP-1 antibody comprises the VH sequence of SEQ ID NO: 46, including post-translational modifications of that sequence. In a particular embodiment, the VH comprises one, two or three HVRs selected from: (a) HVR-H1 comprising the amino acid sequence of SEQ ID NO: 40, (b) HVR-H$_2$ comprising the amino acid sequence of SEQ ID NO: 41, and (c) HVR-H3 comprising the amino acid sequence of SEQ ID NO: 42.

In another aspect, an anti-STEAP-1 antibody of an antibody-drug conjugate is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 47. In certain embodiments, a VL sequence having at least 90%, 91%, 92%, 93%, 94%, 95%, 96%, 97%, 98%, or 99% identity to the amino acid sequence of SEQ ID NO: 47 contains substitutions (e.g., conservative substitutions), insertions, or deletions relative to the reference sequence, but an anti-STEAP-1 antibody comprising that sequence retains the ability to bind to STEAP-1. In certain embodiments, a total of 1 to 10 amino acids have been substituted, inserted and/or deleted in SEQ ID NO: 47 In certain embodiments, a total of 1 to 5 amino acids have been substituted, inserted and/or deleted in SEQ ID NO: 47. In certain embodiments, the substitutions, insertions, or deletions occur in regions outside the HVRs (i.e., in the FRs). Optionally, the anti-STEAP-1 antibody comprises the VL sequence of SEQ ID NO: 47, including post-translational modifications of that sequence. In a particular embodiment, the VL comprises one, two or three HVRs selected from (a) HVR-L1 comprising the amino acid sequence of SEQ ID NO: 43; (b) HVR-L2 comprising the amino acid sequence of SEQ ID NO: 44; and (c) HVR-L3 comprising the amino acid sequence of SEQ ID NO: 45.

In another aspect, an antibody-drug conjugate comprising an anti-STEAP-1 antibody is provided, wherein the antibody comprises a VH as in any of the embodiments provided above, and a VL as in any of the embodiments provided above.

In one embodiment, an antibody-drug conjugate is provided, wherein the antibody comprises the VH and VL sequences in SEQ ID NO: 46 and SEQ ID NO: 47, respectively, including post-translational modifications of those sequences.

In a further aspect, provided herein are antibody-drug conjugate comprising antibodies that bind to the same epitope as an anti-STEAP-1 antibody provided herein. For example, in certain embodiments, an immunoconjugate is provided comprising an antibody that binds to the same epitope as an anti-STEAP-1 antibody comprising a VH sequence of SEQ ID NO: 46 and a VL sequence of SEQ ID NO: 47, respectively.

In a further aspect of the invention, an anti-STEAP-1 antibody of an antibody-drug conjugate according to any of the above embodiments is a monoclonal antibody, including a human antibody. In one embodiment, an anti-STEAP-1 antibody of an antibody-drug conjugate is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

HVR-H$_2$ comprising the amino acid sequence of SEQ ID NO: 49; (c) HVR-H3 comprising the amino acid sequence of SEQ ID NO: 50.

In another aspect, the invention provides an antibody-drug conjugate comprising an antibody that comprises at least one, at least two, or all three VL HVR sequences selected from (a) HVR-L1 comprising the amino acid sequence of SEQ ID NO: 51; (b) HVR-L2 comprising the amino acid sequence of SEQ ID NO: 52; and (c) HVR-L3 comprising the amino acid sequence of SEQ ID NO: 53. In one embodiment, the antibody comprises (a) HVR-L1 comprising the amino acid sequence of SEQ ID NO: 51; (b) HVR-L2 comprising the amino acid sequence of SEQ ID NO: 52; and (c) HVR-L3 comprising the amino acid sequence of SEQ ID NO: 53.

Table of STEAP Antibody Sequences

| SEQ ID NO | Description | Sequence |
|---|---|---|
| 40 | Anti-STEAP-1 HVR-H1 | GYSITSDYAW N |
| 41 | Anti-STEAP-1 HVR-H2 | GYISNSGSTS YNPSLKS |
| 42 | Anti-STEAP-1 HVR-H3 | ERNYDYDDYY YAMDY |
| 43 | Anti-STEAP-1 HVR-L1 | KSSQSLLYRS NQKNYLA |
| 44 | Anti-STEAP-1 HVR-L2 | WASTRES |
| 45 | Anti-STEAP-1 HVR-L3 | QQYYNYPRT |
| 46 | Anti-STEAP-1 heavy chain variable region | EVQLVESGGG LVQPGGSLRL SCAVSGYSIT SDYAVVNWVRQ APGKGLEWVG YISNSGSTSY NPSLKSRFTI SRDTSKNTLY LQMNSLRAED TAVYYCARER NYDYDDYYA MDYWGQGTLV TVSS |
| 47 | Anti-STEAP-1 light chain variable region | DIQMTQSPSS LSASVGDRVT ITCKSSQSLL YRSNQKNYLA WYQQKPGKAP KLLIYWASTR ESGVPSRFSG SGSGTDFTLT ISSLQPEDFA TYYCQQYYNY PRTFGQGTKV EIK |

Anti-NaPi2b Antibodies

In certain embodiments, an ADC comprises anti-NaPi2b antibodies. In some embodiments, the invention provides an antibody-drug conjugate comprising an anti-NaPi2b antibody comprising at least one, two, three, four, five, or six HVRs selected from (a) HVR-H1 comprising the amino acid sequence of SEQ ID NO: 48; (b) HVR-H$_2$ comprising the amino acid sequence of SEQ ID NO: 49; (c) HVR-H3 comprising the amino acid sequence of SEQ ID NO: 50; (d) HVR-L1 comprising the amino acid sequence of SEQ ID NO: 51; (e) HVR-L2 comprising the amino acid sequence of SEQ ID NO: 52 and (f) HVR-L3 comprising the amino acid sequence of SEQ ID NO: 53.

In one aspect, the invention provides an antibody-drug conjugate comprising an antibody that comprises at least one, at least two, or all three VH HVR sequences selected from (a) HVR-H1 comprising the amino acid sequence of SEQ ID NO: 48; (b) HVR-H$_2$ comprising the amino acid sequence of SEQ ID NO: 49; (c) HVR-H3 comprising the amino acid sequence of SEQ ID NO: 50. In a further embodiment, the antibody comprises (a) HVR-H1 comprising the amino acid sequence of SEQ ID NO: 48; (b)

In another aspect, an antibody-drug conjugate of the invention comprises an antibody comprising (a) a VH domain comprising at least one, at least two, or all three VH HVR sequences selected from (i) HVR-H1 comprising the amino acid sequence of SEQ ID NO: 48, (ii) HVR-H$_2$ comprising the amino acid sequence of SEQ ID NO: 49, and (iii) HVR-H3 comprising an amino acid sequence selected from SEQ ID NO: 50; and (b) a VL domain comprising at least one, at least two, or all three VL HVR sequences selected from (i) HVR-L1 comprising the amino acid sequence of SEQ ID NO: 51, (ii) HVR-L2 comprising the amino acid sequence of SEQ ID NO: 52, and (c) HVR-L3 comprising the amino acid sequence of SEQ ID NO: 53.

In another aspect, the invention provides an antibody-drug conjugate comprising an antibody that comprises (a) HVR-H1 comprising the amino acid sequence of SEQ ID NO: 48 (b) HVR-H$_2$ comprising the amino acid sequence of SEQ ID NO: 49; (c) HVR-H3 comprising the amino acid sequence of SEQ ID NO: 50; (d) HVR-L1 comprising the amino acid sequence of SEQ ID NO: 51; (e) HVR-L2 comprising the amino acid sequence of SEQ ID NO: 52; and (f) HVR-L3 comprising the amino acid sequence of SEQ ID NO: 53.

In any of the above embodiments, an anti-NaPi2b antibody of an antibody-drug conjugate is humanized. In one embodiment, an anti-NaPi2b antibody comprises HVRs as in any of the above embodiments, and further comprises a human acceptor framework, e.g. a human immunoglobulin framework or a human consensus framework.

In another aspect, an anti-NaPi2b antibody of an antibody-drug conjugate comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 54. In certain embodiments, a VH sequence having at least 90%, 91%, 92%, 93%, 94%, 95%, 96%, 97%, 98%, or 99% identity to the amino acid sequence of SEQ ID NO: 54 contains substitutions (e.g., conservative substitutions), insertions, or deletions relative to the reference sequence, but an anti-NaPi2b antibody comprising that sequence retains the ability to bind to NaPi2b. In certain embodiments, a total of 1 to 10 amino acids have been substituted, inserted and/or deleted in SEQ ID NO: 54. In certain embodiments, a total of 1 to 5 amino acids have been substituted, inserted and/or deleted in SEQ ID NO: 54. In certain embodiments, substitutions, insertions, or deletions occur in regions outside the HVRs (i.e., in the FRs). Optionally, the anti-NaPi2b antibody comprises the VH sequence of SEQ ID NO: 54, including post-translational modifications of that sequence. In a particular embodiment, the VH comprises one, two or three HVRs selected from: (a) HVR-H1 comprising the amino acid sequence of SEQ ID NO: 48, (b) HVR-H2 comprising the amino acid sequence of SEQ ID NO: 49, and (c) HVR-H3 comprising the amino acid sequence of SEQ ID NO: 50.

In another aspect, an anti-NaPi2b antibody of an antibody-drug conjugate is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 55. In certain embodiments, a VL sequence having at least 90%, 91%, 92%, 93%, 94%, 95%, 96%, 97%, 98%, or 99% identity to the amino acid sequence of SEQ ID NO: 55 contains substitutions (e.g., conservative substitutions), insertions, or deletions relative to the reference sequence, but an anti-NaPi2b antibody comprising that sequence retains the ability to bind to anti-NaPi2b. In certain embodiments, a total of 1 to 10 amino acids have been substituted, inserted and/or deleted in SEQ ID NO: 55. In certain embodiments, a total of 1 to 5 amino acids have been substituted, inserted and/or deleted in SEQ ID NO: 55. In certain embodiments, the substitutions, insertions, or deletions occur in regions outside the HVRs (i.e., in the FRs). Optionally, the anti-NaPi2b antibody comprises the VL sequence of SEQ ID NO: 55, including post-translational modifications of that sequence. In a particular embodiment, the VL comprises one, two or three HVRs selected from (a) HVR-L1 comprising the amino acid sequence of SEQ ID NO: 51; (b) HVR-L2 comprising the amino acid sequence of SEQ ID NO: 52; and (c) HVR-L3 comprising the amino acid sequence of SEQ ID NO: 53.

In another aspect, an antibody-drug conjugate comprising an anti-NaPi2b antibody is provided, wherein the antibody comprises a VH as in any of the embodiments provided above, and a VL as in any of the embodiments provided above.

In one embodiment, an antibody-drug conjugate is provided, wherein the antibody comprises the VH and VL sequences in SEQ ID NO: 54 and SEQ ID NO: 55, respectively, including post-translational modifications of those sequences.

In a further aspect, provided herein are antibody-drug conjugate comprising antibodies that bind to the same epitope as an anti-NaPi2b antibody provided herein. For example, in certain embodiments, an immunoconjugate is provided comprising an antibody that binds to the same epitope as an anti-NaPi2b antibody comprising a VH sequence of SEQ ID NO: 54 and a VL sequence of SEQ ID NO: 55, respectively.

In further aspect of the invention, an anti-NaPi2b antibody of an antibody-drug conjugate according to any of the above embodiments is a monoclonal antibody, including a human antibody. In one embodiment, an anti-NaPi2b antibody of an antibody-drug conjugate is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

Table of NaPi2b Antibody Sequences

| SEQ ID NO | Description | Sequence |
|---|---|---|
| 48 | Anti-NaPi2b HVR-H1 | GFSFSDFAMS |
| 49 | Anti-NaPi2b HVR-H2 | ATIGR VAFHTYYPDSMKG |
| 50 | Anti-NaPi2b HVR-H3 | ARHRGFDVGHFDF |
| 51 | Anti-NaPi2b HVR-L1 | RSSETL VHSSGNTYLE |
| 52 | Anti-NaPi2b HVR-L2 | RVSNRFS |
| 53 | Anti-NaPi2b HVR-L3 | FQGSFNPLT |
| 54 | Anti-NaPi2b heavy chain variable region | EVQLVESGGGL VQPGGSLRLSCAASGFSFSDFAMSWV RQAPGKGLEWVATIGRVAFHTYYPDSMKGRFTISRDN SKNTLYLQMNSLRAEDTAVYYCARHRGFDVGHFDFW GQGTLVTVSS |

-continued

Table of NaPi2b Antibody Sequences

| SEQ ID NO | Description | Sequence |
|---|---|---|
| 55 | Anti-NaPi2b light chain variable region | DIQMTQSPSSLSASVGDRVTITCRSSETL VHSSGNTYLE WYQQKPGKAPKLLIYRVSNRFSGVPSRFSGSGSGTDFT LTISSLQPEDFATYYCFQGSFNPLTFGQGTKVEIKR |

Anti-CD79b Antibodies

In certain embodiments, an ADC comprises anti-CD79b antibodies. In some embodiments, the invention provides an antibody-drug conjugate comprising an anti-CD79b antibody comprising at least one, two, three, four, five, or six HVRs selected from (a) HVR-H1 comprising the amino acid sequence of SEQ ID NO: 58; (b) HVR-H$_2$ comprising the amino acid sequence of SEQ ID NO: 59; (c) HVR-H3 comprising the amino acid sequence of SEQ ID NO: 60; (d) HVR-L1 comprising the amino acid sequence of SEQ ID NO: 61; (e) HVR-L2 comprising the amino acid sequence of SEQ ID NO: 62; and (f) HVR-L3 comprising the amino acid sequence of SEQ ID NO: 63.

In one aspect, the invention provides an antibody-drug conjugate comprising an antibody that comprises at least one, at least two, or all three VH HVR sequences selected from (a) HVR-H1 comprising the amino acid sequence of SEQ ID NO: 58; (b) HVR-H$_2$ comprising the amino acid sequence of SEQ ID NO: 59; and (c) HVR-H3 comprising the amino acid sequence of SEQ ID NO: 60. In a further embodiment, the antibody comprises (a) HVR-H1 comprising the amino acid sequence of SEQ ID NO: 58; (b) HVR-H$_2$ comprising the amino acid sequence of SEQ ID NO: 59; and (c) HVR-H3 comprising the amino acid sequence of SEQ ID NO: 60.

In another aspect, the invention provides an antibody-drug conjugate comprising an antibody that comprises at least one, at least two, or all three VL HVR sequences selected from (a) HVR-L1 comprising the amino acid sequence of SEQ ID NO: 61; (b) HVR-L2 comprising the amino acid sequence of SEQ ID NO: 62; and (c) HVR-L3 comprising the amino acid sequence of SEQ ID NO: 63. In one embodiment, the antibody comprises (a) HVR-L1 comprising the amino acid sequence of SEQ ID NO: 61; (b) HVR-L2 comprising the amino acid sequence of SEQ ID NO: 62; and (c) HVR-L3 comprising the amino acid sequence of SEQ ID NO: 63.

In another aspect, an antibody-drug conjugate of the invention comprises an antibody comprising (a) a VH domain comprising at least one, at least two, or all three VH HVR sequences selected from (i) HVR-H1 comprising the amino acid sequence of SEQ ID NO: 58, (ii) HVR-H$_2$ comprising the amino acid sequence of SEQ ID NO: 59, and (iii) HVR-H3 comprising an amino acid sequence selected from SEQ ID NO: 60; and (b) a VL domain comprising at least one, at least two, or all three VL HVR sequences selected from (i) HVR-L1 comprising the amino acid sequence of SEQ ID NO: 61, (ii) HVR-L2 comprising the amino acid sequence of SEQ ID NO: 62, and (iii) HVR-L3 comprising the amino acid sequence of SEQ ID NO: 63.

In another aspect, the invention provides an antibody-drug conjugate comprising an antibody that comprises (a) HVR-H1 comprising the amino acid sequence of SEQ ID NO: 58; (b) HVR-H$_2$ comprising the amino acid sequence of SEQ ID NO: 59; (c) HVR-H3 comprising the amino acid sequence of SEQ ID NO: 60; (d) HVR-L comprising the amino acid sequence of SEQ ID NO: 61; (e) HVR-L2 comprising the amino acid sequence of SEQ ID NO: 62; and (f) HVR-L3 comprising the amino acid sequence of SEQ ID NO: 63.

In any of the above embodiments, an anti-CD79b antibody of an antibody-drug conjugate is humanized. In one embodiment, an anti-CD79b antibody comprises HVRs as in any of the above embodiments, and further comprises a human acceptor framework, e.g. a human immunoglobulin framework or a human consensus framework.

In another aspect, an anti-CD79b antibody of an antibody-drug conjugate comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 56. In certain embodiments, a VH sequence having at least 90%, 91%, 92%, 93%, 94%, 95%, 96%, 97%, 98%, or 99% identity to the amino acid sequence of SEQ ID NO: 56 contains substitutions (e.g., conservative substitutions), insertions, or deletions relative to the reference sequence, but an anti-CD79b antibody comprising that sequence retains the ability to bind to CD79b. In certain embodiments, a total of 1 to 10 amino acids have been substituted, inserted and/or deleted in SEQ ID NO: 56. In certain embodiments, a total of 1 to 5 amino acids have been substituted, inserted and/or deleted in SEQ ID NO: 56. In certain embodiments, substitutions, insertions, or deletions occur in regions outside the HVRs (i.e., in the FRs). Optionally, the anti-CD79b antibody comprises the VH sequence of SEQ ID NO: 8, including post-translational modifications of that sequence. In a particular embodiment, the VH comprises one, two or three HVRs selected from: (a) HVR-H1 comprising the amino acid sequence of SEQ ID NO: 58, (b) HVR-H$_2$ comprising the amino acid sequence of SEQ ID NO: 59, and (c) HVR-H3 comprising the amino acid sequence of SEQ ID NO: 60.

In another aspect, an anti-CD79b antibody of an antibody-drug conjugate is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 57. In certain embodiments, a VL sequence having at least 90%, 91%, 92%, 93%, 94%, 95%, 96%, 97%, 98%, or 99% identity to the amino acid sequence of SEQ ID NO: 57 contains substitutions (e.g., conservative substitutions), insertions, or deletions relative to the reference sequence, but an anti-CD79b antibody comprising that sequence retains the ability to bind to CD79b. In certain embodiments, a total of 1 to 10 amino acids have been substituted, inserted and/or deleted in SEQ ID NO: 57. In certain embodiments, a total of 1 to 5 amino acids have been substituted, inserted and/or deleted in SEQ ID NO: 57. In certain embodiments, the substitutions, insertions, or deletions occur in regions outside the HVRs (i.e., in the FRs). Optionally, the anti- CD79b antibody comprises the VL sequence of SEQ ID NO: 57, including post-translational modifications of that sequence. In a particular embodiment, the VL comprises one, two or three HVRs selected from (a) HVR-L1 comprising the amino acid sequence of SEQ ID NO: 61; (b) HVR-L2 comprising the amino acid sequence of SEQ ID NO: 62; and (c) HVR-L3 comprising the amino acid sequence of SEQ ID NO: 63.

In another aspect, an antibody-drug conjugate comprising an anti-CD79b antibody is provided, wherein the antibody comprises a VH as in any of the embodiments provided above, and a VL as in any of the embodiments provided above.

In one embodiment, an antibody-drug conjugate is provided, wherein the antibody comprises the VH and VL sequences in SEQ ID NO: 56 and SEQ ID NO: 57, respectively, including post-translational modifications of those sequences.

In a further aspect, provided herein are antibody-drug conjugate comprising antibodies that bind to the same epitope as an anti-CD79b antibody provided herein. For example, in certain embodiments, an immunoconjugate is provided comprising an antibody that binds to the same epitope as an anti-CD79b antibody comprising a VH sequence of SEQ ID NO: 56 and a VL sequence of SEQ ID NO: 57, respectively.

In a further aspect of the invention, an anti-CD79b antibody of an antibody-drug conjugate according to any of the above embodiments is a monoclonal antibody, including a human antibody. In one embodiment, an anti-CD79b antibody of an antibody-drug conjugate is an antibody fragment, e.g., a Fv, Fab, Fab', scFv, diabody, or F(ab')₂ fragment. In another embodiment, the antibody is a substantially full length antibody, e.g., an IgG1 antibody, IgG2a antibody or other antibody class or isotype as defined herein.

Table of CD79b Antibody Sequences

| SEQ ID NO | Description | Sequence |
|---|---|---|
| 56 | anti-CD79b huMA79bv28 heavy chain variable region | EVQLVESGGG LVQPGGSLRL SCAASGYTFS SYWIEWVRQA PGKGLEWIGE ILPGGGDTNY NEIFKGRATF SADTSKNTAY LQMNSLRAED TAVYYCTRRV PIRLDYWGQG TLVTVSS |
| 57 | anti-CD79b huMA79bv28 light chain variable region | DIQLTQSPSS LSASVGDRVT ITCKASQSVD YEGDSFLNWY QQKPGKAPKL LIYAASNLES GVPSRFSGSG SGTDFTLTIS SLQPEDFATY YCQQSNEDPL TFGQGTKVEI KR |
| 58 | anti-CD79b huMA79bv28 HVR-H1 | GYTFSSYWIE |
| 59 | anti-CD79b huMA79bv28 HVR-H2 | GEILPGGGDTNYNEIFKG |
| 60 | anti-CD79b huMA79bv28 HVR-H3 | TRRVPIRLDY |
| 61 | anti-CD79b huMA79bv28 HVR-L1 | KASQSVDYEGDSFLN |
| 62 | anti-CD79b huMA79bv28 HVR-L2 | AASNLES |
| 63 | anti-CD79b huMA79bv28 HVR-L3 | QQSNEDPLT |

Human HER2 Precursor Protein Details of an exemplary human HER2 precursor protein with signal sequences is provided below

| SEQ ID NO | Description | Sequence |
|---|---|---|
| 64 | Exemplary human HER2 precursor protein, with signal sequence | MELAALCRWG LLLALLPPGA ASTQVCTGTD<br>MKLRLPASPE THLDMLRHLY QGCQVVQGNL<br>ELTYLPTNAS LSFLQDIQEV QGYVLIAHNQ<br>VRQVPLQRLR IVRGTQLFED NYALAVLDNG<br>DPLNNTTPVT GASPGGLREL QLRSLTEILK<br>GGVLIQRNPQ LCYQDTILWK DIFHKNNQLA<br>LTLIDTNRSR ACHPCSPMCK GSRCWGESSE<br>DCQSLTRTVC AGGCARCKGP LPTDCCHEQC<br>AAGCTGPKHS DCLACLHFNH SGICELHCPA<br>LVTYNTDTFE SMPNPEGRYT FGASCVTACP<br>YNYLSTDVGS CTLVCPLHNQ EVTAEDGTQR<br>CEKCSKPCAR VCYGLGMEHL REVRAVTSAN<br>IQEFAGCKKI FGSLAFLPES FDGDPASNTA<br>PLQPEQLQVF ETLEEITGYL YISAWPDSLP<br>DLSVFQNLQV IRGRILHNGA YSLTLQGLGI<br>SWLGLRSLRE LGSGLALIHH NTHLCFVHTV<br>PWDQLFRNPH QALLHTANRP EDECVGEGLA<br>CHQLCARGHC WGPGPTQCVN CSQFLRGQEC<br>VEECRVLQGL PREYVNARHC LPCHPECQPQ<br>NGSVTCFGPE ADQCVACAHY KDPPFCVARC<br>PSGVKPDLSY MPIWKFPDEE GACQPCPINC<br>THSCVDLDDK GCPAEQRASP LTSIISAVVG<br>ILLVVVLGVV FGILIKRRQQ KIRKYTMRRL<br>LQETELVEPL TPSGAMPNQA QMRILKETEL<br>RKVKVLGSGA FGTVYKGIWI PDGENVKIPV<br>AIKVLRENTS PKANKEILDE AYVMAGVGSP<br>YVSRLLGICL TSTVQLVTQL MPYGCLLDHV<br>RENRGRLGSQ DLLNWCMQIA KGMSYLEDVR<br>LVHRDLAARN VLVKSPNHVK ITDFGLARLL<br>DIDETEYHAD GGKVPIKWMA LESILRRRFT<br>HQSDVWSYGV TVWELMTFGA KPYDGIPARE<br>IPDLLEKGER LPQPPICTID VYMIMVKCWM<br>IDSECRPRFR ELVSEFSRMA RDPQRFVVIQ<br>NEDLGPASPL DSTFYRSLLE DDDMGDLVDA<br>EEYLVPQQGF FCPDPAPGAG GMVHHRHRSS<br>STRSGGGDLT LGLEPSEEEA PRSPLAPSEG<br>AGSDVFDGDL GMGAAKGLQS LPTHDPSPLQ<br>RYSEDPTVPL PSETDGYVAP LTCSPQPEYV<br>NQPDVRPQPP SPREGPLPAA RPAGATLERP<br>KTLSPGKNGV VKDVFAFGGA VENPEYLTPQ<br>GGAAPQPHPP PAFSPAFDNL YYWDQDPPER<br>GAPPSTFKGT PTAENPEYLG LDVPV |

Antibody Affinity

In certain embodiments, an antibody provided herein has a dissociation constant (Kd) of ≤1 μM, ≤100 nM, ≤50 nM, ≤10 nM≤5 nM, ≤1 nM, ≤0.1 nM, ≤0.01 nM, or ≤0.001 nM, and optionally is ≥$10^{-13}$ M. (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCFT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethyl-aminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$, See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instalments) or a 8000-series SLM-AMINCO spectrophotometer (ThermoSpectronic) with a stirred cuvette.

Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. Nat. Med. 9: 129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9: 129-134 (2003); and Hollinger et al., *Proc. Natl. Acad. Sci. USA* 90: 6444-6448 (1993). Triabodies and tetrabodies are also described in Hudson et al., *Nat. Med.* 9: 129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. *E. coli* or phage), as described herein.

Chimeric and Humanized Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13: 1619-1633 (2008), and are further described, e.g., in Riechmann et al., *Nature* 332:323-329 (1988); Queen et al., *Proc. Nat'l Acad. Sci. USA* 86: 10029-10033 (1989); U.S. Pat. Nos. 5,821,337, 7,527,791, 6,982,321, and 7,087,409; Kashmiri et al, *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol,* 151:2623 (1993)); human mature (somatically mutated) framework regions or human germline framework regions (see, e.g., Almagro and Fransson, *Front. Biosci.* 13: 1619-1633 (2008)); and framework regions derived from screening FR libraries (see, e.g., Baca et al., *J. Biol. Chem.* 272: 10678-10684 (1997) and Rosok et al., *J. Biol. Chem.* 271:22611-22618 (1996)).

Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23: 1117-1125 (2005). See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in L1 et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., J. Mol. Biol. 222: 581-597 (1992); Marks and Bradbury, *Methods in Molecular Biology* 248: 161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, bispecific antibodies may bind to two different epitopes of the same target. Bispecific antibodies may also be used to localize cytotoxic agents to cells which express the target. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). The term "knob-into-hole" or "KnH" technology as used herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces or VH/VL interfaces of antibodies (see, e.g., US 2011/0287009, US2007/0178552, WO 96/027011, WO 98/050431, Zhu et al., 1997, Protein *Science* 6:781-788, and WO2012/106587). In some embodiments, KnHs drive the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can be also be used to pair two different receptor extracellular domains together or any other polypeptide sequences that comprises different target recognition sequences (e.g., including affibodies, peptibodies and other Fc fusions).

The term "knob mutation" as used herein refers to a mutation that introduces a protuberance (knob) into a polypeptide at an interface in which the polypeptide interacts with another polypeptide. In some embodiments, the other polypeptide has a hole mutation.

The term "hole mutation" as used herein refers to a mutation that introduces a cavity (hole) into a polypeptide at an interface in which the polypeptide interacts with another polypeptide. In some embodiments, the other polypeptide has a knob mutation.

A brief nonlimiting discussion is provided below.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g., by altering nucleic acid encoding the interface). In some embodiments, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The side chain volumes of the various amino residues are shown, for example, in Table 1 of US2011/0287009. A mutation to introduce a "protuberance" may be referred to as a "knob mutation."

In some embodiments, import residues for the formation of a protuberance are naturally occurring amino acid residues selected from arginine (R), phenylalanine (F), tyrosine (Y) and tryptophan (W). In some embodiments, an import residue is tryptophan or tyrosine. In some embodiment, the original residue for the formation of the protuberance has a small side chain volume, such as alanine, asparagine, aspartic acid, glycine, serine, threonine or valine.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). In some embodiments, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. In some embodiments, import residues for the formation of a cavity are naturally occurring amino acid residues selected from alanine (A), serine (S), threonine (T) and valine (V). In some embodiments, an import residue is serine, alanine or threonine. In some embodiments, the original residue for the formation of the cavity has a large side chain volume, such as tyrosine, arginine, phenylalanine or tryptophan. A mutation to introduce a "cavity" may be referred to as a "hole mutation."

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity may, in some instances, rely on modeling the protuberance/cavity pair based upon a three-dimensional structure such as that obtained by X-ray crystallography or nuclear magnetic resonance (NMR). This can be achieved using widely accepted techniques in the art.

In some embodiments, a knob mutation in an IgG constant region is T366W (EU numbering). In some embodiments, a hole mutation in an IgG constant region comprises one or more mutations selected from T366S, L368A and Y407V (EU numbering). In some embodiments, a hole mutation in an IgG constant region comprises T366S, L368A and Y407V (EU numbering).

In some embodiments, a knob mutation in an IgG4 constant region is T366W (EU numbering). In some embodiments, a hole mutation in an IgG4 constant region comprises one or more mutations selected from T366S, L368A, and Y407V (EU numbering). In some embodiments, a hole mutation in an IgG4 constant region comprises T366S, L368A, and Y407V (EU numbering).

Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol, 148(5): 1547-1553 (1992)); using "diabody" technology for making bispecific antibody fragments (see, e.g., Hollinger et al., Proc. Natl Acad. Sci. USA, 90:6444-6448 (1993)); and using single-chain Fv (sFv) dimers (see, e.g. Gruber et al., J. Immunol, 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 206/0025576A1).

The antibody or fragment herein also includes a "Dual Acting FAb" or "DAF" comprising an antigen binding site that binds to the target as well as another, different antigen (see, US 2008/0069820, for example).

Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

Substitution, Insertion, and Deletion Variants

In certain embodiments, antibody variants having one or more amino acid substitutions are provided. Sites of interest for substitutional mutagenesis include the HVRs and FRs. Conservative substitutions are shown below in a Table of conservative substitutions under the heading of "preferred substitutions." More substantial changes are provided in the Table under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

| Table of conservative substitutions | | |
|---|---|---|
| Original Residue | Exemplary Substitutions | Preferred Substitutions |
| Ala (A) | Val; Leu; Ile | Val |
| Arg (R) | Lys; Gln; Asn | Lys |
| Asn (N) | Gln; His; Asp; Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |

-continued

Table of conservative substitutions

| Original Residue | Exemplary Substitutions | Preferred Substitutions |
| --- | --- | --- |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gin;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178: 1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244: 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336: 1239-1249 (2004); Yamane-Ohnuki et al. *Biotech. Bioeng.* 87: 614 (2004). Examples of cell lines capable of producing defucosylated antibodies include Led 3 CHO cells deficient in protein fucosylation (Ripka et al. *Arch. Biochem. Biophys.* 249:533-545 (1986); US Pat Appl No US 2003/0157108; and WO 2004/056312, especially at Example 11), and knockout cell lines, such as alpha-1,6-fucosyl transferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82: 1499-1502 (1985); 5,821,337 (see Bruggemann, M. et al., *J. Exp. Med.* 166: 1351-1361 (1987)).

Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202: 163 (1996); Cragg, M. S. et al., *Blood* 101: 1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12): 1759-1769 (2006)).

In some embodiments, one or more amino acid modifications may be introduced into the Fc portion of the antibody provided herein in order to increase IgG binding to the neonatal Fc receptor. In certain embodiments, the antibody comprises the following three mutations according to EU numbering: M252Y, S254T, and T256E (the "YTE mutation") (U.S. Pat. No. 8,697,650; see also Dall'Acqua et al., *Journal of Biological Chemistry* 281(33):23514-23524 (2006). In certain embodiments, the YTE mutation does not affect the ability of the antibody to bind to its cognate antigen. In certain embodiments, the YTE mutation increases the antibody's serum half-life compared to the native (i.e., non-YTE mutant) antibody. In some embodiments, the YTE mutation increases the serum half-life of the antibody by 3-fold compared to the native (i.e., non-YTE mutant) antibody. In some embodiments, the YTE mutation increases the serum half-life of the antibody by 2-fold compared to the native (i.e., non-YTE mutant) antibody. In some embodiments, the YTE mutation increases the serum half-life of the antibody by 4-fold compared to the native (i.e., non-YTE mutant) antibody. In some embodiments, the YTE mutation increases the serum half-life of the antibody by at least 5-fold compared to the native (i.e., non-YTE mutant) antibody. In some embodiments, the YTE mutation increases the serum half-life of the antibody by at least 10-fold compared to the native (i.e., non-YTE mutant) antibody. See, e.g., U.S. Pat. No. 8,697,650; see also Dall'Acqua et al., *Journal of Biological Chemistry* 281(33): 23514-23524 (2006).

In certain embodiments, the YTE mutant provides a means to modulate antibody-dependent cell-mediated cytotoxicity (ADCC) activity of the antibody. In certain embodiments, the YTEO mutant provides a means to modulate ADCC activity of a humanized IgG antibody directed against a human antigen. See, e.g., U.S. Pat. No. 8,697,650; see also Dall'Acqua et al., *Journal of Biological Chemistry* 281(33):23514-23524 (2006).

In certain embodiments, the YTE mutant allows the simultaneous modulation of serum half-life, tissue distribution, and antibody activity (e.g., the ADCC activity of an IgG antibody). See, e.g., U.S. Pat. No. 8,697,650; see also Dall'Acqua et al., *Journal of Biological Chemistry* 281(33): 23514-23524 (2006).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In certain embodiments, the proline at position 329 (EU numbering) (P329) of a wild-type human Fc region is substituted with glycine or arginine or an amino acid residue large enough to destroy the proline sandwich within the Fc/Fc gamma receptor interface, that is formed between the P329 of the Fc and tryptophane residues W87 and W110 of FcgRIII (Sondermann et al., Nature 406, 267-273 (20 Jul. 2000)). In a further embodiment, at least one further amino acid substitution in the Fc variant is S228P, E233P, L234A, L235A, L235E, N297A, N297D, or P331S and still in another embodiment said at least one further amino acid substitution is L234A and L235A of the human IgG1 Fc region or S228P and L235E of the human IgG4 Fc region, all according to EU numbering (U.S. Pat. No. 8,969,526 which is incorporated by reference in its entirety).

In certain embodiments, a polypeptide comprises the Fc variant of a wild-type human IgG Fc region wherein the polypeptide has P329 of the human IgG Fc region substituted with glycine and wherein the Fc variant comprises at least two further amino acid substitutions at L234A and L235A of the human IgG1 Fc region or S228P and L235E of the human IgG4 Fc region, and wherein the residues are numbered according to the EU numbering (U.S. Pat. No. 8,969,526 which is incorporated by reference in its entirety). In certain embodiments, the polypeptide comprising the P329G, L234A and L235A (EU numbering) substitutions exhibit a reduced affinity to the human FcγRIIIA and FcγRIIA, for down-modulation of ADCC to at least 20% of the ADCC induced by the polypeptide comprising the wild-type human IgG Fc region, and/or for down-modulation of ADCP (U.S. Pat. No. 8,969,526 which is incorporated by reference in its entirety).

In a specific embodiment the polypeptide comprising an Fc variant of a wildtype human Fc polypeptide comprises a triple mutation: an amino acid substitution at position Pro329, a L234A and a L235A mutation according to EU numbering (P329/LALA) (U.S. Pat. No. 8,969,526 which is incorporated by reference in its entirety). In specific embodiments, the polypeptide comprises the following amino acid substitutions: P329G, L234A, and L235A according to EU numbering.

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which improve binding of the Fc region to FcRn.

Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, Nature 322:738-40 (1988); U.S. Pat. Nos. 5,648,260; 5,624,821; and WO 94/29351 concerning other examples of Fc region variants.

Cysteine Engineered Antibody Variants

In certain embodiments, it may be desirable to create cysteine engineered antibodies, e.g., a "THIOMAB™" or TDC, in which one or more residues of an antibody are substituted with cysteine residues. In particular embodiments, the substituted residues occur at sites of the antibody that are available for conjugation. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: K149 (Kabat numbering) of the light chain; V205 (Kabat numbering) of the light chain; A118 (EU numbering) of the heavy chain; A140 (EU numbering) of the heavy chain; L174 (EU numbering) of the heavy chain; Y373 (EU numbering) of the heavy chain; and S400 (EU numbering) of the heavy chain Fc region. In specific embodiments, the antibodies described herein comprise the HC-A140C (EU numbering) cysteine substitution. In specific embodiments, the antibodies described herein comprise the LC-K149C (Kabat numbering) cysteine substitution. In specific embodiments, the antibodies described herein comprise the HC-A118C (EU numbering) cysteine substitution. Cysteine engineered antibodies may be generated as described, e.g., in U.S. Pat. No. 7,521,541.

In certain embodiments, the antibody comprises one of the following heavy chain cysteine substitutions:

| Chain (HC/LC) | Residue | EU Mutation Site # | Kabat Mutation Site # |
|---|---|---|---|
| HC | T | 114 | 110 |
| HC | A | 140 | 136 |
| HC | L | 174 | 170 |
| HC | L | 179 | 175 |
| HC | T | 187 | 183 |
| HC | T | 209 | 205 |
| HC | V | 262 | 258 |
| HC | G | 371 | 367 |
| HC | Y | 373 | 369 |
| HC | E | 382 | 378 |
| HC | S | 424 | 420 |
| HC | N | 434 | 430 |
| HC | Q | 438 | 434 |

In certain embodiments, the antibody comprises one of the following light chain cysteine substitutions:

| Chain (HC/LC) | Residue | EU Mutation Site # | Kabat Mutation Site # |
|---|---|---|---|
| LC | I | 106 | 106 |
| LC | R | 108 | 108 |
| LC | R | 142 | 142 |

| Chain (HC/LC) | Residue | EU Mutation Site # | Kabat Mutation Site # |
|---|---|---|---|
| LC | K | 149 | 149 |
| LC | V | 205 | 205 |

A nonlimiting exemplary hu7C2.v2.2.LA light chain (LC) K149C THIOMAB™ has the heavy chain and light chain amino acid sequences of SEQ ID NOs: 26 and 30, respectively. A non limiting exemplary hu7C2.v2.2.LA heavy chain (HC) A118C THIOMAB™ has the heavy chain and light chain amino acid sequences of SEQ ID NOs: 31 and 25, respectively.

Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1, 3, 6-trioxane, ethylene/maleic anhydride copolymer, polyaminoacids (either homopolymers or random copolymers), and dextran or poly(n-vinyl pyrrolidone)polyethylene glycol, propylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Recombinant Methods and Compositions

Antibodies may be produced using recombinant methods and compositions, e.g., as described in U.S. Pat. No. 4,816,567. In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0 Sp20 cell). In one embodiment, a method of making an antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fe effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N T, 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22: 1409-1414 (2004), and L1 et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977); baby hamster kidney cells (BHK); mouse Sertoli cells (TM4 cells as described, e.g., in Mather, *Biol. Reprod.* 23:243-251 (1980); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.*

383:44-68 (1982); MRC 5 cells; and FS4 cells. Other useful mammalian host cell lines include Chinese hamster ovary (CHO) cells, including DHFR CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

Administration & Dose

Compounds of formula (I) or formula (II) or pharmaceutically acceptable salts, solvates, tautomers, stereoisomers or mixtures thereof, may be administered alone or in combination with one or another or with one or more pharmacologically active compounds which are different from the compounds of formula (I) or formula (II).

Compounds of the invention may suitably be combined with various components to produce compositions of the invention. Suitably the compositions are combined with a pharmaceutically acceptable carrier or diluent to produce a pharmaceutical composition (which may be for human or animal use). Suitable carriers and diluents include isotonic saline solutions, for example phosphate-buffered saline. Useful pharmaceutical compositions and methods for their preparation may be found in standard pharmaceutical texts. See, for example, *Handbook for Pharmaceutical Additives*, 3rd Edition (eds. M. Ash and I. Ash), 2007 (Synapse Information Resources, Inc., Endicott, N.Y., USA) and Remington: *The Science and Practice of Pharmacy*, 21st Edition (ed. D. B. Troy) 2006 (Lippincott, Williams and Wilkins, Philadelphia, USA) which are incorporated herein by reference.

The compounds of the invention may be administered by any suitable route. Suitably the compounds of the invention will normally be administered orally or by any parenteral route, in the form of pharmaceutical preparations comprising the active ingredient, optionally in the form of a nontoxic organic, or inorganic, acid, or base, addition salt, in a pharmaceutically acceptable dosage form.

The compounds of the invention, their pharmaceutically acceptable salts, and pharmaceutically acceptable solvates of either entity can be administered alone but will generally be administered in admixture with a suitable pharmaceutical excipient diluent or carrier selected with regard to the intended route of administration and standard pharmaceutical practice.

For example, the compounds of the invention or pharmaceutically acceptable salts, solvates, tautomers, stereoisomers or mixtures thereof, can be administered orally, buccally or sublingually in the form of tablets, capsules (including soft gel capsules), ovules, elixirs, solutions or suspensions, which may contain flavouring or colouring agents, for immediate-, delayed-, modified-, sustained-, controlled-release or pulsatile delivery applications. The compounds of the invention may also be administered via fast dispersing or fast dissolving dosages forms.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients may be present both within the dosage form i.e. within the matrix, and/or on the dosage form i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol.

The compounds of the invention can also be administered parenterally, for example, intravenously, intra-arterially, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Suitably formulation of the invention is optimised for the route of administration e.g. oral, intravenously, etc.

Administration may be in one dose, continuously or intermittently (e.g. in divided doses at appropriate intervals) during the course of treatment. Methods of determining the most effective means and dosage are well known to a skilled person and will vary with the formulation used for therapy, the purpose of the therapy, the target cell(s) being treated, and the subject being treated. Single or multiple administrations can be carried out with the dose level and the dose regimen being selected by the treating physician, veterinarian, or clinician.

Depending upon the disorder and patient to be treated, as well as the route of administration, the compositions may be administered at varying doses. For example, a typical dosage for an adult human may be 100 ng to 25 mg (suitably about 1 micro g to about 10 mg) per kg body weight of the subject per day.

Suitably guidance may be taken from studies in test animals when estimating an initial dose for human subjects. For example when a particular dose is identified for mice, suitably an initial test dose for humans may be approx. 0.5× to 2× the mg/Kg value given to mice.

Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Isomers, Salts and Solvates

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; alpha- and beta-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH.

A reference to a class of structures may well include structurally isomeric forms falling within that class (e.g. $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not apply to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro. In some cases, the compounds of formula (I) can exist as tautomers. Suitably, the compounds of formula (I) include the keto-enol tautomers of the drawn structures.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof.

Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

Compounds formula (I) or formula (II), which include compounds specifically named above, may form pharmaceutically acceptable complexes, salts, solvates and hydrates. These salts include nontoxic acid addition salts (including di-acids) and base salts.

If the compound is cationic, or has a functional group which may be cationic (e.g. —NH$_2$ may be —NH$_3^+$), then an acid addition salt may be formed with a suitable anion. Examples of suitable inorganic anions include, but are not limited to, those derived from the following inorganic acids hydrochloric acid, nitric acid, nitrous acid, phosphoric acid, sulfuric acid, *sulphurous* acid, hydrobromic acid, hydroiodic acid, hydrofluoric acid, phosphoric acid and phosphorous acids. Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfonate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

For example, if the compound is anionic, or has a functional group which may be anionic (e.g. —COOH may be —COO$^-$, or —SO$_2$H may be —SO$_2^-$), then a base salt may be formed with a suitable cation. Examples of suitable inorganic cations include, but are not limited to, metal cations, such as an alkali or alkaline earth metal cation, ammonium and substituted ammonium cations, as well as amines. Examples of suitable metal cations include sodium (Na$^+$) potassium (K$^+$), magnesium (Mg$^{2+}$), calcium (Ca$^{2+}$), zinc (Zn$^{2+}$), and aluminum (Al$^{3+}$). Examples of suitable organic cations include, but are not limited to, ammonium ion (i.e. NH4$^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^-$. Examples of suitable amines include arginine, N,N'-dibenzylethylene-diamine, chloroprocaine, choline, diethylamine, diethanolamine, dicyclohexylamine, ethylenediamine, glycine, lysine, N-methylglucamine, olamine, 2-amino-2-hydroxymethyl-propane-1,3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2011)

Pharmaceutically acceptable salts may be prepared using various methods. For example, one may react a compound of formula (I) of formula (II) with an appropriate acid or base to give the desired salt. One may also react a precursor of the compound of formula (I) of formula (II) with an acid or base to remove an acid- or base-labile protecting group or to open a lactone or lactam group of the precursor. Additionally, one may convert a salt of the compound of formula (I) of formula (II) to another salt through treatment with an appropriate acid or base or through contact with an ion exchange resin. Following reaction, one may then isolate the salt by filtration if it precipitates from solution, or by evaporation to recover the salt. The degree of ionization of the salt may vary from completely ionized to almost non-ionized.

It may be convenient or desirable to prepare, purify, and/or handle a corresponding solvate of the active compound. The term "solvate" describes a molecular complex comprising the compound and one or more pharmaceutically acceptable solvent molecules (e.g., EtOH). The term "hydrate" is a solvate in which the solvent is water. Pharmaceutically acceptable solvates include those in which the solvent may be isotopically substituted (e.g., $D_2O$, acetone-d6, DMSO-d6).

A currently accepted classification system for solvates and hydrates of organic compounds is one that distinguishes between isolated site, channel, and metal-ion coordinated solvates and hydrates. See, e.g., K. R. Morris (H. G. Brittain ed.) Polymorphism in Pharmaceutical Solids (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion. When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. v In such cases, non-stoichiometry will typically be observed.

Compounds of formula (I) or formula (II), include imine, carbinolamine and carbinolamine ether forms of the PBD or PDD. The carbinolamine or the carbinolamine ether is formed when a nucleophilic solvent ($H_2O$, ROH) adds across the imine bond of the PBD or PDD moiety. The balance of these equilibria between these forms depend on the conditions in which the compounds are found, as well as the nature of the moiety itself.

These compounds may be isolated in solid form, for example, by lyophilisation.

Further particular and preferred aspects are set out in the accompanying independent and dependent claims. Features of the dependent claims may be combined with features of the independent claims as appropriate, and in combinations other than those explicitly set out in the claims.

Synthetic Strategies

The compounds of Formula (I) may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, *Comprehensive Organic Transformations, A Guide to Functional Group Preparations*, 2nd Ed (2010), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a diacid, etc.). In addition, in some instances, reaction intermediates may be used in subsequent steps without isolation or purification (i.e., in situ).

In some of the reaction schemes and examples below, certain compounds can be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry*, 4th Edition, (2006) and P. Kocienski, *Protective Groups*, 3rd Edition (2005).

Generally, the chemical transformations described throughout the specification may be carried out using substantially stoichiometric amounts of reactants, though certain reactions may benefit from using an excess of one or more of the reactants.

Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., $-78°$ C. to $0°$ C.). Any reference in the disclosure to a stoichiometric range, a temperature range, a pH range, etc., whether or not expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

Further particular and preferred aspects are set out in the accompanying independent and dependent claims. Features of the dependent claims may be combined with features of the independent claims as appropriate, and in combinations other than those explicitly set out in the claims.

BRIEF DESCRIPTION OF THE DRAWINGS

Embodiments of the present invention will now be described further, with reference to the accompanying drawings, in which:

FIG. 5 shows a sequence of the labelled strands of HexA, TyrT and MS1 DNA fragments used in the biophysical characterisation study.

FIG. 6 shows an autoradiograph of a denaturing polyacrylamide gel showing DNA interstrand cross-linking by 34 in linear $^{32}$P-end-labelled HexA DNA following overnight incubation at 37° C. at various concentrations.

FIG. 7 shows an autoradiograph of a denaturing polyacrylamide gel showing DNA interstrand cross-linking by the PBD dimer Talirine in linear $^{32}$P-end-labelled TyrT DNA following overnight incubation at 37° C. at various concentrations.

FIG. 10 shows fluorescently labelled DNA duplexes used in the FRET melting study to study the formation of interstrand (top) and intrastrand (bottom) cross-links. The labels were fluorescein (F) and dabcyl (Q).

EXAMPLES

General Remarks

Figure 1:
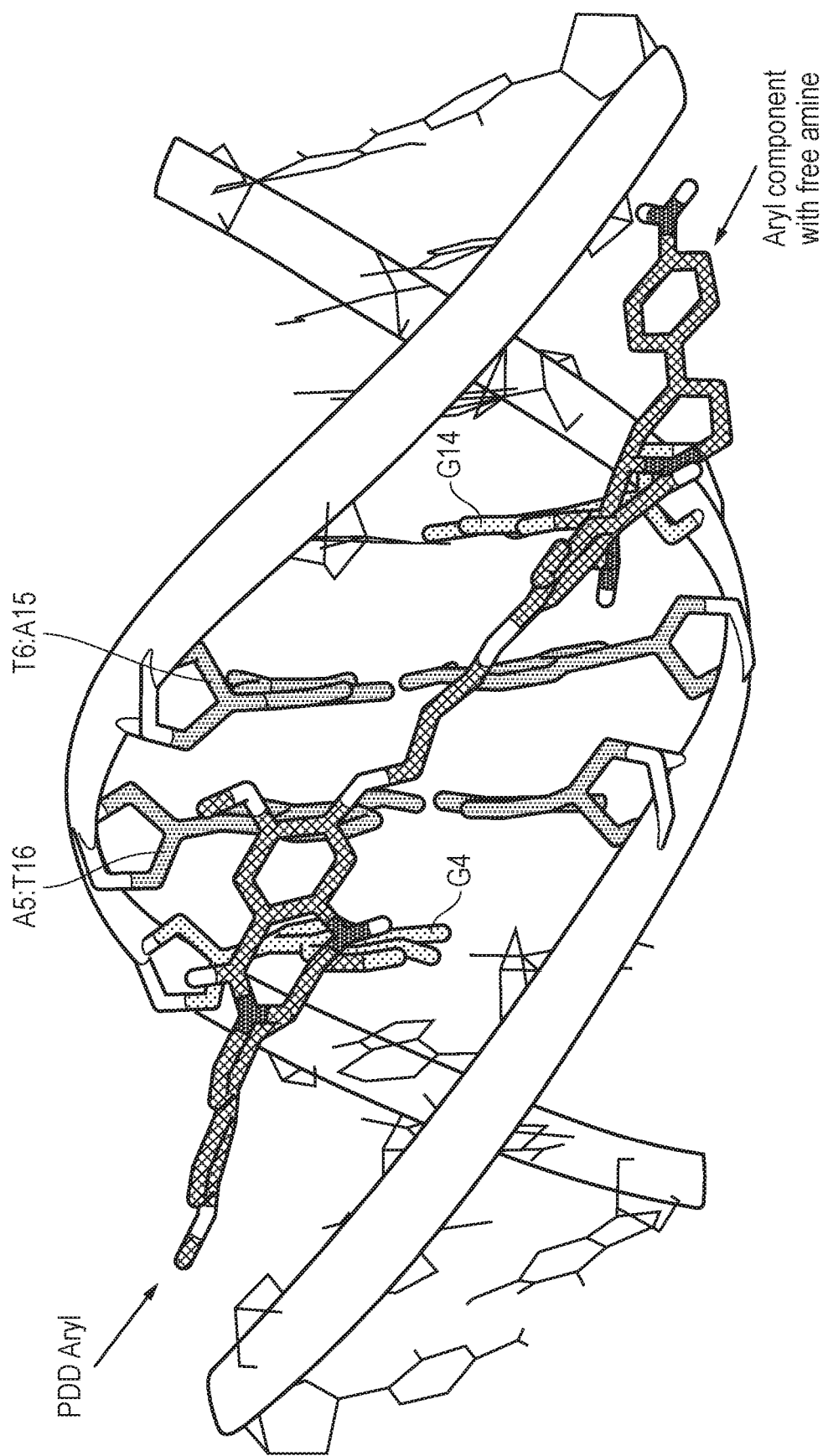
FIG. 1 shows a snapshot of molecular dynamics simulation of a PDD-Aryl Dimer (Structure 1, see Molecular Modelling Section) covalently bound to G4 and G14 of 5'-GCA<u>G</u>ATC(<u>G</u>)TGC-3'.

Unless otherwise stated, all synthetic building blocks and reagents were purchased from standard commercial suppliers including Maybridge Chemicals (UK), Fluorochem (USA), and Sigma-Aldrich (UK) and used as purchased. Solvents were purchased from Sigma-Aldrich (UK), VWR and Fisher Scientific (UK). Anhydrous reactions were carried out in pre-oven-dried glassware under an inert atmosphere of nitrogen. Anhydrous solvents were used as purchased without further drying. Thin Layer Chromatography (TLC) was performed on silica gel aluminium plates (Merck 60, $F_{254}$), and flash column chromatography was carried out either manually, using silica gel (Merck 9385, 230-400 mesh ASTM, 40-63 μM) (whilst monitoring by thin layer chromatography: UV (254 nm) and an aqueous alkaline solution of potassium permanganate as stain), or using a Biotage Isolera 1® automated Flash Chromatography System. All NMR spectra were obtained at room temperature using a Bruker DPX400 spectrometer or a Varian Mercury Vx, Agilent 400 MHz spectrometer, for which chemical shifts are expressed in ppm relative to the solvent and coupling constants are expressed in Hz. Microwave reactions were carried out on an Biotage Initiator® microwave synthesis reactor. Yields refer to isolated material (homogeneous by TLC or NMR) unless otherwise stated and names are assigned according to IUPAC nomenclature. All Liquid Chromatography Mass Spectroscopy (LCMS) analysis was performed on a Waters Alliance 2695 with water (A) and acetonitrile (B) comprising the mobile phases. Formic acid (0.1%) was added to both acetonitrile and water to ensure acidic conditions throughout the analysis. Function type: Diode array (535 scans). Column type: Monolithic C18 50×4.60 mm. Mass spectrometry data were collected using a Waters Micromass ZQ instrument coupled to a Waters 2695 HPLC with a Waters 2996 PDA. Waters Micromass ZQ parameters used were: Capillary (kV), 3.38; Cone (, 35; Extractor (V, 3.0; Source temperature (° C.), 100; De-solvation Temperature (° C.), 200; Cone flow rate (L/h), 50; De-solvation flow rate (L/h), 250. LCMS gradient conditions are described as follows. Hydrophobicity can be determined through computational methods (e.g., calculation of LogP), experimental (measurement of LogP) or through the use of chromatography-based techniques[22,23].

Method A (10 min): from 95% A/5% B to 50% B over 3 min. Then from 50% B to 80% B over 2 min. Then from 80% B to 95% B over 1.5 min and held constant for 1.5 min. This was then reduced to 5% B over 0.2 min and maintained to 5% B for 1.8 min. The flow rate was 0.5 mL/min, 200 μL was split via a zero dead volume T piece which passed into the mass spectrometer. The wavelength range of the UV detector was 220-400 nm.

Method B (5 min): from 95% A/5% B to 90% B over 3 min. Then from 90% B to 95% B over 0.5 min and held constant for 1 min. This was then reduced to 5% B over 0.5 min. The flow rate was 1.0 mL/min, 100 μL was split via a zero dead volume T piece which passed into the mass spectrometer. The wavelength range of the UV detector was 220-500 nm.

Example 1—Molecular Modelling

Molecular dynamics simulations were undertaken on a series of our novel PDD dimers and D-ring containing G-alkylating analogues.

Figure 2:
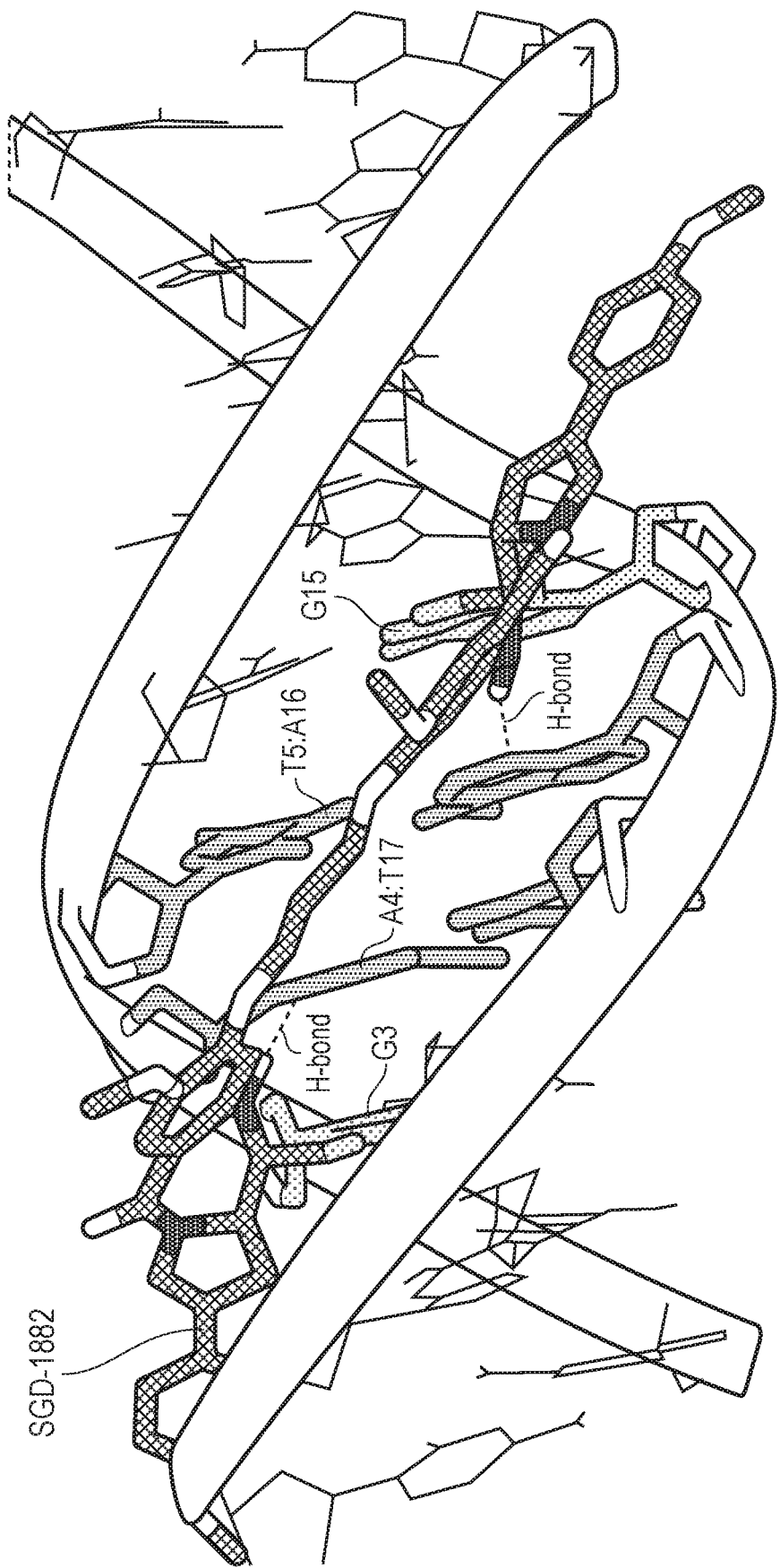
FIG. 2 shows a snapshot of molecular dynamics simulation of SGD-1882 (Seattle Genetics PBD dimer) covalently bound to G3 and G15 of 5'-GC<u>G</u>ATC(<u>G</u>)TCGC-3', illustrating a similar lack of DNA base-pair distortion (yellow).

Simulations (see FIG. 1) suggest that the C2-aryl substituted PDD (Structure 1 shown below) sits in the minor groove in a similar manner to the PBD dimer SGD-1882 (see FIG. 2). Extensive van der Waals interactions are formed between the central methylene linker and minor groove floor (cyan) and both aryl components enhance binding to DNA. As can be seen from FIG. 1 the PDD-Aryl Dimer (Structure 1) is covalently bound to G4 and G14 of 5'-GCA<u>G</u>ATC(<u>G</u>)TGC-3'. Little base-pair distortion (cyan) is observed in the central binding region, and both imines sit in the minor groove in a similar manner to the PBD molecules

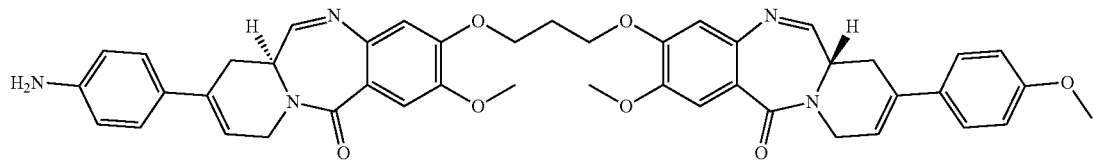

Structure 1-PDD-Aryl Dimer

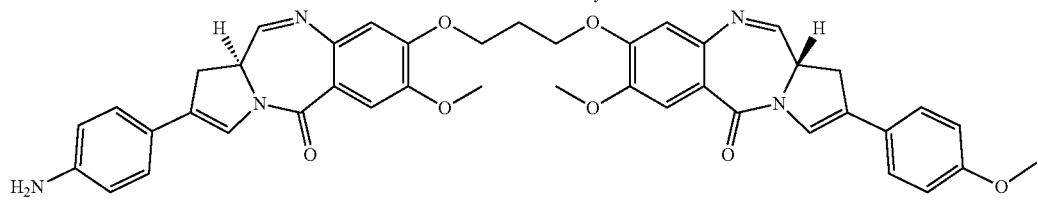

SGD-1882 (Seattle Genetics PBD dimer)

Figure 3:
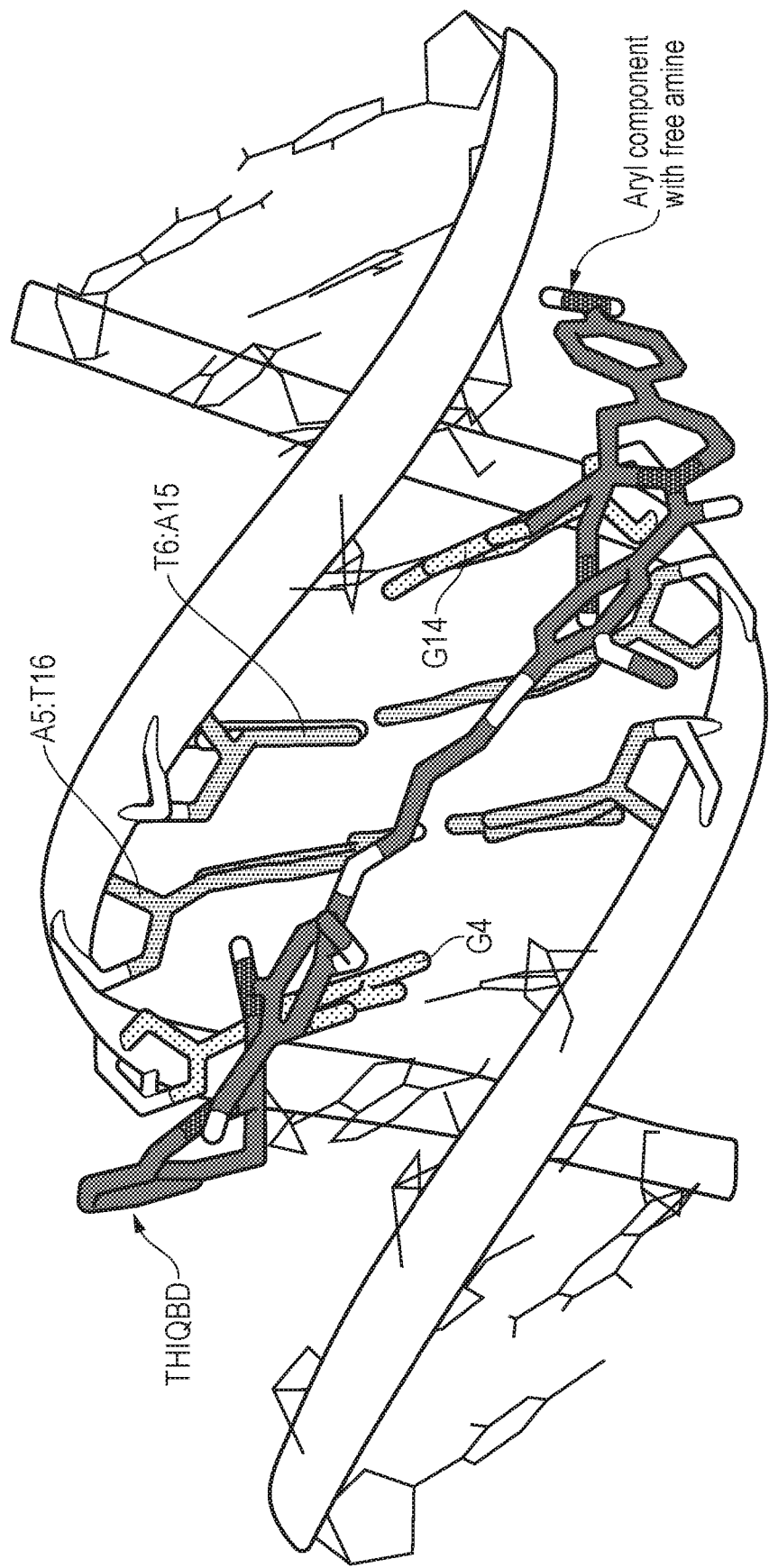
FIG. 3 shows a snapshot of molecular dynamics simulation of a THIQBD-PDD-Aryl Dimer (Structure 2, see Molecular Modelling Section) covalently bound to G4 and G14 of 5'-GCA<u>G</u>ATC(<u>G</u>)TGC-3'.

Similarly, the tetrahydroisoquinoline benzodiazepine fused ring system THIQBD-aryl PDD dimer (see Structure 2 below) shows excellent binding in the DNA with both imines sitting in the minor groove in a similar manner to the PBD dimers (see FIG. 3). Limited DNA distortion (orange) occurs in the central base-pairing, suggesting favourable isohelicity with the minor groove floor. Extensive van der Waals interactions are also formed between the trimethylene linker and DNA bases, which assist in restraining the molecule in the minor groove.

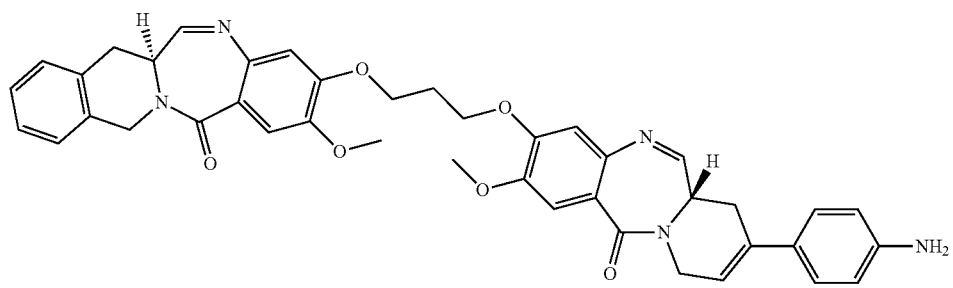

Structure 2 - THIQBD-aryl PDD dimer

Figure 4:
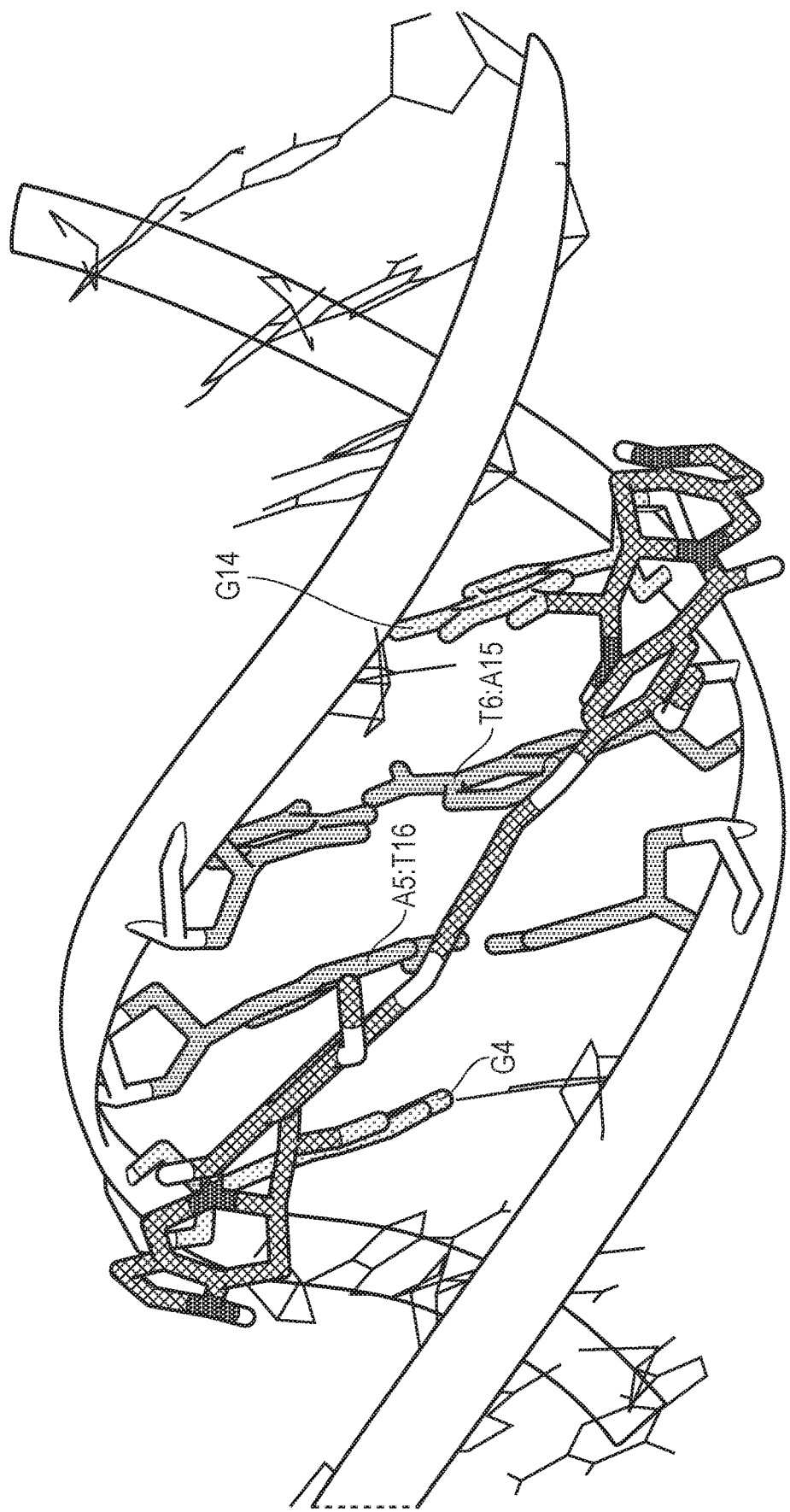
FIG. 4 shows a snapshot of molecular dynamics simulation of a 6-7-6-5 Dimer (Structure 3, see Molecular Modelling Section) covalently bound to G4 and G14 of 5'-GCA<u>G</u>ATC(<u>G</u>)TGC-3'.

The 6-7-6-5 dimer (Structure 3, shown below) also performs similar interactions with the minor groove of DNA, with excellent isohelicity observed (see FIG. 4). The molecular dynamics simulation of this 6-7-6-5 Dimer show that it is covalently bound to G4 and G14 of 5'-GCAGATC (G)TGC-3'. Little base-pair distortion (yellow) is observed in the central binding region, and both imines sit in the minor groove in a similar manner to the PBD molecules.

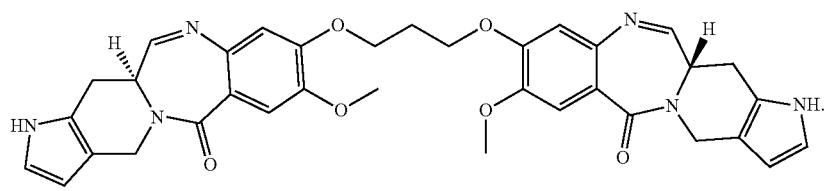

Structure 3 6-7-6-5 dimer

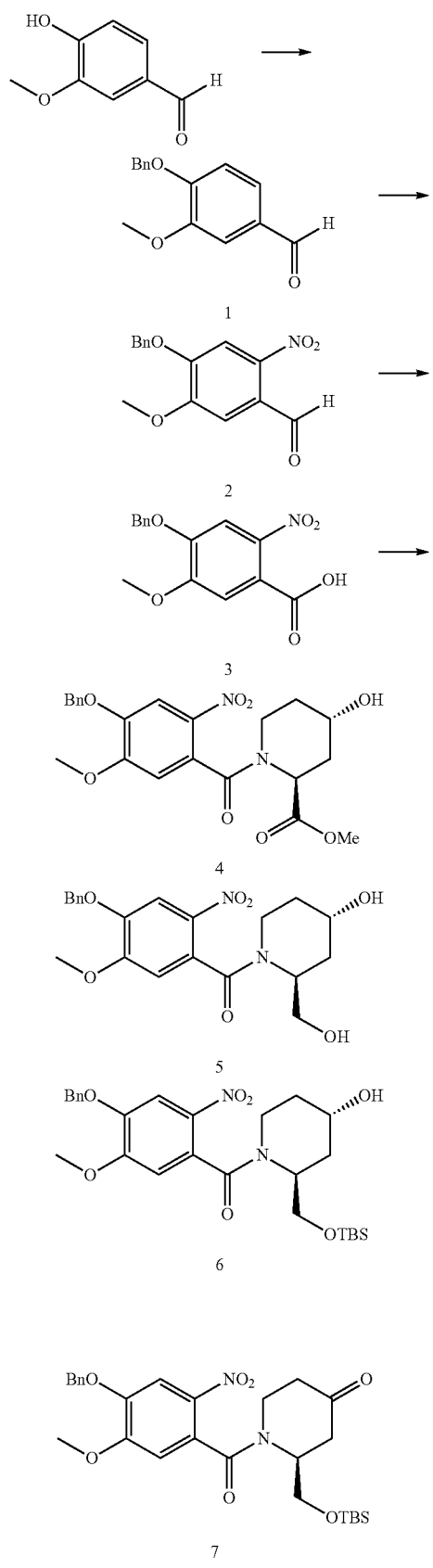
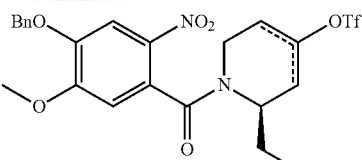
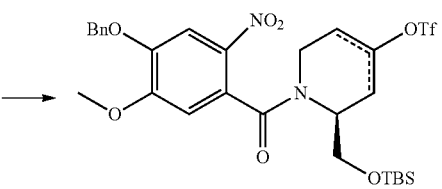

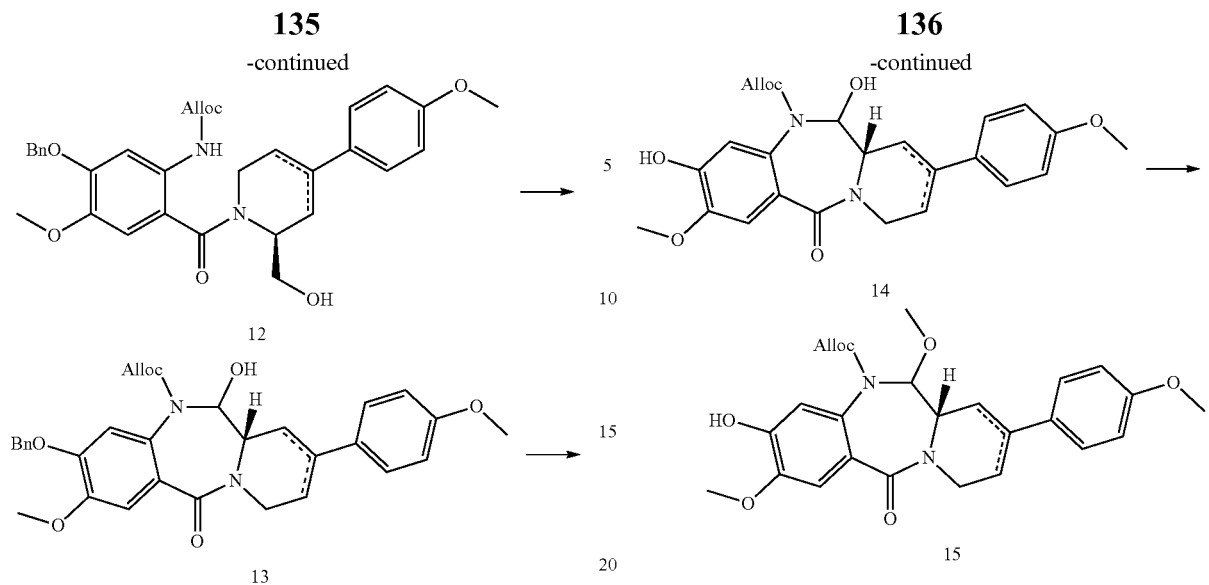
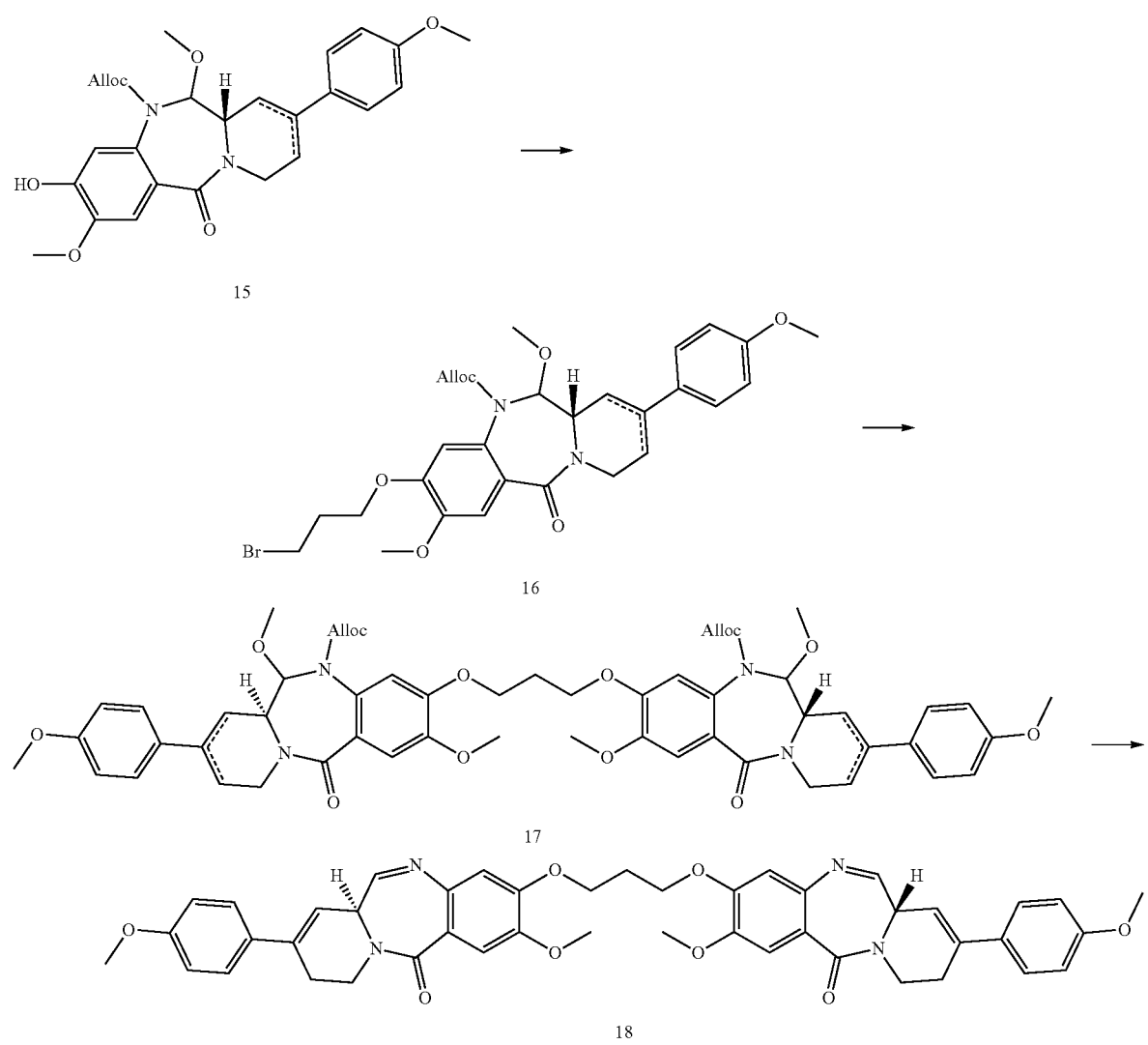
General synthetic scheme 3

General synthetic scheme 4
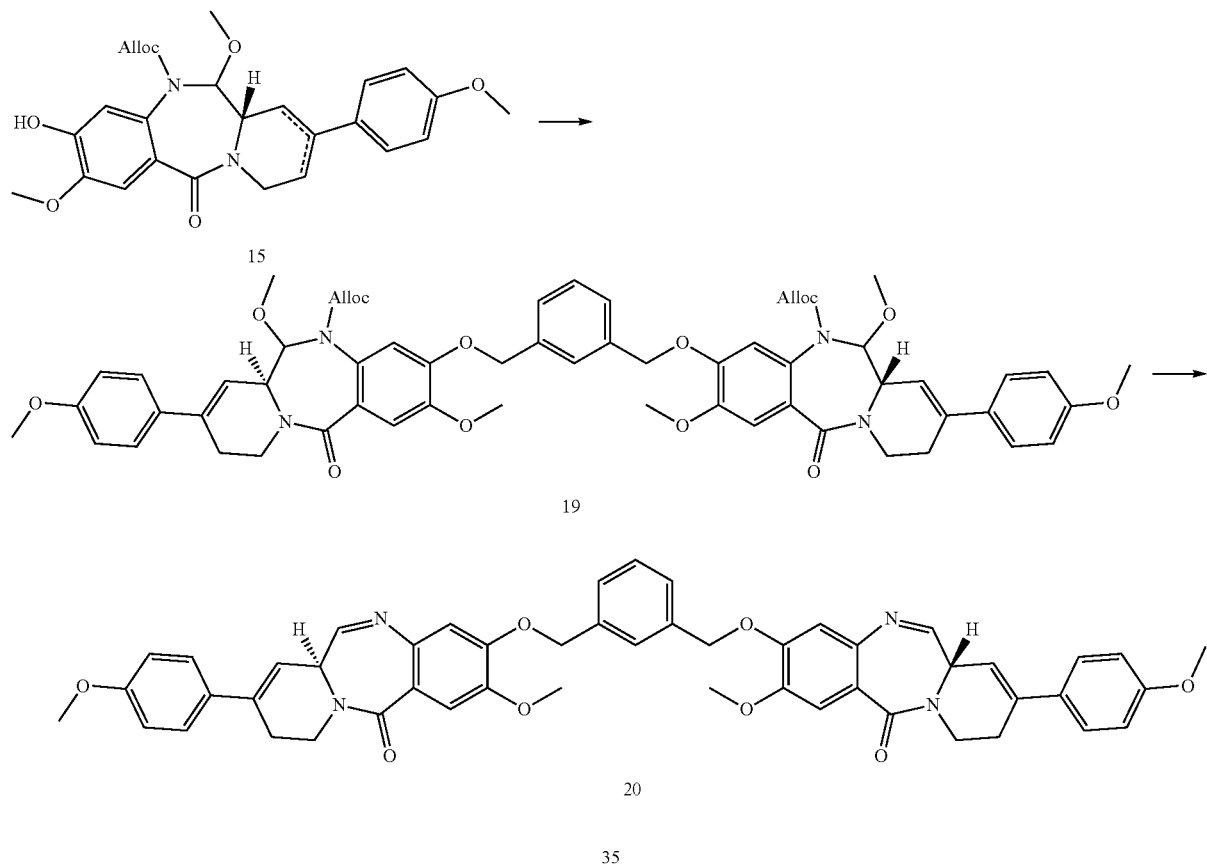
General synthetic scheme 5
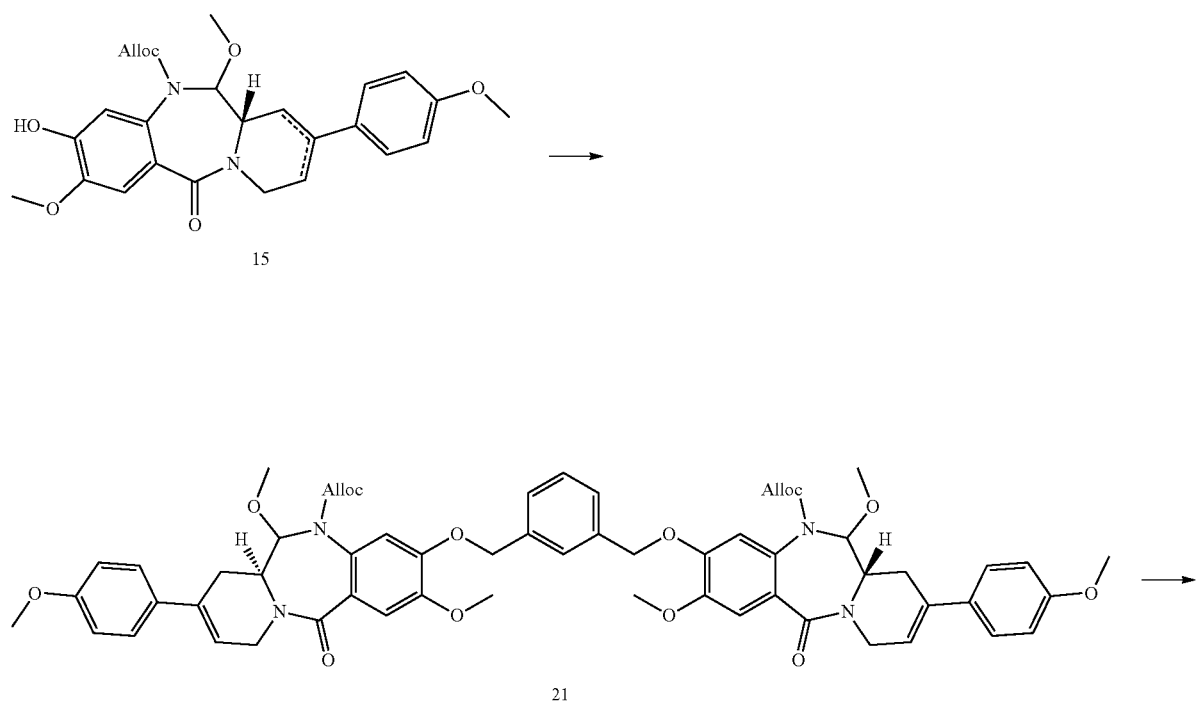

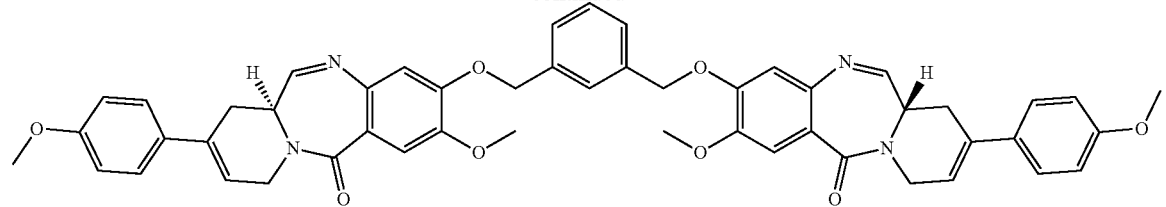
22
General synthetic scheme 6
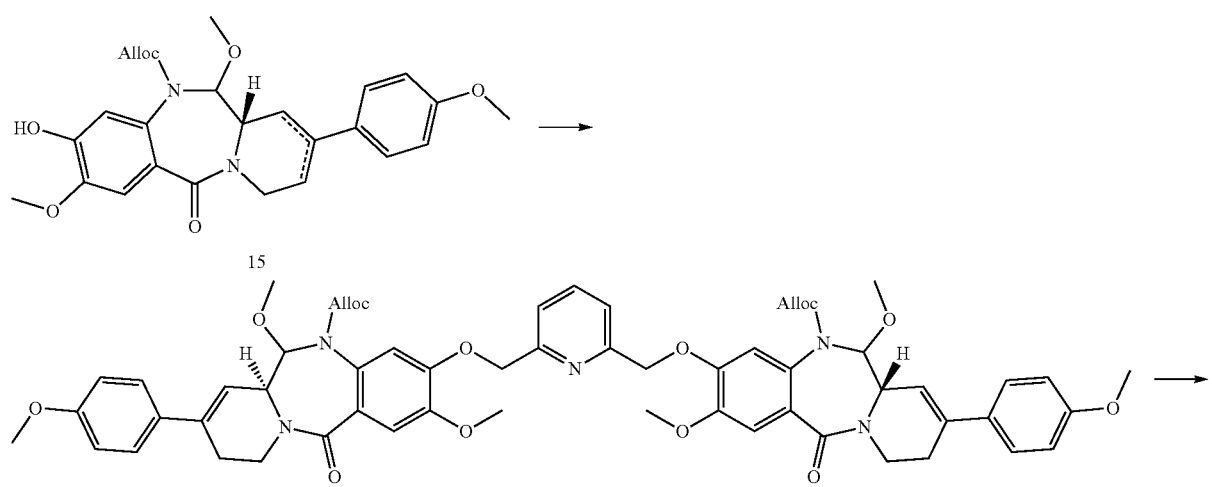
23
24
General synthetic scheme 7
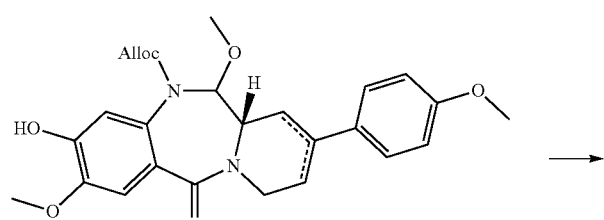
15

-continued
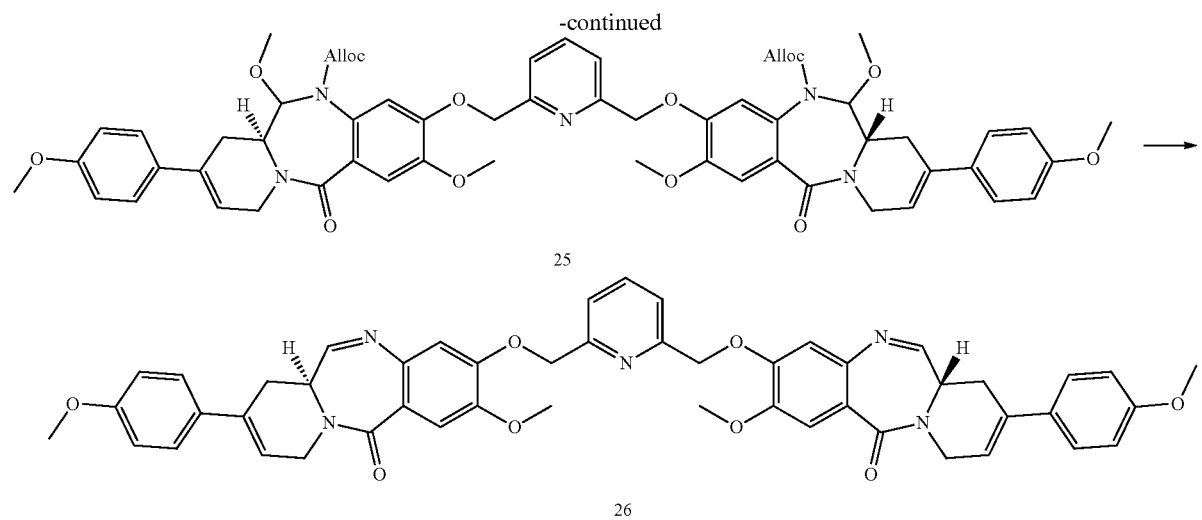
General synthetic scheme 8
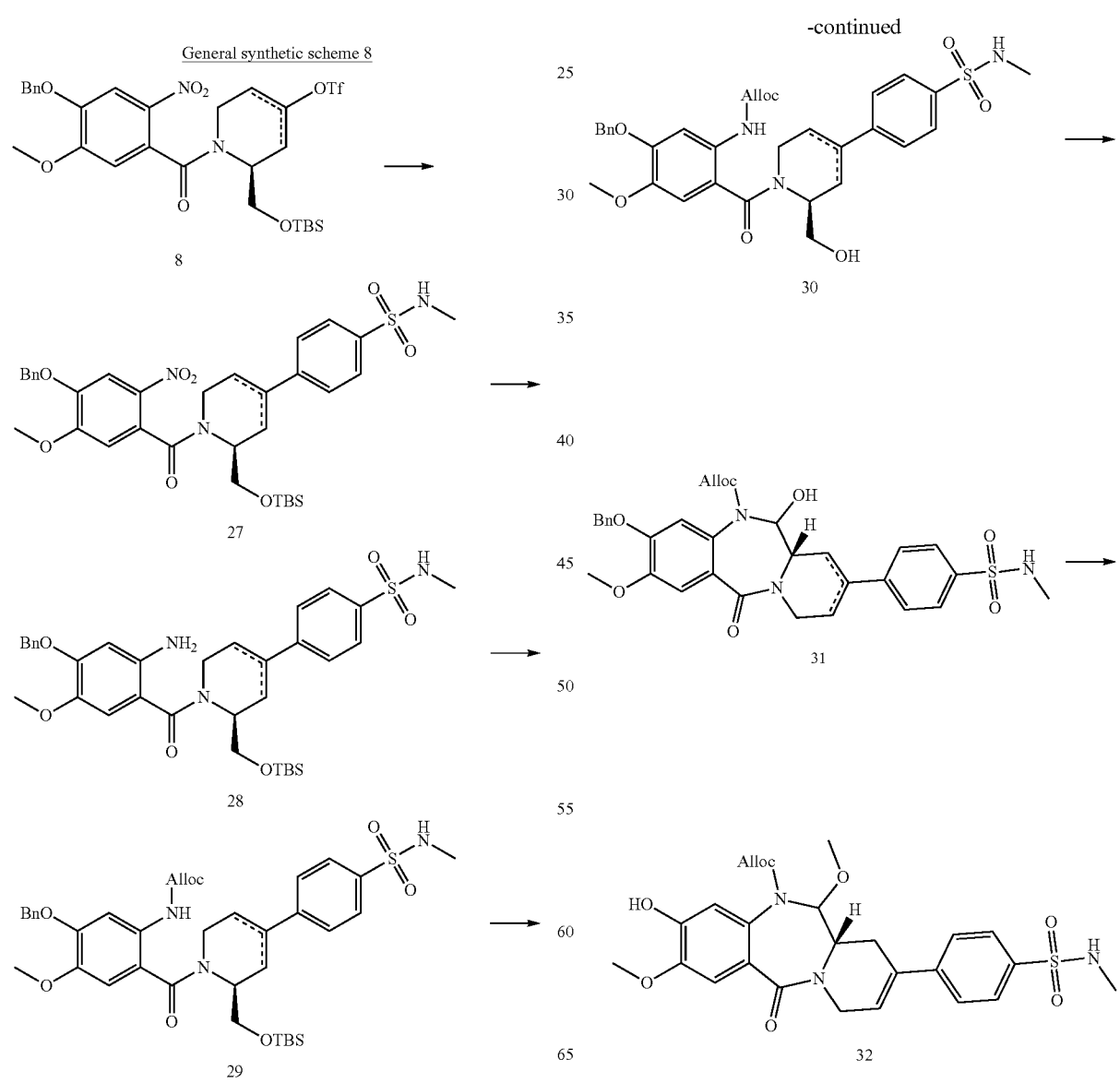

General synthetic scheme 9
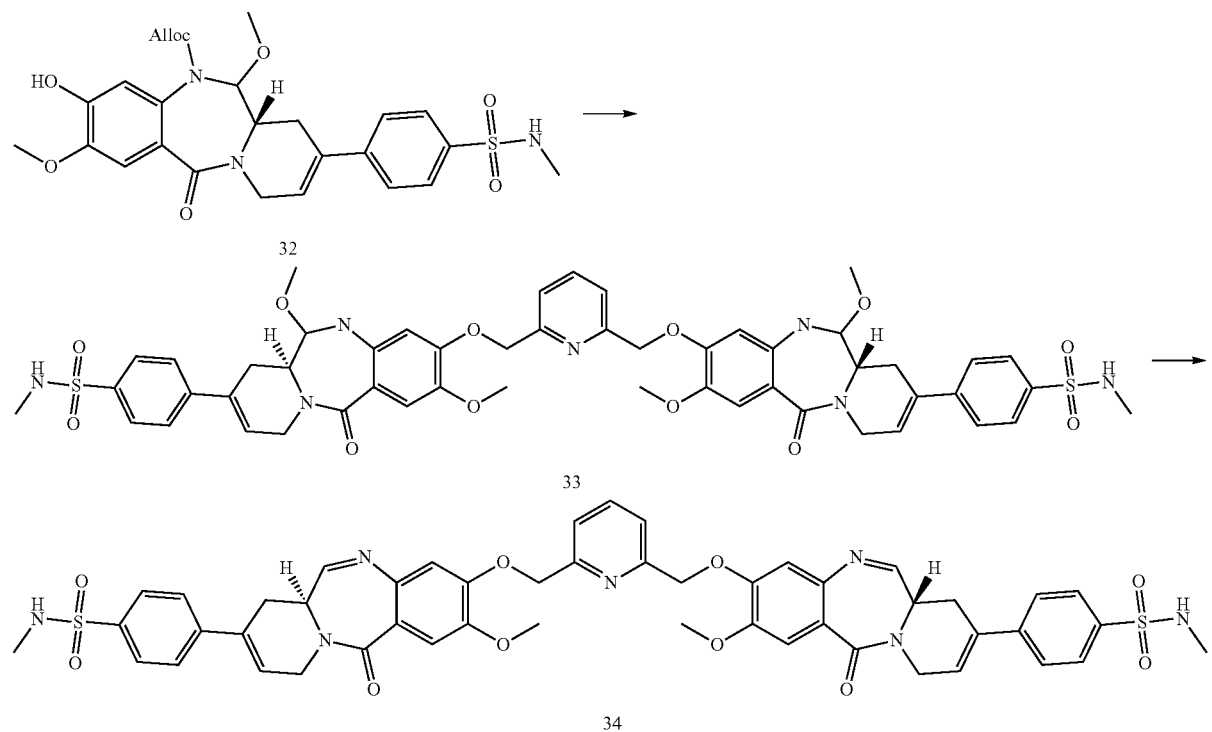
General synthetic scheme 10
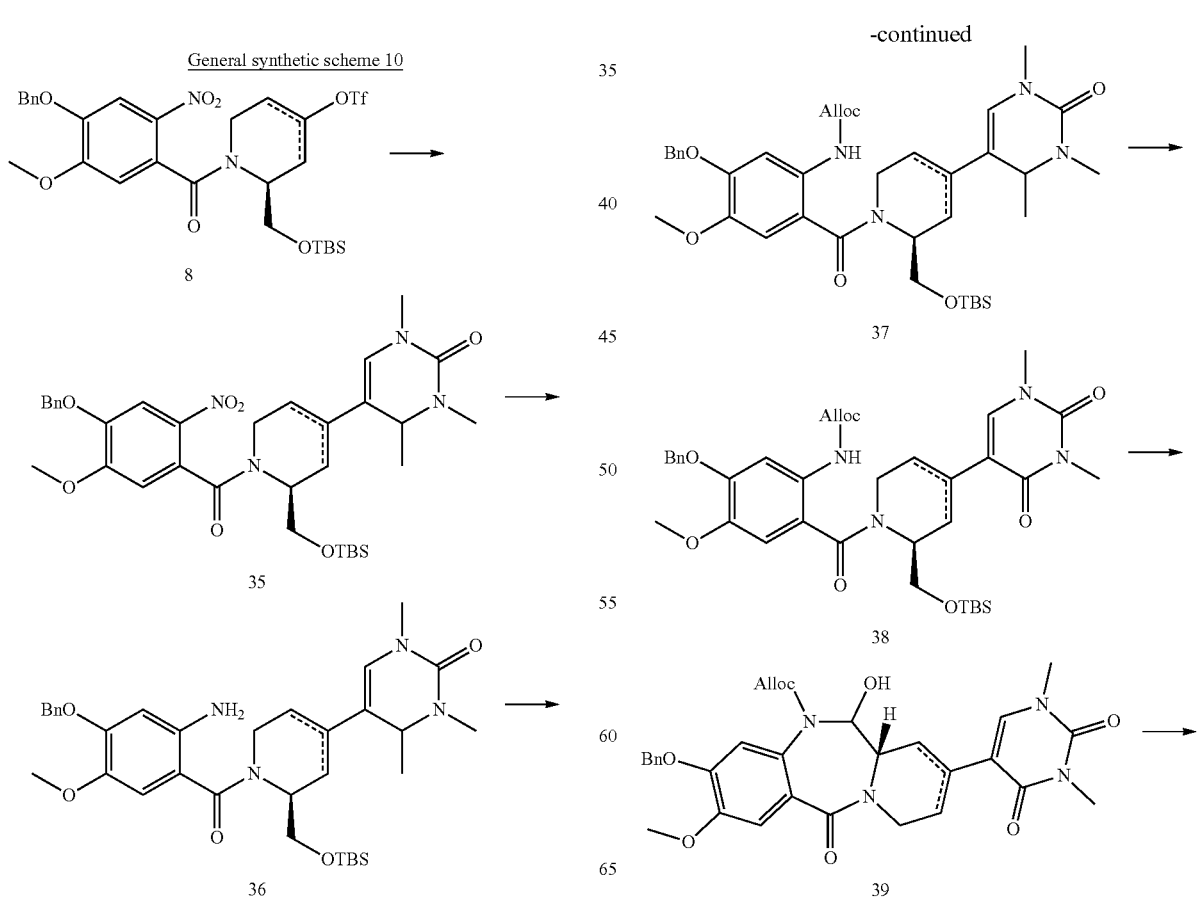

-continued
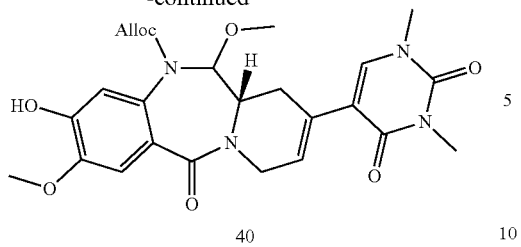
40
General synthetic scheme 11
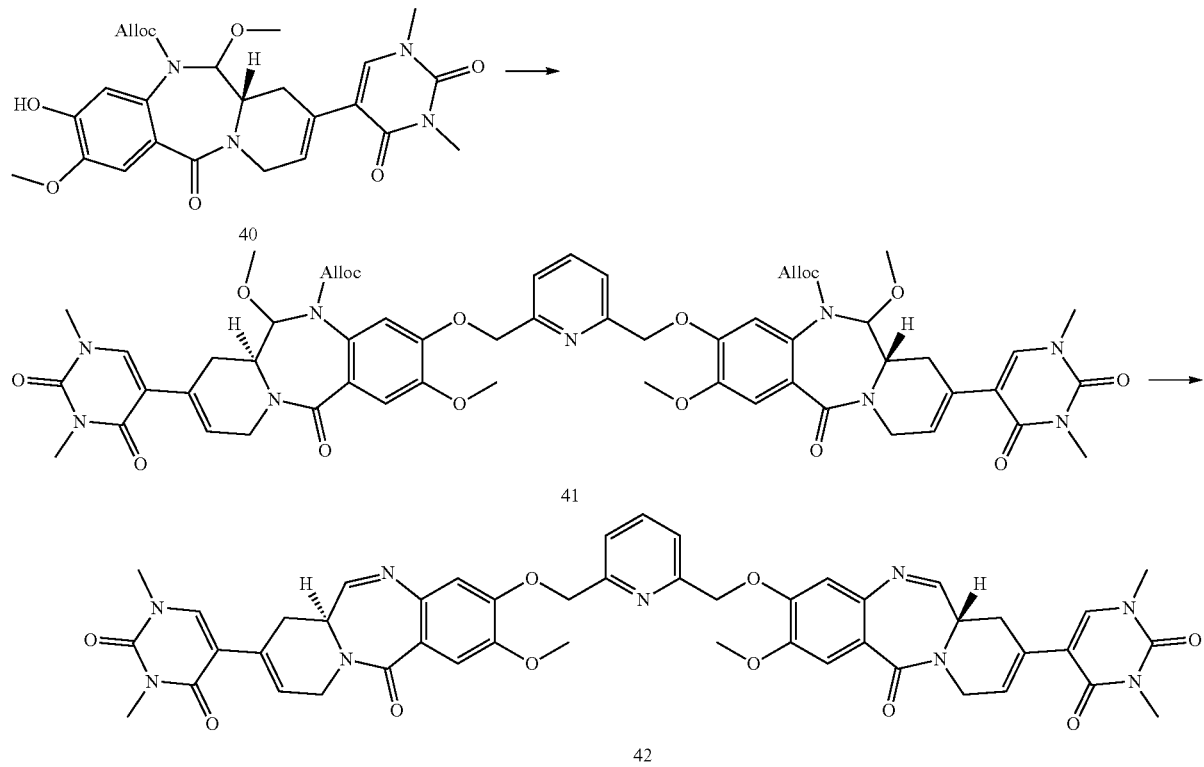
General synthetic scheme 12
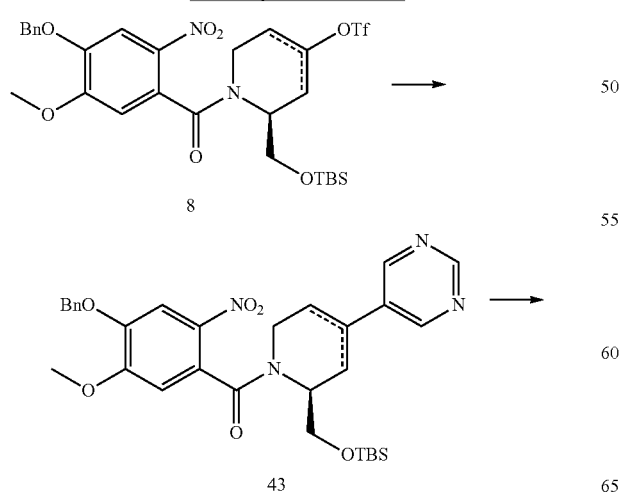

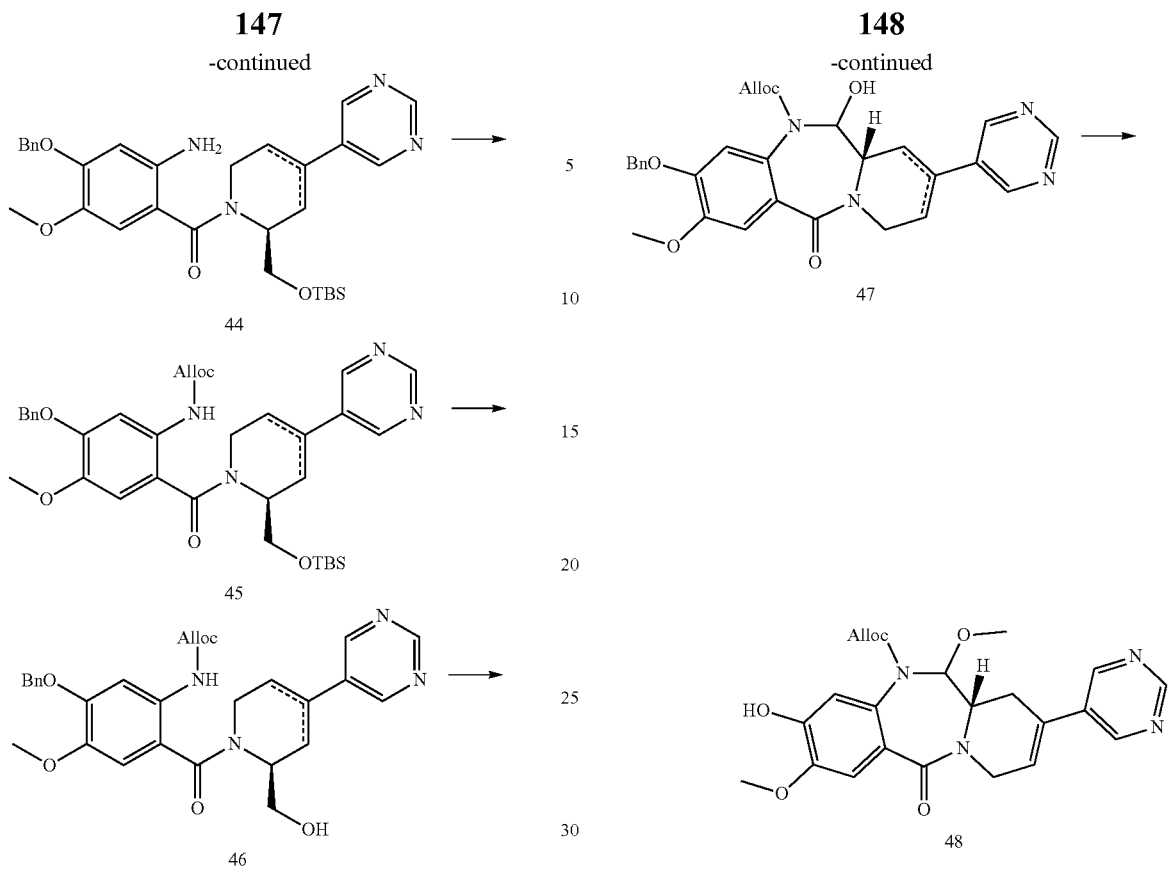
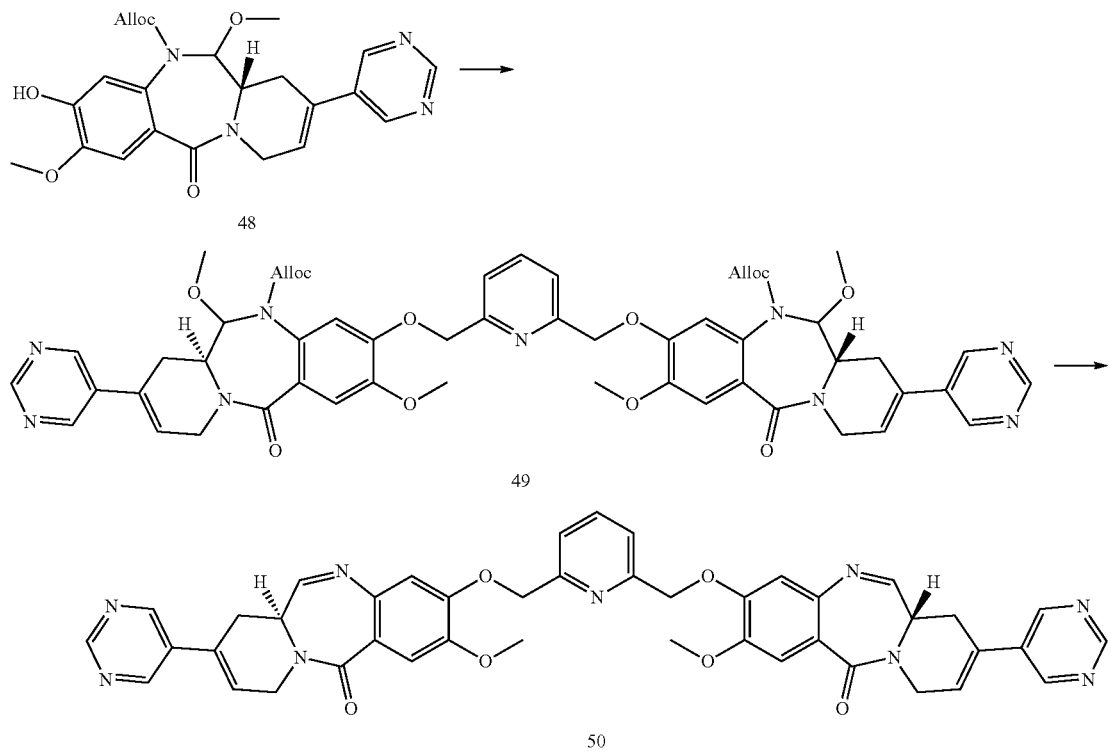
General synthetic scheme 13

General synthetic scheme 14
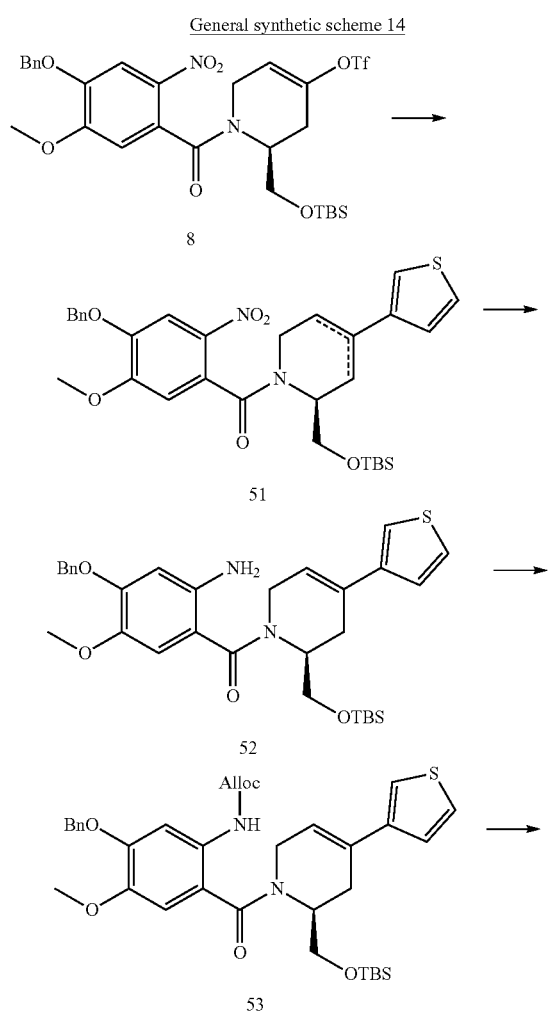
-continued
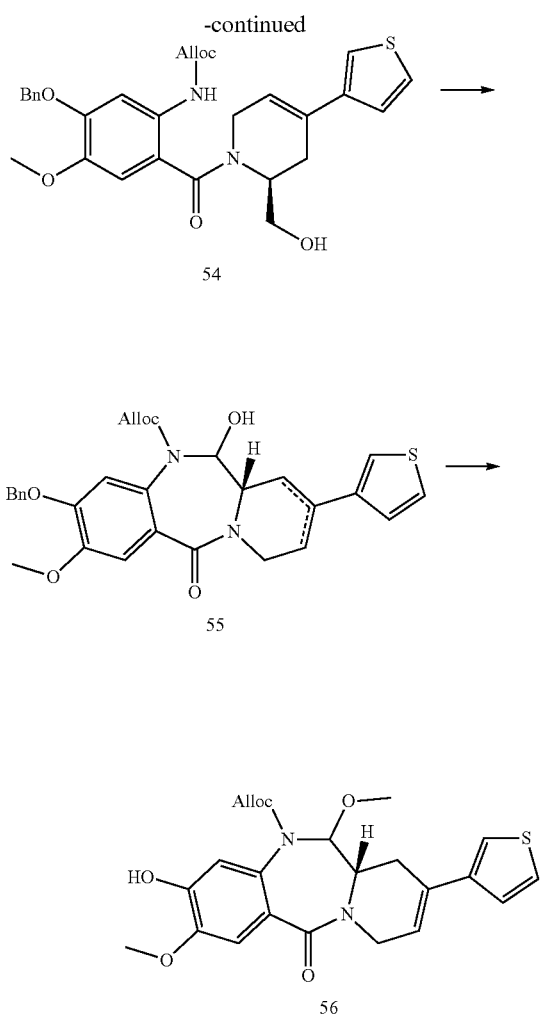
General synthetic scheme 15
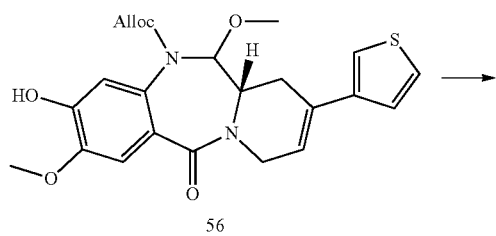
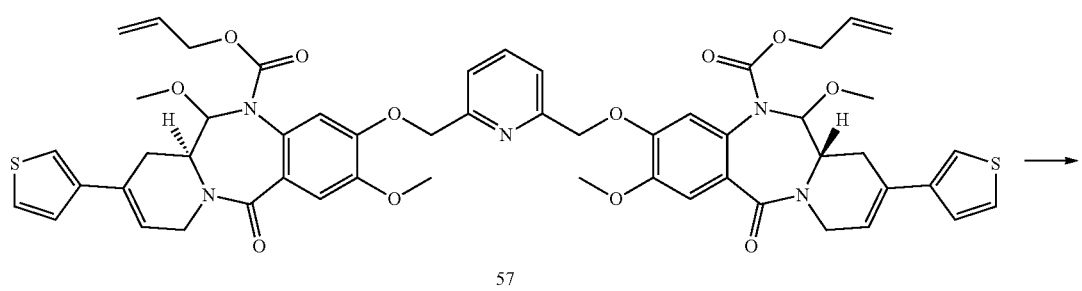

151 152
-continued
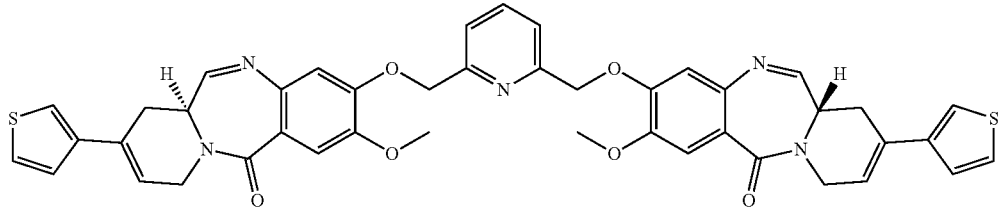
58
General synthetic scheme 16
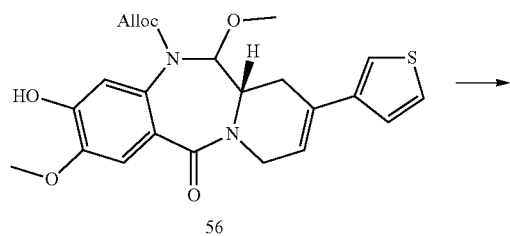
56
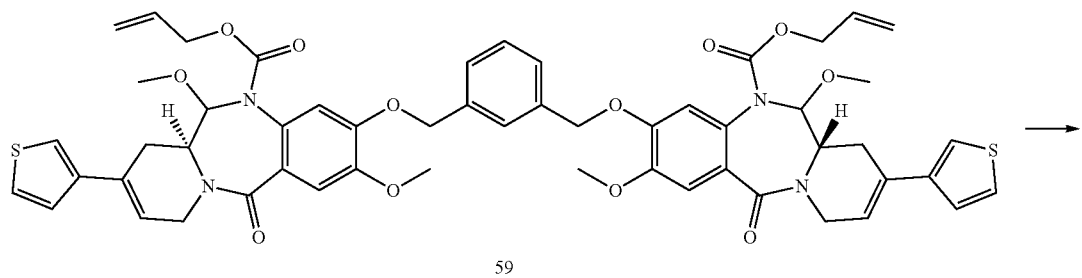
59
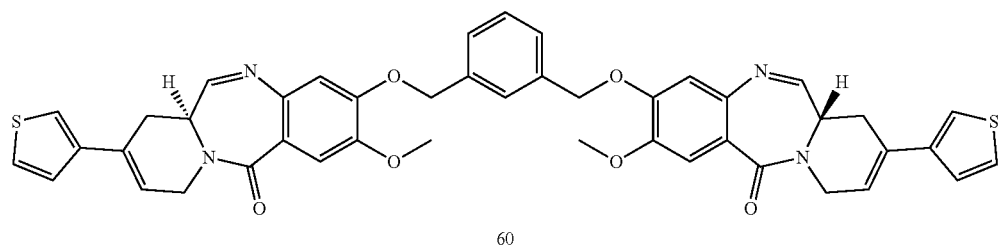
60
General synthetic scheme 17
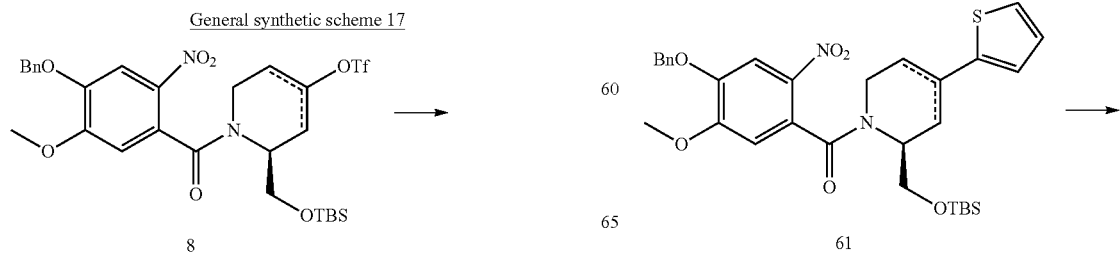
8               61

153
-continued
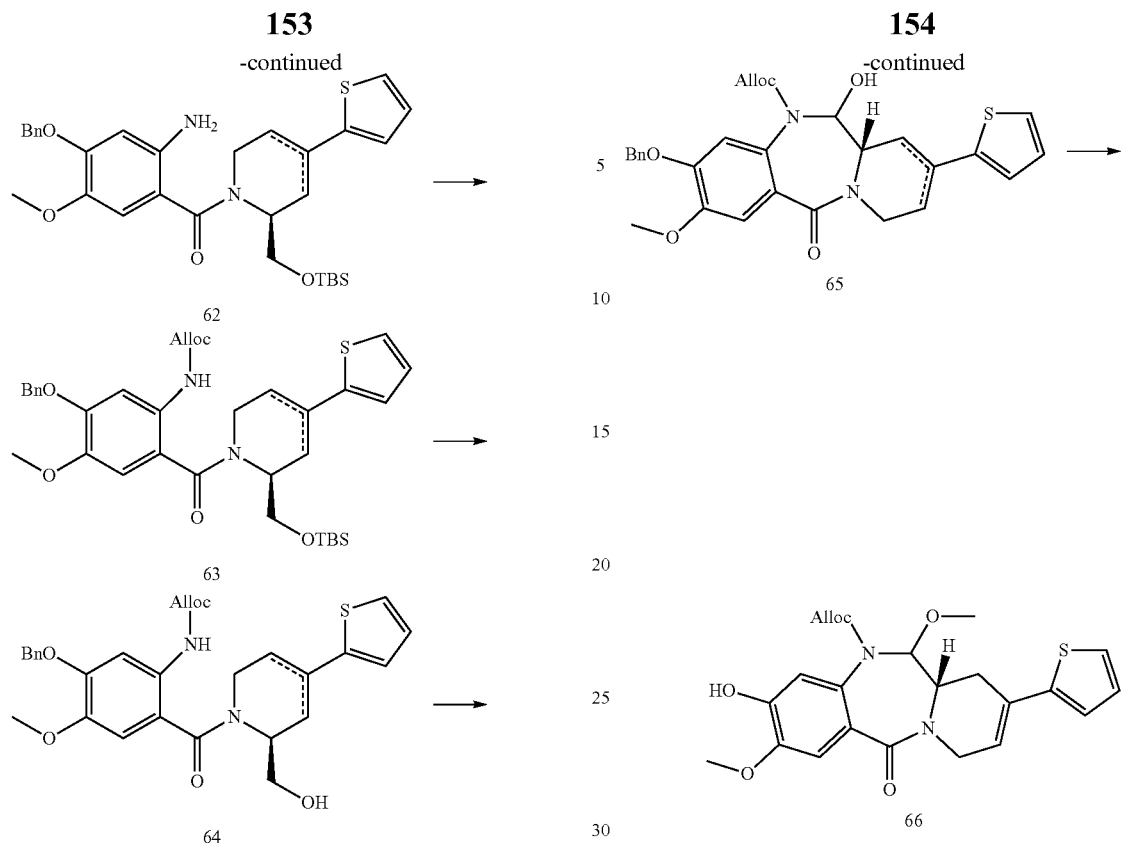
154
-continued
General synthetic scheme 18
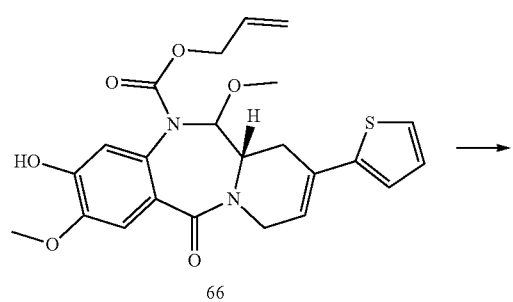
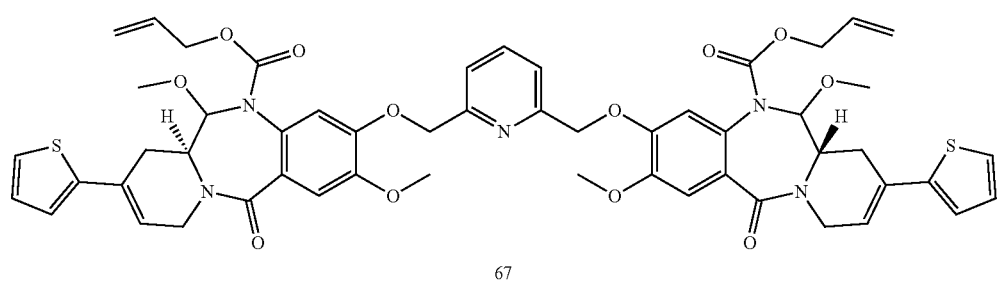

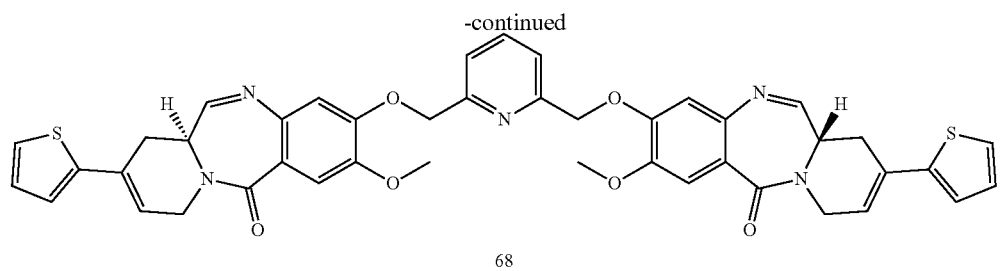
68
General synthetic scheme 19
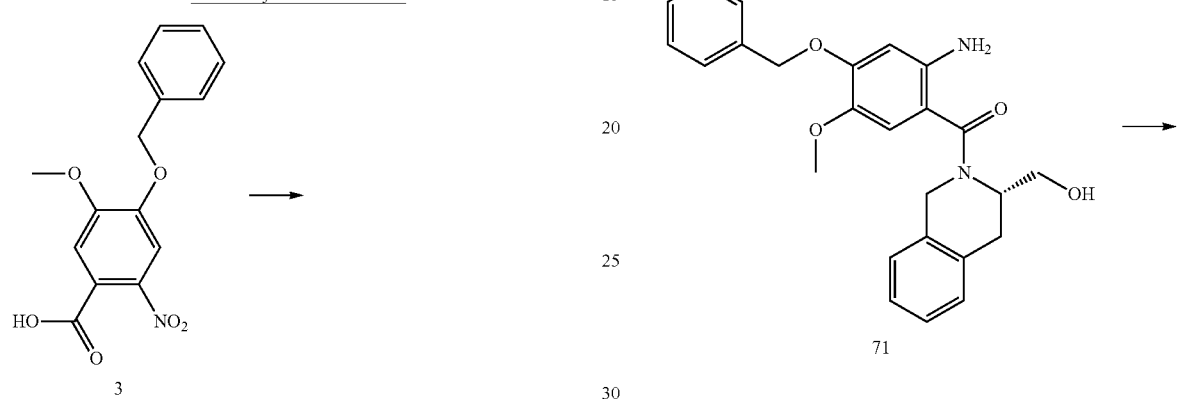
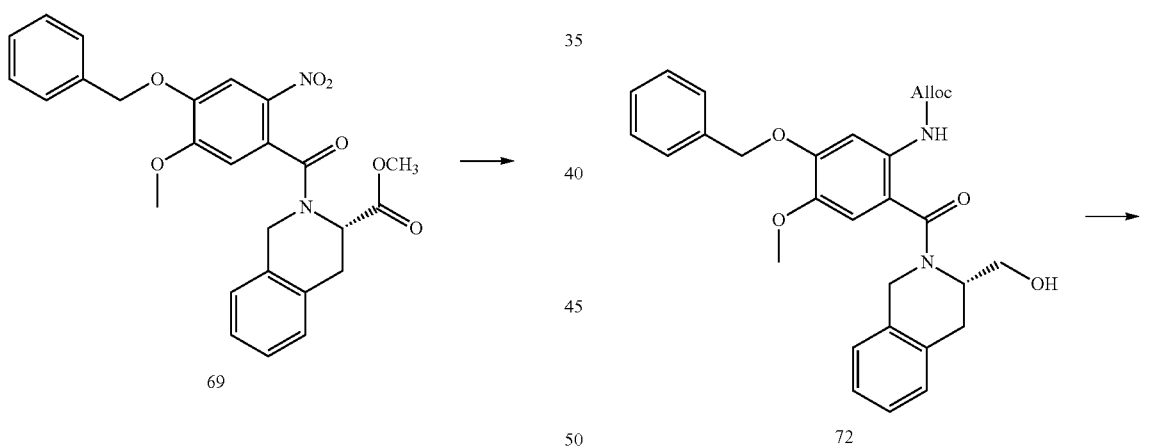
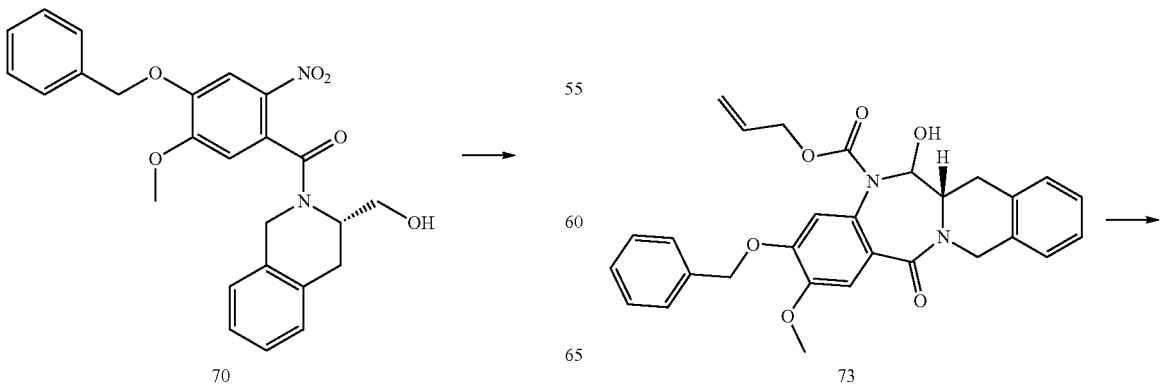

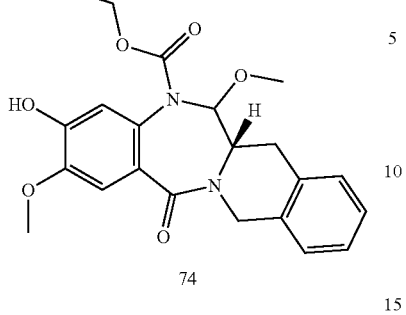
74
General synthetic scheme 20
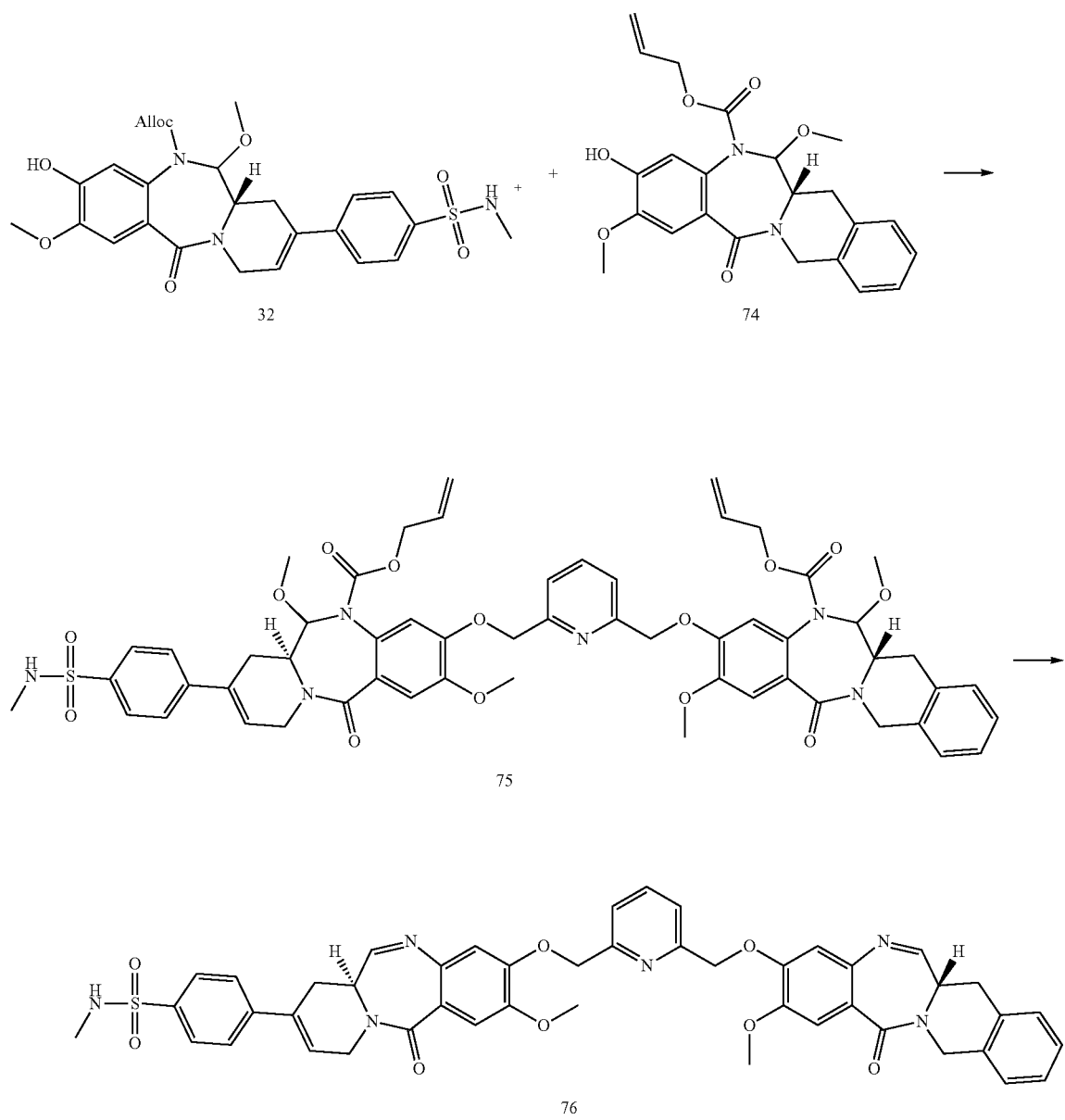

General synthetic scheme 21
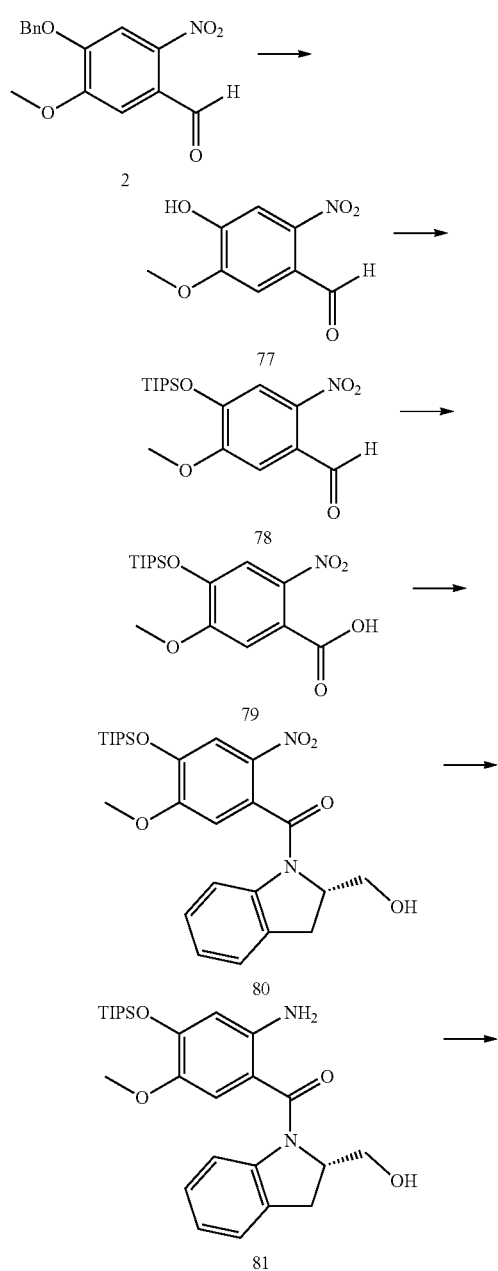
General synthetic scheme 22
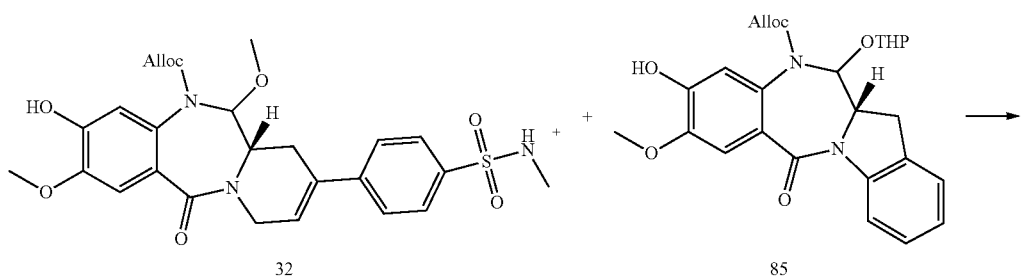

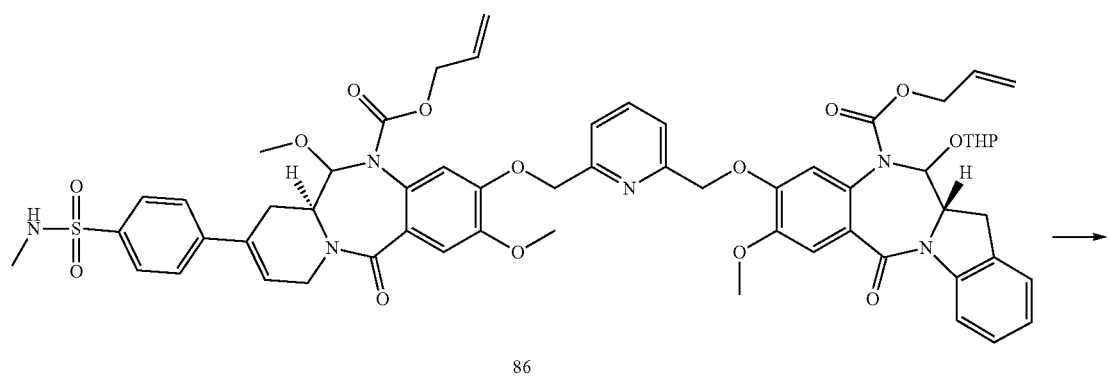
86
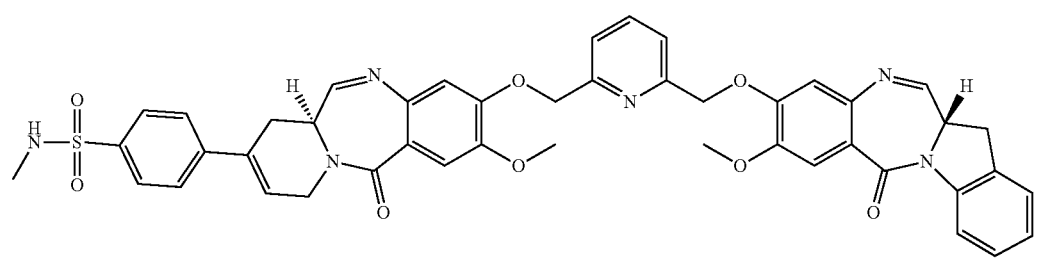
87
General syntheic scheme 23
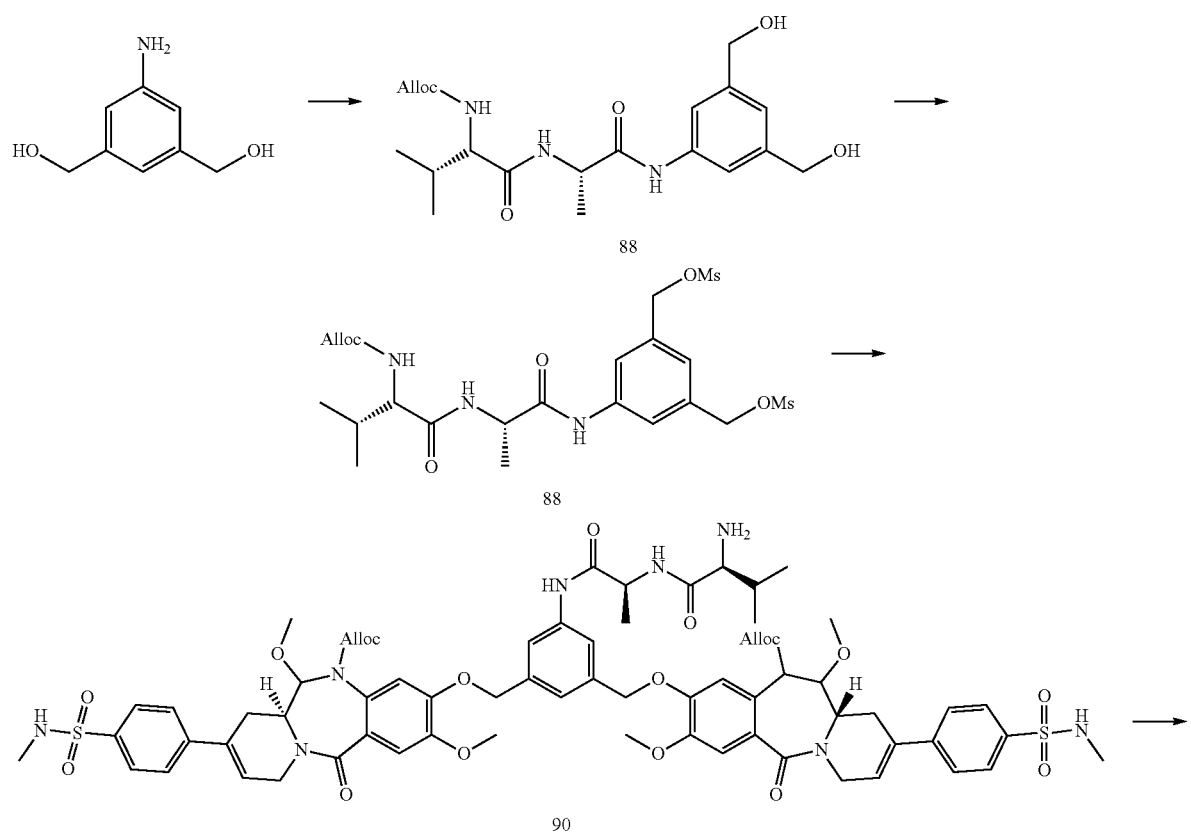

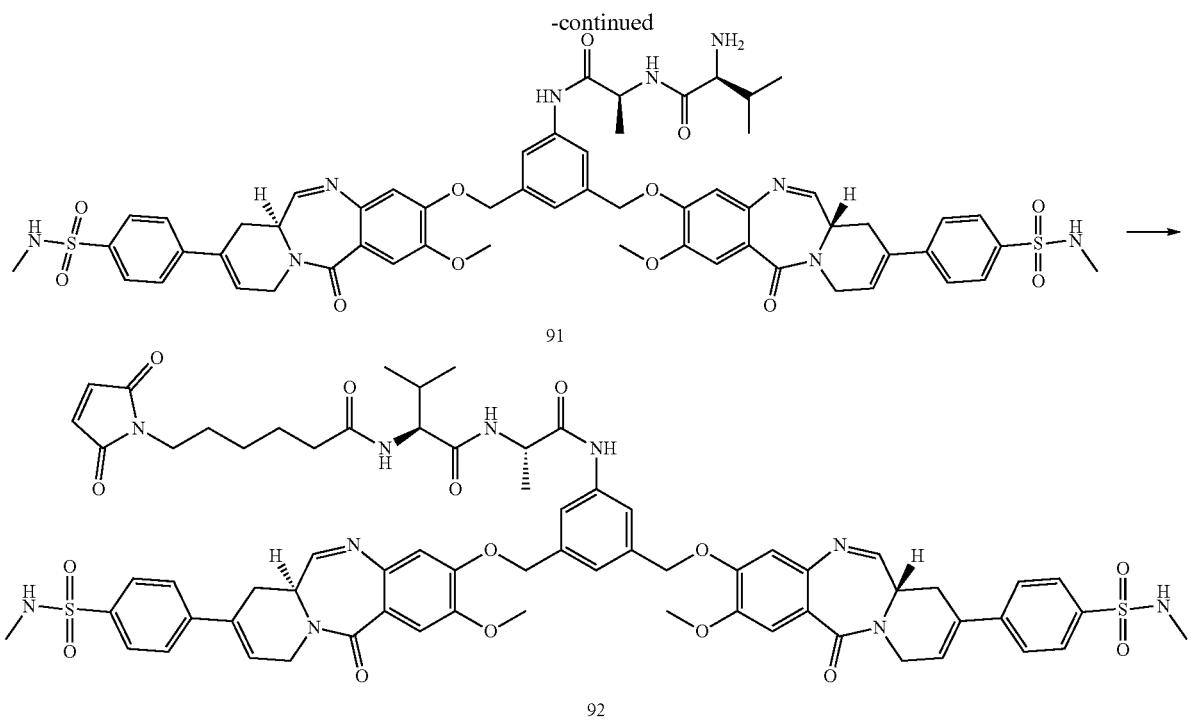

4-(Benzyloxy)-3-methoxybenzaldehyde (1)

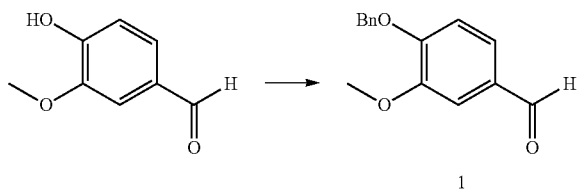 [SMILES: COc1cc(C=O)ccc1O ; COc1cc(C=O)ccc1OCc1ccccc1]

A mixture of compound vanillin (50.0 g, 328.6 mmol), benzyl bromide (59.0 g, 345.1 mmol) and potassium carbonate (136.3 g, 985.9 mmol) in methanol (300 mL) was refluxed for 4 h. The reaction mixture was filtered, and the filtrate evaporated under reduced pressure to afford the title compound (75.0 g, 94%) as a pale yellow solid. $^1$H NMR (400 MHz, CDCl$_3$) δ 9.83 (s, 1H), 7.47-7.35 (m, 6H), 7.33 (d, J=7.2 Hz, 1H), 6.98 (d, J=8.2 Hz, 1H), 5.24 (s, 2H), 3.94 (s, 3H).

4-(Benzyloxy)-5-methoxy-2-nitrobenzaldehyde (2)

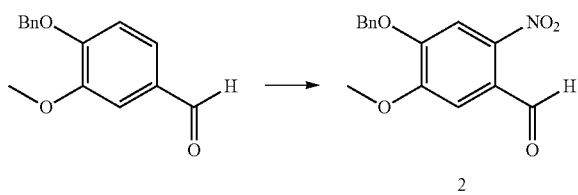 [SMILES: COc1cc(C=O)ccc1OCc1ccccc1 ; COc1cc(C=O)c([N+](=O)[O-])cc1OCc1ccccc1]

A solution of 4-(benzyloxy)-3-methoxybenzaldehyde (1) (65.00 g, 268.3 mmol) in trifluoroacetic acid (300.0 mL) was charged with a solution of potassium nitrate (32.55 g, 322.0 mmol), in trifluoroacetic acid (300 mL) dropwise at 0° C. The reaction mixture was stirred for 1 h and then diluted with water (1.2 L). The resulting precipitate was filtered and washed with cold water (50 mL×2) to afford the title compound (64.0 g, 83%) as a yellow solid. $^1$H NMR (400 MHz, CDCl$_3$) δ 10.43 (s, 1H), 7.67 (s, 1H), 7.46-7.40 (m, 5H), 5.27 (s, 2H), 4.02 (s, 3H).

4-(Benzyloxy)-5-methoxy-2-nitrobenzoic acid (3)

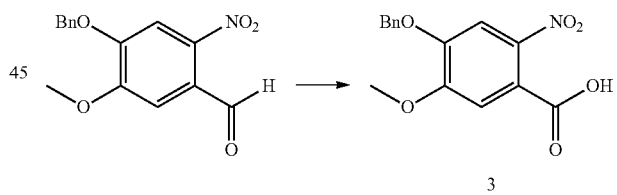

A solution of 4-(benzyloxy)-5-methoxy-2-nitrobenzaldehyde (2) (36.00 g, 125.3 mmol) in acetone (500 mL) was charged with a hot solution of potassium permanganate (10% w/v in water) (19.80 g, 125.3 mmol) and then stirred at 70° C. for 2 h, before cooling to room temperature. The mixture was acidified to pH=4 using hydrochloric acid (2N), and then extracted with ethyl acetate. The combined organic extracts were washed with cold water and dried over anhydrous sodium sulfate, filtered and concentrated in vacuo. The resulting residue was purified by flash chromatography (silica) and eluted with dichloromethane/methanol (20:1) to afford the title compound (24.0 g, 63%) as a yellow solid. $^1$H NMR (400 MHz, DMSO-d6) δ 7.64 (s, 1H), 7.47-7.37 (m, 5H), 7.26 (s, 1H), 5.22 (s, 2H), 3.90 (s, 3H).

Methyl(2S,4S)-1-(4-(benzyloxy)-5-methoxy-2-nitrobenzoyl)-4-hydroxy-piperidine-2-carboxylate (4)

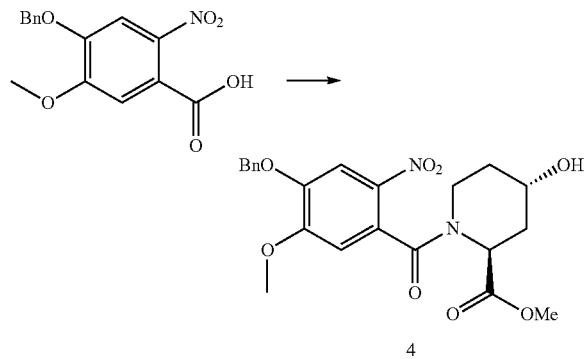

A solution of 4-(benzyloxy)-5-methoxy-2-nitrobenzoic acid (3) (20.00 g, 66.0 mmol) in N,N-dimethylformamide (100 mL) was charged with HATU (37.61 g, 98.9 mmol) and N,N-diisopropylethylamine (21.31 g, 164.9 mmol) and stirred for 30 min. The reaction mixture was then cooled to 0° C. and methyl (2S,4S)-4-hydroxypiperidine-2-carboxylate hydrochloride (12.90 g, 66.0 mmol) was added. After the reaction was judged to have completed by TLC, it was diluted with water (300 mL) and extracted with ethyl acetate (500 mL×3). The combined organic extracts were washed with water and dried over solid anhydrous sodium sulfate, filtered and concentrated in vacuo. The residue was purified by flash column chromatography (silica), eluting with acetone/dichloro-methane, from 5% to 40% acetone, to afford the title compound (22.00 g, 75%) as a pale yellow solid. $^1$H NMR (400 MHz, DMSO-d6) mixture of rotamers, δ 7.77 and 7.72 (2×s, 1H), 7.40-7.33 (m, 2H), 7.31-7.20 (m, 3H), 6.94 and 6.73 (2×s, 1H), 5.14 and 5.12 (2×s, 2H), 4.05-3.99 (m, 1H), 3.91 and 3.89 (2×s, 3H), 3.67 and 3.63 (2×s, 3H) 3.60-3.58 (m, 1H), 3.40-3.30 (m, 1H) 2.52 and 2.24 (2×d, 1H, J=14.4 and 14.1 Hz), 1.99-1.90 (m, 1H) 1.89-1.80 (m, 1H) 1.73-1.60 (m, 1H), 1.57-1.48 (m, 1H); MS (ES+): m/z=445 (M+H)$^+$; LCMS (Method B): $t_R$=3.25 min.

(4-(Benzyloxy)-5-methoxy-2-nitrophenyl)((2S,4S)-4-hydroxy-2-(hydroxyl-methyl)piperidin-1-yl)methanone (5)

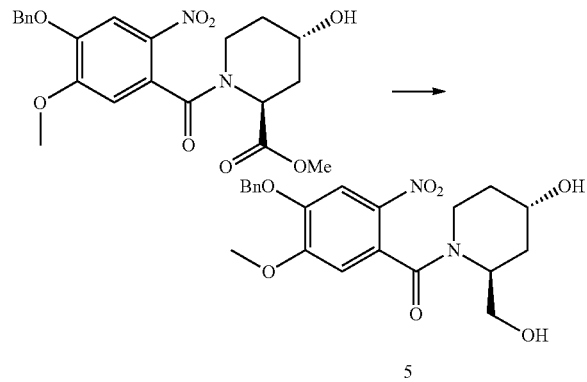

A stirred solution of methyl (2S,4S)-1-(4-(benzyloxy)-5-methoxy-2-nitrobenzoyl)-4-hydroxypiperidine-2-carboxylate (4) (4.70 g, 10.5 mmol) in anhydrous tetrahydrofuran (100 mL) was charged with lithium borohydride (2 M in tetrahydrofuran, 7.9 mL, 15.8 mmol) dropwise at 0° C. The reaction was then stirred at room temperature. After 1 h, the reaction was judged to be complete by TLC and was quenched using water (50 mL) and hydrochloric acid solution (1 N, 10 mL). The mixture was then extracted with ethyl acetate (100 mL×3) and the combined organic extracts were washed with sodium hydrogen carbonate (50 mL×2) and brine (50 mL×2), dried over solid anhydrous sodium sulfate, filtered and concentrated in vacuo to afford the title compound (4.0 g, 91%) as an off-white solid. $^1$H NMR (400 MHz, CD$_3$OD) mixture of rotamers, δ 7.76, 7.74 and 7.71 (3×s, 1H), 7.39-7.22 (m, 5H), 7.01 and 6.91 (2×s, 1H), 5.12 (2×s, 2H), 4.39 (d, J=13.5 Hz, 1H), 4.20 and 4.10 (2×dd, 1H, J=9.8, 12.0 and 8.8, 12.0 Hz), 3.88 and 3.83 (2×s, 3H), 3.65 (dd, J=4.4, 12.0 Hz, 038H), 3.57-352 (m, 0.8H), 3.50-343 (m, 0.6H), 3.34 (dd, J=4.0, 12.0 Hz, 0.6H), 3.26 (dd, J=2.7, 13.3 Hz, 0.5H), 3.12-3.00 (m, 0.5H), 1.90-1.85 (m, 0.5H), 1.85-1.77 (m, 1H), 1.75-1.70 (m, 1H), 1.70-1.55 (m, 2H), 1.52-1.42 (m, 2H); MS (ES+): m/z=417 (M+H)$^+$; LCMS (Method B): $t_R$=3.08 min.

(4-(Benzyloxy)-5-methoxy-2-nitrophenyl)((2S,4S)-2-(((tert-butyldimethyl-silyl)oxy)methyl)-4-hydroxypiperidin-1-yl)methanone (6)

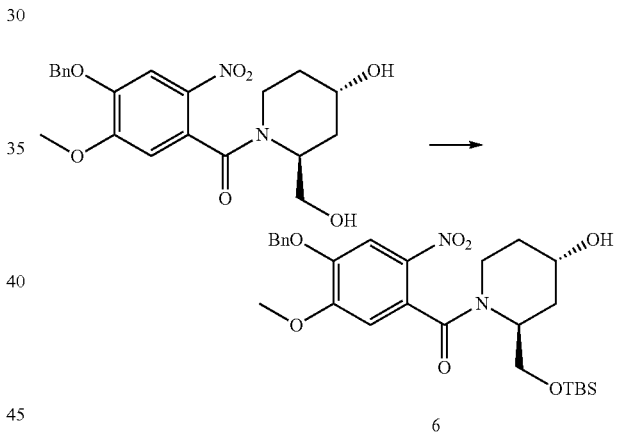

A solution of (4-(benzyloxy)-5-methoxy-2-nitrophenyl)((2S,4S)-4-hydroxy-2-(hydroxylmethyl)piperidin-1-yl) methanone (5) (7.50 g, 18.0 mmol) in dry N,N-dimethylformamide (15 mL) was charged with imidazole (3.68 g, 54.0 mmol) and tert-butyldimethylsilyl chloride (2.99 g, 19.8 mmol) and then stirred at room temperature. After 2 h, the reaction was found to have partially completed. Additional tert-butyl-dimethylsilyl chloride (0.54 g, 3.6 mmol) was then added. After stirring for another 30 min, the reaction was judged to have completed by TLC and was diluted with water (100 mL). The mixture was then extracted with ethyl acetate (300 mL×2) and the combined organic extracts washed with citric acid (1 M) (150 mL) and brine (150 mL) and dried over solid anhydrous sodium sulfate, filtered and concentrated in vacuo. The residue was purified by flash column chromatography (silica), eluting with petroleum spirit, 40-60° C./ethyl acetate (3:1 to 1:1) to afford the title compound (6.17 g, 65%) as an orange oil. $^1$H NMR (400 MHz, CDCl$_3$), mixture of rotamers, δ 7.61, 7.60 and 7.57 (3×s, 1H), 7.30-7.15 (m, 5H), 6.61, 6.56 and 6.50 (3×s, 1H), 5.04 and 5.03 (2×s, 2H), 4.86-4.45 (m, 2H), 4.17 (dd, J=3.2, 10.6 Hz, 0.5H), 4.01-3.84 (m, 2H), 3.69 (dt, J=5.9, 3.9 Hz, 1H), 3.60 (dd, J=10.6, 2.9 Hz, 1H), 3.47-3.34 (m, 1H), 3.11 and 2.96 (2×t, J=12.2 and 14.5 Hz, 1H), 2.15-1.97 (m, 1H), 1.89 and 1.80 (2×d, J=14.4, 14.9 Hz, 1H), 1.63-130 (m, 3H), 0.80-0.67 (m, 9H), 0.15-0.05 (m, 6H); MS (ES+): m/z=531 (M+H)+; LCMS (Method B): t_R=4.38 min.

(S)-1-(4-(Benzyloxy)-5-methoxy-2-nitrobenzoyl)-2-(((tert-butyldimethyl-silyl)oxy)methyl)piperidin-4-one (7)

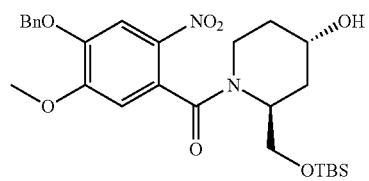

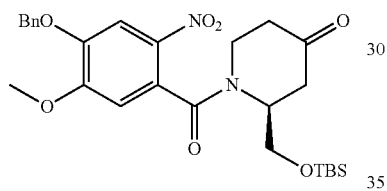

A solution of (4-(benzyloxy)-5-methoxy-2-nitrophenyl)((2S,4S)-2-(((tert-butyldimethylsilyl)oxy)methyl)-4-hydroxypiperidin-1-yl)methanone (6) (14.0 g, 26.4 mmol) in dichloromethane (200 mL) was charged with TEMPO (0.41 g, 2.60 mmol) and (diacetoxyiodo)benzene (11.05 g, 34.3 mmol) and stirred at room temperature. After 24 h, the reaction was judged to have completed by TLC. The mixture was then extracted with ethyl acetate (300 mL×2) and the combined organic extracts were washed with a saturated aqueous solution of sodium metabisulfite (150 mL) and brine (150 mL) and dried over anhydrous sodium sulfate, filtered and concentrated in vacuo. The residue was purified by flash column chromatography (silica), eluting with petroleum spirit, 40-60° C./ethyl acetate (3:1 to 1:1) to afford the title compound (13.00 g, 90%) as a yellow solid. $^1$H NMR (400 MHz, CDCl$_3$), mixture of rotamers, δ 7.69, 7.68 and 7.67 (3×s, 1H), 7.40-7.20 (m, 5H), 6.71, 6.70 and 6.65 (3×s, 1H), 5.14 and 5.13 (2×s, 2H), 4.12 and 3.91 (2×dd, J=10.6, 2.6 and 10.4, 2.7 Hz, 1H), 3.89, 3.88 and 3.87 (3×s, 3H), 3.80-3.35 (m, 3H), 2.77-2.15 (m, 4H), 0.85-0.72 (m, 9H), 0.02--0.10 (m, 6H); $^{13}$C NMR (100 MHz, CDCl$_3$), mixture of rotamers, δ 205.7, 167.5, 154.9, 148.3, 148.2, 137.6, 137.3, 135.2, 130.0, 128.9, 128.7, 128.6, 127.6, 127.3, 127.1, 127.0, 109.9, 109.2, 108.6, 71.4, 65.6, 65.1, 64.6, 56.8, 56.8, 56.7, 56.5, 51.3, 51.2, 43.3, 41.9, 41.5, 41.3, 39.9, 39.8, 39.6, 37.5, 25.8, 25.8, 25.8, 20.3, 18.3, 18.2, 18.2, 18.1, −5.7, −5.7; MS (ES+): m/z=529 (M+H)+; LCMS (Method A): t_R=8.28 min.

(S)-1-(4-(Benzyloxy)-5-methoxy-2-nitrobenzoyl)-2-(((tert-butyldimethyl-silyl)oxy)methyl)-1,2,3,6-tetra-hydropyridin-4-yl trifluoromethanesulfonate and
(S)-1-(4-(benzyloxy)-5-methoxy-2-nitrobenzoyl)-6-(((tert-butyldimethylsilyl)oxy)methyl)-1,2,3,6-tetra-hydropyridin-4-yl trifluoromethanesulfonate (8) (1:1)

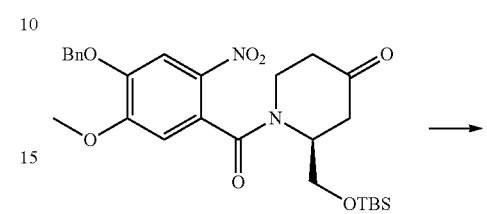

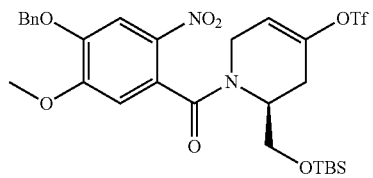

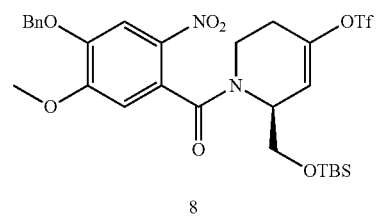

A solution of (S)-1-(4-(benzyloxy)-5-methoxy-2-nitrobenzoyl)-2-(((tert-butyldimethyl-silyl)oxy)methyl)piperidin-4-one (7) (13.00 g, 24.6 mmol) in anhydrous tetrahydro-furan (100 mL) was cooled to −78° C., and charged with sodium bis(trimethylsilyl)amide (2 M in tetrahydrofuran, 18.4 mL, 36.9 mmol) dropwise. The reaction mixture was stirred for 1 h, before a solution of N-phenyl-bis(trifluoromethanesulfonimide) (11.42 g, 32.0 mmol) in anhydrous tetrahydrofuran (100 mL) was added dropwise. The resulting mixture was then allowed to warm to room temperature and stirred for 4 h. At this point, the reaction was judged to have completed by TLC. The mixture was then concentrated in vacuo and the residue purified by flash column chromatography (silica), eluting with petroleum spirit, 40-60° C./ethyl acetate (10:1) then dichloro-methane/acetone (100:1) to afford the title compound (12.8 g, 79%) as a cream solid. $^1$H NMR (400 MHz, CDCl$_3$), mixture of rotamers and regioisomers, δ 7.70-7.60 (m, 1H), 7.39-7.25 (m, 5H), 6.77-6.60 (m, 1H), 5.91-5.45 (m, 1H), 5.15-5.00 (m, 2H), 3.95-377 (m, 1H), 3.90-3.85 (m, 3H), 3.75-3.20 (m, 3H), 2.90-2.08 (m, 2H), 0.85-0.6 (m, 9H), 0.07-0.22 (m, 6H); MS (ES+): m/z=661 (M+H)+; LCMS (Method A): t_R=9.27 min.

(S)-(4-(Benzyloxy)-5-methoxy-2-nitrophenyl)(6-(((tert-butyldimethyl-silyl)oxy)methyl)-4-(4-methoxyphenyl)-3,6-dihydropyridin-1(2H)-yl)-methanone and (S)-(4-(benzyloxy)-5-methoxy-2-nitrophenyl)(2-(((tert-butyldimethylsilyl)oxy)methyl)-4-(4-methoxyphenyl)-3,6-dihydropyridin-1(2H)-yl)methanone (9) (1:1)

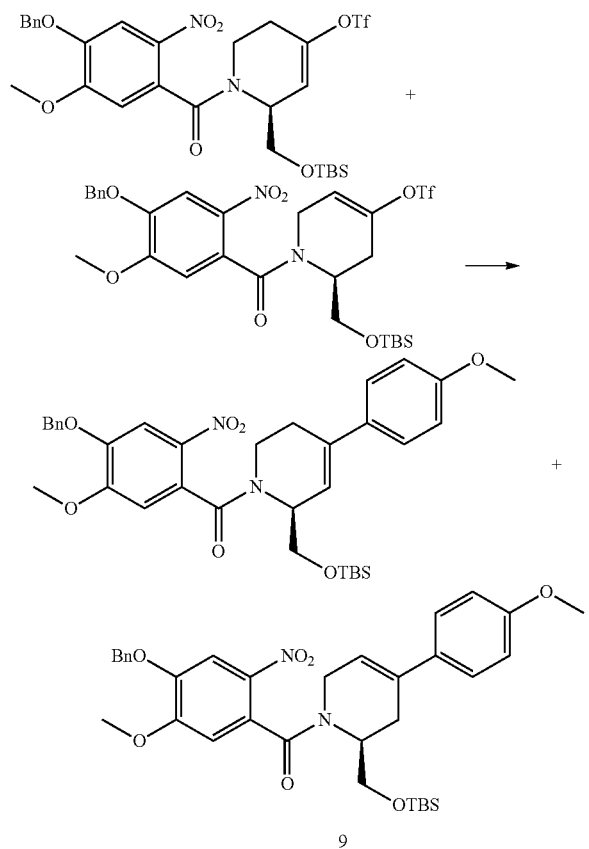

9

A solution of (S)-1-(4-(benzyloxy)-5-methoxy-2-nitrobenzoyl)-2-(((tert-butyldimethyl-silyl)oxy)methyl)-1,2,3,6-tetrahydropyridin-4-yl trifluoromethanesulfonate and(S)-1-(4-(benzyloxy)-5-methoxy-2-nitrobenzoyl)-6-(((tert-butyldimethylsilyl)oxy)methyl)-1,2,3,6-tetrahydropyridin-4-yl trifluoromethanesulfonate (8) (3.00 g, 4.53 mmol) in acetonitrile (5 mL) was charged with [1,1'-bis(diphenylphosphino)ferrocene]dichloro-palladium(II), complex with dichloromethane (0.369 g, 0.45 mmol), 2-(4-methoxyphenyl)-4,4,5,5-tetramethyl-1,3,2-dioxaborolane (1.87 g, 5.90 mmol) and an aqueous solution of potassium carbonate (2 M, 4.5 mL, 9.06 mmol) and irradiated with microwaves at 50° C. for 10 min. The resulting mixture was diluted with ethyl acetate (100 mL) and washed with brine (50 mL), then dried over solid anhydrous magnesium sulfate and concentrated in vacuo. The residual oil was purified by flash column chromatography (silica), eluting with petroleum spirit, 40-60° C./ethyl acetate (4:1) to afford the title compound (2.11 g, 75%) as an off-white solid. $^1$H NMR (400 MHz, CDCl$_3$), mixture of rotamers and regioisomers, δ 7.75-7.60 (m, 1H), 7.40-7.00 (m, 7H), 6.80-6.70 (m, 2H), 6.69-6.62 (m, 1H), 6.11-5.56 (m, 1H), 5.15-476 (m, 2H), 4.04-391 (m, 1H), 3.85 and 3.84 (2×s, 3H), 3.82-3.73 (m, 1H), 3.70-3.69 (2×s, 3H), 3.65-346 (m, 1H), 3.45-3.24 (m, 1H), 3.06-2.55 (m, 1H), 2.55-2.10 (m, 1H), 0.90-0.57 (m, 9H), 0.10-0.37 (m, 6H); MS (ES+): m/z=619 (M+H)$^+$; LCMS (Method A): t$_R$=9.38 min.

(S)-(2-Amino-4-(benzyloxy)-5-methoxyphenyl)(2-(((tert-butyldimethyl-silyl)oxy)methyl)-4-(4-methoxyphenyl)-3,6-dihydropyridin-1(2H)-yl)-methanone and (S)-(2-amino-4-(benzyloxy)-5-methoxyphenyl)(6-(((tert-butyldimethylsilyl)oxy)methyl)-4-(4-methoxyphenyl)-3,6-dihydropyridin-1(2H)-yl)methanone (10) (1:1)

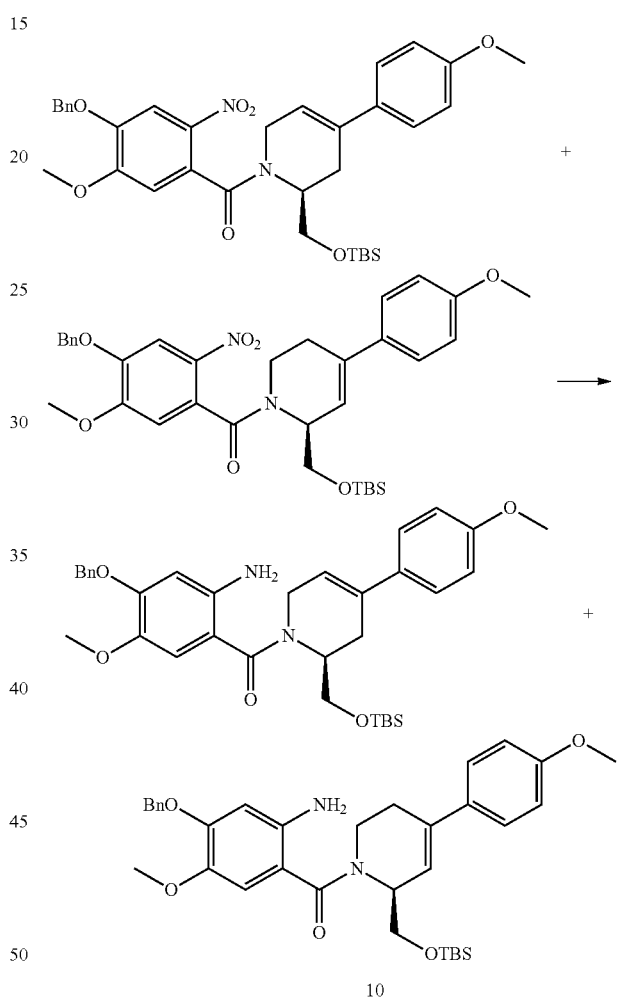

10

A solution of (S)-(4-(benzyloxy)-5-methoxy-2-nitrophenyl)(6-(((tert-butyldimethyl-silyl)oxy)methyl)-4-(4-methoxyphenyl)-3,6-dihydropyridin-1(2H)-yl)methanone and (S)-(4-(benzyloxy)-5-methoxy-2-nitrophenyl)(2-(((tert-butyldimethylsilyl)oxy)methyl)-4-(4-methoxyphenyl)-3,6-dihydropyridin-1(2H)-yl)methanone (9) (0.50 g, 0.80 mmol) in formic acid (5% v/v in absolute ethanol, 10 mL) was charged with zinc powder (1.94 g, 29.6 mmol) and stirred for 10 min, whilst monitoring by TLC and LCMS. Upon completion, the reaction was quenched by addition of a saturated aqueous solution of sodium hydrogen carbonate (10 mL) and concentrated in vacuo. The residue was then partitioned between ethyl acetate (100 mL) and brine (50 mL) and the organic phase dried over magnesium sulfate, filtered, and concentrated in vacuo to give the title compound (0.428 g, 90%) as a yellow oil. $^1$H NMR (400 MHz, CDCl$_3$), mixture of rotamers and regioisomers, δ 7.42-7.27 (m, 7H), 7.26-7.21 (m, 1H), 6.89-6.85 (m, 2H), 6.80-6.74 (m, 1H), 6.28-5.98 (m, 1H), 5.12 (s, 2H), 4.07-3.82 (m, 2H) 3.82, 3.82 and 3.81 (3×s, 3H), 3.79, 3.79 and 3.78 (3×s, 3H), 3.75-3.43 (m, 2H), 2.84-2.50 (m, 1H), 2.49-2.35 (m, 1H), 0.95-0.75 (m, 9H), 0.15-0.10 (m, 6H); MS (ES+): m/z=589 (M+H)$^+$; LCMS (Method A): t$_R$=8.93 min.

Allyl (S)-(5-(benzyloxy)-2-(2-(((tert-butyldimethyl-silyl)oxy)methyl)-4-(4-methoxyphenyl)-1,2,3,6-tetrahydropyridine-1-carbonyl)-4-methoxy-phenyl)carbamate and allyl (S)-(5-(benzyloxy)-2-(6-(((tert-butyldimethyl-silyl)oxy)methyl)-4-(4-methoxyphenyl)-1,2,3,6-tetrahydropyridine-1-carbonyl)-4-methoxyphenyl)carbamate (11) (1:1)

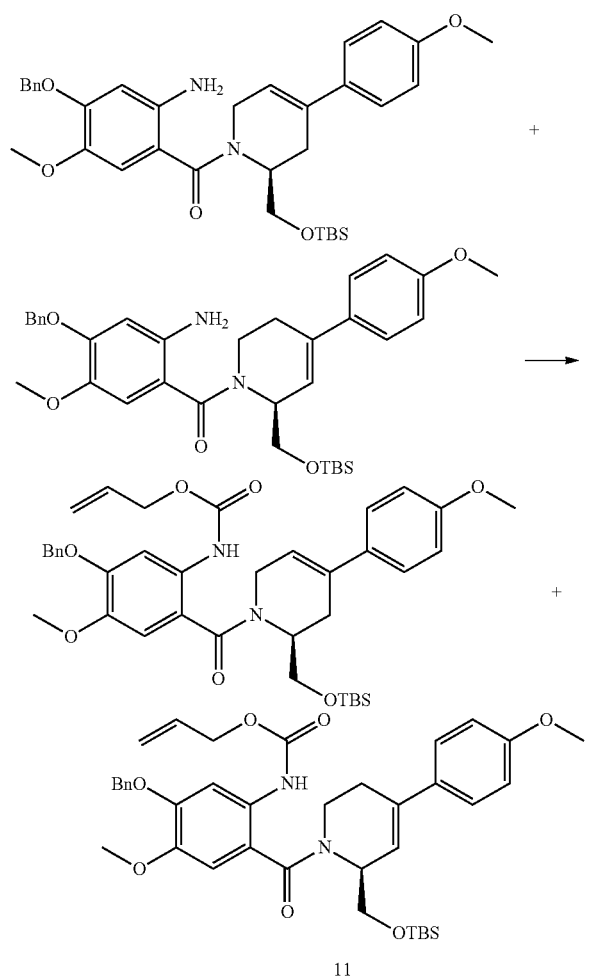

11

A solution of (S)-(2-amino-4-(benzyloxy)-5-methoxyphenyl)(2-(((tert-butyldimethyl-silyl)oxy)methyl)-4-(4-methoxyphenyl)-3,6-dihydropyridin-1(2H)-yl)methanone and (S)-(2-amino-4-(benzyloxy)-5-methoxyphenyl)(6-(((tert-butyldimethylsilyl)oxy)-methyl)-4-(4-methoxyphenyl)-3,6-dihydropyridin-1(2H)-yl)methanone (10) (0.40 g, 0.67 mmol) in dichloromethane (30 mL) was charged with pyridine (0.124 mL, 1.54 mmol) and allyl chloroformate (0.074 mL, 0.70 mmol). After 1 h, the reaction was judged to be complete by TLC and LCMS and was sequentially washed with a saturated aqueous solution of copper sulfate (2×20 mL) and brine (20 mL). The organic extract was then dried over magnesium sulfate and concentrated in vacuo. The resulting oil was then purified by flash column chromatography (silica), eluting with dichloro-methane/acetone (95:5) to afford the title compound (389 mg, 85%) as a brown oil. $^1$H NMR (400 MHz, CDCl$_3$), mixture of rotamers and regioisomers, δ 8.52-7.69 (m, 1H), 7.44-7.35 (m, 2H), 7.34-7.17 (m, 5H), 6.87-6.60 (m, 3H), 6.04-5.90 (br, 1H), 5.85 (ddd, J=16.1, 10.9, 5.7 Hz, 1H), 5.28-5.20 (m, 1H), 5.15-5.05 (m, 3H), 4.59-4.46 (m, 2H), 3.98-3.80 (m, 1H), 3.76 (s, 3H), 3.72 (s, 3H), 3.66-3.33 (m, 2H), 2.77-230 (m, 2H), 0.87-0.68 (m, 9H), 0.15-0.07 (m, 6H); MS (ES+): m/z=673 (M+H)$^+$; LCMS (Method A): t$_R$=9.50 min.

Allyl (S)-(5-(benzyloxy)-2-(2-(hydroxymethyl)-4-(4-methoxyphenyl)-1,2, 3,6-tetrahydropyridine-1-carbonyl)-4-methoxyphenyl)carbamate and allyl (S)-(5-(benzyloxy)-2-(6-(hydroxymethyl)-4-(4-methoxyphenyl)-1,2,3,6-tetrahydropyridine-1-carbonyl)-4-methoxyphenyl)carbamate (12) (1:1)

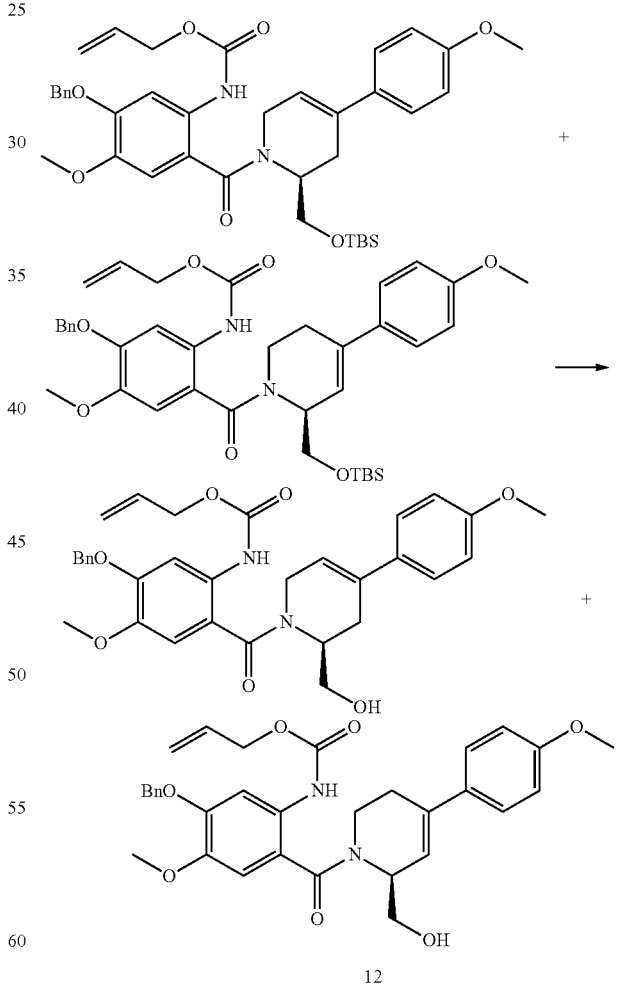

12

A solution of allyl (S)-(5-(benzyloxy)-2-(2-(((tert-butyldimethylsilyl)oxy)methyl)-4-(4-methoxyphenyl)-1,2, 3,6-tetrahydropyridine-1-carbonyl)-4-methoxyphenyl)carbamate and allyl (S)-(5-(benzyloxy)-2-(6-(((tert-butyldimethylsilyl)oxy)methyl)-4-(4-methoxy-phenyl)-1,2, 3,6-tetrahydropyridine-1-carbonyl)-4-methoxyphenyl) carbamate (11) (0.35 g, 0.52 mmol) in tetrahydrofuran (30 mL) was cooled to 0° C. and charged with tetrabutylammonium fluoride (1 M in tetrahydrofuran, 0.65 mL, 0.65 mmol). The reaction was allowed to warm to room temperature and after 1 h, TLC and LCMS confirmed consumption of starting material. Ethyl acetate (100 mL) was added to the reaction mixture and the resulting solution washed with a saturated aqueous solution of ammonium chloride (50 mL) and brine (50 mL) and dried over magnesium sulfate. After concentrating in vacuo, the title compound (276 mg, 95%) was afforded as a brown oil. $^1$H NMR (400 MHz, CDCl$_3$), mixture of rotamers and regioisomers, δ 8.21-7.77 (m, 1H), 7.48 (d, J=8.0 Hz, 2H), 7.42-7.28 (m, 5H), 6.88 (d, J=8.7 Hz, 2H), 6.83 (br, 1H), 6.00-5.83 (m, 2H), 5.37-5.26 (m, 1H), 5.24-5.19 (m, 1H) 5.18 (s, 2H), 4.54-4.44 (t, J=5.5 Hz, 2H), 3.97-3.78 (m, 1H), 3.77 and 3.74 (2×s, 3H), 3.73 and 3.70 (2×s, 3H), 3.69-3.52 (m, 2H), 3.41-3.23 (m, 1H), 2.74-2.17 (m, 3H); MS (ES+): m/z=559 (M+H)$^+$; LCMS (Method B): $t_R$=3.77 min.

Allyl (6aS)-3-(benzyloxy)-6-hydroxy-2-methoxy-8-(4-methoxyphenyl)-12-oxo-6,6a,7,10-tetrahydrobenzo[e]pyrido[1,2-α][1,4]diazepine-5(12H)-carboxylate and allyl (6aS)-3-(benzyloxy)-6-hydroxy-2-methoxy-8-(4-methoxyphenyl)-12-oxo-6,6a,9,10-tetrahydrobenzo[e]pyrido[1,2-α][1,4]-diazepine-5 (12H)-carboxylate (13) (1:1)

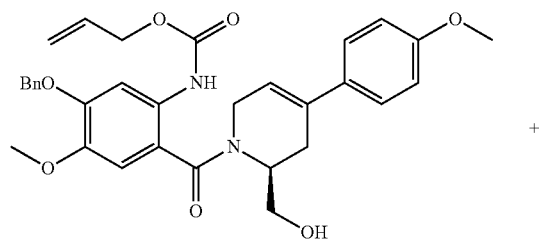

+

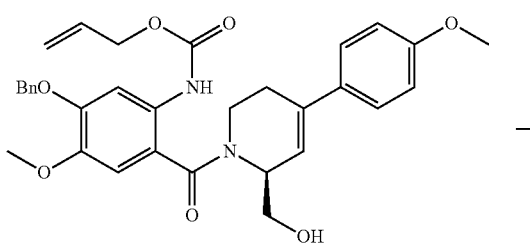

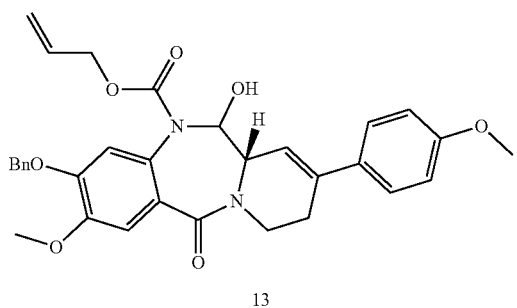

13

A solution of allyl (S)-(5-(benzyloxy)-2-(2-(hydroxymethyl)-4-(4-methoxyphenyl)-1,2,3,6-tetrahydropyridine-1-carbonyl)-4-methoxyphenyl)carbamate and allyl (S)-(5-(benzyloxy)-2-(6-(hydroxymethyl)-4-(4-methoxyphenyl)-1,2,3,6-tetrahydropyridine-1-carbonyl)-4-methoxyphenyl) carbamate (12) (0.25, 0.45 mmol) in dichloromethane (15 mL) was charged with TEMPO (0.017 g, 0.11 mmol) and (diacetoxyiodo)benzene (0.363 g, 1.13 mmol) and stirred for 16 h. Dichloromethane (15 mL) was then added to the reaction mixture, which was washed sequentially with a saturated aqueous solution of sodium metabisulfite (30 mL) and brine (30 mL). The organic extract was then dried over magnesium sulfate and concentrated under reduced pressure. Purification by flash column chromatography (silica), eluting with dichloromethane/acetone (85:15) gave the title compound (137 mg, 55%) as a red oil. $^1$H NMR (400 MHz, CDCl$_3$), mixture of regioisomers, δ 7.35-7.21 (m, 5H) 7.19-7.11 (m, 1H), 7.10-7.04 (m, 2H), 6.84-6.76 (m, 2H), 6.65-6.57 (m, 1H), 6.15-6.01 (m, 1H), 5.73-5.85 and 5.60-5.44 (m, 1H), 5.11-496 (m, 3H), 4.73-4.66 and 4.42-4.28 (m, 2H), 4.23 (dd, J=3.6 Hz, 1H), 4.09-3.90 (m, 1H), 3.84 and 3.82 (2×s, 3H), 3.74 and 3.72 (2×s, 3H) 3.69-3.61 (m, 1H), 3.35-3.26 (m, 1H), 2.99 (d, J=14.9 Hz, 1H), 2.64-2.46 (m, 2H); MS (ES+): m/z=557 (M+H)$^+$; LCMS (Method B): $t_R$=3.50 min.

Allyl (6aS)-3,6-dihydroxy-2-methoxy-8-(4-methoxyphenyl)-12-oxo-6,6a,7,10-tetrahydrobenzo[e]pyrido[1,2-α][1,4]diazepine-5(12H)-carboxylate and allyl (6aS)-3,6-dihydroxy-2-methoxy-8-(4-methoxyphenyl)-12-oxo-6,6a,9,10-tetrahydrobenzo[e]pyrido[1,2-α][1,4]diazepine-5(12H)-carboxylate (14) (1:1)

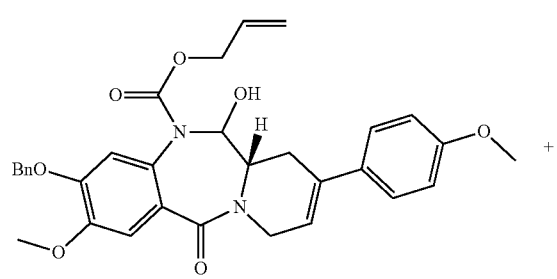 +

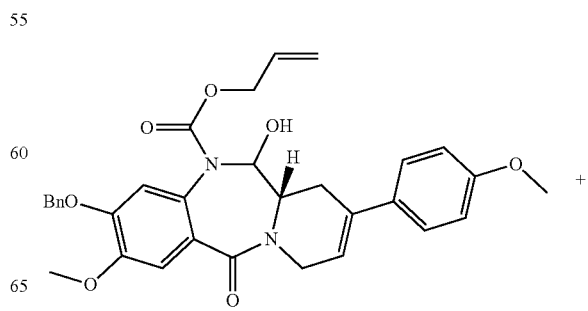 +

-continued

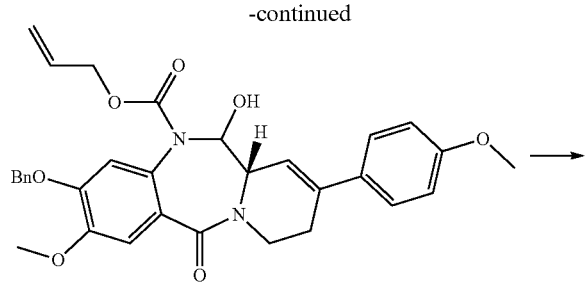

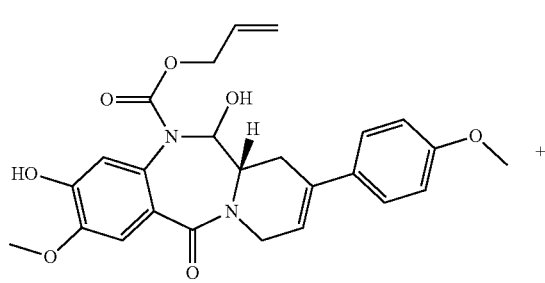

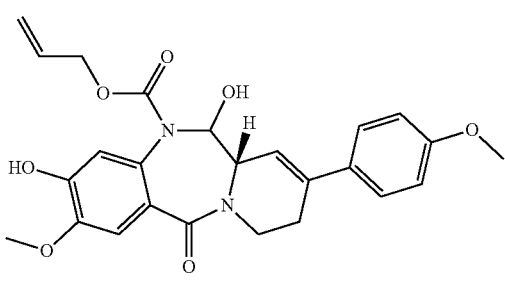

14

A solution of allyl (6aS)-3-(benzyloxy)-6-hydroxy-2-methoxy-8-(4-methoxyphenyl)-12-oxo-6,6a,7,10-tetrahydrobenzo[e]pyrido[1,2-α][1,4]diazepine-5(12H)-carboxylate and allyl(6aS)-3-(benzyloxy)-6-hydroxy-2-methoxy-8-(4-methoxyphenyl)-12-oxo-6,6a,9,10-tetrahydrobenzo[e]pyrido[1,2-α][1,4]diazepine-5(12H)-carboxylate (13) (0.125 g, 0.23 mmol) in anhydrous dichloromethane (10 mL) was charged with boron trichloride (1 M in dichloromethane, 0.67 mL, 0.67 mmol) under an inert atmosphere of nitrogen. After 15 min, the reaction was deemed to have completed by TLC and LCMS and was subsequently cooled to −78° C. and added to a cold saturated aqueous solution of sodium hydrogen carbonate (20 mL). Dichloromethane (20 mL) was then added and after separating layers, the organic extract was washed with brine (20 mL), dried over magnesium sulfate, and concentrated in vacuo. Purification by flash column chromatography (silica), eluting with dichloromethane/acetone (94:6) gave the title compound (44 mg, 42%) as a yellow solid. $^1$H NMR (400 MHz, CDCl$_3$), mixture of regioisomers, δ 9.80 and 9.78 (2×s, 1H), 7.40-7.36 (m, 2H), 7.04 and 7.02 (2×s, 1H), 6.94-6.91 (m, 2H), 6.65 and 6.62 (2×s, 1H), 6.30 and 5.99 (2×s, 1H), 5.86-5.70 (m, 1H), 5.67-5.36 (m, 1H), 5.15-4.95 (m, 1H), 4.65-4.30 (m, 2H), 4.12-3.91 (m, 1H), 3.80 and 3.79 (2×s, 3H), 3.75 and 3.73 (2×s, 3H), 3.68-3.43 (m, 1H), 3.11-2.90 (m, 1H), 2.69-2.35 (m, 2H); MS (ES+): m/z=467 (M+H)$^+$; LCMS (Method B): t$_R$=3.18 min.

Allyl (6aS)-3-hydroxy-2,6-dimethoxy-8-(4-methoxyphenyl)-12-oxo-6,6a,7,10-tetrahydrobenzo[e]pyrido[1,2-α][1,4]diazepine-5(12H)-carboxylate and allyl (6aS)-3-hydroxy-2,6-dimethoxy-8-(4-methoxyphenyl)-12-oxo-6,6a,9,10-tetrahydrobenzo[e]pyrido[1,2-α][1,4]diazepine-5(12H)-carboxylate (15) (1:1)

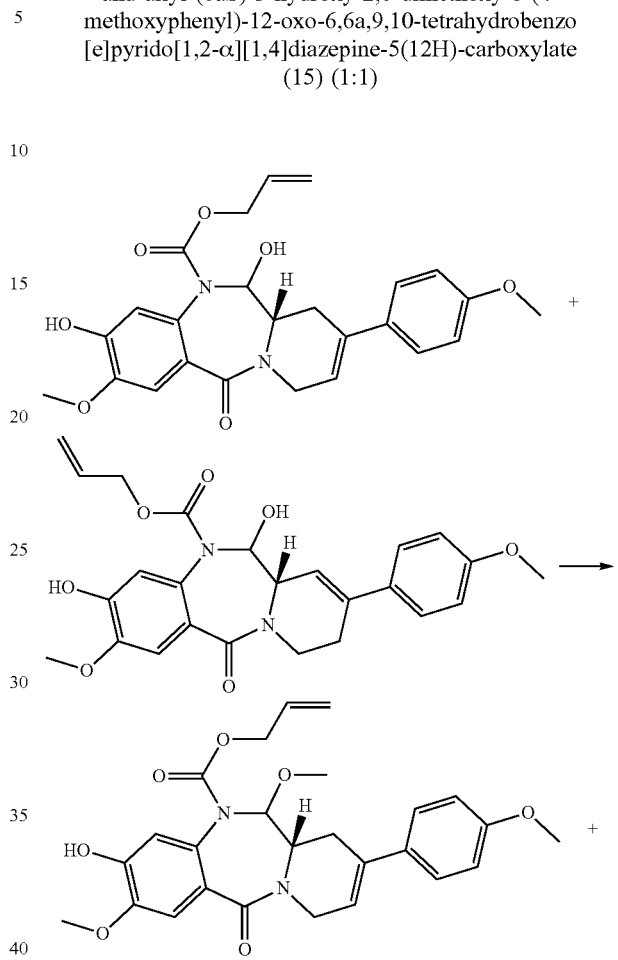

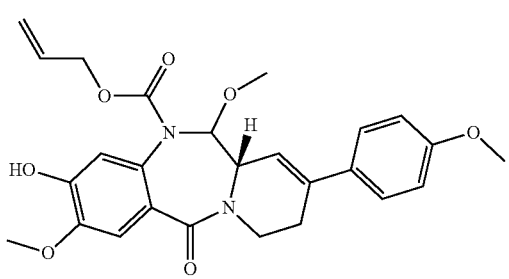

15

A solution of allyl (6aS)-3,6-dihydroxy-2-methoxy-8-(4-methoxyphenyl)-12-oxo-6,6a,7,10-tetrahydrobenzo[e]pyrido[1,2-α][1,4]diazepine-5(12H)-carboxylate and allyl (6aS)-3,6-dihydroxy-2-methoxy-8-(4-methoxyphenyl)-12-oxo-6,6a,9,10-tetrahydrobenzo[e]pyrido[1,2-α][1,4]diazepine-5(12H)-carboxylate (14)(44 mg, 0.094 mmol) in methanol was concentrated in vacuo to afford the title compound (35 mg, 77%) as a yellow solid, which was used in the subsequent step without further purification. MS (ES+): m/z=481 (M+H)$^+$; LCMS (Method B): t$_R$=3.57 min.

177

Allyl (6aS)-3-(3-bromopropoxy)-2,6-dimethoxy-8-(4-methoxyphenyl)-12-oxo-6,6a,7,10-tetrahydrobenzo[e]pyrido[1,2-α][1,4]diazepine-5(12H)-carboxylate and allyl (6aS)-3-(3-bromopropoxy)-2,6-dimethoxy-8-(4-methoxyphenyl)-12-oxo-6,6a,9,10-tetrahydrobenzo[e]pyrido[1,2-α][1,4]diazepine-5(12H)-carboxylate (16) (1:1)

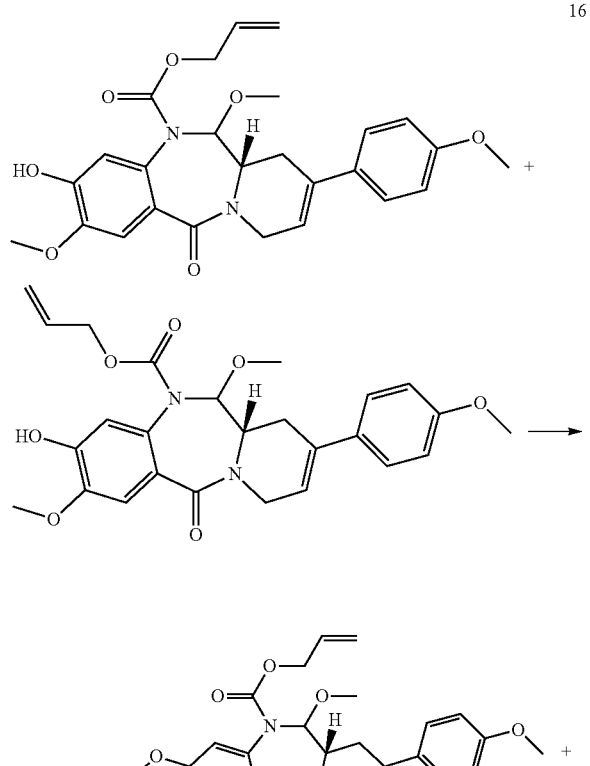

16

178

-continued

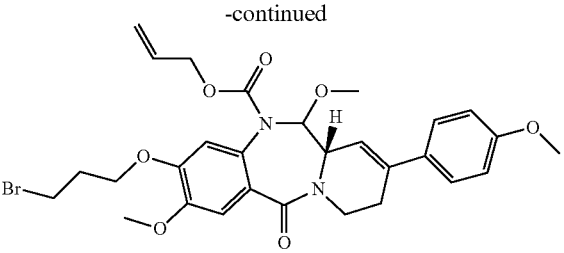

A solution of allyl (6aS)-3-hydroxy-2,6-dimethoxy-8-(4-methoxyphenyl)-12-oxo-6,6a,7,10-tetrahydrobenzo[e]pyrido[1,2-α][1,4]diazepine-5(12H)-carboxylate and allyl (6aS)-3-hydroxy-2,6-dimethoxy-8-(4-methoxyphenyl)-12-oxo-6,6a,9,10-tetrahydrobenzo[e]pyrido[1,2-α][1,4]diazepine-5(12H)-carboxylate (15) (0.035 g, 0.073 mmol) in N,N-dimethylformamide (5 mL) was charged with potassium carbonate (0.010 g, 0.073 mmol) and 1,3-dibromopropane (0.015 mL, 0.15 mmol) and stirred at room temperature for 16 h. Water (50 mL) was then added and the resulting suspension extracted with ethyl acetate (3×50 mL). The combined organic extracts were then washed with a saturated aqueous solution of sodium hydrogen carbonate (50 mL) and brine (3×50 mL), dried over magnesium sulfate and concentrated in vacuo. Flash column chromatography (silica), eluting with petroleum spirit, 40-60° C./ethyl acetate (4:1) gave the title compound (20 mg, impure) as a brown oil. MS (ES+): m/z=603 (M+H)$^+$; LCMS (Method A): $t_R$=8.75 min.

Diallyl 3,3'-(propane-1,3-diylbis(oxy))(6aS,6a'S)-bis(2,6-dimethoxy-8-(4-methoxyphenyl)-12-oxo-6,6a,9,10-tetrahydrobenzo[e]pyrido[1,2-α][1,4]-diazepine-5(12H)-carboxylate) and diallyl 3,3'-(propane-1,3-diylbis(oxy))-(6aS,6a'S)-bis(2,6-dimethoxy-8-(4-methoxyphenyl)-12-oxo-6,6a,7,10-tetrahydrobenzo[e]pyrido[1,2-α][1,4]diazepine-5(12H)-carboxylate) and allyl (6aS)-3-(3-(((6aS)-5-((allyloxy)carbonyl)-2,6-dimethoxy-8-(4-methoxyphenyl)-12-oxo-5,6,6a,7,10,12-hexahydrobenzo[e]pyrido[1,2-α]-[1,4]diazepin-3-yl)oxy)propoxy)-2,6-dimethoxy-8-(4-methoxyphenyl)-12-oxo-6,6a,9,10-tetrahydrobenzo[e]pyrido[1,2-α][1,4]diazepine-5(12H)-carboxylate (17)

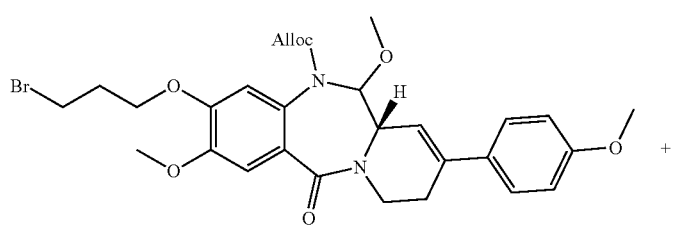

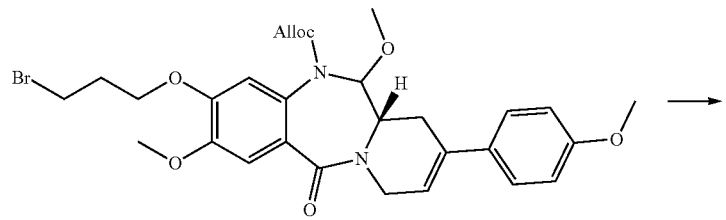

-continued

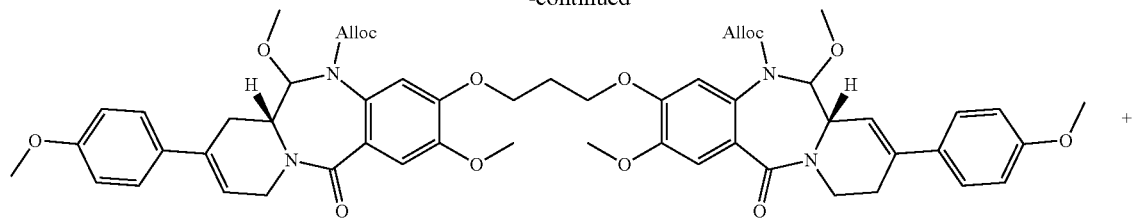

+

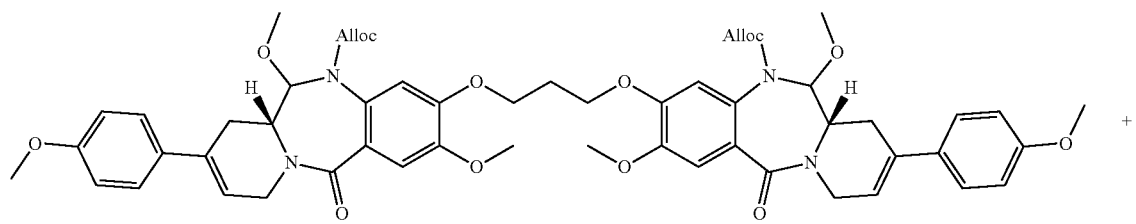

+

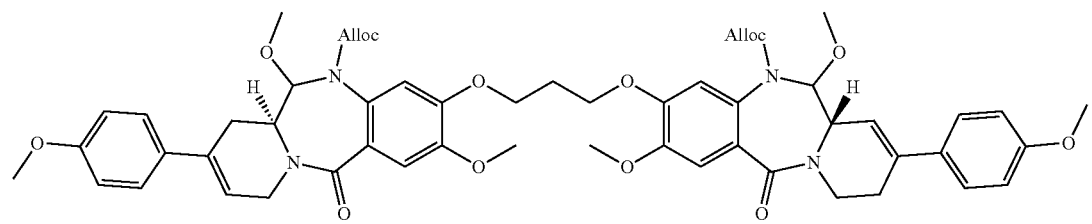

17

A solution of allyl (6aS)-3-(3-bromopropoxy)-2,6-dimethoxy-8-(4-methoxyphenyl)-12-oxo-6,6a,7,10-tetrahydrobenzo[e]pyrido[1,2-α][1,4]diazepine-5(12H)-carboxylate and allyl (6aS)-3-(3-bromopropoxy)-2,6-dimethoxy-8-(4-methoxyphenyl)-12-oxo-6,6a,9,10-tetrahydrobenzo[e]pyrido[1,2-α][1,4]diazepine-5(12H)-carboxylate (16) (0.020 g, 0.033 mmol) in N,N-dimethylformamide (5 mL) was charged with potassium carbonate (0.005 g, 0.033 mmol) and allyl (6aS)-3-hydroxy-2,6-dimethoxy-8-(4-methoxyphenyl)-12-oxo-6,6a,7,10-tetrahydrobenzo[e]pyrido[1,2-α][1,4]diazepine-5(12H)-carboxylate and allyl (6aS)-3-hydroxy-2,6-dimethoxy-8-(4-methoxyphenyl)-12-oxo-6,6a,9,10-tetrahydrobenzo[e]pyrido[1,2-α][1,4]diazepine-5(12H)-carboxylate (15) (0.014 mg, 0.030 mmol). The reaction mixture was heated to 60° C. and stirred for 4 h. Water (50 mL) was then added to the solution and the resulting suspension extracted with ethyl acetate (3×50 mL). The combined organics were washed a saturated aqueous solution of sodium hydrogen carbonate (50 mL) and brine (3×50 mL), dried over magnesium sulfate and concentrated in vacuo. Purification by flash column chromatography (silica), eluting with dichloromethane/acetone (9:1) gave the title compound (17 mg, 51%) as a white solid. $^1$H NMR (400 MHz, CDCl$_3$), mixture of regioisomers, δ 7.48-7.30 (m, 4H), 7.23 and 7.20 (2×s, 2H), 6.97-6.84 (m, 4H), 6.77-6.66 (m, 2H), 6.23 and 6.02 (2× br, 2H), 5.87-5.69 (m, 2H), 5.63 and 5.41 (2× d, J=9.1 and 8.6 Hz, 2H), 5.18-4.99 (m, 3H), 4.77-4.54 (m, 4H), 4.52-4.37 (m, 2H), 4.33-4.08 (m, 5H), 4.01-3.85 (m, 8H), 3.82 and 3.79 (2×s, 6H), 3.69-3.52 (m, 1H), 3.18-2.90 (m, 2H), 2.73-2.51 (m, 3H), 2.45-2.33 (m, 2H); MS (ES+): m/z=1024 (M+Na)$^+$; LCMS (Method A): t$_R$=9.32 min.

(6aS,6a'S)-3,3'-(Propane-1,3-diylbis(oxy))bis(2-methoxy-8-(4-methoxy-phenyl)-9,10-dihydrobenzo[e]pyrido[1,2-α][1,4]diazepin-12(6aH)-one) (18)

18

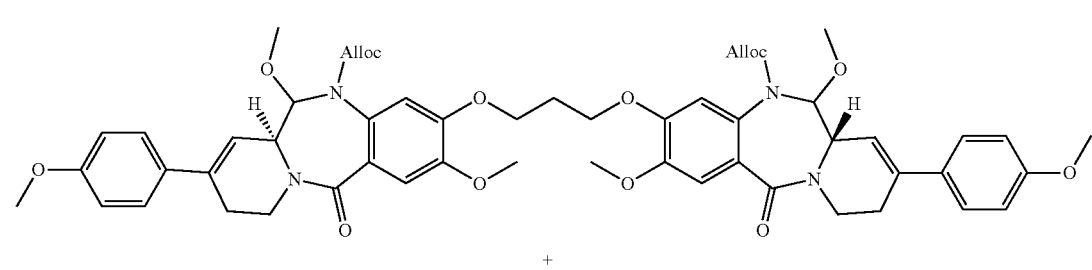

+

-continued

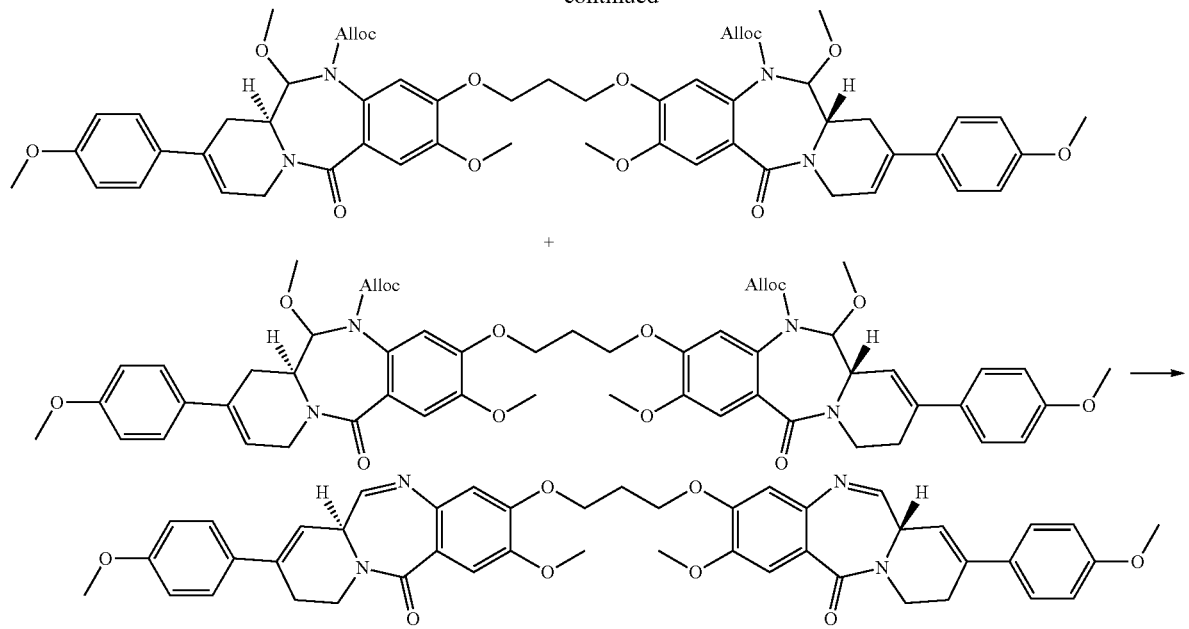

A solution containing diallyl 3,3'-(propane-1,3-diylbis(oxy))(6aS,6a'S)-bis(2,6-dimethoxy-8-(4-methoxyphenyl)-12-oxo-6,6a,9,10-tetrahydrobenzo[e]pyrido[1,2-α][1,4]diazepine-5(12H)-carboxylate) and diallyl 3,3'-(propane-1,3-diylbis(oxy))-(6aS,6a'S)-bis(2,6-dimethoxy-8-(4-methoxyphenyl)-12-oxo-6,6a,7,10-tetrahydrobenzo-[e]pyrido[1,2-α][1,4]diazepine-5(12H)-carboxylate) and allyl (6aS)-3-(3-(((6aS)-5-((allyloxy)carbonyl)-2,6-dimethoxy-8-(4-methoxyphenyl)-12-oxo-5,6,6a,7,10,12-hexahydrobenzo[e]pyrido[1,2-α][1,4]diazepin-3-yl)oxy)propoxy)-2,6-dimethoxy-8-(4-methoxyphenyl)-12-oxo-6,6a,9,10-tetrahydrobenzo[e]pyrido[1,2-α] [1,4]diazepine-5(12H)-carboxylate (17) (0.017 g, 0.017 mmol) in dichloromethane (3 mL) was charged with pyrrolidine (0.0013 mL, 0.02 mmol) and tetrakis(triphenylphosphine)-palladium(o) (0.001 g, 0.00085 mmol). This was stirred for 15 min, then concentrated in vacuo. Diethyl ether (10 mL) was charged and the residue concentrated in vacuo once again and this process was repeated twice more. Purification (separation of regioisomers) was carried out by flash column chromatography (silica), eluting with ethyl acetate (100%) to give the title compound (10 mg, 76%) as a cream solid. $^1$H NMR (400 MHz, CDCl$_3$) δ 7.87 (d, J=5.3 Hz, 2H), 7.47 (s, 2H), 7.39 (d, J=7.2 Hz, 4H), 6.92 (d, J=7.2 Hz, 4H), 6.88 (s, 2H), 6.50 (d, J=3.7 Hz, 2H), 4.56-4.45 (m, 2H), 4.36-4.19 (m, 6H), 3.93 (s, 6H), 3.82-3.76 (m, 6H), 3.48-3.37 (m, 2H), 2.72-2.65 (m, 4H), 2.48-2.36 (m, 2H); MS (ES+): m/z=770 (M+H)$^+$; LCMS (Method A): t$_R$=7.18 min.

Diallyl 3,3'-((1,3-phenylenebis(methylene))bis(oxy))(6aS,6a'S)-bis(2,6-dimethoxy-8-(4-methoxyphenyl)-12-oxo-6,6a,9,10-tetrahydrobenzo[e]-pyrido[1,2-α][1,4]diazepine-5(12H)-carboxylate)(19)

19

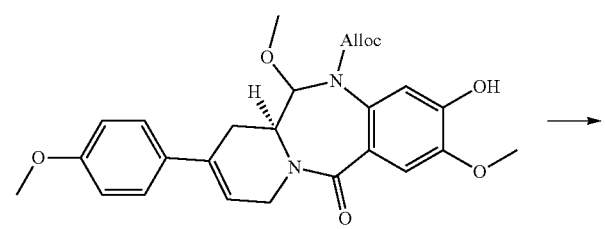

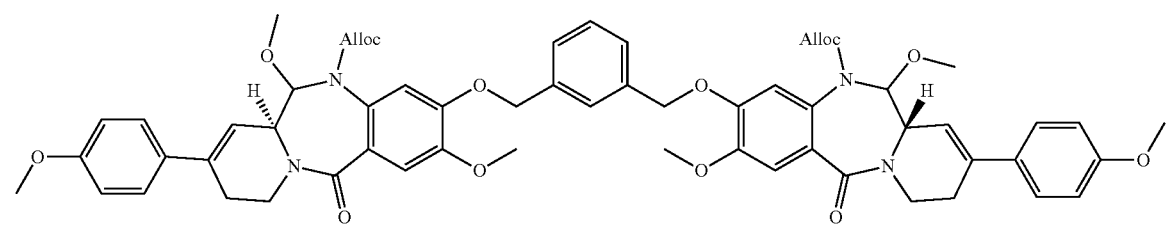

A solution of allyl (6aS)-3-hydroxy-2,6-dimethoxy-8-(4-methoxyphenyl)-12-oxo-6,6a,9,10-tetrahydrobenzo[e]pyrido[1,2-α][1,4]diazepine-5(12H)-carboxylate (15) (0.035 g, 0.073 mmol) in N,N-dimethylformamide (2 mL) was charged with potassium carbonate (0.010 g, 0.073 mmol) and 1,3-bis(bromomethyl)benzene (0.011 g, 0.039 mmol) and irradiated with microwaves 45° C. for 45 min. Water (20 mL) was then added, and the mixture extracted with ethyl acetate (3×50 mL). The combined organic extracts were washed with brine (3×100 mL), dried over magnesium sulfate and concentrated in vacuo. Purification by flash column chromatography (silica), eluting with dichloromethane/acetone (9:1) gave the title compound (28 mg, 73%) as a cream solid. $^1$H NMR (400 MHz, CDCl$_3$) δ 7.54 (s, 2H) 7.41 (br, 4H), 7.33 (d, J=8.1 Hz, 4H), 7.22 (s, 2H), 6.88 (d, J=7.8 Hz, 4H), 6.71 (s, 2H), 6.07-6.00 (m, 2H), 5.80-5.66 (m, 2H), 5.66 (d, J=9.7 Hz, 2H), 5.19-5.00 (m, 8H), 4.72-4.35 (m, 6H), 3.92 (s, 6H), 3.81 (s, 6H), 3.51 (s, 6H), 3.16-3.05 (m, 2H), 2.63-2.51 (m, 4H); MS (ES+): m/z=1064 (M+H)$^+$; LCMS (Method A): $t_R$=9.43 min.

(6aS,6a'S)-3,3'-((1,3-Phenylenebis(methylene))bis(oxy))bis(2-methoxy-8-(4-methoxyphenyl)-9,10-dihydrobenzo[e]pyrido[1,2-α][1,4]diazepin-12-(6aH)-one) (20)

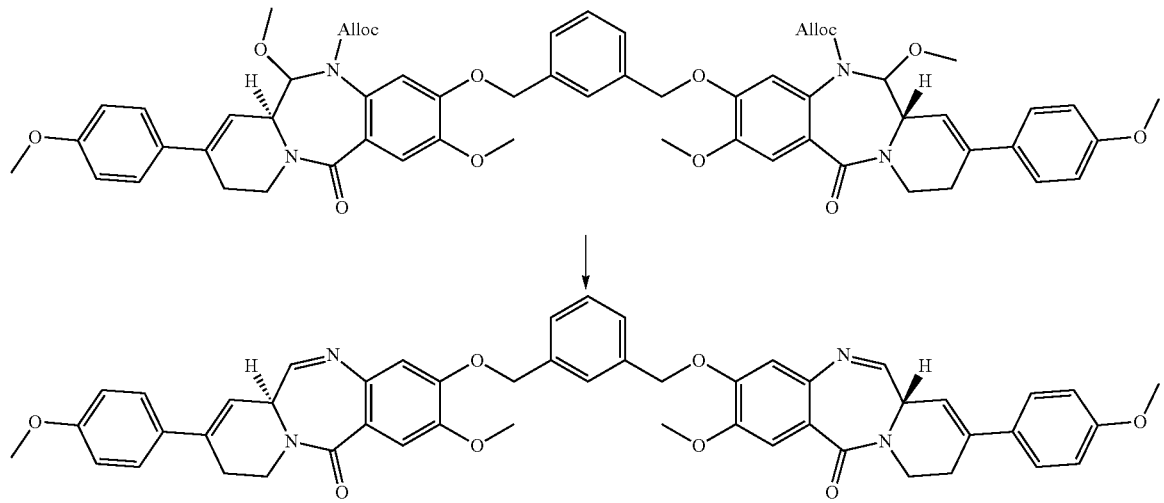

20

A solution of diallyl 3,3'-((1,3-phenylenebis(methylene))bis(oxy))(6aS,6a'S)-bis(2,6-dimethoxy-8-(4-methoxyphenyl)-12-oxo-6,6a,9,10-tetrahydrobenzo[e]pyrido[1,2-α]-[1,4]diazepine-5(12H)-carboxylate) (19) (0.015 g, 0.014 mmol) in dichloromethane (3 mL) was charged with tetrakis(triphenylphosphine)palladium(o) (0.001 g, 0.00085 mmol) and pyrrolidine (0.0026 mL, 0.04 mmol) and stirred for 5 min, then concentrated in vacuo. Diethyl ether (10 mL) was charged and the residue concentrated in vacuo once again, and this process was repeated twice more. Purification was carried out by flash column chromatography (silica), eluting with dichloromethane/acetone (3:1) to give the title compound (7.6 mg, 65%) as a cream solid. 1H NMR (400 MHz, CDCl$_3$) δ 7.84 (d, J=5.3 Hz, 2H), 7.53-7.48 (m, 3H), 7.44-7.35 (m, 7H), 6.91 (d, J=8.4 Hz, 4H), 6.85 (s, 2H), 6.05 (d, J=3.9 Hz, 2H), 5.21 (q, J=12.4 Hz, 4H), 4.54-4.41 (m, 2H), 4.32-4.26 (m, 2H), 3.96 (s, 6H), 3.83 (s, 6H), 3.49-3.37 (td, J=13.9, 7.6 Hz, 2H), 2.72-2.65 (m, 4H); MS (ES+): m/z=831 (M+H)$^+$; LCMS (Method A): $t_R$=7.33 min.

Diallyl 3,3'-((1,3-phenylenebis(methylene))bis(oxy))
(6aS,6a'S)-bis(2,6-dimethoxy-8-(4-methoxyphenyl)-
12-oxo-6,6a,7,10-tetrahydrobenzo[e]-pyrido[1,2-α]
[1,4]diazepine-5(12H)-carboxylate) (21)

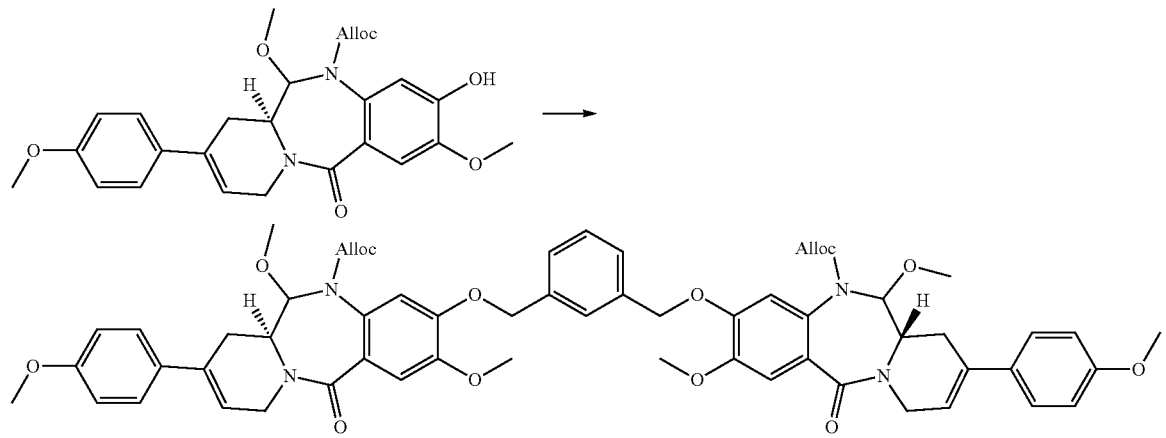

A solution of allyl (6aS)-3-hydroxy-2,6-dimethoxy-8-(4-methoxyphenyl)-12-oxo-6,6a, 7,10-tetrahydrobenzo[e]pyrido[1,2-a][1,4]diazepine-5(12H)-carboxylate (15) (0.010 g, 0.021 mmol) in N,N-dimethylformamide (1 mL) was charged with potassium carbonate (0.0028 g, 0.021 mmol) and 1,3-bis(bromomethyl)benzene (0.003 g, 0.010 mmol) and irradiated with microwaves 45° C. for 45 min. Water (10 mL) was then added, and the mixture extracted with ethyl acetate (3×20 mL). The combined organic extracts were washed with brine (3×30 mL), dried over magnesium sulfate and concentrated in vacuo. Purification by flash column chromatography (silica), eluting with dichloro-methane/acetone (9:1) gave the title compound (7.7 mg, 70%) as a cream solid. $^1$H NMR (400 MHz, CDCl$_3$) δ 7.52 (s, 2H), 7.40 (br, 4H), 7.36 (d, J=8.5 Hz, 4H), 6.90 (d, J=8.5 Hz, 4H), 6.69 (s, 2H), 6.26-6.20 (m, 2H), 5.76-5.64 (m, 2H), 5.45-5.35 (m, 2H), 5.18-4.99 (m, 8H), 4.61-4.36 (m, 4H), 4.31-4.05 (m, 6H), 3.93 (s, 6H), 3.83 (s, 6H), 3.70-3.59 (m, 2H), 3.42-3.38 (s, 6H), 2.99-2.62 (m, 2H); MS (ES+): m/z=1063 (M+H)$^+$; LCMS (Method B): $t_R$=4.17 min.

(6aS,6a'S)-3,3'-((1,3-Phenylenebis(methylene))bis
(oxy))bis(2-methoxy-8-(4-methoxyphenyl)-7,10-
dihydrobenzo[e]pyrido[1,2-α][1,4]diazepin-12
(6aH)-one) (22)

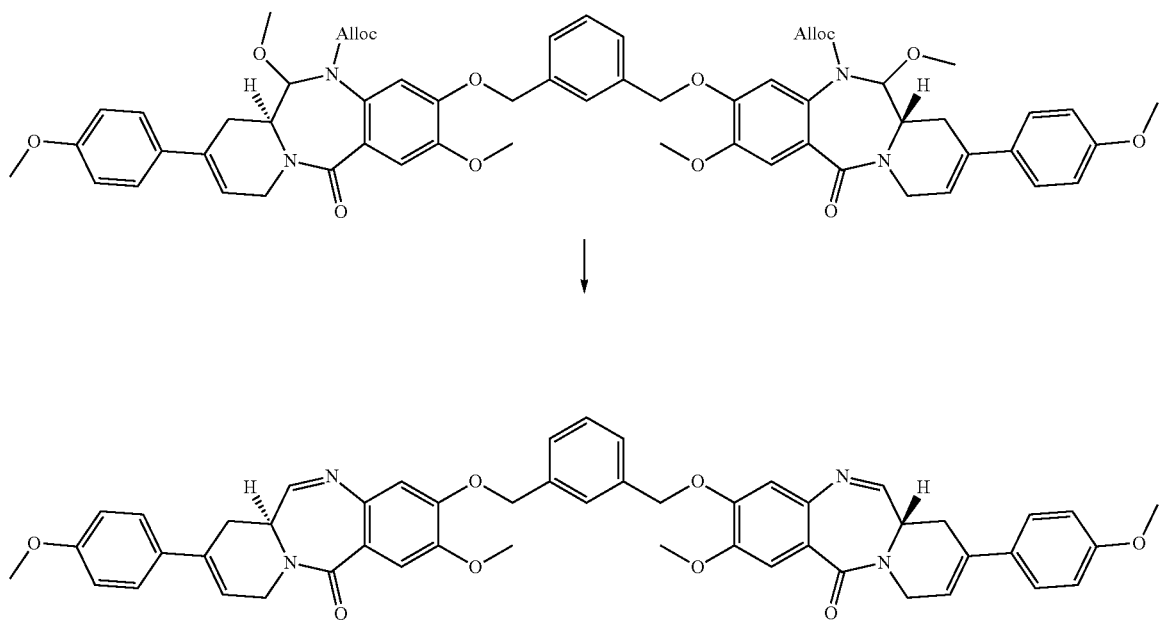

A solution of diallyl 3,3'-((1,3-phenylenebis(methylene))bis(oxy))(6aS,6a'S)-bis(2,6-dimethoxy-8-(4-methoxyphenyl)-12-oxo-6,6a,7,10-tetrahydrobenzo[e]pyrido[1,2-a][1,4]diazepine-5(12H)-carboxylate) (21) (0.0041 g, 0.0039 mmol) in dichloromethane (1 mL) was charged with tetrakis(triphenylphosphine)palladium(o) (1 mg) and pyrrolidine (3 L) and stirred for 5 min, then concentrated in vacuo. Diethyl ether (10 mL) was charged and the residue concentrated in vacuo once again, and this process was repeated twice more. Purification was carried out by flash column chromatography (silica), eluting with dichloromethane/acetone (3:1) to give the title compound (1.9 mg, 60%) as a cream solid. $^1$H NMR (400 MHz, CDCl$_3$) δ 7.59 (d, J=5.4 Hz, 2H), 7.54 (s, 2H), 7.50 (s, 1H), 7.43-7.38 (m, 7H), 6.93 (d, J=7.9 Hz, 4H), 6.83 (s, 2H), 6.39-6.35 (m, 2H), 5.20 (q, J=12.8 Hz, 4H), 4.46 (dd, J=18.0, 6.1 Hz, 2H), 4.11 (d, J=18.1 Hz, 2H), 3.97 (s, 6H), 3.94 (d, J=5.0 Hz, 2H), 3.84 (s, 6H), 2.94 (m, 4H); MS (ES+): m/z=831 (M+H)$^+$; LCMS (Method A): t$_R$=7.42 min.

Diallyl 3,3'-((pyridine-2,6-diylbis(methylene))bis(oxy))(6aS,6a'S)-bis(2,6-dimethoxy-8-(4-methoxyphenyl)-12-oxo-6,6a,9,10-tetrahydrobenzo[e]-pyrido[1,2-α][1,4]d-iazepine-5(12H)-carboxylate) (23)

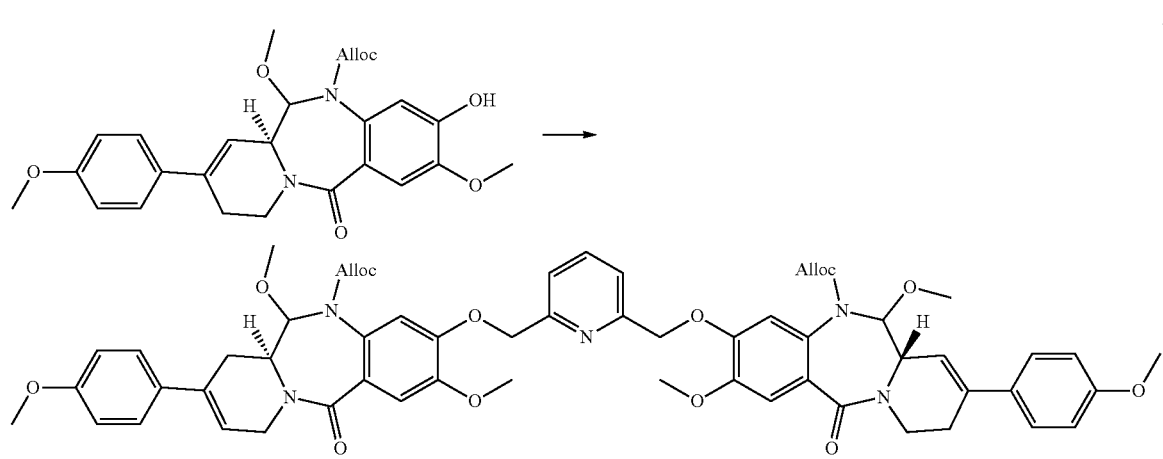

23

A solution of allyl (6aS)-3-hydroxy-2,6-dimethoxy-8-(4-methoxyphenyl)-12-oxo-6,6a,9,10-tetrahydrobenzo[e]pyrido[1,2-α][1,4]diazepine-5(12H)-carboxylate (15) (0.030 g, 0.062 mmol) in N,N-dimethylformamide (1 mL) was charged with potassium carbonate (0.0086 g, 0.062 mmol) and 1,3-bis(bromomethyl)benzene (0.008 g, 0.031 mmol) and irradiated with microwaves 45° C. for 40 min. Water (20 mL) was then added, and the mixture extracted with ethyl acetate (3×50 mL). The combined organic extracts were washed with brine (3×100 mL), dried over magnesium sulfate and concentrated in vacuo. Purification by flash column chromatography (silica), eluting with dichloromethane/acetone (9:1) gave the title compound (24 mg, 73%) as a cream solid. $^1$H NMR (400 MHz, CDCl$_3$) δ 7.79 (t, J=7.7 Hz, 1H), 7.54 (d, J=7.7 Hz, 2H), 7.33 (d, J=8.7 Hz, 4H), 7.24 (s, 2H), 6.88 (d, J=8.8 Hz, 4H), 6.73 (s, 1H), 6.01 (d, J=2.8 Hz, 2H), 5.76-5.34 (m, 2H), 5.59 (d, J=9.1 Hz, 2H), 5.27 (s, 4H), 5.13-4.98 (m, 4H), 4.72 (d, J=12.7 Hz, 2H), 4.61-4.38 (m, 4H), 3.95 (s, 6H), 3.92 (d, J=11.7 Hz, 2H), 3.82 (s, 6H), 3.49 (s, 6H), 3.17-3.07 (m, 2H), 2.66-2.50 (m, 4H); MS (ES+): m/z=1064 (M+H)$^+$; LCMS (Method B): t$_R$=4.17 min.

(6aS,6a'S)-3,3'-((Pyridine-2,6-diylbis(methylene))bis(oxy))bis(2-methoxy-8-(4-methoxyphenyl)-9,10-dihydrobenzo[e]pyrido[1,2-α][1,4]diazepin-12(6aH)-one) (24)

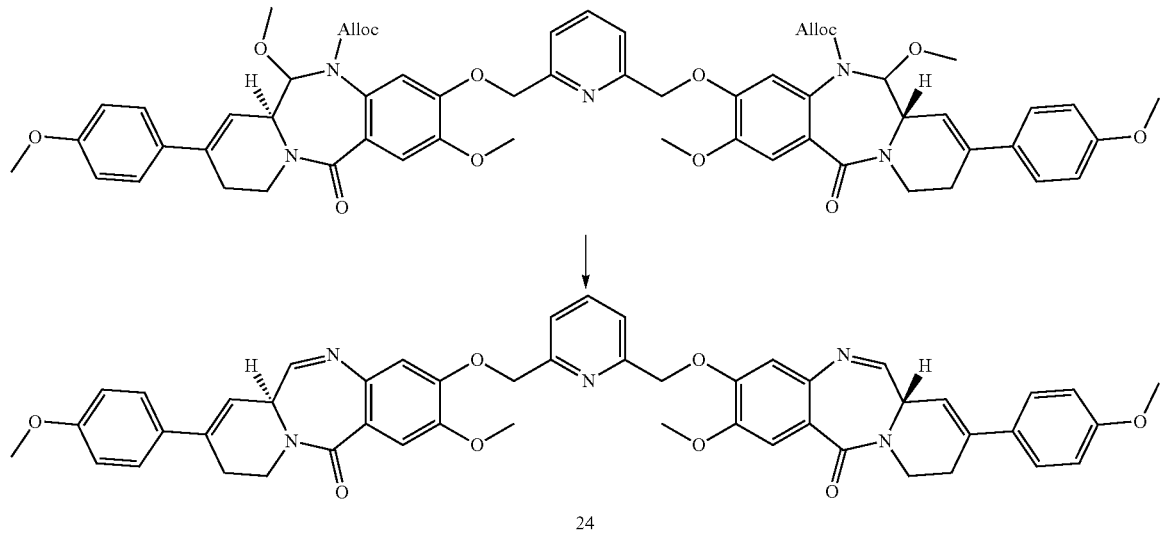

24

A solution of diallyl 3,3'-((pyridine-2,6-diylbis(methylene))bis(oxy))(6aS,6a'S)-bis(2,6-dimethoxy-8-(4-methoxyphenyl)-12-oxo-6,6a,9,10-tetrahydrobenzo[e]pyrido[1,2-α][1,4]diazepine-5(12H)-carboxylate) (23) (0.025 g, 0.023 mmol) in dichloromethane (1 mL) was charged with tetrakis(triphenylphosphine)palladium(o) (2 mg, 0.0013 mmol) and pyrrolidine (4.2 μL, 0.065 mmol) and stirred for 5 min, then concentrated in vacuo. Diethyl ether (10 mL) was charged and the residue concentrated in vacuo once again, and this process was repeated twice more. Purification was carried out by flash column chromatography (silica), eluting with dichloromethane/acetone (3:1) to give the title compound (6.6 mg, 34%) as a cream solid. $^1$H NMR (400 MHz, CDCl$_3$) δ 7.86 (d, J=5.3 Hz, 2H), 7.74 (t, J=7.8 Hz, 1H), 7.48 (d, J=7.8 Hz, 2H), 7.43-7.35 (m, 4H), 6.95-6.89 (m, 4H), 6.86 (s, 2H), 6.06 (d, J=$_{4.0}$ Hz, 2H), 5.34 (s, 4H), 4.51 (dt, J=13.2, 4.6 Hz, 2H), 4.30 (t, J=4.7 Hz, 2H), 4.00 (s, 6H), 3.83 (s, 6H), 3.44 (dt, J=13.3, 6.8 Hz, 2H), 2.76-2.64 (m, 4H); MS (ES+): m/z=832 (M+H)$^+$; LCMS (Method A): t$_R$=7.35 min.

Diallyl 3,3'-((pyridine-2,6-diylbis(methylene))bis(oxy))(6aS,6a'S)-bis(2,6-dimethoxy-8-(4-methoxyphenyl)-12-oxo-6,6a,7,10-tetrahydrobenzo[e]-pyrido[1,2-α][1,4]diazepine-5(12H)-carboxylate) (25)

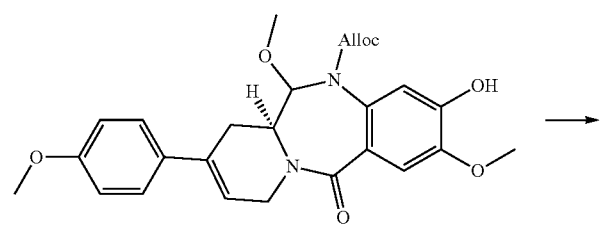

25

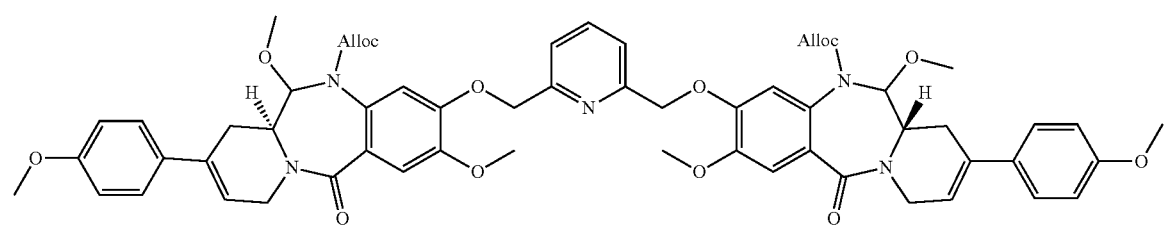

A solution of allyl (6aS)-3-hydroxy-2,6-dimethoxy-8-(4-methoxyphenyl)-12-oxo-6,6a,7,10-tetrahydrobenzo[e]pyrido[1,2-α][1,4]diazepine-5(12H)-carboxylate (15) (0.030 g, 0.062 mmol) in N,N-dimethylformamide (1 mL) was charged with potassium carbonate (0.0086 g, 0.062 mmol) and 1,3-bis(bromomethyl)benzene (0.008 g, 0.031 mmol) and irradiated with microwaves 45° C. for 40 min. Water (20 mL) was then added, and the mixture extracted with ethyl acetate (3×50 mL). The combined organic extracts were washed with brine (3×100 mL), dried over magnesium sulfate and concentrated in vacuo. Purification by flash column chromatography (silica), eluting with dichloromethane/acetone (9:1) gave the title compound (23 mg, 72%) as a cream solid. $^1$H NMR (400 MHz, CDCl$_3$) δ 7.78 (t, J=7.8 Hz, 1H), 7.53 (d, J=7.7 Hz, 2H), 7.35 (d, J=8.6 Hz, 4H), 7.27 (s, 2H), 6.90 (d, J=8.6 Hz, 4H), 6.69 (s, 2H), 6.26-6.19 (m, 2H), 5.74-5.58 (m, 2H), 5.40 (d, J=9.6 Hz, 2H), 5.25 (s, 4H), 5.11-4.95 (m, 4H), 4.58-433 (m, 4H), 4.26 (dd, J=18.1, 5.6 Hz, 2H), 4.14 (d, J=18.1 Hz, 2H), 3.95 (s, 6H), 3.81 (s, 6H), 3.63 (dd, J=8.0, 6.1 Hz, 2H), 3.38 (s, 6H), 2.93 (d, J=15.1 Hz, 2H), 2.72-2.55 (m, 2H); MS (ES+): m/z=1064 (M+H)$^+$; LCMS (Method B): $t_R$=4.02 min.

(6aS,6a'S)-3,3'-((Pyridine-2,6-diylbis(methylene))bis(oxy))bis(2-methoxy-8-(4-methoxyphenyl)-7,10-dihydrobenzo[e]pyrido[1,2-α][1,4]diazepin-12(6aH)-one) (26)

dichloromethane/acetone (3:1) to give the title compound (12 mg, 60%) as a cream solid. $^1$H NMR (400 MHz, CDCl$_3$) δ 7.72 (t, J=7.8 Hz, 1H), 7.58 (d, J=5.5 Hz, 2H), 7.55 (s, 2H), 7.46 (d, J=7.8 Hz, 2H), 7.42-7.36 (m, 4H), 6.95-6.89 (m, 4H), 6.84 (s, 2H), 6.36 (dd, J=3.0, 1.6 Hz, 2H), 5.31 (s, 4H), 4.45 (dd, J=18.3, 5.9 Hz, 2H), 4.15-4.07 (m, 2H), 3.99 (s, 6H), 3.83 (s, 6H), 3.96-3.90 (m, 2H), 2.96-2.91 (m, 4H); MS (ES+): m/z=832 (M+H)$^+$; LCMS (Method A): $t_R$=7.47 min.

(S)-4-(1-(4-(Benzyloxy)-5-methoxy-2-nitrobenzoyl)-6-(((tert-butyl-dimethylsilyl)oxy)methyl)-1,2,3,6-tetrahydropyridin-4-yl)-N-methylbenzenesulfonamide and (S)-4-(1-(4-(benzyloxy)-5-methoxy-2-nitro-benzoyl)-2-(((tert-butyldimethylsilyl)oxy)methyl)-1,2,3,6-tetrahydro-pyridin-4-yl)-N-methylbenzenesulfonamide (27) (1:1)

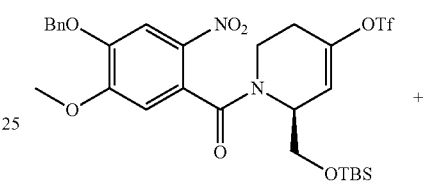

27

+

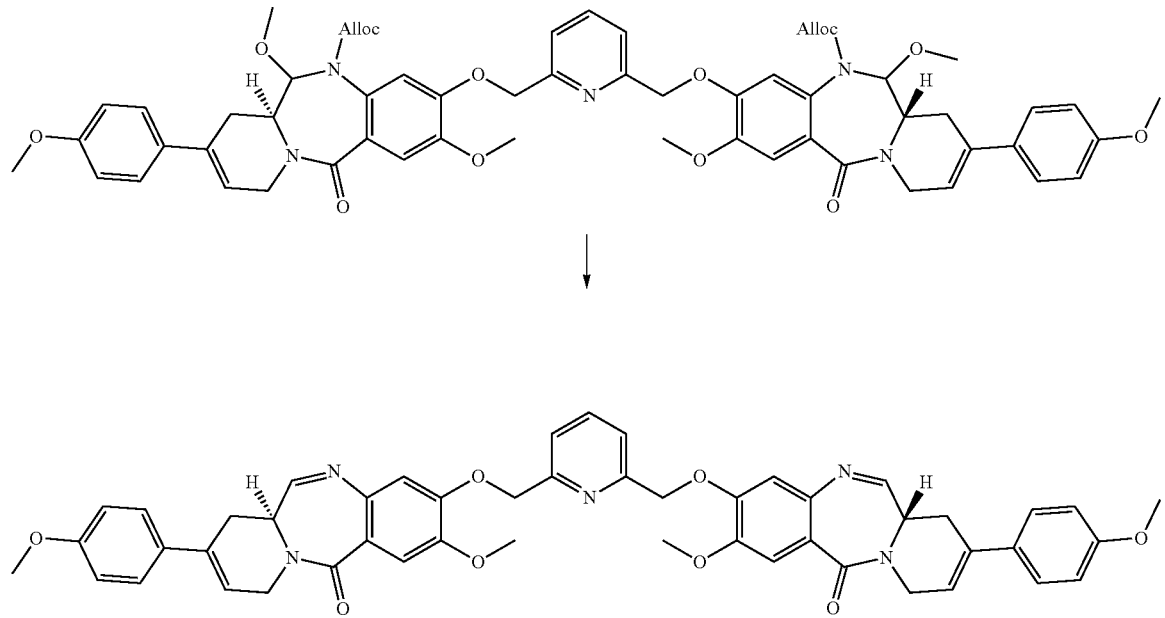

26

A solution of diallyl 3,3'-((pyridine-2,6-diylbis(methylene))bis(oxy))(6aS,6a'S)-bis(2,6-dimethoxy-8-(4-methoxyphenyl)-12-oxo-6,6a,7,10-tetrahydrobenzo[e]pyrido[1,2-a][1,4]diazepine-5(12H)-carboxylate) (25) (0.025 g, 0.023 mmol) in dichloromethane (1 mL) was charged with tetrakis(triphenylphosphine)palladium(o) (2 mg, 0.0013 mmol) and pyrrolidine (4.2 µL, 0.065 mmol) and stirred for 5 min, then concentrated in vacuo. Diethyl ether (10 mL) was charged and the residue concentrated in vacuo once again, and this process was repeated twice more. Purification was carried out by flash column chromatography (silica), eluting with -continued

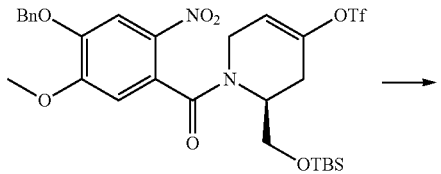

193

-continued

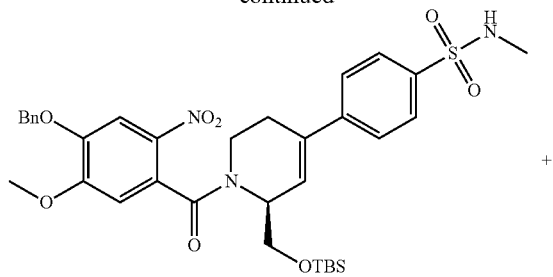

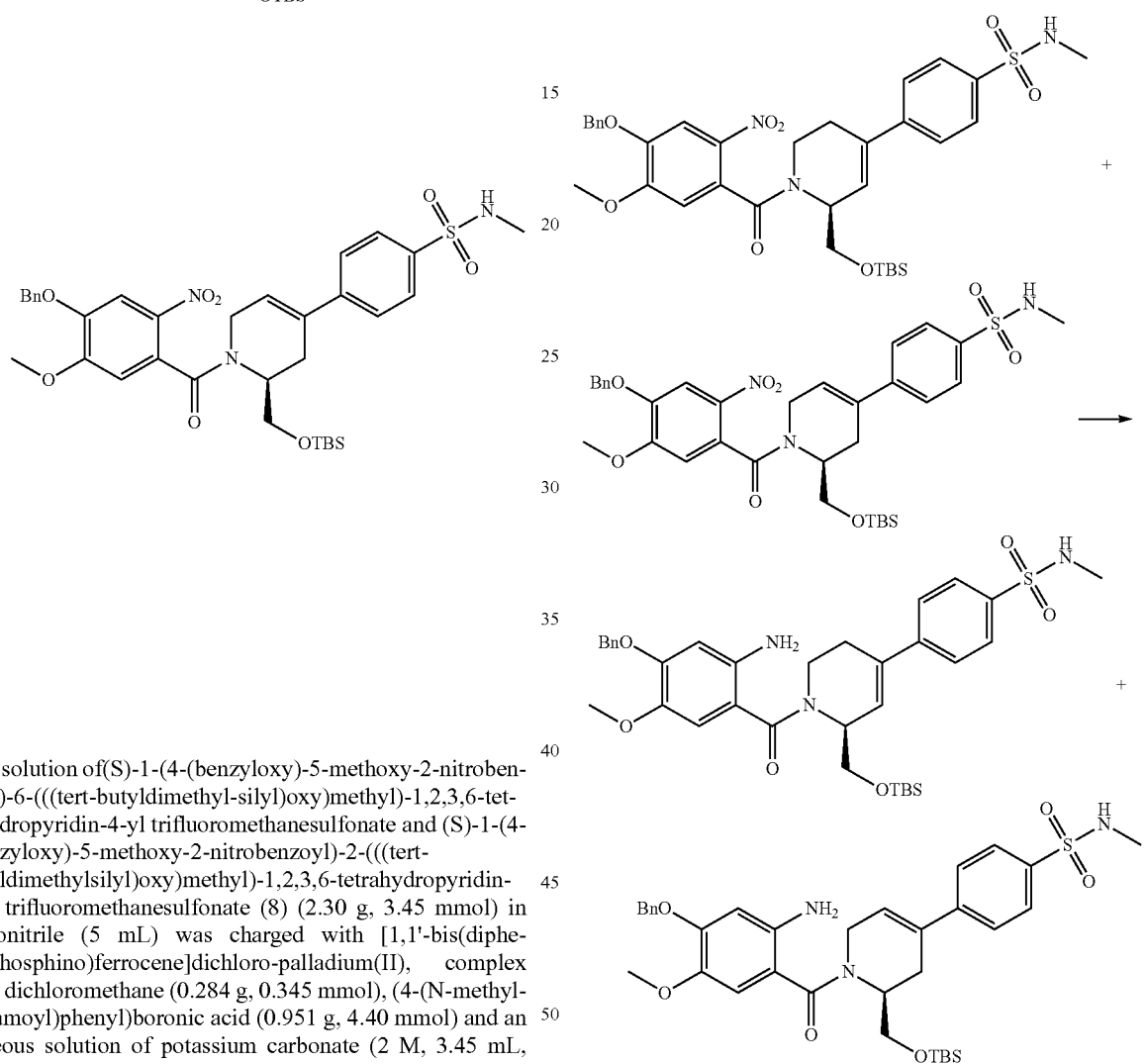

A solution of (S)-1-(4-(benzyloxy)-5-methoxy-2-nitrobenzoyl)-6-(((tert-butyldimethyl-silyl)oxy)methyl)-1,2,3,6-tetrahydropyridin-4-yl trifluoromethanesulfonate and (S)-1-(4-(benzyloxy)-5-methoxy-2-nitrobenzoyl)-2-(((tert-butyldimethylsilyl)oxy)methyl)-1,2,3,6-tetrahydropyridin-4-yl trifluoromethanesulfonate (8) (2.30 g, 3.45 mmol) in acetonitrile (5 mL) was charged with [1,1'-bis(diphenylphosphino)ferrocene]dichloro-palladium(II), complex with dichloromethane (0.284 g, 0.345 mmol), (4-(N-methylsulfamoyl)phenyl)boronic acid (0.951 g, 4.40 mmol) and an aqueous solution of potassium carbonate (2 M, 3.45 mL, 6.90 mmol) and irradiated with microwaves at 50° C. for 10 min. The resulting mixture was diluted with ethyl acetate (100 mL) and washed with brine (50 mL), then dried over solid anhydrous magnesium sulfate and concentrated in vacuo. The residual oil was purified by flash column chromatography (silica), eluting with dichloromethane/acetone (9:1) to afford the title compound (2.09 g, 88%) as an orange solid. $^1$H NMR (400 MHz, CDCl$_3$), mixture of rotamers and regioisomers, δ 7.88-7.71 (m, 3H), 7.55-7.31 (m, 5H), 6.89-6.73 (m, 1H), 6.44-5.93 (m, 4H), 5.28-4.90 (m, 1H), 5.24 and 5.23 (2×s, 2H), 4.38-4.28 (m, 1H), 4.08-3.41 (m, 3H), 3.97 (2×s, 3H), 3.21-2.70 (m, 1H), 2.70-2.63 (m, 3H), 2.61-2.23 (m, 1H), 0.94-0.71 (m, 9H), 0.17-0.15 (m, 6H); MS (ES+): m/z=682 (M+H)$^+$; LCMS (Method B): t$_R$=4.13 min.

194

(S)-4-(1-(2-Amino-4-(benzyloxy)-5-methoxybenzoyl)-6-(((tert-butyl-dimethylsilyl)oxy)methyl)-1,2,3,6-tetrahydropyridin-4-yl)-N-methylbenzenesulfonamide and (S)-4-(1-(2-amino-4-(benzyloxy)-5-methoxy-benzoyl)-2-(((tert-butyldimethylsilyl)oxy)methyl)-1,2,3,6-tetrahydro-pyridin-4-yl)-N-methylbenzenesulfonamide (28) (1:1)

A solution of (S)-4-(1-(4-(Benzyloxy)-5-methoxy-2-nitrobenzoyl)-6-(((tert-butyl-dimethylsilyl)oxy)methyl)-1,2,3,6-tetrahydropyridin-4-yl)-N-methylbenzenesulfonamide and (S)-4-(1-(4-(benzyloxy)-5-methoxy-2-nitrobenzoyl)-2-(((tert-butyldimethylsilyl)oxy)methyl)-1,2,3,6-tetrahydro-pyridin-4-yl)-N-methylbenzene-sulfonamide (27) (2.40 g, 3.52 mmol) in formic acid (5% v/v in absolute ethanol, 80 mL) was charged with zinc powder (8.45 g, 130.2 mmol) and stirred for 30 min, whilst monitoring by TLC and LCMS. Upon completion, the reaction was quenched by addition of a saturated aqueous solution of sodium hydrogen carbonate (10 mL) and concentrated in vacuo. The residue was then partitioned between ethyl acetate (200 mL) and brine (100 mL) and the organic phase dried over magnesium sulfate, filtered, and concentrated in vacuo. Purification by flash column chromatography (silica), eluting with dichloromethane/acetone (9:1) gave the title compound (2.07 g, 90%) as a yellow solid. ¹H NMR (400 MHz, CDCl₃), mixture of rotamers and regioisomers, δ 8.00 (s, 1H), 7.82 (dd, J=8.4, 1.7 Hz, 2H), 7.51 (d, J=8.4 Hz, 2H), 7.45-7.27 (m, 5H), 6.81-6.72 (2×s, 1H), 6.31-6.26 (2×s, 1H), 6.27-6.08 (m, 1H), 5.13 (s, 2H), 4.40 (q, J=5.2 Hz, 1H), 4.05-3.58 (m, 3H), 3.81 (s, 3H), 2.91-2.80 (m, 1H), 2.70-2.62 (m, 3H), 2.53-236 (m, 2H), 0.92-0.78 (m, 9H), 0.13-0.04 (m, 6H); MS (ES+): m/z=652 (M+H)⁺; LCMS (Method B): t_R=3.97 min.

Allyl (S)-(5-(benzyloxy)-2-(6-(((tert-butyldimethylsilyl)oxy)methyl)-4-(4-(N-methylsulfamoyl)phenyl)-1,2,3,6-tetrahydropyridine-1-carbonyl)-4-methoxyphenyl)carbamate and allyl (S)-(5-(benzyloxy)-2-(2-(((tert-butyl-dimethylsilyl)oxy)methyl)-4-(4-(N-methylsulfamoyl)phenyl)-1,2,3,6-tetrahydropyridine-1-carbonyl)-4-methoxyphenyl) carbamate (29) (1:1)

A solution of (S)-4-(1-(2-amino-4-(benzyloxy)-5-methoxybenzoyl)-6-(((tert-butyl-dimethylsilyl)oxy) methyl)-1,2,3,6-tetrahydropyridin-4-yl)-N-methylbenzenesulfonamide and (S)-4-(1-(2-amino-4-(benzyloxy)-5-methoxybenzoyl)-2-(((tert-butyldimethylsilyl)oxy)methyl)-1,2,3,6-tetrahydropyridin-4-yl)-N-methylbenzenesulfonamide (28) (2.20 g, 3.37 mmol) in dichloromethane (200 mL) was charged with pyridine (0.27 mL, 3.38 mmol) and allyl chloroformate (0.429 mL, 4.25 mmol). After 15 min, the reaction was judged to be complete by TLC and LCMS and was sequentially washed with a saturated aqueous solution of copper sulfate (2×100 mL) and brine (100 mL). The organic extract was then dried over magnesium sulfate and concentrated in vacuo. The resulting oil was then purified by flash column chromatography (silica), eluting with dichloromethane/acetone (95:5) to afford the title compound (2.06 g, 83%) as a brown oil. ¹H NMR (400 MHz, CDCl₃), mixture of rotamers and regioisomers, δ 8.43-7.90 (m, 2H), 7.83 (d, J=8.4 Hz, 2H) 7.56-7.28 (m, 7H), 6.97-6.77 (2×s, 1H), 6.23 (s, 1H), 5.92 (ddd, J=22.6, 10.9, 5.7 Hz, 1H), 5.40-5.27 (m, 1H), 5.24-5.12 (m, 3H), 4.08-3.35 (m, 3H), 3.81 (s, 3H), 2.88-2.76 (m, 0.5H), 2.69-2.64 (m, 3H), 2.62-2.36 (m, 1.5H), 0.94-0.75 (m, 9H), 0.20-0.06 (m, 6H); MS (ES+): m/z=736 (M+H)⁺; LCMS (Method B): t_R=4.22 min.

Allyl (S)-(5-(benzyloxy)-2-(6-(hydroxymethyl)-4-(4-(N-methylsulfamoyl)-phenyl)-1,2,3,6-tetrahydropyridine-1-carbonyl)-4-methoxyphenyl)-carbamate and allyl (S)-(5-(benzyloxy)-2-(2-(hydroxymethyl)-4-(4-(N-methylsulfamoyl)phenyl)-1,2,3,6-tetrahydropyridine-1-carbonyl)-4-methoxyphenyl)carbamate (30) (1:1)

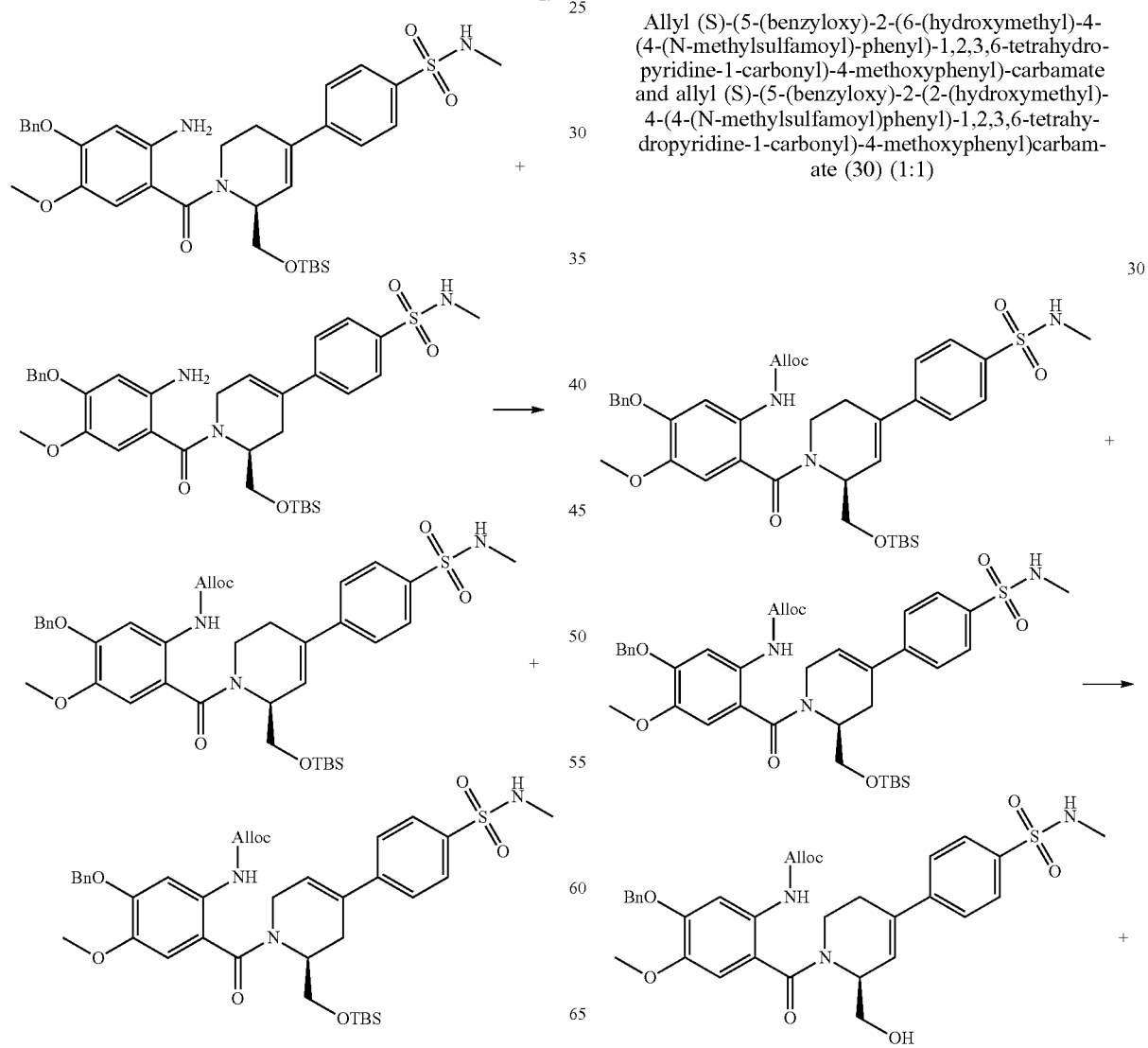

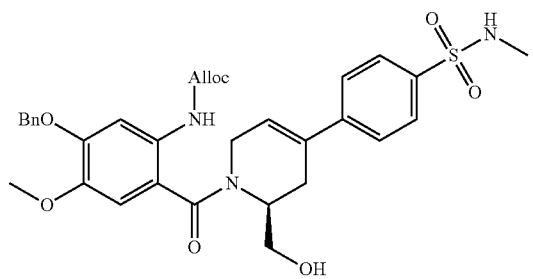

A solution of allyl (S)-(5-(benzyloxy)-2-(6-(((tert-butyldimethylsilyl)oxy)methyl)-4-(4-(N-methylsulfamoyl)phenyl)-1,2,3,6-tetrahydropyridine-1-carbonyl)-4-methoxyphenyl)carbamate and allyl (S)-(5-(benzyloxy)-2-(2-(((tert-butyldimethylsilyl)oxy)-methyl)-4-(4-(N-methylsulfamoyl)phenyl)-1,2,3,6-tetrahydropyridine-1-carbonyl)-4-methoxyphenyl)carbamate (29) (1.90 g, 2.58 mmol) in tetrahydrofuran (50 mL) was cooled to 0° C. and charged with tetrabutylammonium fluoride (1 M in tetrahydrofuran, 0.32 mL, 3.23 mmol). The reaction was allowed to warm to room temperature and after 1 h, TLC and LCMS confirmed consumption of starting material. Ethyl acetate (100 mL) was added to the reaction mixture and the resulting solution washed with a saturated aqueous solution of ammonium chloride (50 mL) and brine (50 mL) and dried over magnesium sulfate. Purification by flash column chromatography (silica), eluting with dichloromethane/acetone (4:1) gave the title compound (1.52 g, 95%) as a cream solid. $^1$H NMR (400 MHz, CDCl$_3$), mixture of rotamers and regioisomers, δ 8.17-8.06 (br, 1H), 7.83-7.70 (m, 3H), 7.53-7.28 (m, 7H), 6.89-6.77 (s, 1H), 6.23-6.08 (m, 1H), 5.91 (ddd, J=22.8, 10.8, 5.6 Hz, 1H), 5.38-5.18 (m, 2H), 5.15 (s, 2H), 4.66-4.57 (m, 2H), 4.54-4.45 (m, 1H), 4.14-3.89 (m, 1H), 3.85-3.83 (2×s, 3H), 3.81-3.32 (m, 2H), 2.91-2.78 (m, 0.5H), 2.68-2.60 (2×d, J=5.4 Hz, 3H), 2.59-2.31 (m, 15H); MS (ES+): m/z=622 (M+H)$^+$; LCMS (Method B): $t_R$=3.37 min.

Allyl (6aS)-3-(benzyloxy)-6-hydroxy-2-methoxy-8-(4-(N-methylsulfamoyl)-phenyl)-12-oxo-6,6a,9,10-tetrahydrobenzo[e]pyrido[1,2-α][1,4]diazepine-5(12H)-carboxylate and allyl (6aS)-3-(benzyloxy)-6-hydroxy-2-methoxy-8-(4-(N-methylsulfamoyl)phenyl)-12-oxo-6,6a,7,10-tetrahydrobenzo[e]-pyrido[1,2-α][1,4]diazepine-5(12H)-carboxylate (31) (1:1)

31

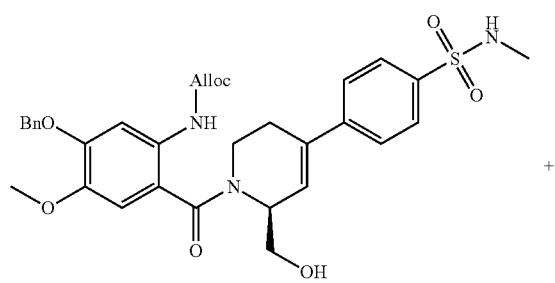

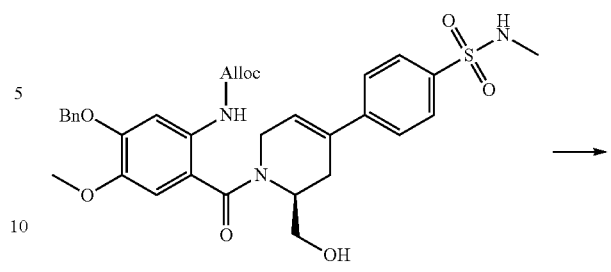

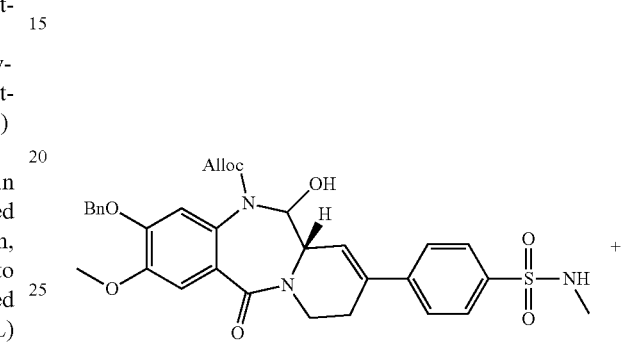

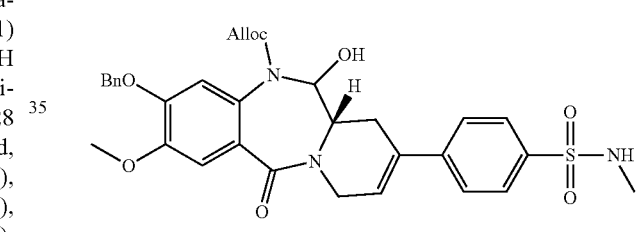

A solution of allyl (S)-(5-(benzyloxy)-2-(6-(hydroxymethyl)-4-(4-(N-methylsulfamoyl)-phenyl)-1,2,3,6-tetrahydropyridine-1-carbonyl)-4-methoxyphenyl)carbamate and allyl (S)-(5-(benzyloxy)-2-(2-(hydroxymethyl)-4-(4-(N-methylsulfamoyl)phenyl)-1,2,3,6-tetrahydropyridine-1-carbonyl)-4-methoxyphenyl)carbamate (30) (1.50 g, 2.41 mmol) in dichloromethane (50 mL) was charged with TEMPO (0.037 g, 0.24 mmol) and (diacetoxyiodo)benzene (0.853 g, 2.61 mmol) and stirred at room temperature for 16 h. Dichloromethane (15 mL) was then added to the reaction mixture, which was quenched by addition of a saturated aqueous solution of sodium metabisulfite (50 mL). The organic phase was separated, washed with brine (50 mL), dried over magnesium sulfate, filtered and concentrated in vacuo. Purification by flash column chromatography (silica), eluting with dichloromethane/acetone (9:1) gave the title compound (748 mg, 50%) as a yellow solid. $^1$H NMR (400 MHz, CDCl$_3$), mixture of rotamers and regioisomers, δ 7.82 (apparent t, J=7.6 Hz, 2H), 7.54 (apparent t, J=7.8 Hz, 2H), 7.46-7.29 (m, 6H), 7.25-7.22 (2×s, 1H), 6.79-6.68 (m, 1H), 6.39-6.29 (m, 1H), 5.87-5.57 (m, 2H), 5.24-5.03 (m, 4H), 4.89-4.79 (m, 1H), 4.59-434 (m, 2H), 4.24-4.01 (m, 1H), 3.95-3.93 (2×s, 3H), 3.81-3.72 (m, 1H), 3.14-3.05 (m, 1H), 2.76-2.73 (m, 3H); MS (ES+): m/z=620 (M+H)$^+$; LCMS (Method B): $t_R$=3.32 min.

Allyl (6aS)-3-hydroxy-2,6-dimethoxy-8-(4-(N-methylsulfamoyl)phenyl)-12-oxo-6,6a,7,10-tetrahydrobenzo[e]pyrido[1,2-α][1,4]diazepine-5(12H)-carboxylate (32)

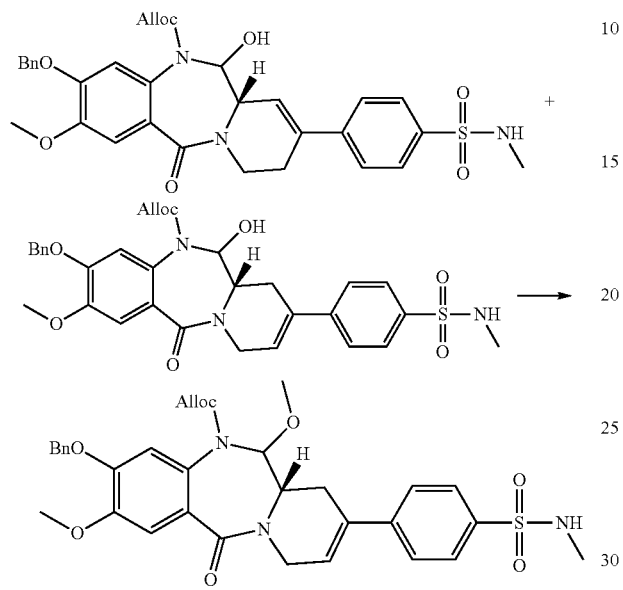

A solution of allyl (6aS)-3-(benzyloxy)-6-hydroxy-2-methoxy-8-(4-(N-methyl-sulfamoyl)phenyl)-12-oxo-6,6a,9,10-tetrahydrobenzo[e]pyrido[1,2-α][1,4]diazepine-5(12H)-carboxylate and allyl (6aS)-3-(benzyloxy)-6-hydroxy-2-methoxy-8-(4-(N-methylsulfamoyl)phenyl)-12-oxo-6,6a,7,10-tetrahydrobenzo[e]pyrido[1,2-α][1,4]-diazepine-5(12H)-carboxylate (31) (700 mg, 1.13 mmol) in anhydrous dichloromethane (20 mL) was charged with boron trichloride (1 M in dichloromethane, 3.39 mL, 3.39 mmol) and stirred under an inert atmosphere of nitrogen for 30 min. Methanol (20 mL) was then charged and the resulting mixture irradiated with microwaves at 55° C. for 1 h. After concentrating the resulting mixture in vacuo, purification was carried out by (multiple) flash column chromatography (silica), eluting with petroleum spirit, 40-60° C./ethyl acetate (4:1) to afford the (regiopure) title compound (203 mg, 33%) as a white solid. $^1$H NMR (400 MHz, CDCl$_3$) δ 7.84 (d, J=8.5 Hz, 2H), 7.57-7.50 (m, 2H), 7.21 (s, 1H), 6.74 (s, 1H), 6.47-6.39 (m, 1H), 5.81-5.68 (m, 1H), 5.40 (d, J=9.6 Hz, 1H), 5.16-5.01 (m, 2H), 4.56 (dd, J=14.6, 4.4 Hz, 1H), 4.45 (dd, J=10.7, 5.3 Hz, 1H), 4.23-4.15 (m, 2H), 3.91 (s, 3H), 3.73-3.64 (m, 1H), 3.42 (s, 3H), 2.96 (d, J=14.9 Hz, 1H), 2.78-2.59 (m, 5H); MS (ES+): m/z=544 (M+H)$^+$; LCMS (Method B): $t_R$=2.97 min.

Allyl (6aS)-3-((6-(((((6aS)-5-((allyloxy)carbonyl)-2,6-dimethoxy-8-(4-(N-methylsulfamoyl)phenyl)-12-oxo-5,6,6a,7,10,12-hexahydrobenzo[e]-pyrido[1,2-α][1,4]diazepin-3-yl)oxy)methyl)pyridin-2-yl)methoxy)-2,6-dimethoxy-8-(4-(N-methylsulfamoyl)phenyl)-12-oxo-6,6a,7,10-tetrahydrobenzo[e]pyrido[1,2-α][1,4]diazepine-5(12H)-carboxylate (33)

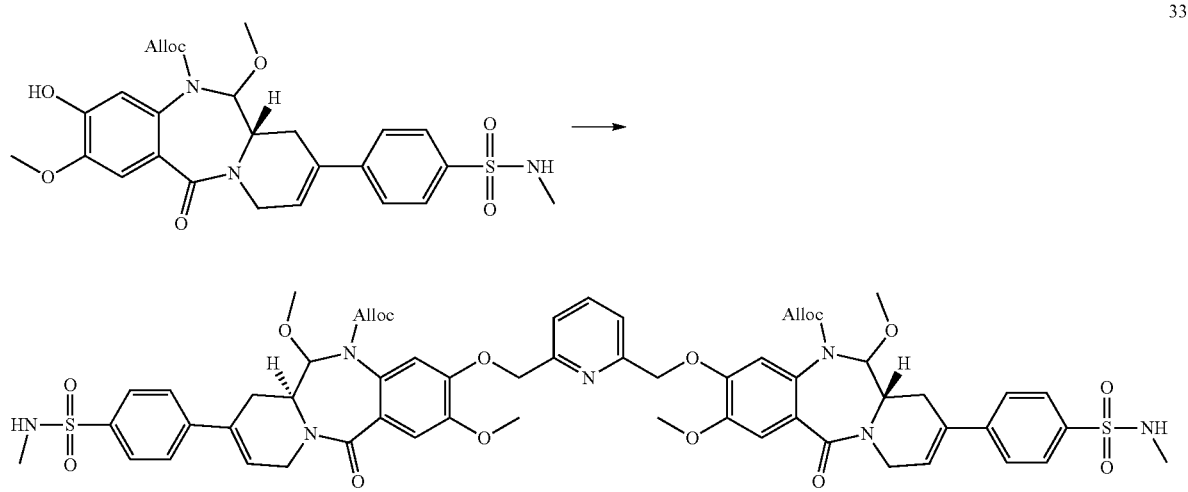

A solution of allyl (6aS)-3-hydroxy-2,6-dimethoxy-8-(4-(N-methylsulfamoyl)phenyl)-12-oxo-6,6a,7,10-tetrahydrobenzo[e]pyrido[1,2-α][1,4]diazepine-5(12H)-carboxylate (32) (0.045 g, 0.083 mmol) in N,N-dimethylformamide (2 mL) was charged with potassium carbonate (0.012 g, 0.083 mmol) and 2,6-bis(bromomethyl)pyridine (0.011 g, 0.042 mmol). The resulting mixture was irradiated with microwaves at 55° C. for 1 h, at which point TLC and LCMS showed completion of the reaction. Water (20 mL) was added and the resulting suspension extracted with ethyl acetate (3×100 mL). The combined organic extracts were then washed with brine (5×100 mL), dried over magnesium sulfate, and concentrated in vacuo. Purification by flash column chromatography (silica), eluting with petroleum spirit, 40-60° C./ethyl acetate (1:4 to 0:1) gave the title compound (22 mg, 44%) as a white solid. $^1$H NMR (400 MHz, CDCl$_3$) δ 7.86 (d, J=8.4 Hz, 4H), 7.79 (t, J=7.8 Hz, 1H), 7.54 (apparent d, J=8.4 Hz, 6H), 6.71 (s, 2H), 6.49-6.41 (m, 2H), 5.74-5.59 (m, 2H), 5.39 (d, J=2 Hz, 2H), 5.25 (s, 4H), 5.05 (d, J=10.3 Hz, 2H), 4.76-4.57 (m, 2H), 4.56-4.36 (m, 4H), 4.36-4.16 (m, 4H), 3.96 (s, 6H), 3.74-3.63 (m, 2H), 3.38 (s, 3H), 2.99-2.91 (m, 2H), 2.78-2.70 (m, 2H), 2.67 (d, J=5.1 Hz, 6H); MS (ES+): m/z=1190 (M+H)$^+$; LCMS (Method B): $t_R$=3.47 min.

4,4'-(((6aS,6a'S)-((Pyridine-2,6-diylbis(methylene))bis(oxy))bis(2-methoxy-12-oxo-6a,7,10,12-tetrahydrobenzo[e]pyrido[1,2-α][1,4]diazepine-3,8-diyl))bis(N-methylbenzenesulfonamide) (34)

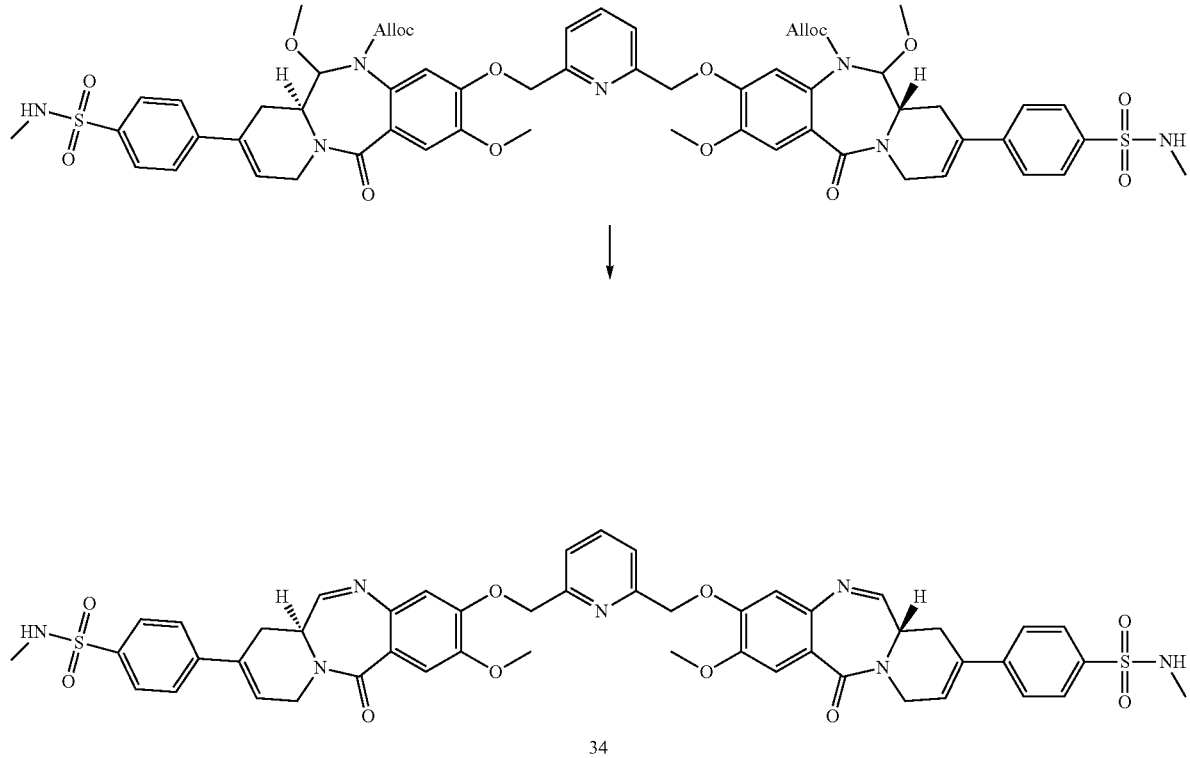

34

A solution of allyl (6aS)-3-((6-(((((6aS)-5-((allyloxy)carbonyl)-2,6-dimethoxy-8-(4-(N-methylsulfamoyl)phenyl)-12-oxo-5,6,6a,7,10,12-hexahydrobenzo[e]pyrido[1,2-α][1,4]-diazepin-3-yl)oxy)methyl)pyridin-2-yl)methoxy)-2,6-dimethoxy-8-(4-(N-methyl-sulfamoyl)phenyl)-12-oxo-6a,6a,7,10-tetrahydrobenzo[e]pyrido[1,2-α][1,4]diazepine-5(12H)-carboxylate (33) (0.022 g, 0.018 mmol) in dichloromethane (2 mL) was charged with tetrakis(triphenylphosphine)palladium(o) (0.001 g, 0.0009 mmol) and pyrrolidine (0.0036 mL, 0.04 mmol). After 5 min, the reaction was observed to have completed via TLC. The reaction mixture was concentrated in vacuo to form an oil, which was charged with diethyl ether (2 mL) and reconcentrated in vacuo (this process was repeated twice more). Purification via flash column chromatography (silica), eluting with dichloromethane/acetone (4:1) gave the title compound (12 mg, 66%) as a white solid. $^1$H NMR (400 MHz, CDCl$_3$) δ 7.91 (d, J=8.6 Hz, 4H), 7.73 (t, J=7.8 Hz, 1H), 7.60 (d, J=8.6 Hz, 4H), 7.57 (d, J=4.7 Hz, 2H), 7.45 (d, J=7.8 Hz, 2H), 6.86 (s, 2H), 6.65-6.56 (m, 2H), 5.34-5.31 (m, 4H), 4.65 (q, J=5.3 Hz, 2H), 4.52 (dd, J=18.7, 5.9 Hz, 2H), 4.22-4.13 (m, 2H), 4.01 (s, 6H), 3.05-2.92 (m, 4H), 2.74-2.64 (m, 6H), 1.61 (m, 2H); MS (ES+): m/z=958 (M+H)$^+$; LCMS (Method A): t$_R$=6.37 min.

(S)-5-(1-(4-(Benzyloxy)-5-methoxy-2-nitrobenzoyl)-6-(((tert-butyl-dimethylsilyl)oxy)methyl)-1,2,3,6-tetrahydropyridin-4-yl)-1,3-dimethyl-pyrimidine-2,4(1H,3H)-dione and (S)-5-(1-(4-(benzyloxy)-5-methoxy-2-nitrobenzoyl)-2-(((tert-butyldimethylsilyl)oxy)methyl)-1,2,3,6-tetrahydropyridin-4-yl)-1,3-dimethylpyrimidine-2,4(1H,3H)-dione (35) (1:1)

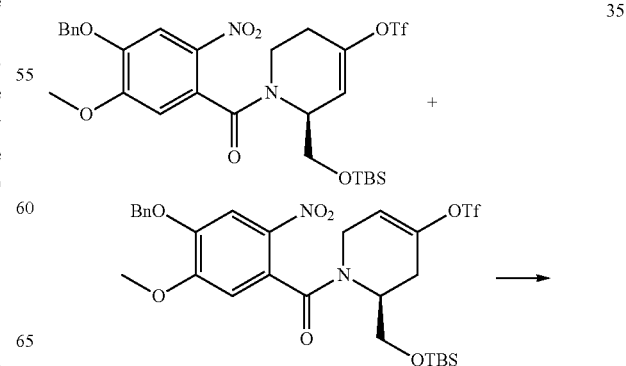

35

203

-continued

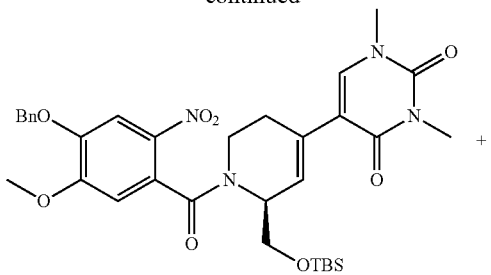

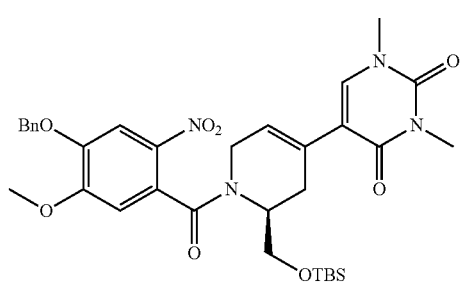

A solution of (S)-1-(4-(benzyloxy)-5-methoxy-2-nitrobenzoyl)-6-(((tert-butyldimethyl-silyl)oxy)methyl)-1,2,3,6-tetrahydropyridin-4-yl trifluoromethanesulfonate and (S)-1-(4-(benzyloxy)-5-methoxy-2-nitrobenzoyl)-2-(((tert-butyldimethylsilyl)oxy)methyl)-1,2,3,6-tetrahydropyridin-4-yl trifluoromethanesulfonate (8) (2.68 g, 4.06 mmol) in acetonitrile (4 mL) was charged with [1,1'-bis(diphenylphosphino)ferrocene]dichloro-palladium(II), complex with dichloromethane (0.334 g, 0.41 mmol), (1,3-dimethyl-2,4-dioxo-1,2,3,4-tetrahydropyrimidin-5-yl)boronic acid (0.968 g, 5.26 mmol) and an aqueous solution of potassium carbonate (2 M, 4.05 mL, 8.10 mmol) and irradiated with microwaves at 50° C. for 40 min. The resulting mixture was diluted with ethyl acetate (100 mL) and washed with brine (50 mL), then dried over solid anhydrous magnesium sulfate and concentrated in vacuo. The residual oil was purified by flash column chromatography (silica), eluting with dichloromethane/acetone (9:1) to afford the title compound (1.93 g, 73%) as a brown solid. $^1$H NMR (400 MHz, CDCl$_3$), mixture of rotamers and regioisomers, δ 7.73-7.70 (m, 1H), 7.49-7.30 (m, 5H), 7.17-7.06 (m, 1H), 6.91-6.72 (m, 1H), 6.36-6.04 (m, 1H), 5.26-5.18 (m, 2H), 5.17-4.76 (m, 1H), 3.96 (s, 3H), 3.93-3.57 (m, 3H), 3.41-3.39 (2×s, 3H), 3.34 (s, 3H), 2.70-2.19 (m, 2H), 0.97-0.69 (m, 9H), 0.19-0.18 (m, 6H); MS (ES+): m/z=651 (M+H)$^+$; LCMS (Method B): $t_R$=4.03 min.

204

(S)-5-(1-(2-Amino-4-(benzyloxy)-5-methoxybenzoyl)-6-(((tert-butyl-dimethylsilyl)oxy)methyl)-1,2,3,6-tetrahydropyridin-4-yl)-1,3-dimethyl-pyrimidine-2,4(1H,3H)-dione and (S)-5-(1-(2-amino-4-(benzyloxy)-5-methoxybenzoyl)-2-(((tert-butyldimethylsilyl)oxy)methyl)-1,2,3,6-tetrahydropyridin-4-yl)-1,3-dimethylpyrimidine-2,4(1H,3H)-dione (36) (1:1)

36

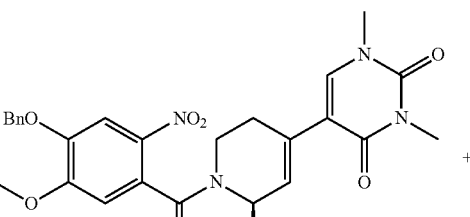

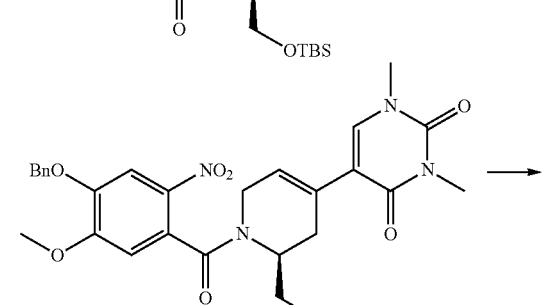

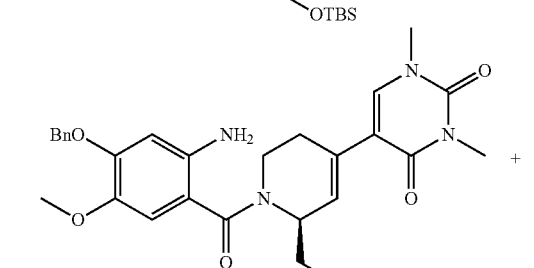

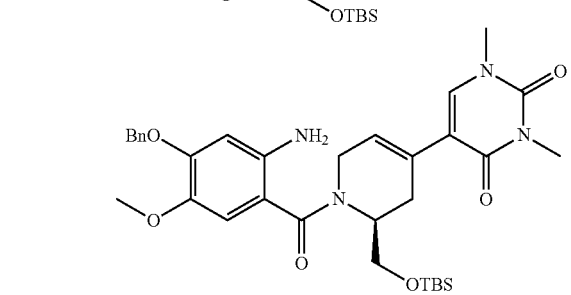

A solution of (S)-5-(1-(4-(benzyloxy)-5-methoxy-2-nitrobenzoyl)-6-(((tert-butyl-dimethylsilyl)oxy)methyl)-1,2,3,6-tetrahydropyridin-4-yl)-1,3-dimethylpyrimidine-2,4(1H,3H)-dione and (S)-5-(1-(4-(benzyloxy)-5-methoxy-2-nitrobenzoyl)-2-(((tert-butyldimethylsilyl)oxy)methyl)-1,2,3,6-tetrahydropyridin-4-yl)-1,3-dimethyl-pyrimidine-2,4(1H,3H)-dione (35) (1.90 g, 2.91 mmol) in formic acid (5% v/v in absolute ethanol, 65 mL) was charged with zinc powder (7.00 g, 108 mmol) and stirred for 30 min, whilst monitoring by TLC and LCMS. Upon completion, the reaction was quenched by addition of a saturated aqueous solution of sodium hydrogen carbonate (10 mL) and concentrated in vacuo. The residue was then partitioned between ethyl acetate (200 mL) and brine (100 mL) and the organic phase dried over magnesium sulfate, filtered, and concentrated in vacuo. Purification by flash column chromatography (silica), eluting with chloroform/acetone (1:0 to 7:3) gave the title compound (1.43 g, 79%) as a yellow solid. $^1$H NMR (400 MHz, CDCl$_3$), mixture of rotamers and regioisomers, δ 7.54-7.24 (m, 5H), 7.13-7.05 (m, 1H), 6.83-6.72 (m, 1H), 6.32-6.16 (m, 2H), 5.12 (s, 2H), 4.03-3.81 (m, 2H), 3.80 (s, 3H), 3.67-3.57 (m, 1H), 3.44-3.37 (m, 3H), 3.35 (s, 3H), 2.66-2.55 (m, 1H), 2.44-2.34 (m, 1H), 0.92-0.76 (m, 9H), 0.13-0.08 (m, 6H); MS (ES+): m/z=621 (M+H)$^+$; LCMS (Method B): t$_R$=3.85 min.

Allyl(S)-(5-(benzyloxy)-2-(6-(((tert-butyldimethylsilyl)oxy)methyl)-4-(1,3-dimethyl-2,4-dioxo-1,2,3,4-tetrahydropyrimidin-5-yl)-1,2,3,6-tetrahydropyridine-1-carbonyl)-4-methoxyphenyl)carbamate and allyl (S)-(5-(benzyloxy)-2-(2-(((tert-butyldimethylsilyl)oxy)methyl)-4-(1,3-dimethyl-2,4-dioxo-1,2,3,4-tetrahydropyrimidin-5-yl)-1,2,3,6-tetrahydropyridine-1-carbonyl)-4-methoxyphenyl)carbamate (37) (1:1)

37

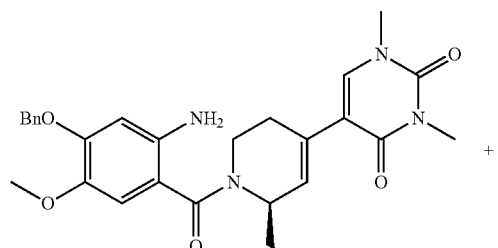

+

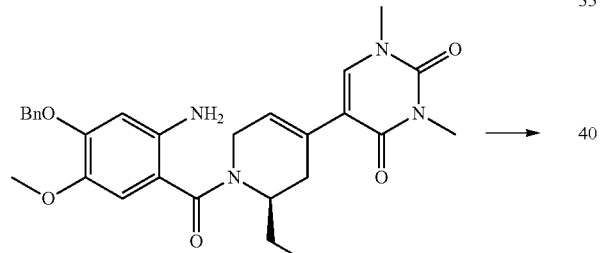

→

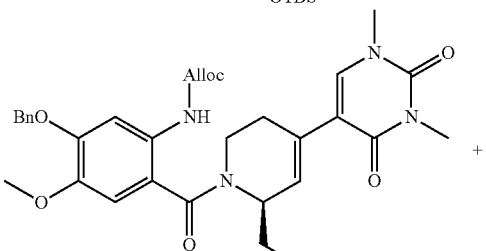

+

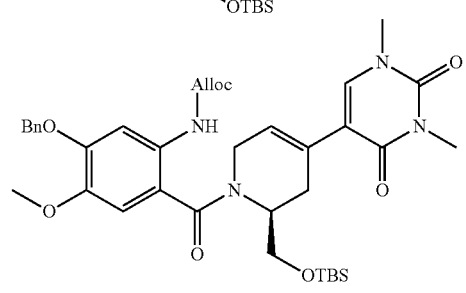

A solution of (S)-5-(1-(2-Amino-4-(benzyloxy)-5-methoxybenzoyl)-6-(((tert-butyl-dimethylsilyl)oxy)methyl)-1,2,3,6-tetrahydropyridin-4-yl)-1,3-dimethylpyrimidine-2,4(1H,3H)-dione and(S)-5-(1-(2-amino-4-(benzyloxy)-5-methoxybenzoyl)-2-(((tert-butyldimethylsilyl)oxy)methyl)-1,2,3,6-tetrahydropyridin-4-yl)-1,3-dimethyl-pyrimidine-2,4(1H,3H)-dione (36) (1.41 g, 2.27 mmol) in dichloromethane (200 mL) was charged with pyridine (0.22 mL, 2.27 mmol) and allyl chloroformate (0.253 mL, 2.38 mmol). After 15 min, the reaction was judged to be complete by TLC and LCMS and was sequentially washed with a saturated aqueous solution of copper sulfate (2×100 mL) and brine (100 mL). The organic extract was then dried over magnesium sulfate and concentrated in vacuo. The resulting oil was then purified by flash column chromatography (silica), eluting with petroleum spirit, 40-60° C./ethyl acetate (4:1) to afford the title compound (1.34 g, 84%) as a brown oil. $^1$H NMR (400 MHz, CDCl$_3$), mixture of rotamers and regioisomers, δ 8.33-7.78 (m, 1H), 7.52-7.28 (m, 5H), 7.10 (s, 1H), 6.90-6.75 (m, 1H), 6.25-6.11 (m, 1H), 6.00-5.88 (m, 1H), 5.34 (dd, J=17.2, 1.5 Hz, 1H), 5.23 (dd, J=10.4, 1.2 Hz, 1H), 5.16 (s, 2H), 4.69-4.54 (m, 2H), 4.09-3.45 (m, 6H), 3.42 (s, 3H), 3.35 (s, 3H), 2.66-2.33 (m, 2H), 0.98-0.75 (m, 9H), 0.12-0.07 (m, 6H); MS (ES+): m/z=705 (M+H)$^+$; LCMS (Method B): t$_R$=4.18 min.

Allyl (S)-(5-(benzyloxy)-2-(4-(1,3-dimethyl-2,4-dioxo-1,2,3,4-tetrahydro-pyrimidin-5-yl)-6-(hydroxymethyl)-1,2,3,6-tetrahydropyridine-1-carbonyl)-4-methoxyphenyl)carbamate and allyl (S)-(5-(benzyloxy)-2-(4-(1,3-dimethyl-2,4-dioxo-1,2,3,4-tetrahydropyrimidin-5-yl)-2-(hydroxymethyl)-1,2,3,6-tetrahydropyridine-1-carbonyl)-4-methoxyphenyl)carbamate (38) (1:1)

38

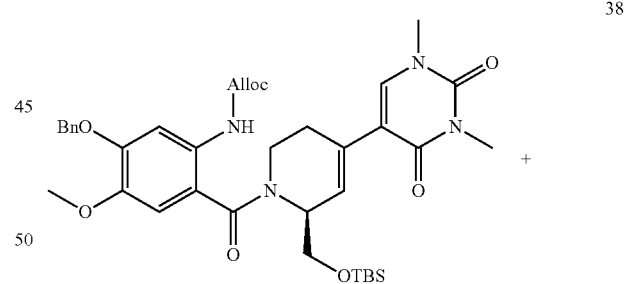

+

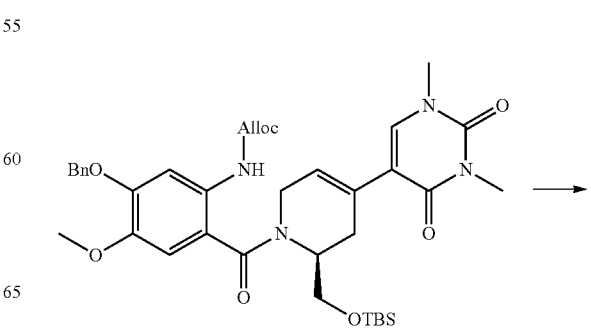

→

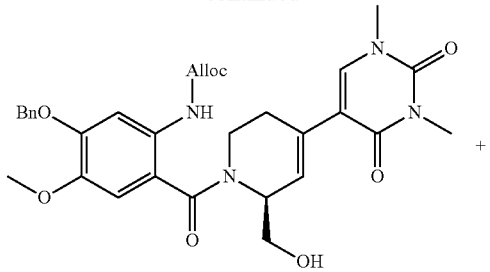

A solution of allyl (S)-(5-(benzyloxy)-2-(6-(((tert-butyldimethylsilyl)oxy)methyl)-4-(1,3-dimethyl-2,4-dioxo-1,2,3,4-tetrahydropyrimidin-5-yl)-1,2,3,6-tetrahydropyridine-1-carbonyl)-4-methoxyphenyl)carbamate and allyl (S)-(5-(benzyloxy)-2-(2-(((tert-butyldimethylsilyl)oxy)methyl)-4-(1,3-dimethyl-2,4-dioxo-1,2,3,4-tetrahydro-pyrimidin-5-yl)-1,2,3,6-tetrahydropyridine-1-carbonyl)-4-methoxyphenyl)carbamate (37) (1.35 g, 1.91 mmol) in tetrahydrofuran (50 mL) was cooled to 0° C. and charged with tetrabutylammonium fluoride (1 M in tetrahydrofuran, 2.38 mL, 2.38 mmol). The reaction was allowed to warm to room temperature and after 1 h, TLC and LCMS confirmed consumption of starting material. Ethyl acetate (100 mL) was added to the reaction mixture and the resulting solution washed with a saturated aqueous solution of ammonium chloride (50 mL) and brine (50 mL) and dried over magnesium sulfate. Purification by flash column chromatography (silica), eluting with dichloromethane/acetone (4:1) gave the title compound (1.04 g, 92%) as a cream solid. $^1$H NMR (400 MHz, CDCl$_3$), mixture of rotamers and regioisomers, δ 8.28-7.70 (m, 1H), 7.51-7.27 (m, 5H), 7.15-7.07 (m, 1H), 6.84-6.75 (m, 1H), 6.20-5.87 (m, 2H), 5.33 (dd, J=17.2, 1.5 Hz, 1H), 5.25-5.20 (m, 1H), 5.16 (s, 2H), 4.64-4.59 (m, 2H), 4.07-3.63 (m, 6H), 3.42-3.41 (2×s, 3H), 3.35-3.34 (2×s, 3H), 2.61-2.37 (m, 2H); MS (ES+): m/z=591 (M+H)$^+$; LCMS (Method B): $t_R$=3.22 min.

Allyl (6aS)-3-(benzyloxy)-8-(1,3-dimethyl-2,4-di-oxo-1,2,3,4-tetrahydro-pyrimidin-5-yl)-6-hydroxy-2-methoxy-12-oxo-6,6a,9,10-tetrahydrobenzo-[e]pyrido[1,2-α][1,4]diazepine-5(12H)-carboxylate and allyl (6aS)-3-(benzyloxy)-8-(1,3-dimethyl-2,4-di-oxo-1,2,3,4-tetrahydropyrimidin-5-yl)-6-hydroxy-2-methoxy-12-oxo-6,6a,7,10-tetrahydrobenzo[e]pyrido[1,2-α][1,4]diazepine-5(12H)-carboxylate (39) (1:1)

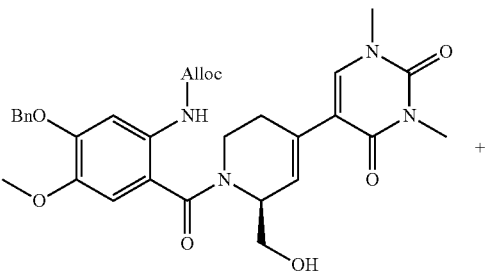

A solution of allyl (S)-(5-(benzyloxy)-2-(4-(1,3-dimethyl-2,4-dioxo-1,2,3,4-tetrahydro-pyrimidin-5-yl)-6-(hydroxymethyl)-1,2,3,6-tetrahydropyridine-1-carbonyl)-4-methoxyphenyl)carbamate and allyl (S)-(5-(benzyloxy)-2-(4-(1,3-dimethyl-2,4-dioxo-1,2,3,4-tetrahydropyrimidin-5-yl)-2-(hydroxymethyl)-1,2,3,6-tetrahydropyridine-1-carbonyl)-4-methoxyphenyl)carbamate (38) (1.05 g, 1.78 mmol) in dichloromethane (50 mL) was charged with TEMPO (0.055 g, 0.35 mmol) and (diacetoxyiodo)benzene (1.25 g, 3.89 mmol) and stirred at room temperature for 16 h, after which TLC showed only partial consumption of starting material. Further TEMPO (0.014 g, 0.090 mmol) and (diacetoxyiodo)benzene (0.224 g, 0.700 mmol) were added and the mixture stirred for a further 2 h. Dichloromethane (15 mL) was then added to the reaction mixture, which was quenched by addition of a saturated aqueous solution of sodium metabisulfite (50 mL). The organic phase was separated, washed with brine (50 mL), dried over magnesium sulfate, filtered and concentrated in vacuo. Purification by flash column chromatography (silica), eluting with dichloromethane/acetone (9:1) gave the title compound (366 mg, 35%) as a yellow solid. $^1$H NMR (400 MHz, CDCl$_3$), mixture of rotamers and regioisomers, δ 7.45-7.27 (m, 5H), 7.23-7.22 (2×s, 1H), 7.20-7.12 (2× S, 2H), 6.85-6.12 (m, 1H), 5.84-5.77 (m, 1H), 5.73-5.59 (m, 1H), 5.20-5.00 (m, 4H), 4.78-4.43 (m, 1H), 4.37 (dd, J=17.8, 6.0 Hz, 1H), 3.99-3.88 (m, 3H), 3.71-3.63 (m, 1H), 3.47-3.39 (m, 3H), 3.39-3.31 (m, 3H), 3.12-2.96 (m, 1H), 2.58-2.37 (m, 1H); MS (ES+): m/z=571 (M+H)$^+$; LCMS (Method B): t$_R$=3.12 min.

Allyl (6aS)-8-(1,3-dimethyl-2,4-dioxo-1,2,3,4-tetra-hydropyrimidin-5-yl)-3-hydroxy-2,6-dimethoxy-12-oxo-6,6a,7,10-tetrahydrobenzo[e]pyrido[1,2-α][1,4] diazepine-5(12H)-carboxylate (40)

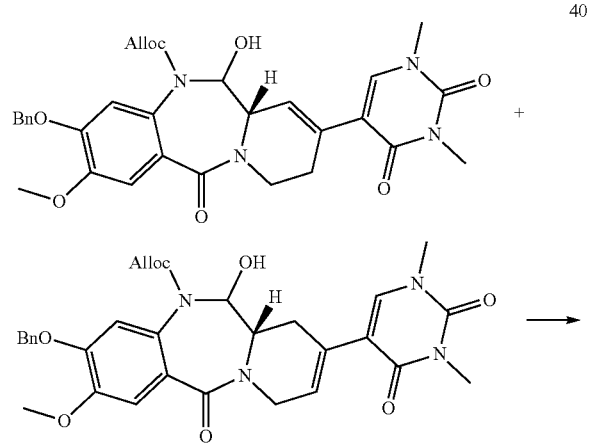

A solution of allyl (6aS)-3-(benzyloxy)-8-(1,3-dimethyl-2,4-dioxo-1,2,3,4-tetrahydro-pyrimidin-5-yl)-6-hydroxy-2-methoxy-12-oxo-6,6a,9,10-tetrahydrobenzo[e]pyrido[1,2-a][1,4]diazepine-5(12H)-carboxylate and allyl (6aS)-3-(benzyloxy)-8-(1,3-dimethyl-2,4-dioxo-1,2,3,4-tetrahydropyrimidin-5-yl)-6-hydroxy-2-methoxy-12-oxo-6,6a,7,10-tetrahydrobenzo[e]pyrido[1,2-α][1,4]diazepine-5(12H)-carboxylate (39) (350 mg, 0.595 mmol) in anhydrous dichloromethane (20 mL) was charged with boron trichloride (1 M in dichloromethane, 1.78 mL, 1.78 mmol) and stirred under an inert atmosphere of nitrogen for 30 min. Methanol (20 mL) was then charged and the resulting mixture irradiated with microwaves at 55° C. for 1 h. After concentrating the resulting mixture in vacuo, purification was carried out by (multiple) flash column chromatography (silica), eluting with petroleum spirit, 40-60° C./ethyl acetate (4:1) to afford the (regiopure) title compound (67 mg, 22%) as a white solid. $^1$H NMR (400 MHz, CDCl$_3$) δ 7.21 (s, 1H), 7.21-7.08 (3×s, 1H), 6.75 (s, 1H), 6.30-6.24 (m, 1H), 5.95 (s, 1H), 5.84-5.71 (m, 1H), 5.52 (d, J=9.6 Hz, 1H), 5.16-5.04 (m, 2H), 4.62-4.54 (m, 1H), 4.51-4.41 (m, 1H), 4.23-4.07 (m, 2H), 3.95 (s, 3H), 3.62-3.54 (m, 1H), 3.50 (s, 3H), 3.44 (s, 3H), 3.37 (s, 3H), 2.82 (d, J=15.1 Hz, 1H), 2.69-2.52 (m, 1H); MS (ES+): m/z=512 (M+H)$^+$; LCMS (Method B): t$_R$=2.85 min.

Diallyl 3,3'-((pyridine-2,6-diylbis(methylene))bis (oxy))(6aS,6a'S)-bis(8-(1,3-dimethyl-2,4-dioxo-1,2,3,4-tetrahydropyrimidin-5-yl)-2,6-dimethoxy-12-oxo-6,6a,7,10-tetrahydrobenzo[e]pyrido[1,2-α][1,4] diazepine-5(12H)-carboxylate) (41)

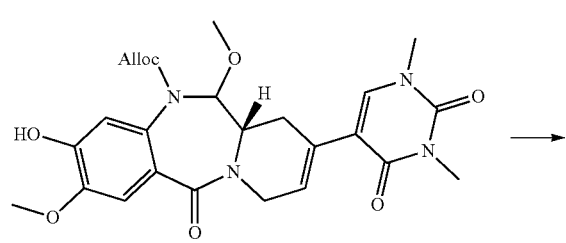

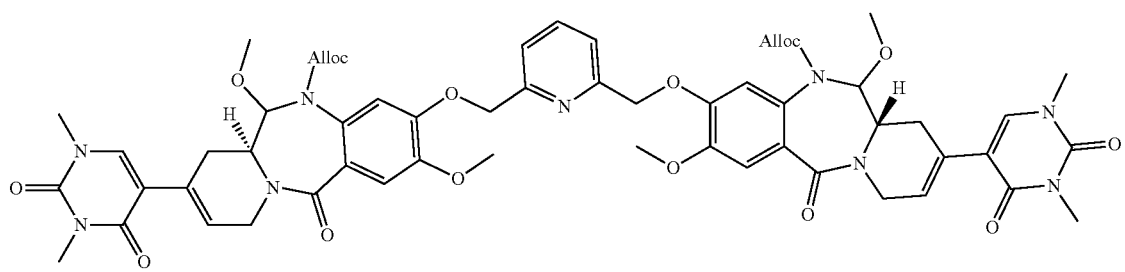

41

A solution of allyl (6aS)-8-(1,3-dimethyl-2,4-dioxo-1,2,3,4-tetrahydropyrimidin-5-yl)-3-hydroxy-2,6-dimethoxy-12-oxo-6,6a,7,10-tetrahydrobenzo[e]pyrido[1,2-α][1,4]diazepine-5(12H)-carboxylate (40) (0.050 g, 0.097 mmol) in N,N-dimethylformamide (2 mL) was charged with potassium carbonate (0.013 g, 0.097 mmol) and 2,6-bis(bromomethyl)pyridine (0.013 g, 0.048 mmol). The resulting mixture was irradiated with microwaves at 55° C. for 1 h, at which point TLC and LCMS showed completion of the reaction. Water (20 mL) was added and the resulting suspension extracted with ethyl acetate (3×100 mL). The combined organic extracts were then washed with brine (5×100 mL), dried over magnesium sulfate, and concentrated in vacuo. Purification by flash column chromatography (silica), eluting with dichloromethane/methanol (95:5) gave the title compound (10 mg, impure) as a brown solid, which was used in the subsequent step without further purification. MS (ES+): m/z=1128 (M+H)$^+$; LCMS (Method B): $t_R$=3.22 min.

5,5'-((6aS,6a'S)-((Pyridine-2,6-diylbis(methylene))bis(oxy))bis(2-methoxy-12-oxo-6a,7,10,12-tetrahydrobenzo[e]pyrido[1,2-α][1,4]diazepine-3,8-diyl))bis(1,3-dimethylpyrimidine-2,4(1H,3H)-dione) (42)

A solution of diallyl 3,3'-((pyridine-2,6-diylbis(methylene))bis(oxy))(6aS,6a'S)-bis(8-(1,3-dimethyl-2,4-dioxo-1,2,3,4-tetrahydropyrimidin-5-yl)-2,6-dimethoxy-12-oxo-6,6a,7,10-tetrahydrobenzo[e]pyrido[1,2-α][1,4]diazepine-5(12H)-carboxylate) (41) (0.010 g, 0.009 mmol) in dichloromethane (2 mL) was charged with tetrakis(triphenyl-phosphine)palladium(o) (0.5 mg) and pyrrolidine (0.002 mL, 0.02 mmol). After 15 min, the reaction was observed to have completed via TLC. The reaction mixture was concentrated in vacuo to form an oil, which was charged with diethyl ether (2 mL) and re-concentrated in vacuo (this process was repeated twice more). Purification via flash column chromatography (silica), eluting with dichloromethane/methanol (9:1) gave the title compound (2.0 mg, 25%) as a cream solid. $^1$H NMR (400 MHz, CDCl$_3$) δ 7.92 (d, J=5.3 Hz, 2H), 7.74 (t, J=8.0 Hz, 1H), 7.54 (s, 2H), 7.48 (d, J=7.9 Hz, 2H), 6.87 (s, 2H), 6.33-6.27 (m, 2H), 5.32 (s, 4H), 5.30 (s, 2H), 4.41 (dd, J=18.8, 5.3 Hz, 2H) 4.05 (d, J=18.1 Hz, 2H), 4.00 (s, 6H), 3.92-3.85 (m, 1H), 3.69-3.60 (m, 1H), 3.46 (s, 6H), 3.38 (s, 6H), 2.99 (d, J=15.7 Hz, 2H), 2.82-2.71 (m, 2H); MS (ES+): m/z=896 (M+H)$^+$; LCMS (Method A): $t_R$=5.78 min.

(S)-(4-(Benzyloxy)-5-methoxy-2-nitrophenyl)(6-(((tert-butyldimethylsilyl)-oxy)methyl)-4-(pyrimidin-5-yl)-3,6-dihydropyridin-1(2H)-yl)methanone and (S)-(4-(benzyloxy)-5-methoxy-2-nitrophenyl)(2-(((tert-butyldimethyl-silyl)oxy)methyl)-4-(pyrimidin-5-yl)-3,6-dihydropyridin-1(2H)-yl)methanone (43) (1:1)

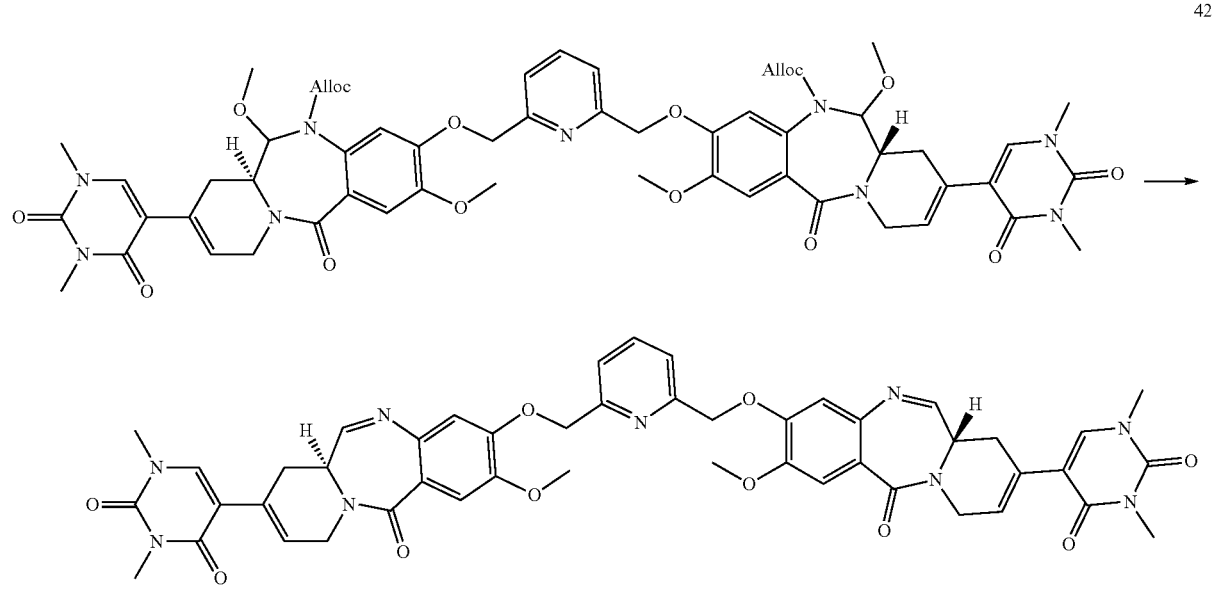

-continued

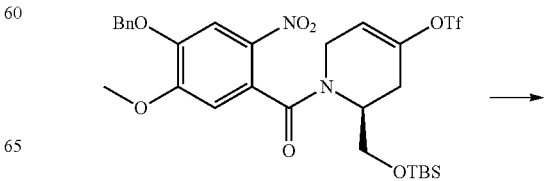

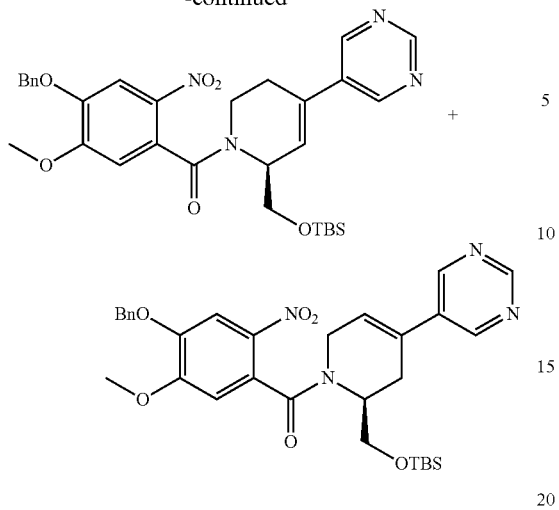

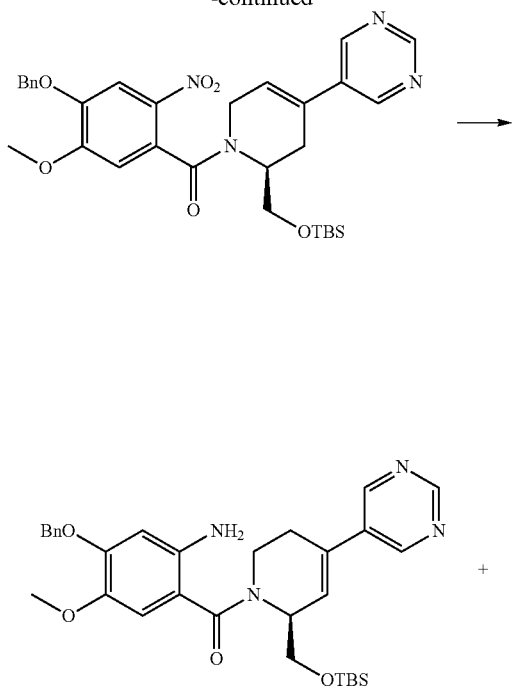

A solution of (S)-1-(4-(benzyloxy)-5-methoxy-2-nitrobenzoyl)-6-(((tert-butyldimethyl-silyl)oxy)methyl)-1,2,3,6-tetrahydropyridin-4-yl trifluoromethane sulfonate and (S)-1-(4-(benzyloxy)-5-methoxy-2-nitrobenzoyl)-2-(((tert-butyldimethylsilyl)oxy)methyl)-1,2,3,6-tetrahydropyridin-4-yl trifluoromethanesulfonate (8) (4.00 g, 6.05 mmol) in acetonitrile (2 mL) was charged with [1,1'-bis(diphenylphosphino)ferrocene]dichloro-palladium(II), complex with dichloromethane (0.497 g, 0.61 mmol), pyrimidin-5-ylboronic acid (0.970 g, 7.86 mmol) and an aqueous solution of potassium carbonate (2 M, 6.05 mL, 12.1 mmol) and irradiated with microwaves at 50° C. for 10 min, at which point TLC showed only partial consumption of starting material. Further pyrimidin-5-ylboronic acid (0.970 g, 7.86 mmol) was charged and the resulting mixture irradiated with microwaves for a further 10 min at 50° C. The mixture was subsequently diluted with ethyl acetate (100 mL) and washed with brine (50 mL), then dried over solid anhydrous magnesium sulfate and concentrated in vacuo. The residual oil was purified by flash column chromatography (silica), eluting with petroleum spirit, 40-60° C./ethyl acetate (4:1) to afford the title compound (2.90 g, 81%) as a yellow solid. MS (ES+): m/z=591 (M+H)$^+$; LCMS (Method B): $t_R$=4.12 min.

(S)-(2-Amino-4-(benzyloxy)-5-methoxyphenyl)(6-(((tert-butyldimethyl-silyl)oxy)methyl)-4-(pyrimidin-5-yl)-3,6-dihydropyridin-1(2H)-yl)methanone and (S)-(2-amino-4-(benzyloxy)-5-methoxyphenyl)(2-(((tert-butyldimethylsilyl)oxy)methyl)-4-(pyrimidin-5-yl)-3,6-dihydropyridin-1(2H)-yl)methanone (44) (1:1)

44

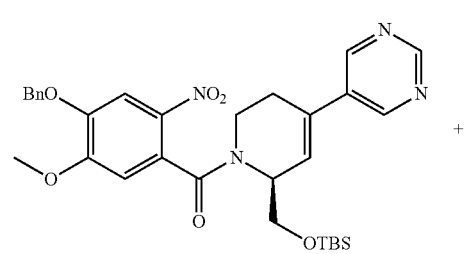

A solution of (S)-(4-(benzyloxy)-5-methoxy-2-nitrophenyl)(6-(((tert-butyldimethyl-silyl)oxy)methyl)-4-(pyrimidin-5-yl)-3,6-dihydropyridin-1(2H)-yl)methanone and (S)-(4-(benzyloxy)-5-methoxy-2-nitrophenyl)(2-(((tert-butyldimethylsilyl)oxy)methyl)-4-(pyrimidin-5-yl)-3,6-dihydropyridin-1(2H)-yl)methanone (43) (2.85 g, 4.82 mmol) in formic acid (5% v/v in absolute ethanol, 61 mL) was charged with zinc powder (11.6 g, 179 mmol) and stirred for 30 min, whilst monitoring by TLC and LCMS. Upon completion, the reaction was quenched by addition of a saturated aqueous solution of sodium hydrogen carbonate (10 mL) and concentrated in vacuo. The residue was then partitioned between ethyl acetate (200 mL) and brine (100 mL) and the organic phase dried over magnesium sulfate, filtered, and concentrated in vacuo. Purification by flash column chromatography (silica), eluting with dichloromethane/acetone (4:1) gave the title compound (2.22 g, 82%) as a yellow solid. $^1$H NMR (400 MHz, CDCl$_3$), mixture of rotamers and regioisomers, δ 9.11 (s, 1H), 8.74 (s, 2H), 7.47-7.27 (m, 5H), 6.83-6.72 (m, 1H), 6.33-6.22 (m, 2H), 3.96-3.83 (m, 2H), 3.81 (s, 3H), 3.76-3.46 (m, 2H), 2.87-2.57 (m, 1H), 2.54-2.35 (m, 1H), 0.90-0.80 (m, 9H), 0.11-0.05 (m, 6H); MS (ES+): m/z=561 (M+H)$^+$; LCMS (Method A): $t_R$=7.97 min.

Allyl (S)-(5-(benzyloxy)-2-(6-(((tert-butyldimethyl-silyl)oxy)methyl)-4-(pyrimidin-5-yl)-1,2,3,6-tetrahydropyridine-1-carbonyl)-4-methoxy-phenyl)carbamate and allyl (S)-(5-(benzyloxy)-2-(2-(((tert-butyldimethyl-silyl)oxy)methyl)-4-(pyrimidin-5-yl)-1,2,3,6-tetrahydropyridine-1-carbonyl)-4-methoxyphenyl)carbamate (45) (1:1)

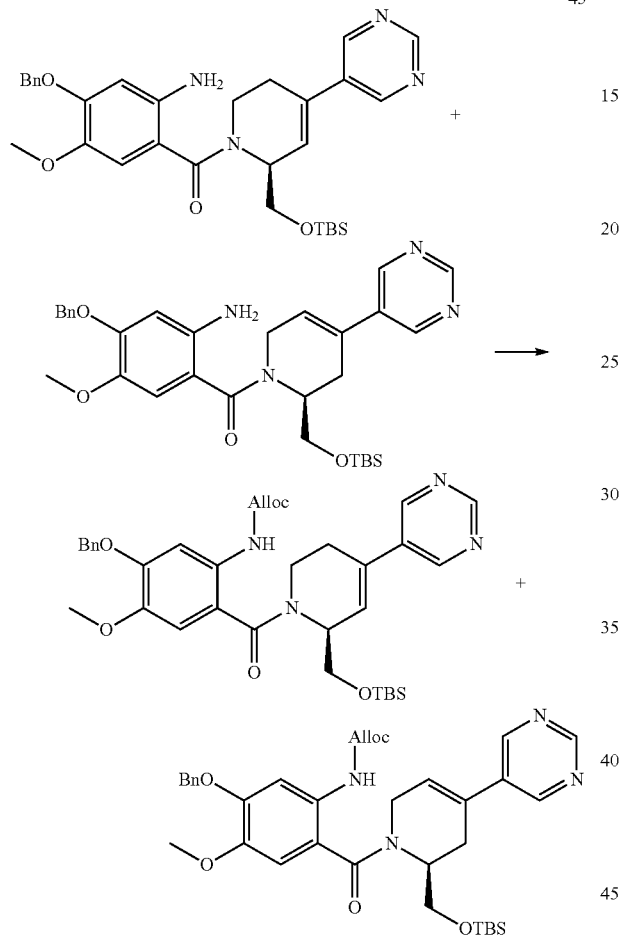

A solution of (S)-(2-amino-4-(benzyloxy)-5-methoxyphenyl)(6-(((tert-butyldimethyl-silyl)oxy)methyl)-4-(pyrimidin-5-yl)-3,6-dihydropyridin-1(2H)-yl)methanone and (S)-(2-amino-4-(benzyloxy)-5-methoxyphenyl)(2-(((tert-butyldimethylsilyl)oxy)methyl)-4-(pyrimidin-5-yl)-3,6-dihydropyridin-1(2H)-yl)methanone (44) (1.00 g, 1.78 mmol) in dichloromethane (200 mL) was charged with pyridine (0.17 mL, 1.78 mmol) and allyl chloroformate (0.196 mL, 1.86 mmol). After 15 min, the reaction was judged to be complete by TLC and LCMS and was sequentially washed with a saturated aqueous solution of copper sulfate (2×100 mL) and brine (100 mL). The organic extract was then dried over magnesium sulfate and concentrated in vacuo. The resulting oil was then purified by flash column chromatography (silica), eluting with dichloromethane/acetone (4:1) to afford the title compound (782 mg, 68%) as a brown solid. $^1$H NMR (400 MHz, CDCl$_3$), mixture of rotamers and regioisomers, δ 9.28-7.20 (m, 4H), 7.52-7.27 (m, 5H), 6.91-6.76 (m, 1H), 6.24 (s, 1H), 5.98-5.85 (m, 1H), 5.32 (dd, J=17.2, 1.4 Hz, 1H), 5.22 (d, J=10.5 Hz, 1H), 5.18 (s, 2H), 4.66-456 (m, 2H), 4.00-3.86 (m, 2H), 3.84 (s, 3H), 3.81-3.43 (m, 2H), 2.88-2.32 (m, 2H), 0.93-0.73 (m, 9H), 0.12-0.07 (m, 6H); MS (ES+): m/z=645 (M+H)$^+$; LCMS (Method A): t$_R$=8.48 min.

Allyl (S)-(5-(benzyloxy)-2-(6-(hydroxymethyl)-4-(pyrimidin-5-yl)-1,2,3,6-tetrahydropyridine-1-carbonyl)-4-methoxyphenyl)carbamate and allyl (S)-(5-(benzyloxy)-2-(2-(hydroxymethyl)-4-(pyrimidin-5-yl)-1,2,3,6-tetrahydropyridine-1-carbonyl)-4-methoxyphenyl)carbamate (46) (1:1)

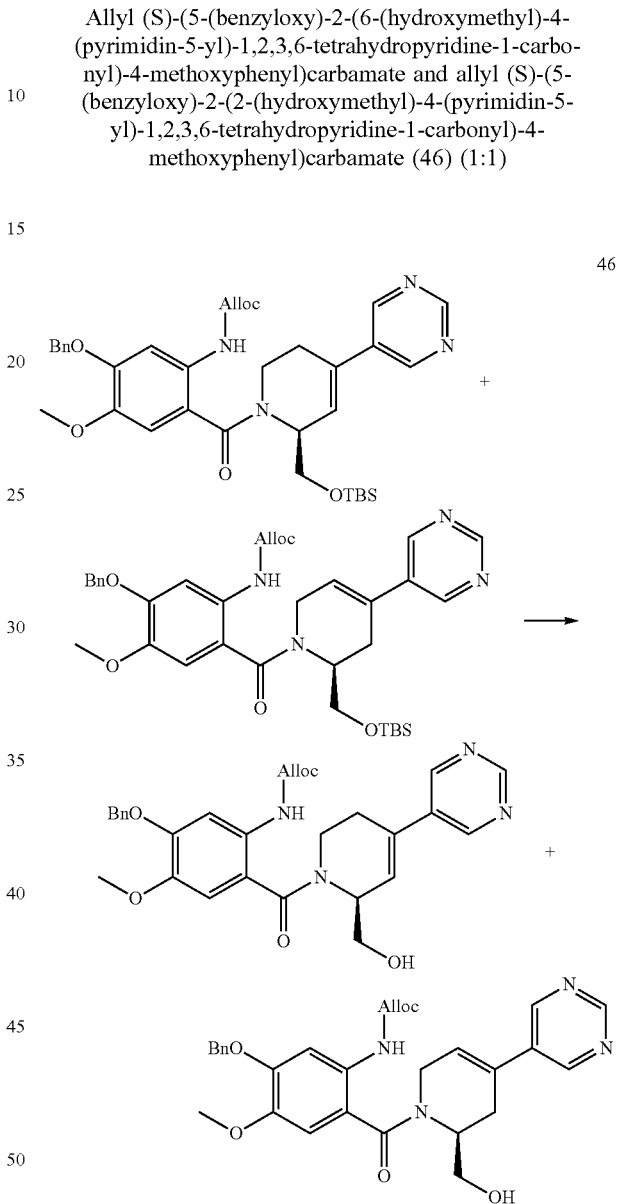

A solution of allyl (S)-(5-(benzyloxy)-2-(6-(((tert-butyldimethylsilyl)oxy)methyl)-4-(pyrimidin-5-yl)-1,2,3,6-tetrahydropyridine-1-carbonyl)-4-methoxyphenyl)carbamate and allyl (S)-(5-(benzyloxy)-2-(2-(((tert-butyldimethylsilyl)oxy)methyl)-4-(pyrimidin-5-yl)-1,2,3,6-tetrahydropyridine-1-carbonyl)-4-methoxyphenyl) carbamate (45) (0.78 g, 1.21 mmol) in tetrahydrofuran (50 mL) was cooled to 0° C. and charged with tetrabutylammonium fluoride (1 M in tetrahydrofuran, 1.51 mL, 1.51 mmol). The reaction was allowed to warm to room temperature and after 15 min, TLC and LCMS confirmed consumption of starting material. Ethyl acetate (100 mL) was added to the reaction mixture and the resulting solution washed with a saturated aqueous solution of ammonium chloride (50 mL)

and brine (50 mL) and dried over magnesium sulfate. Purification by flash column chromatography (silica), eluting with dichloromethane/acetone (4:1) gave the title compound (552 mg, 86%) as a cream solid. $^1$H NMR (400 MHz, CDCl$_3$), mixture of rotamers and regioisomers, δ 9.14 (s, 1H), 8.77 (s, 2H), 8.09 (s, 1H), 7.85-7.69 (m, 1H), 7.54-7.30 (m, 5H), 6.87-6.79 (m, 1H), 6.26-6.13 (m, 1H), 6.01-5.81 (m, 1H), 5.37-5.30 (m, 1H), 5.24-5.18 (m, 1H), 4.61 (t, J=5.6 Hz, 2H), 4.09-3.86 (m, 2H), 3.87-3.82 (2×s, 3H), 3.81-3.38 (m, 2H), 3.00-2.60 (m, 1H), 2.50-235 (m, 1H); MS (ES+): m/z=531 (M+H)$^+$; LCMS (Method B): t$_R$=3.18 min.

Allyl (6aS)-3-(benzyloxy)-6-hydroxy-2-methoxy-12-oxo-8-(pyrimidin-5-yl)-6,6a,9,10-tetrahydrobenzo[e]pyrido[1,2-α][1,4]diazepine-5(12H)-carboxylate and allyl (6aS)-3-(benzyloxy)-6-hydroxy-2-methoxy-12-oxo-8-(pyrimidin-5-yl)-6,6a,7,10-tetrahydrobenzo[e]pyrido[1,2-α][1,4]diazepine-5(12H)-carboxylate (47) (1:1)

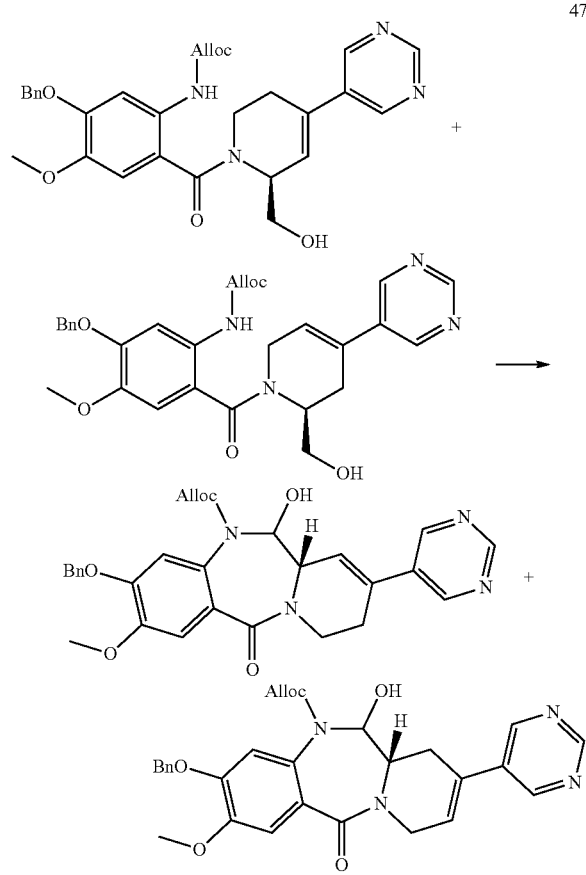

A solution of allyl (S)-(5-(benzyloxy)-2-(6-(hydroxymethyl)-4-(pyrimidin-5-yl)-1,2,3,6-tetrahydropyridine-1-carbonyl)-4-methoxyphenyl)carbamate and allyl (S)-(5-(benzyloxy)-2-(2-(hydroxymethyl)-4-(pyrimidin-5-yl)-1,2,3,6-tetrahydropyridine-1-carbonyl)-4-methoxyphenyl)carbamate (46) (0.55 g, 1.03 mmol) in dichloromethane (50 mL) was charged with TEMPO (0.041 g, 0.26 mmol) and (diacetoxyiodo)benzene (0.78 g, 2.42 mmol) and stirred at room temperature for 16 h, at which point TLC and LCMS showed consumption of starting material. Dichloromethane (15 mL) was then added to the reaction mixture, which was quenched by addition of a saturated aqueous solution of sodium metabisulfite (50 mL). The organic phase was separated, washed with brine (50 mL), dried over magnesium sulfate, filtered and concentrated in vacuo. Purification by flash column chromatography (silica), eluting with dichloromethane/acetone (9:1) gave the title compound (236 mg, 43%) as a brown solid. $^1$H NMR (400 MHz, CDCl$_3$), mixture of rotamers and regioisomers, δ 9.14 (s, 1H), 8.85-8.75 (m, 2H), 7.45-7.29 (m, 5H), 7.26-7.20 (m, 1H), 6.72 (s, 1H), 6.51-6.33 (m, 1H), 5.87-5.60 (m, 2H), 5.21-5.05 (m, 4H), 4.53-4.07 (m, 4H), 3.98-3.90 (m, 3H), 3.87-3.78 (m, 1H), 3.09 (d, J=16.4 Hz, 1H), 2.81-2.71 (m, 1H); MS (ES+): m/z=529 (M+H)$^+$; LCMS (Method A): t$_R$=6.15 min.

Allyl (6aS)-3-hydroxy-2,6-dimethoxy-12-oxo-8-(pyrimidin-5-yl)-6,6a,7,10-tetrahydrobenzo[e]pyrido[1,2-α][1,4]diazepine-5(12H)-carboxylate (48)

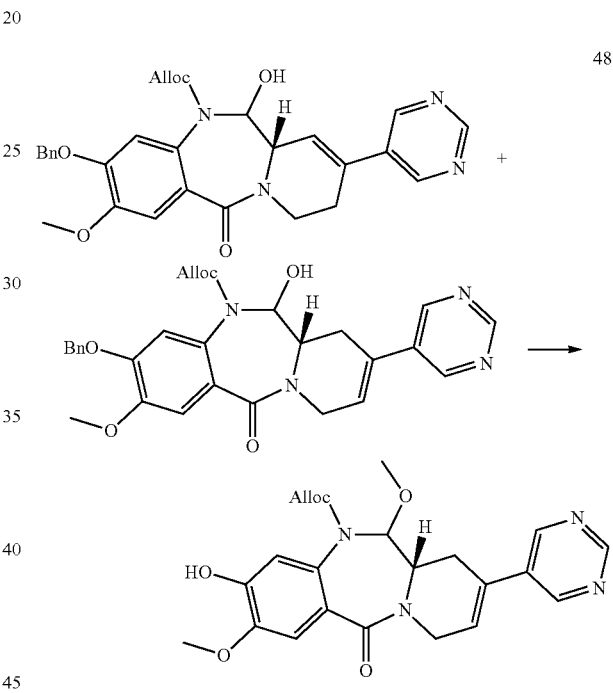

A solution of allyl (6aS)-3-(benzyloxy)-6-hydroxy-2-methoxy-12-oxo-8-(pyrimidin-5-yl)-6,6a,9,10-tetrahydrobenzo[e]pyrido[1,2-α][1,4]diazepine-5(12H)-carboxylate and allyl (6aS)-3-(benzyloxy)-6-hydroxy-2-methoxy-12-oxo-8-(pyrimidin-5-yl)-6,6a,7,10-tetrahydrobenzo[e]pyrido[1,2-α][1,4]diazepine-5(12H)-carboxylate (47) (0.235 g, 0.44 mmol) in anhydrous dichloromethane (20 mL) was charged with boron trichloride (1 M in dichloromethane, 1.32 mL, 1.32 mmol) and stirred under an inert atmosphere of nitrogen for 30 min. Methanol (20 mL) was then charged and the resulting mixture irradiated with microwaves at 55° C. for 1 h. After concentrating the resulting mixture in vacuo, purification was carried out by (multiple) flash column chromatography (silica), eluting with dichloromethane/acetone (2:3) to afford the (regiopure) title compound (36 mg, 18%) as a cream solid. $^1$H NMR (400 MHz, CDCl$_3$) δ 9.16 (S, 1H), 8.81 (s, 2H), 7.21 (s, 1H), 6.76 (s, 1H), 6.48 (s, 1H), 5.85-5.68 (m, 1H), 5.43 (d, J=9.3 Hz, 1H), 5.18-5.03 (m, 1H), 4.66-4.41 (m, 2H), 4.30-4.20 (m, 2H), 3.94 (s, 3H), 3.77-3.69 (m, 1H), 2.94 (d, J=16.0 Hz, 1H), 2.80-2.71 (m, 1H); MS (ES+): m/z=453 (M+H)$^+$; LCMS (Method A): t$_R$=5.45 min.

Diallyl 3,3'-((pyridine-2,6-diylbis(methylene))bis(oxy))(6aS,6a'S)-bis(2,6-dimethoxy-12-oxo-8-(pyrimidin-5-yl)-6,6a,7,10-tetrahydrobenzo[e]pyrido-[1,2-α][1,4]diazepine-5(12H)-carboxylate)(49)

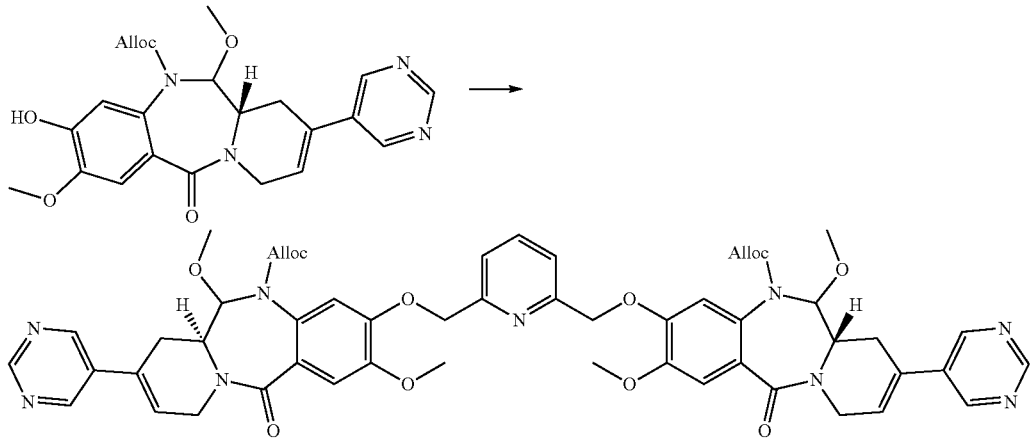

49

A solution of allyl (6aS)-3-hydroxy-2,6-dimethoxy-12-oxo-8-(pyrimidin-5-yl)-6,6a,7,10-tetrahydrobenzo[e]pyrido[1,2-α][1,4]diazepine-5(12H)-carboxylate (48) (0.035 g, 0.077 mmol) in N,N-dimethylformamide (2 mL) was charged with potassium carbonate (0.011 g, 0.077 mmol), 2,6-bis(bromomethyl)pyridine (0.010 g, 0.039 mmol) and water (0.1 mL). The resulting mixture was irradiated with microwaves at 55° C. for 1 h, at which point TLC and LCMS showed completion of the reaction. Water (20 mL) was added and the resulting suspension extracted with ethyl acetate (3×100 mL). The combined organic extracts were then washed with brine (5×100 mL), dried over magnesium sulfate, and concentrated in vacuo. Purification by flash column chromatography (silica), eluting with dichloromethane/methanol (95:5) gave the title compound (22 mg, 57%) as a cream solid. $^1$H NMR (400 MHz, CDCl$_3$) δ 9.16 (s, 2H), 8.80 (s, 4H), 7.80 (t, J=7.8 Hz, 1H), 7.54 (d, J=7.8 Hz, 2H), 7.26 (s, 2H), 6.70 (s, 2H), 6.51-6.45 (m, 2H), 5.41 (d, J=9.3 Hz, 2H), 5.25 (s, 4H), 5.07 (d, J=10.5 Hz, 2H), 4.57-4.36 (m, 4H), 4.33-4.20 (m, 4H), 3.96 (s, 6H), 3.75-3.67 (m, 2H), 3.40 (s, 6H), 2.92 (d, J=15.2 Hz, 2H), 2.81-2.71 (m, 2H); MS (ES+): m/z=1008 (M+H)$^+$; LCMS (Method A): t$_R$=6.80 min.

(6aS,6a'S)-3,3'-((Pyridine-2,6-diylbis(methylene))bis(oxy))bis(2-methoxy-8-(pyrimidin-5-yl)-7,10-dihydrobenzo[e]pyrido[1,2-α][1,4]diazepin-12(6aH)-one)(50)

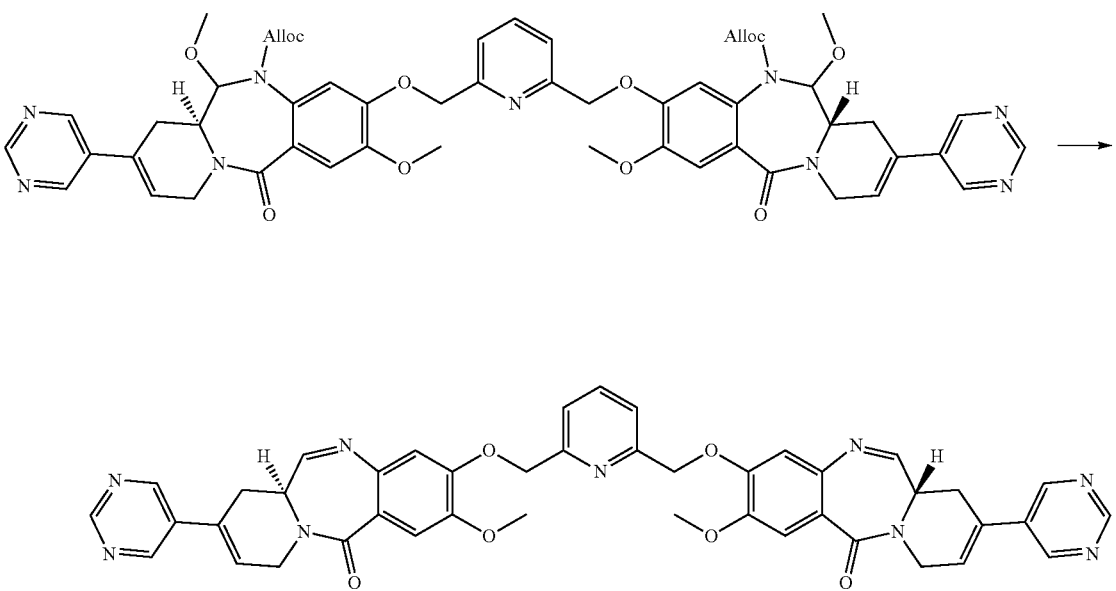

50

A solution of diallyl 3,3'-((pyridine-2,6-diylbis(methylene))bis(oxy))(6aS,6a'S)-bis(2,6-dimethoxy-12-oxo-8-(pyrimidin-5-yl)-6,6a,7,10-tetrahydrobenzo[e]pyrido[1,2-α][1,4]diazepine-5(12H)-carboxylate) (49) (0.024 g, 0.023 mmol) in dichloromethane (2 mL) was charged with tetrakis(triphenylphosphine)palladium(0) (1 mg) and pyrrolidine (5.4 ML). After 5 min, the reaction was observed to have completed via TLC. The reaction mixture was concentrated in vacuo to form an oil, which was charged with diethyl ether (2 mL) and re-concentrated in vacuo (this process was repeated twice more). Purification via flash column chromatography (silica), eluting with dichloromethane/methanol (95:5) gave the title compound (10 mg, 54%) as a cream solid. $^1$H NMR (400 MHz, CDCl$_3$) δ 9.19 (s, 2H), 8.86 (s, 4H), 7.74 (t, J=7.8 Hz, 1H), 7.61 (d, J=5.6 Hz, 2H), 7.55 (s, 2H), 7.47 (d, J=7.5 Hz, 2H), 6.87 (s, 2H), 6.65-6.57 (m, 2H), 5.32 (s, 4H), 4.48 (dd, J=19.3, 5.2 Hz, 2H), 4.31-4.25 (m, 2H), 4.24-4.17 (m, 2H), 4.00 (s, 6H), 3.03 (d, J=15.4 Hz, 2H), 2.93 (d, J=16.4 Hz, 2H); MS (ES+): m/z=776 (M+H)$^+$; LCMS (Method A): t$_R$=5.53 min.

(S)-(4-(benzyloxy)-5-methoxy-2-nitrophenyl)(6-(((tert-butyldimethyl-silyl)oxy)methyl)-4-(thiophen-3-yl)-3,6-dihydropyridin-1(2H)-yl)methanone and (S)-(4-(benzyloxy)-5-methoxy-2-nitrophenyl)(2-(((tert-butyldimethylsilyl)oxy)methyl)-4-(thiophen-3-yl)-3,6-dihydropyridin-1(2H)-yl)methanone (51) (1:1)

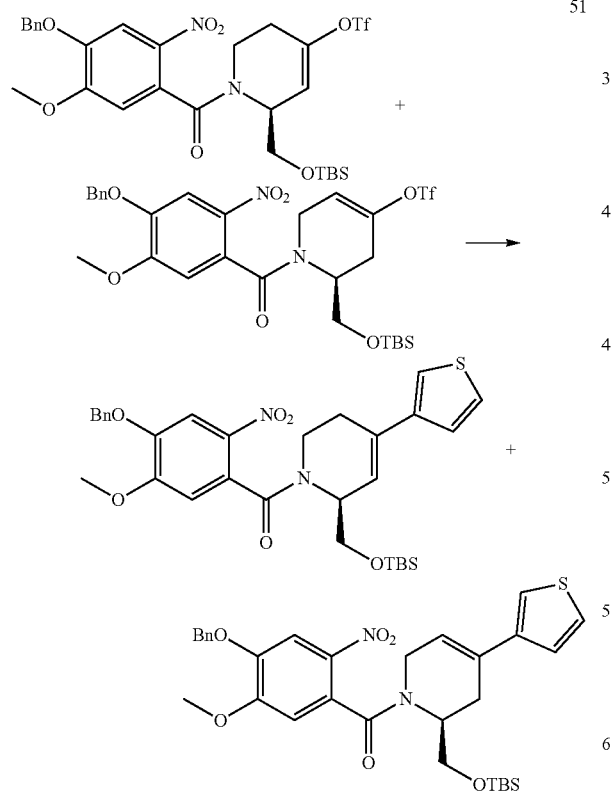

A solution of (S)-1-(4-(benzyloxy)-5-methoxy-2-nitrobenzoyl)-6-(((tert-butyldimethyl-silyl)oxy)methyl)-1,2,3,6-tetrahydropyridin-4-yl trifluoromethanesulfonate and (S)-1-(4-(benzyloxy)-5-methoxy-2-nitrobenzoyl)-2-(((tert-butyldimethylsilyl)oxy)methyl)-1,2,3,6-tetrahydropyridin-4-yl trifluoromethanesulfonate (8) (5.00 g, 7.56 mmol) in acetonitrile (10 mL) was charged with [1,1'-bis(diphenylphosphino)ferrocene]dichloro-palladium(II), complex with dichloromethane (0.617 g, 0.756 mmol), 3-thienylboronic acid (1.07 g, 8.35 mmol) and an aqueous solution of potassium carbonate (2 M, 7.56 mL, 15.1 mmol) and irradiated with microwaves at 50° C. for 20 min. The mixture was subsequently diluted with ethyl acetate (50 mL) and sequentially washed with water (25 mL) and brine (25 mL), then dried over solid anhydrous magnesium sulfate and concentrated in vacuo. The residue was then purified by flash column chromatography (silica), eluting with petroleum spirit, 40-60° C./ethyl acetate (from 1:0 to 0:1) to afford the title compound (3.65 g, 81%) as a yellow solid. $^1$H NMR (400 MHz, CDCl$_3$), mixture of rotamers and regioisomers, δ 7.85-7.73 (m, 1H), 7.49-7.34 (m, 5H), 7.33-7.18 (m, 3H), 7.16-7.06 (m, 1H), 6.81-6.72 (m, 1H), 5.28-5.18 (m, 2H), 5.06 (br. s, 1H), 4.01-3.95 (m, 4H), 3.83 (d, J=7.03 Hz, 1H), 3.76 (d, J=9.76 Hz, 1H), 3.71-3.57 (m, 1H), 3.57-3.36 (m, 1H), 2.41 (d, J=19.14 Hz, 1H), 0.98-0.82 (m, 9H), 0.18-0.06 (m, 6H); $^{13}$C NMR (100 MHz, CDCl$_3$), mixture of rotamers and regioisomers, δ 166.4, 154.7, 148.1, 142.0, 135.3, 134.6, 130.6, 128.8, 128.5, 127.6, 127.5, 126.0, 124.6, 122.1, 119.6, 119.2, 109.1, 71.4, 60.4, 56.7, 56.7, 52.5, 52.3, 42.9, 27.4, 25.9, 25.8, 21.0, 18.2, −5.4; MS (ES+): m/z=595 (M+H)$^+$.

(S)-(2-Amino-4-(benzyloxy)-5-methoxyphenyl)(6-(((tert-butyldimethyl-silyl)oxy)methyl)-4-(thiophen-3-yl)-3,6-dihydropyridin-1(2H)-yl)methanone and (S)-(2-amino-4-(benzyloxy)-5-methoxyphenyl)(2-(((tert-butyldimethylsilyl)oxy)methyl)-4-(thiophen-3-yl)-3,6-dihydropyridin-1(2H)-yl)methanone (52) (1:1)

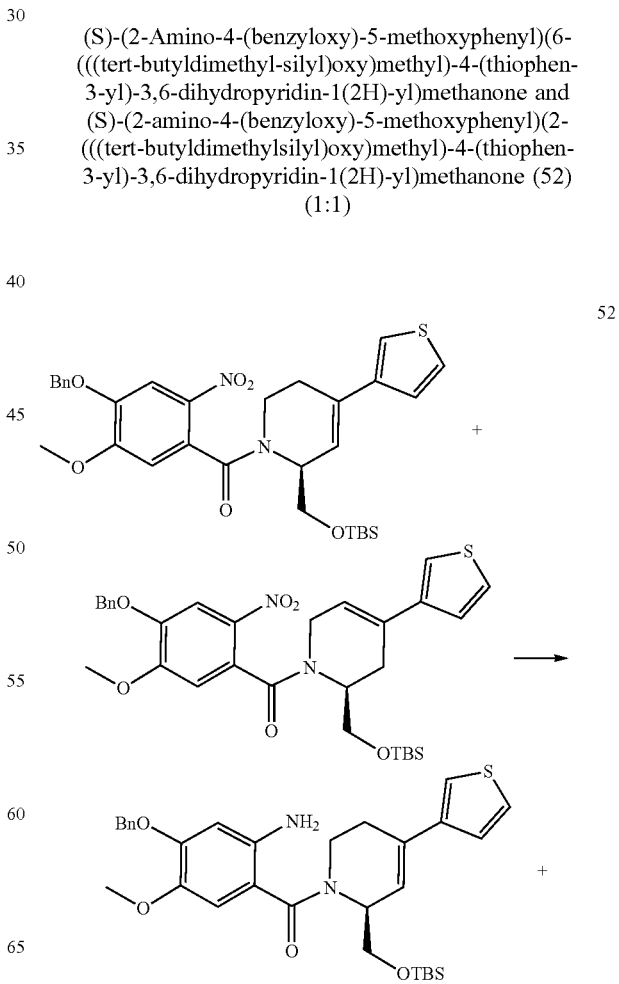

-continued

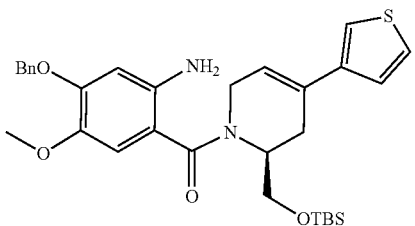

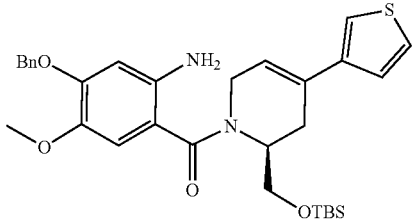

A solution of (S)-(4-(benzyloxy)-5-methoxy-2-nitrophenyl)(6-(((tert-butyldimethyl-silyl)oxy)methyl)-4-(thiophen-3-yl)-3,6-dihydropyridin-1(2H)-yl)methanone and (S)-(4-(benzyloxy)-5-methoxy-2-nitrophenyl)(2-(((tert-butyldimethylsilyl)oxy)methyl)-4-(thiophen-3-yl)-3,6-dihydropyridin-1(2H)-yl)methanone (51) (3.62 g, 6.08 mmol) in formic acid (5% v/v in absolute ethanol, 60 mL) was charged with zinc powder (15.9 g, 243 mmol) and stirred for 1 h, whilst monitoring by TLC and LCMS. Upon completion, the mixture was filtered over a pad of celite and the resulting cake washed with ethyl acetate. A saturated aqueous solution of sodium hydrogen carbonate (10 mL) was then added to the filtrate and the mixture concentrated in vacuo to remove organics. The residue was then partitioned between ethyl acetate (60 mL) and brine (60 mL) and the organic phase dried over magnesium sulfate, filtered, and concentrated in vacuo. Purification by flash column chromatography (silica), eluting with dichloromethane/acetone (1:0 to 4:1) gave the title compound (3.24 g, 80%) as a yellow solid. $^1$H NMR (400 MHz, CDCl$_3$), mixture of rotamers and regioisomers, δ 7.46-7.21 (m, 7H), 7.14 (dd, J=2.7, 1.2 Hz, 1H), 6.82-6.76 (m, 1H), 6.28 (d, J=5.9 Hz, 1H), 6.15 (dd, J=3.9, 2.0 Hz, 1H), 5.13 (s, 2H), 4.10 (d, J=16.8 Hz, 2H), 3.96-3.82 (m, 1H), 3.81 (s, 3H), 3.79-3.69 (m, 1H), 3.69-3.39 (m, 1H), 2.64-2.38 (m, 2H), 0.92-0.85 (m, 9H), 0.07 (s, 3H), 0.02 (br. s, 3H); $^{13}$C NMR (100 MHz, CDCl$_3$), mixture of rotamers and regioisomers, δ 150.8, 141.9, 140.1, 136.8, 131.9, 128.6, 127.9, 127.1, 125.9, 124.5, 121.3, 119.4, 119.3, 118.7, 113.1, 112.3, 103.0, 102.9, 70.7, 64.4, 62.1, 57.1, 30.9, 25.9, 18.3, −5.4; MS (ES+): m/z=565 (M+H)$^+$.

Allyl (S)-(5-(benzyloxy)-2-(2-(((tert-butyldimethyl-silyl)oxy)methyl)-4-(thiophen-3-yl)-1,2,3,6-tetrahydropyridine-1-carbonyl)-4-methoxy-phenyl)carbamate and allyl (S)-(5-(benzyloxy)-2-(6-(((tert-butyldimethyl-silyl)oxy)methyl)-4-(thiophen-3-yl)-1,2,3,6-tetrahydropyridine-1-carbonyl)-4-methoxyphenyl)carbamate (53) (1:1)

53

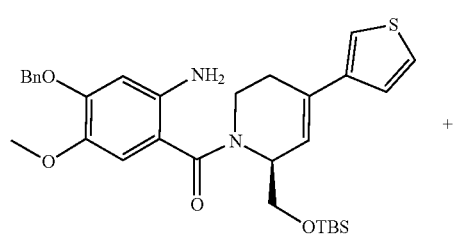

+

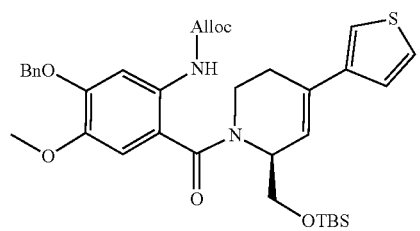

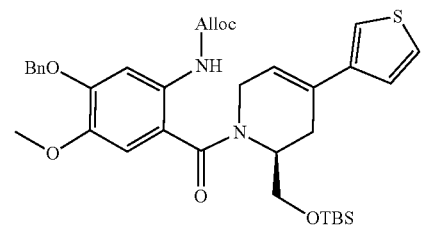

A solution of (S)-(2-amino-4-(benzyloxy)-5-methoxyphenyl)(6-(((tert-butyldimethyl-silyl)oxy)methyl)-4-(thiophen-3-yl)-3,6-dihydropyridin-1(2H)-yl)methanone and(S)-(2-amino-4-(benzyloxy)-5-methoxyphenyl)(2-(((tert-butyldimethylsilyl)oxy)methyl)-4-(thiophen-3-yl)-3,6-dihydropyridin-1(2H)-yl)methanone (52) (3.00 g, 5.30 mmol) in dichloromethane (20 mL) was cooled to −2° C. and charged with pyridine (0.429 mL, 5.30 mmol) and allyl chloroformate (0.564 mL, 5.30 mmol). After 10 min, the reaction was judged to be complete by TLC and LCMS and was sequentially washed with a saturated aqueous solution of copper sulfate (20 mL), water (20 mL) and a saturated aqueous solution of sodium hydrogen carbonate (20 mL). The organic extract was then dried over magnesium sulfate and concentrated in vacuo. The resulting oil was then purified by flash column chromatography (silica), eluting with petroleum spirit, 40-60° C./ethyl acetate (1:0 to 0:1) to afford the title compound (3.33 g, 97%) as a white solid. $^1$H NMR (400 MHz, CDCl$_3$), mixture of rotamers and regioisomers, δ 8.57-7.73 (m, 2H), 7.49 (d, J=7.4 Hz, 2H), 7.42-7.22 (m, 6H), 7.15 (br. s, 1H), 6.85 (d, J=12.9 Hz, 1H), 6.12 (br. s, 1H), 5.99-5.82 (m, 1H), 5.33 (d, J=17.2 Hz, 1H), 5.24-517 (m, 3H), 4.70-453 (m, 2H), 3.85 (s, 4H), 3.75 (br. s, 1H), 3.58 (br. s, 1H), 2.79 (d, J=14.1 Hz, 1H), 2.46 (d, J=16.8 Hz, 1H), 0.92-0.81 (m, 10H), 0.12-0.04 (m, 3H), 0.01 (br. s, 2H); $^{13}$C NMR (100 MHz, CDCl$_3$), mixture of rotamers and regioisomers, δ 153.4, 150.2, 144.8, 141.7, 136.4, 132.5, 128.5, 128.0, 127.7, 126.0, 124.5, 124.4, 119.4, 118.0, 111.6, 70.7, 65.7, 64.3, 62.1, 56.7, 25.9, 18.3, −5.4; MS (ES+): m/z=649 (M+H)$^+$.

225

Allyl (S)-(5-(benzyloxy)-2-(2-(hydroxymethyl)-4-(thiophen-3-yl)-1,2,3,6-tetrahydropyridine-1-carbonyl)-4-methoxyphenyl)carbamate and allyl (S)-(5-(benzyloxy)-2-(6-(hydroxymethyl)-4-(thiophen-3-yl)-1,2,3,6-tetrahydro-pyridine-1-carbonyl)-4-methoxyphenyl)carbamate (54) (1:1)

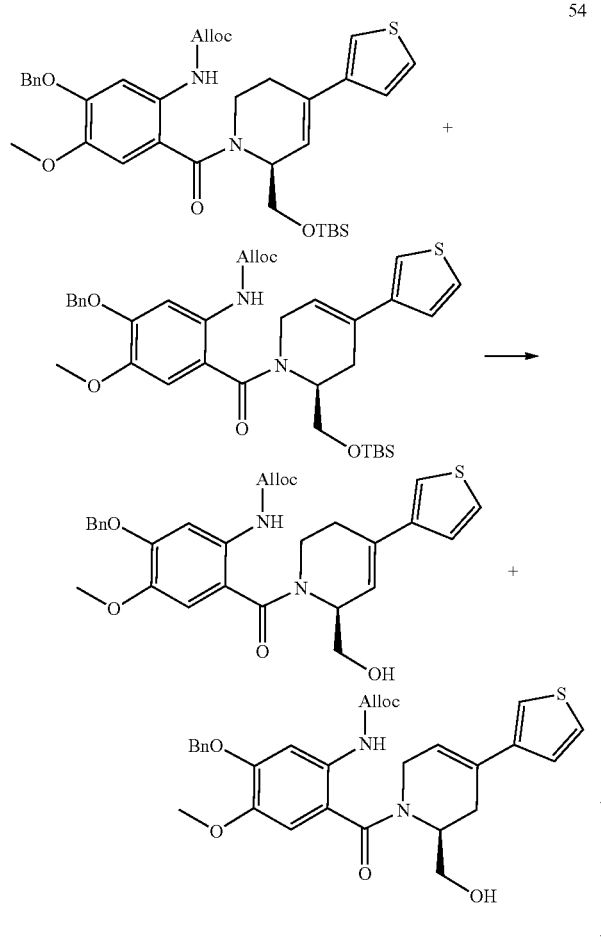

A solution of allyl (S)-(5-(benzyloxy)-2-(2-(((tert-butyldimethylsilyl)oxy)methyl)-4-(thiophen-3-yl)-1,2,3,6-tetrahydropyridine-1-carbonyl)-4-methoxyphenyl)carbamate and allyl (S)-(5-(benzyloxy)-2-(6-(((tert-butyldimethylsilyl)oxy)methyl)-4-(thiophen-3-yl)-1,2,3,6-tetrahydropyridine-1-carbonyl)-4-methoxyphenyl) carbamate (53) (3.27 g, 5.03 mmol) in tetrahydrofuran (20 mL) was cooled to 0° C. and charged with tetrabutylammonium fluoride (1 M in tetrahydrofuran, 6.03 mL, 6.03 mmol). The reaction was allowed to warm to room temperature and after 20 min, TLC and LCMS confirmed consumption of starting material. Ethyl acetate (50 mL) was added to the reaction mixture and the resulting solution washed with a saturated aqueous solution of ammonium chloride (20 mL) and brine (20 mL) and dried over magnesium sulfate. Purification by flash column chromatography (silica), eluting with dichloromethane/acetone (1:0 to 0:1) gave the title compound (2.68 g, 99%) as a pale yellow solid. $^1$H NMR (400 MHz, CDCl$_3$), mixture of rotamers and regioisomers, δ 8.42-8.06 (m, 1H), 7.97-7.64 (m, 1H), 7.47 (d, J=8.2 Hz, 2H), 7.41-7.27 (m, 4H), 7.24-7.10 (m, 2H), 6.84 (br. s, 1H), 6.05 (br. s, 1H), 6.00-5.82 (m, 1H), 5.38-5.26 (m, 1H), 5.24-5.11 (m, 3H), 4.65-4.56 (m, 2H), 3.96-3.85 (m, 1H), 3.83-3.81 (m, 3H), 3.72 (br. s, 1H), 3.64 (d, J=4.7 Hz, 1H), 3.40 (br. s, 1H), 3.22 (br. s, 1H), 2.52-2.40 (m, 2H); $^{13}$C NMR (100 MHz, CDCl$_3$), mixture of rotamers and regioisomers, δ 158.5, 153.9, 150.1, 149.8, 145.3, 141.5, 141.3, 136.4, 136.3, 132.5, 128.5, 127.7, 126.1, 124.5, 120.0, 119.2, 117.9, 110.8, 107.2, 70.8, 65.7, 61.4, 60.4, 56.5, 30.9, 27.9, 25.6, 21.0; MS (ES+): m/z=535 (M+H)$^+$; LCMS (Method B): $t_R$=4.07 min.

Allyl (6S,6aS)-3-(benzyloxy)-6-hydroxy-2-methoxy-12-oxo-8-(thiophen-3-yl)-6,6a,7,10-tetrahydrobenzo[e]pyrido[1,2-α][1,4]diazepine-5(12H)-carboxylate and allyl (6S,6aS)-3-(benzyloxy)-6-hydroxy-2-methoxy-12-oxo-8-(thiophen-3-yl)-6,6a,9,10-tetrahydrobenzo[e]pyrido[1,2-α][1,4]diazepine-5(12H)-carboxylate (55) (1:1)

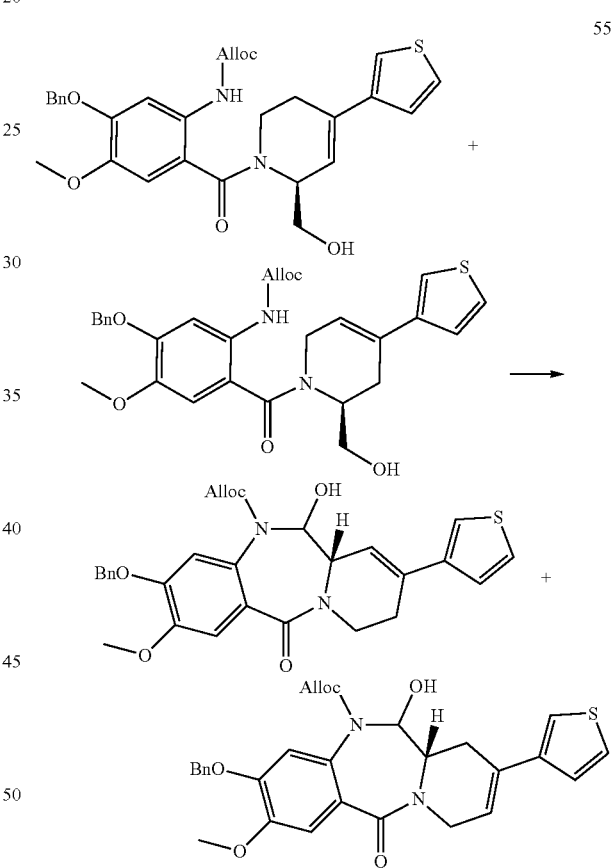

A solution of allyl (S)-(5-(benzyloxy)-2-(2-(hydroxymethyl)-4-(thiophen-3-yl)-1,2,3,6-tetrahydropyridine-1-carbonyl)-4-methoxyphenyl)carbamate and allyl (S)-(5-(benzyloxy)-2-(6-(hydroxymethyl)-4-(thiophen-3-yl)-1,2,3,6-tetrahydropyridine-1-carbonyl)-4-methoxyphenyl) carbamate (54) (2.39 g, 4.48 mmol) in dichloromethane (15 mL) was charged with TEMPO (119 mg, 0.76 mmol) and (diacetoxyiodo)benzene (2.94 g, 9.13 mmol) and stirred at room temperature for 16 h, at which point TLC and LCMS showed consumption of starting material. Dichloromethane (30 mL) was then added to the reaction mixture, which was quenched by addition of a saturated aqueous solution of sodium metabisulfite (20 mL). The organic phase was separated, washed with brine (50 mL), dried over magnesium sulfate, filtered and concentrated in vacuo. Purification by flash column chromatography (silica), eluting with dichloromethane/acetone (1:0 to 0:1) gave the title compound (1.70 g, 71%) as a pale yellow solid. ¹H NMR (400 MHz, CDCl₃), mixture of rotamers and regioisomers, δ 7.47-7.17 (m, 10H), 6.76 (d, J=9.0 Hz, 1H), 6.28 (br. s, 1H), 5.66 (dd, J=1.2, 4.3 Hz, 2H), 5.25-5.03 (m, 2H), 4.46 (br. s, 2H), 4.33-4.15 (m, 1H), 4.04 (br. s, 1H), 3.96-3.88 (m, 3H), 3.80-3.64 (m, 1H), 3.13-2.98 (m, 1H), 2.69-2.55 (m, 2H); ¹³C NMR (100 MHz, CDCl₃), mixture of rotamers and regioisomers, δ 168.9, 167.6, 149.1, 141.4, 136.2, 133.3, 131.8, 130.5, 128.6, 128.1, 127.3, 126.1, 125.3, 120.2, 119.0, 118.0, 117.6, 114.3, 110.8, 84.5, 84.1, 71.0, 66.7, 60.4, 56.1, 55.9, 54.6, 41.3, 37.1; MS (ES+): m/z=533 (M+H)⁺; LCMS (Method A): $t_R$=7.62 min.

Allyl(6aS)-3-hydroxy-2,6-dimethoxy-12-oxo-8-(thiophen-3-yl)-6,6a,7,10-tetrahydrobenzo[e]pyrido[1,2-α][1,4]diazepine-5(12H)-carboxylate (56)

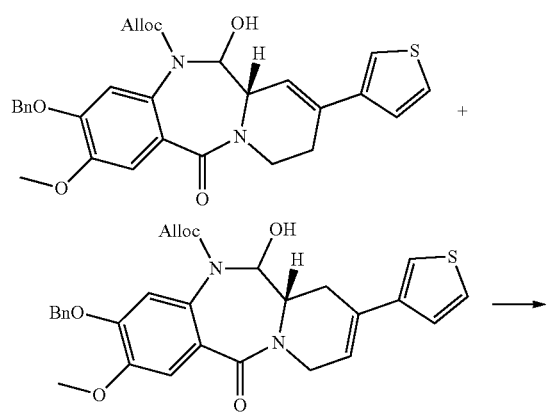

56

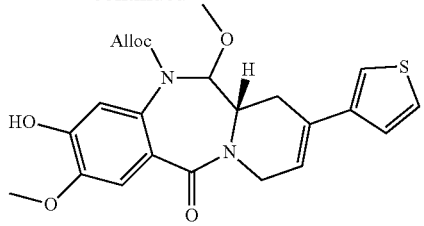

A solution of allyl (6S,6aS)-3-(benzyloxy)-6-hydroxy-2-methoxy-12-oxo-8-(thiophen-3-yl)-6,6a,7,10-tetrahydrobenzo[e]pyrido[1,2-α][1,4]diazepine-5(12H)-carboxylate and allyl (6S,6aS)-3-(benzyloxy)-6-hydroxy-2-methoxy-12-oxo-8-(thiophen-3-yl)-6,6a,9,10-tetrahydrobenzo[e]pyrido[1,2-α][1,4]diazepine-5(12H)-carboxylate (55) (1.59 g, 2.89 mmol) in anhydrous dichloromethane (10 mL) was charged with boron trichloride (1 M in dichloromethane, 8.94 mL, 8.94 mmol) and stirred at room temperature under an inert atmosphere of nitrogen for 15 min. Methanol (30 mL) was then charged and the resulting mixture irradiated with microwaves at 55° C. for 1 h. After filtering through a cotton pad, washing with dichloromethane and concentrating in vacuo, purification was carried out by (multiple) flash column chromatography (silica), eluting with petroleum spirit, 40-60° C./ethyl acetate (1:0 to 0:1) to afford the (regiopure) title compound (138 mg, 10%) as a cream solid. ¹H NMR (400 MHz, CDCl₃) δ 7.31 (dd, J=5.1, 2.7 Hz, 1H), 7.25-7.23 (m, 1H), 7.20-7.17 (m, 2H), 6.78-6.69 (m, 2H), 6.28 (br. s, 1H), 5.73 (br. s, 1H), 5.41 (d, J=9.4 Hz, 1H), 5.07 (d, J=10.9 Hz, 2H), 4.55 (dd, J=13.1, 5.7 Hz, 1H), 4.44 (br. s, 1H), 4.23-4.16 (m, 2H), 3.87-3.83 (m, 3H), 3.44-3.41 (m, 3H), 2.98-2.89 (m, 1H), 2.70-2.60 (m, 1H); ¹³C NMR (100 MHz, CDCl₃) δ 169.4, 156.0, 148.4, 146.7, 141.2, 131.9, 130.6, 128.8, 126.4, 124.6, 119.9, 119.2, 117.3, 116.1, 110.3, 91.3, 66.4, 56.1, 54.9, 41.2, 26.9; MS (ES+): m/z=457 (M+H)⁺; LCMS (Method A): $t_R$=7.00 min.

Diallyl 3,3'-((pyridine-2,6-diylbis(methylene))bis(oxy))(6aS,6a'S)-bis(2,6-dimethoxy-12-oxo-8-(thiophen-3-yl)-6,6a,7,10-tetrahydrobenzo[e]-pyrido[1,2-α][1,4]diazepine-5(12H)-carboxylate) (57)

57

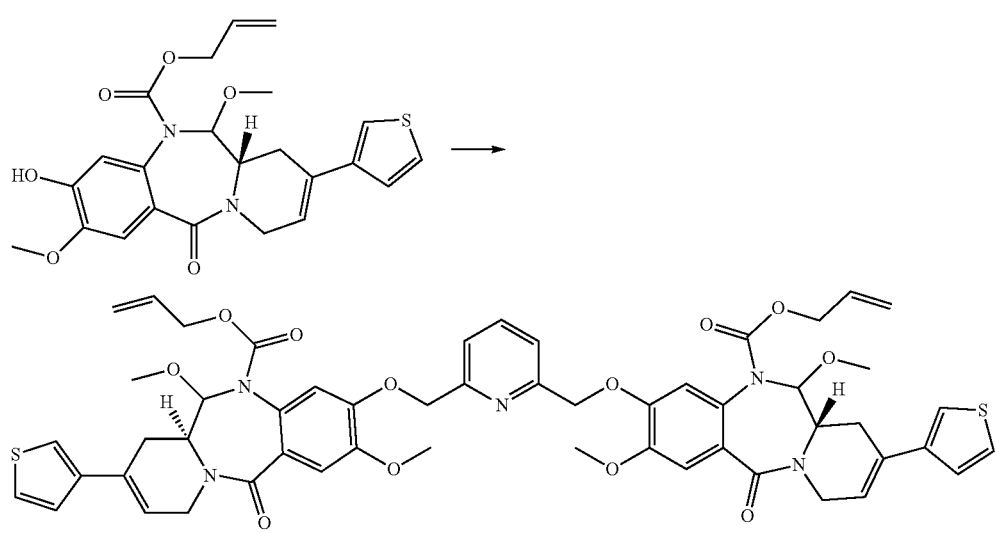

A solution of allyl (6aS)-3-hydroxy-2,6-dimethoxy-12-oxo-8-(thiophen-3-yl)-6,6a,7,10-tetrahydrobenzo[e]pyrido[1,2-α][1,4]diazepine-5(12H)-carboxylate (56) (69 mg, 0.15 mmol) in N,N-dimethylformamide (1 mL) was charged with potassium carbonate (21 mg, 0.15 mmol), 2,6-bis(bromomethyl)pyridine (19.9 mg, 0.075 mmol) and water (0.1 mL). The resulting mixture was irradiated with microwaves at 55° C. for 1 h, at which point TLC and LCMS showed completion of the reaction. Ethyl acetate (10 mL) was added and the mixture extracted with water (5 mL) and brine (5 mL). The organic phase was then dried over magnesium sulfate, and concentrated in vacuo. Purification by flash column chromatography (silica), eluting with petroleum spirit, 40-60° C./ethyl acetate (1:0 to 0:1) gave the title compound (35 mg, 46%) as a pale yellow solid. $^1$H NMR (400 MHz, CDCl$_3$) δ 7.84-7.74 (m, 1H), 7.54 (d, J=7.4 Hz, 2H), 7.33 (dd, J=5.1, 2.7 Hz, 2H), 7.31-7.25 (m, 4H), 7.24-7.16 (m, 2H), 6.70 (br. s, 2H), 6.37-6.26 (m, 2H), 5.67 (br. s, 1H), 5.40 (d, J=9.4 Hz, 1H), 5.31-5.22 (m, 4H), 5.13-4.97 (m, 3H), 4.57-4.45 (m, 2H), 4.42 (br. s, 2H), 4.30-4.18 (m, 3H), 4.00-3.92 (m, 8H), 3.69-3.57 (m, 2H), 3.45-3.36 (m, 6H), 3.00-2.84 (m, 2H), 2.75-2.57 ppm (m, 2H); $^{13}$C NMR (100 MHz, CDCl$_3$) δ 169.0, 156.0, 149.4, 141.2, 137.9, 131.9, 130.6, 126.4, 124.6, 120.4, 119.9, 119.3, 114.6, 110.9, 91.3, 73.7, 71.4, 66.4, 60.3, 56.2, 54.8, 41.2, 26.9; MS (ES+): m/z=1017 (M+H)$^+$; LCMS (Method A): t$_R$=8.63 min.

(6aS,6a'S)-3,3'-((Pyridine-2,6-diylbis(methylene))bis(oxy))bis(2-methoxy-8-(thiophen-3-yl)-7,10-dihydrobenzo[e]pyrido[1,2-α][1,4]diazepin-12(6aH)-one) (58)

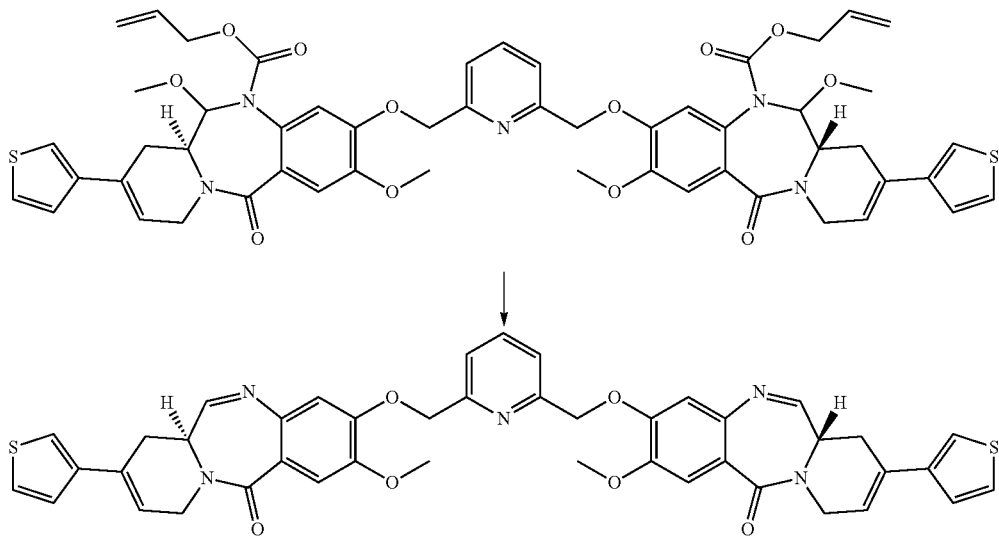

58

A solution of diallyl 3,3'-((pyridine-2,6-diylbis(methylene))bis(oxy))(6aS,6'S,6a'S)-bis(2,6-dimethoxy-12-oxo-8-(thiophen-3-yl)-6,6a,7,10-tetrahydrobenzo[e]pyrido[1,2-a][1,4]diazepine-5(12H)-carboxylate) (57) (35 mg, 0.034 mmol) in dichloromethane (2 mL) was charged with tetrakis(triphenylphosphine)palladium(o) (1 mg) and pyrrolidine (5 µL). After 5 min, the reaction was observed to have completed via TLC. The reaction mixture was concentrated in vacuo to form an oil, which was charged with diethyl ether (2 mL) and re-concentrated in vacuo (this process was repeated twice more). Purification via flash column chromatography (silica), eluting with dichloromethane/methanol (95:5) gave the title compound (15 mg, 55%) as a cream solid. $^1$H NMR (400 MHz, CDCl$_3$) δ 7.76-7.70 (m, 1H), 7.60 (d, J=5.9 Hz, 2H), 7.56 (s, 2H), 7.47 (d, J=7.8 Hz, 2H), 7.37 (dd, J=5.1, 2.7 Hz, 2H), 7.31 (dd, J=5.1, 1.2 Hz, 2H), 6.86 (s, 2H), 6.49-6.43 (m, 2H), 5.32 (s, 4H), 4.45 (dd, J=18.5, 5.7 Hz, 2H), 4.14 (d, J=18.7 Hz, 2H), 4.01 (s, 6H), 3.97-3.91 (m, 2H), 3.78-3.64 (m, 2H), 2.98-2.91 (m, 4H); MS (ES+): m/z=784 (M+H)$^+$; LCMS (Method A): t$_R$=7.23 min.

Diallyl 3,3'-((1,3-phenylenebis(methylene))bis(oxy))(6S,6aS,6'S,6a'S)-bis(2,6-dimethoxy-12-oxo-8-(thiophen-3-yl)-6,6a,7,10-tetrahydrobenzo[e]-opyrido[1,2-α][1,4]diazepine-5(12H)-carboxylate) (59)

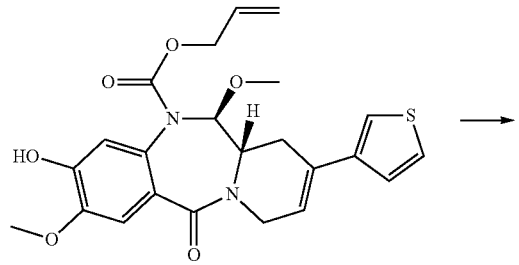

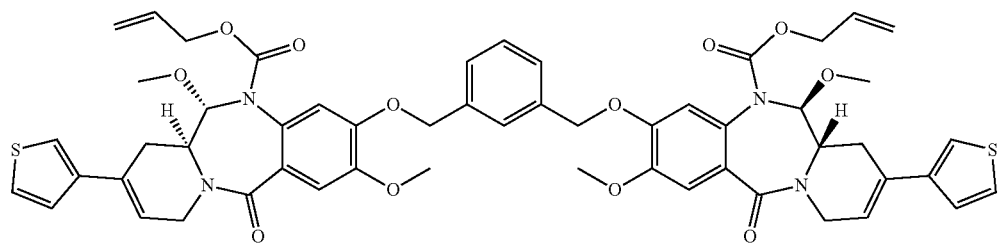

59

A solution of allyl (6aS)-3-hydroxy-2,6-dimethoxy-12-oxo-8-(thiophen-3-yl)-6,6a,7,10-tetrahydrobenzo[e]pyrido[1,2-α][1,4]diazepine-5(12H)-carboxylate (56) (63 mg, 0.13 mmol) in N,N-dimethylformamide (1 mL) was charged with potassium carbonate (18 mg, 0.13 mmol), 1,3-bis(bromomethyl)benzene (17.2 mg, 0.065 mmol) and water (0.1 mL). The resulting mixture was irradiated with microwaves at 55° C. for 1 h, at which point TLC and LCMS showed completion of the reaction. Ethyl acetate (10 mL) was added and the mixture extracted with water (5 mL) and brine (5 mL). The organic phase was then dried over magnesium sulfate and concentrated in vacuo. Purification by flash column chromatography (silica), eluting with petroleum spirit, 40-60° C./ethyl acetate (1:0 to 0:1) gave the title compound (45 mg, 69%) as a pale yellow solid. $^1$H NMR (400 MHz, CDCl$_3$) δ 7.55 (s, 1H), 7.48-7.38 (m, 4H), 7.38-7.34 (m, 2H), 7.34 (s, 1H), 7.31-7.28 (m, 2H), 7.25-7.20 (m, 2H), 6.72 (br. s, 2H), 6.40-6.31 (m, 2H), 5.71 (d, J=3.9 Hz, 1H), 5.42 (d, J=9.8 Hz, 1H), 5.17 (s, 5H), 5.14-5.01 (m, 4H), 4.54 (d, J=12.9 Hz, 2H), 4.45 (br. s, 2H), 4.33-4.17 (m, 4H), 3.95 (s, 6H), 3.67 (t, J=7.0 Hz, 2H), 3.49-3.39 (m, 7H), 2.78-2.58 (m, 2H), 2.24 (br. s, 2H); $^{13}$C NMR (100 MHz, CDCl$_3$) δ 169.0, 149.4, 141.2, 136.6, 131.9, 130.6, 128.9, 126.3, 124.6, 119.9, 119.2, 117.2, 114.7, 110.8, 91.3, 73.7, 71.0, 66.3, 56.1, 41.1, 29.5, 26.7; MS (ES+): m/z=1016 (M+H)$^+$; LCMS (Method A): t$_R$=8.87 min.

(6aS,6a'S)-3,3'-((1,3-Phenylenebis(methylene))bis(oxy))bis(2-methoxy-8-(thiophen-3-yl)-7,10-dihydrobenzo[e]pyrido[1,2-α][1,4]diazepin-12(6aH)-one) (60)

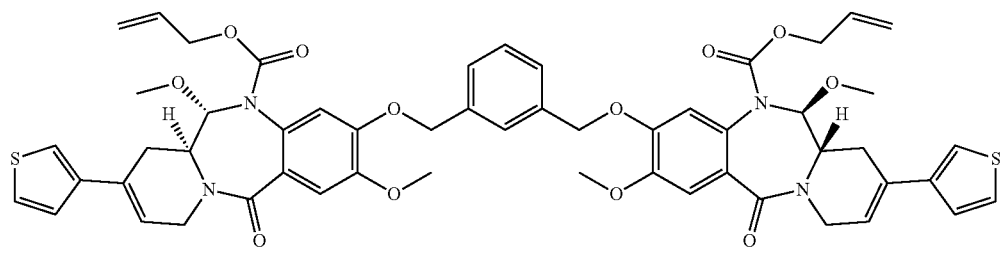

↓

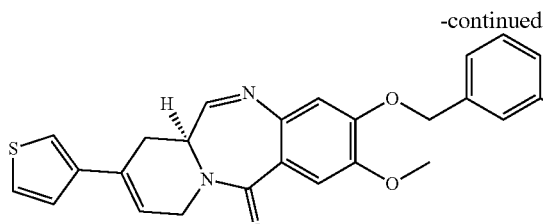
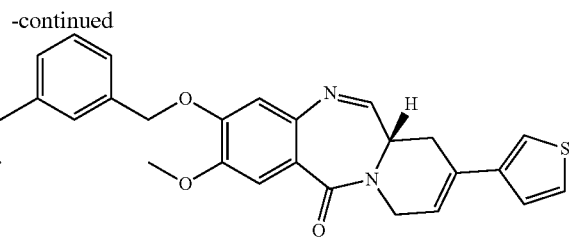

60

A solution of diallyl 3,3'-((1,3-phenylenebis(methylene))bis(oxy))(6S,6aS,6'S,6a'S)-bis(2,6-dimethoxy-12-oxo-8-(thiophen-3-yl)-6,6a,7,10-tetrahydrobenzo[e]pyrido[1,2-α][1,4]diazepine-5(12H)-carboxylate) (59) in dichloromethane (2 mL) was charged with tetrakis(triphenylphosphine)palladium(o) (1 mg) and pyrrolidine (5 μL). After 5 min, the reaction was observed to have completed via TLC. The reaction mixture was concentrated in vacuo to form an oil, which was charged with diethyl ether (2 mL) and re-concentrated in vacuo (this process was repeated twice more). Purification via flash column chromatography (silica), eluting with dichloromethane/acetone (1:0 to 0:1) gave the title compound (12.7 mg, 74%) as a pale yellow solid. $^1$H NMR (400 MHz, CDCl$_3$) δ 7.61 (d, J=5.5 Hz, 2H), 7.54 (s, 2H), 7.51 (s, 1H), 7.42-7.37 (m, 5H), 7.32 (dd, J=5.1, 1.2 Hz, 2H), 6.84 (s, 2H), 6.47 (dt, J=4.9, 2.6 Hz, 2H), 5.29-5.13 (m, 5H), 4.45 (dd, J=18.4, 5.9 Hz, 2H), 4.14 (d, J=18.4 Hz, 2H), 3.99-3.98 (m, 6H), 3.95 (dt, J=5.4, 2.6 Hz, 2H), 2.95 (d, J=2.7 Hz, 4H); MS (ES+): m/z=783 (M+H)$^+$; LCMS (Method A): $t_R$=7.50 min.

(S)-(4-(Benzyloxy)-5-methoxy-2-nitrophenyl)(6-(((tert-butyldimethyl-silyl)oxy)methyl)-4-(thiophen-2-yl)-3,6-dihydropyridin-1(2H)-yl)methanone and (S)-(4-(benzyloxy)-5-methoxy-2-nitrophenyl)(2-(((tert-butyldimethylsilyl)oxy)methyl)-4-(thiophen-2-yl)-3,6-dihydropyridin-1(2H)-yl)methanone (61) (1:1)

61

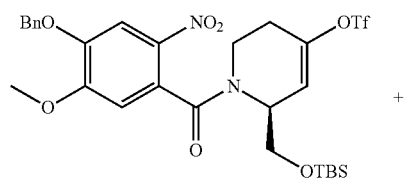

+

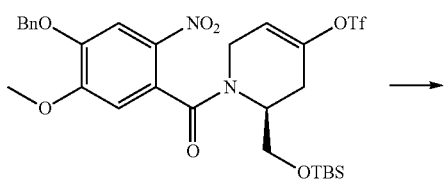

→

[Structures continued on right column]

A solution of (S)-1-(4-(benzyloxy)-5-methoxy-2-nitrobenzoyl)-6-(((tert-butyldimethyl-silyl)oxy)methyl)-1,2,3,6-tetrahydropyridin-4-yl trifluoromethane sulfonate and (S)-1-(4-(benzyloxy)-5-methoxy-2-nitrobenzoyl)-2-(((tert-butyldimethylsilyl)oxy)methyl)-1,2,3,6-tetrahydropyridin-4-yl trifluoromethanesulfonate (8) (2.50 g, 3.78 mmol) in acetonitrile (5 mL) was charged with [1,1'-bis(diphenylphosphino)ferrocene]dichloro-palladium(II), complex with dichloromethane (310 mg, 0.38 mmol), 2-thienylboronic acid (534 mg, 4.17 mmol) and an aqueous solution of potassium carbonate (2 M, 3.78 mL, 7.56 mmol) and irradiated with microwaves at 50° C. for 20 min. The mixture was subsequently diluted with ethyl acetate (25 mL) and sequentially washed with water (15 mL) and brine (15 mL), then dried over solid anhydrous magnesium sulfate and concentrated in vacuo. The residue was then purified by flash column chromatography (silica), eluting with petroleum spirit, 40-60° C./ethyl acetate (from 1:0 to 0:1) to afford the title compound (1.78 g, 80%) as a yellow solid. $^1$H NMR (400 MHz, CDCl$_3$), mixture of rotamers and regioisomers, δ 7.87-7.72 (m, 1H), 7.51-7.33 (m, 5H), 7.18 (d, J=6.2 Hz, 1H), 7.09-6.88 (m, 2H), 6.77 (d, J=$_{5.9}$ Hz, 1H), 6.47-5.78 (m, 1H), 5.24 (d, J=3.5 Hz, 2H), 4.01-3.95 (m, 4H), 3.75 (br. s, 2H), 3.65 (br. s, 1H), 3.10-233 (m, 2H), 1.03-0.81 (m, 9H), 0.78 (s, 1H), 0.20-0.02 (m, 6H); $^{13}$C NMR (100 MHz, CDCl$_3$) δ 177.0, 176.6, 137.3, 135.3, 128.8, 128.5, 122.6, 122.3, 119.6, 109.1, 100.1, 96.5, 71.4, 56.7, 52.0, 35.7, 27.6, 25.9, 18.2, 18.0, −5.4; MS (ES+): m/z=595 (M+H)$^+$; LCMS (Method A): $t_R$=9.28 min.

235

(S)-(2-Amino-4-(benzyloxy)-5-methoxyphenyl)(6-(((tert-butyldimethyl-silyl)oxy)methyl)-4-(thiophen-2-yl)-3,6-dihydropyridin-1(2H)-yl)methanone and (S)-(2-amino-4-(benzyloxy)-5-methoxyphenyl)(2-(((tert-butyldimethylsilyl)oxy)methyl)-4-(thiophen-2-yl)-3,6-dihydropyridin-1(2H)-yl)methanone (62) (1:1)

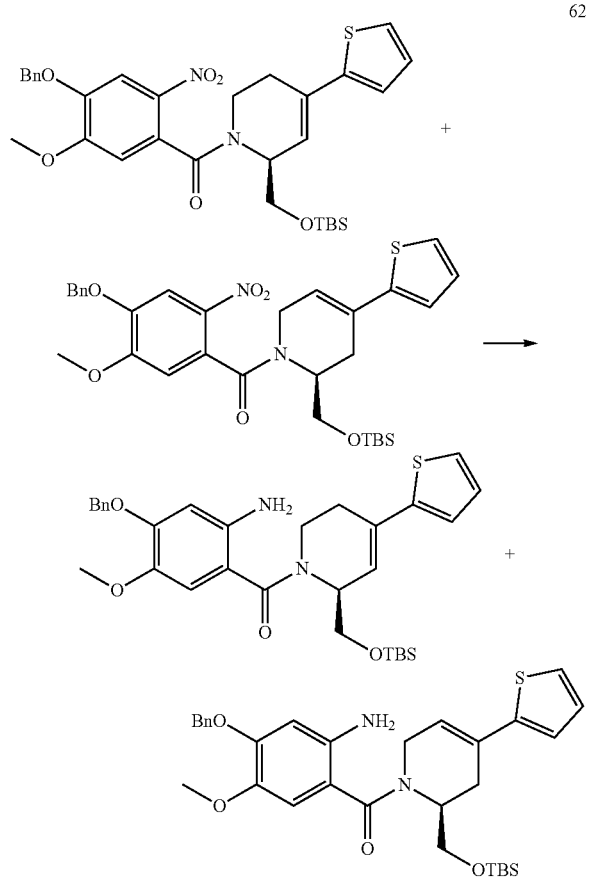

A solution of (S)-(4-(Benzyloxy)-5-methoxy-2-nitrophenyl)(6-(((tert-butyldimethyl-silyl)oxy)methyl)-4-(thiophen-2-yl)-3,6-dihydropyridin-1(2H)-yl)methanone and (S)-(4-(benzyloxy)-5-methoxy-2-nitrophenyl)(2-(((tert-butyldimethylsilyl)oxy)methyl)-4-(thiophen-2-yl)-3,6-dihydropyridin-1(2H)-yl)methanone (61) in formic acid (5% v/v in absolute ethanol, 30 mL) was cooled to 0° C. and charged with zinc powder (7.71 g, 118 mmol), then stirred for 2 h, whilst monitoring by TLC and LCMS. Upon completion, the mixture was filtered over a pad of celite and the resulting cake washed with ethyl acetate. A saturated aqueous solution of sodium hydrogen carbonate (10 mL) was then added to the filtrate and the mixture concentrated in vacuo to remove organics. The residue was then partitioned between ethyl acetate (30 mL) and brine (30 mL) and the organic phase dried over magnesium sulfate, filtered, and concentrated in vacuo. Purification by flash column chromatography (silica), eluting with petroleum spirit, 40-60° C./ethyl acetate (from 1:0 to 7:3) gave the title compound (1.53 g, 92%) as a yellow solid. $^1$H NMR (400 MHz, CDCl$_3$), mixture of rotamers and regioisomers, δ 7.46-7.29 (m, 5H), 7.20-7.14 (m, 1H), 7.01-6.96 (m, 2H), 6.83-6.73

236

(m, 1H), 6.28 (d, J=$_{5-9}$ Hz, 1H), 6.18-6.00 (m, 1H), 4.19-4.01 (m, 2H), 3.97-3.85 (m, 1H), 3.83-3.79 (m, 4H), 3.79-3.69 (m, 1H), 3.69-3.60 (m, 1H), 2.82 (dq, J=17.2, 3.1 Hz, 1H), 2.57-2.41 (m, 1H), 0.93-0.82 (m, 9H), 0.10-0.03 (m, 6H); $^{13}$C NMR (100 MHz, CDCl$_3$) δ 150.8, 144.6, 141.8, 140.1, 136.8, 128.6, 127.9, 127.1, 123.8, 122.2, 120.4, 118.5, 113.1, 112.2, 102.9, 70.8, 64.4, 62.0, 57.0, 25.9, 18.3, −5.4; MS (ES+): m/z=565 (M+H)$^+$; LCMS (Method A): t$_R$=9.65 min.

Allyl (S)-(5-(benzyloxy)-2-(6-(((tert-butyldimethyl-silyl)oxy)methyl)-4-(thiophen-2-yl)-1,2,3,6-tetrahydropyridine-1-carbonyl)-4-methoxyphenyl)-carbamate and allyl (S)-(5-(benzyloxy)-2-(2-(((tert-butyldimethylsilyl)-oxy)methyl)-4-(thiophen-2-yl)-1,2,3,6-tetrahydropyridine-1-carbonyl)-4-methoxyphenyl)carbamate (63) (1:1)

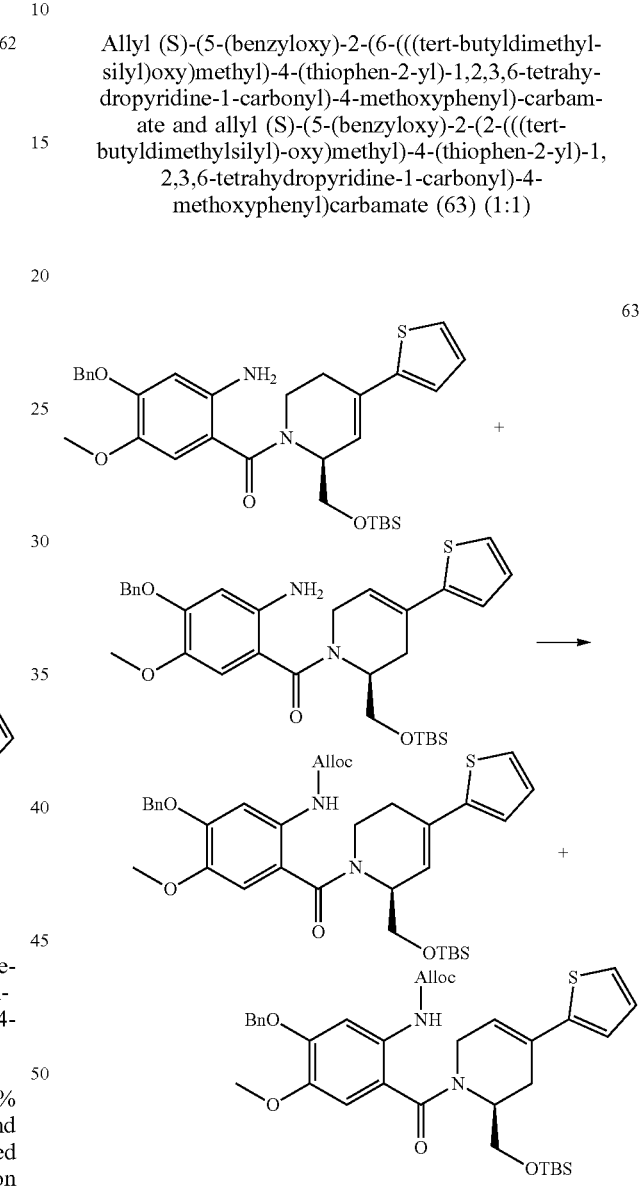

A solution of (S)-(2-Amino-4-(benzyloxy)-5-methoxyphenyl)(6-(((tert-butyldimethyl-silyl)oxy)methyl)-4-(thiophen-2-yl)-3,6-dihydropyridin-1(2H)-yl)methanone and(S)-(2-amino-4-(benzyloxy)-5-methoxyphenyl)(2-(((tert-butyldimethylsilyl)oxy)methyl)-4-(thiophen-2-yl)-3,6-dihydropyridin-1(2H)-yl)methanone (62) (1.50 g, 2.65 mmol) in dichloromethane (10 mL) was cooled to −2° C. and charged with pyridine (214 µL, 2.65 mmol) and allyl chloroformate (282 µL, 2.65 mmol). After 10 min, the reaction was judged to be complete by TLC and LCMS and was sequentially washed with a saturated aqueous solution of copper sulfate (10 mL), water (10 mL) and a saturated aqueous solution of sodium hydrogen carbonate (1 mL). The organic extract was then dried over magnesium sulfate and concentrated in vacuo. The resulting oil was then purified by flash column chromatography (silica), eluting with petroleum spirit, 40-60° C./ethyl acetate (1:0 to 0:1) to afford the title compound (1.48 g, 87%) as a white solid. $^1$H NMR (400 MHz, CDCl$_3$), mixture of rotamers and regioisomers, δ 8.14 (br. s, 1H), 7.49 (d, J=7.8 Hz, 2H), 7.42-7.30 (m, 3H), 7.21-7.17 (m, 1H), 7.02-6.98 (m, 2H), 6.84 (d, J=11.7 Hz, 1H), 6.13 (br. s, 1H), 5.99-5.85 (m, 1H), 5.33 (dt, J=17.2, 1.6 Hz, 1H), 5.26-514 (m, 4H), 4.69-4.53 (m, 3H), 3.88-3.79 (m, 4H), 3.76 (d, J=4.7 Hz, 1H), 2.51 (d, J=17.2 Hz, 1H), 0.89 (s, 9H), 0.86 (s, 3H), 0.13-0.04 (m, 3H), 0.01 (br. s, 2H); $^{13}$C NMR (100 MHz, CDCl$_3$) δ 153.6, 150.3, 144.3, 136.4, 132.5, 128.5, 127.7, 127.4, 124.0, 122.4, 118.0, 70.7, 65.7, 64.2, 62.0, 56.7, 25.9, 18.3, −5.5; MS (ES+): m/z=649 (M+H)$^+$.

Allyl (S)-(5-(benzyloxy)-2-(6-(hydroxymethyl)-4-(thiophen-2-yl)-1,2,3,6-tetrahydropyridine-1-carbonyl)-4-methoxyphenyl)carbamate and allyl (S)-(5-(benzyloxy)-2-(2-(hydroxymethyl)-4-(thiophen-2-yl)-1,2,3,6-tetrahydro-pyridine-1-carbonyl)-4-methoxyphenyl)carbamate (64) (1:1)

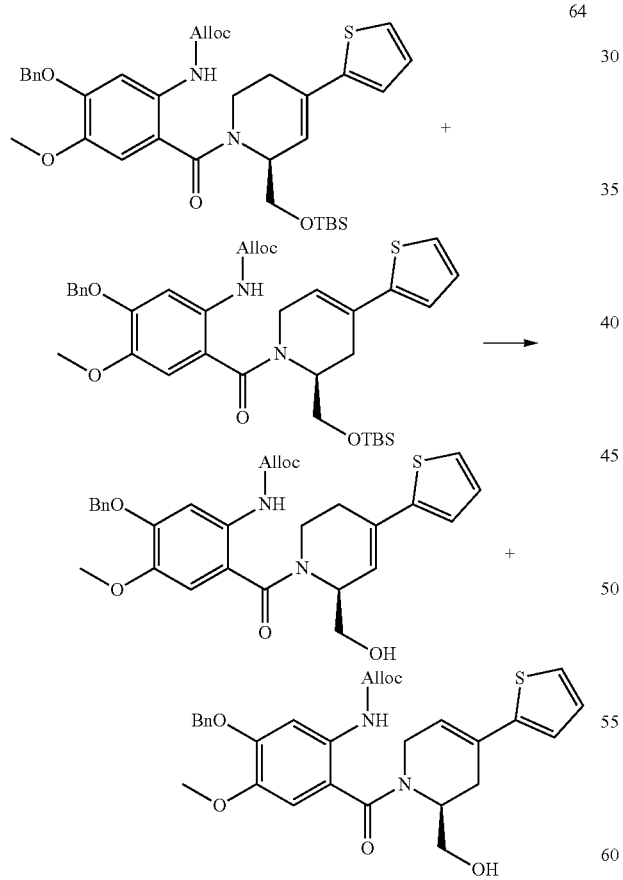

A solution of allyl (S)-(5-(benzyloxy)-2-(6-(((tert-butyldimethylsilyl)oxy)methyl)-4-(thiophen-2-yl)-1,2,3,6-tetrahydropyridine-1-carbonyl)-4-methoxyphenyl)carbamate and allyl (S)-(5-(benzyloxy)-2-(2-(((tert-butyldimethylsilyl)oxy)methyl)-4-(thiophen-2-yl)-1,2,3,6-tetrahydropyridine-1-carbonyl)-4-methoxyphenyl) carbamate (63) (1.45 g, 2.23 mmol) in tetrahydrofuran (10 mL) was cooled to 0° C. and charged with tetrabutylammonium fluoride (1 M in tetrahydrofuran, 2.67 mL, 2.67 mmol). The reaction was allowed to warm to room temperature and after 1 h, TLC and LCMS confirmed consumption of starting material. Ethyl acetate (25 mL) was added to the reaction mixture and the resulting solution washed with a saturated aqueous solution of ammonium chloride (10 mL) and brine (10 mL) and dried over magnesium sulfate. Purification by flash column chromatography (silica), eluting with dichloromethane/acetone (1:0 to 0:1) gave the title compound (1.19 g, 100%) as a pale yellow solid. $^1$H NMR (400 MHz, CDCl$_3$), mixture of rotamers and regioisomers, δ 8.19 (br. s, 1H), 7.73 (br. s, 1H), 7.47 (d, J=8.2 Hz, 2H), 7.41-7.29 (m, 3H), 7.19 (ddd, J=9.8, 4.7, 1.6 Hz, 1H), 7.02-6.95 (m, 2H), 6.83 (br. s, 1H), 6.21-5.75 (m, 2H), 5.39-5.31 (m, 1H), 5.24-5.04 (m, 4H), 4.74-4.52 (m, 2H), 3.88-3.79 (m, 4H), 3.79-3.65 (m, 2H), 3.40 (br. s, 1H), 3.06-2.29 (m, 2H); $^{13}$C NMR (100 MHz, CDCl$_3$) δ 170.5, 153.9, 153.8, 144.1, 143.8, 136.3, 132.4, 128.5, 127.7, 127.4, 124.4, 122.9, 122.4, 117.8, 110.7, 70.8, 65.8, 56.5, 53.4, 30.9, 27.9; MS (ES+): m/z=535 (M+H)$^+$; LCMS (Method A): t$_R$=7.70 min.

Allyl (6aS)-3-(benzyloxy)-6-hydroxy-2-methoxy-12-oxo-8-(thiophen-2-yl)-6,6a,9,10-tetrahydrobenzo[e]pyrido[1,2-α][1,4]diazepine-5(12H)-carboxylate and allyl (6aS)-3-(benzyloxy)-6-hydroxy-2-methoxy-12-oxo-8-(thiophen-2-yl)-6,6a,7,10-tetrahydrobenzo[e]pyrido[1,2-α][1,4]diazepine-5(12H)-carboxylate (65) (1:1)

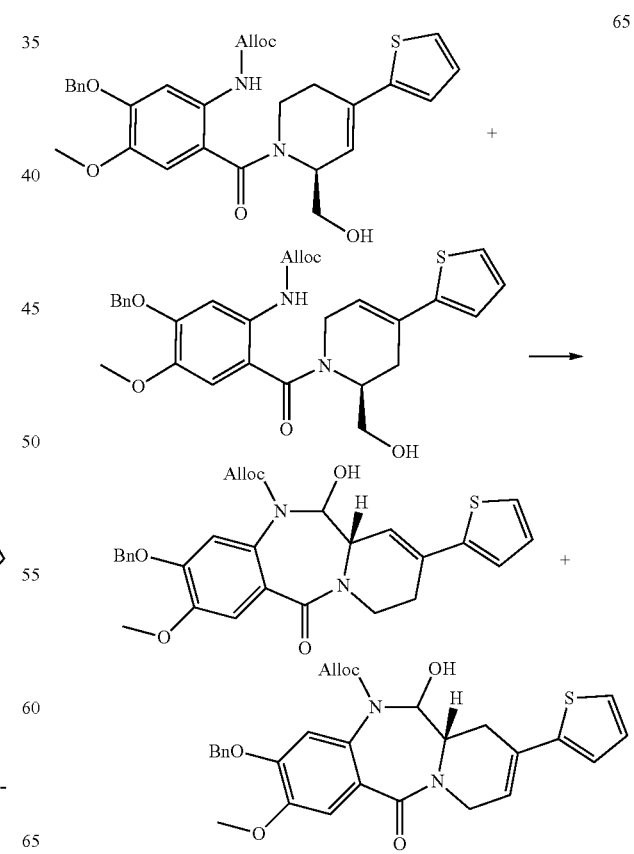

A solution of allyl (S)-(5-(benzyloxy)-2-(6-(hydroxymethyl)-4-(thiophen-2-yl)-1,2,3,6-tetrahydropyridine-1-carbonyl)-4-methoxyphenyl)carbamate and allyl (S)-(5-(benzyloxy)-2-(2-(hydroxymethyl)-4-(thiophen-2-yl)-1,2,3,6-tetrahydropyridine-1-carbonyl)-4-methoxyphenyl)carbamate (64) (1.16 g, 2.17 mmol) in dichloromethane (10 mL) was charged with TEMPO (33 mg, 0.21 mmol) and (diacetoxyiodo)benzene (837 mg, 2.60 mmol) and stirred at room temperature for 16 h, at which point TLC and LCMS showed consumption of starting material. Dichloromethane (15 mL) was then added to the reaction mixture, which was quenched by addition of a saturated aqueous solution of sodium metabisulfite (10 mL). The organic phase was separated, washed with a saturated aqueous solution of sodium hydrogen carbonate (10 mL), brine (10 mL), dried over magnesium sulfate, filtered and concentrated in vacuo. Purification by flash column chromatography (silica), eluting with dichloromethane/ethyl acetate (1:0 to 0:1) gave the title compound (574 mg, 50%) as a yellow solid. $^1$H NMR (400 MHz, CDCl$_3$), mixture of rotamers and regioisomers, δ 7.52-7.29 (m, 6H), 7.25-7.20 (m, 1H), 7.26-7.19 (m, 1H), 7.08-6.98 (m, 2H), 6.76 (br. s, 1H), 6.40-6.13 (m, 1H), 5.93-5.58 (m, 1H), 5.22-5.06 (m, 3H), 4.87-4.72 (m, 1H), 4.56-4.37 (m, 1H), 4.33-4.19 (m, 2H), 4.03 (br. s, 1H), 3.98-3.91 (m, 3H), 3.80-3.69 (m, 1H), 3.12 (d, J=15.2 Hz, 1H), 2.77-2.54 (m, 2H); $^{13}$C NMR (100 MHz, CDCl$_3$) δ 171.2, 168.8, 149.1, 143.7, 136.2, 129.6, 128.6, 127.5, 127.3, 125.3, 124.6, 123.1, 118.7, 117.3, 114.2, 110.8, 84.0, 71.1, 66.7, 60.4, 56.2, 41.3, 37.1, 27.2, 21.0, 14.2; MS (ES+): m/z=533 (M+H)$^+$; LCMS (Method A): t$_R$=7.55 min.

Allyl (6aS)-3-hydroxy-2,6-dimethoxy-12-oxo-8-(thiophen-2-yl)-6,6a,7,10-tetrahydrobenzo[e]pyrido[1,2-α][1,4]diazepine-5(12H)-carboxylate (66)

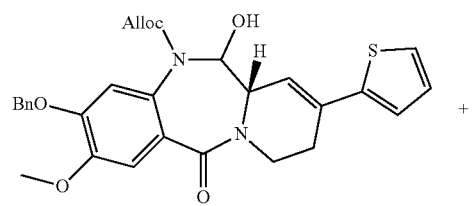

66

+

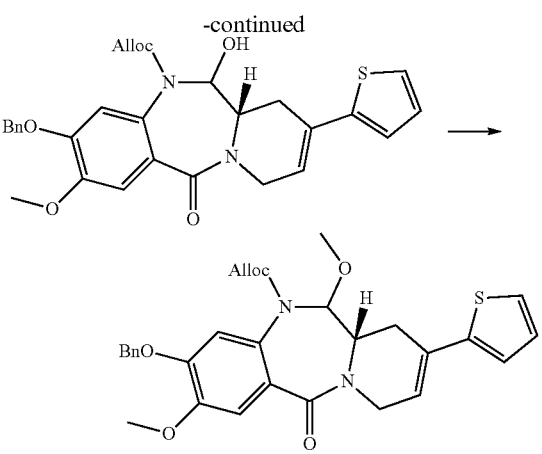

A solution of allyl (6aS)-3-(benzyloxy)-6-hydroxy-2-methoxy-12-oxo-8-(thiophen-2-yl)-6,6a,9,10-tetrahydrobenzo[e]pyrido[1,2-α][1,4]diazepine-5(12H)-carboxylate and allyl (6aS)-3-(benzyloxy)-6-hydroxy-2-methoxy-12-oxo-8-(thiophen-2-yl)-6,6a,7,10-tetrahydrobenzo[e]pyrido[1,2-α][1,4]diazepine-5(12H)-carboxylate (65) (529 mg, 0.99 mmol) in anhydrous dichloromethane (3.7 mL) was charged with boron trichloride (1 M in dichloromethane, 2.97 mL, 2.97 mmol) and stirred at room temperature under an inert atmosphere of nitrogen for 15 min. Methanol (5.3 mL) was then charged and the resulting mixture irradiated with microwaves at 55° C. for 1 h. After filtering through a cotton pad, washing with dichloromethane and concentrating in vacuo, purification was carried out by (multiple) flash column chromatography (silica), eluting with petroleum spirit, 40-60° C./ethyl acetate (1:0 to 0:1) to afford the (regiopure) title compound (16 mg, 3%) as a white solid. $^1$H NMR (400 MHz, CDCl$_3$) δ 7.25-7.21 (m, 1H), 7.08-7.04 (m, 1H), 7.04-7.00 (m, 1H), 6.77 (s, 1H), 6.35 (dt, J=5.6, 2.9 Hz, 1H), 6.18-5.71 (m, 1H), 5.45 (d, J=9.4 Hz, 1H), 5.16-5.04 (m, 2H), 4.63-4.55 (m, 1H), 4.49-4.41 (m, 1H), 4.25-4.19 (m, 2H), 3.97-3.92 (m, 3H), 3.89 (d, J=6.2 Hz, 1H), 3.69-3.62 (m, 1H), 3.48-3.43 (m, 3H), 3.03-2.97 (m, 1H), 2.76-2.65 (m, 1H); MS (ES+): m/z=457 (M+H)$^+$; LCMS (Method A): t$_R$=7.08 min.

Diallyl 3,3'-((pyridine-2,6-diylbis(methylene))bis(oxy))(6aS,6a'S)-bis(2,6-dimethoxy-12-oxo-8-(thiophen-2-yl)-6,6a,7,10-tetrahydrobenzo[e]pyrido-[1,2-α][1,4]diazepine-5(12H)-carboxylate)(67)

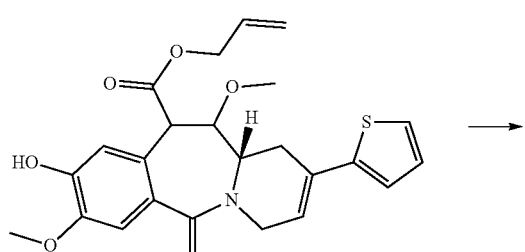

66

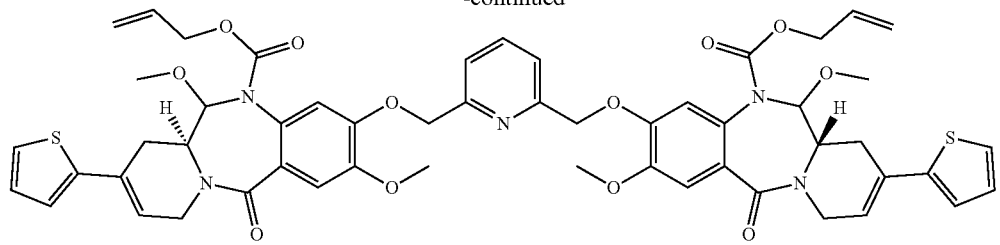

67

A solution of allyl (6aS)-3-hydroxy-2,6-dimethoxy-12-oxo-8-(thiophen-2-yl)-6,6a,7,10-tetrahydrobenzo[e]pyrido[1,2-α][1,4]diazepine-5(12H)-carboxylate (66) (15 mg, 0.032 mmol) in N,N-dimethylformamide (0.5 mL) was charged with potassium carbonate (4.42 mg, 0.032 mmol), 2,6-bis(bromomethyl)pyridine (4.23 mg, 0.016 mmol) and water (0.1 mL). The resulting mixture was irradiated with microwaves at 55° C. for 2 h, at which point TLC and LCMS showed completion of the reaction. Ethyl acetate (10 mL) was added and the mixture extracted with water (5 mL) and brine (5 mL). The organic phase was then dried over magnesium sulfate and concentrated in vacuo. Purification by flash column chromatography (silica), eluting with petroleum spirit, 40-60° C./ethyl acetate (1:0 to 0:1) gave the title compound (7 mg, 22%) as a white solid. $^1$H NMR (400 MHz, CDCl$_3$) δ 7.85-7.76 (m, 1H), 7.59-7.51 (m, 2H), 7.26-7.20 (m, 2H), 7.08-6.97 (m, 5H), 6.71 (br. s, 2H), 6.39-6.31 (m, 2H), 5.68 (br. s, 1H), 5.43 (d, J=9.0 Hz, 1H), 5.34-5.23 (m, 6H), 5.12-4.98 (m, 4H), 4.50 (br. s, 2H), 4.43 (br. s, 2H), 4.27-4.19 (m, 3H), 4.01-3.93 (m, 8H), 3.68-3.59 (m, 2H), 3.43 (s, 6H), 3.03-2.92 (m, 2H), 2.71 (d, J=10.2 Hz, 2H); MS (ES+): m/z=1016 (M+H)$^+$; LCMS (Method B): t$_R$=4.58 min.

(6aS,6a'S)-3,3'-((Pyridine-2,6-diylbis(methylene))bis(oxy))bis(2-methoxy-8-(thiophen-2-yl)-7,10-dihydrobenzo[e]pyrido[1,2-α][1,4]diazepin-12(6aH)-one) (68)

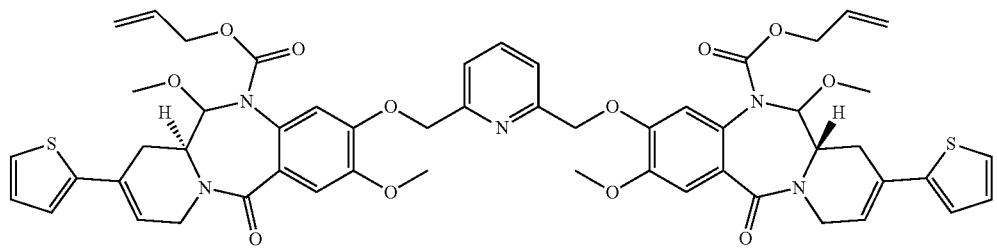

↓

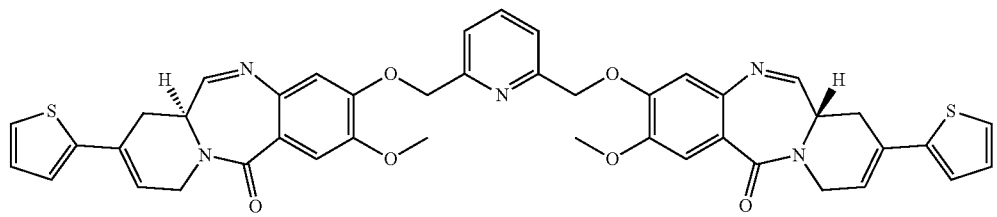

68

A solution of diallyl 3,3'-((pyridine-2,6-diylbis(methylene))bis(oxy))(6aS,6a'S)-bis(2,6-dimethoxy-12-oxo-8-(thiophen-2-yl)-6,6a,7,10-tetrahydrobenzo[e]pyrido[1,2-α][1,4]diazepine-5(12H)-carboxylate) (67) (7 mg, 0.0068 mmol) in dichloromethane (0.5 mL) was charged with tetrakis(triphenylphosphine)palladium(o) (0.39 mg) and pyrrolidine (1.5 ML). After 5 min, the reaction was observed to have completed via TLC. The reaction mixture was concentrated in vacuo to form an oil, which was charged with diethyl ether (2 mL) and re-concentrated in vacuo (this process was repeated twice more). Purification via flash column chromatography (silica), eluting with dichloromethane/acetone (1:0 to 0:1) gave the title compound (2.0 mg, 38%) as a pale yellow solid. $^1$H NMR (400 MHz, CDCl$_3$) δ 7.76-7.65 (m, 1H), 7.64-7.60 (m, 1H), 7.45 (d, J=7.4 Hz, 2H), 7.09 (d, J=3.5 Hz, 2H), 7.06-6.98 (m, 2H), 6.87-6.78 (m, 2H), 6.46 (dt, J=5.5, 2.7 Hz, 2H), 5.35-5.24 (m, 5H), 4.43 (dd, J=18.7, 5.9 Hz, 2H), 4.11 (d, J=18.4 Hz, 2H), 4.01-3.95 (m, 7H), 3.93 (dt, J=5.6, 2.9 Hz, 2H), 3.74-3.58 (m, 2H), 3.02-2.86 (m, 4H); MS (ES+): m/z=784 (M+H)$^+$; LCMS (Method A): t$_R$=7.17 min.

Methyl (S)-2-(4-(benzyloxy)-5-methoxy-2-nitrobenzoyl)-1,2,3,4-tetrahydro-isoquinoline-3-carboxylate (69)

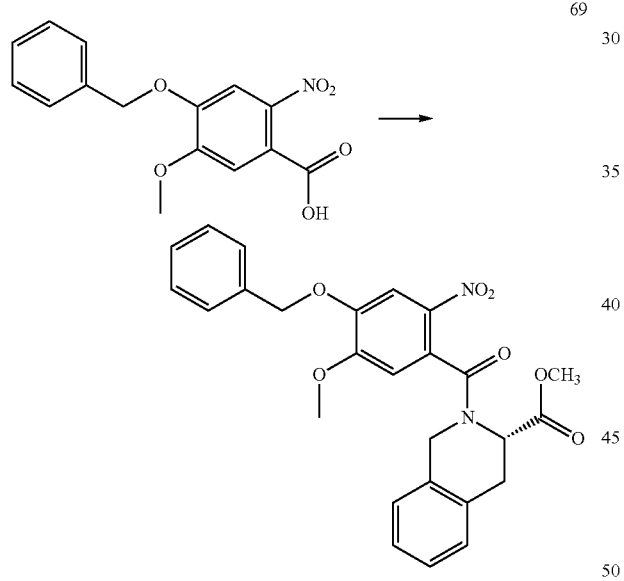

A mixture of 4-(benzyloxy)-5-methoxy-2-nitrobenzoic acid (3) (2.0 g, 6.6 mmol), oxalyl chloride (1.70 mL, 19.8 mmol) and anhydrous N,N-dimethylformamide (2 drops) in anhydrous dichloromethane (40 mL) was stirred at room temperature for 3 h. Anhydrous toluene (8 mL) was added to the reaction mixture which was then concentrated in vacuo. A solution of the resulting residue in anhydrous dichloromethane (10 mL) was added dropwise to a solution of methyl (S)-1,2,3,4-tetrahydroisoquinoline-3-carboxylate (1.65 g, 7.26 mmol) and triethylamine (2.0 mL, 14.5 mmol) in anhydrous dichloromethane (30 mL), at −10° C. The reaction mixture was stirred at room temperature for 2 h and then washed with hydrochloric acid (1 M, 20 mL) and brine (20 mL), dried over sodium sulfate, filtered and concentrated. The resulting residue was purified by column chromatography (silica), eluting with acetone/dichloromethane (from 0% to 30%), to give the title compound (2.5 g, 79%) as a yellow oil. $^1$H NMR (400 MHz, CDCl$_3$) δ 7.49-7.42 (m, 6H), 7.24-7.19 (m, 5H), 5.25 (s, 2H), 4.64-4.60 (m, 1H), 4.38-4.26 (m, 2H), 3.93 (s, 3H), 3.58 (s, 3H), 3.33-3.23 (m, 2H); $^{13}$C NMR (100 MHz, CDCl$_3$) δ 170.8, 170.3, 154.6, 148.4, 135.3, 133.5, 130.5, 130.1, 128.9, 128.8, 128.6, 128.4, 127.7, 127.4, 126.7, 109.3, 109.1, 71.4, 56.8, 52.6, 31.8, 31.0, 30.5; MS (ES+): m/z=477 (M+H)$^+$; LCMS (Method B): t$_R$=4.10 min.

(S)-(4-(Benzyloxy)-5-methoxy-2-nitrophenyl)(3-(hydroxymethyl)-3,4-dihydroisoquinolin-2(1H)-yl)methanone (70)

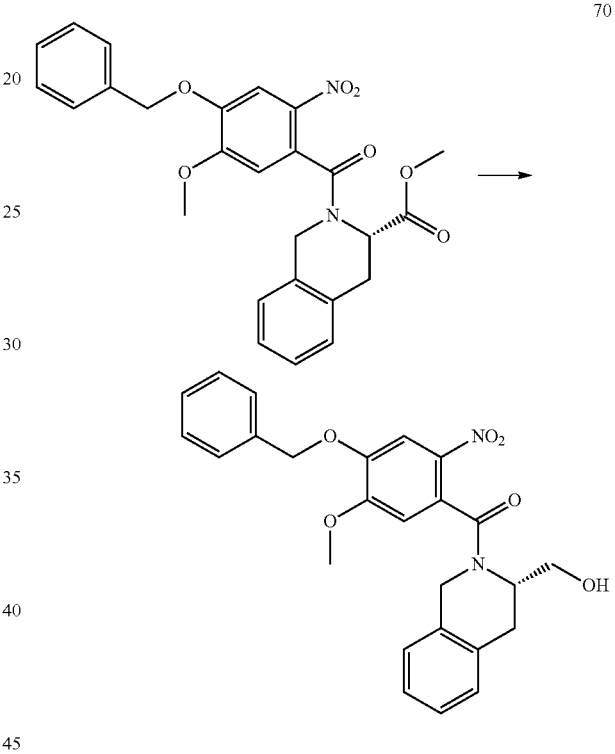

A solution of methyl (S)-2-(4-(benzyloxy)-5-methoxy-2-nitrobenzoyl)-1,2,3,4-tetrahydroisoquinoline-3-carboxylate (69) (2.4 g, 5.0 mmol) in anhydrous tetrahydrofuran (48 mL) was charged with a solution of lithium borohydride (2 M in tetrahydrofuran, 3.8 mL, 8.7 mmol) at 0° C. The reaction mixture was stirred at room temperature for 3 hours. Water (150 mL) was added dropwise at 0° C. and the reaction mixture was then extracted with ethyl acetate (2×100 mL). The combined organic extracts were then concentrated in vacuo. The resulting residue was purified by column chromatography (silica), eluting with acetone/dichloromethane (from 0% to 30%), to give the title compound (2.2 g, 97%) as creamy oil. $^1$H NMR (400 MHz, CDCl$_3$) δ 7.42-7.39 (m, 4H), 7.36-7.34 (m, 5H), 7.30 (s, 1H), 7.29 (s, 1H), 5.17 (s, 2H), 4.62 (s, 1H), 4.36-4.25 (m, 1H), 4.23-4.16 (m, 2H), 3.87 (s, 3H), 3.70-3.63 (m, 1H), 3.58-3.50 (m, 1H), 3.05-2.97 (m, 2H); $^{13}$C NMR (100 MHz, CDCl$_3$) δ 168.2, 150.2, 148.3, 133.7, 128.9, 128.9, 128.8, 128.6, 127.7, 127.6, 127.5, 127.0, 126.5, 114.4, 110.6, 108.9, 103.9, 91.6, 71.4, 65.4, 54.4, 33.3; MS (ES+): m/z=449 (M+H)$^+$; LCMS (Method B): t$_R$=3.78 min.

245

(S)-(2-Amino-4-(benzyloxy)-5-methoxyphenyl)(3-(hydroxymethyl)-3,4-dihydroisoquinolin-2(1H)-yl)methanone (71)

246

Allyl (S)-(5-(benzyloxy)-2-(3-(hydroxymethyl)-1,2,3,4-tetrahydro-isoquinoline-2-carbonyl)-4-methoxyphenyl)carbamate (72)

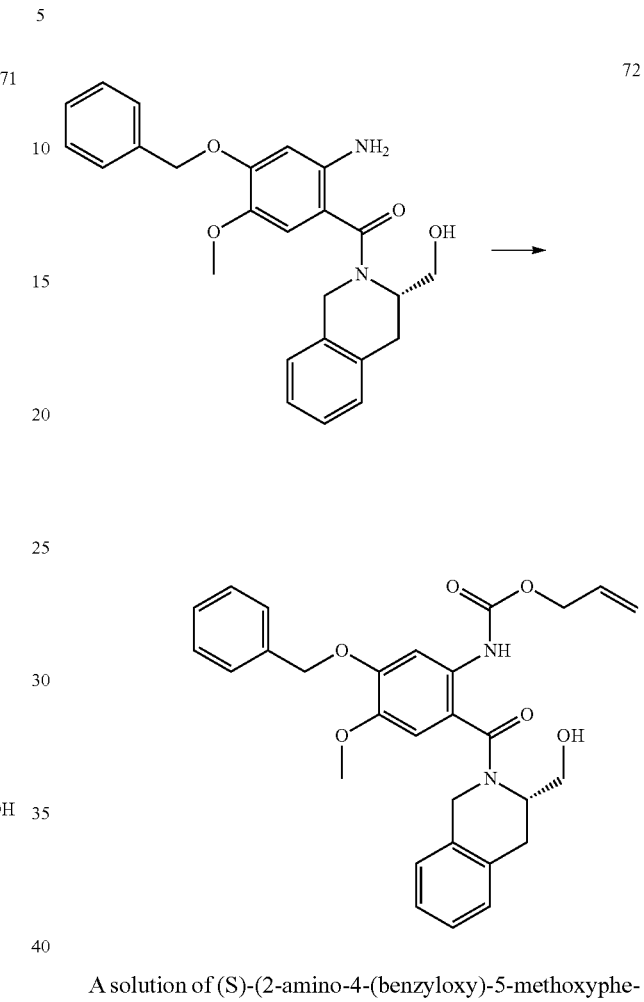

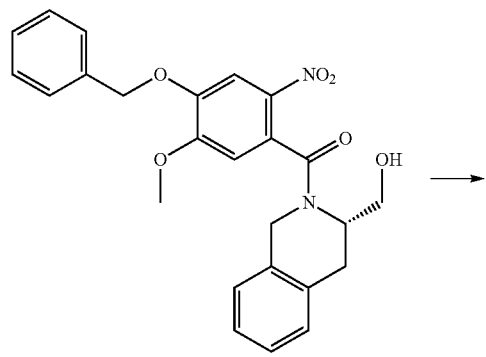

A solution of (S)-(4-(benzyloxy)-5-methoxy-2-nitrophenyl)(3-(hydroxymethyl)-3,4-dihydroisoquinolin-2(1H)-yl)methanone (70) (2.20 g, 4.90 mmol) in tetrahydrofuran (50 mL) and methanol (50 mL) was charged with iron (III) chloride hexahydrate (0.80 g, 2.90 mmol), activated charcoal (2.60 g, 221 mmol) and hydrazine (2.90 mL, 58.9 mmol). The reaction mixture was then stirred at reflux (85° C.) for 16 h. The mixture was subsequently allowed to cool to room temperature and filtered through a plug of celite. The filter cake was washed with ethyl acetate and methanol and then concentrated in vacuo to give the title compound (1.7 g, 83%) as brown solid. $^1$H NMR (400 MHz, MeOD) δ 7.48 (s, 1H), 7.46 (s, 1H), 7.41-733 (m, 4H), 7.20-7.18 (m, 3H), 6.84 (s, 1H), 6.56 (s, 1H), 5.11 (s, 2H), 4.61 (s, 1H), 4.54-4.40 (m, 1H), 3.77 (s, 3H), 3.62-3.54 (m, 2H), 3.19 (dd, J=16.2, 5.9 Hz, 2H), 2.92-2.80 (m, 2H); $^{13}$C NMR (100 MHz, MeOD) δ 169.1, 149.8, 141.0, 135.5, 130.7, 129.0, 128.7, 128.6, 128.5, 128.4, 128.2, 127.4, 127.0, 126.7, 110.1, 109.1, 71.0, 68.7, 64.8, 56.4, 50.3, 27.9; MS (ES+): m/z=419 (M+H)$^+$; LCMS (Method B): $t_R$=3.50 min.

A solution of (S)-(2-amino-4-(benzyloxy)-5-methoxyphenyl)(3-(hydroxymethyl)-3,4-dihydroisoquinolin-2(1H)-yl)methanone (71) (1.50 g, 3.6 mmol) and anhydrous pyridine (696 μL, 8.97 mmol) in anhydrous dichloromethane (50 mL) at −10° C. was slowly charged with a solution of allylchloroformate (343 μL, 3.23 mmol) in anhydrous dichloromethane (30 mL). The reaction mixture was stirred at room temperature for 30 min and then sequentially washed with a saturated aqueous solution of copper (II) sulfate (50 mL), water (50 mL) and a saturated aqueous solution of sodium hydrogen carbonate (50 mL). The organic layer was dried over sodium sulfate, filtered and concentrated in vacuo. The resulting residue was purified by column chromatography (silica), eluting with acetone/dichloromethane (from 0% to 20%), to give the title compound (1.47 g, 81%) as an off-white solid. $^1$H NMR (400 MHz, MeOD) δ 8.14 (s, 1H), 7.81 (s, 1H), 7.51 (s, 1H), 7.49 (s, 1H), 7.42-7.32 (m, 4H), 7.23-7.17 (m, 3H), 6.82 (s, 1H), 5.97-5.87 (m, 1H), 5.33 (dq, J=17.2, 1.5 Hz, 1H), 5.22 (dq, J=10.6, 1.3 Hz, 1H), 5.19 (s, 2H), 4.68-4.64 (m, 1H), 4.61 (dd, J=5.5, 1.3 Hz, 2H), 4.44 (br. s, 2H), 3.82 (s, 3H), 3.70-3.64 (m, 1H), 3.21-3.15 (m, 1H), 2.74 (br. s, 1H); $^{13}$C NMR (100 MHz, CDCl$_3$) δ 169.4, 152.9, 148.7, 144.1, 140.1, 135.3, 131.4, 130.5, 129.1, 128.1, 127.5, 127.0, 126.7, 125.9, 125.5, 117.9, 116.8, 109.6, 105.7, 69.7, 67.4, 66.0, 64.7, 55.3, 53.8, 26.8; MS (ES+): m/z=503 (M+H)$^+$; LCMS (Method B): $t_R$=3.95 min.

247

Allyl (6aS)-3-(benzyloxy)-6-hydroxy-2-methoxy-14-oxo-6,6a,7,12-tetrahydrobenzo[5,6][1,4]diazepino[1,2-b]isoquinoline-5(14H)-carboxylate (73)

248

Allyl (6aS)-3-hydroxy-2,6-dimethoxy-14-oxo-6,6a,7,12-tetrahydrobenzo-[5,6][1,4]diazepino[1,2-b]isoquinoline-5(14H)-carboxylate (74)

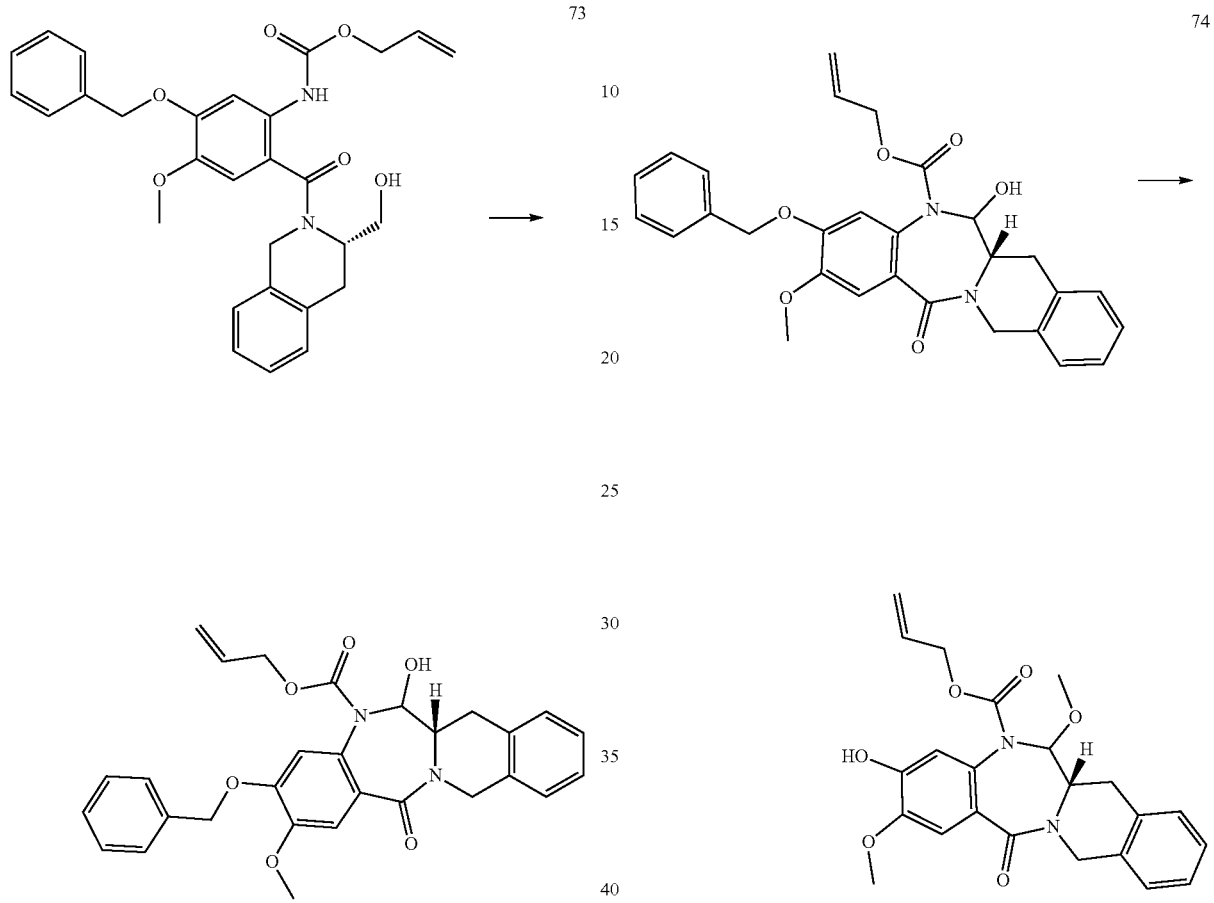

A solution of allyl (S)-(5-(benzyloxy)-2-(3-(hydroxymethyl)-1,2,3,4-tetrahydro-isoquinoline-2-carbonyl)-4-methoxyphenyl)carbamate (72) (1.4 g, 2.78 mmol) in dichloromethane (80 mL) was charged with 2,2,6,6-tetramethyl-1-piperidinyloxy (44 mg, 0.28 mmol) and (diacetoxyiodo)benzene (1.0 g, 3.33 mmol). The reaction mixture was stirred at room temperature for 16 h and was then sequentially washed with a saturated aqueous solution of sodium metabisulfite (40 mL), a saturated aqueous solution of sodium hydrogen carbonate (40 mL), water (30 mL) and brine (30 mL). The organic layer was then dried over sodium sulfate, filtered and concentrated. The resulting residue was purified by column chromatography (silica), eluting with acetone/dichloromethane (from 0% to 20%), to give the title compound (1.2 g, 86%) as an off-white solid. $^1$H NMR (400 MHz, CDCl$_3$) δ 7.44-7.31 (m, 6H), 7.28-7.26 (m, 5H), 6.72 (s, 1H), 5.70-5.61 (m, 1H), 5.31 (d, J=9.8 Hz, 1H), 5.20-5.17 (m, 1H), 5.11-5.07 (m, 3H), 4.83 (d, J=15.6 Hz, 1H), 4.58 (d, J=15.6 Hz, 1H), 4.48-4.34 (m, 2H), 3.94 (s, 3H), 3.74-3.69 (m, 1H), 3.17-3.05 (m, 2H); $^{13}$C NMR (100 MHz, CDCl$_3$) δ 169.0, 149.0, 136.2, 134.3, 133.7, 131.8, 126.7, 128.2, 127.9, 127.8, 127.3, 126.7, 118.1, 114.0, 111.2, 84.8, 71.0, 66.7, 56.2, 53.5, 50.8, 44.3, 30.2; MS (ES+): m/z=501(M+H)$^+$; LCMS (Method B): $t_R$=3.80 min.

A solution of allyl (6aS)-3-(benzyloxy)-6-hydroxy-2-methoxy-14-oxo-6,6a,7,12-tetrahydrobenzo[5,6][1,4]diazepino[1,2-b]isoquinoline-5(14H)-carboxylate (73) (100 mg, 0.199 mmol) in dichloromethane (1 mL) was charged with boron trichloride (1 M solution in dichloromethane, 600 μL, 0.600 mmol) and the resulting suspension was stirred at room temperature for 10 min, then methanol (2 mL) was added to the reaction mixture which was irradiated with microwaves 60 min at 55° C. The reaction mixture was subsequently filtered through a cotton pad that was washed with dichloromethane and concentrated in vacuo. Purification by flash column chromatography (silica), eluting with petroleum spirit 40-60° C./ethyl acetate (1:0 to 0:1) gave the title compound (40 mg, 48%) as a cream powder.

MS (ES+): m/z=424 (M+H)$^+$; LCMS (Method B): $t_R$=3.53 min.

Allyl (6aS)-3-((6-(((((6aS)-5-((allyloxy)carbonyl)-2,6-dimethoxy-8-(4-(N-methylsulfamoyl)phenyl)-12-oxo-5,6,6a,7,10,12-hexahydrobenzo[e]pyrido-[1,2-α][1,4]diazepin-3-yl)oxy)methyl)pyridin-2-yl)methoxy)-2,6-dimethoxy-14-oxo-6,6a,7,12-tetrahydrobenzo[5,6][1,4]diazepino[1,2-b]isoquinoline-5(14H)-carboxylate (75)

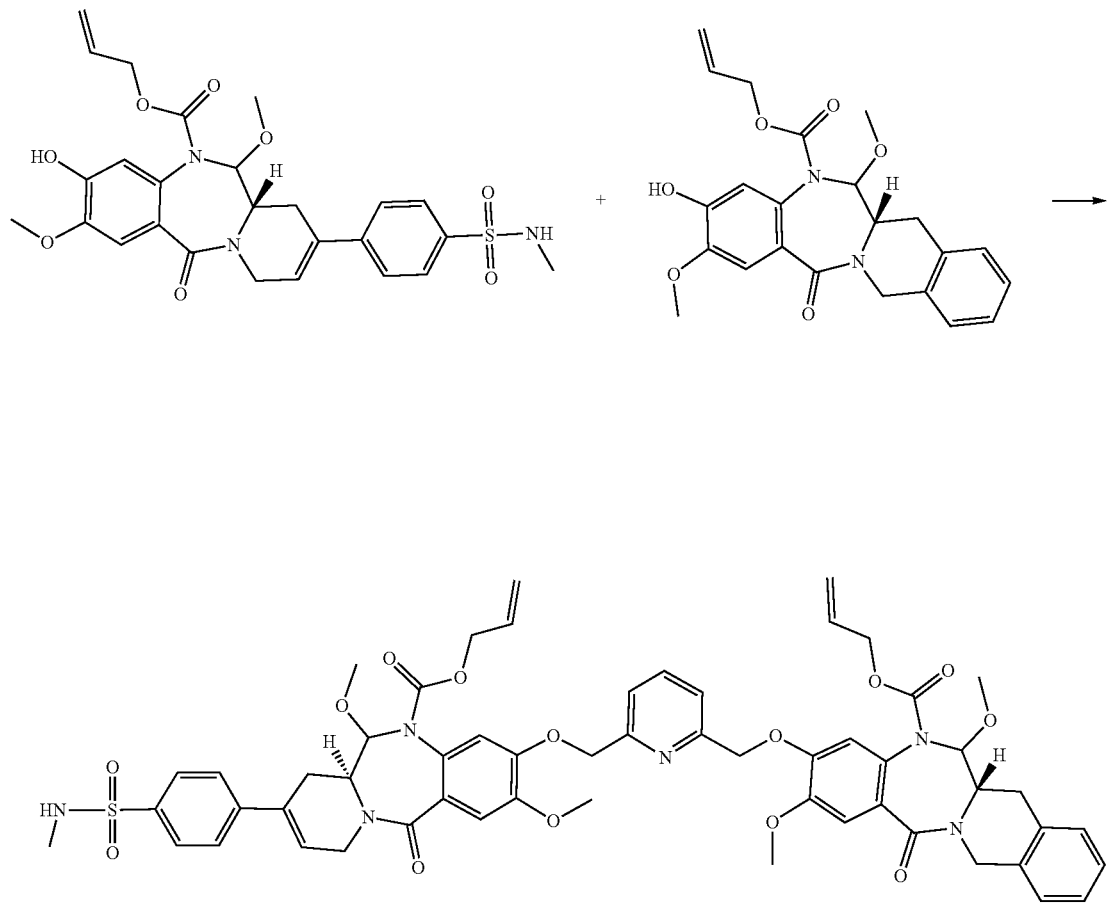

A solution of allyl (6aS)-3-hydroxy-2,6-dimethoxy-8-(4-(N-methylsulfamoyl)phenyl)-12-oxo-6,6a,7,10-tetrahydrobenzo[e]pyrido[1,2-α][1,4]diazepine-5(12H)-carboxylate (32) (43 mg, 0.080 mmol) and allyl (6aS)-3-hydroxy-2,6-dimethoxy-14-oxo-6,6a,7,12-tetrahydrobenzo[5,6][1,4]diazepino[1,2-b]isoquinoline-5(14H)-carboxylate (74) (34 mg, 0.080 mmol) in N,N-dimethylformamide (1 mL) was charged with potassium carbonate (22 mg, 0.016 mmol), water (0.1 mL) and 2,6-bis(bromomethyl)pyridine (19 mg, 0.072 mmol) and irradiated with microwaves for 1 h at 55° C., then diluted with ethyl acetate (10 mL), washed with brine (2×10 mL), dried over anhydrous magnesium sulfate and concentrated in vacuo. Purification by flash column chromatography (silica), eluting with dichloromethane/ethyl acetate (from 1:0 to 0:1) gave the title compound (18 mg, 21%) as a white solid. $^1$H NMR (400 MHz, CDCl$_3$) δ 7.87 (d, J=8.2 Hz, 2H), 7.83-7.76 (m, 1H), 7.58-7.52 (m, 4H), 7.32-7.28 (m, 5H), 7.26-7.22 (m, 1H), 6.78-6.65 (m, 2H), 6.47 (d, J=2.7 Hz, 1H), 5.79-5.59 (m, 1H), 5.41 (d, J=9.8 Hz, 1H), 5.26 (d, J=5.1 Hz, 4H), 5.19-5.00 (m, 4H), 4.81-4.68 (m, 1H), 4.65-4.38 (m, 5H), 4.38-4.20 (m, 3H), 4.01-3.93 (m, 6H), 3.75-3.65 (m, 1H), 3.60 (d, J=3.5 Hz, 1H), 3.44-337 (m, 6H), 3.12-2.92 (m, 3H), 2.76 (d, J=10.2 Hz, 1H), 2.73-2.65 (m, 3H); $^{13}$C NMR (100 MHz, CDCl$_3$) δ 157.8, 155.9, 153.3, 143.9, 137.9, 127.9, 127.7, 127.5, 127.3, 126.7, 126.5, 125.7, 120.5, 117.4, 114.6, 111.7, 110.9, 108.6, 92.0, 71.4, 70.3, 66.5, 60.4, 56.2, 56.2, 44.1, 41.6, 30.6, 30.4, 29.7, 29.3; MS (ES+): m/z=1071(M+H)$^+$; LCMS (Method A): $t_R$=7.78 min.

4-((S)-2-Methoxy-3-((6-(((((S)-2-methoxy-14-oxo-6a,7,12,14-tetrahydrobenzo[5,6][1,4]diazepino[1,2-b]isoquinolin-3-yl)oxy)methyl)pyridin-2-yl)methoxy)-12-oxo-6a,7,10,12-tetrahydrobenzo[e]pyrido[1,2-α][1,4]-diazepin-8-yl)-N-methylbenzenesulfonamide (76)

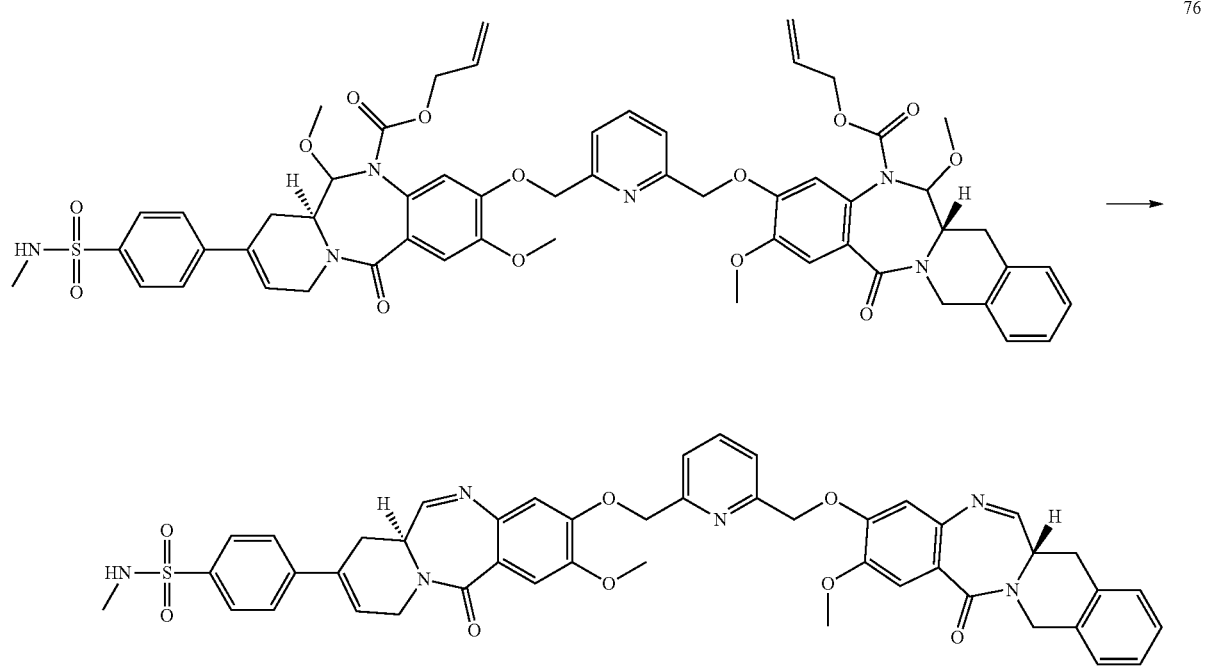

A solution of allyl (6aS)-3-((6-(((((6aS)-5-((allyloxy)carbonyl)-2,6-dimethoxy-8-(4-(N-methylsulfamoyl)phenyl)-12-oxo-5,6,6a,7,10,12-hexahydrobenzo[e]pyrido[1,2-α][1,4]-diazepin-3-yl)oxy)methyl)pyridin-2-yl)methoxy)-2,6-dimethoxy-14-oxo-6,6a,7,12-tetrahydrobenzo[5,6][1,4]diazepino[1,2-b]isoquinoline-5(14H)-carboxylate (75) (18 mg, 0.016 mmol) in dichloromethane (0.5 mL) was charged with tetrakis(triphenyl-phosphine)palladium(o) (0.92 mg) and pyrrolidine (3.2 ML). After 5 min, the reaction was observed to have completed via TLC. The reaction mixture was concentrated in vacuo to form an oil, which was charged with diethyl ether (1 mL) and re-concentrated in vacuo (this process was repeated twice more). Purification via flash column chromatography (silica), eluting with dichloromethane/acetone (from 1:0 to 0:1) gave the title compound (13 mg, 96%) as a pale yellow solid. $^1$H NMR (400 MHz, CDCl$_3$) δ 7.92-7.88 (m, 2H), 7.77-7.71 (m, 1H), 7.61 (d, J=2.7 Hz, 1H), 7.60-7.55 (m, 3H), 7.50-7.44 (m, 3H), 7.38-7.29 (m, 3H), 6.86 (d, J=9.4 Hz, 2H), 6.64-6.55 (m, 1H), 5.34-5.28 (m, 4H), 4.99 (d, J=15.2 Hz, 1H), 4.62-4.44 (m, 3H), 4.20 (dd, J=18.9, 2.5 Hz, 1H), 4.03-3.98 (m, 7H), 3.96-3.91 (m, 2H), 3.77-3.66 (m, 1H), 3.27 (dd, J=15.2, 5.5 Hz, 1H), 3.15 (dd, J=15.6, 4.3 Hz, 1H), 3.07-2.92 (m, 2H), 2.73-2.67 (m, 3H); $^{13}$C NMR (100 MHz, CDCl$_3$) δ 166.8, 166.4, 161.8, 156.1, 150.5, 150.3, 148.1, 148.0, 143.7, 140.3, 140.2, 138.2, 137.8, 133.1, 128.0, 127.8, 127.8, 127.5, 126.7, 125.8, 125.7, 120.3, 112.3, 111.9, 110.9, 105.8, 96.5, 71.2, 62.0, 56.2, 49.4, 48.8, 44.0, 41.7, 35.0, 33.7, 31.9, 30.8, 29.3; MS (ES+): m/z=839 (M+H)$^+$; LCMS (Method A): t$_R$=6.43 min.

4-Hydroxy-5-methoxy-2-nitrobenzaldehyde (77)

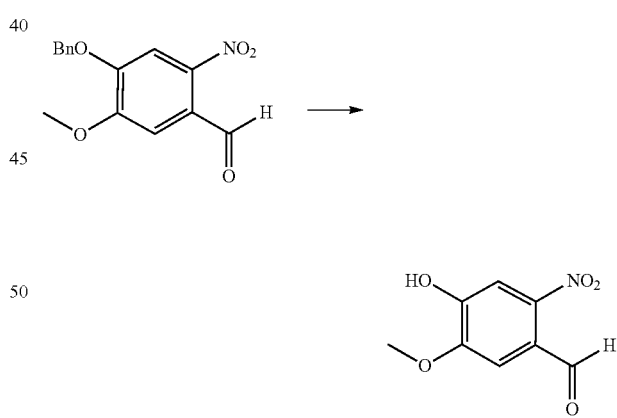

A solution of 4-(benzyloxy)-5-methoxy-2-nitrobenzaldehyde (2) (100 g, 348 mmol) in glacial acetic acid (800 mL) was charged with an aqueous solution of hydrobromic acid (48% v/v, 88.0 mL, 522 mmol) and heated to 85° C., with stirring for 1 h, after which the reaction was judged to be complete by TLC. After allowing the resulting mixture to cool to room temperature, it was then diluted in water (1.60 L), and the resulting precipitate filtered, and washed with cold water (100 mL×3) to give the title compound (50.0 g, 73%) as a yellow solid. TLC: R$_f$=0.2 (eluent: petroleum spirit, 40-60° C./ethyl acetate=3:1, v/v)

5-Methoxy-2-nitro-4-((triisopropylsilyl)oxy)benzaldehyde (78)

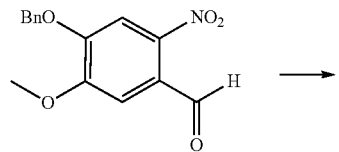

A mixture of 4-hydroxy-5-methoxy-2-nitrobenzaldehyde (77) (50.0 g, 254 mmol), triisopropylsilyl chloride (59.7 mL, 279 mmol) and imidazole (51.8 g, 761 mmol) was heated and stirred at 100° C. for 30 min. The reaction mixture was poured onto ice-water and extracted with ethyl acetate (500 mL×3). The organic extract was dried over sodium sulfate, filtered and concentrated under reduced pressure. The resulting residue was purified by flash column chromatography (silica), eluting with petroleum spirit, 40-60° C./ethyl acetate (20:1) to give the title compound (57.5 g, 64%) as a yellow solid. TLC: R$_f$=0.6 (eluent: petroleum spirit, 40-60° C./ethyl acetate=20:1, v/v)

5-Methoxy-2-nitro-4-((triisopropylsilyl)oxy)benzoic acid (79)

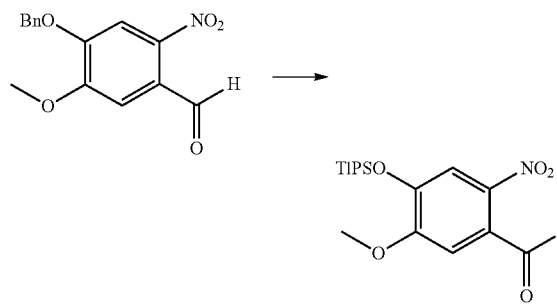

A solution of sodium chlorite (80%, 46.0 g, 407 mmol) and sodium phosphate monobasic dihydrate (35.5 g, 228 mmol) in water (200 mL) was added to a solution of 5-methoxy-2-nitro-4-((triisopropylsilyl)oxy)benzaldehyde (78) (57.5 g, 163 mmol) in tetrahydrofuran (800 mL) at room temperature. Hydrogen peroxide (30% w/w, 235 mL, 2.28 mol) was immediately added to the vigorously stirred biphasic mixture. The starting material dissolved, and the temperature of the reaction mixture rose to 45° C. After 30 min, the reaction was judged to have completed by TLC. The mixture was subsequently acidified to pH=3-4 with citric acid and extracted with ethyl acetate (500 mL×3). The combined organic extracts were washed with water (150 mL) and brine (150 mL), dried over anhydrous sodium sulfate, filtered and concentrated in vacuo. The residue was then purified by flash column chromatography (silica), eluting with petroleum spirit, 40-60° C./ethyl acetate (10:1) then dichloromethane/methanol (10:1) to afford the title compound (38.0 g, 63%) as a yellow oil. $^1$H NMR (400 MHz, CDCl$_3$) δ 9.81 (s, 1H), 7.35 (s, 1H), 7.25 (s, 1H), 3.91 (s, 3H), 1.26 (q, J=7.4 Hz, 3H), 1.09 (d, J=7.4 Hz, 18H); MS (ES−): m/z=368 (M−1)⁻.

(S)-(2-(Hydroxymethyl)indolin-1-yl)(5-methoxy-2-nitro-4-((triisopropyl-silyl)oxy)phenyl)methanone (80)

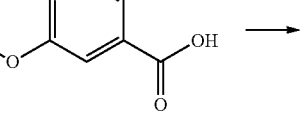

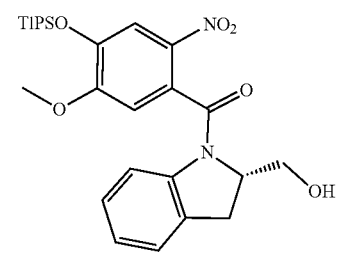

A solution of 5-methoxy-2-nitro-4-((triisopropylsilyl) oxy)benzoic acid (79) (1.00 g, 2.71 mmol) in dichloromethane (25 mL) was charged with (S)-(+)-2-indolinemethanol (404 mg, 2.71 mmol), HATU (0.54 g, 4.06 mmol) and N,N-diisopropylethylamine (875 mg, 6.77 mmol). The reaction mixture was stirred at room temperature for 3 h and then diluted with water (100 mL) and extracted with dichloromethane (100 mL×2). The combined organic extracts were then dried over anhydrous sodium sulfate, filtered and concentrated in vacuo. The residue was purified by flash column chromatography (silica), eluting with petroleum spirit, 40-60° C./ethyl acetate (9:1 to 0:1) to afford the title compound (800 mg, 58%) as a yellow oil. $^1$H NMR (400 MHz, CDCl$_3$) δ 7.22-7.14 (m, 1H), 7.08-7.00 (m, 1H), 6.95-6.90 (m, 1H), 6.80-6.70 (m, 1H), 5.69-5.65 (m, 1H), 5.23-5.06 (m, 1H), 4.00-3.82 (m, 3H), 2.80 (s, 5H), 2.04 (s, 1H), 1.34-1.25 (m, 3H), 1.15-1.10 (m, 18H); MS (ES+): m/z=501(M+H)⁺.

(S)-(2-Amino-5-methoxy-4-((triisopropylsilyl)oxy)phenyl)(2-(hydroxyl-methyl)indolin-1-yl)methanone (81)

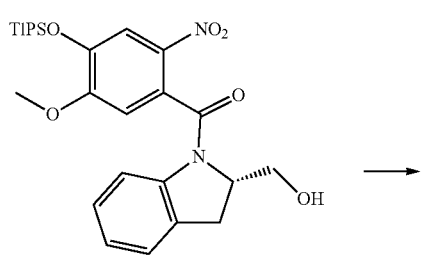

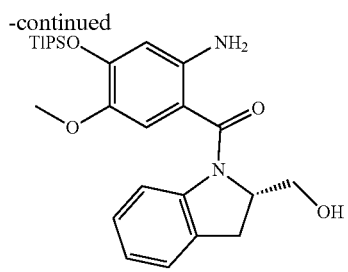

A solution of (S)-(2-(hydroxymethyl)indolin-1-yl)(5-methoxy-2-nitro-4-((triisopropyl-silyl)oxy)phenyl)methanone (80) (800 mg, 1.60 mmol) in methanol (1 mL) was charged with palladium (10 wt. % loading on carbon, 80 mg). The mixture was stirred at room temperature under an atmosphere of hydrogen for 16 h then filtered through a pad of Celite. The resulting cake was then washed with ethyl acetate (50 mL) and concentrated under reduced pressure. The residue was then purified by flash column chromatography (silica), eluting with petroleum spirit, 40-60° C./ethyl acetate (4:1 to 1:1) to afford the title compound (500 mg, 66%) as a yellow oil. $^1$H NMR (400 MHz, DMSO-d6) δ 7.22 (d, J=6.8 Hz, 1H), 7.08 (s, 1H), 7.00-6.93 (m, 2H), 6.75 (s, 1H), 6.37 (d, J=2.8 Hz, 1H), 4.98-4.88 (m, 3H), 4.61-4.57 (m, 1H), 3.58 (s, 3H), 3.47-3.44 (m, 1H), 3.32-3.26 (m, 1H), 3.01-2.97 (m, 1H), 2.69 (s, 1H), 1.27-1.21 (m, 3H), 1.08 (d, J=7.2 Hz, 18H); MS (ES+): m/z=471(M+H)$^+$.

Allyl(S)-(2-(2-(hydroxymethyl)indoline-1-carbonyl)-4-methoxy-5-((triisopropylsilyl)oxy)phenyl)carbamate (82)

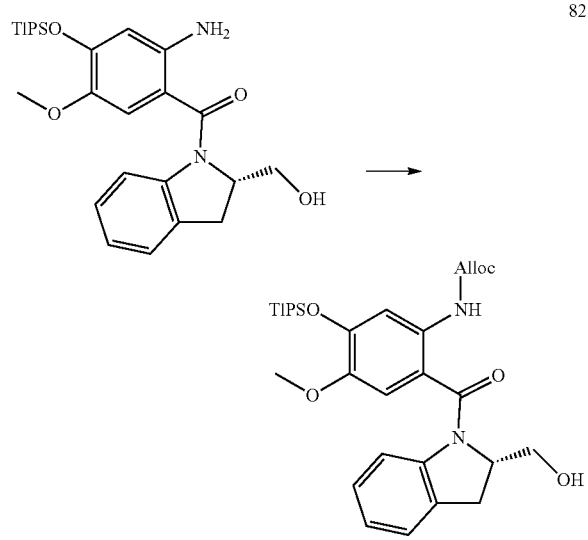

A solution of (S)-(2-amino-5-methoxy-4-((triisopropylsilyl)oxy)phenyl)(2-(hydroxylmethyl)indolin-1-yl)methanone (81) (470 mg, 1.00 mmol) in dichloromethane (1 mL) at −10° C. was charged with anhydrous pyridine (158 mg, 2.00 mmol) and allyl chloroformate (127 mg, 1.05 mmol). After 30 min, the reaction was judged to have completed by TLC and was then diluted with dichloromethane (100 mL), then washed with a saturated aqueous solution of copper sulfate (10 mL), water (100 mL) and a saturated aqueous solution of sodium hydrogen carbonate (1 mL). The organic layer was then dried over anhydrous sodium sulfate, filtered and concentrated in vacuo. The residue was purified by flash column chromatography (silica), eluting with petroleum spirit, 40-60° C./ethyl acetate (5%) to afford the title compound (400 mg, 72%) as a yellow oil. $^1$H NMR (400 MHz, CDCl$_3$) δ 8.36 (s, 1H), 7.74 (s, 1H), 7.19 (d, J=7.2 Hz, 1H), 6.97-6.87 (m, 2H), 6.72 (s, 1H), 6.40 (s, 1H), 5.98-5.87 (m, 1H), 5.31 (d, J=16.8 Hz, 1H), 5.22 (d, J=10.4 Hz, 1H), 4.94-4.91 (m, 1H), 4.60 (d, J=5.6 Hz, 2H), 3.76 (d, J=6.0 Hz, 2H), 3.54 (s, 3H), 3.45-338 (m, 1H), 2.81-2.76 (m, 1H), 1.35-1.28 (m, 3H), 1.12 (d, J=7.6 Hz, 18H); MS (ES+): m/z=555 (M+H)$^+$.

Allyl (12aS)-12-hydroxy-8-methoxy-6-oxo-9-((triisopropylsilyl)oxy)-12a,13-dihydro-6H-benzo[5,6][1,4]diazepino[1,2-α]indole-11(12H)-carboxylate (83)

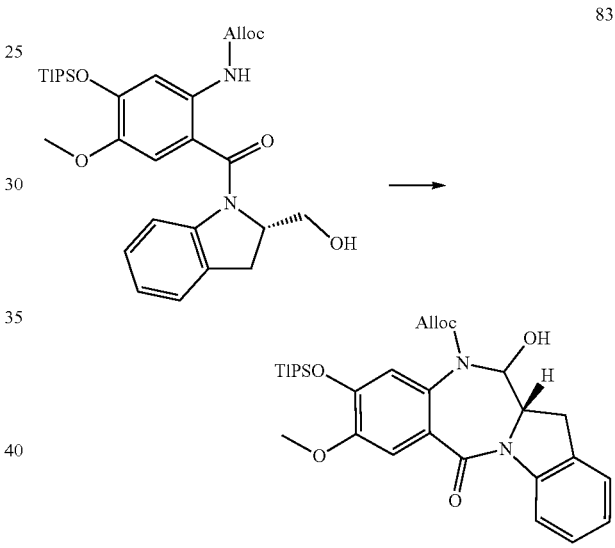

A solution of allyl (S)-(2-(2-(hydroxymethyl)indoline-1-carbonyl)-4-methoxy-5-((triisopropylsilyl)oxy)phenyl)carbamate (82) (391 mg, 0.71 mmol) in dichloromethane (13 mL) was charged with TEMPO (11 mg, 0.07 mmol) and (diacetoxyiodo)benzene (274 mg, 0.85 mmol). The reaction mixture was stirred at room temperature for 18 h and then diluted in dichloromethane (40 mL), washed with a saturated aqueous solution of sodium metabisulfite (1 mL), then a saturated aqueous solution of sodium hydrogen carbonate (10 mL) and lastly, brine (1 mL). The organic layer was then dried over anhydrous sodium sulfate, filtered and concentrated in vacuo. The residue was purified by flash column chromatography (silica), eluting with petroleum spirit, 40-60° C./ethyl acetate (10%) to afford the title compound (290 mg, 74%) as a yellow oil. $^1$H NMR (500 MHz, CDCl$_3$) 8.19 (d, J=8.0 Hz, 1H), 7.21 (d, J=7.5 Hz, 1H), 7.08 (t, J=7.5 Hz, 1H), 6.71 (s, 1H), 5.78 (s, 1H), 5.73 (d, J=10.0 Hz, 1H), 5.20-5.14 (m, 2H), 4.62-4.58 (m, 1H), 4.46 (s, 1H), 4.15-4.06 (m, 2H), 3.86-3.84 (m, 3H), 3.49-3.43 (m, 1H), 3.21 (d, J=17.0 Hz, 1H), 2.04 (d, J=2.0 Hz, 1H), 1.28-1.21 (m, 3H), 1.09-1.08 (m, 18H); MS (ES+): m/z=553 (M+H)$^+$.

257

Allyl (12aS)-8-methoxy-6-oxo-12-((tetrahydro-2H-pyran-2-yl)oxy)-9-((triisopropylsilyl)oxy)-12a,13-dihydro-6H-benzo[5,6][1,4]diazepino[1,2-α]indole-11(12H)-carboxylate (84)

258

Allyl (12aS)-9-hydroxy-8-methoxy-6-oxo-12-((tetrahydro-2H-pyran-2-yl)oxy)-12a,13-dihydro-6H-benzo[5,6][1,4]diazepino[1,2-α]indole-11(12H)-carboxylate (85)

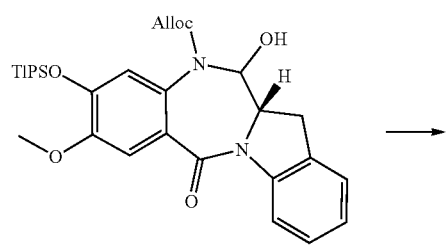

84

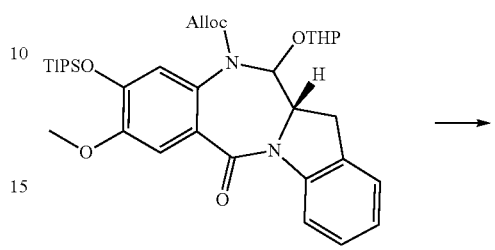

85

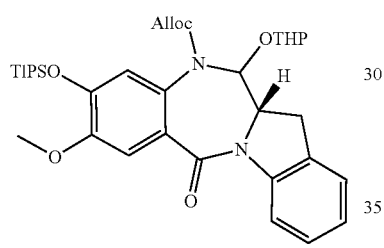

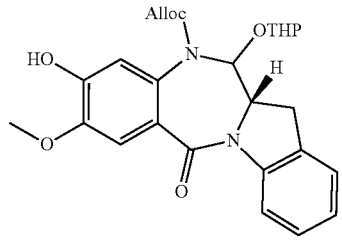

A solution of allyl (12aS)-12-hydroxy-8-methoxy-6-oxo-9-((triisopropylsilyl)oxy)-12a,13-dihydro-6H-benzo[5,6][1,4]diazepino[1,2-α]indole-11(12H)-carboxylate (83) (280 mg, 0.510 mmol) in tetrahydrofuran (5 mL) was charged with 3,4-dihydro-2H-pyran (429 mg, 5.10 mmol) and para-toluenesulfonic acid monohydrate (3 mg, 1% w/w). The reaction mixture was stirred at room temperature for 18 h and then diluted with ethyl acetate (30 mL), washed with a saturated aqueous solution of sodium hydrogen carbonate (10 mL) and brine (1 mL), then dried over anhydrous sodium sulfate, filtered and concentrated in vacuo. The residue was purified by flash column chromatography (silica), eluting with petroleum spirit, 40-60° C./ethyl acetate (20%) to afford the title compound (300 mg, 92%) as a colourless oil. $^1$H NMR (500 MHz, CDCl$_3$) δ 8.20-8.13 (m, 1H), 7.25-7.21 (m, 2H), 7.08-6.61 (m, 2H), 5.94 (m, 1H), 5.78-5.66 (m, 1H), 5.13-5.04 (m, 2H), 4.96-4.94 (m, 2H), 4.89 (d, J=6.0 Hz, 1H), 3.86 (d, J=2.0 Hz, 3H), 3.65-3.61 (m, 1H), 3.47-3.42 (m, 1H), 2.07-2.01 (m, 1H), 1.98-1.95 (m, 1H), 1.79-1.73 (m, 6H), 1.33-1.26 (m, 3H), 1.11-1.08 (m, 18H); MS (ES+): m/z=637 (M+H)$^+$.

A solution of allyl (12aS)-8-methoxy-6-oxo-12-((tetrahydro-2H-pyran-2-yl)oxy)-9-((triisopropylsilyl)oxy)-12a,13-dihydro-6H-benzo[5,6][1,4]diazepino[1,2-α]indole-11(12H)-carboxylate (84) (290 mg, 0.46 mmol) in tetrahydrofuran (5 mL) under an inert atmosphere of nitrogen was charged with tetrabutylammonium fluoride (1 M in tetrahydrofuran, 0.65 mL, 0.65 mmol). The mixture was stirred at room temperature for 1 h and then charged with water (1 mL), extracted with ethyl acetate (30 mL×2) and the combined organic phases washed with brine (10 mL), dried over anhydrous sodium sulfate, filtered and concentrated in vacuo. The residue was purified by flash column chromatography (silica), eluting with petroleum spirit, 40-60° C./ethyl acetate (20%) to afford the title compound (100 mg, 45%) as a white solid. $^1$H NMR (500 MHz, DMSO-d6) δ 8.16 (dd, J=21.0, 8.0 Hz, 1H), 7.28 (d, J=5.0 Hz, 1H), 7.25-7.20 (m, 1H), 7.10-7.05 (m, 1H), 6.77 (m, 1H), 6.02 (s, 1H), 5.81-5.72 (m, 1H), 5.20-5.14 (m, 1H), 5.13-4.84 (m, 1H), 4.66-4.48 (m, 2H), 4.15-4.07 (m, 1H), 3.95 (s, 3H), 3.60-3.42 (m, 2H), 3.30-3.18 (m, 1H), 1.88-1.54 (m, 7H), 1.29-1.24 (m, 1H); MS (ES+): m/z=481(M+H)$^+$.

Allyl (12aS)-9-((6-(((((6aS)-5-((allyloxy)carbonyl)-2,6-dimethoxy-8-(4-(N-methylsulfamoyl)phenyl)-12-oxo-5,6,6a,7,10,12-hexahydrobenzo[e]pyrido-[1,2-α][1,4]diazepin-3-yl)oxy)methyl)pyridin-2-yl)methoxy)-8-methoxy-6-oxo-12-((tetrahydro-2H-pyran-2-yl)oxy)-12a,13-dihydro-6H-benzo[5,6]-[1,4]diazepino[1,2-α]indole-11(12H)-carboxylate (86)

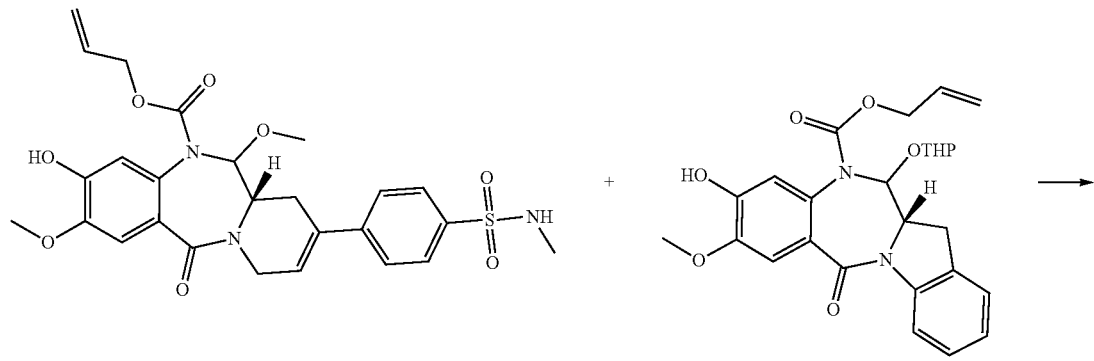

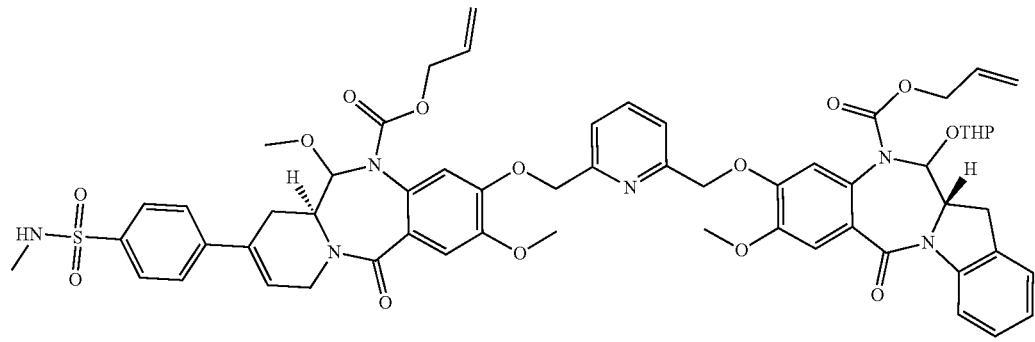

A solution of allyl (6aS)-3-hydroxy-2,6-dimethoxy-8-(4-(N-methylsulfamoyl)phenyl)-12-oxo-6,6a,7,10-tetrahydrobenzo[e]pyrido[1,2-α][1,4]diazepine-5(12H)-carboxylate (32) (76 mg, 0.141 mmol) and allyl (12aS)-9-hydroxy-8-methoxy-6-oxo-12-((tetrahydro-2H-pyran-2-yl)oxy)-12a,13-dihydro-6H-benzo[5,6][1,4]diazepino[1,2-a]indole-11(12H)-carboxylate (85) (68 mg, 0.141 mmol) in N,N-dimethylformamide (1 mL) was charged with potassium carbonate (39 mg, 0.282 mmol), water (0.1 mL) and 2,6-bis(bromomethyl)pyridine (33 mg, 0.126 mmol) and irradiated with microwaves for 1 h at 55° C. The resulting mixture was then diluted in ethyl acetate (10 mL), washed with brine (10 mL×2), dried over magnesium sulphate, filtered and concentrated in vacuo. Purification by flash column chromatography (silica), eluting with petroleum spirit, 40-60° C./ethyl acetate (from 1:0 to 0:1), followed by acetone (100%) gave the title compound (25 mg, impure) as a white solid. MS (ES+): m/z=1127 (M+H)$^+$; LCMS (Method A): $t_R$=8.33 min.

4-((S)-2-Methoxy-3-((6-((((S)-8-methoxy-6-oxo-12a,13-dihydro-6H-benzo[5,6][1,4]diazepino[1,2-α]indol-9-yl)oxy)methyl)pyridin-2-yl)methoxy)-12-oxo-6a,7,10,12-tetrahydrobenzo[e]pyrido[1,2-a][1,4]diazepin-8-yl)-N-methylbenzenesulfonamide (87)

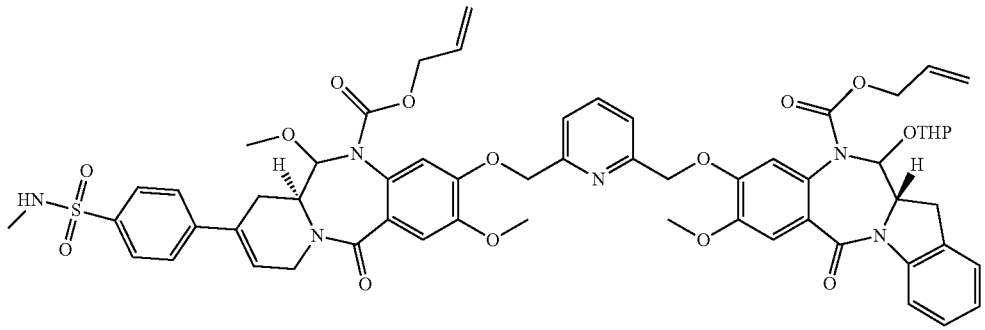

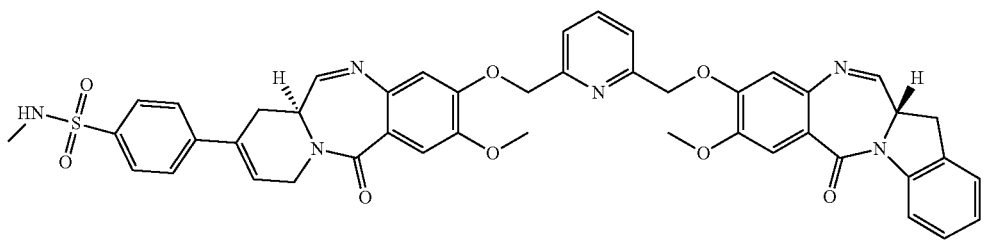

87

A solution of allyl (12aS)-9-((6-(((((6aS)-5-((allyloxy)carbonyl)-2,6-dimethoxy-8-(4-(N-methylsulfamoyl)phenyl)-12-oxo-5,6,6a,7,10,12-hexahydrobenzo[e]pyrido[1,2-α][1,4]diazepin-3-yl)oxy)methyl)pyridin-2-yl)methoxy)-8-methoxy-6-oxo-12-((tetrahydro-2H-pyran-2-yl)oxy)-12a,13-dihydro-6H-benzo[5,6][1,4]diazepino[1,2-α]indole-11(12H)-carboxylate (86) (25 mg, 0.022 mmol) in dichloromethane (0.5 mL) was charged with tetrakis(triphenylphosphine)palladium(o) (1.3 mg) and pyrrolidine (4.4 µL). After 5 min, the reaction was observed to have completed via TLC. The reaction mixture was concentrated in vacuo to form an oil, which was charged with diethyl ether (1 mL) and re-concentrated in vacuo (this process was repeated twice more). Purification via flash column chromatography (silica), eluting with dichloromethane/acetone (from 1:0 to 0:1) gave the title compound (9.5 mg, 53%) as a pale yellow solid. ¹H NMR (400 MHz, CDCl₃) δ 8.27 (d, J=7.8 Hz, 1H), 7.94-7.69 (m, 4H), 7.66-7.45 (m, 6H), 7.12 (d, J=7.4 Hz, 1H), 7.01 (s, 1H), 6.92-6.85 (m, 1H), 6.59 (d, J=3.1 Hz, 1H), 5.37-5.28 (m, 4H), 4.55 (d, J=5.1 Hz, 1H), 4.47 (dd, J=6.6, 4.7 Hz, 1H), 4.18 (br. s, 1H), 4.04-3.97 (m, 6H), 3.95-3.85 (m, 3H), 3.78-3.64 (m, 1H), 3.49 (s, 1H), 3.05-2.94 (m, 2H), 2.74-2.58 (m, 4H); MS (ES+): m/z=825 (M+H)⁺; LCMS (Method A): t_R=6.58 min.

Allyl ((S)-1-(((S)-1-((3,5-bis(hydroxymethyl)phenyl)amino)-1-oxopropan-2-yl)amino)-3-methyl-1-oxobutan-2-yl)carbamate (88)

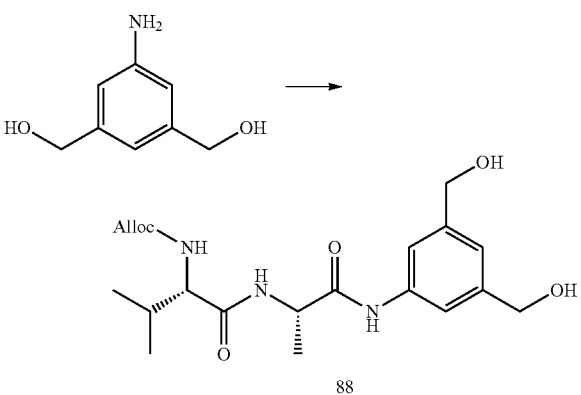

88

A solution of (5-amino-1,3-phenylene)dimethanol (0.50 g, 3.26 mmol) in N,N-dimethylacetamide (20 mL) was charged with which allyl ((S)-1-(((S)-1-amino-1-oxopropan-2-yl)amino)-3-methyl-1-oxobutan-2-yl)carbamate (0.93 g, 3.42 mmol) and N-(3-dimethylaminopropyl)-N'-ethylcarbodiimide hydrochloride (1.25 g, 6.52 mmol) and stirred for 4 h at room temperature. Water (100 mL) was then added, and the mixture extracted with ethyl acetate (3×100 mL). The combined organic extracts were then washed with brine (5×100 mL), dried over magnesium sulfate and concentrated in vacuo. Purification by flash column chromatography (silica), eluting with petroleum spirit, 40-60° C./ethyl acetate (3:7), gave the title compound (505 mg, 38%) as a white solid. $^1$H NMR (400 MHz, CDCl$_3$) δ 7.57 (s, 1H), 7.49 (s, 2H), 7.10 (s, 1H), 6.01-5.82 (m, 1H), 5.29 (ddd, J=17.3, 11.1, 1.5 Hz, 1H), 5.20-5.10 (m, 1H), 4.57 (s, 4H), 4.56-4.44 (m, 3H), 3.95 (d, J=6.7 Hz, 1H), 2.12-1.93 (m, 1H), 1.44 (dd, J=7.1, 4.0 Hz, 3H), 1.06-0.86 (m, 6H); MS (ES+): m/z=408 (M+H)$^+$; LCMS (Method A): t$_R$=5.22 min.

(5-((S)-2-((S)-2-(((Allyloxy)carbonyl)amino)-3-methylbutanamido)-propanamido)-1,3-phenylene)bis(methylene) dimethanesulfonate (89)

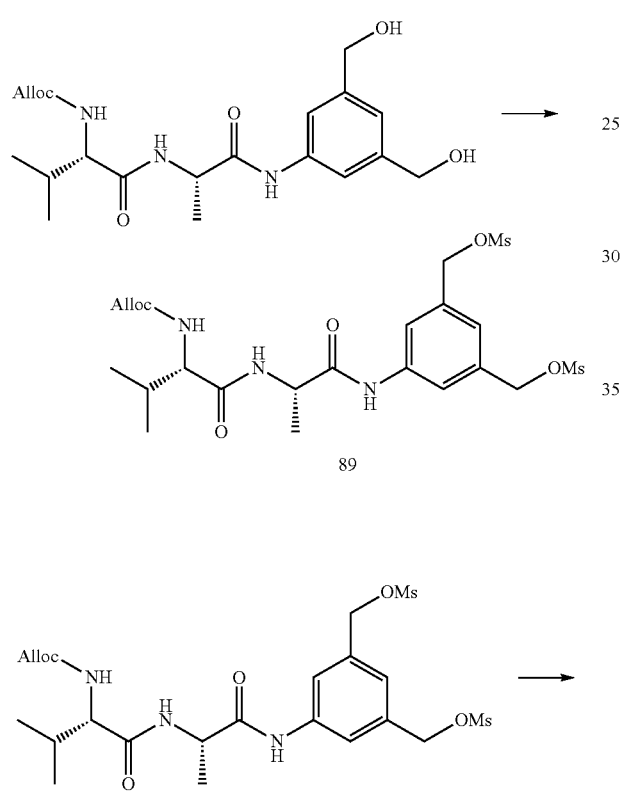

89

A suspension of allyl ((S)-1-(((S)-1-((3,5-bis(hydroxymethyl)phenyl)amino)-1-oxopropan-2-yl)amino)-3-methyl-1-oxobutan-2-yl)carbamate (88) (0.50 g, 1.22 mmol) in anhydrous dichloromethane (100 mL) and cooled to −5° C., to which anhydrous triethylamine (0.51 mL, 3.66 mmol) was added, followed by methanesulfonyl chloride (0.09 mL, 1.22 mmol). Immediate consumption of starting material was observed by TLC. The reaction mixture was washed with brine (2×50 mL), dried over magnesium sulfate and concentrated under reduced pressure. The resulting foam was purified by flash column chromatography (silica), eluting with petroleum spirit, 40-60° C./ethyl acetate (1:9), to give the title compound (263 mg, 38%) as a cream solid. $^1$H NMR (400 MHz, CDCl$_3$), mixture of rotamers, δ 7.68 (s, 2H), 7.14 (s, 1H), 6.98-6.81 (m, 1H), 5.99-5.76 (m, 1H), 5.65 and 5.49 (2× d, J=7.2 Hz, 1H), 5.32-5.26 (m, 1H), 5.26-5.18 (m, 1H), 5.15 (s, 2H), 4.70 (tt, J=14.2, 7.0 Hz, 1H), 4.61-4.49 (m, 2H), 4.03 and 3.92 (2× t, J=6.7 Hz, 1H), 2.99 (s, 6H), 2.21-2.10 (m, 1H), 1.50-1.42 (m, 3H), 1.05-0.91 (m, 6H); MS (ES+): m/z=564 (M+H)$^+$; LCMS (Method A): t$_R$=6.37 min.

Allyl(6aS)-3-((3-(((((6aS)-5-((allyloxy)carbonyl)-2,6-dimethoxy-8-(4-(N-methylsulfamoyl)phenyl)-12-oxo-5,6,6a,7,10,12-hexahydrobenzo[e]-pyrido[1,2-α][1,4]diazepin-3-yl)oxy)methyl)-5-((2S)-2-(2-(((allyloxy)-carbonyl)amino)-3-methylbutanamido)propanamido)benzyl)oxy)-2,6-dimethoxy-8-(4-(N-methylsulfamoyl)phenyl)-12-oxo-6,6a,7,10-tetrahydrobenzo[e]pyrido[1,2-α][1,4]diazepine-5(12H)-carboxylate (90)

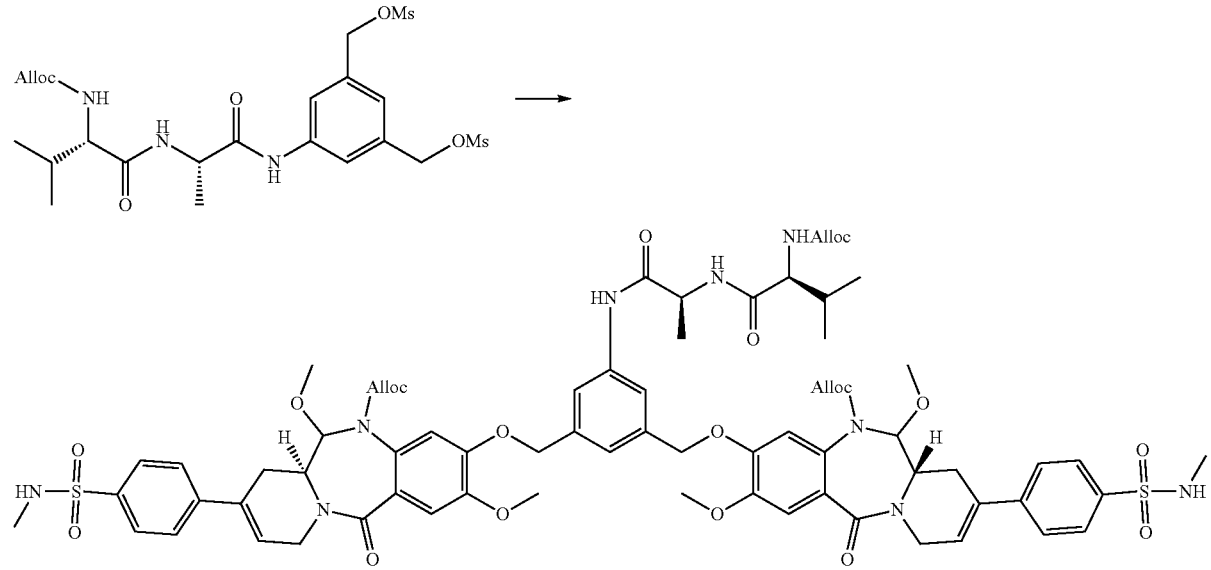

90

A solution of (5-((S)-2-((S)-2-(((Allyloxy)carbonyl)amino)-3-methylbutanamido)-propanamido)-1,3-phenylene)bis(methylene) dimethanesulfonate (89) (60 mg, 0.11 mmol) in anhydrous N,N-dimethylformamide (5 ml), was charged with allyl (6aS)-3-hydroxy-2,6-dimethoxy-8-(4-(N-methylsulfamoyl)phenyl)-12-oxo-6,6a,7,10-tetrahydrobenzo[e]pyrido[1,2-α][1,4]diazepine-5(12H)-carboxylate (32) (100 mg, 0.22 mmol) and potassium carbonate (0.06 g, 0.22 mmol) and the resulting mixture stirred at room temperature for 15 h. Water (50 ml) was then added and the resulting solution extracted with ethyl acetate (3×50 mL). The combined organic extracts were washed with brine (5×50 mL), then dried over anhydrous magnesium sulphate, filtered and concentrated under reduced pressure. The resulting oil was purified by flash column chromatography (silica), eluting with dichloromethane/acetone (1:1) to give the title compound (30 mg, 19%) as a beige solid. $^1$H NMR (400 MHz, CDCl$_3$) δ 8.80 (m, 1H), 7.85 (d, J=8.2 Hz, 4H), 7.61-7.59 (m, 2H), 7.53 (d, J=8.3 Hz, 4H), 7.30 (s, 1H), 7.25-7.20 (m, 2H), 6.84-6.81 (m, 1H), 6.70 (s, 2H), 6.45 (s, 2H), 5.91-5.58 (m, 3H), 5.50-5.33 (m, 2H), 5.25-5.12 (m, 2H), 5.13-4.97 (m, 7H), 4.88 (d, J=4.7 Hz, 2H), 4.71-4.59 (m, 1H), 4.59-4.36 (m, 6H), 4.34-4.17 (m, 4H), 3.89 (s, 6H), 3.73-3.63 (m, 2H), 3.40 (s, 6H), 3.00-3.86 (m, 2H), 2.79-2.69 (m, 2H), 2.66 (d, J=5.1 Hz, 6H), 2.16-2.14 (m, 1H), 1.43 (d, J=6.3 Hz, 3H), 1.05-0.86 (m, 6H); MS (ES+): m/z=1458 (M+H)$^+$; LCMS (Method A): t$_R$=7.08 min.

(S)-2-Amino-N—((S)-1-((3,5-bis((((S)-2-methoxy-8-(4-(N-methylsulfamoyl)-phenyl)-12-oxo-6a,7,10,12-tetrahydrobenzo[e]pyrido[1,2-α][1,4]diazepin-3-yl)oxy)methyl)phenyl)amino)-1-oxopropan-2-yl)-3-methylbutanamide (91)

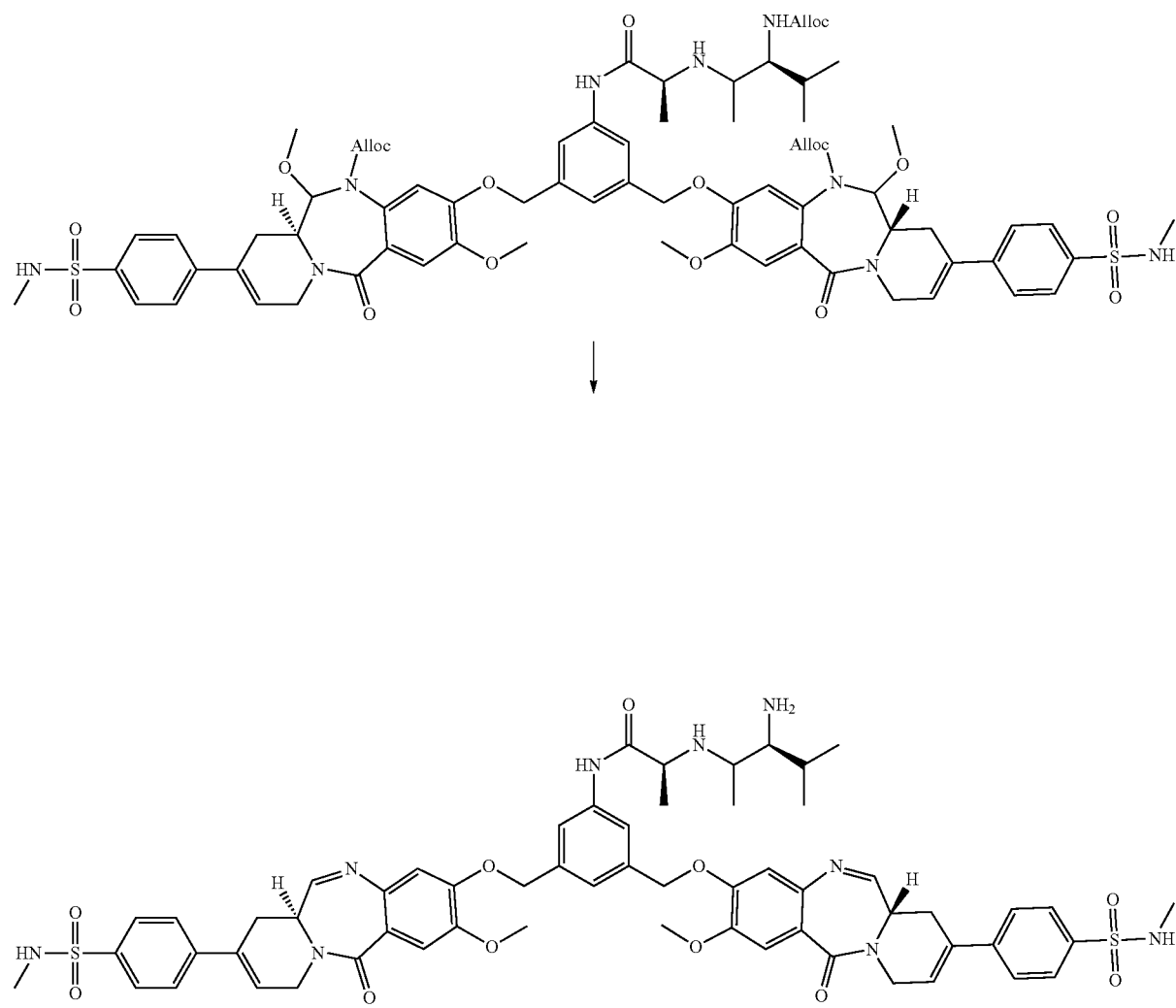

A solution of allyl (6aS)-3-((3-(((((6aS)-5-((allyloxy)carbonyl)-2,6-dimethoxy-8-(4-(N-methylsulfamoyl)phenyl)-12-oxo-5,6,6a,7,10,12-hexahydrobenzo[e]pyrido[1,2-α][1,4]-diazepin-3-yl)oxy)methyl)-5-((2S)-2-(2-(((allyloxy)carbonyl)amino)-3-methylbutan-amido)propanamido)benzyl)oxy)-2,6-dimethoxy-8-(4-(N-methylsulfamoyl)phenyl)-12-oxo-6,6a,7,10-tetrahydrobenzo[e]pyrido[1,2-α][1,4]diazepine-5(12H)-carboxylate (90) (0.030 g, 0.020 mmol) in dichloromethane (2 mL) was charged with tetrakis(triphenyl-phosphine)palladium(o) (1 mg) and pyrrolidine (6.5 µL). After 5 min, the reaction was observed to have only partially completed by LCMS (deprotection of imines). Further tetrakis(triphenylphosphine)palladium(o) (1 mg) and pyrrolidine (6.5 µL) were added to the reaction mixture, which resulted in immediate completion of the reaction. The reaction mixture was concentrated under reduced pressure to form an oil, which was re-dissolved in diethyl ether (2 mL) and re-concentrated under reduced pressure to remove any residual pyrrolidine (this process was repeated twice more). Purified by flash column chromatography (silica), eluting with dichloromethane/methanol (95:5) gave the title compound (30 mg, 85%) as a yellow solid. MS (ES+): m/z=1142 (M+H)$^+$; LCMS (Method A): $t_R$=5.43 min.

N—((S)-1-(((S)-1-((3,5-bis((((S)-2-Methoxy-8-(4-(N-methylsulfamoyl)-phenyl)-12-oxo-6a,7,10,12-tetrahydrobenzo[e]pyrido[1,2-α][1,4]diazepin-3-yl)oxy)methyl)phenyl)amino)-1-oxopropan-2-yl)amino)-3-methyl-1-oxobutan-2-yl)-6-(2,5-dioxo-2,5-dihydro-1H-pyrrol-1-yl)hexanamide (92)

A solution of (S)-2-amino-N—((S)-1-((3,5-bis((((S)-2-methoxy-8-(4-(N-methyl-sulfamoyl)phenyl)-12-oxo-6a,7,10,12-tetrahydrobenzo[e]pyrido[1,2-α][1,4]diazepin-3-yl)oxy)methyl)phenyl)amino)-1-oxopropan-2-yl)-3-methylbutanamide (91)(20 mg, 0.018 mmol) in N,N-dimethylacetamide (2 mL) was charged with 6-maleimido-hexanoic acid (4.0 mg, 0.018 mmol) and N-(3-dimethylaminopropyl)-N'-ethyl-carbodiimide hydrochloride (3.0 mg, 0.018 mmol) and stirred for 15 h, at which point consumption of starting material was observed by LCMS. Water (10 mL) was added to the reaction mixture and the resulting suspension extracted with ethyl acetate (50 mL×4). The combined organic extracts were washed with brine (40 mL×5), dried over magnesium sulfate and concentrated in vacuo. Purification by flash column chromatography (silica), eluting with dichloromethane/acetone (5:95) gave the title compound (4.9 mg, 21%) as a light brown solid. $^1$H NMR (400 MHz, DMSO-d6) δ 10.08 (br, 1H), 9.95 (br, 1H), 8.39 (m, 1H), 8.15 (d, J=6.3 Hz, 2H), 7.92 (s, 1H), 7.70 (d, J=6.8 Hz, 2H), 7.65-7.62 (m, 1H), 7.47 (d, J=5.1 Hz, 2H), 7.38 (d, J=2.6 Hz, 2H), 7.24 (br, 2H), 7.11 (s, 2H), 6.96 (dd, J=10.2, 9.0 Hz, 2H), 6.92 (d, J=7.2 Hz, 2H), 6.68 (d, J=13.6 Hz, 2H), 6.58 (br, 2H), 5.91 (d, J=6.8 Hz, 2H), 5.39 (br, 1H), 5.25-5.15 (m, 2H), 5.05 (br, 2H), 4.53 (s, 3H), 4.39 (br, 1H), 4.36-4.26 (m, 2H), 4.20-4.13 (m, 2H), 3.94 (br, 3H), 3.86 (s, 2H), 3.71 (s, 2H), 3.51 (s, 6H), 3.11 (d, J=14.4 Hz, 2H), 3.04-2.86 (m, 6H), 2.79-2.59 (m, 2H), 2.42 (dd, J=10.3, 5.7 Hz, 3H), 1.47-1.30 (m, 2H), 0.88-0.79 (m, 6H); MS (ES+): m/z=1336 (M+H)$^+$; LCMS (Method A): $t_R$=6.62 min.

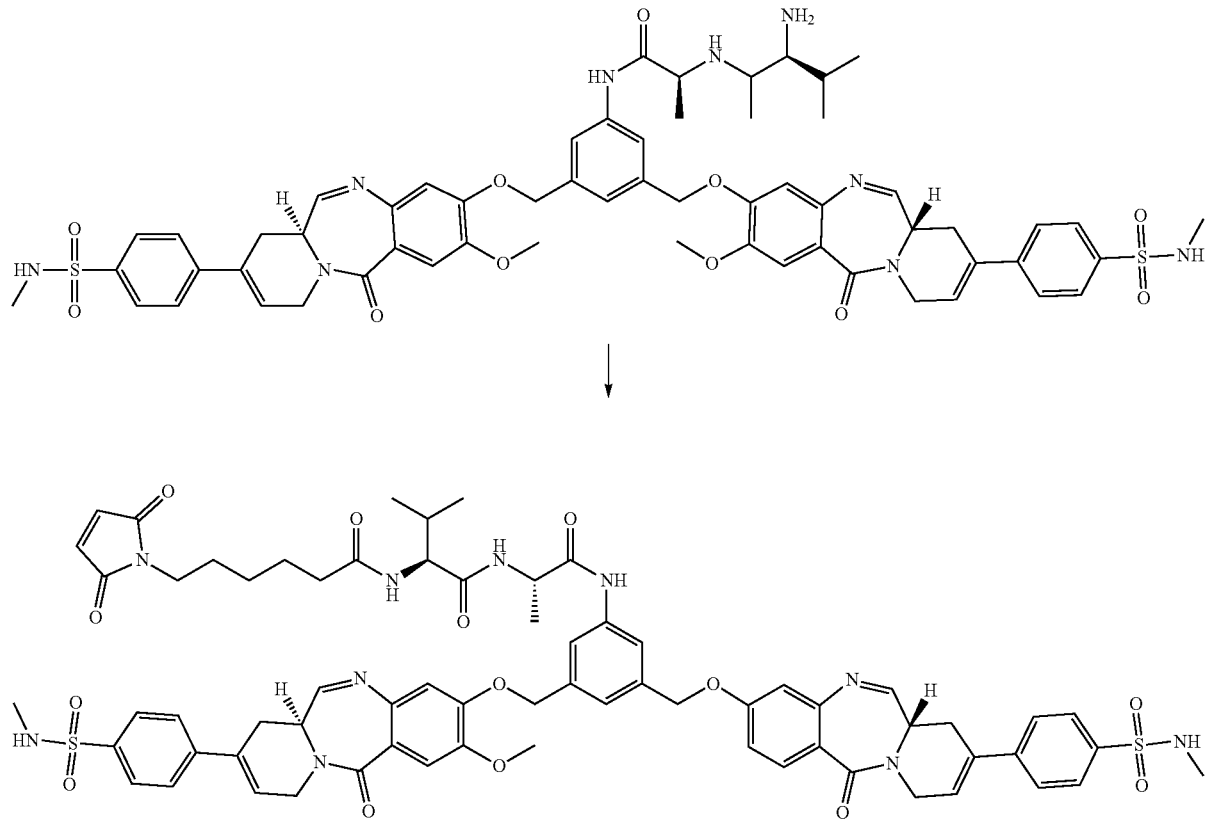

General synthetic scheme 24
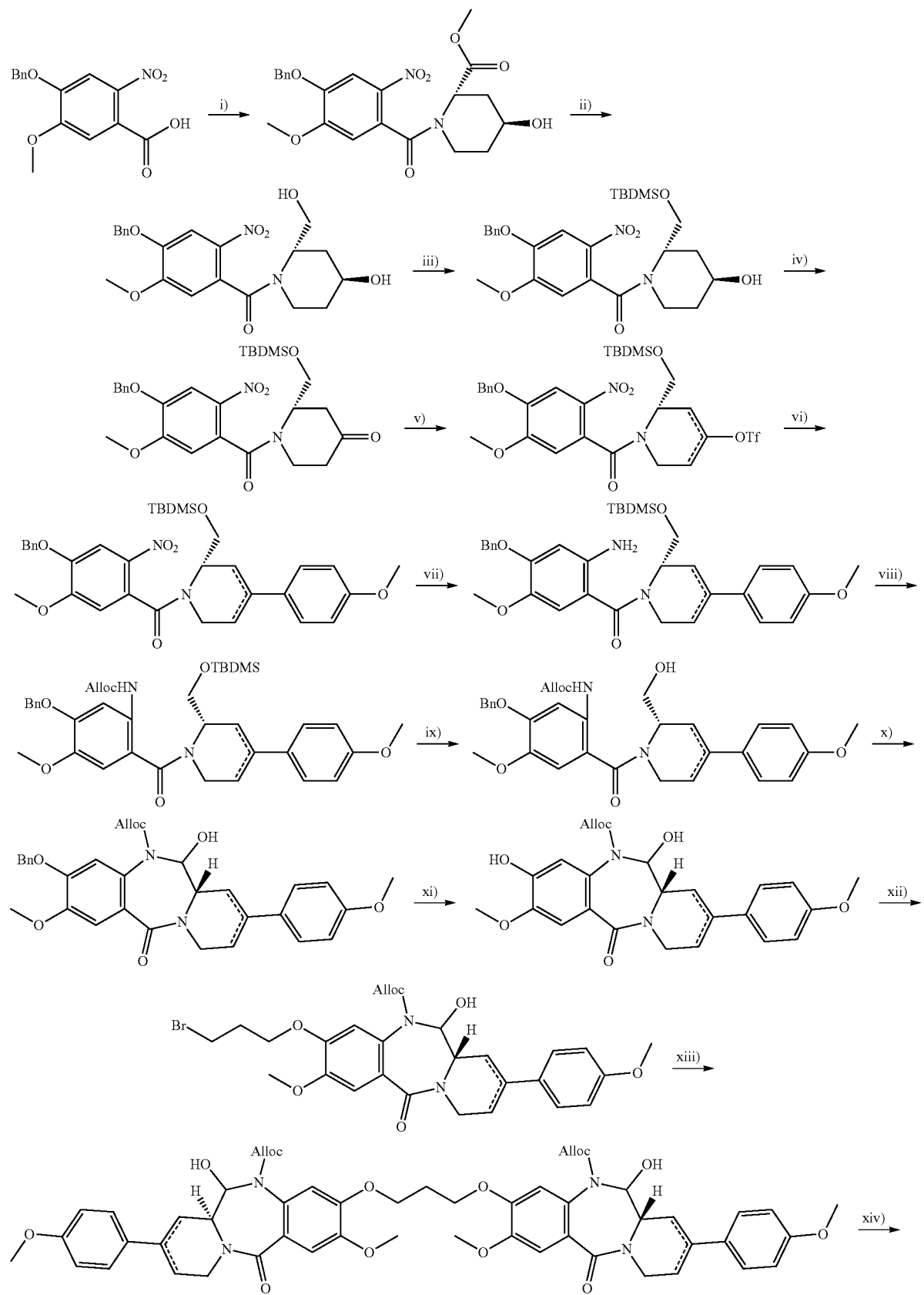

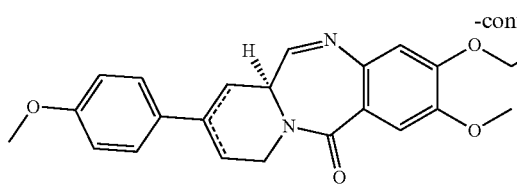
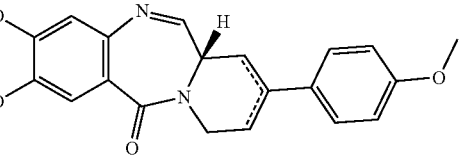

i) HATU, Et₃N, 4-(benzyloxy)-5-methoxy-2-nitrobenzoic acid, DMF ii) NaBH₄, THF iii) TBDMSCl, DMAP, Imidazole, DMF iv) TEMPO, BAIB, DCM v) Sodium bis trimethylsilyl amide, N,N-Bis(trifluoromethylsulfonyl)aniline, THF, −60° C. vi) 2-(4-methoxyphenyl)-4,4,5,5-tetramethyl-1,3,2-dioxaborolane, K₂CO₃, Pd(dppf)Cl₂.CH₂Cl₂, acetonitrile, 50° C. vii) Zinc, formic acid, EtOH viii) Allyl chloroformate, pyridine, DCM ix) TBAF, THF x) TEMPO, BAIB, DCM xi) BCl₃, THF xii) 1, 3-dibromopropane, K₂CO₃, DMF xiii) 12, K₂CO₃ DMF, 60° C. xiv) pyrrolidine, Tetrakis(triphenylphosphine)-palladium(o), DCM Methyl(2S,4S)-1-(4-(benzyloxy)-5-methoxy-2-nitrobenzoyl)-4-hydroxy-piperidine-2-carboxylate ((93)

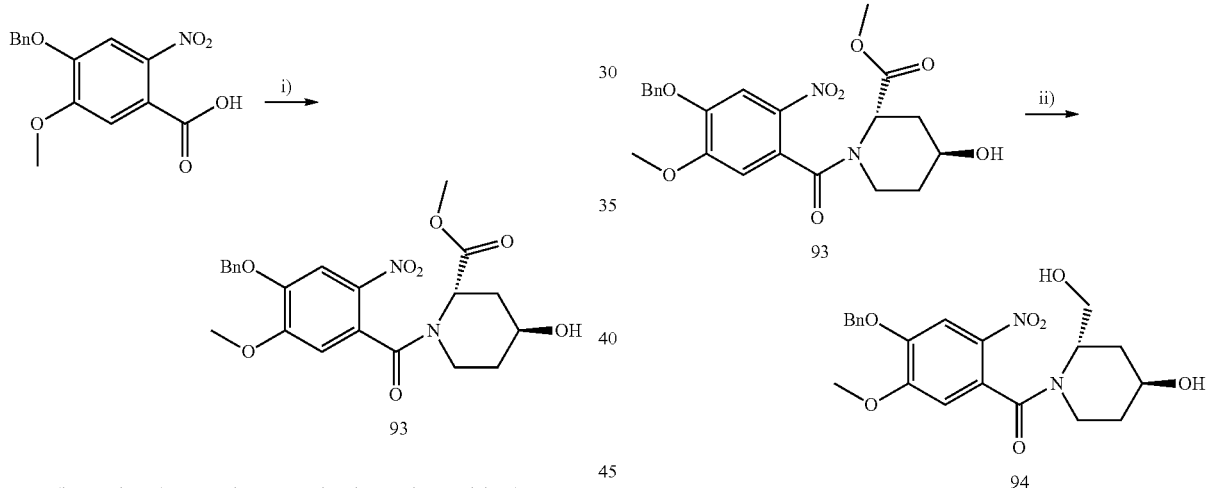

4-(benzyloxy)-5-methoxy-2-nitrobenzoic acid (5.0 g, 16.5 mmol), was dissolved in N,N-dimethylformamide (50 mL). To this solution, HATU (9.4 g, 24-75 mmol) and trimethylamine (9.67 ml 69.3 mmol) was added. The solution was allowed to stir for 30 minutes. The solution was then cooled to 0° C. and methyl (2S,4S)-4-hydroxypiperidine-2-carboxylate (2.6 g, 16.5 mmol) was then added to the mixture. After four hours, the reaction was judged to have completed by LC-MS analysis. Water (500 ml) was then added to the solution, causing the formation of a suspension. The crude product was extracted using ethyl acetate (3×500 ml) and the combined organic extract was washed sequentially with bicarbonate solution (500 ml) and brine (500 ml) and dried with magnesium sulphate. The crude product was purified using flash column chromatography (acetone/dichloromethane, from 5% to 40% acetone), resolving a white solid in 82% yield. ¹H NMR (400 MHz, CD₃OD), rotameric mixture, S 7.77 and 7.72 (2×s, 1H), 7.40-7.33 (m, 2H), 7.31-7.20 (m, 3H), 6.94 and 6.73 (2×s, 1H), 5.14 and 5.12 (2×s, 2H), 4.05-3.99 (m, 1H), 3.91 and 3.89 (2×s, 3H), 3.67 and 3.63 (2×s, 3H) 3.60-3.58 (m, 1H), 3.40-3.30 (m, 1H) 2.52 and 2.24 (2×d, 1H, J=14.4, 14.1 Hz), 1.99-1.90 (m, 1H) 1.89-1.80 (m, 1H) 1.73-1.60 (m, 1H), 1.57-1.48 (m, 1H); MS (ES+): m/z=445.0 (M+H)⁺; LC Retention Time (Method B): t$_R$=3.25 min.

The addition of the methyl (2S,4S)-4-hydroxypiperidine-2-carboxylate C ring to the A ring precursor generates rotameric intermediates. The addition of the triflate (step v) generated a regioisomeric mix in a 50:50 ratio which was separated the Suzuki step (step vi). This complicated the NMR spectra obtained, causing peak broadening and splitting.

(4-(Benzyloxy)-5-methoxy-2-nitrophenyl)((2S,4S)-4-hydroxy-2-(hydroxymethyl)piperidin-1-yl)methanone (94)

93 (4-7 g, 10.5 mmol) was dissolved in tetrahydrofuran (100 ml). The solution was cooled to 0° C. using ice and lithium borohydride (0.342 g, 15.75 mmol) was added portionwise to the mixture. Some effervescence was observed. After one hour, the reaction was judged to have completed by TLC and LC-MS analysis. The reaction was quenched using water (50 ml) and hydrochloric acid solution (1M, 10 ml). The tetrahydrofuran was removed under reduced pressure and the resulting concentrated solution extracted using ethyl acetate (3×100 ml). The combined organic layer was washed sequentially with bicarbonate solution (50 ml) and brine (50 ml), dried with magnesium sulphate and concentrated under reduced pressure to resolve a white solid in 85% yield. No further purification was carried out and the intermediate 94 was carried through to the next step in the synthesis. ¹H NMR (400 MHz, CD₃OD), rotameric mixture, δ 7.76, 7.74 and 7.71 (3×s, 1H), 7.39-7.22 (m, 5H), 7.01 and 6.91 (2×s, 1H), 5.12 (2×s, 2H), 4.39 (d, 1H, J=13.5 Hz), 4.20 and 4.10 (2× dd, 1H, J=9.8, 12.0 and 8.8, 12.0 Hz), 3.88 and 3.83 (2×s, 3H), 3.65 (dd, 0.38H, J=4.4, 12.0 Hz), 3.57-3.52 (m, 0.8H), 3.50-3.43 (m, 0.6H), 3.34 (dd, 0.6H, J=4.0, 12.0 Hz), 3.26 (dd, 0.5H, 2.7, 13.3 Hz), 3.12-3.00 (m, 0.5H), 1.90-1.85 (m, 0.5H), 1.85-1.77 (m, 1H), 1.75-1.70 (m, 1H), 1.70-1.55 (m, 2H), 1.52-1.42 (m, 2H); MS (ES+): m/z=417.0 (M+H)+; LC Retention Time (Method B): t_R=3.08 min.

(4-(Benzyloxy)-5-methoxy-2-nitrophenyl)((2S,4S)-2-(((tert-butyldimethyl-silyl)oxy)methyl)-4-hydroxypiperidin-1-yl)methanone (95)

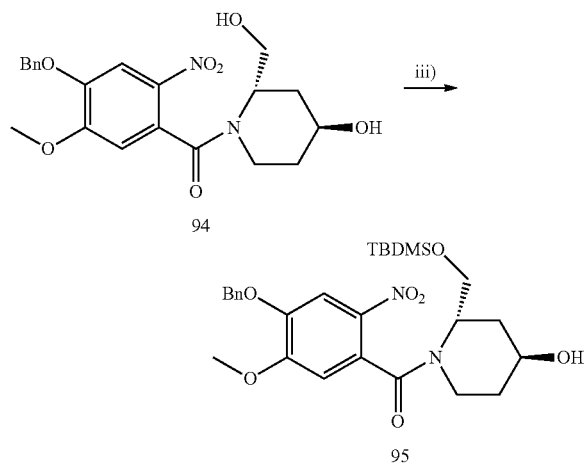

94 (4.0 g, 9.61 mmol) was dissolved in dichloromethane (100 ml). To this solution, imidazole (1.98 g, 28.83 mmol) and tert-Butyldimethylsilyl chloride (1.52 g, 10.09 mmol) was added. After two hours, the reaction was judged to have completed by LC-MS analysis. The reaction mixture was washed sequentially with saturated citric acid solution (100 ml) and brine (100 ml), dried with magnesium sulphate and the dichloromethane was removed under reduced pressure. The resulting crude oil was purified using flash column chromatography (acetone/DCM, from 5% to 20% acetone), resolving an orange oil 95 in 82% yield. ¹H NMR (400 MHz, CDCl₃), rotameric mixture, δ 7.61, 7.60 and 7.57 (3×s, 1H), 7.30-7.15 (m, 5H), 6.61, 6.56 and 6.50 (3×s, 1H), 5.04 and 5.03 (2×s, 2H), 4.86-4.45 (m, 2H), 4.17 (dd, 0.5H, 3.2, 10.6 Hz), 4.01-3.84 (m, 2H), 3.69 (dt, 1H, 5.9, 3.9 Hz), 3.60 (dd, 1H, 10.6, 2.9 Hz), 3.47-3.34 (m, 1H), 3.11 and 2.96 (2× t, 1H, J=12.2 and 14.5 Hz), 2.15-1.97 (m, 1H), 1.89 and 1.80 (2× d, 1H, J=14.4, 14.9 Hz), 1.63-130 (m, 3H), 0.80-0.67 (m, 9H), 0.05--0.15 (m, 6H); MS (ES+): m/z=531.1 (M+H)+; LC Retention Time (Method B): t_R=4.38 min.

(S)-1-(4-(Benzyloxy)-5-methoxy-2-nitrobenzoyl)-2-(((tert-butyldimethyl-silyl)oxy)methyl)piperidin-4-one (96)

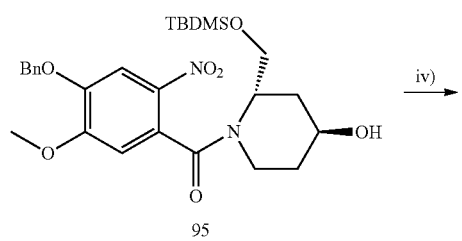

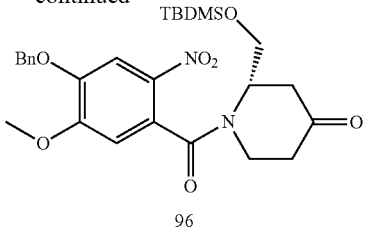

95 (3.7 g, 6.98 mmol) was dissolved in dichloromethane (100 ml). To this solution, TEMPO (0.11 g, 0.698 mmol) and bis(acetoxy)iodobenzene (2.92 g, 9.07 mmol) was added, and the solution allowed to stir at room temperature for 16 hours. At this point, the reaction was judged to have completed by LC-MS and TLC analysis. (Note: On some occasions, the reaction was found to have partially completed. In this case, more TEMPO was added until the oxidation was completed). The reaction mixture was washed sequentially with saturated copper sulphate solution (2×100 ml) and brine (100 ml), dried with magnesium sulphate and the dichloromethane was removed under reduced pressure. The crude product was purified using flash column chromatography (acetone/dichloromethane, from 1% to 8% acetone), resolving a white solid 96 in 90% yield. ¹H NMR (400 MHz, CDCl₃), rotameric mixture, δ 7.69, 7.68 and 7.67 (3×s, 1H), 7.40-7.20 (m, 5H), 6.71, 6.70 and 6.65 (3×s, 1H), 5.14 and 5.13 (2×s, 2H), 4.12 and 3.91 (2× dd, 1H, J=10.6, 2.6 and 10.4, 2.7 Hz), 3.89, 3.88 and 3.87 (3×s, 3H), 3.80-3.35 (m, 3H), 2.77-2.15 (m, 4H), 0.85-0.72 (m, 9H), 0.02--0.10 (m, 6H); ¹³C NMR (400 MHz, CDCl3), rotameric mixture. δ 205.7, 167.5, 154.9, 148.3, 148.2, 137.6, 137.3, 135.2, 130.0, 128.9, 128.7, 128.6, 127.6, 127.3, 127.1, 127.0, 109.9, 109.2, 108.6, 71.4, 65.6, 65.1, 64.6, 56.8, 56.8, 56.7, 56.5, 51.27, 51.22, 43.3, 41.9, 41.5, 41.3, 39.9, 39.8, 39.6, 37.5, 25.8, 25.8, 25.8, 20.3, 18.3, 18.2, 18.2, 18.1, -5.7, -5.7; MS (ES+): m/z=529.0 (M+H)+; LC Retention Time (Method A): t_R=8.28 min.

(S)-1-(4-(benzyloxy)-5-methoxy-2-nitrobenzoyl)-2-(((tert-butyldimethyl-silyl)oxy)methyl)-1,2,3,6-tetrahydropyridin-4-yl trifluoromethanesulfonate and (S)-1-(4-(benzyloxy)-5-methoxy-2-nitrobenzoyl)-6-(((tert-butyldimethylsilyl)oxy)methyl)-1,2,3,6-tetrahydropyridin-4-yl trifluoromethanesulfonate (97)

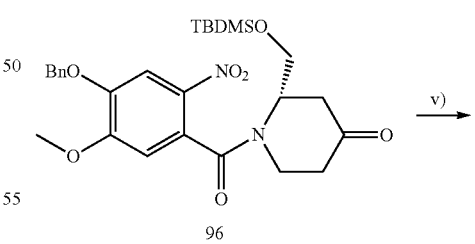

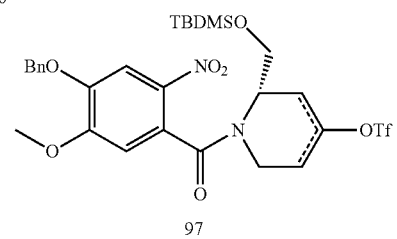

96 (3.3 g, 6.23 mmol) was added to a stirred solution of sodium bis(trimethylsilyl)amide (1.73 g, 9.34 mmol) in tetrahydrofuran (50 ml) which was cooled to −78° C. The solution was allowed to stir for one hour. N-Phenyl-bis(trifluoromethanesulfonimide) (2.89 g, 8.09 mmol) was separately dissolved in tetrahydrofuran (50 ml). The N-Phenyl-bis(trifluoromethanesulfonimide) solution was then added to the flask containing 96 and sodium bis(trimethylsilyl)amide. The combined solution was allowed to warm to room temperature and the reaction mixture left to stir for four hours. At this point, the reaction was judged to have completed by TLC and LC-MS analysis. The tetrahydrofuran was removed under reduced pressure and the crude material was immediately purified using flash column chromatography (acetone/dichloromethane, from 1% to 3% acetone) to yield an off-white foam 97 in 75% yield. $^1$H NMR (400 MHz, CDCl3), rotameric and regiomeric mixture, δ 7.70-7.60 (m, 1H), 7.39-7.25 (m, 5H), 6.77-6.60 (m, 1H), 5.91-5.45 (m, 1H), 5.15-5.00 (m, 2H), 3.95-3.77 (m, 1H), 3.90-3.85 (m, 3H), 3.75-3.20 (m, 3H), 2.90-2.08 (m, 2H), 0.85-0.6 (m, 9H), 0.07-−0.22 (m, 6H); MS (ES+): m/z=661.1 (M+H)$^+$; LC Retention Time (Method A): $t_R$=9.27 min.

(S)-(4-(benzyloxy)-5-methoxy-2-nitrophenyl)(6-(((tert-butyl-dimethyl-silyl)oxy)methyl)-4-(4-methoxyphenyl)-3,6-dihydropyridin-1(2H)-yl)methanone (98a) and (S)-(4-(benzyloxy)-5-methoxy-2-nitrophenyl)(2-(((tert-butyldimethylsilyl)oxy)methyl)-4-(4-methoxyphenyl)-3,6-dihydropyridin-1(2H)-yl)methanone (98b)

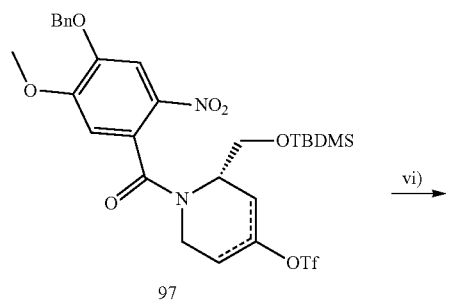

97

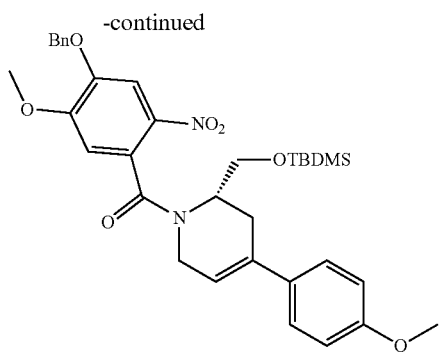

98b 97 (3 g, 4.53 mmol) was dissolved in acetonitrile (2 ml). To this solution, 1,1'-bis(diphenylphosphino)ferrocene (0.369 g, 0.45 mmol), methoxyphenyl)-4,4,5,5-tetramethyl-1,3,2-dioxaborolane (1.87 g, 5.9 mmol) and potassium carbonate (1.25, 9.06 mmol) were added. The solution was heated at 50° C. for 10 minutes under microwave conditions. The solution was diluted in ethyl acetate (100 ml), washed with brine (50 ml), dried under magnesium sulphate and concentrated under reduced pressure. The resulting oil was purified using flash column chromatography (80:20 petroleum ether/ethyl acetate) repeatedly and the two regioisomers resulting from the introduction of the triflate were separated as an orange solid 98a and creamy white solid 98b. The overall yield (both regioisomers combined) was 75%.

98a Characterisation $^1$H NMR (400 MHz, CDCl$_3$), rotameric mixture, δ 7.81-7.72 (m, 1H), 7.49-7.27 (m, 7H), 6.92-6.83 (m, 2H), 6.78/6.76 (2×s, 1H), 6.20/6.02 (2×s, 1H), 5.27-5.17 (m, 2H), 5.06-4.88 (m, 1H), 4.07-3.86 (m, 5H), 3.81 (s, 3H), 3.75-3.34 (m, 3H), 2.59-2.21 (m, 1H), 0.97-0.69 (m, 9H), 0.17-−0.19 (m, 6H); MS (ES+): m/z=619.2 (M+H)$^+$; LC Retention Time (Method B): $t_R$=4.80.

98b Characterisation $^1$H NMR (400 MHz, CDCl$_3$), rotameric mixture, δ7.84-7.72 (m, 1H), 7.49-7.26 (m, 7H), 6.91-6.82 (m, 2H), 6.78-6.72 (m, 1H), 6.02/5.73 (2×s, 1H), 5.25-4.88 (m, 3H), 3.96 (s, 3H), 3.88-3.67 (m, 6H), 3.76-3.67 (m, 2H), 3.75-3.54 (m, 1H), 3.00-2.34 (m, 2H), 1.29-1.19 (m, 9H), 0.96-0.72 (m, 6H); MS (ES+): m/z=619.2 (M+H)$^+$; LC Retention Time (Method A): $t_R$=9.38

(S)-(2-amino-4-(benzyloxy)-5-methoxyphenyl)(6-(((tert-butyldimethyl-silyl)oxy)methyl)-4-(4-methoxyphenyl)-3,6-dihydropyridin-1(2H)-yl)methanone (99a) and (S)-(2-amino-4-(benzyloxy)-5-methoxy-phenyl)(2-(((tert-butyldimethylsilyl)oxy)methyl)-4-(4-methoxyphenyl)-3,6-dihydropyridin-1(2H)-yl)methanone (99b)

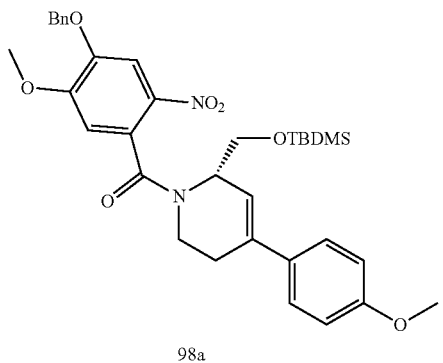

98a

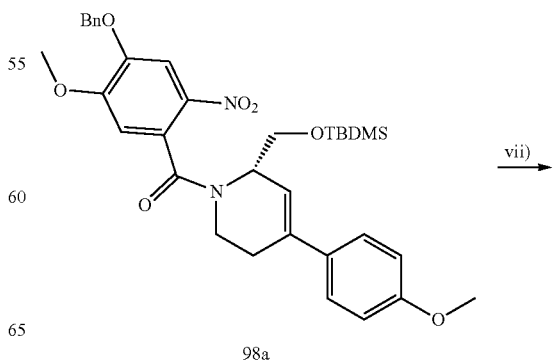

98a

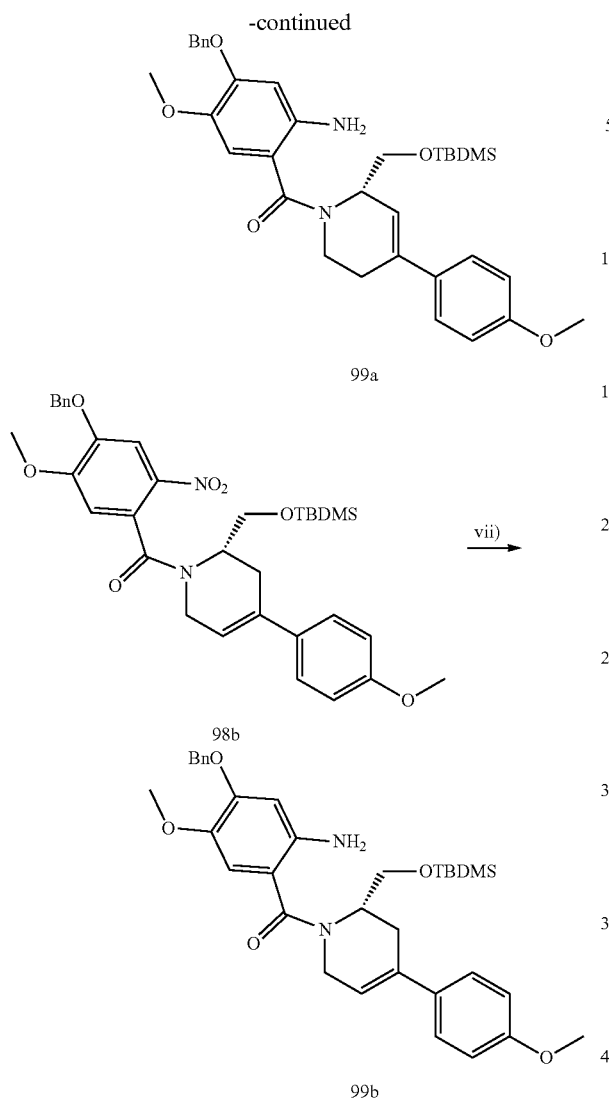

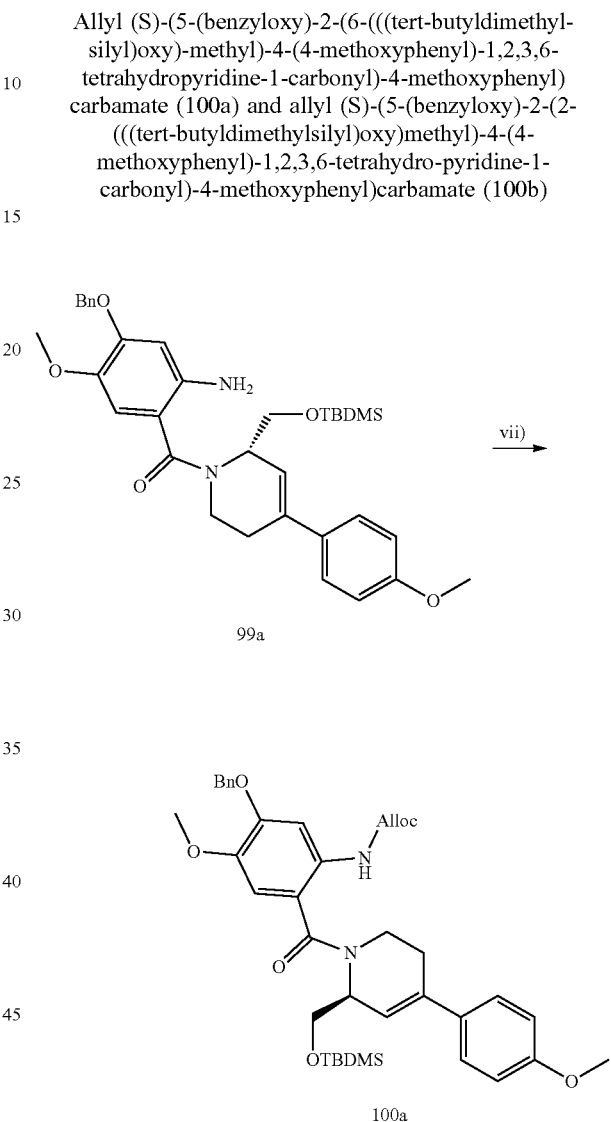

98a (0.5 g, 0.8 mmol) was dissolved in a 5% solution of formic acid in ethanol (10 ml). To this solution, zinc powder (1.94 g, 29.6 mmol) was added. After approximately 10 minutes, the reaction was observed to have proceeded to completion via TLC and LC-MS analysis. The reaction mixture was quenched through addition of saturated sodium bicarbonate solution (10 ml) and the solution concentrated under reduced pressure. The concentrated aqueous solution was partitioned between brine (50 ml) and ethyl acetate (100 ml). The organic layer was isolated, dried with magnesium sulphate and concentrated under reduced pressure to resolve a yellow oil 99a in 90% yield. The intermediate was carried to the next step without further purification.

A similar reaction procedure was carried out to generate 99b from 98b in 87% yield. 99a Characterisation $^1$H NMR (400 MHz, CDCl$_3$) Rotameric Mixture, δ7.99 (s, 1H), 7.43 (d, 2H, J=7.8 Hz), 7.37 (m, 2H), 7.34-7.28 (m, 3H), 6.87 (d, 2H, J=8.0 Hz), 6.78 (s, 1H), 6.41/6.00 (2×s, 1H), 5.15 (s, 2H), 4.04-3.83 (m, 3H), 3.81 (s, 3H), 3.72-3.27 (m, 2H), 2.67-2.37 (m, 2H), 0.94-0.77 (m, 9H), 0.16--0.03 (m, 6H); MS (ES+): m/z=589.3 LC Retention Time (Method B): t$_R$=4.58.

99b Characterisation $^1$H NMR (400 MHz, CDCl$_3$) Rotameric Mixture, δ 7.99 (s, 1H), 7.43 (d, 2H, J=7.8 Hz) 7.39-7.30 (m, 5H), 6.86 (d, 2H, J=8.2 Hz), 6.82 (s, 1H), 6.42/5.91 (2×s, 1H), 5.12 (s, 2H), 4.97-4.32 (br, 4H), 3.81 (s, 3H), 3.78-3.56 (m, 3H), 2.80 (d, 1H, J=14.7 Hz), 2.44 (d, 1H, J=16.7 Hz), 0.97-0.72 (m, 9H), 0.13--0.07 (m, 6H); MS (ES+): m/z=589.3 LC Retention Time (Method B): t$_R$=4.57.

Allyl (S)-(5-(benzyloxy)-2-(6-(((tert-butyldimethyl-silyl)oxy)-methyl)-4-(4-methoxyphenyl)-1,2,3,6-tetrahydropyridine-1-carbonyl)-4-methoxyphenyl) carbamate (100a) and allyl (S)-(5-(benzyloxy)-2-(2-(((tert-butyldimethylsilyl)oxy)methyl)-4-(4-methoxyphenyl)-1,2,3,6-tetrahydro-pyridine-1-carbonyl)-4-methoxyphenyl)carbamate (100b)

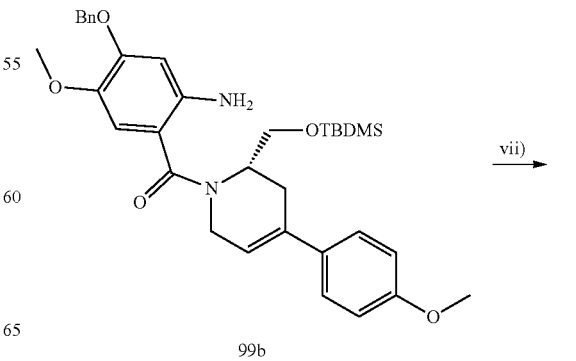

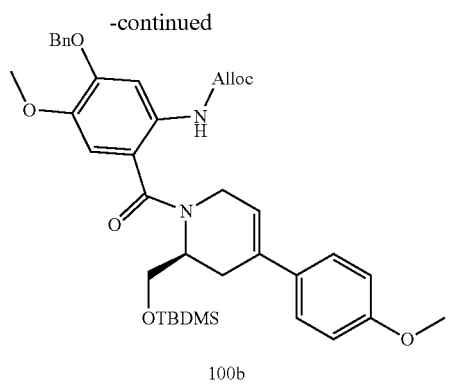

100b 99a (0.4 g, 0.67 mmol) was dissolved in DCM (30 ml). To this solution, pyridine (0.124 ml, 1.54 mmol) and allyl chloroformate (0.074 ml, 0.70 mmol) were added sequentially. After one hour, the reaction was judged to have completed by LC-MS analysis. The reaction solution was then washed with saturated copper sulphate solution (2×20 ml) and brine (20 ml). The organic layer was then dried with magnesium sulphate and concentrated under reduced pressure. The resulting oil was purified using flash column chromatography (5:95 acetone/DCM) to resolve a brown oil 100a in 85% yield.

A similar experimental procedure was carried out to produce 100b from 99b in similar yields (90%).

100a Characterisation $^1$H NMR (400 MHz, CDCl$_3$) δ 8.15 (s, 1H), 7.86 (s, 1H), 7.48 (d, 2H, J=7.9 Hz), 7.38 (t, 2H, J=7.2 Hz), 7.34-7.28 (m, 3H), 6.88 (d, 2H, J=8.4 Hz), 6.83 (s, 1H), 6.03-5.85 (m, 2H), 5.31 (d, 1H, J=17.3 Hz), 5.24-5.15 (m, 3H), 4.65-4.45 (s, 2H), 3.98-3.85 (m, 1H), 3.84-3.77 (m, 9H), 3.69-3.31 (m, 1H), 2.62-2.36 (m, 2H), 0.93-0.78 (m, 9H), 0.12-0.02 (m, 6H); MS (ES+): m/z=673.3 (M+H)$^+$; LC Retention Time (Method B) $t_R$=4.92.

100b Characterisation $^1$H NMR (400 MHz, CDCl$_3$) δ 8.39 (s, 1H), 7.96 (s, 1H), 7.48 (d, 2H, J=7.4 Hz), 7.37 (t, 2H, 7.6 Hz), 7.33-7.27 (m, 3H), 6.88 (d, 2H, 8.7 Hz), 6.07-5.94 (bs, 1H), 5.92 (ddd, 1H, J=22.6, 11.0, 5.7 Hz), 5.23-5.10 (m, 2H), 4.67-4.52 (m, 2H), 3.83 (s, 3H), 3.81 (s, 3H), 3.78-3.52 (m, 3H), 2.82-2.69 (m, 1H), 2.44 (d, 1H, 17.1 Hz), 0.94-0.66 (m, 9H), 0.14--0.13 (m, 6H); MS (ES+): m/z=673.4 (M+H)$^+$; LC Retention Time (Method B) $t_R$=4.87.

Allyl (S)-(5-(benzyloxy)-2-(6-(hydroxymethyl)-4-(4-methoxy-phenyl)-1,2,3,6-tetrahydropyridine-1-carbonyl)-4-methoxyphenyl)-carbamate (iota) and allyl (S)-(5-(benzyloxy)-2-(2-(hydroxymethyl)-4-(4-methoxyphenyl)-1,2,3,6-tetrahydropyridine-1-carbonyl)-4-methoxy-phenyl)carbamate (101b)

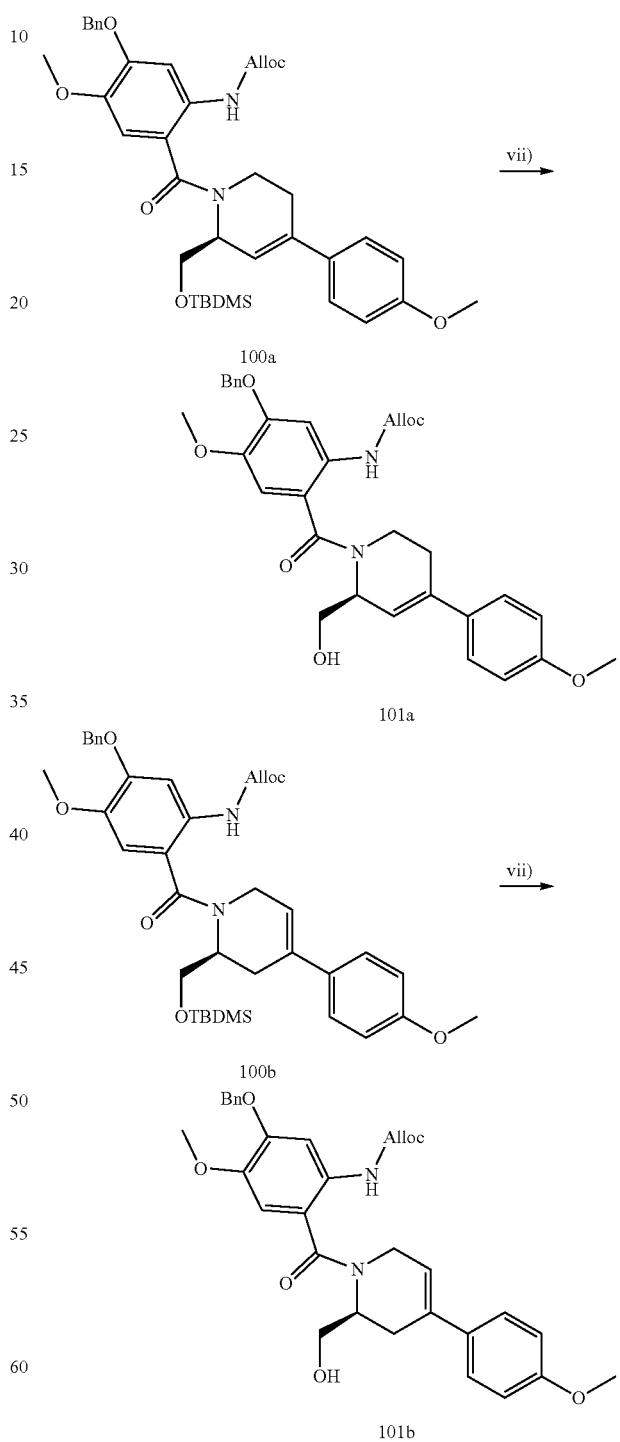

100a (0.35 g, 0.52 mmol) was dissolved in THF (30 ml) and the resulting solution cooled to 0° C. To this solution, tetra-n-butylammonium fluoride (0.17 g, 0.65 mmol) was then added to the reaction mixture as a 1M solution in THF. The reaction was allowed to warm to room temperature and after 1 hour, TLC and LC-MS confirmed complete reaction of the starting material. Ethyl acetate (100 ml) was added to the reaction mixture, with the resulting solution washed with saturated ammonium chloride solution (50 ml), brine (50 ml) and dried with magnesium sulphate. The solution was then concentrated under reduced pressure to yield 101a as a brown oil (95%). No further purification was carried out on the material.

An analogous procedure was carried out to convert 100b to 101b in 90% yield.

101a Characterisation $^1$H NMR (400 MHz, CDCl$_3$) δ 8.18 (s, 1H), 7.80 (s, 1H), 7.47 (d, 2H, J=8.0 Hz), 7.38 (t, 2H, J=7.9 Hz), 7.34-7.27 (m, 3H), 6.88 (d, 2H, J=8.5 Hz), 6.83 (s, 1H), 6.00-5.84 (m, 2H), 5.33 (d, 1H, J=17.4 Hz), 5.21 (d, 1H, 10.3 Hz), 5.17 (s, 2H), 4.62 (d, 2H, J=5.4 Hz), 4.15-3.88 (m, 2H), 3.84 (s, 3H), 3.82-3.77 (m, 5H), 3.47-3.31 (br, 1H), 2.69-2.54 (m, 1H), 2.47 (d, 1H, J=14.4 Hz); MS (ES+): m/z=559.2 (M+H)$^+$; LC Retention Time (Method B): t$_R$=3.72.

101b Characterisation $^1$H NMR (400 MHz, CDCl$_3$) δ 8.14 (s, 1H), 7.82 (s, 1H), 7.47 (d, 2H, J=7.8 Hz), 7.37 (t, 2H, J=7.6 Hz), 7.34-7.27 (m, 3H), 6.92-6.79 (m, 3H), 5.91 (ddd, 1H, J=22.8, 10.8, 5.6 Hz), 5.36-5.28 (m, 1H), 5.20 (d, 1H, J=10.4 Hz), 5.16 (s, 2H), 4.60 (d, 2H, J=5.5 Hz), 4.07-3.84 (m, 1H), 3.82 (s, 3H), 3.81-3.48 (m, 6H), 2.88-2.73 (m, 1H), 2.36 (d, 1H, J=17.9 Hz); MS (ES+): m/z=559.3 (M+H)$^+$; LC Retention Time (Method B): t$_R$=3.70.

Allyl (6aS)-3-(benzyloxy)-6-hydroxy-2-methoxy-8-(4-methoxy-phenyl)-12-oxo-6,6a,9,10-tetrahydrobenzo[e]pyrido[1,2-α][1,4]diazepine-5(12H)-carboxylate (102a) and allyl (6aS)-3-(benzyloxy)-6-hydroxy-2-methoxy-8-(4-methoxyphenyl)-12-oxo-6,6a,7,10-tetrahydrobenzo[e]-pyrido[1,2-α][1,4]diazepine-5(12H)-carboxylate (102b)

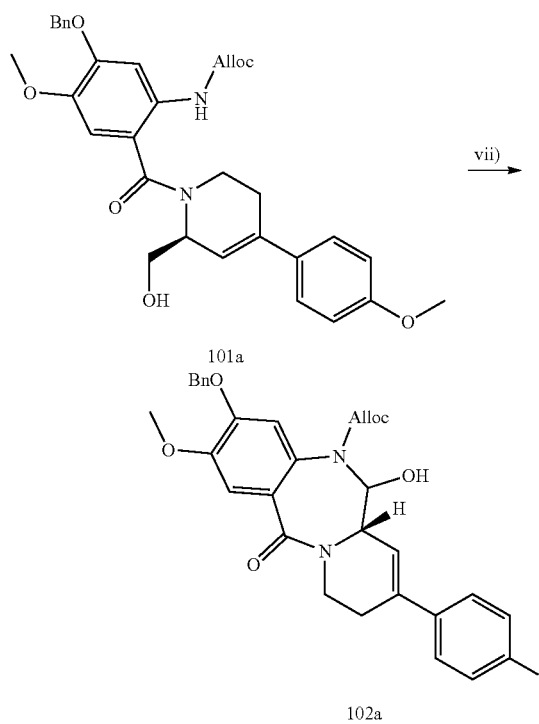

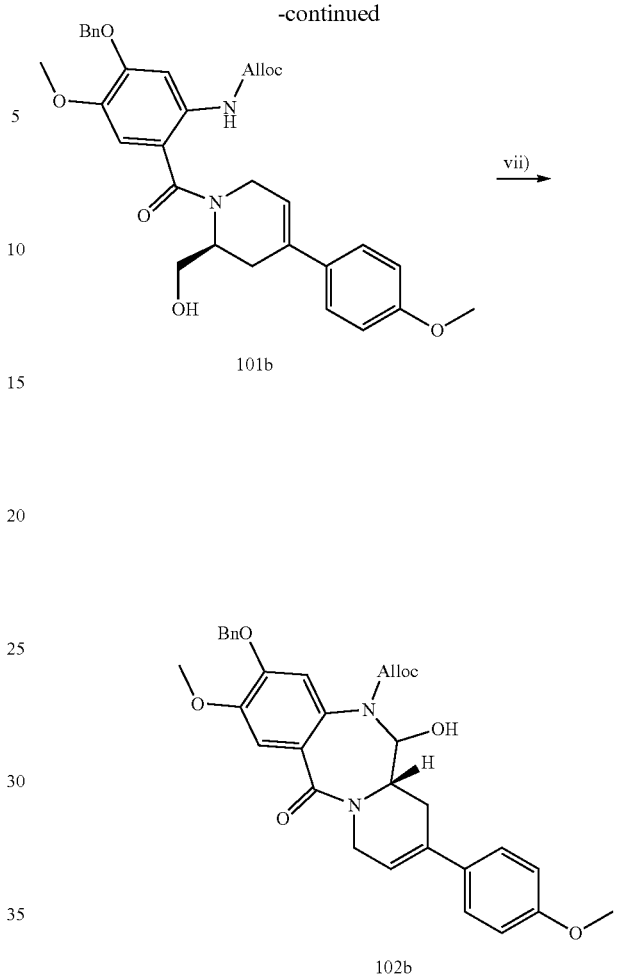

101a (0.25 g, 0.45 mmol) was dissolved in DCM (15 ml). To this solution, 2,2,6,6-tetramethyl-1-piperidinyloxy (0.017 g, 0.11 mmol) and (diacetoxyiodo)benzene (0.363 g, 1.13 mmol) were added. The reaction was allowed to stir for 16 hours, at which point TLC showed consumption of the starting material. DCM (15 ml) was added to the reaction mixture and the organic solution washed with saturated sodium metabisulphite solution (30 ml) and brine (30 ml). The organic layer was dried with magnesium sulphate and concentrated under reduced pressure. Flash column chromatography (15:85 acetone/DCM) was then used to purify 102a as a red oil in 55% yield. 101b was converted to 102b using the conditions described above in 58% yield.

102a Characterisation $^1$H NMR (400 MHz, CDCl$_3$) δ 7.46-7.30 (m, 7H), 7.22 (s, 1H), 6.87 (d, 2H, J=8.4 Hz), 6.73 (s, 1H), 6.10 (d, 1H, J=3.6 Hz), 5.79 (d, 1H, J=10.1 Hz), 5.68 (br, 1H), 5.23-5.06 (m, 4H), 4.78 (d, 1H, J=13.0 Hz), 4.57-4.36 (m, 2H), 4.02 (d, 1H, J=8.9 Hz), 3.92 (s, 3H), 3.80 (s, 3H), 3.77-3.61 (m, 1H), 3.10 (dt, 1H, J=14.4, 7.1 Hz), 2.64-2.52 (m, 2H); MS (ES+): m/z=557.2 (M+H)$^+$; LC Retention Time (Method B): t$_R$=3.68.

102b Characterisation $^1$H NMR (400 MHz, CDCl$_3$) δ 7.45-7.28 (m, 7H), 6.89 (d, 2H, J=8.5 Hz), 6.70 (s, 1H), 6.19 (s, 1H), 5.74-5.57 (m, 2H), 5.20-5.04 (m, 4H), 4.52-4.35 (m, 2H), 4.31 (dd, 1H, J=18.1, 5.8 Hz), 4.14 (d, 1H, J=18.2 Hz), 3.94 (s, 3H), 3.82 (s, 3H), 3.77-3.69 (m, 1H), 3.07 (d, 1H, J=16.2 Hz), 2.73-2.63 (m, 1H); MS (ES+): m/z=557.2 (M+H)$^+$; LC Retention Time (Method B): t$_R$=3.62.

Allyl (6aS)-3-hydroxy-2,6-dimethoxy-8-(4-methoxyphenyl)-12-oxo-6,6a,9,10-tetrahydrobenzo[e]pyrido[1,2-α][1,4]diazepine-5(12H)-carboxylate (103a) and allyl (6aS)-3-hydroxy-2,6-dimethoxy-8-(4-methoxy-phenyl)-12-oxo-6,6a,7,10-tetrahydrobenzo[e]pyrido[1,2-α][1,4]diazepine-5(12H)-carboxylate (103b)

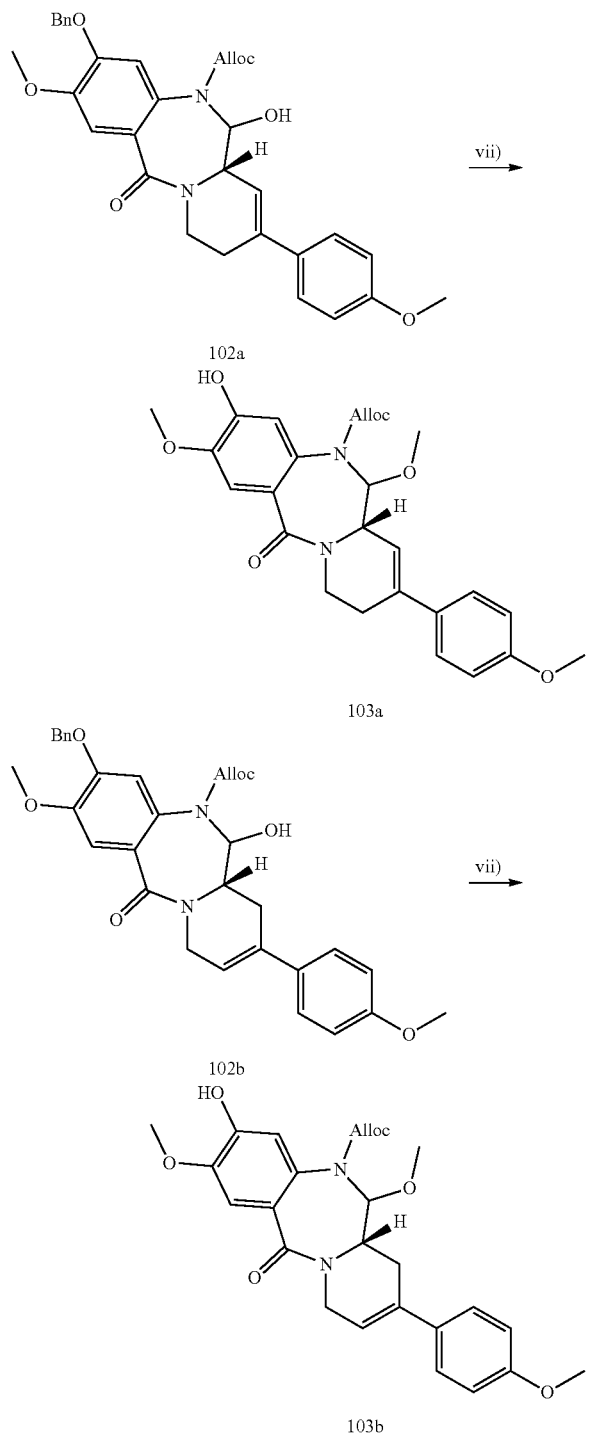

102a (0.125 g, 0.23 mmol) was dissolved in anhydrous DCM (10 ml) under nitrogen. To this solution, boron trichloride (0.079 g, 0.67 mmol) was added as a 1 M solution in DCM. After fifteen minutes, it was determined that the starting material had been completely consumed via LC-MS and TLC analysis. An excess of methanol (50 ml) was then added to the reaction mixture and the solution stirred for a further three hours. At this point, LC-MS and TLC analysis showed the formation of 11a. The reaction mixture was then concentrated to yield a yellow oil. Further purification using flash column chromatography (80:20 ethyl acetate/petroleum ether) yielded 103a as an orange solid in 42% yield*.

* Some interconversion of 103a to 103b (and vice versa) was observed during purification of the reaction mixture. This olefinic interconversion is possibly borane-catalysed. The regiomeric mix obtained in both cases was separated using the flash column chromatography conditions described above.

Using this procedure, 102b was converted to 103b in similar yields (45%, grey solid).

103a Characterisation $^1$H NMR (400 MHz, CDCl$_3$) δ 7.35 (d, 2H, J=8.0 Hz), 7.20 (s, 1H), 6.88 (d, 2H, J=8.2 Hz), 6.78 (s, 1H), 6.04-6.01 (m, 1H), 5.92 (s, 1H), 5.85-5.72 (br, 1H), 5.61 (d, 1H, J=9.3 Hz), 5.18-5.06 (m, 2H), 4.71 (d, 1H, J=13.1 Hz), 4.63 (dd, 1H, J=13.5, 5.1 Hz), 4.52-4.49 (m, 1H), 3.94 (s, 3H), 3.92-3.89 (m, 1H), 3.81 (s, 3H), 3.53 (s, 3H), 3.17-3.06 (m, 1H), 2.62-2.55 (m, 2H); MS (ES+): m/z=481.0 (M+H)$^+$; LC Retention Time (Method A): t$_R$=3.43.

103b Characterisation MS (ES+): m/z=481.0 (M+H)$^+$; LC Retention Time (Method A): t$_R$=3.32.

Allyl (6aS)-3-(3-bromopropoxy)-2,6-dimethoxy-8-(4-methoxyphenyl)-12-oxo-6,6a,9,10-tetrahydrobenzo[e]pyrido[1,2-α][1,4]diazepine-5(12H)-carboxylate (104a)

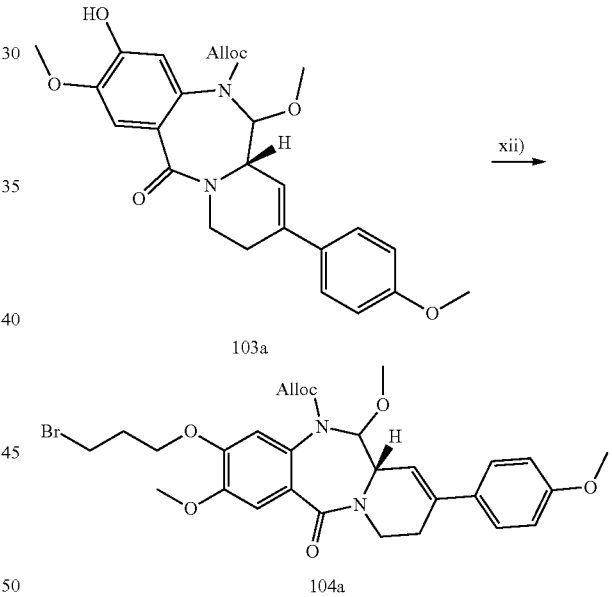

103a (0.035 g, 0.073 mmol) was dissolved in DMF (5 ml). To this solution, potassium carbonate (0.010 g, 0.073 mmol) and 1,3-dibromopropane (0.015 ml, 0.15 mmol) were added, and the solution allowed to stir for 16 hours. At this point, LC-MS analysis confirmed the consumption of the starting material. Water (50 ml) was added to the reaction mixture and the resulting suspension was extracted with ethyl acetate (3×50 ml). The combined organic extracts were washed with saturated sodium bicarbonate (50 ml) and brine (3×50 ml), dried with magnesium sulphate and concentrated under reduced pressure. The resulting oil was further purified using flash column chromatography (80:20 petroleum ether/ethyl acetate) to produce 104a as a brown oil in of 75% purity. This impure intermediate was carried through to the next step with LC-MS analysis only; MS (ES+): m/z=603.1 (M+H)$^+$; LC Retention Time (Method A): t$_R$=8.75.

Diallyl 3,3'-(propane-1,3-diylbis(oxy))(6aS,6a'S)-bis (2,6-dimethoxy-8-(4-methoxyphenyl)-12-oxo-6,6a,9, 10-tetrahydrobenzo[e]-pyrido[1,2-a][1,4]diazepine-5 (12H)-carboxylate) (105a)

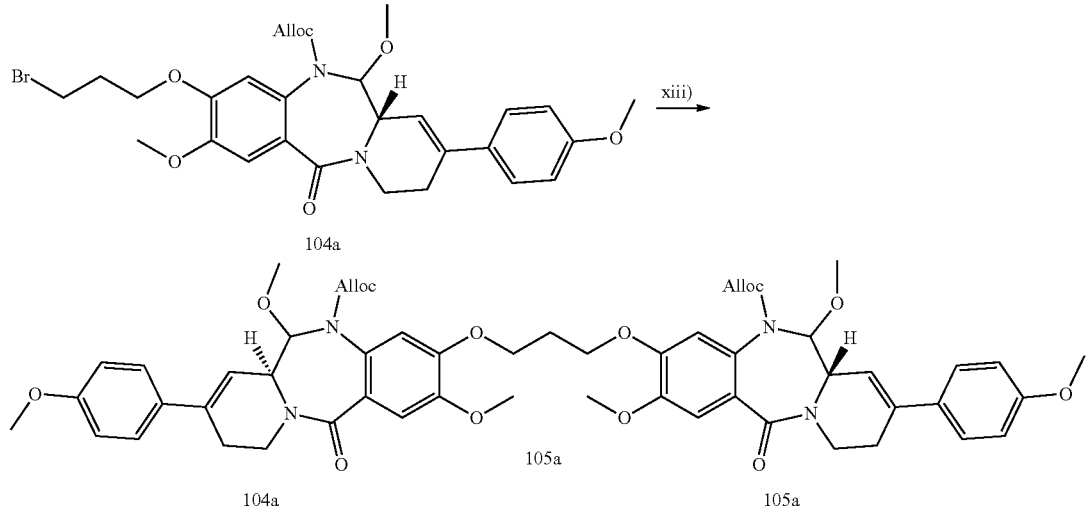

104a (0.020 g, 0.033 mmol) was dissolved in DMF (5 ml). To this solution, potassium carbonate (0.005 g, 0.033 mmol) and 103a (0.014 g, 0.030 mmol) was added. The reaction mixture was heated to 60° C. and stirred for four hours. At this point, formation of the dimer was observed via LC-MS analysis of the reaction mixture. Water (50 ml) was added to the solution, with the resulting suspension extracted with ethyl acetate (3×50 ml). The organic layer was washed with saturated sodium bicarbonate solution (50 ml) and brine (3×50 ml), dried with magnesium sulphate and concentrated under reduced pressure. Flash column chromatography was carried out on the sample obtained (10:90 acetone/DCM) to resolve 105a as a white solid in 51% yield. $^1$H NMR (400 MHz, CDCl$_3$) δ 7.33 (d, 4H, J=8.5 Hz), 7.25 (s, 2H), 6.88 (d, 4H, J=8.2 Hz), 6.71 (s, 2H), 6.05-5.99 (m, 2H), 5.83-5.69 (br, 2H), 5.61 (d, 2H, J=9.1 Hz), 5.09 (d, 4H, J=10.7 Hz), 4.71 (d, 2H, J=12.3 Hz), 4.68-4.57 (m, 2H), 4.50-4.40 (m, 2H), 4.32-4.19 (m, 4H), 3.90 (s, 6H), 3.81 (s, 6H), 3.56 (s, 6H), 3.17-3.06 (m, 2H), 2.64-2.54 (m, 4H), 2.45-2.34 (m, 2H); MS (ES+): m/z=1023.5 (M+Na)$^+$; LC Retention Time (Method A): $t_R$=9.32.

Diallyl 3,3'-(propane-1,3-diylbis(oxy))(6aS,6a'S)-bis (2,6-dimethoxy-8-(4-methoxyphenyl)-12-oxo-6,6a,9, 10-tetrahydrobenzo[e]-pyrido[1,2-a][1,4]diazepine-5 (12H)-carboxylate)(106a)

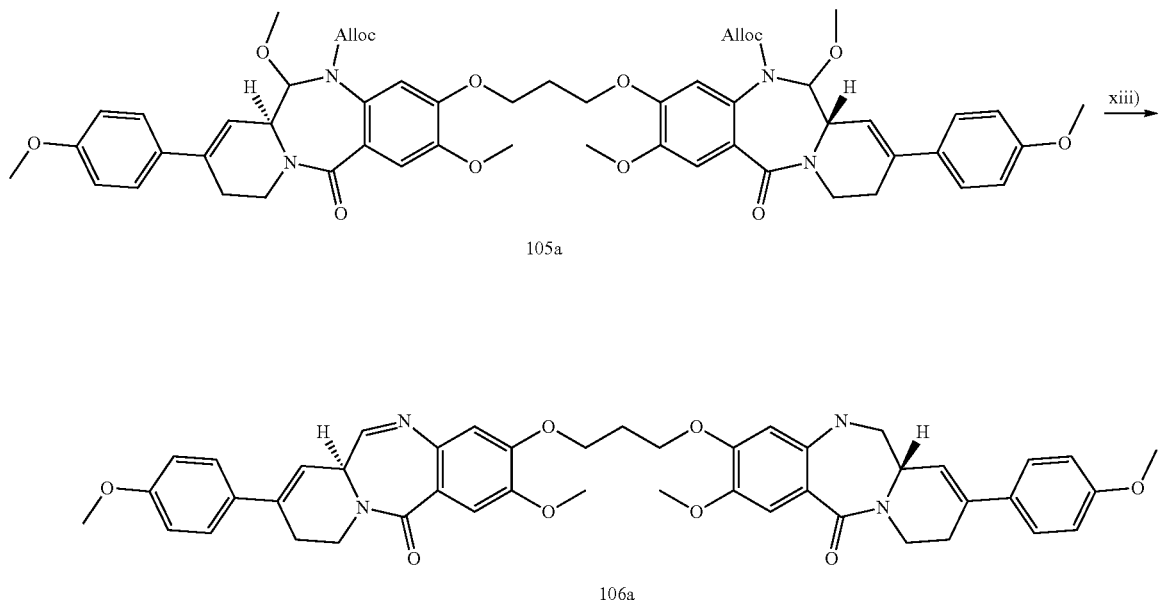

105a (0.017 g, 0.017 mmol) was dissolved in DCM (3 ml). To this solution, tetrakis-(triphenylphosphine)palladium(o) (0.001 g, 0.00085 mmol) and pyrrolidine 0.0013 ml, 0.02 mmol) were added. After fifteen minutes, the reaction was observed to have completed via TLC analysis. The reaction mixture was concentrated under reduced pressure to form an oil, which was re-dissolved in diethyl ether (2 ml) and concentrated under reduced pressure (×3) to remove any residual pyrrolidine. The solid obtained was then purified via flash column chromatography (100% ethyl acetate) to resolve 106a in 76% yield. The dimer obtained was estimated 80% regiopure via the NMR reported below.
¹H NMR (400 MHz, CDCl₃) 7.87 (d, 2H, J=5.3 Hz), 7.47 (s, 2H), 7.39 (d, 4H, J=7.2 Hz), 6.92 (d, 4H, J=7.2 Hz), 6.88 (s, 2H), 6.50 (d, 2H, J=3.7 Hz), 4.56-4.45 (m, 2H), 4.36-4.19 (m, 6H), 3.93 (s, 6H), 3.82 (s, 6H), 3.48-3.37 (m, 2H), 2.72-2.65 (m, 4H), 2.48-2.36 (m, 2H); MS (ES+): m/z=769.5 (M+H)⁺; LC Retention Time (Method A): $t_R$=7.18 (Method B): $t_R$=3.48.

Further Dimer Examples

Four further dimer examples are detailed below as two regioisomer pairs.

Pair One: Aryl Linker

Diallyl 3,3'-((1,3-phenylenebis(methylene))bis(oxy))
(6aS,6a'S)-bis(2,6-dimethoxy-8-(4-methoxyphenyl)-
12-oxo-6,6a,9,10-tetrahydrobenzo[e]-pyrido[1,2-α]
[1,4]diazepine-5(12H)-carboxylate) (107a) and
diallyl 3,3'-((1,3-phenylenebis(methylene))bis(oxy))
(6aS,6a'S)-bis(2,6-dimethoxy-8-(4-methoxyphenyl)-
12-oxo-6,6a,7,10-tetrahydrobenzo[e]pyrido[1,2-α]-
[1,4]-diazepine-5(12H)-carboxylate) (107b)

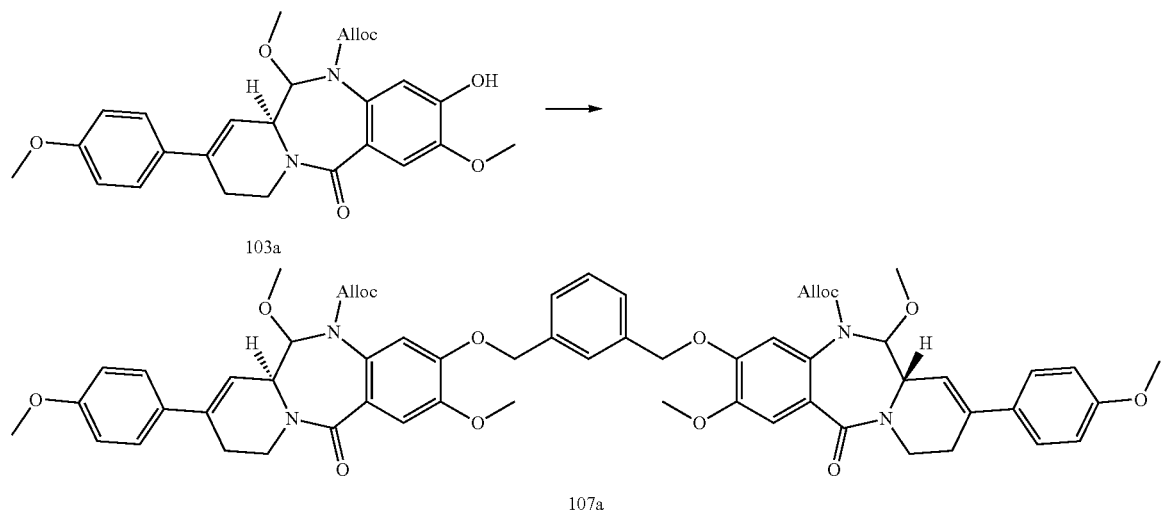

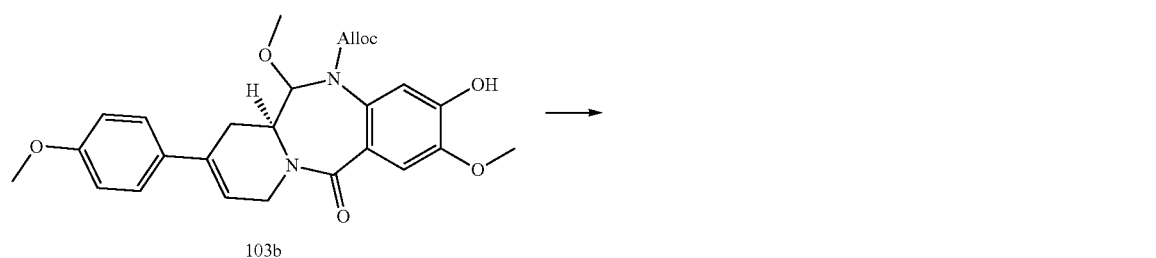

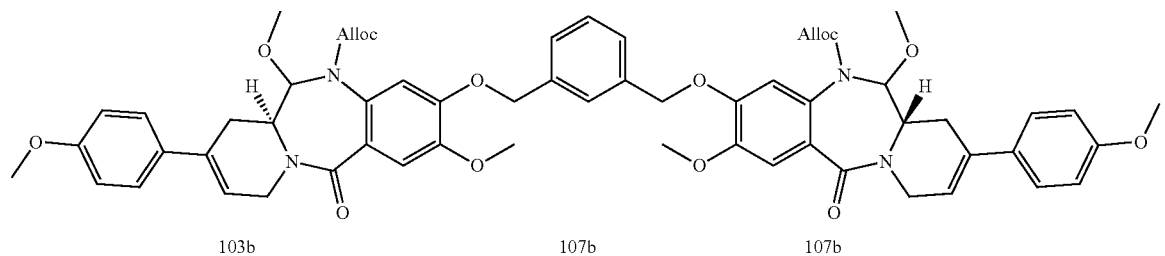

103a (0.035 g, 0.073 mmol) was dissolved in DMF (2 ml). To this solution, 1,3-bis(bromomethyl)benzene (0.011 g, 0.039 mmol) and potassium carbonate (0.010 g, 0.073 mmol) were added and the solution heated at 45° C. for 45 minutes under microwave conditions. At this point the reaction was judged to have proceeded effectively by LC-MS analysis. Water (20 ml) was then added to the reaction mixture and the resulting suspension extracted with ethyl acetate (3×50 ml). The organic extracts were combined and washed with brine (3×100 ml), dried using magnesium sulphate and concentrated under reduced pressure to produce a yellow oil. Further purification using flash column chromatography (10:90 acetone/dichloromethane) produced a cream coloured solid 107a in 73% yield.

A similar procedure was carried out using 103b to generate 107b in 70% yield. 107a Characterisation $^1$H NMR (400 MHz, CDCl$_3$) δ 7.54 (s, 2H) 7.41 (bs, 4H), 7.33 (d, 4H, J=8.1 Hz), 7.22 (s, 2H), 6.88 (d, 4H, J=7.8 Hz), 6.71 (s, 2H), 6.07-6.00 (m, 2H), 5.80-5.66 (m, 2H), 5.66 (d, 2H, J=9.7 Hz), 5.19-5.00 (m, 8H), 4.72-4.35 (m, 6H), 3.92 (s, 6H), 3.81 (s, 6H), 3.51 (s, 6H), 3.16-3.05 (m, 2H), 2.63-2.51 (m, 4H); MS (ES+): m/z=1063.7 (M+H)$^+$; LC Retention Time (Method A): $t_R$=9.43.

107b Characterisation $^1$H NMR (400 MHz, CDCl$_3$) δ 7.52 (s, 2H), 7.40 (bs, 4H), 7.36 (d, 4H, J=8.5 Hz), 6.90 (d, 4H, J=8.5 Hz), 6.69 (s, 2H), 6.26-6.20 (m, 2H), 5.76-5.64 (m, 2H), 5.45-5.35 (m, 2H), 5.18-4.99 (m, 8H), 4.61-4.36 (m, 4H), 4.31-4.05 (m, 6H), 3.93 (s, 6H), 3.83 (s, 6H), 3.70-3.59 (m, 2H), 3.42-3.38 (s, 6H), 2.99-2.86 (m, 2H), 2.75-2.62 (m, 2H); MS (ES+): m/z=1063.2 (M+H)$^+$; LC Retention Time (Method A): $t_R$=4.17.

(6aS,6a'S)-3,3'-((1,3-phenylenebis(methylene))bis(oxy))bis(2-methoxy-8-(4-methoxyphenyl)-9,10-dihydrobenzo[e]pyrido[1,2-α][1,4]-diazepin-12(6aH)-one) (108a) and (6aS,6a'S)-3,3'-((1,3-phenylenebis-(methylene))bis(oxy))bis(2-methoxy-8-(4-methoxyphenyl)-7,10-dihydrobenzo[e]pyrido[1,2-α][1,4]diazepin-12(6aH)-one) (108b)

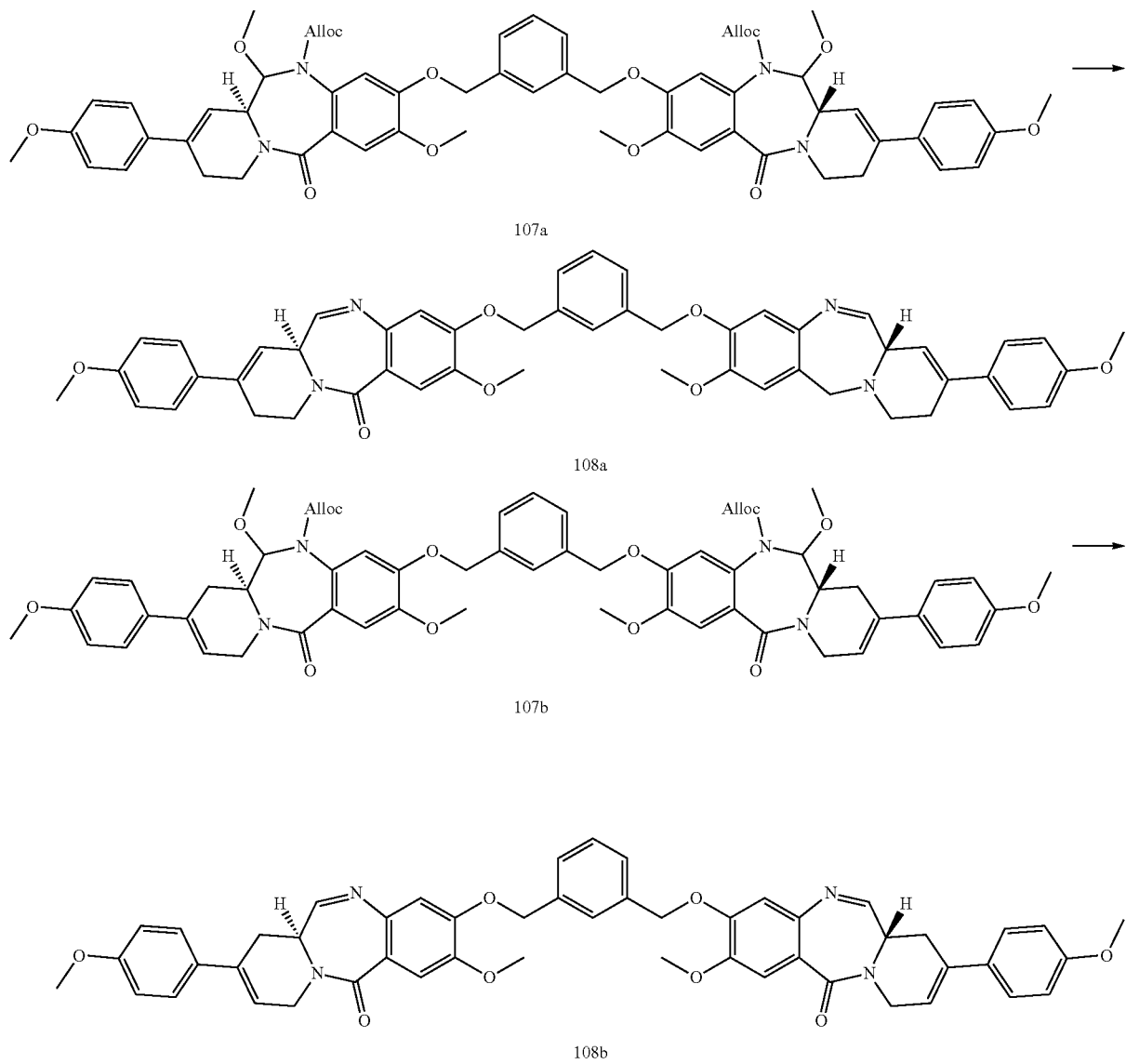

107a

108a

107b

108b 107a (0.015 g, 0.014 mmol) was dissolved in DCM (3 ml). To this solution, tetrakis-(triphenylphosphine)palladium(o) (0.001 g, 0.00085 mmol) and pyrrolidine 0.0026 ml, 0.04 mmol) were added. After five minutes, the reaction was observed to have completed via TLC analysis. The reaction mixture was concentrated under reduced pressure to form an oil, which was re-dissolved in diethyl ether (2 ml) and concentrated under reduced pressure (×3) to remove any residual pyrrolidine. The solid obtained was then purified via flash column chromatography (25:75 acetone/dichloromethane) to resolve 108a in 65% yield. The dimer obtained was obtained 84% regiopure based upon the NMR reported below.

A similar procedure was carried out for the regioisomer 108b. The yield was 60% and the regiopurity estimated as 88% based upon integration of the NMR reported below.

108a Characterisation $^1$H NMR (400 MHz, CDCl$_3$) 0.84 (d, 2H, 5.3 Hz), 7.53-7.48 (m, 3H), 7.44-7.35 (m, 7H), 6.91 (d, 4H, J=8.4 Hz), 6.85 (s, 2H), 6.05 (d, 2H, J=3.9 Hz), 5.21 (q, 4H, J=12.4 Hz), 4.54-4.41 (m, 2H), 4.32-4.26 (m, 2H), 3.96 (s, 6H), 3.83 (s, 6H), 3.49-3.37 (td, 2H, J=13.9, 7.6 Hz), 2.72-2.65 (m, 4H); MS (ES+): m/z=831.4 (M+H)$^+$; LC Retention Time (Method A): t$_R$=7.33 (Method B): t$_R$=3.58.

108b Characterisation $^1$H NMR (400 MHz, CDCl$_3$) δ 7.59 (d, 2H, J=5.4 Hz), 7.54 (s, 2H), 7.50 (s, 1H), 7.43-7.38 (m, 7H), 6.93 (d, 4H, J=7.9 Hz), 6.83 (s, 2H), 6.39-6.35 (m, 2H), 5.20 (q, 4H, J=12.8 Hz), 4.46 (dd, 2H, J=18.0, 6.1 Hz), 4.11 (d, 2H, J=18.1 Hz), 3.97 (s, 6H), 3.94 (d, 2H, 5.0 Hz), 3.84 (s, 6H), 2.94 (m, 4H); MS (ES+): m/z=831.3 (M+H)$^+$; LC Retention Time (Method A): t$_R$=7.42 (Method B): t$_R$=3.55.

Pair Two: Pyridine Linker

Diallyl 3,3'-((pyridine-2,6-diylbis(methylene))bis(oxy))(6aS,6a'S)-bis(2,6-dimethoxy-8-(4-methoxyphenyl)-12-oxo-6,6a,9,10-tetrahydrobenzo[e]pyrido[1,2-α][1,4]diazepine-5(12H)-carboxylate) (109a) and diallyl 3,3'-((pyridine-2,6-diylbis(methylene))bis(oxy))(6aS,6a'S)-bis(2,6-dimethoxy-8-(4-methoxyphenyl)-12-oxo-6,6a,7,10-tetrahydrobenzo[e]-pyrido[1,2-α][1,4]diazepine-5(12H)-carboxylate) (109b)

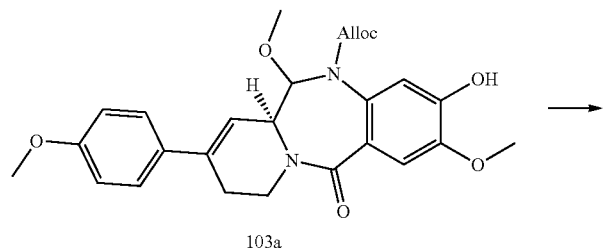

103a

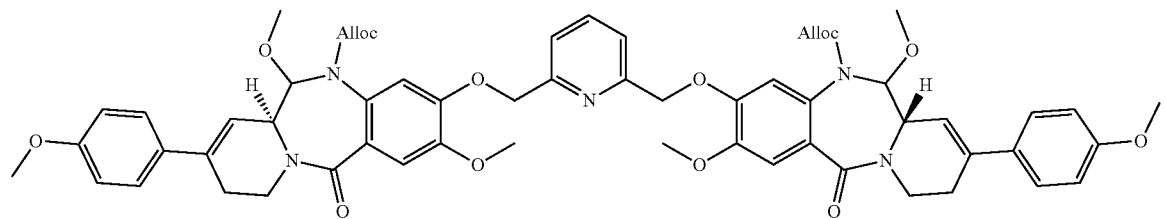

109a

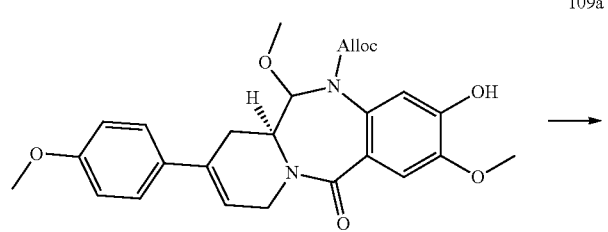

103b

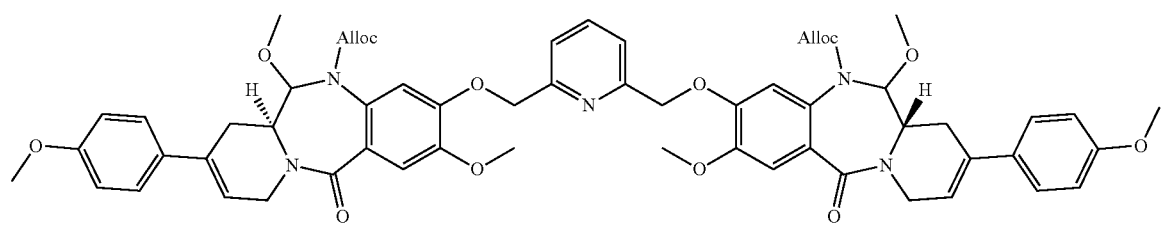

109b 103a (0.035 g, 0.073 mmol) was dissolved in DMF (2 ml). To this solution, 2,6-bis(bromomethyl)pyridine (0.011 g, 0.039 mmol) and potassium carbonate (0.010 g, 0.073 mmol) were added and the solution heated at 45° C. for 45 minutes under microwave conditions. At this point the reaction was judged to have proceeded effectively by LC-MS analysis. Water (20 ml) was then added to the reaction mixture and the resulting suspension extracted with ethyl acetate (3×50 ml). The organic extracts were combined and washed with brine (3×100 ml), dried using magnesium sulphate and concentrated under reduced pressure to produce a yellow oil. Further purification using flash column chromatography (20:90 acetone/dichloromethane) produced a cream coloured solid 109a in 68% yield.

A similar procedure was carried out for the regioisomer 103b to produce the compound 109b in 74% yield.

109a Characterisation $^1$H NMR (400 MHz, CDCl$_3$) δ 7.79 (t, 1H, J=7.7 Hz), 7.54 (d, 2H, J=7.7 Hz), 7.33 (d, 4H, J=8.7 Hz), 7.24 (s, 2H), 6.88 (d, 4H, J=8.8 Hz), 6.73 (s, 1H), 6.01 (d, 2H, J=2.8 Hz), 5.76-5.34 (m, 2H), 5.59 (d, 2H, J=9.1 Hz), 5.27 (s, 4H), 5.13-4.98 (m, 4H), 4.72 (d, 2H, J=12.7 Hz), 4.61-4.38 (m, 4H), 3.95 (s, 6H), 3.92 (d, 2H, J=11.7 Hz), 3.82 (s, 6H), 3.49 (s, 6H), 3.17-3.07 (m, 2H), 2.66-2.50 (m, 4H); MS (ES+): m/z=1064.2 (M+H)$^+$; LC Retention Time (Method B): t$_R$=4.17.

109b Characterisation $^1$H NMR (400 MHz, CDCl$_3$) δ 7.78 (t, 1H, J=7.8 Hz), 7.53 (d, 2H, J=7.7 Hz), 7.35 (d, 4H, J=8.6 Hz), 7.27 (s, 2H), 6.90 (d, 4H, J=8.6 Hz), 6.69 (s, 2H), 6.26-6.19 (m, 2H), 5.74-5.58 (m, 2H), 5.40 (d, 2H, J=9.6 Hz), 5.25 (s, 4H), 5.11-4.95 (m, 4H), 4.58-4.33 (m, 4H), 4.26 (dd, 2H, J=18.1, 5.6 Hz), 4.14 (d, 2H, J=18.1 Hz), 3.95 (s, 6H), 3.81 (s, 6H), 3.63 (dd, 2H, J=8.0, 6.1 Hz), 3.38 (s. 6H), 2.93 (d, 2H, J=15.1 Hz), 2.72-2.55 (m, 2H); MS (ES+): m/z=1064.3 (M+H)$^+$; LC Retention Time (Method B): t$_R$=4.02.

(6aS,6a'S)-3,3'-((pyridine-2,6-diylbis(methylene))bis(oxy))-bis(2-methoxy-8-(4-methoxyphenyl)-9,10-dihydrobenzo[e]pyrido[1,2-α][1,4]diazepin-12(6aH)-one) (110a) and (6aS,6a'S)-3,3'-((pyridine-2,6-diylbis(methylene))bis(oxy))bis(2-methoxy-8-(4-methoxyphenyl)-7,10-dihydrobenzo[e]pyrido[1,2-α][1,4]diazepin-12(6aH)-one) (110b)

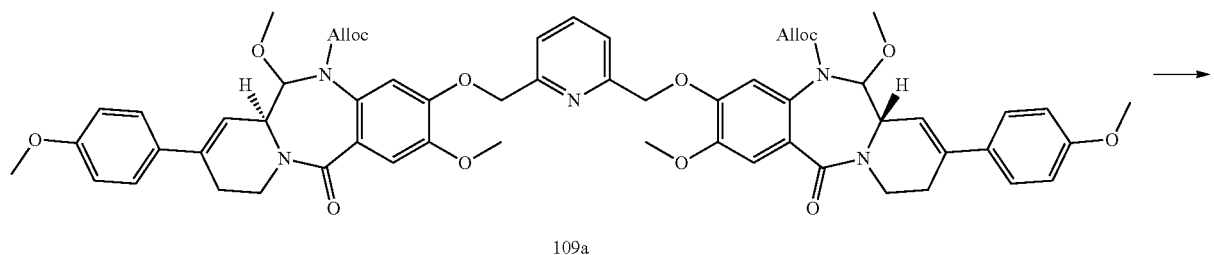

109a

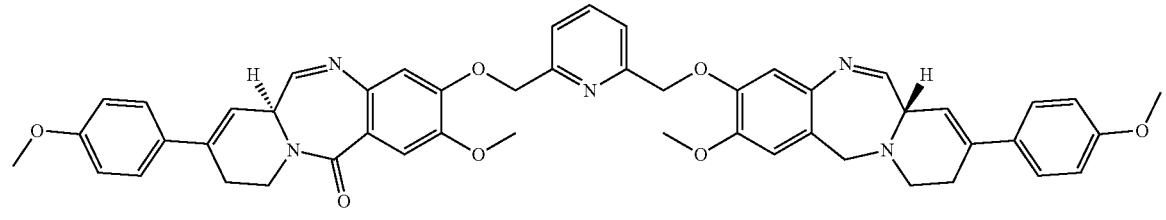

110a

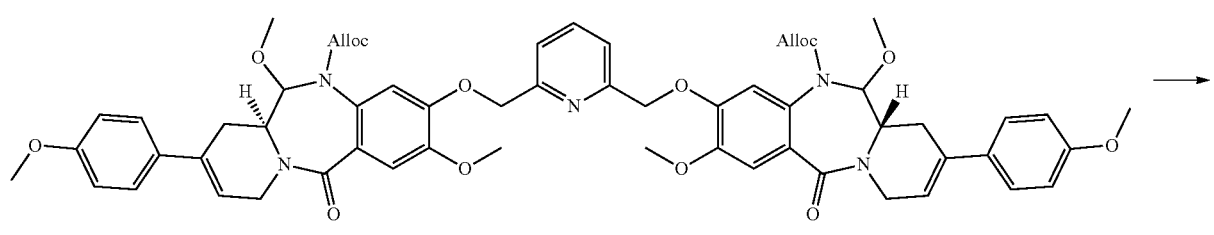

109b

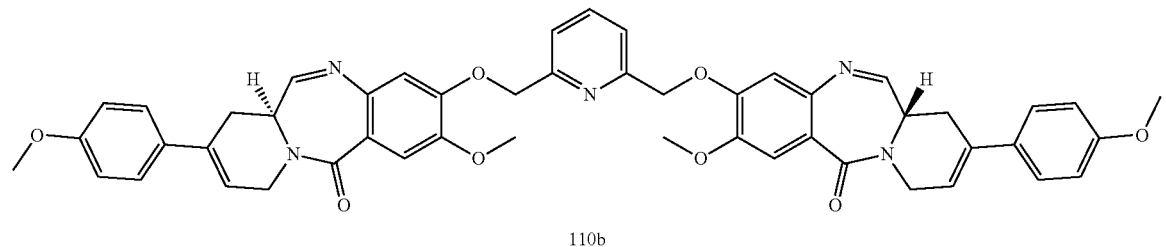

110b 109a (0.025 g, 0.023 mmol) was dissolved in DCM (3 ml). To this solution, tetrakis-(triphenylphosphine)palladium(o) (0.002 g, 0.0013 mmol) and pyrrolidine 0.0042 ml, 0.065 mmol) were added. After five minutes, the reaction was observed to have completed via TLC analysis. The reaction mixture was concentrated under reduced pressure to form an oil, which was re-dissolved in diethyl ether (2 ml) and concentrated under reduced pressure (×3) to remove any residual pyrrolidine. The solid obtained was then purified via flash column chromatography (35:75 acetone/dichloromethane) to resolve 110a in 34% yield. The dimer obtained was obtained was >90% regiopure based upon the NMR reported below.

A similar procedure was carried out for the regioisomer 109b to generate the compound 110b. The yield was 67% and the regiopurity estimated as >90% based upon integration of the NMR reported below.

110a Characterisation $^1$H NMR (400 MHz, CDCl$_3$) δ 7.86 (d, 2H, J=5.3 Hz), 7.74 (t, 1H, J=7.8 Hz), 7.48 (d, 2H, J=7.8 Hz), 7.43-7.35 (m, 4H), 6.95-6.89 (m, 4H), 6.86 (s, 2H), 6.06 (d, 2H, J=4.0 Hz), 5.34 (s, 4H), 4.51 (dt, 2H, J=13.2, 4.6 Hz), 4.30 (t, 2H, J=4.7 Hz), 4.00 (s, 6H), 3.83 (s, 6H), 3.44 (dt, 2H, J=13.3, 6.8 Hz), 2.76-2.64 (m, 4H); MS (ES+): m/z=832.1 (M+H)$^+$; LC Retention Time (Method A): $t_R$=7.35 (Method B): $t_R$=3.40.

110b Characterisation $^1$H NMR (400 MHz, CDCl$_3$) δ 7.72 (t, 1H, J=7.8 Hz), 7.58 (d, 2H, J=5.5 Hz), 7.55 (s, 2H), 7.46 (d, 2H, J=7.8 Hz), 7.42-7.36 (m, 4H), 6.95-6.89 (n, 4H), 6.84 (s, 2H), 6.36 (dd, 2H, J=3.0, Hz), 5.31 (s, 4H), 4.45 (dd, 2H, 18.3, 5.9 Hz), 4.15-4.07 (m, 2H), 3.99 (s, 6H), 3.83 (s, 6H), 3.96-3.90 (m, 2H), 2.96-2.91 (n, 4H); MS (ES+): m/z=832.3 (M+H)$^+$; LC Retention Time (Method A): $t_R$=7.47 (Method B): $t_R$=3.43.

Biological and Biophysical Characterisation Write-Up for Patent 6 Cytotoxicity in Cell Lines The cytotoxicity of compounds 26, 34, 50, 58 and 68 were evaluated in a variety of cell lines using the standard MTT assay for a 72 hour incubation period (Table 1).

of an interstrand cross-link holds the denatured strands in close proximity, and cross-linked adducts therefore run as double-stranded DNA on polyacrylamide gel. Talirine and 34 were tested at >10 different concentrations, and the assay was repeated twice. The cross-linking ability of 34 is shown in FIG. 6. FIG. 6 shows an autoradiograph of a denaturing polyacrylamide gel showing DNA interstrand cross-linking by 34 in linear $^{32}$P-end-labelled HexA DNA following overnight incubation at 37° C. at various concentrations. C1 and C2 represent controls where C1 is DNA without formic acid, and C2 is DNA without formic acid, but heated thereby forming single strands. Cross-links are clearly detectable at concentrations as low as 10 nM. Using the same assay, the PBD dimer Talirine was also shown to cross-link DNA down to a concentration of 10 nM (FIG. 7). These results demonstrate that 34 can produce DNA cross-links at concentrations comparable to the PBD dimer Talirine.

DNA Footprinting

The sequence selectivity of 26 and 34 was investigated using a modification of the previously established DNA footprinting assay[25]. Following an overnight incubation of the ligand-DNA complexes, the mixture was mixed with strand separation buffer containing 10 mM EDTA, 10 mM NaOH, 0.1% bromophenol blue, 80% formamide and incubated at 100° C. for 3 min. The mixture was then immediately cooled on ice and run on an 8% denaturing gel. Examination of the obtained gel (FIG. 8) shows distinct footprints produced by 26 and 34. Furthermore, both DNA fragments contain multiple potential binding sites for 26 and 34 (i.e., multiple examples of potential G-G cross-linking sites), but surprisingly only three preferred sites were observed during this experiment. These footprints correspond to the general code XYWWYWYX, where X is any base, Y is G or C and W is A or T. This suggests that the molecule acts in a highly sequence selective manner. The possible adducts formed within both sequences are shown in FIG. 9.

| Code | Cytotoxicity (72 hours) nM | | | | | |
|---|---|---|---|---|---|---|
| | SK-BR-3 | Std Dev (3 runs) | MCF-7 | Std Dev (3 runs) | ZR 75-1 | Std Dev (3 runs) |
| 26 | 0.006 | 0.001 | 0.006 | 0.001 | 0.005 | 0.001 |
| 34 | 0.041 | 0.013 | 0.057 | 0.008 | 0.159 | 0.061 |

| Code | Cytotoxicity (72 hours) nM | | | | | |
|---|---|---|---|---|---|---|
| | SW48 | Std Dev (3 runs) | LIM 1215 | Std Dev (3 runs) | SW 620 | Std Dev (3 runs) |
| Talirine | 0.003 | 0.002 | 0.434 | 0.025 | 0.017 | 0.002 |
| 26 | 0.006 | 0.001 | 0.006 | 0.001 | 0.005 | 0.001 |
| 34 | 0.0077 | 0.002 | 0.0003 | 0.00005 | 0.325 | N/A |
| 50 | 0.0031 | 0.011 | 0.0037 | 0.003 | 1.35 | N/A |
| 58 | 0.0086 | 0.0031 | 0.023 | 0.003 | 0.092 | 0.008 |
| 68 | 0.012 | 0.0001 | 0.013 | 0.0001 | 0.03 | 0.005 |

Biophysical Characterisation

The ability of 26 and 34 to cross-link DNA was determined using an assay involving linear double-stranded HexA. TyrT and MS1 DNA fragments (FIG. 5). The PBD dimer Talirine (SGD1882) was used as a positive control, as PBD dimers have previously been shown to cross-link DNA[24].

Following denaturation conditions (treatment with formamide and heating at 65° C. for 5 min) the DNA strands were completely separated (see control C2, FIG. 6). The presence FRET DNA Melting FRET DNA melting studies were undertaken on 26 and 34 using a number of fluorescently labelled sequences. The sequences (FIG. 10) were designed to provide additional evidence that 26 and 34 can form inter- and intrastrand cross-links at the site 5'-XYWWYWYX-3'.

The short duplexes used in this FRET study are relatively unstable in the duplex form with a melting temperature below 30° C. so that, in the absence of ligand, a large part of the melting occurs below the starting temperature of the experiment. However, the intrastrand cross-links formed by 34 stabilize the duplex form, producing large increases in melting temperature with $T_m$ values of ~71° C. for 5'-AAAAAAGAGAAGAAAAAA-3' (FIG. 11, 1st panel) suggesting intrastrand cross-link formation in the DNA-footprinting derived binding site and 66° C. for AAAAAAGAGAGAAAAAA-3' (FIG. 11, 3rd panel) suggesting intra-strand cross-link formation and two sites. Interestingly, 5'-AAAAAAGAGAAGAAAAAA-3' directly corresponds to a footprint derived for 34, whereas 5'-AAAAAAGAGAGAAAAAA-3' represents an intra-strand cross-link with one less base-pair, and it is evident from FRET stabilisation that the GAGAAG adduct is preferred. In the case of inter-strand cross-link studies, 34 stabilises 5'-AAAAAAGAGAACAAAAAA-3' with a $T_m$ value of ~71° C., which suggests strong DNA interactivity. Furthermore, 34 exhibits limited stabilisation of 5'-AAAAAAGATCAAAAAA-3' (which represents a traditional PBD binding site), suggesting the molecules outlined possess an alternative DNA sequence selectivity profile to the prior art.

Figure 11:
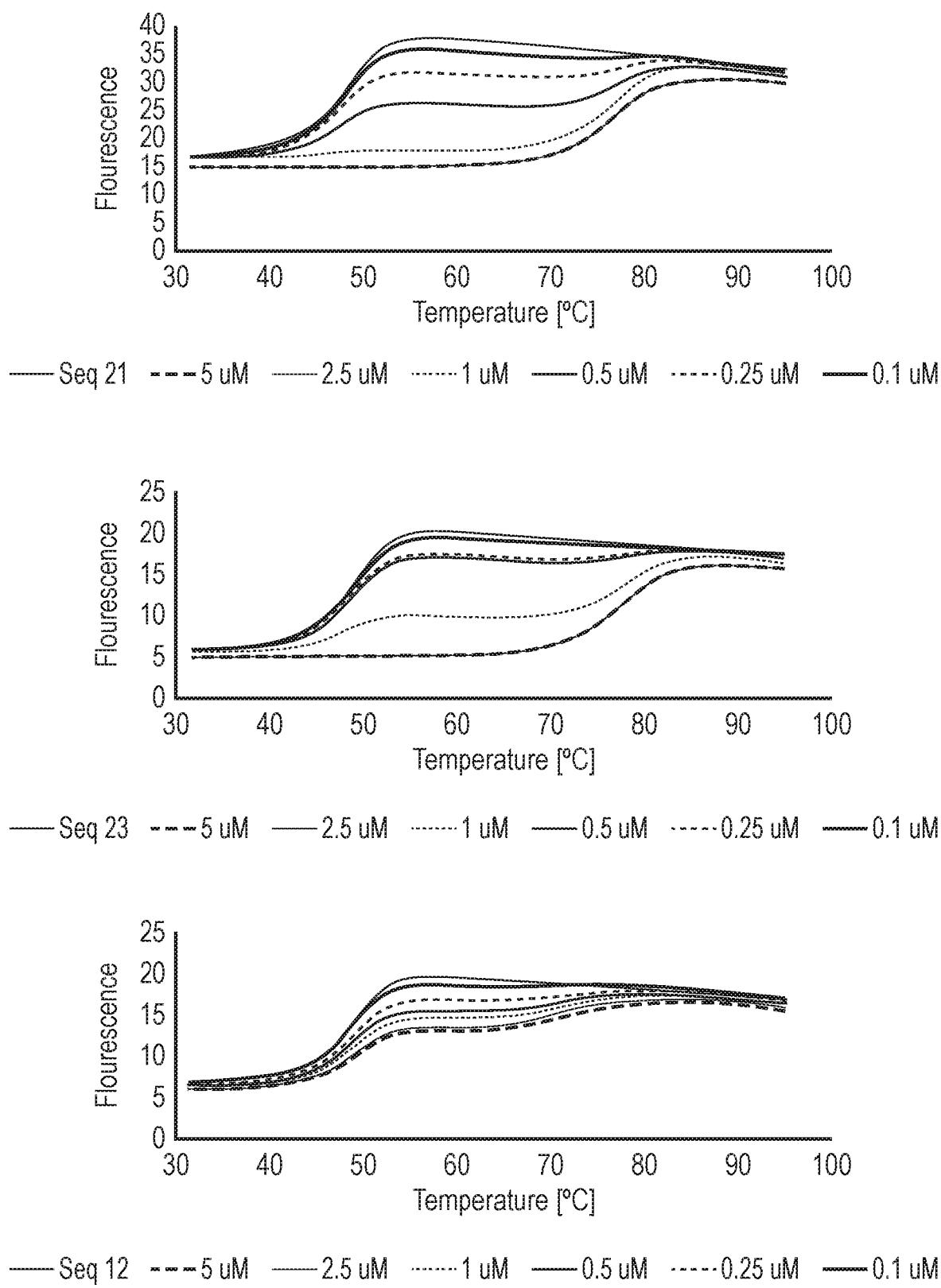
FIG. 11 shows FRET Denaturation data for 5'-AAAAAAGAGAAGAAAAAA-3' (Seq 21) and 5'-AAAAAAGAGAGAAAAAA-3' (Seq 20), 5'-AAAAAAGAGAACAAAAAA-3' (Seq 23) and 5'-AAAAAAGATCAAAAAA-3' (Seq 12) shown in FIG. 6.

As can be seen from FIG. 11, the melting temperature of each duplex increases significantly in proportion to the concentration of 34 present, providing strong supporting evidence that the compound can produce intra- and inter-strand cross-links.

Summary of Cross-Linking Data

Figure 8:
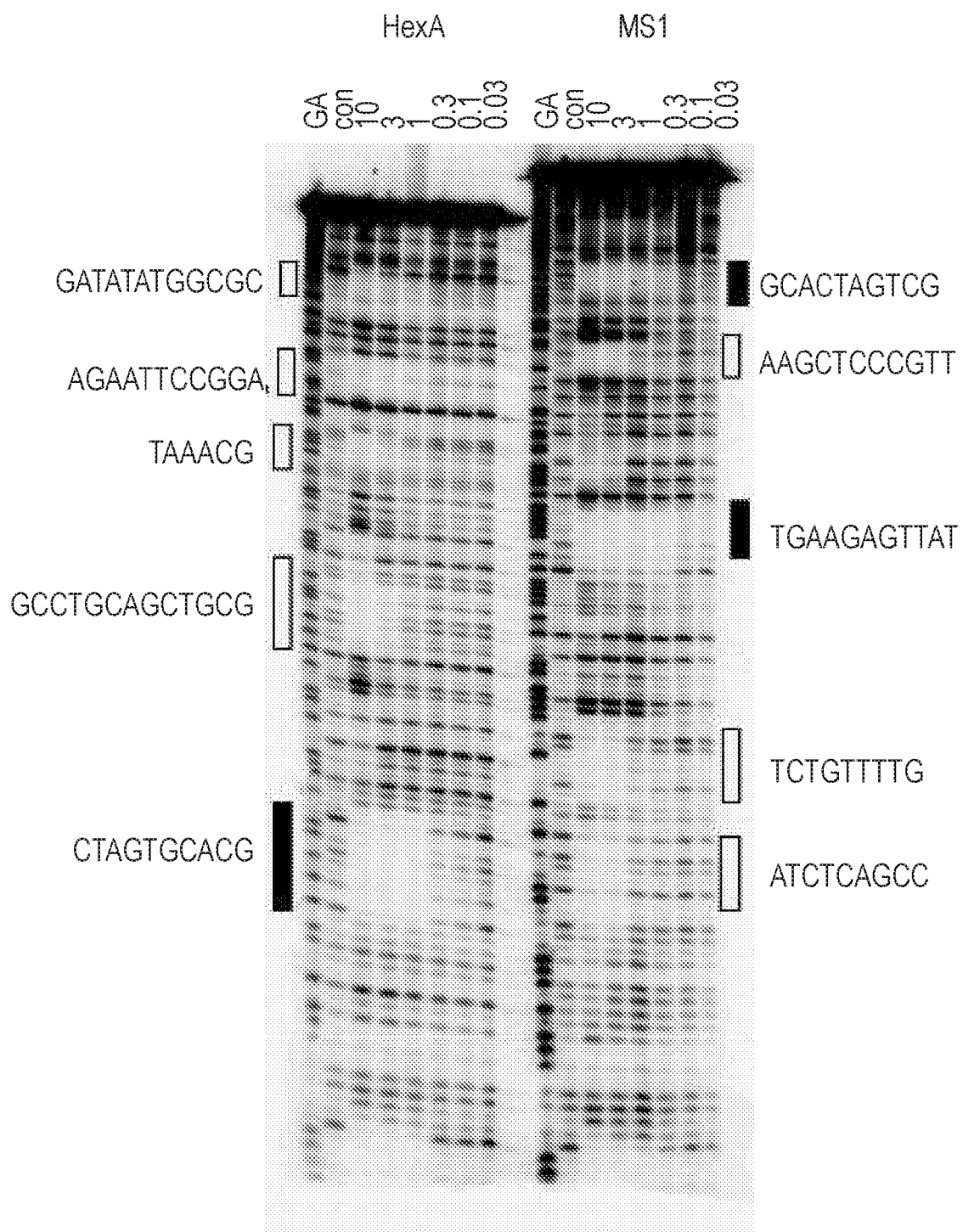
FIG. 8 shows DNA footprinting gel showing the interaction of 26 (bottom panel) and 34 (top panel) with HexA and MS1 DNA fragments. Ligand concentrations are shown at the top of the gel. Tracks labelled "GA" are markers for specific purines, and solid black lines represent strong footprints.
Figure 8:
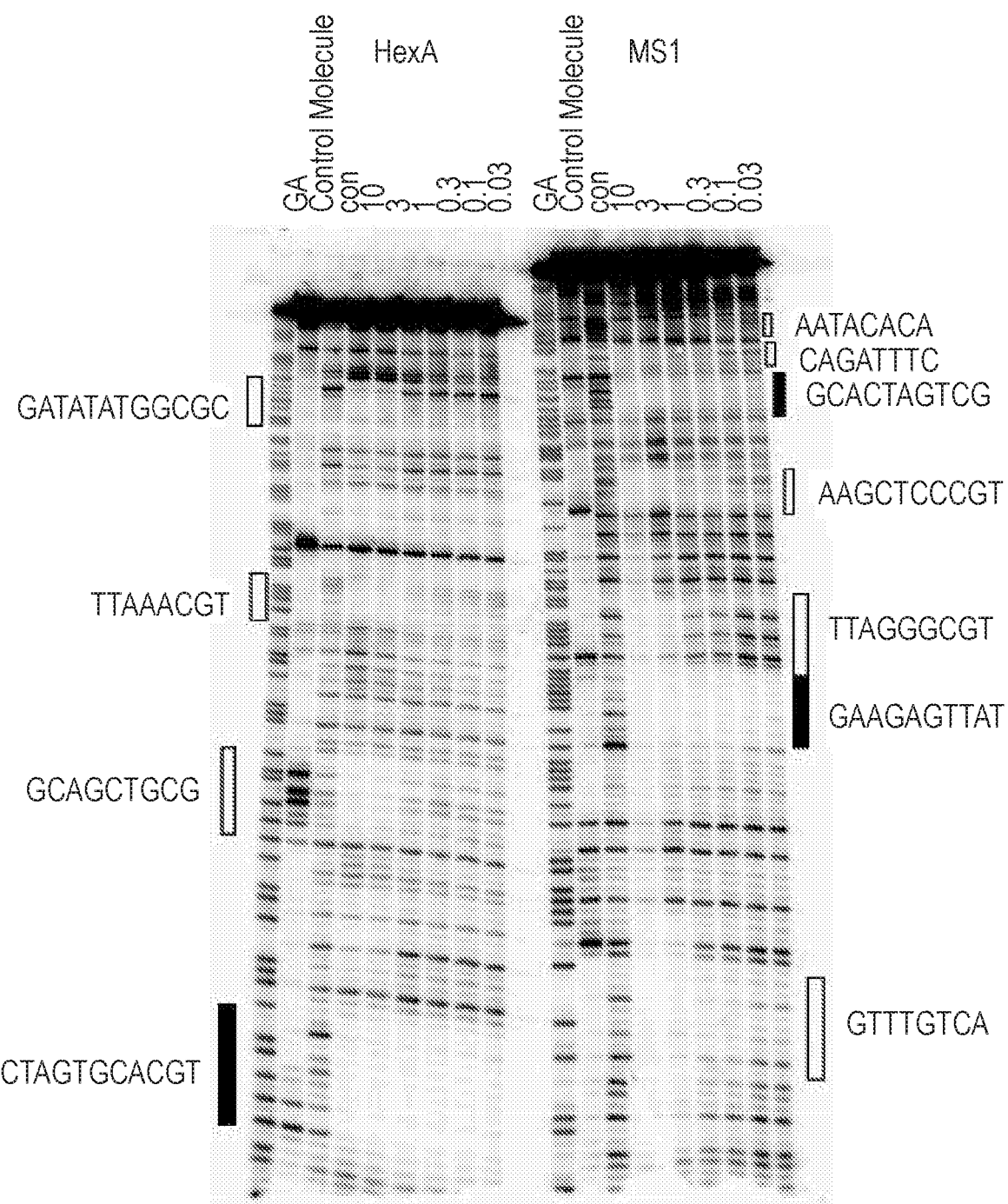
Figure 9:
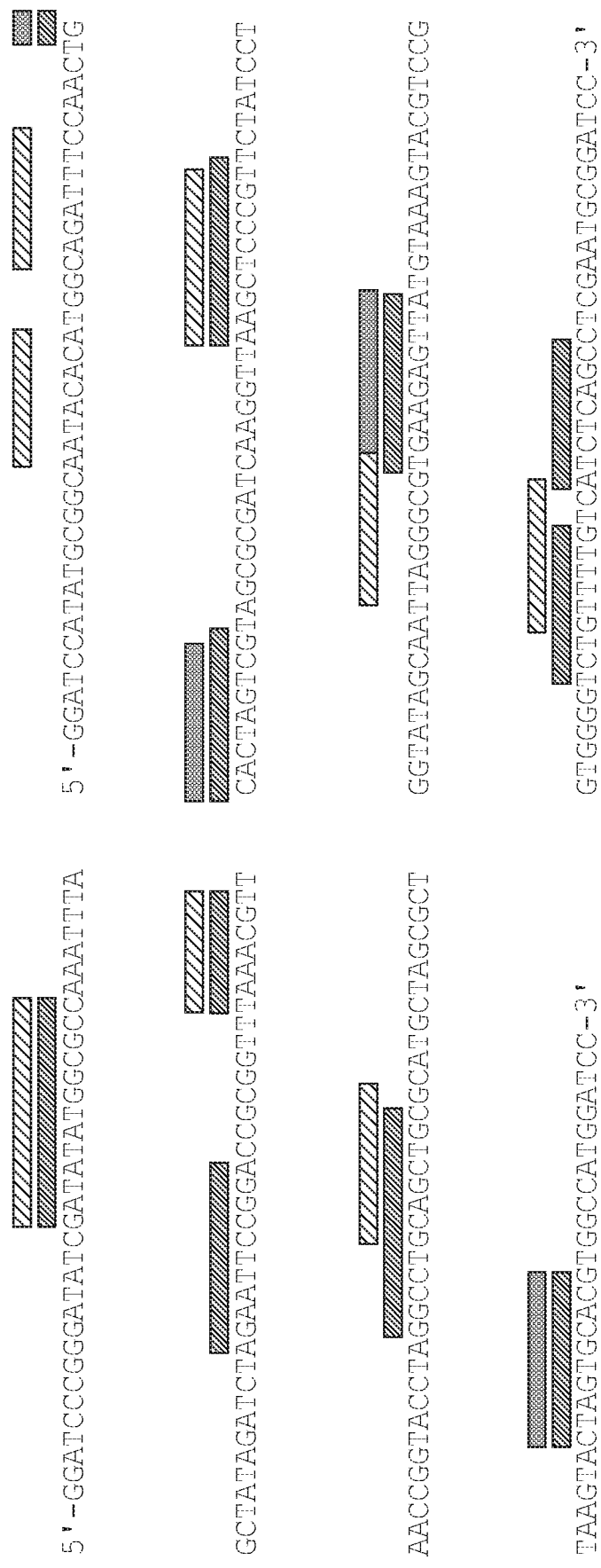
FIG. 9 shows a sequence of the HEXA and MS1 DNA fragments showing the possible adducts formed relating to both 26 and 34.

Taken together, the cross-linking data presented above provide strong evidence that 34 (and its analogues—data not shown) produces both intrastrand and interstrand cross-links which appear to form with a high degree of sequence-specificity (e.g., FIGS. 8 and 9). It is possible that the compound may also form mono-alkylated adducts with guanines. Together, this population of DNA adduct types may account for the cytotoxicity of this family of compounds in cells.

Biophysical Characterisation Methodology

1. Material 1.1. DNA Fragment

The preparation of the DNA fragments (FIG. 5) has been previously described[4]. Briefly, the sequence which had been cloned into the BamHI site of pUC18 was obtained by cutting with HindIII and EcoRI. Radiolabelled DNA fragments were prepared by filling in the 3'-end of the HindIII site with [α-$^{32}$P]dATP using Klenow DNA polymerase (exo-).

The radiolabelled DNA fragment was separated from the remainder of the plasmid DNA on a 6% non-denaturing polyacrylamide gel. The gel (20 cm long, 0.3 mm thick) was run at 400 V in 1×TBE running buffer for about 1-2 h, until the bromophenol blue had run most of the way down the gel. The glass plates were separated and the position of the labelled DNA fragment was established by short (1 min) exposure to an X-ray film. The relevant band was then cut from the gel and the radiolabelled DNA eluted by adding 300 μL 10 mM Tris-HCl, pH 7.5 containing 0.1 mM EDTA and gently agitating overnight at room temperature. The eluted DNA was finally precipitated with ethanol and re-suspended in a suitable volume of 10 mM Tris-HCl, pH 7.5 containing 0.1 mM EDTA buffer so as to give at least 10 counts per second/μL on a hand-held Geiger counter. With fresh plasmid and α-$^{32}$P-dATP this process typically generated about 150 μL of radiolabelled fragment DNA. The absolute concentration of the DNA is not important, and it is typically lower than 10 nM.

Footprinting reactions were performed as previously described[5] using the DNA fragments HexA and HexB, which together contain all 64 symmetrical hexanucleotide sequences[6], and MS1 that contains all possible 134 tetra-nucleotide sequences[7]. The DNA fragments were obtained by cutting the parent plasmids with HindIII and SacI (for HexA and MS1) or EcoRI and PstI (for HexB), and were labelled at the 3'-end of the HindIII or EcoRI sites with [α-$^{32}$P]dATP using reverse transcriptase or exo-Klenow fragment. After gel purification, the radiolabelled DNA was dissolved in 10 mM Tris-HCl pH 7.5 containing 0.1 mM EDTA, at a concentration of about 10 c.p.s per μL as determined on a hand held Geiger counter. 1.5 μL of radiolabelled DNA was mixed with 1.5 μL ligand that had been freshly diluted in 10 mM Tris-HCl pH 7.5, containing 10 mM NaCl. The complexes were left to equilibrate for at least 12 hours before digesting with 2 μL DNase I (final concentration about 0.01 units/mL). The reactions were stopped after 1 minute by adding 4 μL of formamide containing 10 mM EDTA and bromophenol blue (0.1% w/v). The samples were then heated at 100° C. for 3 minutes before loading onto 8% denaturing polyacrylamide gels containing 8 M urea. Gels were fixed in 10% acetic acid, transferred to 3MM paper, dried and exposed to a phosphor screen overnight, before analysing with a Typhoon phosphorimager.

1.2. Compounds 32 was synthesised as described above and the PBD dimer Talirine was obtained from Aurum Pharmatech LLC. Stock solution was prepared by dissolving the ligands in DMSO to give a concentration of 10 mM. From this stock solution, working solutions of the desired concentration were prepared by diluting with 10 mM Tris-HCl, pH 7.5 containing 10 mM NaCl.

2. Cleavage Assay 2.1. Preparation of Ligand-DNA Complexes

Radiolabelled DNA (1.5 μL) was mixed with 1.5 μL ligand solution of various concentrations (10 μM-10 nM) and incubated overnight at 37° C.

2.2. Preparation of GA Marker

Labelled DNA (1.5 μL) was mixed with 20 μL sterile water and 5 μL of denaturing loading solution (80% formamide containing 10 mM EDTA, 10 mM NaOH, 0.01% bromophenol blue). The sample was then incubated at 100° C. for 20 min with the micro-centrifuge tube cap open to allow evaporation.

3. Cross-Linking Assay 3.1. Preparation of Ligand-DNA Complexes

Radiolabelled DNA (1.5 μL) was mixed with 1.5 μL ligand solution of various concentrations (10 μM-10 nM) and incubated overnight at 37° C.

3.2 Cross-Linking Assay

After overnight incubation, the samples were mixed with 7 μL loading solution (80% formamide containing 10 mM EDTA, 10 mM NaOH, 0.1% bromophenol blue) and incubated at 65° C. for 5 min. Control 1 (C1) for native double-stranded DNA consisted of 1.5 μL labelled DNA, 1.5 μL 10 mM Tris-HCl, pH 7.5 containing 0.1 mM EDTA and 7 μL 1× loading dye. Control 2 (C2) for denatured native single-stranded DNA was composed of 1.5 μL labelled DNA, 1.5 μL 10 mM Tris-HCl, pH 7.5 containing 0.1 mM EDTA which was incubated at 65° C. for 5 min. Control 3 (C3) for native double-stranded DNA consisted of 1.5 μL labelled DNA, 1.5 μL 10 mM Tris-HCl, pH 7.5 containing 0.1 mM EDTA and 7 μL SSB. Control 4 (C4) for denatured native single-stranded DNA was composed of 1.5 μL labelled DNA, 1.5 μL 10 mM Tris-HCl, pH 7.5 containing 0.1 mM EDTA and 7 μL SSB which was incubated at 65° C. for 5 min. Separation was performed on a 7.5% denaturing polyacrylamide gel (20 cm long, 0.3 mm thick) at 500V for about 4 h until the dye reached the bottom of the gel. The gel plates were then separated, the gels fixed by immersing in 10% (v/v) acetic acid, followed by transfer to Whatmann 3MM paper and drying under vacuum at 80° C. The dried gel was then exposed to a phosphorimager screen overnight before scanning using a Typhon FLA 7000 instrument.

FRET Studies Methodology

1. General 1.1. Oligonucleotides

Oligonucleotides were obtained from ATDbio (Southampton, UK) in lyophilised form. They were labelled with a fluorophore molecule (F=fluorescein) at the 5'-end and a quencher molecule (Q=dabcyl) at the 3'-end of the complementary strand. Each oligonucleotide was dissolved in distilled $H_2O$ to form stock solutions of 100 µM. Working solutions of 5 µM were prepared by diluting the stock solution with distilled $H_2O$.

1.2. Buffers

The following buffers were used: 250 mM phosphate buffer pH 7.4 (consisting of sodium dihydrogen phosphate and sodium phosphate diluted in distilled $H_2O$) and 5 M sodium chloride buffer. All buffers and distilled $H_2O$ were filtered through a 0.2 µM filter prior to use.

1.3. Compound

For the FRET experiments a stock solution of 18 was prepared by dissolving it in DMSO to give a concentration of 10 mM. From this stock solution, working solutions of the desired concentration were prepared by diluting the stock solution with distilled $H_2O$.

1.4. Preparation of Ligand-DNA Complexes

The reaction mixture was comprised of 4 µL of 250 mM phosphate buffer (final concentration of 50 mM), 4 µL flourophor and 4 µL quencher molecule of the appropriate oligonucleotide for a final concentration of 0.2 µM, 4 µL 5 M sodium chloride (final concentration of 1 M NaCl), and 4 µL of distilled $H_2O$. This mixture was heated in an Eppendorf tube at 90° C. for 1 min and slowly cooled down to room temperature. This process was carried out to anneal the single strands to double-stranded DNA. Following this, 4 µL of the ligand was added in the desired concentration and the mixture incubated overnight either at room temperature or 4° C. A control sample of DNA only was prepared by mixing 4 µL 250 mM phosphate buffer (final concentration of 50 mM) with 4 µL fluorophore-labelled and 4 µL quencher-labelled oligonucleotides (of the appropriate sequence) to give a final concentration of 0.2 µM, 4 µL 5 M sodium chloride (final concentration of 1 M NaCl) and 4 µL distilled $H_2O$. This mixture was analysed without prior annealing.

1.5. Fluorescence Melting

Fluorescence melting profiles were measured using a Roche LightCycler using a total reaction volume of 20 µL. Initially, the samples were denatured by heating to 95° C. at a rate of 1° C. $min^{-1}$. The samples were then maintained at 95° C. for 5 min before annealing by cooling to 25° C. at 1° C. $min^{-1}$. The samples were then held at 25° C. for a further 5 min and finally melted by heating to 95° C. at 1° C. $min^{-1}$. Annealing steps and melting steps were all recorded and changes in fluorescence were measured at 520 nm.

1.6. Data Analysis $T_m$ values were obtained from the first derivates of the melting profiles using the Roche LightCycler software.

MTT Cytotoxicity Methodology

Tumor cell lines were maintained in RPMI1640 medium supplemented with 10% heat-inactivated fetal bovine serum, 2 mM L-glutamine and 1 mM sodium pyruvate. 1800 cells per well were seeded in a volume of 180 µl in a 96-well flat bottom polystyrene plate. The cells were allowed to adhere overnight at 37° C. in a $CO_2$ incubator. Ligands were initially formulated in DMSO, and stocks stored at −80° C. They were then further formulated at lox concentration in RPMI1640 medium. 20 ul of diluted samples were added into each treatment well. On each plate, blank wells with no cells, and untreated wells containing cells, were included. Plates were then cultured at 37° C. in a $CO_2$ incubator for 72 hrs. Cytotoxicity was evaluated using a tetrazolium salt-based assay, the MT assay. After 72 hours, the supernatant was removed from each well and 200 µl of a sterile filtered 500 µg/ml MT solution in water added to each well. The plates were then incubated at 37° C. in a $CO_2$ incubator for 4 hrs. The supernatant was then removed and the formazan crystals formed solubilized by adding 150 µl of DMSO to each well. The plate was then read on a plate reader at 540 nm, and percentage cell survival calculated as follows: ((mean absorbance treated wells at concentration x—mean absorbance blank wells)÷(mean absorbance untreated wells at concentration x—mean absorbance blank wells))×100. Data were plotted as concentration in nM vs. % cell survival in Microsoft Excel, and $IC_{50}$ values (concentration where cell survival is reduced by a half) were determined from the graph.

REFERENCES

1. Antonow, D., Jenkins, T. C., Howard, P. W., and Thurston, D. E. (2007) S, *Bioorganic &Medicinal Chemistry* 15, 3041-3053
2. Antonow, D., and Thurston, D. E. (2011) Synthesis of DNA-interactive pyrrolo[2,1-c][1,4]benzodiazepines (PBDs), *Chem Rev* 111, 2815-2864.
3. Cipolla, L., Araujo, A. C., Airoldi, C., and Bini, D. (2009) Pyrrolo[2,1-c][1,4]benzodiazepine as a scaffold for the design and synthesis of anti-tumour drugs, *Anticancer Agents Med Chem* 9, 1-31.
4. Gerratana, B. (2012) Biosynthesis, synthesis, and biological activities of pyrrolobenzodiazepines, *Med Res Rev* 32, 254-293.
5. Hartley, J. A. (2011) The development of pyrrolobenzodiazepines as antitumour agents, *Expert Opin Investig Drugs* 20, 733-744.
6. Kamal, A., Reddy, K. L., Devaiah, V., Shankaraiah, N., and Reddy, D. R. (2006) Recent advances in the solid-phase combinatorial synthetic strategies for the benzodiazepine based privileged structures, *Mini Rev Med Chem* 6, 53-69.
7. Bose, D. S., Jones, G. B., and Thurston, D. E. (1992) New Approaches to Pyrrolo[2,1-C][1,4]Benzodiazepines—Synthesis, DNA-Binding and Cytotoxicity of Dc-81, *Tetrahedron* 48, 751-758.
8. Hurley, L. H., Reck, T., Thurston, D. E., Langley, D. R., Holden, K. G., Hertzberg, R. P., Hoover, J. R., Gallagher, G., Jr., Faucette, L. F., Mong, S. M., and et al. (1988) Pyrrolo[1,4]benzodiazepine antitumor antibiotics: relationship of DNA alkylation and sequence specificity to the biological activity of natural and synthetic compounds, *Chem Res Toxicol* 1, 258-268.
9. Wells, G., Martin, C. R., Howard, P. W., Sands, Z. A., Laughton, C. A., Tiberghien, A., Woo, C. K., Masterson, L. A., Stephenson, M. J., Hartley, J. A., Jenkins, T. C., Shnyder, S. D., Loadman, P. M., Waring, M. J., and Thurston, D. E. (2006) Design, synthesis, and biophysical and biological evaluation of a series of pyrrolobenzodiazepine-poly(N-methylpyrrole) conjugates, *Journal of medicinal chemistry* 49, 5442-5461.

10. Brucoli, F., Hawkins, R. M., James, C. H., Jackson, P. J., Wells, G., Jenkins, T. C., Ellis, T., Kotecha, M., Hochhauser, D., Hartley, J. A., Howard, P. W., and Thurston, D. E. (2013) An Extended Pyrrolobenzodiazepine-Polyamide Conjugate with Selectivity for a DNA Sequence Containing the ICB2 Transcription Factor Binding Site, *Journal of medicinal chemistry* 56, 6339-6351.

11. Kotecha, M., Kluza, J., Wells, G., O'Hare, C. C., Forni, C., Mantovani, R., Howard, P. W., Morris, P., Thurston, D. E., Hartley, J. A., and Hochhauser, D. (2008) Inhibition of DNA binding of the NF-Y transcription factor by the pyrrolobenzodiazepine-polyamide conjugate GWL-78, *Mol Cancer Ther* 7, 1319-1328.

12. Puvvada, M. S., Hartley, J. A., Jenkins, T. C., and Thurston, D. E. (1993) A quantitative assay to measure the relative DNA-binding affinity of pyrrolo[2,1-c][1,4]benzodiazepine (PBD) antitumour antibiotics based on the inhibition of restriction endonuclease BamHI, *Nucleic Acids Res* 21, 3671-3675.

13. Clingen, P. H., De Silva, I. U., McHugh, P. J., Ghadessy, F. J., Tilby, M. J., Thurston, D. E., and Hartley, J. A. (2005) The XPF-ERCC1 endonuclease and homologous recombination contribute to the repair of minor groove DNA interstrand crosslinks in mammalian cells produced by the pyrrolo[2,1-c][1,4]benzodiazepine dimer SJG-136, *Nucleic Acids Res* 33, 3283-3291.

14. Puvvada, M. S., Forrow, S. A., Hartley, J. A., Stephenson, P., Gibson, I., Jenkins, T. C., and Thurston, D. E. (1997) Inhibition of Bacteriophage T7 RNA Polymerase In Vitro Transcription by DNA-Binding Pyrrolo[2,1-c][1,4]benzodiazepines, *Biochemistry* 36, 2478-2484.

15. Barkley, M. D., Cheatham, S., Thurston, D. E., and Hurley, L. H. (1986) Pyrrolo[1,4]benzodiazepine antitumor antibiotics: evidence for two forms of tomaymycin bound to DNA, *Biochemistry* 25, 3021-3031.

16. Seifert, J., Pezeshki, S., Kamal, A., and Weisz, K. (2012) Inter- and intrastrand DNA crosslinks by 2-fluoro-substituted pyrrolobenzodiazepine dimers: stability, stereochemistry and drug orientation, *Organic & Biomolecular Chemistry* 10, 6850-6860.

17. Smellie, M., Bose, D. S., Thompson, A. S., Jenkins, T. C., Hartley, J. A., and Thurston, D. E. (2003) Sequence-selective recognition of duplex DNA through covalent interstrand cross-linking: kinetic and molecular modeling studies with pyrrolobenzodiazepine dimers, *Biochemistry* 42, 8232-8239.

18. Kopka, M. L., Goodsell, D. S., Baikalov, I., Grzeskowiak, K., Cascio, D., and Dickerson, R. E. (1994) Crystal structure of a covalent DNA-drug adduct: anthramycin bound to C-C-A-A-C-G-T-T-G-G and a molecular explanation of specificity, *Biochemistry* 33, 13593-13610.

19. Kizu, R., Draves, P. H., and Hurley, L. H. (1993) Correlation of DNA sequence specificity of anthramycin and tomaymycin with reaction kinetics and bending of DNA, *Biochemistry* 32, 8712-8722.

20. Gregson, S. J., Howard, P. W., Hartley, J. A., Brooks, N. A., Adams, L. J., Jenkins, T. C., Kelland, L. R., and Thurston, D. E. (2001) Design, synthesis, and evaluation of a novel pyrrolobenzodiazepine DNA-interactive agent with highly efficient cross-linking ability and potent cytotoxicity, *Journal of medicinal chemistry* 44, 737-748.

21. Puzanov, I., Lee, W., Chen, A. P., Calcutt, M. W., Hachey, D. L., Vermeulen, W. L., Spanswick, V. J., Liao, C. Y., Hartley, J. A., Berlin, J. D., and Rothenberg, M. L. (2011) Phase I pharmacokinetic and pharmacodynamic study of SJG-136, a novel DNA sequence selective minor groove cross-linking agent, in advanced solid tumors, *Clinical Cancer Research* 17, 3794-3802.

22. H. L. Bolt, C. E. J. Williams, R. V. Brooks, R. N. Zuckermann, S. L. Cobb, E. H. C. Bromley, *Biopolymers* 2017,108, e23014.

23. K. Valkó, C. Bevan, D. Reynolds, *Analytical Chemistry* 1997, 69, 2022-2029.

24. K. M. Rahman, A. S. Thompson, C. H. James, M. Narayanaswamy, D. E. Thurston, *Journal of the American Chemical Society* 2009,131, 13756-13766.

25. Drew, H. R. and A. A. Travers, *DNA structural variations in the E. coli tyrT promoter.* Cell, 1984. 37(2): p. 491-502.

All publications mentioned in the above specification are herein incorporated by reference. Although illustrative embodiments of the invention have been disclosed in detail herein, with reference to the accompanying drawings, it is understood that the invention is not limited to the precise embodiment and that various changes and modifications can be effected therein by one skilled in the art without departing from the scope of the invention as defined by the appended claims and their equivalents.

The invention claimed is:
1. A compound of formula (I) or formula (II):

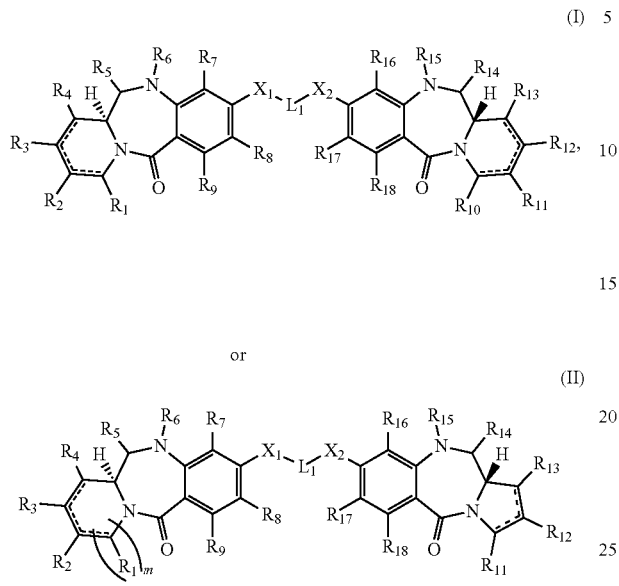

wherein;
each double line --- independently represents a single bond or a double bond;
m is 0 or 1;
$R_1$, $R_2$, $R_3$ and $R_4$ are independently H or $R_{19}$;
or one of $R_1$ and $R_2$, $R_2$ and $R_3$, or $R_3$ and $R_4$, together with the carbon atoms to which they are attached form a 6-membered aryl, or a 5- or 6-membered cyclic, heterocyclic, or heteroaryl ring optionally substituted with 1, 2 or 3 independently selected $R_{20}$ groups;
$R_5$ and $R_6$ are selected such that either (i) $R_5$ is selected from the group consisting of H, OH and $OC_{1-6}$ alkyl; and $R_6$ is selected from the group consisting of H, $SO_3H$, nitrogen protecting groups, -$L_2$-$R_{28}$ and RA; (ii) $R_5$ is oxo or H, and $R_6$ is H or $C_{1-6}$ alkyl; or (iii) $R_5$ and $R_6$ together form a double bond;
$R_7$, $R_9$, $R_{16}$ and $R_{18}$ are independently selected from the group consisting of H and $R_{20}$;
$R_8$ and $R_{17}$ are independently selected from the group consisting of H, $SR_{22}$, $SCH_2Ph$ and $R_{20}$;
$R_{10}$, $R_{11}$, $R_{12}$ and $R_{13}$, are independently selected from the group consisting of H and $R_{19}$;
or one of $R_{10}$ and $R_{11}$, $R_{12}$ and $R_{12}$, $R_{12}$ and $R_{13}$, or $R_{13}$ and $R_{14}$ together with the carbon atoms to which they are attached form a 6-membered aryl, or a 5- or 6-membered cyclic, heterocyclic, or heteroaryl ring optionally substituted with 1, 2 or 3 independently selected optional $R_{20}$ groups;
$R_{14}$ and $R_{15}$ are selected such that either (iv) $R_{14}$ is selected from the group consisting of H, OH and $OC_{1-6}$ alkyl; and $R_{15}$ is selected from the group consisting of H, $SO_3H$, nitrogen protecting groups, -$L_2$-$R_{28}$ and $R_B$; (V) $R_{14}$ is oxo or H, and $R_{15}$ is H or $C_{1-6}$ alkyl; or (vi) $R_{14}$ and $R_{15}$ together form a double bond; with the proviso that if $R_5$ and $R_6$ are selected from (ii) then $R_{14}$ and $R_{15}$ are selected from (iv) or (vi); and if $R_{14}$ and $R_{15}$ are selected from (v) then $R_5$ and $R_6$ are selected from (i) or (iii);

each $R_A$ and $R_B$ is independently selected from the group consisting of $(CH_2)_j$—OH, $(CH_2)_j$—$CO_2R_{26}$, C(=O)—O—$(CH_2)_k$—$NR_{26}R_{27}$, $(CH_2)_j$—$NR_{26}R_{27}$, C(=O)—NH—$(CH_2)_j$—$NR_{26}R_{27}$ and C(=O)—NH—$(CH_2)_k$—C(=NH)$NR_{26}R_{27}$;
$X_1$ is O, S, $NR_{24}$, $CR_{24}R_{25}$, $CR_{24}R_{25}O$, C(=O), C(=O)$NR_{24}$, $NR_{24}C$(=O), O—C(O), C(O)—O or is absent;
$L_1$ is selected from the group consisting of an amino acid, a peptide chain having from 2 to 12 amino acids, a paraformaldehyde chain —$(OCH_2)_{1-24}$—, a polyethylene glycol chain —$(OCH2CH_2)_{1-12}$— and —$(CH_2)_n$—$Y_1$—$(CH_2)_p$— wherein
n is selected from 0, 1, 2, 3, 4, 5, 6, 7, 8, 9, 10, 11 or 12;
p is selected from 0, 1, 2, 3, 4, 5, 6, 7, 8, 9, 10, 11 or 12; and
$Y_1$ is selected from the group consisting of —$(CH_2)_{1-5}$—, —C(O)—NH—, —NH—, —$S(O)_{0-2}$—, —C$[(CH_2)_{0-5}Y_2]$—, —$Ar_1$—C(O)— NH—$(Ar_2)_O$-1 $Ar_3$—, —$Ar_3$—$(Ar_2)_{0-1}$—NH—C(O)—$Ar_1$—, optionally substituted 3- to 7-membered cycloalkylene or heterocycloalkene, optionally substituted 6-membered arylene, and optionally substituted 5- to 9-membered heteroarylene;
$Y_2$ is H or $R_{20}$;
$Ar_1$ is an optionally substituted 5-membered heteroarylene;
$Ar_2$ is an optionally substituted 6-membered arylene or heteroarylene;
$Ar_3$ is an optionally substituted 5- to 9-membered heteroaryl ring;
wherein the optionally substituted groups of $Y_1$, $Ar_1$, $Ar_2$ and $Ar_3$ are optionally substituted with 1, 2 or 3 independently selected $R_{20}$ groups;
$X_2$ is O, S, $NR_{24}$, $CR_{24}R_{25}$, $CR_{24}R_{25}O$, C(=O), C(=O)$NR_{24}$, $NR_{24}C$(=O), O—C(O), C(O)—O or is absent;
each $R_{19}$ is independently selected from the group consisting of $R_{20}$, $R_{21}$, =CH—$(CH_2)_S$, $CH_3$, =CH—$(CH_2)_S$—$R_{21}$, =O, $(CH_2)_s$—$OR_{21}$, $(CH_2)_s$—$CO_2R_{21}$, $(CH_2)_s$—$NR_{21}R_{23}$, O—$(CH_2)_t$—$NR_{21}R_{23}$, NH—C(O)—$R_{21}$, O—$(CH_2)_t$NH—C(O)—$R_{21}$, O—$(CH_2)_t$—C(O)—NH—$R_{21}$, $(CH_2)_s$—$SO_2R_{21}$, O—$SO_2R_{21}$, $(CH_2)_s$—C(O)$R_{21}$ and $(CH_2)_s$—C(O)$NR_{21}R_{23}$;
each $R_{20}$ is independently selected from the group consisting of F, Cl, Br, $(CH_2)_j$—OH, $C_{1-6}$ alkyl, $OC_{1-6}$ alkyl, $OCH_2Ph$, $(CH_2)_j$—$CO_2R_{26}$, O—$(CH_2)_k$—$NR_{26}R_{26}$, C(=O)—O—$(CH_2)_k$—$NR_{26}R_{27}$, C(=O)—$NR_{26}R_{27}$, $(CH_2)_j$—$NR_{26}R_{27}$, $NR_{26}NH_2$, C(=O)—NH—$(CH_2)_j$—$NR_{26}R_{27}$, C(=O)—O—$(CH_2)_k$—$NR_{26}R_{27}$, C(=O)—C(=O)—NH—$(CH_2)_k$—C(=NH)$NR_{26}R_{27}$, -$L_2$-$R_{28}$, $S(O)_2$—($C_{1-6}$ alkyl), O—$(CH_2)_k$—O—($C_{1-6}$ alkyl), $(CH_2)j$-$S(O)_2$—$NR_{26}R_{27}$, C(=NH)—O—($C_{1-6}$ alkyl), $(CH_2)_k$—O—($C_{1-6}$ alkyl), CN, NCO, Cy, C(O)—NH—$(CH_2)_j$-Cy, C(O)-Cy, NH—C(O)—$NR_{26}R_{27}$ and

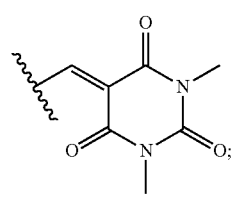 [SMILES: *C=C1C(=O)N(C)C(=O)N(C)C1=O]

each j and s is independently 0, 1, 2, 3, 4, 5 or 6;
each k and t is independently 1, 2, 3, 4, 5 or 6;

each $R_{21}$ is independently selected from the group consisting of H, $C_{1-12}$ alkyl, $C_{5-6}$ heterocyclyl, $C_{5-9}$ heteroaryl, $C_{6-15}$ heteroarylalkyl, phenyl and $C_{7-12}$ aralkyl groups; wherein the heterocyclyl, heteroaryl, heteroarylalkyl, phenyl and aralkyl groups are optionally substituted with 1, 2 or 3 independently selected $R_{20}$ groups;

each $R_{22}$, $R_{23}$, $R_{24}$, $R_{25}$, $R_{26}$ and $R_{27}$ is independently selected from the group consisting of H and $C_{1-12}$ alkyl;

each $C_y$ is independently selected from the group consisting of $C_{5-6}$ heterocyclyl or $C_{5-6}$ heteroaryl group, wherein the heterocyclyl or heteroaryl groups are optionally substituted with 1 or 2 $R_{20}$ groups;

$L_2$ is a bond or a linker moiety having 1-200 non-hydrogen atoms selected from C, N, O, S or halogen, and optionally incorporates ether, oxo, carboxamidyl, urethanyl, branched, cyclic, unsaturated, heterocyclyl, aryl, or heteroaryl moieties; and $R_{28}$ is an azide, alkyne, bisulfone, carbohydrazide, hydrazine, hydroxylamine, iodoacetamide, isothiocyanate, maleimide, phosphine, pyrridopyridazine, semihydrazide, succinimidyl ester, sulfodichlorophenol ester, sulfonyl halide, sulfosuccinimidyl ester, 4-sulfotetrafluorophenyl ester, tetrafluorophenyl ester, thiazole, $R_A$, O—$(CH_2)_k$—$NR_{26}R_{26}$, $NHNH_2$, or is a targeting agent wherein the targeting agent is selected from a protein, a portion of a protein, a peptide, a nucleic acid, or an antibody;

or pharmaceutically acceptable salts, solvates, tautomers, stereoisomers or mixtures thereof;

with the proviso that either the compound is:

(a) a compound of formula (I), wherein at least one of $R_3$ or $R_{12}$ is an optionally substituted $C_{5-6}$ heterocyclyl, an optionally substituted $C_{5-9}$ heteroaryl or an optionally substituted phenyl;

(b) a compound of formula (I), wherein both $R_2$ and $R_3$, and $R_{11}$ and $R_{12}$, together with the carbon atoms to which they are attached form an optionally substituted 5-membered cyclic, heterocyclic, or heteroaryl ring;

(c) a compound of formula (II), wherein m is 1; Ru is an optionally substituted $C_5$-6 heterocyclyl, an optionally substituted $C_{5-9}$ heteroaryl or an optionally substituted phenyl; and $R_1$, $R_2$, $R_3$, $R_4$, $R_{10}$, $R_{11}$ and $R_{13}$ are independently selected from the group consisting of H and $R_{19}$, (d) a compound of formula (II), wherein m is 1; $R_{11}$ and $R_{12}$, or Ru and $R_{13}$, together with the carbon atoms to which they are attached form an optionally substituted 6-membered aryl, or a 5- or 6-membered cyclic, heterocyclic, or heteroaryl ring; and $R_1$, $R_2$, $R_3$, $R_4$, are independently selected from the group consisting of H and $R_{19}$;

(e) a compound of formula (II), wherein m is 0; $R_{12}$ is an optionally substituted $C_{5-6}$ heterocyclyl, an optionally substituted $C_{5-9}$ heteroaryl or an optionally substituted phenyl; and $R_2$ and $R_3$, or $R_3$ and $R_4$, together with the carbon atoms to which they are attached form an optionally substituted 6-membered aryl, or a 5- or 6-membered cyclic, heterocyclic, or heteroaryl ring; or (f) a compound of formula (II), wherein m is 1; $R_{12}$ is =$CH_2$, =CH—$(CH_2)_S$—$CH_3$ or =CH—$(CH_2)_S$—$R_{21}$; and $R_1$, $R_2$, $R_3$, $R_4$, $R_{10}$, $R_{11}$, and $R_{13}$ are independently selected from the group consisting of H and $R_{19}$.

2. A compound of formula (I) or formula (II) according to claim 1, wherein only one $R_{20}$ group is selected from the group consisting of $(CH_2)_j$—OH, $(CH_2)_j$—$CO_2R_{26}$, O—$(CH_2)_k$—$NHR_{27}$, $(CH_2)_j$—$NHR_{27}$, $NHNH_2$, C(=O)—NH—$(CH_2)_j$—$NHR_{27}$, C(=O)—NH—$(CH_2)_k$—C(=NH)$NHR_{27}$ and -$L_2$-$R_{28}$; and the remaining $R_{20}$ groups are independently selected from the group consisting of Cl, Br, $C_{1-6}$ alkyl, $OC_{1-6}$ alkyl, $OCH_2Ph$, O—$(CH_2)_k$—$N(C_{1-6}$ alkyl)($C_{1-6}$ alkyl), $(CH_2)_j$—$N(C_{1-6}$ alkyl)($C_{1-6}C$(=O)—NH—$(CH_2)_j$—$N(C_{1-6}$ alkyl)($C_{1-6}$ alkyl) and C(=O)—NH—$C_6H_4$—$(CH_2)_j$—$R_{26}$.

3. A compound of formula (I) or formula (II) according to claim 1, wherein $R_8$ and $R_{17}$ are independently selected from $O(C_{1-6}$ alkyl) or $OCH_2Ph$.

4. A compound of formula (I) or formula (II) according to claim 1, wherein $R_7$, $R_9$, $R_{16}$ and $R_{18}$ are H.

5. A compound of formula (I) or formula (II) according to claim 1, wherein if present $R_1$ and $R_{10}$ are H.

6. A compound of formula (I) or formula (II) according to claim 1, wherein $R_4$ and $R_{16}$ are H.

7. A compound of formula or formula (II) according to claim 1, wherein $X_1$ and $X_2$ are independently selected from the group consisting of O, $CH_2$, C(=O) and NHC(=O).

8. A compound of formula (I) or formula (II) according to claim 1, wherein $L_1$ is selected from —$(CH_2)_m$—$(CH_2)_q$—$(CH_2)_n$—, —$(CH_2)_m$—$Ar_1$—C(O)—NH—$(Ar_2)_{0-1}$—$Ar_3$—$(CH_2)_n$—, —$(CH_2)_m$—$Ar_3$—$(Ar_2)_{0-1}$—NH—C(O)—$Ar_1$—$(CH_2)_n$—,

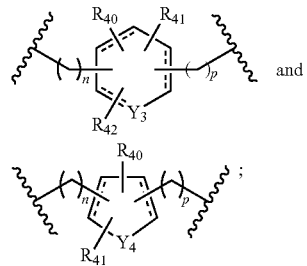

wherein q is 1, 2, 3, 4 or 5;
$Y_3$ is C—H or N;
$Y_4$ is N—$R_{43}$, O or S; and
$R_{40}$, $R_{41}$ and $R_{42}$ are independently selected from the group consisting of H and $R_{20}$; and
$R_{43}$ is H or methyl.

9. A compound of formula (I) or formula (II) according to claim 1, wherein the compound is (a) a compound of formula (I) and at least one of $R_3$ or $R_{12}$ is a substituted $C_{5-9}$ heteroaryl or a substituted phenyl substituted with at least one $R_{20}$ group.

10. A compound of formula (I) or formula (II) according to claim 1, having the structure of formula (A3):

(A3)

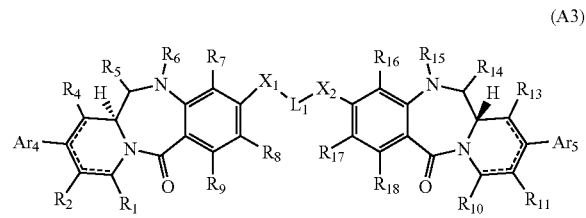

wherein $Ar_4$ and $Ar_5$ are independently selected from the group consisting of optionally substituted $C_{5-9}$ heteroaryl and optionally substituted phenyl, optionally substituted with 1, 2 or 3 independently selected optional $R_{20}$ groups.

11. A compound of formula or formula (II) according to claim 1, having the structure of formula (A6):

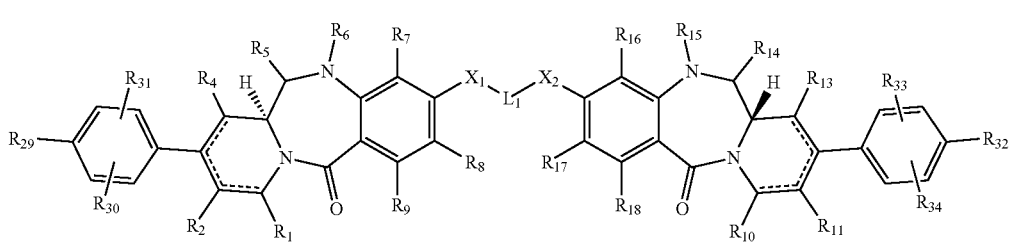

(A6)

wherein $R_{29}$, $R_{30}$, $R_{31}$, $R_{32}$, $R_{33}$ and $R_{34}$ are each independently selected from the group consisting of H and $R_{20}$.

12. A compound of formula (I) or formula (II) according to claim 1, having the structure of formula (A15) or (A16):

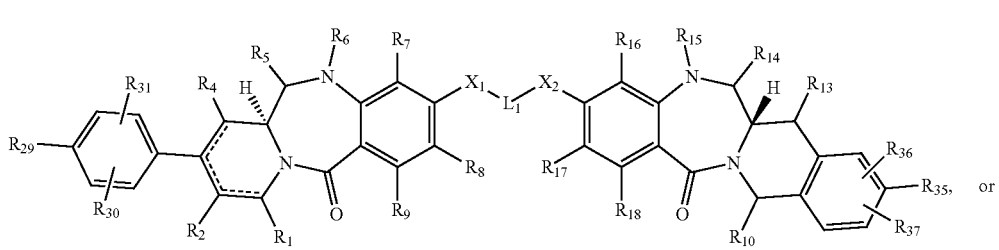

(A15)

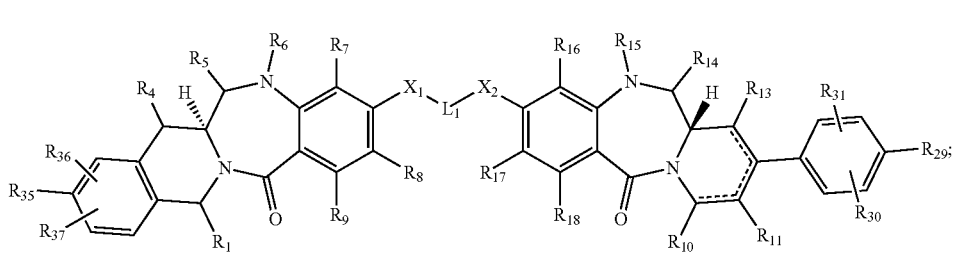

(A16)

wherein $R_{29}$, $R_{30}$, $R_{31}$, $R_{35}$, $R_{36}$ and $R_{37}$ are each independently selected from the group consisting of H and $R_{20}$.

13. A compound of formula (I) or formula (II) according to claim 1, having the structure of formula (B1):

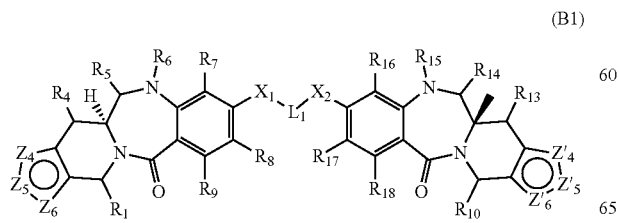

(B1)

wherein $Z_4$ is selected from the group consisting of NH, $N(C_{1-6}$ alkyl), S and O; and $Z_5$ and $Z_6$ are independently selected from the group consisting of N, CH, and C—$R_{20}$; or $Z_4$ and $Z_5$ are independently selected from the group consisting of N, CH, and C—$R_{20}$, and $Z_6$ is selected from the group consisting of NH, —$N(C_{1*6}$ alkyl), S and O; and $Z'_4$ is selected from the group consisting of NH, $N(C_{1-6}$ alkyl), S and O; and $Z'_5$ and $Z'_6$ are independently selected from the group consisting of N, CH, and C—$R_{20}$; or $Z'_4$ and $Z'_5$ are independently selected from the group consisting of N, CH, and C—$R_{20}$, and $Z'_6$ is selected from the group consisting of NH, $N(C_{1-6}$ alkyl) S and O.

14. A compound of formula (I) or formula (II) according to claim 1, having the structure of formula (C2):

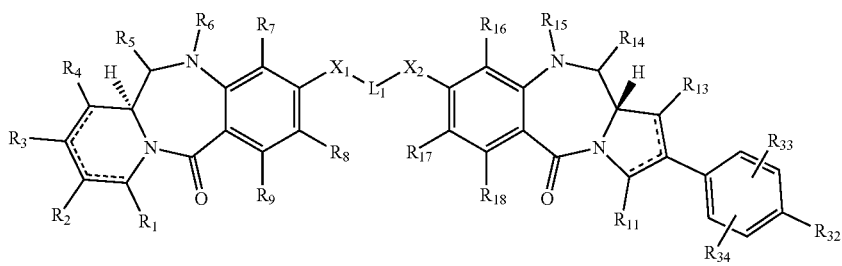

(C2)

wherein $R_{22}$, $R_{33}$ and $R_{34}$ are each independently selected from the group consisting of H and $R_{20}$.

15. An antibody-drug conjugate comprising a compound of formula (I) or formula (II) according to claim 1.

16. A pharmaceutical composition comprising a compound of formula (I) or formula (II) according to claim 1, and a pharmaceutically acceptable carrier or diluent.

17. A method of treating reversing, alleviating or inhibiting the progress of cancer in a subject, the method comprising administering a compound of formula (I) or formula (II) according to claim 1, either alone or as a part of a pharmaceutical composition, to the subject, or administering a pharmaceutical composition according to claim 16, to the subject.

18. The method according to claim 17, wherein the cancer is selected from the group consisting of bladder cancer, bone cancer, bowel cancer, brain cancer, breast cancer, cervical cancer, colon cancer, head and neck cancer, leukemia, liver cancer, lung cancer, lymphoma, melanoma, oesophageal cancer, oral cancer, ovarian cancer, pancreatic cancer, prostate cancer, rectal cancer, renal cancer, retinoblastoma, sarcoma, skin cancer, stomach cancer, testicular cancer, thyroid cancer and uterine cancer.

* * * * *